US011128636B1

(12) United States Patent
Jorasch et al.

(10) Patent No.: US 11,128,636 B1
(45) Date of Patent: Sep. 21, 2021

(54) SYSTEMS, METHODS, AND APPARATUS FOR ENHANCED HEADSETS

(71) Applicant: Science House LLC, New York, NY (US)

(72) Inventors: James Jorasch, New York, NY (US); Christopher Capobianco, Hastings-on-Hudson, NY (US); Isaac W. Hock, Chicago, IL (US); Michael Werner, Germantown, TN (US); Geoffrey Gelman, New York, NY (US); Gennaro Rendino, Horseheads, NY (US)

(73) Assignee: Science House LLC, New York, NY (US)

( * ) Notice: Subject to any disclaimer, the term of this patent is extended or adjusted under 35 U.S.C. 154(b) by 0 days.

(21) Appl. No.: 17/320,164

(22) Filed: May 13, 2021

Related U.S. Application Data

(60) Provisional application No. 63/023,965, filed on May 13, 2020.

(51) Int. Cl.
*H04L 29/06* (2006.01)
*G07C 9/37* (2020.01)
(Continued)

(52) U.S. Cl.
CPC ............ *H04L 63/102* (2013.01); *A61B 5/291* (2021.01); *A61B 5/369* (2021.01); *G06F 1/163* (2013.01); *G06F 3/012* (2013.01); *G06F 3/017* (2013.01); *G06K 9/00664* (2013.01); *G06K 9/6201* (2013.01); *G06T 7/70* (2017.01); *G07C 9/37* (2020.01); *G10L 15/22* (2013.01);
(Continued)

(58) Field of Classification Search
CPC ... H04L 63/102; H04L 63/0861; G10L 15/22; G10L 2015/225; A61B 5/369; A61B 5/291; G07C 9/37; G06T 7/70; G06Q 50/01; G06K 9/00664
See application file for complete search history.

(56) References Cited

U.S. PATENT DOCUMENTS 3,541,541 A 11/1970 Englebart
3,611,358 A 10/1971 Dalmasso
(Continued)

FOREIGN PATENT DOCUMENTS

AU 2017232174 10/2017
CN 1431575 9/2005
(Continued)

OTHER PUBLICATIONS

Bruce Schneier, "Applied Cryptography," Wiley, 1996.
(Continued)

*Primary Examiner* — Vernal U Brown
(74) *Attorney, Agent, or Firm* — RowanTree Law Group PLLC; Carson C.K. Fincham

(57) ABSTRACT

In accordance with some embodiments, systems, apparatus, interfaces, methods, and articles of manufacture are provided for ascertaining aspects of a user, such as the user's identity, competence, health, and state of mind. In various embodiments, data is captured about a user via a headset worn by the user. Based on the data, a determination may be made about an aspect of the user, and the user may accordingly be granted or denied access to a resource.

30 Claims, 117 Drawing Sheets

(51) Int. Cl.
    *G06F 1/16*         (2006.01)
    *G06K 9/62*         (2006.01)
    *G06K 9/00*         (2006.01)
    *G06F 3/01*         (2006.01)
    *G06T 7/70*         (2017.01)
    *H04N 5/232*       (2006.01)
    *G10L 15/22*       (2006.01)
    *A61B 5/369*      (2021.01)
    *A61B 5/291*      (2021.01)
    *G16H 40/67*      (2018.01)
    *G06Q 10/10*      (2012.01)
    *G06Q 50/00*      (2012.01)
    *G06Q 50/20*      (2012.01)

(52) U.S. Cl.
    CPC ......... *G16H 40/67* (2018.01); *H04L 63/0861* (2013.01); *H04N 5/23222* (2013.01); *G06Q 10/101* (2013.01); *G06Q 50/01* (2013.01); *G06Q 50/205* (2013.01); *G10L 2015/225* (2013.01)

(56) References Cited

U.S. PATENT DOCUMENTS

| | | | |
|---|---|---|---|
| 4,280,135 | A | 7/1981 | Schlossberg |
| 5,025,255 | A | 6/1991 | Mould |
| 5,080,516 | A | 1/1992 | Ward |
| 5,204,768 | A | 4/1993 | Tsakiris et al. |
| 5,348,405 | A | 9/1994 | Lupkas |
| 5,646,648 | A | 7/1997 | Bertram |
| 5,669,015 | A | 9/1997 | Chidester et al. |
| 5,680,157 | A | 10/1997 | Bidiville et al. |
| 5,684,279 | A | 11/1997 | Burgett |
| 5,729,008 | A | 3/1998 | Blalock et al. |
| 5,779,549 | A | 7/1998 | Walker et al. |
| 5,879,088 | A | 3/1999 | English |
| 5,971,340 | A | 10/1999 | Murphy |
| 6,040,539 | A | 3/2000 | Hiegel |
| 6,043,809 | A | 3/2000 | Holehan |
| 6,056,193 | A | 5/2000 | MCauliffe et al. |
| 6,330,022 | B1 | 12/2001 | Seligmann |
| 6,400,356 | B1 | 6/2002 | Bidiville et al. |
| 6,630,895 | B1 | 10/2003 | Dong |
| 6,694,391 | B2 | 2/2004 | Blood |
| 6,710,769 | B2 | 3/2004 | Loughran et al. |
| 6,715,881 | B2 | 4/2004 | Fujiwara |
| 6,980,136 | B2 | 12/2005 | Tsai et al. |
| 6,992,656 | B2 | 1/2006 | Hughes |
| 7,015,833 | B1 | 3/2006 | Ambuehl et al. |
| 7,079,049 | B2 | 7/2006 | Giordani |
| 7,165,901 | B2 | 1/2007 | McLoone et al. |
| 7,189,017 | B2 | 3/2007 | McLoone |
| 7,212,655 | B2 | 5/2007 | Tumey et al. |
| 7,397,932 | B2 | 7/2008 | McAlpine et al. |
| 7,434,153 | B2 | 10/2008 | Liu et al. |
| 7,679,518 | B1 | 3/2010 | Pabla et al. |
| 7,693,736 | B1 | 4/2010 | Chu et al. |
| 7,738,468 | B2 | 6/2010 | Strandridge et al. |
| 7,786,411 | B2 | 8/2010 | Li et al. |
| 7,808,484 | B1 | 10/2010 | Bareli |
| 7,808,488 | B2 | 10/2010 | Martin et al. |
| 7,847,204 | B2 | 12/2010 | Tsai |
| 8,094,193 | B2 | 1/2012 | Peterson |
| 8,200,520 | B2 | 6/2012 | Chen et al. |
| D665,439 | S | 8/2012 | Khamsepoor et al. |
| 8,242,412 | B2 | 8/2012 | Liu et al. |
| 8,255,151 | B2 | 8/2012 | Bourque et al. |
| 8,255,152 | B2 | 8/2012 | Barth et al. |
| 8,289,363 | B2 | 10/2012 | Buckler |
| 8,315,876 | B2 | 11/2012 | Reuss |
| 8,334,843 | B1 | 12/2012 | Charlton et al. |
| 8,346,590 | B2 | 1/2013 | Norton et al. |
| 8,432,485 | B1 | 4/2013 | Martinez et al. |
| 8,622,798 | B2 | 1/2014 | Lockton |
| 8,705,195 | B2 | 4/2014 | Lockton |
| 8,721,204 | B2 | 5/2014 | Sauvage |
| 8,738,432 | B2 | 5/2014 | Hamilton et al. |
| 8,805,141 | B2 | 8/2014 | Fewkes et al. |
| 8,830,312 | B2 | 9/2014 | Hummel et al. |
| 8,887,052 | B1 | 11/2014 | Young |
| 8,892,999 | B2 | 11/2014 | Nims et al. |
| 9,001,120 | B2 | 4/2015 | Steedly et al. |
| 9,042,589 | B2 | 5/2015 | Depallens et al. |
| 9,153,231 | B1 | 10/2015 | Salvador et al. |
| 9,166,979 | B2 | 10/2015 | Hoard et al. |
| 9,176,595 | B2 | 11/2015 | Chao |
| 9,235,977 | B2 | 1/2016 | Deutsch |
| 9,336,594 | B2 | 5/2016 | Kyal et al. |
| 9,344,745 | B2 | 5/2016 | Gottlieb |
| 9,360,948 | B2 | 6/2016 | Al Nabulsi et al. |
| 9,400,930 | B2 | 7/2016 | Moeglein et al. |
| 9,697,418 | B2 | 7/2017 | Shamaie |
| 9,707,482 | B2 | 7/2017 | Lockton et al. |
| 9,807,342 | B2 | 10/2017 | Fogarty et al. |
| 9,821,226 | B2 | 11/2017 | Leyvant et al. |
| 9,858,496 | B2 | 1/2018 | Sun et al. |
| 9,953,214 | B2 | 4/2018 | Yin et al. |
| 9,972,144 | B2 | 5/2018 | Klein et al. |
| 10,044,871 | B2 | 8/2018 | Bargetzi et al. |
| 10,048,917 | B2 | 8/2018 | Vaughan et al. |
| 10,076,279 | B2 | 9/2018 | Nahum |
| 10,121,113 | B1 | 11/2018 | Swieter et al. |
| 10,185,027 | B2 | 1/2019 | O'Keeffe |
| 10,190,792 | B2 | 1/2019 | Jacobson et al. |
| 10,379,635 | B2 | 8/2019 | Wang et al. |
| 10,389,769 | B2 | 8/2019 | Gudipaty et al. |
| 10,482,698 | B2 | 11/2019 | Caterino et al. |
| 10,489,793 | B2 | 11/2019 | Ohnemus et al. |
| RE47,837 | E | 2/2020 | Barefoot et al. |
| 10,650,244 | B2 | 5/2020 | Meisser et al. |
| 10,672,167 | B2 | 6/2020 | Albouze |
| 10,782,682 | B2 | 9/2020 | Li et al. |
| 10,810,409 | B2 | 10/2020 | Bacivarov et al. |
| 10,880,520 | B2 | 12/2020 | Jiang et al. |
| 2001/0054971 | A1 | 12/2001 | King |
| 2002/0005834 | A1 | 1/2002 | Oh |
| 2002/0084986 | A1 | 7/2002 | Armstrong |
| 2002/0109675 | A1 | 8/2002 | Kuan |
| 2002/0126088 | A1 | 9/2002 | Abdelhadi et al. |
| 2003/0025884 | A1 | 2/2003 | Hamana et al. |
| 2003/0052863 | A1 | 3/2003 | Hsia |
| 2003/0076369 | A1 | 4/2003 | Resner et al. |
| 2003/0078970 | A1 | 4/2003 | Leaders et al. |
| 2003/0160813 | A1 | 8/2003 | Raju |
| 2003/0191690 | A1 | 10/2003 | McIntyre et al. |
| 2003/0206759 | A1 | 11/2003 | Emerson |
| 2003/0208324 | A1 | 11/2003 | Bellwood et al. |
| 2003/0208404 | A1 | 11/2003 | Michie |
| 2004/0100447 | A1 | 5/2004 | Ozolins |
| 2005/0007343 | A1 | 1/2005 | Butzer |
| 2005/0057514 | A1 | 3/2005 | Bathiche |
| 2005/0122706 | A1 | 6/2005 | Sung |
| 2005/0128180 | A1 | 6/2005 | Wang |
| 2005/0246642 | A1 | 11/2005 | Valderas et al. |
| 2006/0011461 | A1 | 1/2006 | Chan et al. |
| 2006/0248462 | A1 | 11/2006 | Ofek et al. |
| 2006/0250367 | A1 | 11/2006 | Tabasso et al. |
| 2007/0143679 | A1 | 6/2007 | Resner |
| 2007/0230794 | A1 | 10/2007 | McAlpine et al. |
| 2008/0013262 | A1 | 1/2008 | Stanford et al. |
| 2008/0133803 | A1 | 6/2008 | Liu et al. |
| 2008/0158157 | A1 | 7/2008 | Chang et al. |
| 2008/0288864 | A1 | 11/2008 | Qu et al. |
| 2008/0298613 | A1 | 12/2008 | Slamka et al. |
| 2009/0132926 | A1 | 5/2009 | Bucha |
| 2009/0237358 | A1 | 9/2009 | Chang |
| 2010/0146496 | A1 | 6/2010 | Stoddart et al. |
| 2010/0157167 | A1 | 6/2010 | Lawther et al. |
| 2010/0225584 | A1 | 9/2010 | Cauchi |
| 2010/0318916 | A1 | 12/2010 | Wilkins |
| 2011/0053556 | A1 | 3/2011 | Masaryk et al. |
| 2011/0291931 | A1 | 12/2011 | Wu et al. |

(56) References Cited

U.S. PATENT DOCUMENTS

| | | |
|---|---|---|
| 2013/0013327 A1 | 1/2013 | Horseman |
| 2013/0117693 A1 | 5/2013 | Anderson et al. |
| 2013/0234945 A1 | 9/2013 | Goktekin |
| 2014/0078061 A1 | 3/2014 | Simons et al. |
| 2014/0198445 A1 | 7/2014 | Kwok |
| 2014/0310660 A1 | 10/2014 | Rosen et al. |
| 2015/0113795 A1 | 4/2015 | Depallens et al. |
| 2015/0153847 A1 | 6/2015 | Irani et al. |
| 2015/0278730 A1 | 10/2015 | Goldsmith et al. |
| 2016/0092053 A1 | 3/2016 | Loganathan et al. |
| 2016/0117029 A1 | 4/2016 | Short et al. |
| 2016/0143554 A1* | 5/2016 | Lim .................. A61B 5/6803 600/383 |
| 2017/0036110 A1 | 2/2017 | Lockton et al. |
| 2017/0347906 A1* | 12/2017 | Intrator .................. A61B 5/165 |
| 2018/0074785 A1* | 3/2018 | Ohmura .................. G06F 3/0487 |
| 2018/0173494 A1* | 6/2018 | Choi .................. G10L 15/30 |
| 2019/0192974 A1 | 6/2019 | Eatedali et al. |
| 2020/0018973 A1 | 1/2020 | Klug et al. |
| 2020/0019232 A1 | 1/2020 | Rouvinez et al. |
| 2020/0026348 A1 | 1/2020 | Nienstedt et al. |
| 2020/0034028 A1 | 1/2020 | Merminod et al. |
| 2020/0034401 A1 | 1/2020 | Scannell |
| 2020/0050292 A1 | 2/2020 | O'Conaire et al. |
| 2020/0054941 A1 | 2/2020 | Aronzon et al. |
| 2020/0150788 A1 | 5/2020 | Su et al. |
| 2020/0257787 A1* | 8/2020 | Eyole .................. A61B 5/7264 |
| 2020/0267162 A1 | 8/2020 | Koottayi et al. |

FOREIGN PATENT DOCUMENTS

| | | |
|---|---|---|
| CN | 2929837 Y | 8/2007 |
| CN | 201097315 Y | 8/2008 |
| CN | 104238758 A | 12/2014 |
| CN | 105677056 | 6/2016 |
| CN | 205375405 U | 7/2016 |
| DE | 10047112 | 4/2002 |
| DE | 102006012614 | 8/2011 |
| EP | 0146276 | 6/1985 |
| EP | 0763791 | 3/1997 |
| EP | 1605340 | 12/2005 |
| EP | 2698687 | 2/2014 |
| JP | 6189953 | 8/2017 |
| WO | WO1998002312 A1 | 1/1998 |
| WO | WO0177954 | 10/2001 |
| WO | WO2006046815 | 5/2006 |
| WO | WO2007100951 A2 | 9/2009 |
| WO | WO2010097777 | 9/2010 |
| WO | WO2010148483 | 12/2010 |
| WO | WO2013133686 | 9/2013 |
| WO | WO2016095051 | 6/2016 |
| WO | WO2019246562 A1 | 12/2019 |
| WO | WO2020018938 A1 | 1/2020 |

OTHER PUBLICATIONS

Angel Abcede "2017 Heat-Map Study Defines Multiple Paths to Purchase" Company News, Oct. 30, 2017; 4 pps.
Bailey, Jason M. "Adaptice Video Game Controllers Open Worlds for Gamers with Disabilities" The New York Times, Feb. 20, 2019. 2 pps.
"How does FX work?" 4 pps.
"Ambient Products" Energy Utilities, 1 pps.
Harwell, Drew AI baby monitors attract anxious parents: 'Fear is the quickest way to get people's attention' The Washington Post, Feb. 25, 2020; 6 pps.
"Friendship Lamp" 4 pps.
"Release the true Power" ConsoleTuner 2 pps.
"Co-Pilot, XBox One's New Accessibility Feature" Cerebral Palsy Foundation. 1 pps.
Tze Zhi Chin et al. "Exploring EEG based Authentication for Imaginary and Non-imaginary tasks using Power Spectral Density Method" 2019 IOP Conf. Ser.: Mater. Sci. Eng. 557 012031; 6 pps.
"Technical White-Paper" Logitech Flow White Paper v.1.0; 7 pps.
PainStaton 1; "Enhanced Duelling Artefact, 2001" download date Aug. 3, 2020; 11 pps.
Scott et al.; Ambient Video Awareness: "It's Great, but I Still Don't Want It". Knowledge Media Institute, The Open University, United Kingdom; Conference Paper—Jan. 2006; 9 pps.
Maiberg, Emanuel; "Is Using a Mouse and Keyboard on Consoles Cheating?" website: https://www.vice.com/en_us/article/g5pxjx/using-leaked-nintendo-source-code-poses-serious-legal-risk-to-emulators; May 7, 2019; 23 pps.
Born to Connect. Bond Touch. 7 pps.
"Logitech Attempts to Reinvent Presentation Remotes With Spotlight"; Website https://me.pcmag.com/input-devices/10278/logitech-attempts-to-reinvent-presentation-remote-with-spotlight: download date Mar. 21, 2020; 3 pps.
The Master Series by Logitech; 1 pps.
Hillen, Brittany "NVIDIA Research develops a neural network to replace traditional video compression" Oct. 6, 2020; 1 pps.
The World's First Intelligent Cooling Assistant. Get updated about our launch. 2 pps.
Using Smart Video Analytics to Improve Operation in healthcare facilities. Insights Nov. 2020. Issue 1. 20 pps.
Levy, Steven; Videoconferencing Needs to Climb out of the Uncanny Valley. Wired. Download date: Jun. 25, 2020.

* cited by examiner

700

| USER ID 702 | NAME 704 | EMAIL ADDRESS 706 | PASSWORD 708 | PHONE NUMBER 710 |
|---|---|---|---|---|
| u637483 | Allen Jones | a.jones@xyz.com | tZ78nm3$ | 111-222-3333 |
| u637484 | Susan Brown | susanb@bigschool.edu | eagledove | 222-333-4444 |
| u637485 | Thomas Winters | thomas@peace.org | 4getmeknot | 333-444-5555 |

703

| NICKNAMES 712 | ADDRESS 714 | FINANCIAL ACCOUNT INFORMATION 716 | BIRTHDATE 718 |
|---|---|---|---|
| crusher987 | 567 Main Street, Anytown, USA 65432 | 1111-2222-3333-4444, Expires 06/2026 | 04/19/1982 |
| dragonfly123 | 222 Cedar Lane, Somewhere, USA, 89012 | Paypal susanb@bigschool.edu | 11/23/2002 |
| monoskate | 321 Memory Drive, Pleasantville, USA 76543 | 2222-3333-4444-5555, Expires 08/2025 | 02/21/1990 |

713

| MARITAL STATUS 720 | GENDER 722 | PRIMARY LANGUAGE 724 | IMAGES 726 |
|---|---|---|---|
| Single | Male | English | <image data> |
| Single | Female | Spanish | <image data> |
| Married | Male | English | <image data> |

| Network ID 802 | Network Name 804 | Network IP Address 806 | User ID 808 | Specified Connection Speed 810 |
|---|---|---|---|---|
| n423940 | Bob_apt | 3.98.106.14 | u193753 | 10 MB/s |
| n423941 | hr_dept | 6.116.10.122 | u827124 | 25 MB/s |
| n423942 | suite_28 | 16.215.67.44 | u328190 | 900 MB/s |

| Actual Upload-speed 812 | Actual Download-speed 814 | Encryption Type 816 | Uptime Percentage 818 |
|---|---|---|---|
| 12 MB/s | 10 MB/s | WPA | 99.98 |
| 22 MB/s | 26 MB/s | WPA2-AES | 99.0 |
| 600 MB/s | 900 MB/s | WPA-TKIP | 96.2 |

| User Device ID 902 | Form Factor 904 | Model 906 | Processor 908 | Processor Speed 910 | Number of Cores 912 |
|---|---|---|---|---|---|
| ud200187 | Desktop PC | XPS Tower | Intel® Core™ i7 9700 | 4.7 GHz | 8 |
| ud200188 | Laptop | Dell Inspiron 15 3000 | Intel® Core™ i5-1035G1 | 3.6 GHz | 4 |
| ud200189 | Tablet | Samsung Galaxy Tab S6 | Qualcomm Snapdragon 855 | 2.8 GHz | 8 |

| Graphics Card 914 | RAM 916 | Storage 918 | Year of manufacture 920 | Purchase year 922 | Operating System 924 |
|---|---|---|---|---|---|
| NVIDIA® GeForce RTX™ 2060 | 32 GB | 256GB SSD (Boot) + 1TB Hard Drive | 2020 | 2020 | Windows 10 |
| Intel® UHD Graphics | 8 GB | 1 TB Hard Drive | 2018 | 2019 | Windows 10 |
| Adreno 640 | 8 GB | 128GB | 2020 | 2020 | Android 10 |

| MAC Address 926 | Physical Location 928 | Timezone 930 | Owner ID 932 | Network ID(s) 934 | IP Address 936 |
|---|---|---|---|---|---|
| AC-98-2D-02-CA-1B | <owner's address> | Pacific | u498795 | n738511 | (N/A) |
| 00-1A-D2-7B-07-47 | 975 Red Brick Lane, Plainville, CT 98765 | Mountain | u399811 | n423942 | (N/A) |
| AF-98-2D-39-CA-1B | 468 Bluebird Drive, Shoreville, NC 23456 | Eastern | u455309 | NULL | 3.34.90.111 |

| Peripheral Device ID 1002 | Type 1004 | Model 1006 | Purchase year 1008 | IP Address 1010 |
|---|---|---|---|---|
| pd7218901 | mouse | FastByte VX983 | 2022 | 4.91.21.111 |
| pd7218902 | mouse | Tailspin A900-1 | 2021 | 3.59.10.98 |
| pd7218903 | keyboard | ActionKey UZ840A | 2024 | N/A |
| pd7218904 | headset | Rezon8 boom45 | 2023 | N/A |

| Physical Location 1012 | Owner ID 1014 | Linked User Device ID (s) 1016 | Communication modalities available 1018 | Network ID(s) 1020 |
|---|---|---|---|---|
| 369 Pebble Lane, Greenville, USA 01234 | u830269 | ud209412 | video, audio | NULL |
| 468 Seashell Drive, Beach Town USA 65432 | u302483 | ud100006 | audio | NULL |
| 8095 Palm Tree Lane, Woodgrove, USA 35921 | u284851 | ud370189 | video, LEDs | n587120 |
| 492 Greenbrook Lane, Brookville, USA 98421 | u948539 | ud370189 | audio | n995198 |

| Configuration ID 1102 | Peripheral Device ID 1104 | Variable 1106 | Default Setting 1108 |
|---|---|---|---|
| cf20093812 | pd8500000 | Headset camera resolution | High |
| cf20093813 | pd8500000 | Mouse color | Red |
| cf20093814 | pd9203664 | Key height | 1mm |

| Third-Party Control 1110 | Current Setting 1112 | Setting Expiration Time 1114 |
|---|---|---|
| Yes | Medium | 12:07PM 01/17/2023 |
| Yes | Green | After 300 clicks |
| No | 1mm | 2:10:17AM 06/02/2022 |

| Connection ID 1202 | Peripheral Device 1 ID 1204 | Peripheral Device 2 ID 1206 |
|---|---|---|
| pc100268421 | pd9471134 | pd4511008 |
| pc100268422 | pd8854811 | pd4427879 |
| pc100268423 | pd9858002 | pd1874206 |

| Time 1208 | Action 1210 | Maximum daily messages 1212 |
|---|---|---|
| 6:43PM 02/12/2023 | Initiate Connection | 1000 |
| 8:23PM 09/24/2025 | Terminate Connection | None |
| 11:43AM 02/26/2024 | Initiate limited connection | 5 |

| Peripheral Device Group ID 1302 | Group Name 1304 | Group Type 1306 | Settings 1308 |
|---|---|---|---|
| pg3719319 | Fortnite_kings | Game team | Direct device-to-device messaging |
| pg3719320 | Accounting_department | Functional | Any device can control any other |
| pg3719321 | Sams_home | Proximity | All can interact with the dragon slayer game |

| Formation Time 1310 | Group Leader Device 1312 | Member Peripheral Devices 1314 |
|---|---|---|
| 12:47 p.m. August 2nd 2022 | pd6551873 | pd6551873, pd9431820, pd7463109 |
| 4:39 p.m. October 23rd 2024 | NULL | pd1665578, pd5646120, pd6755008, pd1554075 |
| 3:49 p.m. January 15th 2025 | pd6886461 | pd6886461, pd5725876, pd2538754, pd4372186, pd9845009 |

| Connection ID 1402 | User 1 ID 1404 | User 2 ID 1406 | Time 1408 |
|---|---|---|---|
| uc491325973 | u204401 | u522978 | 2:27 p.m. January 3rd 2021 |
| uc491325974 | u376123 | u982396 | 9:42 a.m. March 15th 2024 |
| uc491325975 | u986456 | u255087 | 12:09 a.m. January 17th 2024 |

| Action 1410 | Relationship 1412 | Maximum daily messages 1414 |
|---|---|---|
| Initiate Connection | Friends | 100 |
| Terminate Connection | Teammates | none |
| Initiate limited connection | Co-workers | 1000 |

| User Group ID 1502 | Group Name 1504 | Group Type 1506 | Formation Time 1508 |
|---|---|---|---|
| ug8739534 | Finance Fanatics | Department | 7:58 p.m. July 13th 2023 |
| ug2948204 | Safety Squad | Safety experts | 1:24 p.m. April 17th 2024 |
| ug7385798 | The Pack | Meeting Group | 11:04 a.m. November 16th 2024 |

| Group Leader 1510 | Member Users 1512 |
|---|---|
| u167392 | u167392, u940342, u394583 |
| u201543 | u201543, u301234, u276109, u125427 |
| None | u386409, u876923, u932642, u899984, u487671, u465630 |

| Role assignment ID 1602 | User Group ID 1604 | User ID 1606 | Role 1608 |
|---|---|---|---|
| ra47980028 | ug4875303 | u984567 | Project Manager |
| ra47980029 | ug2489763 | u867113 | Map Keeper |
| ra47980030 | ug4775431 | u956512 | Coach |

| Achievement ID 1702 | User ID 1704 | Time/Date 1706 | Achievement Type 1708 |
|---|---|---|---|
| ac3949229 | u592001 | 5 p.m. September 23rd, 2021 | Professional |
| ac3949230 | u487651 | 11:30 a.m. May 18th, 2024 | Gaming |
| ac3949231 | u476116 | 1:50 p.m. October 3rd, 2023 | Educational |

| Achievement 1710 | Reward 1712 | Provided 1714 |
|---|---|---|
| Got through all three out of three meeting agenda items | Office mouse glows purple for whole day of 7/22/20 | Yes |
| Reached level 10 in Star Attack Blasters | Congratulatory message sent to all users in same game group | Yes |
| Learned pivot tables in Excel | Three free music downloads | Yes |

| Stored Value Account ID 1802 | Owner(s) 1804 | Password 1806 |
|---|---|---|
| sv389410 | u110392 | rabbitpaw5 |
| sv3894103 | u473894; | b85fjyK |
| sv3894104 | u138490 | jaybird99 |

| Currency Type 1808 | Balance 1810 | Hold amount 1812 |
|---|---|---|
| Dollars | 985 | 100 |
| Bitcoin | 12 | 0 |
| Wizard World magic rubies | 355 | 0 |

| Asset ID *1902* | Type *1904* | Title *1906* | Director *1908* | Artist *1910* |
|---|---|---|---|---|
| as40192382 | Movie | Getting Even | Ariel Lightfoot | N/A |
| as40192383 | Music | Anchors Away | N/A | Rikka Lunard |
| as40192384 | Video Game | Volcano Adventure | N/A | World's End Gaming |

| Duration *1912* | Size *1914* | Synopsis *1916* | Reviews *1918* |
|---|---|---|---|
| 2:08:10 | 2 GB | "Comedy/Drama, two con-men turn their lives around…" | 2.5 stars |
| 4:23 | 100 MB | "Jazz: Reminiscing about getting away from it all" | 67% |
| N/A | 1.5 GB | "Explore the terrifying World beneath" | Riveting |

| User Rights/License ID 2002 | Asset ID 2004 | User ID(s) 2006 | Rights 2008 |
|---|---|---|---|
| rl5682900125 | as9302355 | u404588 | Unlimited use |
| rl5682900126 | as3972653 | u622291 | Use until 2025 |
| rl5682900127 | as9864609 | u685999 | 3 downloads |

| User Device State Log ID 2102 | User Device ID 2104 | Time 2106 |
|---|---|---|
| ds200031945 | ud439555 | 1:45:10AM 3/15/2022 |
| ds200031946 | ud439007 | 3:11 p.m. April 17th 2024 |
| ds200031947 | ud752096 | 5:18 p.m. July 31st 2021 |
| ds200062387 | ud752879 | 7:24 p.m. May 7th 2023 |

| Program/App 2108 | Sub-App 2110 | Prominence 2112 |
|---|---|---|
| Chrome browser | Webpage - nytimes.com | Forefront |
| Microsoft Word | NULL | Background |
| Solitaire | NULL | Minimized |
| Photos | NULL | Sleeping |

| Peripheral Activity ID 2202 | Peripheral ID 2204 | Start Time 2206 | End Time 2208 |
|---|---|---|---|
| pa57482391122 | pd3582234 | 3:54:10.073PM 12/04/2024 | 3:54:10.215PM 12/04/2024 |
| pa574823911223 | pd3582235 | 10:42:09.836PM 06/01/2025 | 10:42:10.116PM 06/01/2025 |
| pa574823911224 | pd3582236 | 7:03:55.239PM 09/22/2023 | 7:03:55.469PM 09/22/2023 |

| Component 2210 | Action 2212 | Recipient Program 2214 |
|---|---|---|
| Left mouse button | Pressing | Microsoft Paint |
| "j" key on keyboard | Tapping | Operating system |
| Moving, delta x of 120, delta y of -80 | Delta x of 120 | Chrome browser |

| Sensor Reading ID 2302 | Peripheral ID 2304 | Sensor 2306 |
|---|---|---|
| sr982053195710 | pd9022583 | Heart rate |
| sr982053195711 | pd3492501 | Galvanic skin response |
| sr982053195712 | pd7773631 | Temperature |

| Start Time 2308 | End Time 2310 | Reading 2312 |
|---|---|---|
| 8:11:55.091AM 5/27/2023 | 8:11:59.744AM 5/27/2023 | Heart 110 Beats/minute |
| 11:30:21.05AM 2/13/2025 | 11:30:26.05AM 2/13/2025 | 3.4 micro-Siemens (µS) |
| 6:15:21PM 7/08/2024 | 6:15:26PM 7/08/2024 | 99.6F |

| Message ID 2402 | Time 2404 |
|---|---|
| pm58393092245 | 3:58:01.46AM 12/07/2024 |
| pm58393092246 | 9:45:33.98 4/12/2024 |
| pm58393092247 | 6:25:51.03 3/19/2023 |

| Initiating Peripheral ID 2406 | Receiving Peripheral ID 2408 | Message Content 2410 |
|---|---|---|
| pd3693772 | pd9389422, pd9389566 | Light up LED light #3 for 3 seconds |
| pd1349652 | pd6833341 | Play the following audio <audio data> |
| pd2849155 | pd8603200 | Enemy character is approaching |

| Generic Action ID 2502 | Action/Message 2504 |
|---|---|
| ga283493 | "Nice going" |
| ga283494 | "Cover me" |
| ga283495 | Next slide |
| ga283496 | "Be there in five minutes" |
| ga283497 | Order cheese pizza |

| Mapping ID 2602 | Peripheral Type 2604 | Mode of peripheral 2606 |
|---|---|---|
| mp38279832 | Mouse | Action mode |
| mp38279833 | Headset | Messaging mode |
| mp38279834 | Keyboard | In-use mode |
| mp38279867 | Mouse | Idle mode |

| Input Sequence 2608 | Action 2610 |
|---|---|
| left-click, right-click | ga908665 |
| right-click | Fire rocket |
| hit "j" three times quickly | "I'm going in" |
| ctrl-shift-click | Waiting for command |

| User Game Profile ID 2702 | Game ID 2704 | User ID 2706 | Password 2708 | Screen Name 2710 |
|---|---|---|---|---|
| gp57493489 | gm48227 | u829102 | rnviw45%# | jamboree987 |
| gp57493490 | gm16673 | u395823 | osmosis3 | slyfox88 |

| Preferred Character 2712 | Preferred Avatar 2714 | Preferred Background music 2716 | Rating / Skill Level 2718 | Last Login 2720 |
|---|---|---|---|---|
| Wizard | Blue cone-hat turtle | Theme 45 | Apprentice | 11:45PM 7/9/2023 |
| Ninja | White-robed panda | Theme 21 | Distinguished magician | 4:41PM 8/4/2024 |

| Game Record ID 2802 | Game ID 2804 | Start Time 2806 | End Time 2808 |
|---|---|---|---|
| gr47197713 | gm15823 | 1:45:08PM 2/26/2024 | 2:49:16PM 2/26/2024 |
| gr47197714 | gm38451 | 10:06:55PM 3/5/2023 | 1:24:31AM 3/6/2023 |

| Participant ID(s) 2810 | Score 2812 | Winner 2814 | Highest Level Achieved 2816 | Location(s) played from 2818 |
|---|---|---|---|---|
| u930229 | 19500000 | Nancy Jones | Moon Level | Someplace, USA 20983 |
| u584266, u584488 | 289000, 456000 | N/A | 12 | IP Address 3.184.008.82 |

| Game Activity ID 2902 | Game ID 2904 | Participant ID 2906 | Start Time 2908 |
|---|---|---|---|
| ga483091204578 | gm62703 | u558091 | 2:02:19.091PM 12/04/2024 |
| ga483091204579 | gm48514 | u867421 | 6:19:21.087PM 12/19/2023 |
| ga483091204580 | gm29664 | u483993 | 1:55:17.722AM 5/01/2024 |

| End Time 2910 | Game State 2912 | Activity 2914 |
|---|---|---|
| 2:02:19.185PM 12/04/2024 | Level 6, 3rd screen | Shoot |
| 6:19:21.554PM 12/19/2023 | On spaceship | Switch to laser weapon |
| 1:55:19.210AM 5/01/2024 | Player 1 holds As, Jd, 9h, 9c, 2s, player 2 holds Kc, Qd, Jc, 10h, 10s, $50 in pot, player 1's turn | Player 1 checks |

| Game State ID 3002 | Game ID 3004 | Game Record ID 3006 | Time Remaining 3008 |
|---|---|---|---|
| gs48392382 | gm28744 | gr50991473 | 0:53:21 |
| gs48392383 | gm68402 | gr29569544 | N/A |

| Level 3010 | Score 3012a | Location 3014a | Power 3016a | Ammunition 3018a |
|---|---|---|---|---|
| 8 | 340,000 | 129 leagues North and 369 leagues West | 57% | 18 Silver bullets |
| Cliff Dwelling | 18950 | Mystic Waterfalls | 2380 | 5 Magic hatchets |

| Score 3012b | Location 3014b | Power 3016b | Ammunition 3018b |
|---|---|---|---|
| 275,000 | 131 leagues North and 358 leagues West | 70% | 12 Silver bullets |
| 41290 | Shrouded Mountain | 2174 | 6 winged arrows |

| Project ID 3102 | Project type 3104 | Participants 3106 | Data 3108 |
|---|---|---|---|
| pj8200983 | Text document, spreadsheet, presentation deck, whiteboard | u382014, u899281 | <Text> |
| pj8200984 | Architectural design, paintings, sculptures, drawings, virtual visual arrangements of interiors | u434592, u784338, u649311 | <Cell data> |
| pj8200985 | Music | u403809, u583044, u583924, u358432, u682251 | <Images> |

| Contribution ID 3202 | Project ID 3204 | Participant ID 3206 |
|---|---|---|
| cb383028347988 | pj4738230 | u348411 |
| cb383028347988 | pj7584579 | u292604 |

| Time of Contribution 3208 | Contribution type 3210 | Contribution content 3212 |
|---|---|---|
| 3:18PM 7/30/2023 | Main doc, Side chat message | "We should go aggressively into the rural market because of pent-up demand and no existing options." |
| 9:36AM 8/14/2026 | Thumbs up, vote | <image> |

| Advertisement ID 3302 | Advertiser 3304 | Ad server or Agency 3306 | Target Demographics 3308 |
|---|---|---|---|
| ad382941 | MobileSolutions Inc. | Google Ad Server | Males over 40 |
| ad382942 | SoapStuff Co. | PG One | Females in Northeast |

| Ad Trigger 3310 | Limits 3312 | Presenting Devices 3314 |
|---|---|---|
| User's rate of play slows down 10% | No more than 1000 per day | Keyboard |
| Time is between 12pm and 2pm | Maximum 2 per user | Mouse |

| Modalities 3316 | Ad Content 3318 |
|---|---|
| Image and Tactile | <image data> |
| Video | <video data> |

| Advertisement Presentation ID 3402 | Advertisement ID 3404 | User ID 3406 | Presentation Device 3408 |
|---|---|---|---|
| ap2986100595 | ad583923 | u583123 | ud903412 |
| ap2986100596 | ad793254 | u292675 | ud155230, ud178342 |

| Time 3410 | User Response 3412 |
|---|---|
| 7:23:20PM 2/27/2023 | click, open |
| 4:41:24PM 11/30/2024 | view, purchase |

| AI Model ID 3502 | Model Type 3504 | 'X' Data Source 3506 | 'Y' Data Source 3508 |
|---|---|---|---|
| ai4931 | Linear Regression | Game scores after first 5 minutes of play for game gm14821 | Final game scores for game gm14821 |
| ai4932 | Neural Network | Team messages passed for for game gm94813 | Final team scores gm94813 |

| Parameter Values 3510 | Accuracy 3512 | Last Update 3514 | Update Trigger 3516 |
|---|---|---|---|
| Intercept 5.8, Slope 21.2 | Root Mean Squared Error 5.44 | 12:00:00AM 5/11/2025 | Daily at midnight |
| -.053 x^2 + 10.14x + 1609.21 | Root Mean Squared Error 10.21 | 1:00:00PM 2/22/2024 | 1000 new data points come in |

| Authentication ID 3602 | User ID 3604 | Image(s) 3606 |
|---|---|---|
| au659946 | u384921 | <image data> |
| au659947 | u589402 | NULL |
| au659948 | u389120 | <image data> |

| Fingerprint Images 3608 | Retinal Scans 3610 | Voiceprint 3612 |
|---|---|---|
| <image data> | <image data> | <audio data> |
| <image data> | <image data> | <audio data> |
| NULL | <image data> | <audio data> |

| Privilege ID 3702 | Privilege 3704 | Authentication Points Required 3706 |
|---|---|---|
| pr39302482 | Read documents | 3 |
| pr39302483 | Edit documents | 5 |
| pr39302484 | Message group | 4 |

| Employee ID Number 5002 | Name 5004 | Start Date 5006 | Employee Level 5008 | Supervisor 5010 | Office/Cube Location 5012 |
|---|---|---|---|---|---|
| eid123456 | Chelsea Jones | 11/1/2021 | 1 | eid922210 | Room 123 |
| eid129342 | Rafael Smith | 3/5/1999 | Manager | eid841326 | Cube A, Floor 7 |
| eid492143 | Frank Astor | 8/17/2015 | Individual Contributor | eid961066 | Cube 23 |
| eid294023 | Anne Wong | 7/12/2010 | Vice President | eid875312 | Suite 4 |

| Subject Matter Expertise 5014 | Personality 5016 | Security Level 5018 | Security Credentials 5020 |
|---|---|---|---|
| Software Architecture | Agreeable | Basic | Password - 'sunrise' |
| Widget Markets | Data-oriented | 7 | <voiceprint data> |
| Finance, GAAP | Argumentative | Basic | <fingerprint data> |
| Project Dragon | Focused | High | <retinal scan data> |

| Preferences 5022 | Preferred Standard Device Configurations 5024 | Email 5026 | Phone 5028 |
|---|---|---|---|
| Meetings after 10AM | Voice messaging, alerts via audio | cjones@xyz.com | 883-651-5650 |
| Meet in rooms with windows | Text messaging, alerts with vibration | rafaels@xyz.com | 883-481-9623 |
| Meetings that have fewer than 12 participants | Show live transcript of meeting | fastor@xyz.com | 212-004-6528 |
| No alignment meetings | Alerts with vibration | awong@xyz.com | 212-707-2187 |

| Meeting Id 5102 | Meeting Name 5104 | Meeting Owner 5106 | Meeting Type 5108 | Level 5110 | Location 5112 |
|---|---|---|---|---|---|
| mt4839483 | Angle Bracket Troubleshooting | eid420345 | Innovation | General | Building 4 |
| mt2930421 | Widget Status Update | eid390294 | Alignment | Managers | Clarkville Campus |
| mt2940213 | Strategic Planning | N/A | Commitment | Vice Presidents | N/A |
| mt2940213 | Blockchain Informational | eid593103 | Learning | General | New York Office |

| Room Id 5114 | Start Date 5116 | Time 5118 | Duration (minutes) 5119 | Frequency 5120 | End Date 5122 |
|---|---|---|---|---|---|
| rm294 | 2/17/2025 | 10:00AM MST | 90 | One-time | 2/17/2025 |
| rm103 | 2/1/2025 | 2:30PM EST | 30 | Weekly | 3/29/2025 |
| zoom292012 | 9/21/2025 | 3:00PM PST | 60 | Monthly | 9/21/2026 |
| Webex292019 | 8/21/2025 | 12:30PM GMT | 120 | One-time | 8/21/2025 |

| Phone Number 5124 | Tags 5126 | Project Number or Cost Center Assoc. 5128 | Ratings 5130 | Priority 5132 | Related Meetings 5134 |
|---|---|---|---|---|---|
| 222-333-4444 | Problem Solving | pr20489523 | 3 | 5 | mt2309421 |
| 333-444-5555 | Widget | cc224 | Good | Medium | mt4921039 |
| 555-666-7777 | Status | pr49201521 | Fair | High | NULL |
| 444-555-6666 | Strategy | cc113 | 4 | Low | mt4293112 |

| Meeting Identifier 5202 | Date 5203 | Attendee Identifier 5204 | Role 5206 | Manner 5208 |
|---|---|---|---|---|
| mt4839483 | All | eid420345 | Owner | Video Conference |
| mt2930421 | 4/19/2025 | eid205831 | Note keeper | In-person |
| mt2940213 | 5/6/2025, 5/13/2025 | eid392091 | Attendee | Web Conference, Web Conference |
| mt2940213 | All | Jerry Fisherman (contractor) | Subject Matter Expert | Phone |

| Meeting Identifier 5302 | Date 5304 | Time 5306 | Attendee Identifier 5308 |
|---|---|---|---|
| mt5156875 | 3/22/2025 | 11:43AM | eid894259 |
| mt4884719 | 5/18/2025 | 3:14PM | eid776146 |
| mt4370171 | 4/2/2025 | 10:43:25AM | eid830851 |
| mt9293624 | 7/15/2025 | 3:58:21PM | eid282108 |

| Engagement Level 5310 | Engagement Indicator(s) 5312 | Burnout Risk 5314 | Burnout Indicators 5316 |
|---|---|---|---|
| High | Voice Detection, Rapid Speech | High | Loud Voice |
| Average | Posture, Heart Rate | Low | Steady Engagement |
| Low | Skin Conductivity | Low | None |
| None | Eye Tracking | Medium | 67% rate of declining invites, 95% calendar time full |

| Meeting Identifier 5402 | Effectiveness of Facilitation 5404 | Meeting Energy Level 5406 | Did the Meeting Stay on Track? 5408 |
|---|---|---|---|
| mt9176309 | 5 | 4 | 5 |
| mt1655325 | 2 | High | 3 |
| mt5813512 | High | Medium | Yes |
| mt2869394 | High | Low | 1 |

| Did the Meeting Start/End on Time? 5410 | Room Comfort 5412 | Presentation Quality 5414 | Overall Rating 5416 | Food Quality 5418 |
|---|---|---|---|---|
| Yes | 3 | High | 5 | 3 stars |
| Started on time, Ended 5 minutes late | High | N/A | 3 | 4 stars |
| No | Low | Low | Medium | 4 stars |
| 3 | 4 | 3 | Low | 2 stars |

| Room lighting 5420 | Clarity of purpose 5422 | Projector quality 5424 | Ambient noise levels 5426 |
|---|---|---|---|
| Excellent | 5 | Colors washed out | Loud |
| Too much sun in afternoon | 5 | Generates a lot of heat | Bird noises are a distraction |
| Lighting controls are difficult to understand | 4 | Hard to focus the image | AC is too loud |
| Average | 4.3 | Colors washed out | Voices can be heard from the adjacent meeting room |

| Strength of WiFi signal 5428 | Room cleanliness 5430 | View from room 5432 |
|---|---|---|
| Excellent | Trash cans need to be emptied | Fantastic view of the pond outside the north window |
| Weak | Empty soda cans in food service area | Overlooks the main building entrance |
| Connection droped three times in a one hour meeting | Food in refrigerator needs to be thrown out | No view |
| Excellent | Whiteboard has marks that are hard to erase | Only window faces the wall of the adjacent building |

| Meeting ID 5502 | Meeting Date 5504 | Employee 5506 | Role 5508 | Confirmed/ Declined Meeting 5510 |
|---|---|---|---|---|
| mt2197509 | 8/2/2025 | eid732447 | Owner | Confirmed |
| mt5020142 | 9/14/2025 | eid419542 | Observer | Confirmed |
| mt2997037 | 1/12/2025 | eid136319 | Attendee | Declined |
| mt2997037 | 1/12/2025 | eid410080 | Presenter | Confirmed |

| Time Arrived 5512 | Time Departed 5514 | Travel Time to Meeting Location 5516 | Travel Time from Meeting Location 5518 | Employee Rating by Others 5520 |
|---|---|---|---|---|
| 10:00AM | 11:00AM | 3 min | 4 min | 4.1 |
| 10:03AM | 10:45AM | 14 min | 14 min | 2.5 |
| N/A | N/A | N/A | N/A | N/A |
| 10:00AM | 11:00AM | Remote | Remote | High |

| Employee ID 5602 | Meeting ID 5604 | Subject 5606 | Category 5608 |
|---|---|---|---|
| eid238292 | mt2948201 | Status update | Meeting |
| eid202942 | N/A | Doctor call | Personal |
| eid992913 | mt4920191 | Strategy discussion | Meeting |
| eid284199 | N/A | Solitary work time | Individual |

| Date 5610 | Start Time 5612 | Duration in Minutes 5614 | Company / Personal 5616 |
|---|---|---|---|
| 3/4/2025 | 10AM | 120 | Company |
| 9/2/2025 | 3PM | 30 | Personal |
| 8/21/2025 | 11:30AM | 90 | Company |
| 11/5/2025 | 2PM | 180 | Company |

| Project ID 5702 | Name 5704 | Summary 5706 | Start Date 5708 |
|---|---|---|---|
| pr37697850 | OS Switch | Switch all employees to Linux | 1/18/2025 |
| pr53595075 | Remote Work Securitization | Set up secure environments for remote work | 7/12/2025 |
| pr22004632 | App Launch | Launch new customer app | 2/28/2025 |
| pr40311966 | Supplier Refresh | Re-bid supplier contracts | 9/12/2025 |

| Priority 5710 | Expected Duration 5712 | Percent Completion 5714 | Budget 5716 | Personnel Requirements 5718 |
|---|---|---|---|---|
| High | 10 weeks | 100% | $1 million | 5 @ full-time |
| 1 | 3 weeks | 20% | $5 million | 40 @ full-time |
| Medium | 1 month | 90% | $500,000 | 10 @ 75% time |
| Medium | 6 months | Not started | $20,000 | 1 @ 50% time |

| Project ID 5802 | Employee ID 5804 | Role 5806 |
|---|---|---|
| pr59552104 | eid528092 | Project manager |
| pr97886395 | eid906544 | Lead developer |
| pr80172431 | eid605192 | Communications strategist |
| pr34813883 | eid326860 | Procurement specialist |

| Project ID 5902 | Milestone ID 5904 | Sequence Number 5906 | Summary 5908 |
|---|---|---|---|
| pr14413154 | ml76882780 | 1 | Draft request for proposal |
| pr21180052 | ml68108100 | 3A | Implement pilot with legal group |
| pr79281479 | ml46682502 | 2 | Stress test of grinding machine |
| pr61684854 | ml46174624 | 5 | Completion of laser work with vendor |

| Due Date 5910 | Percent Complete 5912 | Approver(s) 5914 | Violations 5916 |
|---|---|---|---|
| 01/10/2025 | 100% | eid628141 | None |
| 10/24/2025 | 40% | eid305993, eid449341 | None |
| 11/27/2025 | 25% | eid628761 | Additional training required |
| 07/13/2025 | 0% | eid239875, eid832449 | One vendor was not tracked with a headset |

| Asset ID 6002 | Asset Type 6004 | Meeting ID 6006 | Creation Date 6008 | Author 6010 |
|---|---|---|---|---|
| mtas10766643 | Deck | mt1859273 | 08/18/2025 | eid687447 |
| mtas16529041 | Notes | mt4731407 | 03/22/2025 | eid727665 |
| mtas29505046 | Meeting minutes | mt1418640 | 02/18/2025 | eid179157 |
| mtas75112623 | Decisions | mt2850507 | 11/02/2025 | Linda Smith |
| mtas78228629 | Meeting Summary | mt4636463 | 07/17/2025 | eid749134 |
| mtas80458235 | Action Items | mt1778988 | 11/04/2025 | eid892632 |
| mtas71269039 | Photo of whiteboard | mt4460322 | 09/25/2025 | eid923890 |

| Version 6012 | Tags 6014 | Keywords 6016 | Rating 6018 | Asset Data 6020 |
|---|---|---|---|---|
| 3.1 | Rated 8/10 | Market impact | 4 | <data> |
| 2 | Author eid204920 | Breakeven | 5 | <data> |
| 1 | Computer transcription | Fibre cables | 3 | <data> |
| 1 | Needs VP confirmation | Cloud | 4 | <data> |
| 1 | Short-term items | Personnel, resources | 5 | <data> |
| 2 | All items approved by Legal | European market | Medium | <data> |
| 1 | Medium quality | SWOT analysis | High | <data> |

| Asset ID 6102 | Number of Slides 6104 | Number of Words 6106 | Size of the File 6108 | Presentation Software Version 6110 | Number of Graphics 6112 |
|---|---|---|---|---|---|
| mtas63999831 | 38 | 8333 | 12 Mb | Microsoft PowerPoint for Mac version 16.35 | 60 |
| mtas99765120 | 66 | 3124 | 2 Mb | Keynote | 76 |
| mtas89473810 | 26 | 7429 | 190 Kb | Google Slides | 10 |

| Number and Type of Tags 6114 | Number of Times Presented 6116 | Template Used 6118 | Time to Create Presentation 6120 | Key Points 6122 | Take Away Summary Included 6124 |
|---|---|---|---|---|---|
| 12 Descriptive, 19 Ratings | 5 | Learning template #3 | 12 hours | Sales decline | Yes |
| 20 Descriptive, 8 Ratings | 5 | Business Plan template #8 | 17 hours | Important defects | No |
| 5 Descriptive, 4 Ratings | 4 | Financials template #3 | 8 hours 45 minutes | Rollout Plans | Yes |

| Security Level 6126 | Presentation Creation Date 6130 | Presentation Rating 6132 | Acronyms 6134 | Tags4 6136 |
|---|---|---|---|---|
| General | 06/23/2025 | 4 | DCE - Data communications equipment | pr75660791, pr71427249, DCE, Learning |
| Manager+ | 05/29/2025 | 3 | IMAP – Internet Message Access Protocol | Business plan, Market assessment |
| VP + | 05/05/2025 | 3 | FCE – Frame check sequence | Projections, Financials, pr96358600 |

| Asset ID 6202 | Component ID 6204 | Component Type 6206 | Average Rating 6208 |
|---|---|---|---|
| mtas97783941 | cpt3178759788 | Slide 7 | 7.5 |
| mtas76262658 | cpt4506080307 | Graphic #2 | 8.7 |
| mtas83890682 | cpt8656264119 | Topic 3 | 8.2 |

| Room ID 6402 | Address 6404 | Building 6406 | Floor 6408 | Room Number 6410 | Room Name 6412 |
|---|---|---|---|---|---|
| rm703 | 123 Main St, Lincoln, Nebraska | John Casey Building | 7 | 703 | Casey Auditorium |
| rm486 | 456 Gold St, New York, NY | Building 1 | 4 | 486 | N/A |
| rm799 | 890 Riverside Road, Lakeville, Florida | Marketing Building | 7 | 799 | The Barn |

| Room Area 6414 | Room Height 6416 | Capacity 6418 | Energy Usage 6420 | Sun Exposure 6422 | Temperature Control 6424 |
|---|---|---|---|---|---|
| 10000 sq feet | 30 feet | 300 | 34000 BTU | None | Fine control |
| 100 sq feet | 10 feet | 5 | 200 BTU | High direct | None |
| 400 sq feet | 9 feet | 20 standing, 8 seated | 1000 BTU | 11 sq meters of windows facing southwest | Moderate |

| Room Setup 6426 | Tables 6428 | Number of Chairs Present 6430 | Last Cleaned Date/Time 6432 |
|---|---|---|---|
| Classroom/lecture | None | 300 | 03/14/2025 9:00AM |
| Chairs surrounding table | Large circular table | 5 | 12/08/2025 10:00PM |
| Horseshoe | 6 rectangular tables, Movable | 8 | 01/19/2025 1:00PM |

| AV Status 6434 | AV Configuration 6436 | AV Quality 6438 | Acoustics Ratings 6440 |
|---|---|---|---|
| Working | Learning | 5 | Good |
| 1 of 2 screens working | Innovation | Medium | Good |
| Flicker on screen | Alignment | Low | 3 |

| Whiteboard Status 6442 | Catering Availability 6444 | Wheelchair Accessibility 6446 |
|---|---|---|
| Excellent | Yes | Yes |
| Fair, Some permanent marks | No | Yes |
| Good, 3 markers left | Yes | No |

| Room ID 6502 | Peripheral ID 6504 | Location in Room 6506 |
|---|---|---|
| rm898 | pd2765435 | Center of the north wall |
| rm640 | pd5549904 | Corner of the far wall and right wall |
| rm128 | pd6544295 | On the floor |

| Vendor ID 6602 | Name 6604 | Category 6606 | Price 6608 |
|---|---|---|---|
| vnd3220 | Mchine Cleaners Express | Cleaning | $40/hour |
| vnd5880 | Printer Helper | Printing | $35/hour |
| vnd2756 | Swift Copy Repair | Repair | $150/hour |

| Min Time 6610 | Hours 6612 | Ratings 6614 | Website 6616 | Phone 6618 |
|---|---|---|---|---|
| 90 minutes | 8AM - 5PM | 4.5 | cleanmachine.com | 392-459-4920 |
| 60 minutes | 11AM-3PM | High | bprinterhelper.com | 143-420-4583 |
| 15 minutes | 10AM-4PM | 4.2 | swiftco.com | 529-919-2049 |

| Video ID 7002 | Content Summary 7004 |
|---|---|
| mtvd283542 | Training video |
| mtvd719065 | Training video |
| mtvd954661 | Course on lasers |
| mtvd462943 | Instruction Manual |

| Sensor Identifier 7302 | Sensor Type 7304 | Sensor location 7306 | Authorized user 7308 |
|---|---|---|---|
| sid900437 | Camera | rm706 | u905598 |
| sid900437 | Camera | rm706 | u686362 |
| sid674526 | Microphone | rm297 | u626794 |
| sid741925 | Motion Sensor | rm662 | u297685 |

| Subject 7310 | Resolution 7312 | Sampling rate 7314 | Sensitivity 7316 |
|---|---|---|---|
| u755419 | 480p | 30 frames/sec | Low |
| u755419 | 720p | 30 frames/sec | ISO 600 |
| u262782 | N/A | 44.1 kHz | 50 db+ |
| u166850 | N/A | 1/sec | 50 pounds+ |

| Sensor ID 7402 | Trigger 7404 | Updated resolution 7406 | Updated sample rate 7408 |
|---|---|---|---|
| sid900437 | Manual | 720p | 30 frames/sec |
| sid900437 | u693029 | 1080p | 60 frames/sec |
| sid674526 | Occupant detected | N/A | 44.1 kHz |
| sid741925 | Game play initiated | N/A | 2/sec |
| sid852925 | Revert to default setting | N/A | 1/sec |

| Updated sensitivity 7410 | Configuration duration 7412 |
|---|---|
| Low | 11/14/2025 8:58:21 PM |
| ISO 800 | 10/11/2025 5:21:16 AM - 10/11/2025 6:30:00 AM |
| 30 db+ | 11/25/2025 21:31:37 - 12/26/2025 18:07:25 |
| 50 pounds+ | 09/02/2025 15:55:16 |
| 65 pounds+ | 03/21/2025 07:24:29 |

| Appliance Sensor Reading ID 7502 | Appliance ID 7504 | Description 7506 | Start Time 7508 |
|---|---|---|---|
| asr774618611569 | appl660123 | Refrigerator door | 12/29/2025 22:36:59.139 |
| asr147115559837 | appl502005 | Microwave door | 04/27/2025 15:14:57.758 |
| asr793863106572 | appl758422 | Motion sensor 1 | 09/23/2025 03:24:59.146 |
| asr760810715578 | appl618340 | Motion sensor 2 | 08/09/2025 17:34:17.384 |
| asr962280973369 | appl534580 | Closed circuit TV | 09/24/2025 17:47:37.715 |
| asr143309929000 | appl391530 | Thermostat | 10/22/2025 04:39:15.668 |
| asr676084740727 | appl871181 | Refrigerator contents imager | 09/16/2025 01:09:26.709 |
| asr744345646698 | appl938298 | Refrigerator contents imager | 09/11/2025 21:13:52.632 |

| End Time 7510 | Reading 7512 |
|---|---|
| N/A | Open |
| N/A | Close |
| 09/23/2025 03:25:04.391 | Motion - 98% confidence |
| 08/09/2025 17:34:22.275 | Motion - 36% confidence |
| 09/24/2025 17:47:47.924 | <video data> |
| N/A | Set to 20 degrees Celsius |
| N/A | Milk put in |
| N/A | Cookie removed |

| Location 7602 | Date 7604 | Time 7606 | Temperature 7608 | Humidity 7610 |
|---|---|---|---|---|
| 298 Elm St, Somewhere, USA | 5/19/2023 | 8:35AM | 75 | 35% |
| 836 Dodge Lane, Somewhere, USA | 3/08/2022 | 3:22PM | 55 | 96% |
| 378 Main St., Anywhere, USA | 9/17/2024 | 4:35PM | 28 | 22% |
| 221 Crossville St, Anywhere, USA | 9/18/2023 | 1:24P | 80 | 48% |

| Wind Speed 7612 | Type of precipitation 7614 | Precipitation rate 7616 | Light level 7618 | Cloud cover 7620 |
|---|---|---|---|---|
| 8 mph | None | N/A | 9,000 lux | 15% |
| 3 mph | Rain | 0.15 inches/hour | 1,200 lux | 67% |
| 15 mph | Snow | 0.46 inches/hour | 900 lux | 85% |
| 12 mph | None | N/A | 10,500 lux | 30% |

| Asset ID 7702 | Asset type 7704 | Trigger ID 7706 | Time 7708 |
|---|---|---|---|
| as8611893 | Movie | tr54923486 | 00:24 |
| as4661703 | Television episode | tr13713968 | 00:36 |
| as4682177 | Audio book | tr40741438 | 01:24 |

| Target output device 7710 | Output 7712 | Duration 7714 |
|---|---|---|
| Color lighting | Blue lighting | 90 seconds |
| Speakers | Sound file of thunderstorm | 10 seconds |
| Projector | Image of map | 3 minutes |

| Game character ID 8702 | Independently controllable elements 8704 | Time of control 8706 |
|---|---|---|
| chr24976433 | Aim, Trigger pulls, Movement | 5 minutes |
| chr68551097 | Aim, Trigger pulls, Movement, Selection of Armor, Dance move selection | Until game ends |
| chr65470068 | Steering, Accelerator, Brake | Three laps of driving |
| chr61199241 | Even numbered turns, Odd numbered turns | One chess game |
| chr64647219 | Poker action taken, Size of bets | Duration of tournament |

| Peripheral ID<br>8802 | User ID normally in control<br>8804 | User ID taking over control<br>8806 | End time of user taking over control<br>8808 |
|---|---|---|---|
| pd3498509 | u797621 | u883642 | 5:25PM September 23rd 2021 |
| pd3367098 | u205891 | u413251 | 6:12PM August 9th 2023 |
| pd2549037 | u641777 | u645516 | 11:45AM May 16th 2022 |

| Component Type Identifier 9502 | Component Description 9504 | Manufacturer 9506 | Model 9508 |
|---|---|---|---|
| cmpt794967 | LED Red Diffused 3mm (T-1) 643nm 65mcd 60VA | Jameco Valuepro | UT6371-41-M1-R |
| cmpt666516 | MEMS Gauge Pressure Sensor +/-50kPa SOP6 | Omron Electronic Components | 2SMPP-03 |
| cmpt507611 | Conduction Sensor | EISCO Scientific and Science Educational Systems (SES) | ADGR-NL-NUL217 |
| cmpt309210 | Galvanic Skin Response Sensor | Fabrication Enterprises | GSR 2 |

| Component Identifier 9602 | Component Type 9604 | Reference Name 9606 | Address 9608 |
|---|---|---|---|
| cpnt20511457 | cmpt684363 | Left light #1 | 10010101 |
| cpnt39476632 | cmpt873911 | Right LED #2 | 11011011 |
| cpnt89848302 | cmpt799676 | Front speaker | 01010111 |
| cpnt52220341 | cmpt779842 | Top left pressure sensor | 0010110 |

| Signal Identifier 9702 | Component Type 9704 | Incoming/ Outgoing 9706 | Description 9708 | Signal 9710 |
|---|---|---|---|---|
| sign33733400 | cmpt62449166 | Outgoing | Turn light on | 11101110 |
| sign96676896 | cmpt62449166 | Outgoing | Turn light on dim | 11101111 |
| sign71312051 | cmpt22060346 | Outgoing | Tone at 440 hz for 0.5 sec | 00100110 |
| sign33878745 | cmpt28770733 | Incoming | Button pressed | 00010001 |

*FIG. 97*

SYSTEMS, METHODS, AND APPARATUS FOR ENHANCED HEADSETS

CROSS-REFERENCE TO RELATED APPLICATIONS

The present application is a Non-Provisional of, and claims benefit and priority to U.S. Provisional Patent Application No. 63/023,965, titled "SYSTEMS, METHODS, AND APPARATUS FOR ENHANCED HEADSETS", and filed May 13, 2020 in the name of Jorasch et al., the entirety of which is hereby incorporated by reference herein for all purposes.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND

People use headsets for listening to music and for providing data to computers for enabling communications. For example, headsets are commonly used to enhance the audio quality of video calls, such as business meetings, online classes, or video game team communications.

SUMMARY

Various embodiments comprise systems, methods, and apparatus for enhancing headsets with additional capabilities. Various embodiments enable an integration of data from many sources, and enable intelligent processing of that data such that many elements of the system can be optimized and enhanced. In addition to enhancing online calls, game experiences, and the consumption of music and audio files, the various embodiments also address the need to enhance the use of business software applications, safety protocols, authentication, gameplay experiences, recreational activities, social interactions and educational activities.

BRIEF DESCRIPTION OF THE DRAWINGS

An understanding of embodiments described herein and many of the attendant advantages thereof may be readily obtained by reference to the following detailed description when considered with the accompanying drawings, wherein:

FIGS. 7 through 37 are block diagrams of example data storage structures consistent with at least some embodiments described herein;

FIGS. 50 through 53 are block diagrams of example data storage structures consistent with at least some embodiments described herein;

FIG. 54A and FIG. 54B are block diagrams of example data storage structures consistent with at least some embodiments described herein;

FIGS. 55 through 62 are block diagrams of example data storage structures consistent with at least some embodiments described herein;

FIGS. 64A and 64B together show a block diagram of an example data storage structure consistent with at least some embodiments described herein;

FIGS. 65 through 66 are block diagrams of example data storage structures consistent with at least some embodiments described herein;

FIG. 70 is block diagram of an example data storage structure consistent with at least some embodiments described herein;

FIGS. 73 through 78 are block diagrams of example data storage structures consistent with at least some embodiments described herein;

FIGS. 87 through 88 are block diagrams of example data storage structures consistent with at least some embodiments described herein;

FIGS. 95 through 97 are block diagrams of example data storage structures consistent with at least some embodiments described herein;

DETAILED DESCRIPTION

Figure 1:
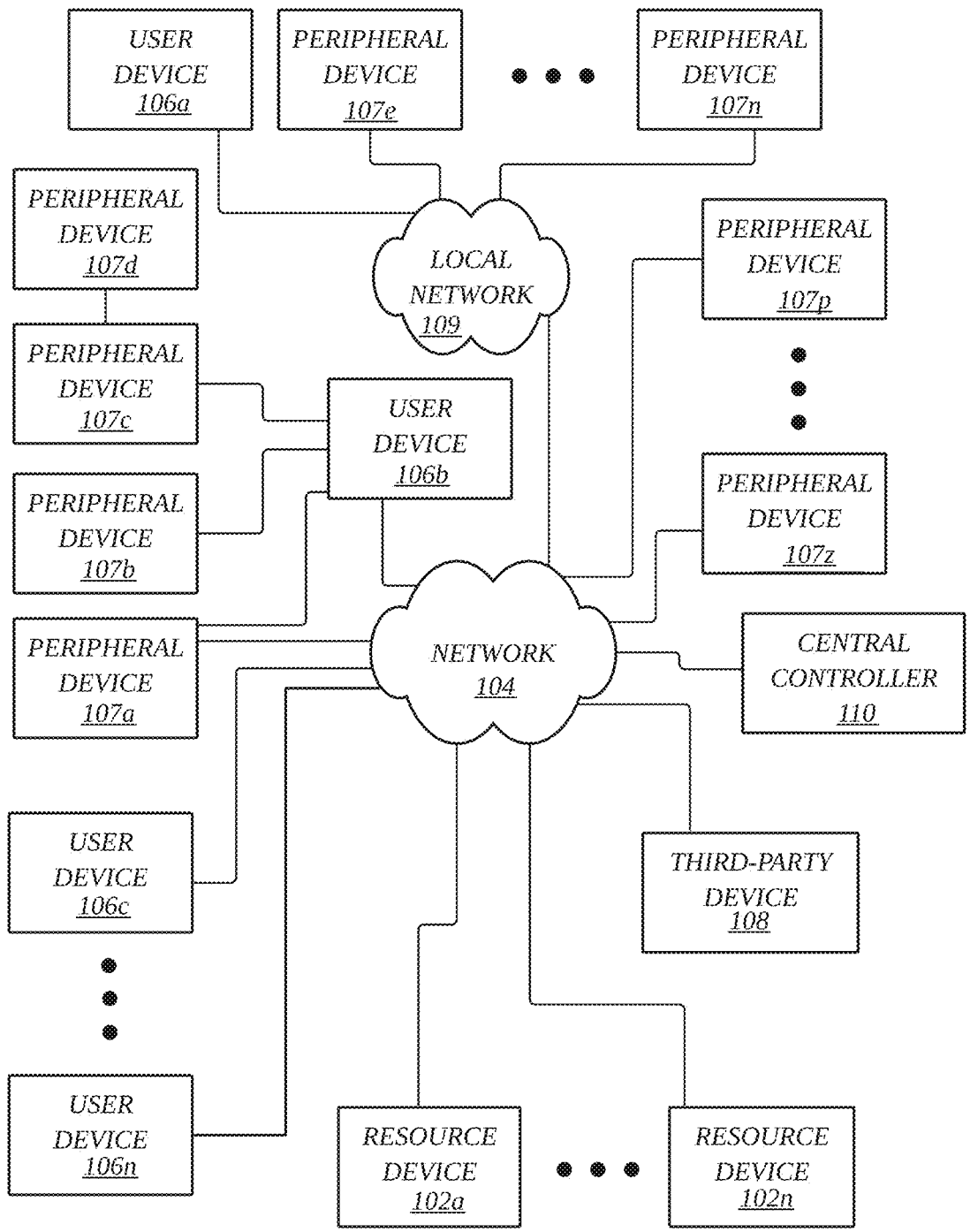
FIG. 1 is a block diagram of a system consistent with at least some embodiments described herein.

Embodiments described herein are descriptive of systems, apparatus, methods, interfaces, and articles of manufacture for utilizing devices and/or for managing meetings.

Headings, section headings, and the like are used herein for convenience and/or to comply with drafting traditions or requirements. However, headings are not intended to be limiting in any way. Subject matter described within a section may encompass areas that fall outside of or beyond what might be suggested by a section heading; nevertheless, such subject matter is not to be limited in any way by the wording of the heading, nor by the presence of the heading. For example, if a heading says "Mouse Outputs", then outputs described in the following section may apply not only to computer mice, but to other peripheral devices as well.

As used herein, a "user" may include a human being, set of human beings, group of human beings, an organization, company, legal entity, or the like. A user may be a contributor to, beneficiary of, agent of, and/or party to embodiments described herein. For example, in some embodiments, a users actions may result in the user receiving a benefit.

In various embodiments, the term "user" may be used interchangeably with "employee", "attendee", or other party to which embodiments are directed.

A user may own, operate, or otherwise be associated with a computing device, such as a personal computer, desktop, Apple Macintosh, or the like, and such device may be referred to herein as "user device". A user device may be associated with one or more additional devices. Such additional devices may have specialized functionality, such as for receiving inputs or providing outputs to users. Such devices may include computer mice, keyboards, headsets, microphones, cameras, and so on, and such devices may be referred to herein as "peripheral devices". In various embodiments, a peripheral device may exist even if it is not associated with any particular user device. In various embodiments, a peripheral device may exist even if it is not associated with any particular other device.

As used herein, a "skin" may refer to an appearance of an outward-facing surface of a device, such as a peripheral device. The surface may include one or more active elements, such as lights, LEDs, display screens, electronic ink, e-skin, or any other active elements. In any case, the surface may be capable of changing its appearance, such as by changing its color, changing its brightness, changing a displayed image, or making any other change. When the outward service of a device changes its appearance, the entire device may appear to change its appearance. In such cases, it may be said that the device has taken on a new "skin".

As used herein, pronouns are not intended to be gender-specific unless otherwise specified or implied by context. For example, the pronouns "he", "his", "she", and "her" may refer to either a male or a female.

As used herein, a "mouse-keyboard" refers to a mouse and/or a keyboard, and may include a device that has the functionality of mouse, a device that has the functionality of a keyboard, a device that has some functionality of a mouse and some functionality Of a keyboard and/or a device that has the functionality of both a mouse and a keyboard.

Systems

Referring first to FIG. 1, a block diagram of a system 100 according to some embodiments is shown. In some embodiments, the system 100 may comprise a plurality of resource devices 102a-n in communication via or with a network 104. According to some embodiments, system 100 may comprise a plurality of user devices 106a-n, a plurality of peripheral devices 107a-n and 107p-z, third-party device 108, and/or a central controller 110, In various embodiments, any or all of devices 106c-n, 107a, 107p-z, may be in communication with the network 104 and/or with one another via the network 104.

Various components of system 100 may communicate with one another via one or more networks (e.g., via network 104). Such networks may comprise, for example, a mobile network such as a cellular, satellite, or pager network, the Internet, a wide area network, a Wi-Fi® network, another network, or a combination of such networks. For example, in one embodiment, both a wireless cellular network and a Wi-Fi® network may be involved in routing communications and/or transmitting data among two or more devices or components. The communication between any of the components of system 100 (or of any other system described herein) may take place over one or more of the following: the Internet, wireless data networks, such as 802.11 Wi-Fi®, PSTN interfaces, cable modem DOCSIS data networks, or mobile phone data networks commonly referred to as 3G, LTE, LTE-advanced, etc.

In some embodiments, additional devices or components that are not shown in FIG. 1 may be part of a system for facilitating embodiments as described herein. For example, one or more servers operable to serve as wireless network gateways or routers may be part of such a system. In other embodiments, some of the functionality described herein as being performed by system 100 may instead or in addition be performed by a third party server operating on behalf of the system 100 (e.g., the central controller 110 may outsource some functionality, such as registration of new game players). Thus, a third party server may be a part of a system such as that illustrated in FIG. 1.

It should be understood that any of the functionality described herein as being performed by a particular component of the system 100 may in some embodiments be performed by another component of the system 100 and/or such a third party server. For example, one or more of the functions or processes described herein as being performed by the central controller 110 (e.g., by a module or software application of the central controller) or another component of system 100 may be implemented with the use of one or more cloud-based servers which, in one embodiment, may be operated by or with the help of a third party distinct from the central controller 110. In other words, while in some embodiments the system 100 may be implemented on servers that are maintained by or on behalf of central controller 110, in other embodiments it may at least partially be implemented using other arrangements, such as in a cloud-computing environment, for example.

In various embodiments, peripheral devices 107b and 107c may be in communication with user device 106b, such as by wired connection (e.g., via USB cable), via wireless connection (e.g., via Bluetooth®) or via any other connection means. In various embodiments, peripheral devices 107b and 107c may be in communication with one another via user device 106b (e.g., using device 106b as an intermediary). In various embodiments, peripheral device 107d may be in communication with peripheral device 107c, such as by wired, wireless, or any other connection means. Peripheral device 107d may be in communication with peripheral device 107b via peripheral device 107c and user device 106b (e.g., using devices 107c and 106b as intermediaries). In various embodiments, peripheral devices 107b and/or 107c may be in communication with network 104 via user device 106b (e.g., using device 106b as an intermediary). Peripheral devices 107b and/or 107c may thereby communicate with other devices (e.g., peripheral device 107p or central controller 110) via the network 104. Similarly, peripheral device 107d may be in communication with network 104 via peripheral device 107c and user device 106b (e.g., by using both 107c and 106b as intermediaries). In various embodiments, peripheral device 107d may thereby communicate with other devices via the network 104.

In various embodiments, local network 109 is in communication with network 104. Local network 109 may be, for example, a Local Area Network (LAN), Wi-Fi® network, Ethernet-based network, home network, school network, office network, business network, or any other network. User device 106a and peripheral devices 107e-n may each be in communication with local network 109. Devices 106a and 107e-n may communicate with one another via local network 109. In various embodiments, one or more of devices 106a and 107e-n may communicate with other devices (e.g., peripheral device 107p or central controller 110) via both the local network 109 network 104. It will be appreciated that the depicted devices 106a and 107e-n are illustrative of some embodiments, and that various embodiments contemplate more or fewer user devices and/or more or fewer peripheral devices in communication with local network 109.

It will be appreciated that various embodiments contemplate more or fewer user devices than the depicted user devices 106a-n. Various embodiments contemplate fewer or more local networks, such as local network 109. In various embodiments, each local network may be in communication with a respective number of user devices and/or peripherals. Various embodiments contemplate more or fewer peripheral devices than the depicted peripheral devices 107a-n and 107p-z. Various embodiments contemplate more or fewer resource devices than the depicted resource devices 102a-n. Various embodiments contemplate more or fewer third-party devices than the depicted third-party device 108. In a similar vein, it will be understood that ranges of reference numerals, such as "102a-n", do not imply that there is exactly one such device corresponding to each alphabet letter in the range (e.g., in the range "a-n"). Indeed, there may be more or fewer such devices than the number of alphabet letters in the indicated range.

In various embodiments, resource devices 102a-n may include devices that store data and/or provide one or more services used in various embodiments. Resource devices 102a-n may be separate from the central controller 110. For example, a resource device may belong to a separate entity to that of the central controller. In various embodiments, one or more resource devices are part of the central controller, have common ownership with the central controller, or are otherwise related to the central control. In various embodiments, resource devices 102a-n may include one or more databases, cloud computing and storage services, calling platforms, video conferencing platforms, streaming services, voice over IP services, authenticating services, certificate services, cryptographic services, anonymization services, biometric analysis services, transaction processing services, financial transaction processing services, digital currency transaction services, file storage services, document storage services, translation services, transcription services, providers of imagery, image/video processing services, providers of satellite imagery, libraries for digital videos, libraries for digital music, library for digital lectures, libraries for educational content, libraries for digital content, providers of shared workspaces, providers of collaborative workspaces, online gaming platforms, game servers, advertisement aggregation services, advertisement distribution services, facilitators of online meetings, email servers, messaging platforms, Wiki hosts, website hosts, providers of software, providers of software-as-a-service, providers of data, providers of user data, and/or any other data storage device and/or any other service provider.

For example, a resource device (e.g., device 102a), may assist the central controller 110 in authenticating a user every time the user logs into a video game platform associated with the central controller. As another example, a resource device may store digital music files that are downloaded to a user device as a reward for the user's performance in a video game associated with the central controller. As another example, a resource device may provide architectural design software for use by users designing a building in a shared workspace associated with the central controller. According to some embodiments, communications between and/or within the devices 102a-n, 106a-n, 107*a-n* and 107*p-z*, 108, and 110 of the system 100 may be utilized to (i) conduct a multiplayer game, (ii) conduct a meeting, (iii) facilitate a collaborative project, (iv) distribute advertisements, (v) provide teaching, (vi) provide evaluations and ratings or individuals or teams, (vii) facilitate video conferencing services, (viii) enhance educational experiences, and/or for any other purpose.

Figure 79A:
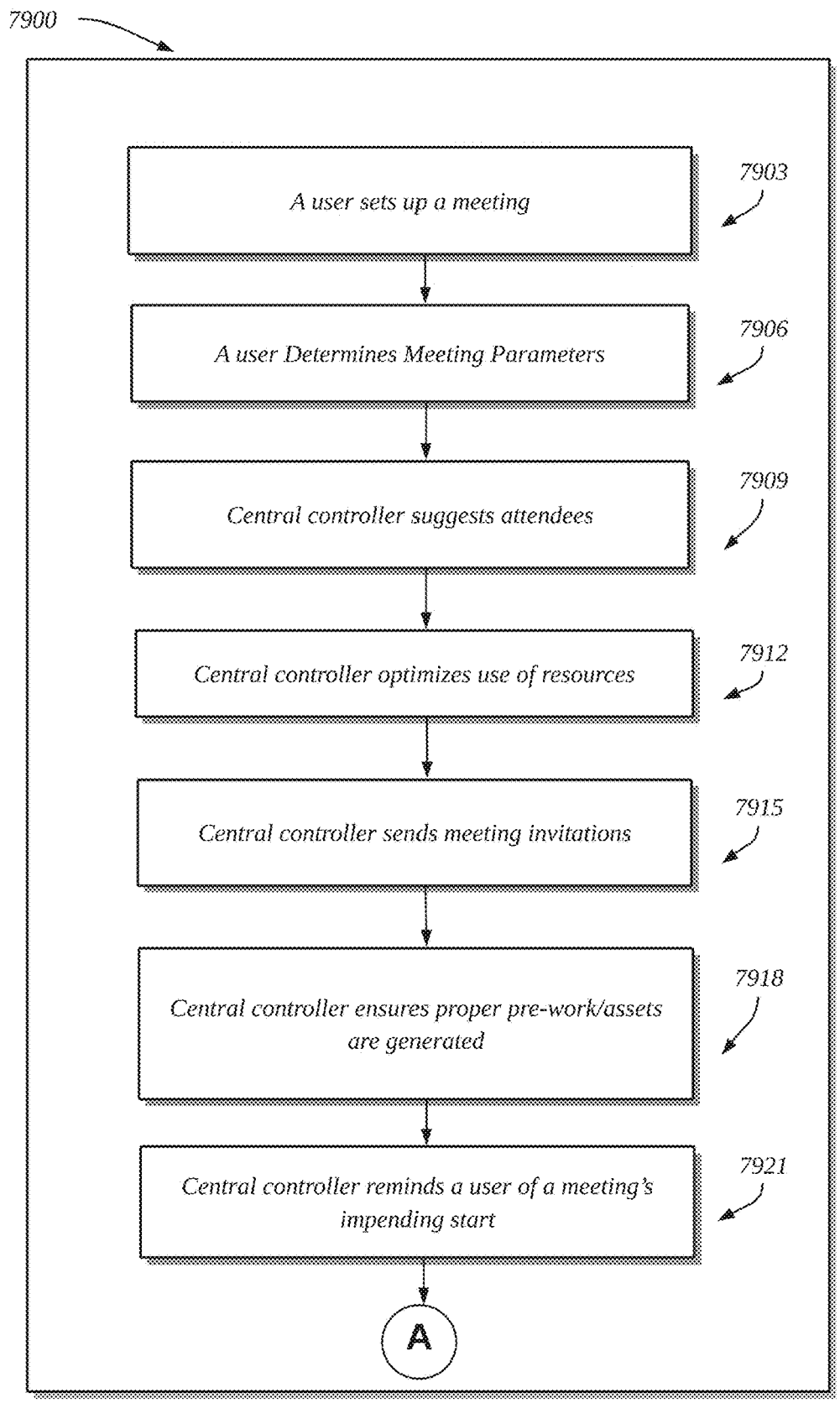
FIG. 79A, FIG. 79B, and FIG. 79C, together show a diagram of a process flow consistent with at least some embodiments described herein.
Figure 79B:
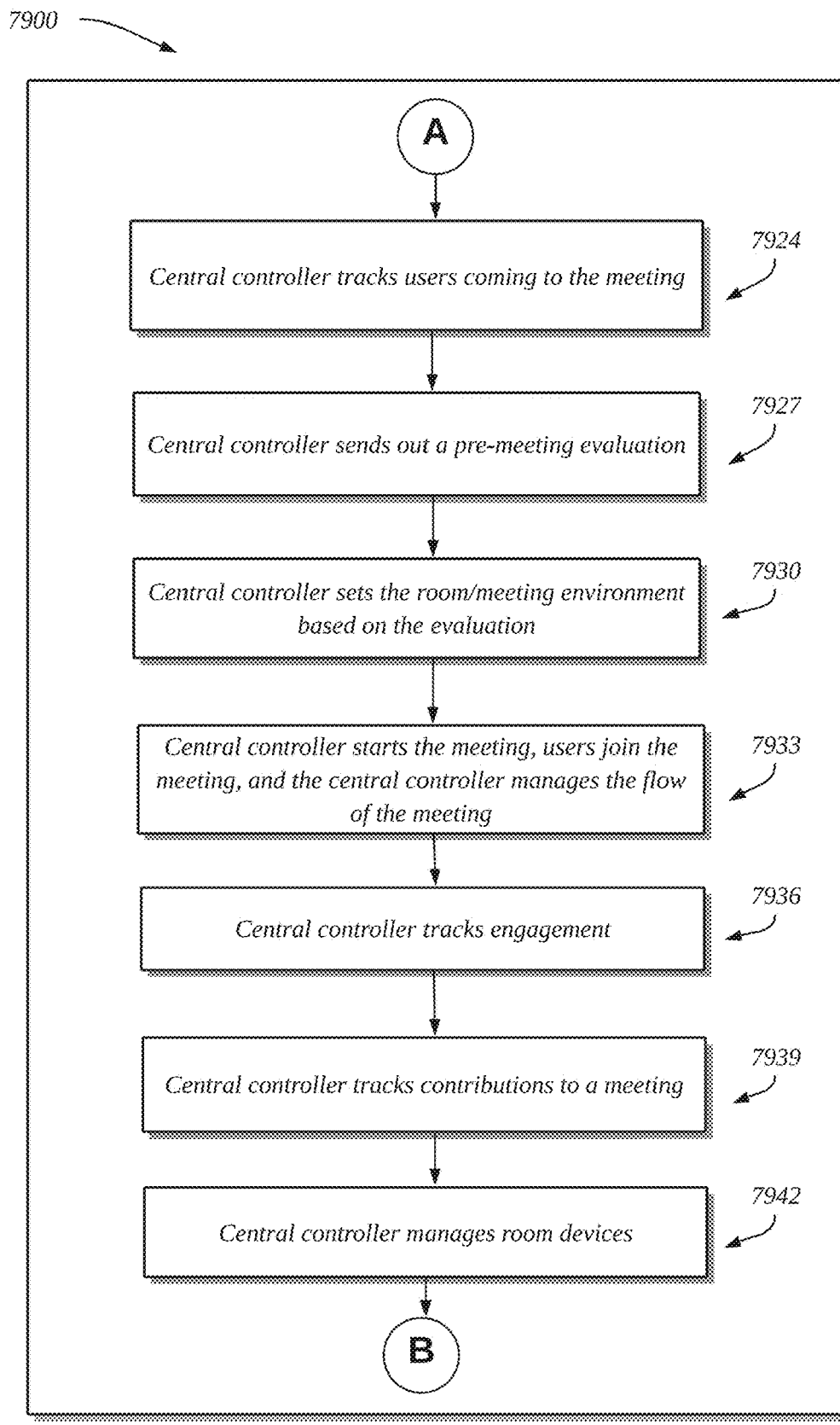
Figure 79C:
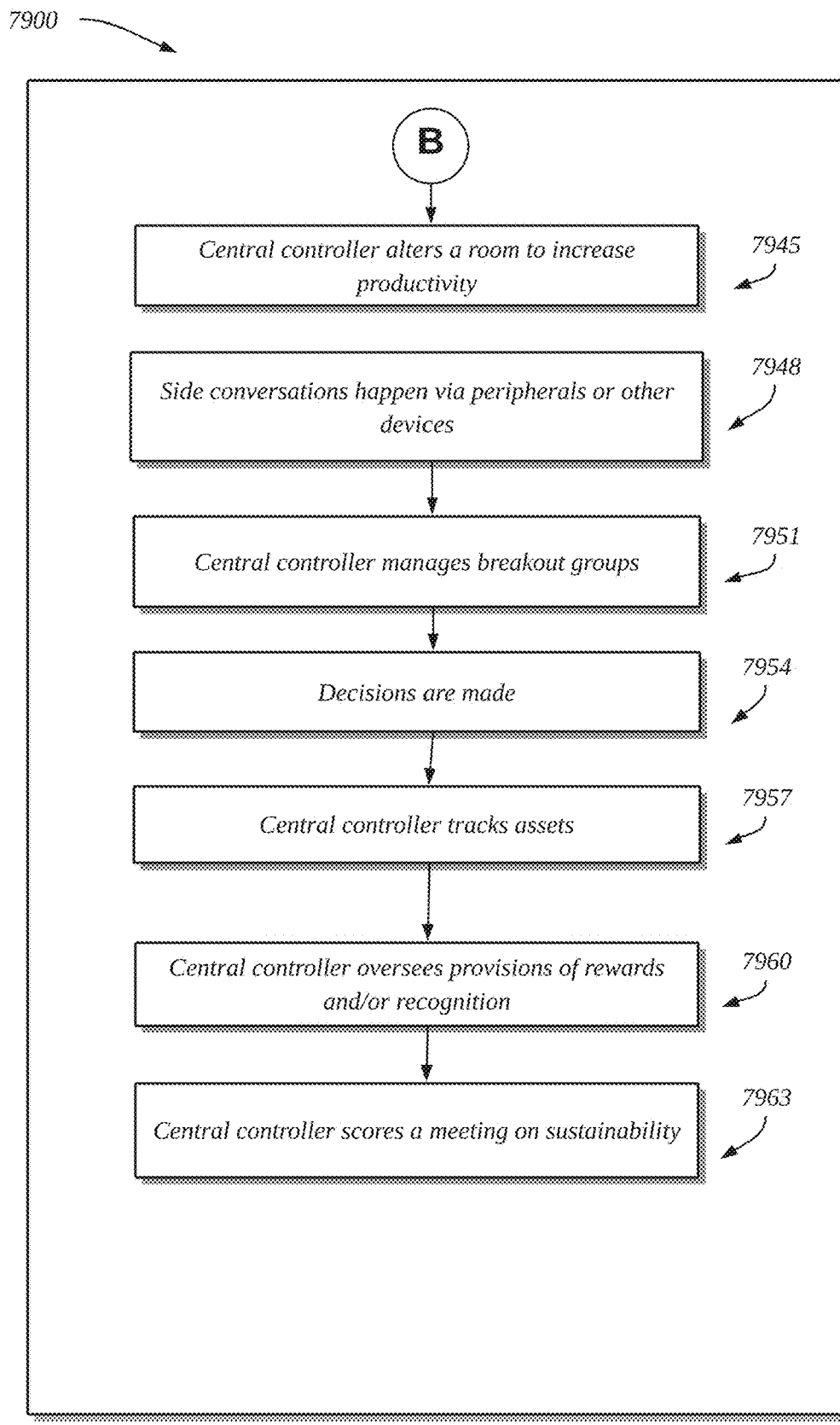

Fewer or more components 102*a-n*, 104, 106*a-n*, 107*a-n*, 107*p-z*, 108, 110 and/or various configurations of the depicted components 102*a-n*, 104, 106*a-n*, 107*a-n*, 107*p-z*, 108, 110 may be included in the system 100 without deviating from the scope of embodiments described herein. In some embodiments, the components 102*a-n*, 104, 106*a-n*, 107*a-n*, 107*p-z*, 108, 110 may be similar in configuration and/or functionality to similarly named and/or numbered components as described herein. In some embodiments, the system 100 (and/or portion thereof) may comprise a platform programmed and/or otherwise configured to execute, conduct, and/or facilitate the methods (e.g., 7900 of FIGS. 79A-C, e.g., 8600 of FIGS. 86A-C, e.g., 9800 of FIG. 98, e.g., 9900 of FIG. 99, e.g., 10000 of FIG. 100, e.g., 10100 of FIG. 101, e.g., 10200 of FIGS. 102A-B) herein, and/or portions thereof.

According to some embodiments, the resource devices 102*a-n* and/or the user devices 106*a-n* may comprise any type or configuration of computing, mobile electronic, network, user, and/or communication devices that are or become known or practicable. The resource devices 102*a-n* and/or the user devices 106*a-n* may, for example, comprise one or more Personal Computer (PC) devices, computer workstations, server computers, cloud computing resources, video gaming devices, tablet computers, such as an iPad® manufactured by Apple®, Inc. of Cupertino, Calif., and/or cellular and/or wireless telephones, such as an iPhone® (also manufactured by Apple®, Inc.) or an LG V50 THINQ™ 5G smart phone manufactured by LG® Electronics, Inc. of San Diego, Calif., and running the Android® operating system from Google®, Inc. of Mountain View, Calif. In some embodiments, the resource devices 102*a-n* and/or the user devices 106*a-n* may comprise one or more devices owned and/or operated by one or more users (not shown), such as a Sony PlayStation® 5, and/or users/account holders (or potential users/account holders). According to some embodiments, the resource devices 102*a-n* and/or the user devices 106*a-n* may communicate with the central controller 110 either directly or via the network 104 as described herein.

According to some embodiments, the peripheral devices 107*a-n*, 107*p-z* may comprise any type or configuration of computing, mobile electronic, network, user, and/or communication devices that are or become known or practicable. The peripheral devices 107*a-n*, 107*p-z* may, for example, comprise one or more of computer mice, computer keyboards, headsets, cameras, touchpads, joysticks, game controllers, watches (e.g., smart watches), microphones, etc. In various embodiments, peripheral devices may comprise one or more of Personal Computer (PC) devices, computer workstations, video game consoles, tablet computers, laptops, and the like. The network 104 may, according to some embodiments, comprise a Local Area Network (LAN; wireless and/or wired), cellular telephone, Bluetooth®, Near Field Communication (NFC), and/or Radio Frequency (RF) network with communication links between the central controller 110, the resource devices 102*a-n*, the user devices 106*a-n*, and/or the third-party device 108. In some embodiments, the network 104 may comprise direct communication links between any or all of the components 102*a-n*, 104, 106*a-n*, 107*a-n*, 107*p-z*, 108, 110 of the system 100. The resource devices 102*a-n* may, for example, be directly interfaced or connected to one or more of the central controller 110, the user devices 106*a-n*, the peripheral devices 107*a-n*, 107*p-z* and/or the third-party device 108 via one or more wires, cables, wireless links, and/or other network components, such network components (e.g., communication links) comprising portions of the network 104. In some embodiments, the network 104 may comprise one or many other links or network components other than those depicted in FIG. 1. The central controller 110 may, for example, be connected to the resource devices 102*a-n* via various cell towers, routers, repeaters, ports, switches, and/or other network components that comprise the Internet and/or a cellular telephone (and/or Public Switched Telephone Network (PSTN)) network, and which comprise portions of the network 104.

While the network 104 is depicted in FIG. 1 as a single object, the network 104 may comprise any number, type, and/or configuration of networks that is or becomes known or practicable. According to some embodiments, the network 104 may comprise a conglomeration of different sub-networks and/or network components interconnected, directly or indirectly, by the components 102*a-n*, 104, 106*b-n*, 107*a*, 107*p-z*, 108, 109, 110 of the system 100. The network 104 may comprise one or more cellular telephone networks with communication links between the user devices 106*b-n* and the central controller 110, for example, and/or may comprise an NFC or other short-range wireless communication path, with communication links between the resource devices 102*a-n* and the user devices 106*b-n*, for example.

According to some embodiments, the third-party device 108 may comprise any type or configuration of a computerized processing device, such as a PC, laptop computer, computer server, database system, and/or other electronic device, devices, or any combination thereof. In some embodiments, the third-party device 108 may be owned and/or operated by a third-party (i.e., an entity different than any entity owning and/or operating either the resource devices 102*a-n*, the user devices 106*a-n*, the peripheral devices 107*a-n* and 107*p-z*, or the central controller 110; such as a business customer or client of the central controller). The third-party device 108 may, for example, comprise an advertiser that provides digital advertisements for incorporation by the central controller 110 into a multiplayer video game, and which pays the central controller to do this. The third-party device 108 may, as another example, comprise a streaming channel that purchases footage of video games from the central controller.

According to some embodiments, the third-party device 108 may comprise a plurality of devices and/or may be associated with a plurality of third-party entities. In some embodiments, the third-party device 108 may comprise the memory device (or a portion thereof), such as in the case the third-party device 108 comprises a third-party data storage service, device, and/or system, such as the Amazon® Simple Storage Service (Amazon® S3™) available from Amazon®.com, Inc. of Seattle, Wash. or an open-source third-party database service, such as MongoDB™ available from MongoDB, Inc. of New York, N.Y. In some embodiments, the central controller 110 may comprise an electronic and/or computerized controller device, such as a computer server and/or server cluster communicatively coupled to interface with the resource devices 102*a-n* and/or the user devices 106*a-n*, and/or the peripheral devices 107*a-n* and 107*p-z*, and/or local network 109 (directly and/or indirectly).

The central controller 110 may, for example, comprise one or more PowerEdge™ M910 blade servers manufactured by Dell®, Inc. of Round Rock, Tex., which may include one or more Eight-Core Intel® Xeon® 7500 Series electronic processing devices. According to some embodiments, the central controller 110 may be located remotely from one or more of the resource devices 102*a-n* and/or the user devices 106*a-n* and/or the peripheral devices 107*a-n* and 107*p-z*. The central controller 110 may also or alternatively comprise a plurality of electronic processing devices located at one or more various sites and/or locations (e.g., a distributed computing and/or processing network).

According to some embodiments, the central controller 110 may store and/or execute specially programmed instructions (not separately shown in FIG. 1) to operate in accordance with embodiments described herein. The central controller 110 may, for example, execute one or more programs, modules, and/or routines (e.g., AI code and/or logic) that facilitate the analysis of meetings (e.g., contributors to the emissions of a meeting; e.g., of contributors to the performance of a meeting), as described herein. According to some embodiments, the central controller 110 may execute stored instructions, logic, and/or software modules to (i) determine meeting configurations consistent with requirements for a meeting, (ii) determine emissions associated with heating a room, (iii) determine emissions associated with a meeting, (iv) determine a route for a participant to take on his way to a meeting, (v) conduct an online game, (vi) facilitate messaging to and between peripheral devices, (vii) determine alterations to a room that may enhance meeting productivity, (ix) provide an interface via which a resource and/or a customer (or other user) may view and/or manage meetings, and/or (x) perform any other task or tasks, as described herein.

In some embodiments, the resource devices 102*a-n*, the user devices 106*a-n*, the third-party device 108, the peripheral devices 107*a-n* and 107*p-z* and/or the central controller 110 may be in communication with and/or comprise a memory device (not shown). The memory device may comprise, for example, various databases and/or data storage mediums that may store, for example, user information, meeting information, cryptographic keys and/or data, login and/or identity credentials, and/or instructions that cause various devices (e.g., the central controller 110, the third-party device 108, resource devices 102*a-n*, the user devices 106*a-n*, the peripheral devices 107*a-n* and 107*p-z*) to operate in accordance with embodiments described herein.

The memory device may store, for example, various AI code and/or mobile device applications and/or interface generation instructions, each of which may, when executed, participate in and/or cause meeting enhancements, improvements to meeting performance, reductions in emissions associated with meeting, enhancements to online gameplay, or any other result or outcome as described herein. In some embodiments, the memory device may comprise any type, configuration, and/or quantity of data storage devices that are or become known or practicable. The memory device may, for example, comprise an array of optical and/or solid-state hard drives configured to store predictive models (e.g., analysis formulas and/or mathematical models and/or models for predicting emissions), credentialing instructions and/or keys, and/or various operating instructions, drivers, etc. In some embodiments, the memory device may comprise a solid-state and/or non-volatile memory card (e.g., a Secure Digital (SD) card such as an SD Standard-Capacity (SDSC), an SD High-Capacity (SDHC), and/or an SD eXtended-Capacity (SDXC)) and any various practicable form-factors, such as original, mini, and micro sizes, such as are available from Western Digital Corporation of San Jose, Calif. In various embodiments, the memory device may be a stand-alone component of the central controller 110. In various embodiments, the memory device 140 may comprise multiple components. In some embodiments, a multi-component memory device may be distributed across various devices and/or may comprise remotely dispersed components. Any or all of the resource devices 102*a-n*, the user devices 106*a-n*, the peripheral devices 107*a-n* and 107*p-z*, the third-party device 108, and/or the central controller 110 may comprise the memory device or a portion thereof, for example.

Resource Devices

Figure 2:
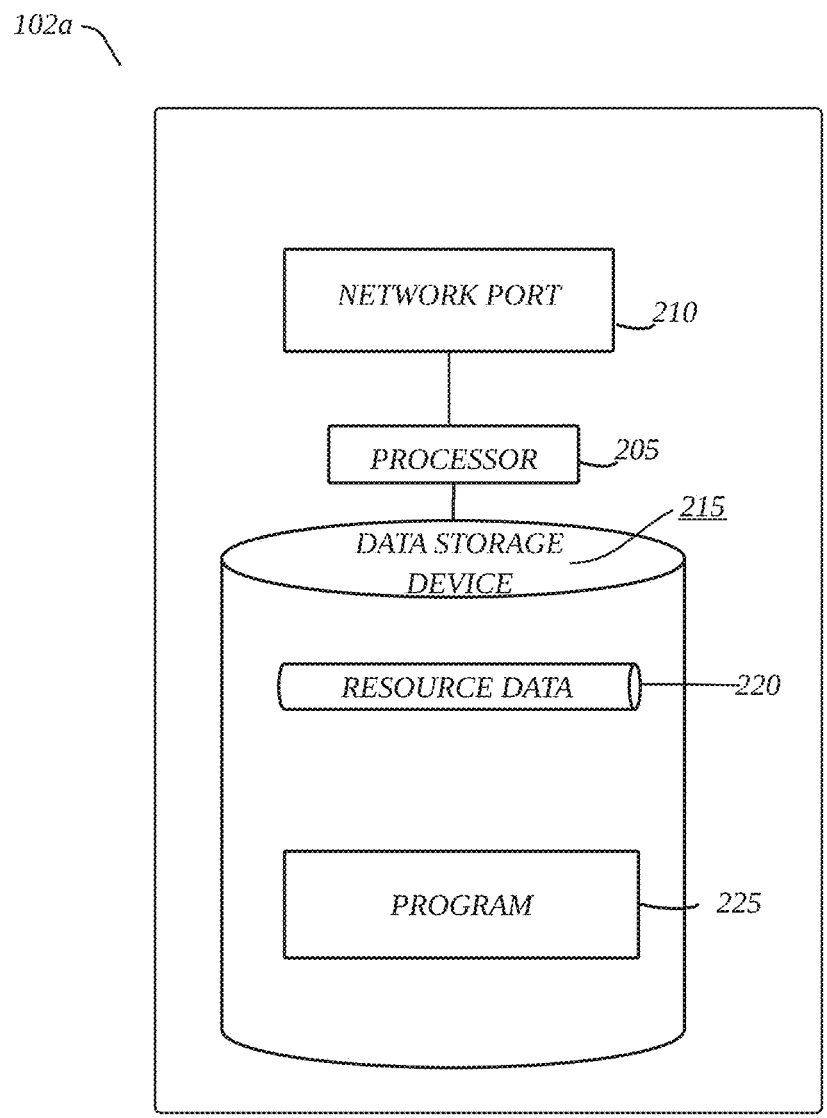
FIG. 2 is a block diagram of a resource device consistent with at least some embodiments described herein.

Turning now to FIG. 2, a block diagram of a resource device 102*a* according to some embodiments is shown. Although FIG. 2 depicts resource device 102*a*, it will be appreciated that other resource devices (e.g., resource devices 102*b-n*, may have similar constructions). In various embodiments, different resource devices may have different constructions. With reference to FIG. 2 (and to any other figures depicting software, software modules, processors, computer programs, and the like), it should be understood that any of the software module(s) or computer programs illustrated therein may be part of a single program or integrated into various programs for controlling processor 205 (or the processor depicted in the relevant figure). Further, any of the software module(s) or computer programs illustrated therein may be stored in a compressed, uncompiled, and/or encrypted format and include instructions which, when performed by the processor, cause the processor to operate in accordance with at least some of the methods described herein. Of course, additional and/or different software module(s) or computer programs may be included and it should be understood that the example software module(s) illustrated and described with respect to FIG. 2 (or to any other relevant figure) are not necessary in any embodiments. Use of the term "module" is not intended to imply that the functionality described with reference thereto is embodied as a stand-alone or independently functioning program or application. While in some embodiments functionality described with respect to a particular module may be independently functioning, in other embodiments such functionality is described with reference to a particular module for ease or convenience of description only and such functionality may in fact be a part of integrated into another module, program, application, or set of instructions for directing a processor of a computing device.

According to an embodiment, the instructions of any or all of the software module(s) or programs described with respect to FIG. 2 (or to any other pertinent figure) may be read into a main memory from another computer-readable medium, such from a ROM to RAM. Execution of sequences of the instructions in the software module(s) or programs causes processor 205 (or other applicable processor) to perform at least some of the process steps described herein. In alternate embodiments, hard-wired circuitry may be used in place of, or in combination with, software instructions for implementation of the processes of the embodiments described herein. Thus, the embodiments described herein are not limited to any specific combination of hardware and software. In various embodiments, resource device 102*a* comprises a processor 205. Processor 205 may be any suitable processor, logic chip, neural chip, controller, or the like, and may include any component capable of executing instructions (e.g., computer instructions, e.g., digital instructions). Commercially available examples include the Apple® eight-core M1 chip with Neural Engine, AMD® Ryzen™ Threadripper 3990x with 64 cores, and the Intel eight-core Core i9-11900K chip.

In various embodiments, processor 205 is in communication with a network port 210 and a data storage device 215. Network port 210 may include any means for resource device 102a to connect to and/or communicate over a network. Network port 210 may include any means for resource device 102a to connect to and/or communicate with another device (e.g., with another electronic device). For example, network port 210 may include a network interface controller, network interface adapter, LAN adapter, or the like. Network port 210 may include a transmitter, receiver, and/or transceiver. Network port 210 may be capable of transmitting signals, such as wireless, cellular, electrical, optical, NFC, RFID, or any other signals. In various embodiments, network port 210 may be capable of receiving signals, such as wireless, cellular, electrical, optical, or any other signals. Storage device 215 may include memory, storage, and the like for storing data and/or computer instructions. Storage device 215 may comprise one or more hard disk drives, solid state drives, random access memory (RAM), read only memory (ROM), and/or any other memory or storage. Storage device 215 may store resource data 220, which may include tables, files, images, videos, audio, or any other data. Storage device 215 may store program 225. Program 225 may include instructions for execution by processor 205 in order to carry out various embodiments described herein. Further, resource data 220 may be utilized (e.g., referenced) by processor 205 in order to carry out various embodiments described herein. It will be appreciated that, in various embodiments, resource device 102a may include more or fewer components than those explicitly depicted.

User Devices

Figure 3:
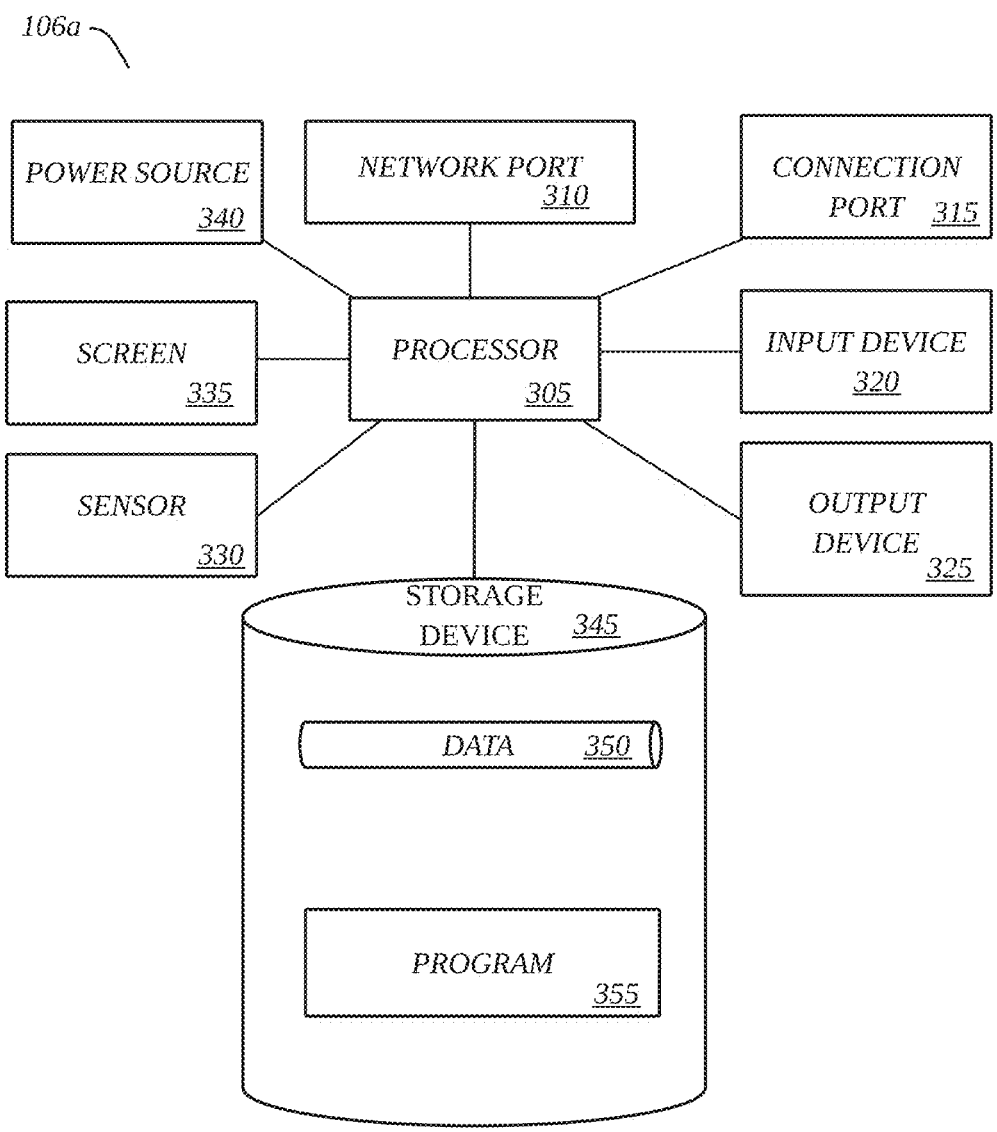
FIG. 3 is a block diagram of a user device consistent with at least some embodiments described herein.

Turning now to FIG. 3, a block diagram of a user device 106a according to some embodiments is shown. Although FIG. 3 depicts user device 106a, it will be appreciated that other user devices (e.g., user devices 106b-n, may have similar constructions). In various embodiments, different user devices may have different constructions. The user device manages the various peripheral devices associated with one or more users, facilitating communication between them and passing information back to the user device. In some embodiments the user device is a Mac® or PC personal computer with suitable processing power, data storage, and communication capabilities to enable various embodiments. In various embodiments, a user device may include a PC, laptop, tablet, smart phone, smart watch, netbook, room AV controller, desktop computer, Apple Macintosh computer, a gaming console, a workstation, or any other suitable device.

Suitable devices that could act as a user device include: Laptops (e.g., MacBook® Pro, MacBook® Air, HP® Spectre™ x360, Google® Pixelbook™ Go, Dell® XPS™ 13); Desktop computers (e.g., Apple® iMac 5K, Microsoft® Surface™ Studio 2, Dell® Inspiron™ 5680); Tablets (e.g., Apple® iPad® Pro 12.9, Samsung® Galaxy™ Tab S6, iPad® Air, Microsoft® Surface™ Pro); Video game systems (e.g., PlayStation® 5, Xbox® One, Nintendo® Switch™, Super NES® Classic Edition, Wii U®); Smartphones (e.g., Apple® iPhone® 12 Pro or Android® device such as Google® Pixel™ 4 and OnePlus™ 7 Pro); IP enabled desk phone; Watches (e.g., Samsung® Galaxy® Watch, Apple® Watch 5, Fossil® Sport, TicWatch™ E2, Fitbit® Versa™ 2); Room AV Controller (e.g., Crestron® Fusion, Google® Meet hardware); Eyeglasses (e.g., Iristick.Z1™ Premium, Vuzix® Blade, Everysight® Raptor™ Solos®, Amazon® Echo™ Frames); Wearables (e.g., watch, headphones, microphone); Digital assistant devices (e.g., Amazon® Alexa® enabled devices, Google® Assistant, Apple® Siri™); or any other suitable devices. In various embodiments, user device 106a comprises a processor 305. As with processor 205, processor 305 may be any suitable processor, logic chip, controller, or the like.

In various embodiments, processor 305 is in communication with a network port 310, connection port 315, input device 320, output device 325, sensor 330, screen 335, power source 340, and a data storage device 345. As with network port 210, network port 310 may include any means for user device 106a to connect to and/or communicate over a network. Network port 310 may comprise similar components and may have similar capabilities as does network port 210, so the details need not be repeated. Connection port 315 may include any means for connecting or interfacing with another device or medium, such as with a peripheral device (e.g., a headset, mouse, a keyboard), a storage medium or device (e.g., a DVD, a thumb drive, a memory card, a CD), or any other device or medium. Connection port 315 may include a USB port, HDMI port, DVI port, VGA port, Display port, Thunderbolt, Serial port, a CD drive, a DVD drive, a slot for a memory card, or any variation thereof, or any iteration thereof, or any other port. Input device 320 may include any component or device for receiving user input or any other input. Input device 320 may include buttons, keys, trackpads, trackballs, scroll wheels, switches, touch screens, cameras, microphones, motion sensors, biometric sensors, or any other suitable component or device. Input device 320 may include a keyboard, power button, eject button, fingerprint button, or any other device.

Output device 325 may include any component or device for outputting or conveying information, such as to a user. Output device 325 may include a display screen, speaker, light, backlight, projector, LED, touch bar, haptic actuator, or any other output device. Sensor 330 may include any component or device for receiving or detecting environmental, ambient, and/or circumstantial conditions, situations, or the like. Sensor 330 may include a microphone, temperature sensor, light sensor, motion sensor, accelerometer, inertial sensor, gyroscope, contact sensor, angle sensor, or any other sensor. Screen 335 may include any component or device for conveying visual information, such as to a user. Screen 335 may include a display screen and/or a touch screen. Screen 335 may include a CRT screen, LCD screen, projection screen, plasma screen, LED screen, OLED screen, DLP screen, laser projection screen, virtual retinal display, or any other screen.

Power source 340 may include any component or device for storing, supplying and/or regulating power to user device 106a and/or to any components thereof. Power source 340 may include a battery, ultra-capacitor, power supply unit, or any other suitable device. Power source 340 may include one or more electrical interfaces, such as a plug for connecting to an electrical outlet. Power source 340 may include one or more cords, wires, or the like for transporting electrical power, such as from a wall outlet and/or among components of user device 106a.

Storage device 345 may include memory, storage, and the like for storing data and/or computer instructions. Storage device 345 may comprise one or more hard disk drives, solid state drives, random access memory (RAM), read only memory (ROM), and/or any other memory or storage. Storage device 345 may store data 350, which may include tables, files, images, videos, audio, or any other data. Storage device 345 may store program 355. Program 355 may include instructions for execution by processor 305 in order to carry out various embodiments described herein. Further, data 350 may be utilized (e.g., referenced) by processor 305 in order to carry out various embodiments described herein. It will be appreciated that, in various embodiments, user device 106a may include more or fewer components than those explicitly depicted. It will be appreciated that components described with respect to user device 106a need not necessarily be mutually exclusive. For example, in some embodiments, an input device 320 and a screen 335 may be the same (e.g., a touch screen). For example, in some embodiments, an input device 320 and a sensor 330 may be the same (e.g., a microphone). Similarly, components described herein with respect to any other device need not necessarily be mutually exclusive.

Peripheral Devices

Figure 4:
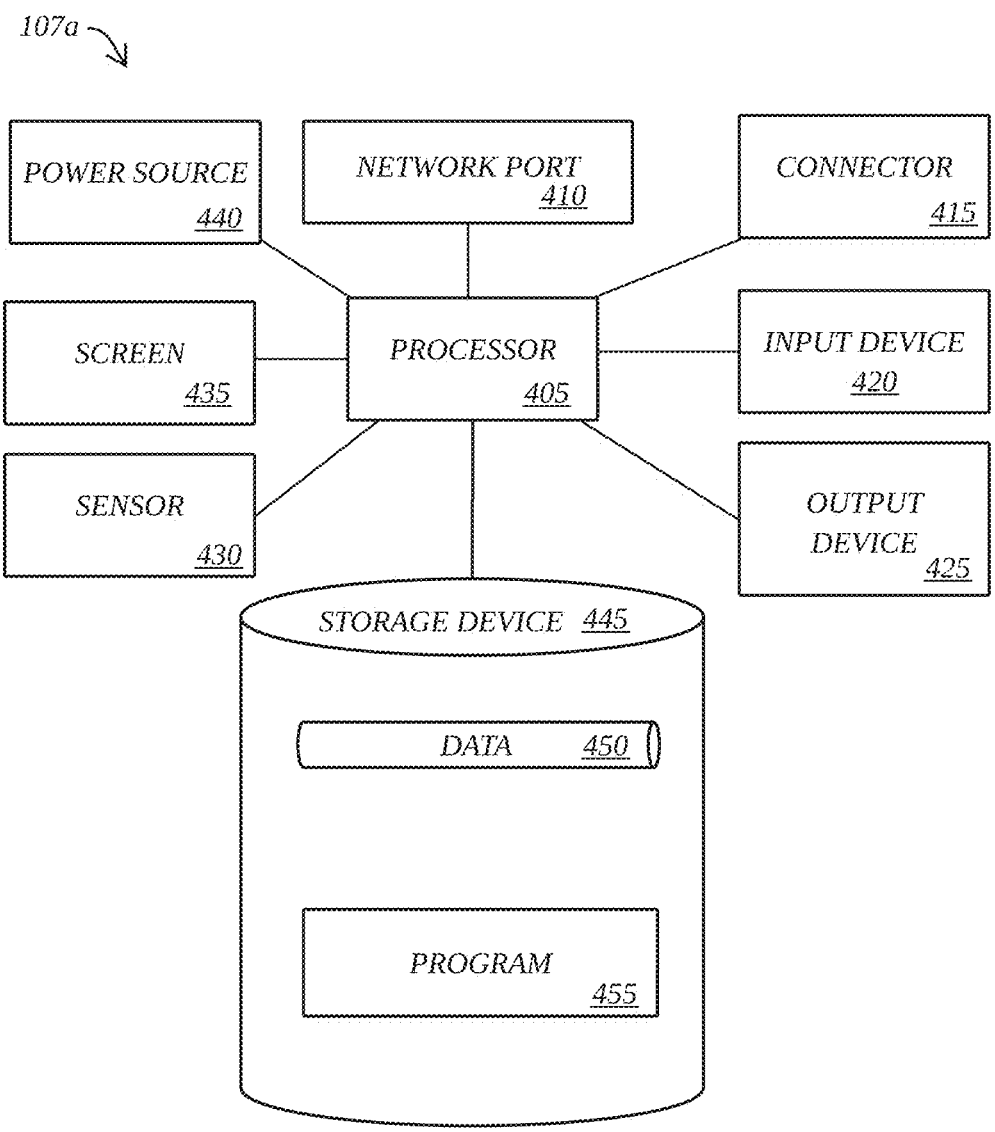
FIG. 4 is a block diagram of a peripheral device consistent with at least some embodiments described herein.

Turning now to FIG. 4, a block diagram of a peripheral device 107a according to some embodiments is shown. Although FIG. 4 depicts peripheral device 107a, it will be appreciated that other peripheral devices (e.g., peripheral devices 107b-n and 107p-z, may have similar constructions). In various embodiments, different peripheral devices may have different constructions. Peripheral devices 107a according to various embodiments include: mouse, trackpad, trackball, joystick, video game controller, wheel, camera, exercise device, footpad, pedals, pedal, foot pedal, yoke, keyboard, headset, watch, stylus, soft circuitry, drone or other action camera (e.g., GoPro®), or any other suitable device. Peripheral devices 107a might include suitably adapted furniture, accessories, clothing, or other items. For example, furniture might include built-in sensors and/or built-in electronics. Peripherals may include: chair, musical instrument, ring, clothing, hat, shoes, shirt, collar, mousepad, or any other suitable object or device. Peripheral devices 107a might include: green screens or chroma key screens; lights such as task lights, or specialized key lights for streaming; webcams; a desk itself, including a conventional or sit-stand desk; desk surface; monitor stand (e.g., which is used to alter the height of a monitor) or laptop computer stand (which may include charger and connections); monitor mount or swing arms; speakers; dongles, connecters, wires, cables; printers and scanners; external hard drives; pens; phones and tablets (e.g., to serve as controllers, second screens, or as a primary device); other desk items (e.g., organizers, photos and frames, coaster, journal or calendar); glasses; mugs; water bottles; etc.

Peripheral device 107a may include various components. Peripheral device 107a may include a processor 405, network port 410, connector 415, input device 420, output device 425, sensor 430, screen 435, power source 440, and storage device 445. Storage device 445 may store data 450 and program 455. A number of components for peripheral device 107a depicted in FIG. 4 have analogous components in user device 106a depicted in FIG. 3 (e.g., processor 405 may be analogous to processor 305), and so such components need not be described again in detail. However, it will be appreciated that any given user device and any given peripheral device may use different technologies, different manufacturers, different arrangements, etc., even for analogous components. For example, a particular user device may comprise a 20-inch LCD display screen, whereas a particular peripheral device may comprise a 1-inch OLED display screen. It will also be appreciated that data 450 need not necessarily comprise the same (or even similar) data as does data 350, and program 455 need not necessarily comprise the same (or even similar) data or instructions as does program 350.

In various embodiments, connector 415 may include any component capable of interfacing with a connection port (e.g., with connection port 315). For example, connector 415 may physically complement connection port 315. Thus, for example, peripheral device 107a may be physically connected to a user device via the connector 415 fitting into the connection port 315 of the user device. The interfacing may occur via plugging, latching, magnetic coupling, or via any other mechanism. In various embodiments, a peripheral device may have a connection port while a user device has a connector. Various embodiments contemplate that a user device and a peripheral device may interface with one another via any suitable mechanism. In various embodiments, a user device and a peripheral device may interface via a wireless connection (e.g., via Bluetooth®, Near Field Communication, or via any other means).

A peripheral may include one or more sensors 430. These may include mechanical sensors, optical sensors, photo sensors, magnetic sensors, biometric sensors, or any other sensors. A sensor may generate one or more electrical signals to represent a state of a sensor, a change in state of the sensor, or any other aspect of the sensor. For example, a contact sensor may generate a "1" (e.g., a binary one, e.g., a "high" voltage) when there is contact between two surfaces, and a "0" (e.g., a binary "0", e.g., a "low" voltage) when there is not contact between the two surfaces. A sensor may be coupled to a mechanical or physical object, and may thereby sense displacement, rotations, or other perturbations of the object. In this way, for example, a sensor may detect when a button has been depressed (e.g., contact has occurred between a depressible surface of a button and a fixed supporting surface of the button), when a wheel has been turned (e.g., a spoke of the wheel has blocked incident light onto an optical sensor), or when any other perturbation has occurred. In various embodiments, sensor 430 may be coupled to input device 420, and may thereby sense user inputs at the input device (e.g., key presses; e.g., mouse movements, etc.).

In various embodiments, sensor 430 may detect more than binary states. For example, sensor 430 may detect any of four different states, any of 256 different states, or any of a continuous range of states. For example, a sensor may detect the capacitance created by two parallel surfaces. The capacitance may change in a continuous fashion as the surfaces grow nearer or further from one another. The processor 405 may detect the electrical signals generated by sensor 430. The processor may translate such raw sensor signals into higher-level, summary, or aggregate signals. For example, processor 405 may receive a series of "1-0" signals from the sensor that is repeated 45 times. Each individual "1-0" signal may represent the rotation of a mouse wheel by 1 degree. Accordingly, the processor may generate a summary signal indicating that the mouse wheel has turned 45 degrees. As will be appreciated, aggregate or summary signals may be generated in many other ways. In some embodiments, no aggregate signal is generated (e.g., a raw sensor signal is utilized).

In various embodiments, processor 405 receives an electrical signal from sensor 430 that is representative of 1 out of numerous possible states. For example, the electrical signal may represent state number 139 out of 256 possible states. This may represent, for example, the displacement by which a button has been depressed. The processor may then map the electrical signal from sensor 430 into one of only two binary states (e.g., 'pressed' or 'not pressed'). To perform the mapping, the processor 405 may compare the received signal to a threshold state. If the state of the received signal is higher than the threshold state, then the processor may map the signal to a first binary state, otherwise the signal is mapped to a second binary state. In various embodiments, the threshold may be adjustable or centrally configurable. This may allow, for example, the processor 405 to adjust the amount of pressure that is required to register a "press" or "click" of a button.

Processor 405 may create data packets or otherwise encode the summary signals. These may then be transmitted to a user device (e.g., device 106*b*) via connector 415 (e.g., if transmitted by wired connection), via network port 410 (e.g., if transmitted by network; e.g., if transmitted by wireless network), or via any other means. User device 106*b* may include a computer data interface controller (e.g., as network port 410; e.g., as connector 415; e.g., as part of network port 410; e.g., as part of connector 415; e.g., in addition to network port 410 and/or connector 415), which may receive incoming data from peripheral device 107*a*. The incoming data may be decoded and then passed to a peripheral driver program on the user device 106*b*. In various embodiments, different models or types of peripheral devices may require different drivers. Thus, for example, user device 106*b* may include a separate driver for each peripheral device with which it is in communication. A driver program for a given peripheral device may be configured to translate unique or proprietary signals from the peripheral device into standard commands or instructions understood by the operating system on the user device 106*b*. Thus, for example, a driver may translate signals received from a mouse into a number of pixels of displacement of the mouse pointer. The peripheral device driver may also store a current state of the peripheral device, such as a position of the device (e.g., mouse) or state of depression of one or more buttons. A driver may pass peripheral device states or instructions to the operating system as generated, as needed, as requested, or under any other circumstances. These may then be used to direct progress in a program, application, process, etc.

Sensors

Various embodiments may employ sensors (e.g., sensor 330; e.g., sensor 430). Various embodiments may include algorithms for interpreting sensor data. Sensors may include microphones, motion sensors, tactile/touch/force sensors, voice sensors, light sensors, air quality sensors, weather sensors, indoor positioning sensors, environmental sensors, thermal cameras, infrared sensors, ultrasonic sensors, fingerprint sensors, brainwave sensors (e.g., EEG sensors), heart rate sensors (e.g., EKG sensors), muscle sensors (e.g., EMG electrodes for skeletal muscles), barcode and magstripe readers, speaker/ping tone sensors, galvanic skin response sensors, sweat and sweat metabolite sensors and blood oxygen sensors (e.g., pulse oximeters), electrodermal activity sensors (e.g., EDA sensors), or any other sensors. Algorithms may include face detection algorithms, voice detection algorithms, or any other algorithms.

Motion sensors may include gyroscopes, accelerometers, Wi-Fi® object sensing (e.g. using Wi-Fi® signals that bounce off of objects in a room to determine the size of an object and direction of movement), magnetometer combos (inertia measurement units), or any other motion sensors. Motion sensors may be 6 or 9 axis sensors, or sensors along any other number of axes. Motion sensors may be used for activity classification. For example, different types of activities such as running, walking, cycling, typing, etc., may have different associated patterns of motion. Motion sensors may therefore be used in conjunction with algorithms for classifying the recorded motions into particular activities. Motion sensors may be used to track activity in a restricted zone of a building, identify whether an individual is heading toward or away from a meeting, as a proxy for level of engagement in a meeting, steps taken, calories burned, hours slept, quality of sleep, or any other aspect of user activity. Motion sensors may be used to quantify the amount of activity performed, e.g., the number of steps taken by a user. Motion sensors can also be used to track the movement of objects, such as the velocity or distance traveled of a user's mouse. Motion sensors may be used to identify whether an individual is approaching an entry to a house, and if so, trigger a doorbell within the house, and send an alert to a user device or peripheral devices of a user associated with the house.

Motion sensors may use passive infrared (PIR) technology which can detect body and changes in body temperatures. Motion sensors using microwave technology send out microwave pulses and measure how those pulses bounce off moving objects. Ultrasonic motion sensors are another option. Motion sensors can also employ dual use technology by combining multiple detection methods, such as using both passive infrared and microwave technologies. Vibration motion sensors can pick up vibrations caused by people walking through a room. Area reflective motion sensors use infrared waves from an LED and can calculate the distance to an object based on the reflection of the waves.

Motion sensors may be used in conjunction with reminders, such as reminders to change activity patterns. For example, if motion sensors have been used to detect that a user has been sitting for a predetermined period of time, or that the user has otherwise been sedentary, a reminder may be generated for the user to encourage the user to stand up or otherwise engage in some physical activity.

Motion sensors may be used to detect wrist gestures, such as shakes, taps or double taps, or twists. Motion sensors may detect device orientation (e.g., landscape/portrait mode, vertical orientation). A motion sensor may include a freefall sensor. A freefall sensor may be used to monitor handling of packages/devices (e.g., that packages were not dropped or otherwise handled too roughly) or to protect hard drives (e.g., to refrain from accessing the hard drive of a device if the device is undergoing too much motion). In various embodiments, accelerometers may be used as microphones. For example, accelerometers may detect vibrations in air, in a membrane, or in some other medium caused by sound waves.

Tactile/touch/force sensors may include sensors that are sensitive to force, such as physical pressure, squeezing, or weight. Flex sensors may sense bending. 3-D accelerometers, such as the Nunchuck®/Wiichuck®, may sense motion in space (e.g., in three dimensions). Light sensors may sense ambient light. Light sensors, such as RGB sensors, may sense particular colors or combinations of colors, such as primary colors (e.g., red green and blue). Light sensors may include full spectrum luminosity sensors, ultraviolet (UV) sensors, infrared (IR) sensors, or any other sensors. Light sensors may include proximity sensors. Indoor positioning sensors may include sensors based on dead reckoning, pedestrian dead reckoning (such as the combination of accelerometer and gyroscope, including systems unreliable on infrastructure), geomagnetic or RF signal strength mapping, Bluetooth® beacons, or based on any other technology. Environmental sensors may include barometers, altimeters, humidity sensors, smoke detectors, radiation detectors, noise level sensors, gas sensors, temperature sensors (e.g., thermometers), liquid flow sensors, and any other sensors. Infrared sensors may be used to detect proximity, body temperature, gestures, or for any other application. Ultrasonic sensors may be used for range-finding, presence/proximity sensing, object detection and avoidance, position tracking, gesture tracking, or for any other purpose.

Outputs

In various embodiments, outputs may be generated by various components, devices, technologies, etc. For example, outputs may be generated by output device 325 and/or by output device 425. Outputs may take various forms, such as lights, colored lights, images, graphics, sounds, melodies, music, tones, vibrations, jingles, spoken words, synthesized speech, sounds from games, sounds from video games, etc. Light outputs may be generated by light emitting diodes (LED's), liquid crystals, liquid crystal displays (LCD's), incandescent lights, display screens, electronic ink (E-ink), e-skin, or by any other source. In various embodiments, outputs may include vibration, movement, or other motion. Outputs may include force feedback or haptic feedback. Outputs may include temperature, such as through heating elements, cooling elements, heat concentrating elements, fans, or through any other components or technologies. In various embodiments, an output component may include a motor. A motor may cause a mouse to move on its own (e.g., without input of its owner). In various embodiments, a first mouse is configured to mirror the motions of a second mouse. That is, for example, when the other second mouse is moved by a user, the motor in the first mouse moves the first mouse in a series of motions that copy the motions of the second mouse. In this way, for example, a first user can see the motions of another user reflected in his own mouse. In various embodiments, outputs may take the form of holograms. In various embodiments, outputs may take the form of scents or odors or vapors. These may be generated with dispensers, for example. In various embodiments, outputs may consist of alterations to an in-home (or other indoor) environment. Outputs may be brought about by home control systems. Alterations to the environment may include changing temperature, humidity, light levels, state of window shades (e.g., open are closed), state of door locks, security cameras settings, light projections onto walls, or any other alteration.

Third-Party Devices

Figure 5:
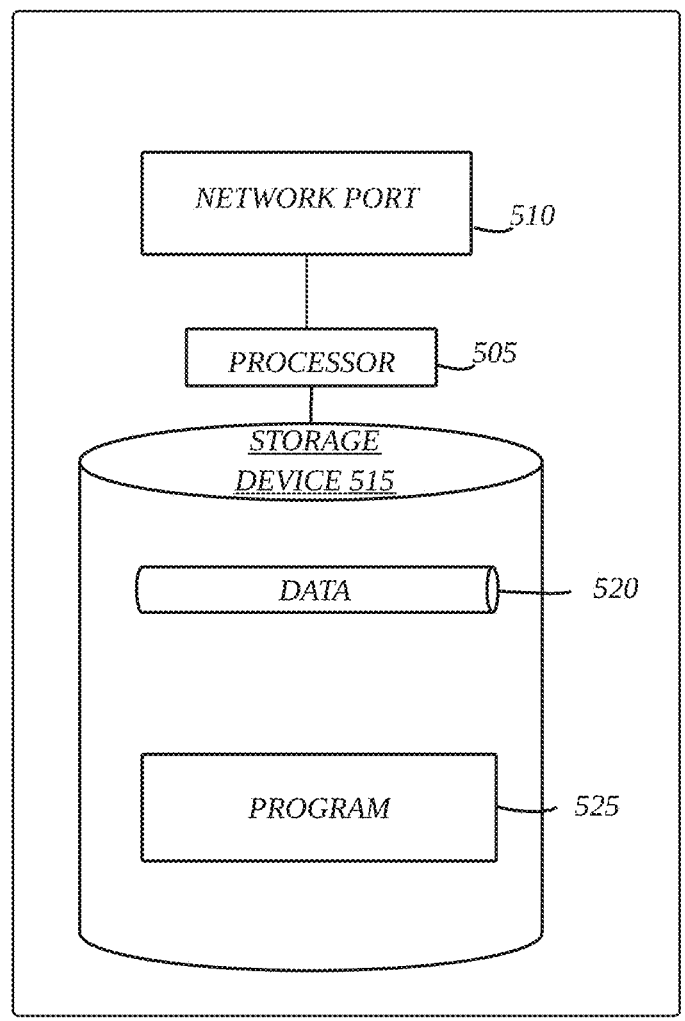
FIG. 5 is a block diagram of a third-party device consistent with at least some embodiments described herein.

Turning now to FIG. 5, a block diagram of a third-party device 108 according to some embodiments is shown. In various embodiments, a third-party device 108 may be a server or any other computing device or any other device. Third-party device 108 may include various components. Third-party device 108 may include a processor 505, network port 510, and storage device 515. Storage device 515 may store data 520 and program 525. A number of components for third-party device 108 depicted in FIG. 5 have analogous components in resource device 102*a* depicted in FIG. 2 (e.g., processor 505 may be analogous to processor 205), and so such components need not be described again in detail. However, it will be appreciated that any given resource device and any given third-party device may use different technologies, different manufacturers, different arrangements, etc., even for analogous components. It will also be appreciated that data 520 need not necessarily comprise the same (or even similar) data as does data 220, and program 525 need not necessarily comprise the same (or even similar) data or instructions as does program 225.

Central Controllers

Figure 6:
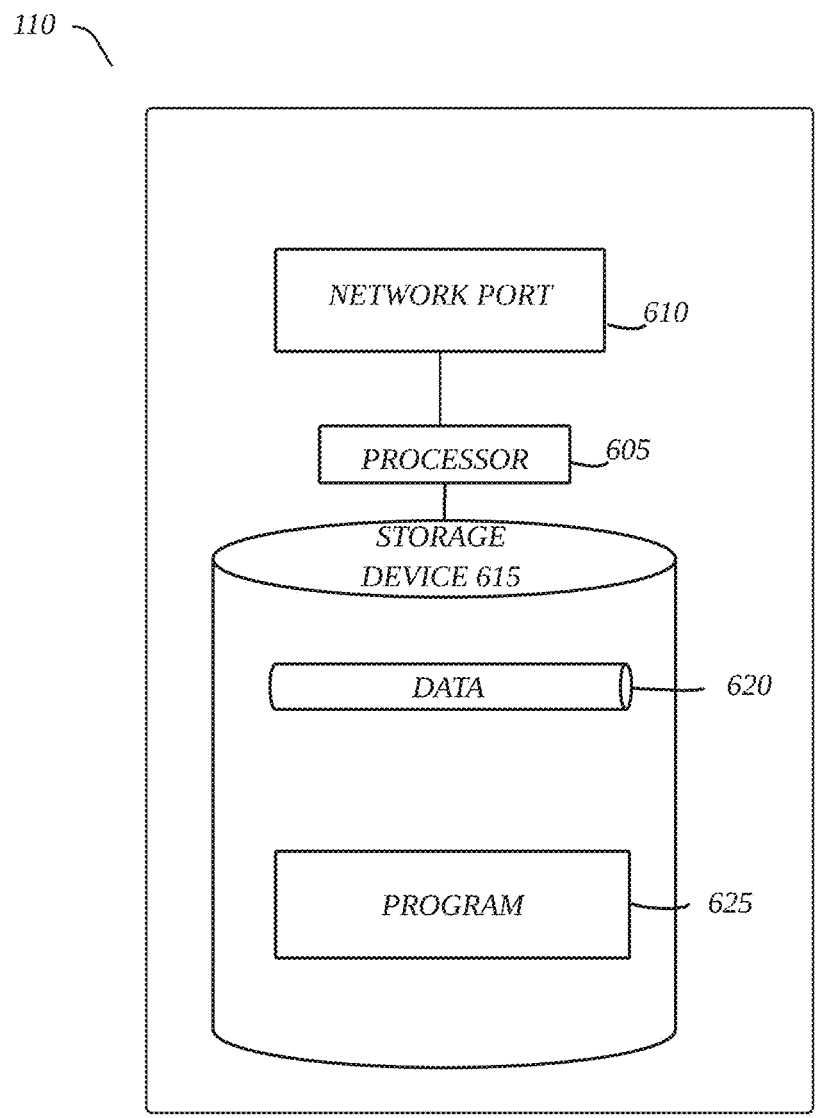
FIG. 6 is a block diagram of a central controller consistent with at least some embodiments described herein.

Turning now to FIG. 6, a block diagram of a central controller 110 according to some embodiments is shown. In various embodiments, central controller 110 may be a server or any other computing device or any other device. Central controller 110 may include various components. Central controller 110 may include a processor 605, network port 610, and storage device 615. Storage device 615 may store data 620 and program 625. A number of components for central controller 110 depicted in FIG. 6 have analogous components in resource device 102*a* depicted in FIG. 2 (e.g., processor 605 may be analogous to processor 205), and so such components need not be described again in detail. However, it will be appreciated that any given resource device and central controller 110 may use different technologies, different manufacturers, different arrangements, etc., even for analogous components. It will also be appreciated that data 620 need not necessarily comprise the same (or even similar) data as does data 220, and program 625 need not necessarily comprise the same (or even similar) data or instructions as does program 225.

In various embodiments, the central controller may include one or more servers located at the headquarters of a company, a set of distributed servers at multiple locations throughout the company, or processing/storage capability located in a cloud environment—either on premise or with an outside vendor such as Amazon® Web Services, Google® Cloud Platform, or Microsoft® Azure™. In various embodiments, the central controller may be a central point of processing, taking input from one or more of the devices herein, such as a user device or peripheral device. The central controller has processing and storage capability along with the appropriate management software as described herein. In various embodiments, the central controller may include an operating system, such as Linux, Windows® Server, Mac® OS X Server, or any other suitable operating system.

Communications with the central controller could include user devices, game controllers, peripheral devices, outside websites, conference room control systems, video communication networks, remote learning communication networks, game consoles, streaming platforms, corporate data systems, etc. In various embodiments, the central controller may include hardware and software that interfaces with user devices and/or peripheral devices in order to facilitate communications. The central controller may collect analytics from devices (e.g., user device, e.g., peripheral devices). Analytics may be used for various purposes, such as for the purpose of enhancing the experience of a user.

In various embodiments, the central controller may perform various other functions, such as authenticating users, maintaining user accounts, maintaining user funds, maintaining user rewards, maintaining user data, maintaining user work products, hosting productivity software, hosting game software, hosting communication software, facilitating the presentation of promotions to the user, allowing one user to communicate with another, allowing a peripheral device to communicate with another, or any other function.

In various embodiments, the central controller may include software for providing notifications and/or status updates. The central controller may notify a user when one or more other users is present (e.g., at their respective office locations, e.g., at their respective home computers), when another user wishes to communicate with the user, when a collaborative project has been updated, when the user has been mentioned in a comment, when the user has been assigned work, when the user's productivity has fallen, when the user has been invited to play in a game, or in any other circumstance. Notifications or status updates may be sent to peripheral devices, user devices, smartphones, or to any other devices.

In various embodiments, the central controller may include voting software. The voting software may facilitate voting, decision-making, or other joint or group action. Example votes may determine a plan of action at a company, or a strategy in a team video game. Voting software may permit users or other participants to receive notification of votes, receive background information about decisions or actions they are voting on, cast their votes, and see the results of votes. Voting software may be capable of instituting various protocols, such as multiple rounds of runoffs, win by the majority, win by the plurality, win by unanimous decision, anonymous voting, public voting, secure voting, differentially weighted votes, voting for slates of decisions, or any other voting protocol, or any other voting format. Voting results may be stored in data storage device 615, or sent to other devices for storage.

Game Controllers

In various embodiments, a game controller may include software and/or hardware that interfaces with the user device in order to facilitate game play. Example games include Pokemon®, Call of Duty®, Wii®, League of Legends®, Clash of Clans™, Madden® NFL®, Minecraft®, Guitar Hero®, Fortnite®, solitaire, poker, chess, go, backgammon, bridge, Magic: The Gathering®, Scrabble®, etc. In various embodiments, a game controller may be part of the central controller 110. In various embodiments, a game controller may be in communication with the central controller 110, and may exchange information as needed. In various embodiments, a game controller may be a standalone device or server (e.g., a server accessed via the internet). In various embodiments, a game controller could be housed within a user computer. In various embodiments, a game controller may be part of, or may operate on any suitable device. In various embodiments, the game controller enables gameplay and can communicate with a user device and one or more computer peripherals. In various embodiments, a game controller may perform such functions as maintaining a game state, updating a game state based on user inputs and game rules, creating a rendering of a game state, facilitating chat or other communication between players of a game, maintaining player scores, determining a winner of a game, running tournaments, determining a winner of a tournament, awarding prizes, showing in-game advertisements, are performing any other function related to a game, or performing any other function.

Data Structures

FIGS. 7-37, 50-62, 64-66, 70, 73-78, 87-88, and 95-97, show example data tables according to some embodiments. A data table may include one or more fields, which may be shown along the top of the table. A given field may serve as a category, class, bucket, or the like for data in the table corresponding to the given field (e.g., for data in cells shown beneath the field). Each cell or box in a data table may include a data element. Data elements within the same row of a table may be associated with one another (e.g., each data element in a row may be descriptive of the same underlying person, object, entity, or the like). In various embodiments, data elements may include identifiers or indexes, which may serve to identify (e.g., uniquely identify) the current row and/or the underlying person, object, or entity. In various embodiments, data elements may include keys, which may allow a row from a first table to be associated with a row from a second table (e.g., by matching like keys in the first and second tables). Through use of keys (or through any other means) two or more data tables may be relatable to one other in various ways. In various embodiments, relationships may include one-to-one, one-to-many, many-to-many, or many-to-one relationships.

It will be appreciated that FIGS. 7-37, 50-62, 64-66, 70, 73-78, 87-88, and 95-97 represent some ways of storing, representing, and/or displaying data, but that various embodiments contemplate that data may be stored, represented and/or displayed in any other suitable fashion. It will be appreciated that, in various embodiments, one or more tables described herein may include additional fields or fewer fields, that a given field may be split into multiple fields (e.g., a "name" field could be split into a "first name" field and a "last name" field), that two or more fields may be combined, that fields may have different names, and/or that fields may be structured within tables in any other suitable fashion. It will be appreciated that, in various embodiments, one or more tables described herein may include additional rows, that rows may be split or combined, that rows may be re-ordered, that rows may be split amongst multiple tables, and/or that rows may be rearranged in any other suitable fashion.

It will be appreciated that, in various embodiments, one or more tables described herein may show representative rows of data elements. Rows are not necessarily shown in any particular order. The rows are not necessarily shown starting from the beginning nor approaching the end in any conceivable ordering of rows. Consecutive rows are not necessarily shown. In some embodiments, fewer or more data fields than are shown may be associated with the data tables (e.g., of FIGS. 7-37, 50-62, 64-66, 70, 73-78, 87-88, and 95-97). Only a portion of one or more databases and/or other data stores is necessarily shown in the data table 700 of FIG. 7, for example, and other fields, columns, structures, orientations, quantities, and/or configurations may be utilized without deviating from the scope of some embodiments. Further, the data shown in the various data fields is provided solely for exemplary and illustrative purposes and does not limit the scope of embodiments described herein. In various embodiments, data or rows that are depicted herein as occurring in the same data table may actually be stored in two or more separate data tables. These separate data tables may be distributed in any suitable fashion, such as being stored within separate databases, in separate locations, on separate servers, or in any other fashion.

In various embodiments, data or rows that are depicted herein as occurring in separate or distinct data tables may actually be stored in the same data tables. In various embodiments, two or more data tables may share the same name (e.g., such data tables may be stored in different locations, on different devices, or stored in any other fashion). Such data tables may or may not store the same types of data, may or may not have the same fields, and may or may not be used in the same way, in various embodiments. For example, central controller 110 may have a "user" data table, and third-party device 108 may be an online gaming platform that also has a "user" data table. However, the two tables may not refer to the same set of users (e.g., one table may store owners of peripheral devices, while the other table may store rated online game players), and the two tables may store different information about their respective users. In various embodiments, data tables described herein may be stored using a data storage device (e.g., storage device 615) of central controller 110. For example, "data" 620 may include data tables associated with the central controller 110, which may reside on storage device 615. Similarly, "data" 520 may include data tables associated with the third-party device 108, which may reside on storage device 515. In various embodiments, data tables associated with any given device may be stored on such device and/or in association with such device.

Referring to FIG. 7, a diagram of an example user table 700 according to some embodiments is shown. User table 700 may, for example, be utilized to store, modify, update, retrieve, and/or access various information related to users. The user table may comprise, in accordance with various embodiments, a user ID field 702, a name field 704, an email address field 706, a password field 708, a phone number field 710, a nicknames field 712, an address field 714, a financial account information field 716, a birthdate field 718, a marital status field 720, a gender field 722, a primary language field 724, and an image(s) field 726. Although not specifically illustrated in user table 700, various additional fields may be included, such as fields containing unique identifiers of friends, user achievements, value earned, statistics (e.g., game statistics), character unique identifiers, game login information, preferences, ratings, time spent playing games, game software owned/installed, and any other suitable fields.

As depicted in FIG. 7, user table 700 is broken into three sections. However, this is only due to space limitations on the page, and in fact user table 700 is intended to depict (aside from the field names) three continuous rows of data elements. In other words, data elements 703 and 713 are in the same row. Of course, FIG. 7 is merely an illustrative depiction, and it is contemplated that a real world implementation of one or more embodiments described herein may have many more than three rows of data (e.g. thousands or millions of rows). Although not specifically referred to in all cases, other tables described herein may similarly be broken up for reasons of space limitations on the printed page, when in actuality it is contemplated that such tables would contain continuous rows of data, in various embodiments. User ID field 702 may store an identifier (e.g., a unique identifier) for a user. Password field 708 may store a password for use by a user. The password may allow the user to confirm his identity, log into a game, log into an app, log into a website, access stored money or other value, access sensitive information, access a set of contacts, or perform any other function in accordance with various embodiments.

Nicknames field 712 may store a user nickname, alias, screen name, character name, or the like. The nickname may be a name by which a user will be known to others in one or more contexts, such as in a game or in a meeting. In various embodiments, a user may have more than one nickname (e.g., one nickname in a first context and another nickname in a second context). Financial account information field 716 may store information about a financial account associated with the user, such as a credit or debit card, bank account, stored value account, PayPal® account, Venmo® account, rewards account, coupons/discounts, crypto currency account, bitcoin account, or any other account. With this information stored, a user may be given access to peruse his account balances or transaction history, for example. A user may be rewarded through additions to his account, and charged through deductions to his account. In various embodiments, a user may utilize his account to pay another user or receive payment from another user. Various embodiments contemplate other uses for financial account information. User table 700 depicts several fields related to demographic information (e.g., marital status field 720, gender field 722, and primary language field 724). In various embodiments, other items of demographic information may be stored, such as number of children, income, country of origin, etc. In various embodiments, fewer items of demographic information may be stored. Images field 726 may store one or more images associated with a user. An image may include an actual photograph of a user (e.g., through a webcam). The image may be used to help other users recognize or identify with the user. In various embodiments, image field 726 may store an item favored by the user, such as the users pet or favorite vacation spot. In various embodiments, image field 726 may store an image of a character or avatar (e.g., an image by which the user wishes to be identified in a game or other online environment).

Referring to FIG. 8, a diagram of an example networks table 800 according to some embodiments is shown. In various embodiments, a local network may include one or more devices that are in communication with one another either directly or indirectly. Communication may occur using various technologies such as ethernet Wi-Fi®, Bluetooth® or any other technology. In various embodiments, devices on a local network may have a local or internal address (e.g., IP address) that is visible only to other devices on the local network. In various embodiments, the network may have one or more external-facing addresses (e.g., IP addresses), through which communications may be transmitted to or received from external devices or Networks. Networks table 800 may store characteristics of a user's local network, such as their connection speed, bandwidth, encryption strength, reliability, etc. With knowledge of a user's Network characteristics, the central controller may determine the content that is transmitted to or requested from a user. For example if the user has a slow network connection, then the central controller may transmit to the user lower bandwidth videos or live game feeds. The central controller may also determine the frequency at which to poll data from a user device or a peripheral device. For example, polling may occur less frequently if the user has a slower network connection. In another example, the central controller may determine whether or not to request sensitive information from the user (such as financial account information) based on the security of the user's network. As will be appreciated, Various other embodiments may consider information about a user's Network and may utilize such information in making one or more decisions.

In various embodiments, network table 800 may store characteristics of any other network. Network ID field 802 may include an identifier (e.g., unique identifier) for a user's network. Network name field 804 may store a name, such as a human readable name, nickname, colloquial name, or the like for a users network. Network IP address field 806 may store an IP address for the network, such as an externally facing IP address. User ID field 808, may store an indication of a user who owns this network, if applicable. In various embodiments, the network may be owned by some other entity such as a company, office, government agency etc. Specified connection speed field 810 may store a specified, advertised, and/or promised connection speed for a network. The connection speed that is realized in practice may differ from the specified connection speed. Actual upload-speed field 812 may store an indication of an upload speed that is or has been realized in practice. For example, the upload speed may store an indication of the upload speed that has been realized in the past hour, in the past 24 hours, or during any other historical time frame. The upload speed may measure the rate at which a network is able to transmit data.

Actual download-speed field 814 may store an indication of a download speed that is or has been realized in practice (such as during some historical measurement period). The download speed may measure the rate at which a network is able to receive data. The download speed may be important, for example, in determining what types of videos may be streamed to a user network and/or user device. Encryption type field 816 may store an indication of the security that is present on the network. In some embodiments, field 816 stores the type of encryption used by the network. For example, this type of encryption may be used on data that is communicated within the network. In some embodiments, field 816 may store an indication of the security measures that a user must undergo in order to access data that has been transmitted through the network. For example, field 816 may indicate that a user must provide a password or biometric identifiers in order to access data that has been transmitted over the network. Uptime percentage field 818 may store an indication of the amount or the percentage of time when a network is available and/or functioning as intended. For example, if a network is unable to receive data for a one-hour period (perhaps due to a thunderstorm), then the one-hour period may count against the network uptime percentage. In various embodiments, an uptime percentage may be used to determine activities in which a user may engage. For example, a user may be allowed to participate in a multi-person video conference or video game requiring extensive team communication, only if the user's network uptime exceeds a certain minimum threshold.

Referring to FIG. 9, a diagram of an example user device table 900 according to some embodiments is shown. User device table 900 may store one or more specifications for user devices. The specifications may be used for making decisions or selections, in various embodiments. For example, a user may be invited to play in a graphically intensive video game or participate in a collaborative conference call only if the user device can handle the graphics requirements (such as by possessing a graphics card). In another example, a user interface for configuring a peripheral device may be displayed with a layout that depends on the screen size of the user device. As will be appreciated, many other characteristics of a user device may be utilized in making decisions and or carrying out steps according to various embodiments. User device ID field 902 may include an identifier (e.g., a unique identifier) for each user device. Form factor field 904 may include an indication of the form factor for the user device. Example form factors may include desktop PC, laptop, tablet, notebook, game console, or any other form factor.

Model field 906 may indicate the model of the user device. Processor field 908 may indicate the processor, CPU, Neural Chip, controller, logic, or the like within the device. In various embodiments, more than one processor may be indicated. Processor speed field 910 may indicate the speed of the processor. Number of cores field 912 may indicate the number of physical or virtual cores in one or more processors of the user device. In various embodiments, the number of cores may include the number of processors, the number of cores per processor, the number of cores amongst multiple processors, or any other suitable characterization. Graphics card field 914 may indicate the graphics card, graphics processor, or other graphics capability of the user device. RAM field 916 may indicate the amount of random access memory possessed by the user device. Storage field 918 may indicate the amount of storage possessed by that user device. Year of manufacture field 920 may indicate the year when the user device was manufactured. Purchase year field 922 may indicate the year in which the user device was purchased by the user.

Operating System field 924 may indicate the operating system that user device is running. MAC Address field 926 may indicate the media access control address (MAC address) of the user device. Physical location field 928 may indicate the physical location of the user device. This may be the same as the owner's residence address, or it may differ (e.g., if the owner has carried the user device elsewhere or is using it at the office, etc.). Timezone field 930 may indicate the time zone in which the user device is located, and or the time zone to which the user device is set. In one example, the central controller may schedule the user device to participate in a video conference call with a particular shared start time for all participants. In another example, the central controller may schedule the user device to participate in a multiplayer game, and wish to alert the user device as to the game's start time using the user device's time zone. Owner ID field 932 may indicate the owner of the user device. The owner may be specified for example in terms of a user ID, which may be cross-referenced to the user table 700 if desired. Network ID(s) field 934 may indicate a network, such as a local network, on which the user device resides. The network may be indicated in terms of a network ID, which may be cross-referenced to the network table 800 if desired.

IP address field 936 may indicate the IP address (or any other suitable address) of the user device. In some embodiments, such as if the user device is on a local network, then the user device's IP address may not be listed. In some embodiments, IP address field 936 may store an internal IP address. In some embodiments, IP address field 936 may store a network IP address, such as the public-facing IP address of the network on which the user device resides. As well be appreciated, user device table 900 may store various other features and characteristics of a user device.

Referring to FIG. 10, a diagram of an example peripheral device table 1000 according to some embodiments is shown. Peripheral device table 1000 may store specifications for one or more peripheral devices. Peripheral device ID field 1002 may store an identifier (e.g., a unique identifier) for each peripheral device. Type field 1004 may store an indication of the type of peripheral device, e.g., mouse, keyboard, headset, exercise bike, camera, presentation remote, projector, chair controller, light controller, coffee maker, etc. Model field 1006 may store an indication of the model of the peripheral device. Purchase year field 1008 may store the year in which the peripheral device was purchased.

IP Address field 1010 may store the IP address, or any other suitable address, of the peripheral device. In some embodiments, such as if the peripheral device is on a local network, then the peripheral device's IP address may not be listed. In some embodiments, IP address field 1010 may store an internal IP address. In some embodiments, IP address field 1010 may store a network IP address, such as the public-facing IP address of the network on which the peripheral device resides. In some embodiments, IP address field 1010 may store the IP address of a user device to which the associated peripheral device is connected.

Physical location field 1012 may store an indication of the physical location of the peripheral device. Owner ID field 1014 may store an indication of the owner of the peripheral device. Linked user device ID(s) field 1016 may store an indication of one or more user devices to which the peripheral device is linked. For example, if a peripheral device is a mouse that is connected to a desktop PC, then field 1016 may store an identifier for the desktop PC. Communication modalities available field 1018 may indicate one or more modalities through which the peripheral device is able to communicate. For example, if a peripheral device possesses a display screen, then video may be listed as a modality. As another example, if a peripheral device has a speaker, then audio may be listed as a modality. In some embodiments, a modality may be listed both for input and for output. For example, a peripheral device with a speaker may have 'audio' listed as an output modality, and a peripheral with a microphone may have 'audio' listed as an input modality.

In various embodiments, a peripheral device might have the capability to output images, video, characters (e.g., on a simple LED screen), lights (e.g., activating or deactivating one or more LED lights or optical fibers on the peripheral device), laser displays, audio, haptic outputs (e.g., vibrations), altered temperature (e.g. a peripheral device could activate a heating element where the user's hand is located), electrical pulses, smells, scents, or any other sensory output or format. In various embodiments, any one of these or others may be listed as modalities if applicable to the peripheral device. In various embodiments, a peripheral device may have the capability to input images (e.g., with a camera), audio (e.g., with a microphone), touches (e.g., with a touchscreen or touchpad), clicks, key presses, motion (e.g., with a mouse or joystick), temperature, electrical resistance readings, positional readings (e.g., using a positioning system, e.g., using a global positioning system, e.g., by integrating motion data), or any other sensory or any other sensor or any other information. Such input modalities may be listed if applicable to the peripheral device.

In some embodiments, modalities may be specified in greater detail. For example, for a given peripheral device, not only is the video modality specified, but the resolution of the video that can be displayed is specified. For example, a keyboard with a display screen may specify a video modality with up to 400 by 400 pixel resolution. Other details may include number of colors available, maximum and minimum audio frequencies that can be output, frame refresh rate that can be handled, or any other details. Network ID(s) field 1020 may store an indication of a network (e.g., a local network) on which a peripheral device resides. If the peripheral device does not reside on a network, or is not known, then a network may not be indicated. As will be appreciated, peripheral device table 1000 may store one or more other features or characteristics of a peripheral device, in various embodiments.

Referring to FIG. 11, a diagram of an example peripheral configuration table 1100 according to some embodiments is shown. Peripheral configuration table 1100 may store configuration variables like mouse speed, color, audio level, pressure required to activate a button, etc. A peripheral device may have one or more input and/or sensor components. The peripheral device may, in turn, process any received inputs before interpreting such inputs or converting such inputs into an output or result. For example, a mouse may detect a raw motion (i.e., a change in position of the mouse itself), but may then multiply the detected motion by some constant factor in order to determine a corresponding motion of the cursor. As another example, a mouse may receive input in the form of pressure or depressing of a button. The mouse might, in turn, pass such pressure information through a step function to determine whether or not to register the pressure as a click or not. The form of the step function may determine the minimum pressure required to register as a click. Table 1100 may store one or more parameters used in the process of converting a raw input into an output or a result. In various embodiments, parameters can be altered. Thus, for example, the sensitivity with which a mouse registers a click may be altered, the ratio of cursor motion to mouse motion may be altered, the ratio of page motion to scroll wheel motion may be altered, and so on.

Table 1100 may also store one or more parameters controlling how a peripheral device outputs information. A parameter might include the color of an LED light, the brightness of an LED light, the volume at which audio is output, the temperature to which a heating element is activated, the brightness of a display screen, the color balance of a display screen, or any other parameter of an output. Table 1100 may also store one or more parameters controlling a physical aspect or configuration of a peripheral device. A parameter might include the default height of a key on a keyboard, the angle at which a keyboard is tilted, the direction in which a camera is facing, or any other aspect of a peripheral device. Table 1100 may also store one or more parameters controlling the overall functioning of a peripheral device. In some embodiments, parameters may control a delay with which a peripheral device transmits information, a bandwidth available to the peripheral, a power available to the peripheral, or any other aspect of a peripheral device's function or operation.

In various embodiments, table 1100 may also store constraints on how parameters may be altered. Constraints may describe, for example, who may alter a parameter, under what circumstances the parameter may be altered, the length of time for which an alteration may be in effect, or any other constraint. Configuration ID field 1102 may store an identifier (e.g., a unique identifier), of a given configuration for a peripheral device. Peripheral device ID field 1104 may store an indication of the peripheral device (e.g., a peripheral device ID) to which the configuration applies. Variable field 1106 may include an indication of which particular parameter, variable, or aspect of a peripheral device is being configured. Example variables include mouse speed, mouse color, key height, etc. Default setting field 1108 may include a default setting for the variable. For example, by default a mouse speed may be set to "fast". In some embodiments, a default setting may take effect following a temporary length of time in which a parameter has been altered.

Outsider third-party control field 1110 may indicate whether or not the parameter can be modified by an outsider (e.g., by another user; e.g., by an opponent). For example, in some embodiments, a user playing a multiplayer video game may have their peripheral device's performance degraded by an opposing player as part of the ordinary course of the game (e.g., if the opposing player has landed a strike on the player). In some embodiments, table 1100 may specify the identities of one or more outside third-parties that are permitted to alter a parameter of a peripheral device. In some embodiments, an outsider is permitted to alter a parameter of a peripheral device only to within a certain range or subset of values. For example, an outsider is permitted to degrade the sensitivity of a user's mouse, however the sensitivity can only be degraded to as low as 50% of maximum sensitivity.

Current setting field 1112 may store the current setting of a parameter for a peripheral device. In other words, if the user were to use the peripheral device at that moment, this would be the setting in effect. Setting expiration time field 1114 may store the time at which a current setting of the parameter will expire. Following expiration, the value of the parameter may revert to its default value, in some embodiments. For example, if the performance of a user's peripheral device has been degraded, the lower performance may remain in effect only for 30 seconds, after which the normal performance of the peripheral device may be restored. As will be appreciated, an expiration time can be expressed in various formats, such as an absolute time, as an amount of time from the present, or in any other suitable format. Expiration time can also be expressed in terms of a number of actions completed by the user. For example, the current setting may expire once a user has clicked the mouse button 300 times.

Referring to FIG. 12, a diagram of an example peripheral device connections table 1200 according to some embodiments is shown. In various embodiments, table 1200 stores an indication of which peripheral devices have been given permission to communicate directly with one another. Peripheral devices may communicate with one another under various circumstances. In some embodiments, two users may pass messages to one another via their peripheral devices. A message sent by one user may be displayed on the peripheral device of the other user. In some embodiments, user inputs to one peripheral device may be transferred to another peripheral device in communication with the first. In this way, for example, a first user may control the peripheral device of a second user by manipulating his own peripheral device (i.e., the peripheral device of the first user). For example, the first user may guide a second users game character through a difficult phase of a video game. As will be appreciated, there are various other situations in which one peripheral device may communicate with another peripheral device.

In various embodiments, peripheral devices may communicate directly with one another, such as with a direct wireless signal sent from one to the other. In various embodiments, one peripheral device communicates with another peripheral device via one or more intermediary devices. Such intermediary devices may include, for example, a user device, a router (e.g., on a local network), the central controller, or any other intermediary device. In other embodiments, one peripheral device may communicate with two or more other peripheral devices at the same time.

As shown, table 1200 indicates a connection between a first peripheral device and a second peripheral device in each row. However, as will be appreciated, a table may store information about connections in various other ways. For example, in some embodiments, a table may store information about a three-way connection, a four-way connection, etc. Connection ID field 1202 may store an identifier (e.g., a unique identifier) for each connection between a first peripheral device and a second peripheral device. Peripheral device 1 ID field 1204 may store an indication of the first peripheral device that is part of the pair of connected devices. Peripheral device 2 ID field 1206 may store an indication of the second peripheral device that is part of the pair of connected devices. Time field 1208 may store the time when the connection was made and/or terminated. Action field 1210 may store the action that was taken. This may include the relationship that was created between the two peripheral devices. Example actions may include initiating a connection, terminating a connection, initiating a limited connection, or any other suitable action.

Maximum daily messages field 1212 may store one or more limits or constraints on the communication that may occur between two peripheral devices. For example, there may be a limit of one thousand messages that may be exchanged between peripheral devices in a given day. As another example, there may be constraints on the number of words that can be passed back and forth between peripheral devices in a given day. Placing constraints on communications may serve various purposes. For example, the owner of a peripheral device may wish to avoid the possibility of being spammed by too many communications from another peripheral device. As another example, the central controller may wish to limit the communications traffic that it must handle.

Referring to FIG. 13, a diagram of an example peripheral device groups table 1300 according to some embodiments is shown. Peripheral device groups may include peripherals that have been grouped together for some reason. For example, any peripheral device in a group is permitted to message any other device in the group, all peripheral devices in a group are on the same video game team, all peripheral devices are on the same network, any peripheral device is allowed to take control of any other, or any peripheral device in the group is allowed to interact with a particular app on a computer. Peripheral device group ID field 1302 may include an identifier (e.g., a unique identifier) for a group of peripheral devices. Group name field 1304 may include a name for the group. Group type field 1306 may include a type for the group. In some embodiments, the group type may provide an indication of the relationship between the peripheral devices in the group. For example, peripheral devices in a group may all belong to respective members of a team of users that participate in a video game together. This group type may be called a game team. In some embodiments, a group of peripheral devices may belong to respective members who have a particular job function in a company, such as people who work in an accounting department of the company. This group type may be called a functional group. Another group type may be for peripheral devices that are proximate to one another. For example, such peripheral devices may all be in the same home, or office, or city. Other types of groups may include groups of peripheral devices with the same owner, groups of peripheral devices belonging to the same company, groups of peripheral devices that are all being used to participate in the same meeting, or any other type of group.

Settings field 1308 may include one or more settings or guidelines or rules by which peripheral devices within the group may interact with one another and/or with an external device or entity. In various embodiments, a setting may govern communication between the devices. For example, one setting may permit device-to-device messaging amongst any peripheral devices within the group. One setting may permit any peripheral device in a group to control any other peripheral device in the group. One setting may permit all peripheral devices in a group to interact with a particular online video game. As will be appreciated, these are but some examples of settings and many other settings are possible and contemplated according to various embodiments. Formation time field 1310 may store an indication of when the group was formed. Group leader device field 1312 may store an indication of which peripheral device is the leader of the group. In various embodiments, the peripheral device that is the leader of a group may have certain privileges and/or certain responsibilities. For example, in a meeting group, the group leader device may be the only device that is permitted to start the meeting or to modify a particular document being discussed in the meeting.

Member peripheral devices field 1314 may store an indication of the peripheral devices that are in the group. Referring to FIG. 14, a diagram of an example user connections table 1400 according to some embodiments is shown. User connections table 1400 may store connections between users. Connections may include "co-worker" connections as during a video conference call, "friend" connections as in a social network, "teammate" connections, such as in a game, etc. In various embodiments, table 1400 may include connections that have been inferred or deduced and were not explicitly requested by the users. For example, the central controller may deduce that two users are members of the same company, because they are each members of the same company as is a third user. Connection ID field 1402 may include an identifier (e.g., a unique identifier) that identifies the connection between two users. User 1 ID field 1404 may identify a first user that is part of a connection. User 2 ID field 1406 may identify a second user that is part of a connection.

Time field 1408 may indicate a time when a connection was made, terminated, or otherwise modified. Action field 1410 may indicate an action or status change that has taken effect with respect to this connection. For example, the action field may be 'initiate connection', 'terminate connection', 'initiate limited connection', or any other modification to a connection. Relationship field 1412 may indicate a type of relationship or a nature of the connection. For example, two users may be related as friends, teammates, family members, co-workers, neighbors, or may have any other type of relationship or connection. Maximum daily messages field 1414 may indicate one or more constraints on the amount of communication between two users. For example, a user may be restricted to sending no more than one hundred messages to a connected user in a given day. The restrictions may be designed to avoid excessive or unwanted communications or to avoid overloading the central controller, for example. Various embodiments may include many other types of restrictions or constraints on the connection or relationship between two users.

Referring to FIG. 15, a diagram of an example user groups table 1500 according to some embodiments is shown. Table 1500 may store an indication of users that belong to the same group. User group ID field 1502 may include an identifier (e.g., a unique identifier) of a user group. Group name field 1504 may include a name for the group. Group type field 1506 may include an indication of the type of group. The type of group may provide some indication of the relationship between users in the group, of the function of the group, of the purpose of the group, or of any other aspect of the group. Examples of group types may include 'safety experts', Department, 'project team x', 'meeting group', 'call group', 'functional area', or any other group type. In some embodiments, a group type may refer to a group of people in the same functional area at a company, such as a group of lawyers, a group of developers, a group of architects or a group of any other people at a company. Formation Time field 1508 may indicate the time/date at which a group was formed. Group leader field 1510 may indicate the user who is the group leader. In some cases, there may not be a group leader. Member users field 1512 may store indications of the users who are members of the group.

Referring to FIG. 16, a diagram of an example 'user roles within groups' table 1600 according to some embodiments is shown. Table 1600 may store an indication of which users have been assigned to which roles. In some embodiments, there are standard predefined roles for a group. In some embodiments, a group may have unique roles. Role assignment ID field 1602 may include an identifier (e.g., a unique identifier) for a particular assignment of a user to a role. User group ID field 1604 may store an indication of the group in which this particular role has been assigned. User ID field 1606 may store an indication of the user to which the role has been assigned. Role field 1608 may store an indication of the particular role that has been assigned, such as 'Project Manager', 'Minutes Keeper', 'Facilitator', 'Coach', 'Navigator', 'Mentor', 'Leader', 'Teacher', etc.

Referring to FIG. 17, a diagram of an example user achievements table 1700 according to some embodiments is shown. User achievements table 1700 may store achievements, accolades, commendations, accomplishments, records set, positive reviews, or any other noteworthy deeds of a user. Achievements may be from a professional setting, from a game setting, from an educational setting, or from any other setting. Achievement ID field 1702 may store an identifier (e.g., a unique identifier) of a particular achievement achieved by a user. User ID field 1704 may store an indication of the user (or multiple users) that has made the achievement. Time/date field 1706 may store the date and time when the user has achieved the achievement. Achievement type field 1708 may indicate the type of achievement, the context in which the achievement was made, the difficulty of the achievement, the level of the achievement, or any other aspect of the achievement. Examples of achievement types may include 'professional', 'gaming', 'educational', or any other achievement type. Achievement field 1710 may store an indication of the actual achievement. Example achievements may include: the user got through all three out of three meeting agenda items; the user reached level 10 in Star Attack Blasters; the user learned pivot tables in Excel; or any other achievement.

Reward field 1712 may indicate a reward, acknowledgement, or other recognition that has or will be provided to the user for the achievement. Example rewards may include: the users office mouse glows purple for the whole day of Jul. 22, 2020; a congratulatory message is sent to all users in the same game group; the user receives three free music downloads; the user receives a financial payment (such as money, digital currency, game currency, game items, etc.); the user receives a discount coupon or promotional pricing, the users name is promoted within a game environment; the users video conference photo is adorned with a digital crown, or any other reward. Provided field 1714 may indicate whether or not the reward has been provided yet. In some embodiments, table 1700 may also store an indication of a time when a reward has been or will be provided.

Referring to FIG. 18, a diagram of an example stored value accounts table 1800 according to some embodiments is shown. Stored value accounts table 1800 may store records of money, currency, tokens, or other value that a user has on deposit, has won, is owed, can receive on demand, or is otherwise associated with a user. A users stored-value account may store government currency, crypto-currency, game currency, game objects, etc. A user may utilize a stored-value account in order to make in-game purchases, in order to pay another user for products or services, in order to purchase a product or service, or for any other purpose. Stored value account ID field 1802 may store an identifier (e.g., a unique identifier) for a user's stored-value account. Owner(s) field 1804 may store an indication of the owner of a stored-value account. Password field 1806 may store an indication of a password required in order for a user to gain access to a stored-value account (e.g., to her account). For example, the password may be required from a user in order for the user to withdraw funds from a stored-value account. In other embodiments, password field 1806 includes biometric values like a digital fingerprint or voice recording that are used to access stored value. In various embodiments, a table such as table 1800 may store a username as well. The username may be used to identify the user when the user is accessing the stored-value account.

Currency type field 1808 may store an indication of the type of currency in the stored-value account. The currency may include such traditional currencies as dollars or British pounds. The currency may also include stock certificates, bonds, cryptocurrency, game currency, game tokens, coupons, discounts, employee benefits (e.g. one or more extra vacation days), game skins, game objects (e.g. a +5 sword, a treasure map), cheat codes, merchant rewards currency, or any other type of currency or stored value. Balance field 1810 may store a balance of funds that the user has in her stored-value account. In some embodiments, a negative balance may indicate that a user has overdrawn an account and/or owes funds to the account. Hold amount field 1812 may indicate an amount of a hold that has been placed on funds in the user account. The hold may restrict the user from withdrawing funds beyond a certain amount, and/or may require the user to leave at least a certain amount in the account. The hold may ensure, for example, that that the user is able to meet future obligations, such as financial obligations.

Referring to FIG. 19, a diagram of an example asset library table 1900 according to some embodiments is shown. Asset library table 1900 may store records of digital assets, such as music, movies, TV shows, videos, games, books, e-books, textbooks, presentations, spreadsheets, newspapers, blogs, graphic novels, comic books, lectures, classes, interactive courses, exercises, cooking recipes, podcasts, software, avatars, etc. These assets may be available for purchase, license, giving out as rewards, etc. For example, a user may be able to purchase a music file from the central controller 110. As another example, a user who has achieved a certain level in a video game may have the opportunity to download a free electronic book. In various embodiments, asset library table 1900 may store analog assets, indications of physical assets (e.g., a catalog of printed books or magazines), or any other asset, or an indication of any other asset.

Asset ID field 1902 may store an identifier (e.g., a unique identifier) for a digital asset. Type field 1904 may store an indication of the type of asset, such as 'movie', 'music', 'video game', 'podcast', etc. Title field 1906 may store a title associated with the asset. For example, this might be the title of a movie, the title of a song, the title of a class, etc. Director field 1908 may store an indication of a director of a movie or other asset. In various embodiments, table 1900 may store an indication of any contributor to the making of a digital asset. For example, table 1900 may store an indication of a songwriter, producer, choreographer, creator, developer, author, streamer, editor, lecturer, composer, cinematographer, dancer, actor, singer, costume designer, or of any other contributor. Artist field 1910 may store an indication of the artist associated with an asset. The artist may be, for example, the singer of a song. The artist could also be the name of a production company that created the asset. Duration field 1912 may store the duration of a digital asset. For example, the duration may refer to the length of a movie, the length of a song, the number of words in a book, the number of episodes in a podcast, or to any other suitable measure of duration. Size field 1914 may store an indication of the size of the digital asset. The size may be measured in megabytes, gigabytes, or in any other suitable format. Synopsis field 1916 may store a synopsis, summary, overview, teaser, or any other descriptor of the digital asset. Reviews field 1918 may store an indication of one or more reviews that are associated with the digital asset. The reviews may come from professional critics, previous users, or from any other source. Reviews may take various forms, including a number of stars, number of thumbs up, an adjective, a text critique, an emoji, or any other form.

Referring to FIG. 20, a diagram of an example 'user rights/licenses to assets' table 2000 according to some embodiments is shown. Table 2000 may store an indication of music, videos, games, books, software, etc. that a user has acquired access to, such as through purchasing or winning a prize. Table 2000 may also store an indication of the nature of the rights or the license that a user has obtained to the acquired asset. User rights/license ID field 2002 may store an identifier (e.g., a unique identifier) for a particular instance of rights being assigned. The instance may include, for example, the assignment of a particular asset to a particular user with a particular set of rights in the asset. Asset ID field 2004 may store an indication of the asset to which rights, license and/or title have been assigned. User ID(s) field 2006 may store an indication of the user or users that has (have) acquired rights to a given asset. Rights field 2008 may store an indication of the nature of rights that have been conferred to the user in the asset. For example, the user may have acquired unlimited rights to view a movie, but not to show the movie in public. A user may have acquired rights to listen to a song up to ten times. A user may have acquired rights to download an asset on up to five user devices. A user may have acquired rights to view an image on a particular peripheral device (e.g. she can listen to a song only via a headset that she has identified). A user may have acquired rights to play a video game for up to seventy-two hours. A user may have acquired rights to view a television series through the end of a particular season. A user may have acquired rights to download a lecture up to three times. A user may have acquired rights to use a software application on up to three devices. A user may have a right to use a movie clip in a presentation deck. As will be appreciated, the aforementioned are but some examples according to some embodiments, and various embodiments contemplate that a user may receive other types of rights or licenses to an asset.

Referring to FIG. 21, a diagram of an example user device state log table 2100 according to some embodiments is shown. User device state log table 2100 may store a log of what programs or apps are/were in use at any given time. Table 2100 may include what program or app was at the forefront, what web pages were open, which app was the last to receive input (e.g., user input), which app occupies the most screen real estate, which app is visible on the larger of two screens, which app is using the most processor cycles, etc. Data stored in table 2100 may, for example, help to ascertain productivity of a user. Data stored in table 2100 may help to link keystrokes (or mouse movements, or other peripheral device activity) to a particular app the user was using. For instance, data stored in table 2100 may allow a determination that a particular set of keystrokes was intended to control the Excel app. In various embodiments, table 2100 may provide snapshots over time of the prominence of different programs, apps, or other processes. Data stored in table 2100 may also be used to detect cheating in a game or educational environment. In other embodiments, it provides an indication of the level of engagement of a person participating in a meeting or video conferencing session.

In various embodiments, table 2100 does not store a comprehensive state. Rather, for example, table 2100 may indicate the state of one or more apps, programs, or processes on a user device, such as at a given point in time. In various embodiments, table 2100 may store a substantially complete indication of a state of a user device, such as at a given point in time. In various embodiments, individual rows or records in table 2100 may store a partial state of a user device (e.g., each row may store information about a single app on the user device, such as the prominence of the app). In various embodiments, a more complete or a substantially complete indication of a state of a user device may be ascertained by combining information from multiple rows of table 2100. User device state log ID field 2102 may store an identifier (e.g., a unique identifier) of a state or partial state of a user device. User device ID field 2104 may store an indication of a user device for which the state or partial state is recorded. Time field 2106 may store an indication of a time at which the user device was in a particular state or partial state. Program/app field 2108 may store an indication of a program, app, or other process, such as a program that was running at the time indicated in field 2106. Program/app field 2108 could also store an indication of the operating system version of the user device. Sub-app field 2110 may store an indication of a subordinate program, app, or process, such as a subordinate program that was running at the time indicated in field 2106. The subordinate program, app, or process may be subordinate to the program, app, or process which is stored in field 2108. For example, field 2108 may refer to a browser (e.g., to the Chrome browser), while field 2110 may refer to a particular web page that is being visited by the browser (e.g., to the Google®.com page). Prominence field 2112 may indicate the prominence of the program or app of field 2108 and/or the prominence of the subordinate program or app of field 2110. The prominence may refer to the visibility, or other state of usage for the program, app, etc. Example prominence values may include 'forefront', 'background', 'minimized', 'sleeping', 'first tab', '50% of processor cycles', 'last used', 'full screen', or any other indication of a state of usage, etc.

Referring to FIG. 22, a diagram of an example 'peripheral activity log' table 2200 according to some embodiments is shown. Peripheral activity log table 2200 may keep track of activities of a peripheral device. Activities may include mouse movement and clicks, keystrokes, which lights on a peripheral device lit up, what direction a joystick was moved in, what image was displayed on a mouse, what direction a camera was facing, how much a headset was shaken, what direction a presentation remote is pointed, how fast an exercise bike wheel is spinning, or any other activity. Peripheral activity ID field 2202 may store an identifier (e.g., a unique identifier) of an activity in which a peripheral device was engaged. Peripheral ID field 2204 may store an indication of the peripheral device that was involved in the activity. Start time field 2206 may store the time at which the activity started. End time field 2208 may store the time at which the activity ended. For example, if an activity is a mouse motion, the activity start time may be recorded as the time when the mouse first started moving in a given direction, and the end time may be recorded as the time when the mouse either stopped moving or changed directions.

Component field 2210 may store the particular component or part of a peripheral device that was involved in an activity. The component field 2210 may store an indication of a button on a mouse, a key on a keyboard, a microphone on a headset, a scroll wheel on a mouse, or any other relevant component of a peripheral device. In some embodiments, the component may be the entire peripheral device, such as when an entire mouse is moved. Action field 2212 may store the action that was performed. Actions may include pressing, tapping, moving, shaking, squeezing, throwing, lifting, changing position (e.g., moving 120 mm in an 'x' direction and moving −80 mm in a 'y' direction) or any other action. Recipient program field 2214 may store the application, program, or other computer process towards which an action was directed. For example, if a user was using the program Microsoft® Paint, then a given action may have been directed towards doing something in Microsoft® Paint, such as drawing a line. In some embodiments, an action may be directed towards an operating system, a browser, or to any other process. In various embodiments, peripheral device activities may be recorded at varying levels of granularity. In some embodiments, every keystroke on a keyboard may be recorded as a separate activity. In some embodiments, the typing of an entire sentence at a keyboard may be recorded as a single activity. In some embodiments, a series of related activities is recorded as a single activity. For example, when a headset shakes back and forth, this may be recorded as a single shake of the headset. In some embodiments, each individual motion of the headset within the shake is recorded as a separate activity. As will be appreciated, various embodiments contemplate that peripheral device activities may be tracked or recorded at any suitable level of granularity.

Referring to FIG. 23, a diagram of an example 'peripheral sensing log' table 2300 according to some embodiments is shown. Peripheral sensing log table 2300 may store a log of sensor readings. In various embodiments, a peripheral device may contain one or more sensors. The sensors may, from time to time (e.g., periodically, e.g., when triggered, etc.) capture a sensor reading. In various embodiments, such sensor readings may capture passive or involuntary activities, such as a user's temperature, skin conductivity, glucose levels, brain wave readings, pupil dilation, breathing rate, breath oxygen levels, or heart rate. A sensor may capture ambient conditions, such as a temperature, ambient level of lighting, ambient light polarization, ambient level of noise, air pressure, pollution level, presence of a chemical, presence of a pollutant, presence of an allergen, presence of a microorganism, wind speed, wind direction, humidity, pollen count, or any other ambient condition or conditions. In various embodiments, a sensor may capture a position, location, relative position, direction of gaze, orientation, tilt, or the like. In various embodiments, a sensor may capture any suitable data.

Sensor reading ID field 2302 may store an identifier (e.g., a unique identifier) of a particular sensor reading. Peripheral ID field 2304 may store an indication of the peripheral device at which the sensor reading has been captured. Sensor field 2306 may store an indication of which sensor has captured the reading. For example, sensor field 2306 may explicitly identify a single sensor or type of sensor from among multiple sensors that are present on a peripheral device. The sensor may be identified, for example, as a heart rate sensor. In some embodiments, a sensor may have a given identifier, serial number, component number, or some other means of identification, which may be stored in field 2306. Start time field 2308 may store the time at which a sensor began to take a reading. End time field 2310 may store the time at which a sensor finished taking a reading. As will be appreciated, different sensors may require differing amounts of time in order to capture a reading. For instance, capturing a reading of a heart rate may require the reading to be taken over several seconds in order to allow for multiple heartbeats. Reading field 2312 may store the actual reading that was captured. For example, the field may store a reading of 110 beats per minute for a heart rate. In other embodiments, the reading may be a recording of an EKG signal from the start time to an end time.

Referring to FIG. 24, a diagram of an example peripheral message log table 2400 according to some embodiments is shown. Peripheral message log table 2400 may store messages that were passed from one peripheral to another. Message ID field 2402 may store an identifier (e.g., a unique identifier) for each message that is passed. Time field 2404 may store the time of the message. In various embodiments, the time represents the time when the message was transmitted. In other embodiments, the time represents the time that the message was received by a user. In various embodiments, the time may represent some other relevant time pertaining to the message. Initiating peripheral ID field 2406 may store an indication of the peripheral device that originated or sent the message. Receiving peripheral ID field 2408 may store an indication of the peripheral device(s) that received the message. Message content field 2410 may store the content of the message. In various embodiments, a message may comprise instructions, such as instructions for the receiving peripheral device. An example instruction might be that the receiving peripheral device light up LED light #3 for 3 seconds, play an attached advertising jingle, or disable the left button (e.g., of a mouse). In some embodiments, the message may include human-readable content. The content might be intended for display by the receiving peripheral device. For example, the message might include the text "enemy character is approaching" or "good job", which would then be displayed by the receiving peripheral device. In various embodiments, the message may include further instructions as to how, when, where, or under what circumstances the message should be displayed.

Referring to FIG. 25, a diagram of an example 'generic actions/messages' table 2500 according to some embodiments is shown. Generic actions/messages table 2500 may store a set of generic or common actions or messages that might be initiated by a user. For example, in the context of a multiplayer video game, it may be common for one team member to send to another team member a message such as "nice going", or "cover me". In the context of a business meeting, messages could include expressions such as "good idea" or "excellent facilitation." In the context of an educational setting, messages might include "it's your turn" or "that answer is correct." In situations where certain messages or actions may be commonplace, it may be beneficial that a user have a quick way of sending such messages or taking such actions. In various embodiments, there may be a shortcut for a given action. The shortcut may comprise a predefined series of motions, button presses, key presses, or voice commands, in various embodiments. In some embodiments, having a shortcut to sending a message or taking an action may allow a user to overcome an inherent barrier of a given peripheral device. For example, a mouse may not have keys with letters on them, so sending a custom text message using a mouse might otherwise be cumbersome. Generic action ID field 2502 may store an identifier (e.g., a unique identifier) for a particular action. Action/message field 2504 may store an actual message or action. Example messages might include, "got him" or "you're the best". Example actions might include a command to proceed to the next slide in a PowerPoint® presentation, an instruction to paste a stored format to a highlighted portion of a document, an instruction to order cheese pizza, or any other message action or instruction.

Referring to FIG. 26, a diagram of an example 'mapping of user input to an action/message' table 2600 according to some embodiments is shown. Mapping of user input to an action/message table 2600 may store a mapping or correspondence between a user input and an associated action or message. The user input may be essentially a shortcut for the desired action or message. The user input may provide a quick or accessible means for sending what might otherwise be a more complicated or cumbersome message. The user input may provide a quick or accessible means for taking an action or issuing an instruction that would otherwise be cumbersome or difficult to specify. A user input may be, for example, a particular sequence of mouse clicks or keystrokes, a particular motion of the head, or any other user input. Actions might include giving a thumbs-up to another user, ordering a pizza, or any action specified in table generic actions/messages table 2500. Mapping ID field 2602 may store an identifier (e.g., a unique identifier) for a particular mapping between a user input and an action or message. Peripheral type field 2604 may store an indication of the type of peripheral on which the user input would be valid or relevant. For example, inputting a set of alpha-numeric keys may only be valid on a keyboard. Shaking one's head may only be valid using a headset, for example.

In various embodiments, a peripheral device may be in any of two or more different modes or states. For example, a peripheral device might be in "in use" mode, or it might be in "idle" mode. For example, a peripheral device might be in "game" mode, or it might be in "work" mode. When a peripheral device is in a first mode, it may be operable to initiate one or more actions. However, when a peripheral device is in a second mode, it may not be operable to initiate one or more actions. For instance, when a peripheral device is in "game" mode, the peripheral device may be operable to send a message to a teammate with just a few predetermined keystrokes. However, when the same peripheral device is in "work" mode, the same message might, at best, be meaningless, and at worst interfere with work. Mode of peripheral field 2606 may be a mode or state of a peripheral device that is relevant to a particular action. For example, field 2606 may store a mode in which a peripheral device is operable to take an associated action. In some embodiments, field 2606 may store a mode in which a peripheral device is not operable to take an associated action. In various embodiments, a given input sequence may be valid in more than one mode of a peripheral device, however the input sequence may have different meanings in the different modes. Example modes may include action mode, messaging mode, in-use mode, idle mode, etc.

Input Sequence field 2608 may store the user inputs that will trigger an associated action. User inputs may comprise a set of clicks, button presses, motions, or any other set of inputs. Action field 2610 may store an action that the user wishes to take when he provides the user inputs. The action may include a generic action from table 2500, in which case an identifier for such an action from table 2500 may be stored in field 2610. The action may include any other action, message, instruction or the like. In some embodiments, certain actions may be valid only when both an originating peripheral device and a receiving peripheral device are both in the proper modes. For example, in order for a text message to be sent from one peripheral device to another peripheral device, the initiating peripheral device must be in "text" mode, and the receiving peripheral device must be in "idle" mode. In such embodiments, for example, table 2600 may store modes for two peripheral devices (e.g., for both an initiating and for a receiving peripheral device). In some embodiments, the relevant mode is the mode of the receiving peripheral device. In such embodiments, for example, table 2600 made store modes for the receiving peripheral device.

Referring to FIG. 27, a diagram of an example 'user game profiles' table 2700 according to some embodiments is shown. User game profiles table 2700 may store a user's profile with respect to a particular game, a particular gaming environment, a tournament, a game site, or any other situation. A user's profile may include login information, identifying information, information about preferences for playing the game, information about when a user is available for playing a game, information about users' communications preferences during a game, and/or any other information. User game profile ID field 2702 may store an identifier (e.g., a unique identifier) for a user game profile. Game ID field 2704 may store an indication of the game for which the user profile applies. In various embodiments, the game refers to a generic game such as "Call of Duty" rather than to a specific instance of that game. In other words, for example, a user's profile may govern how the user plays any game of a particular title. User ID field 2706 may store an indication of the user corresponding to the present user profile. Password field 2708 may store an indication of a password to be used by the user. The password may be used when the user logs in to a gaming site to play a game. In some embodiments, the password may be entered by the user when making an in-game purchase. In some embodiments, the password is stored in an encrypted form. As will be appreciated, the user may utilize the password for various other purposes. In some embodiments, table 2700 may store other or alternative identifying information, such as a user image, a user fingerprint, or some other biometric of the user. In some embodiments, a user may login via other means, such as by using credentials from another user account (e.g., a Google® or Facebook account belonging to the same user). Such alternative identifying information may also be encrypted while stored.

Screen name field 2710 may store a screen name, nickname, character name, alias, username, or any other name by which new user may be referenced in a game environment, or in any other environment. Preferred character field 2712 may store an indication of a user's preferred character to use in a game. For example, a game may allow a user to select a particular character to control within the game. Different characters may have different capabilities, different weaknesses, different looks, or other differences. In some embodiments, table 2700 may store a user's preferred role or function within a multiplayer game. For example, users on a team may assume different roles. For example, one user might be a navigator while another user is a gunner. Preferred avatar field 2714 may store an indication of a user's preferred avatar for use in a game, or in any other situation. A user's avatar may represent the way that the user or the user's character appears on screen. An avatar might appear as a human being dressed in a particular way, as a mythical being, as an animal, as a machine, or in any other form. Preferred background music field 2716 may store an indication of a user's preferred background music for use in a game, or in any other environment. Background music may include a melody, a song, a rhythm, a jingle, or any other music. In some embodiments, there may be multiple available music themes, which may be labeled numerically, such as theme 1, theme 2, etc. Field 2716 may then store a theme number as the user's preferred theme. Rating/skill level field 2718 may store an indication of a user's rating, skill level, experience, or any other metric of aptitude within the game. In one example, a user's FIDE chess rating could be stored for use on a chess playing website. Last login field 2720 may store an indication of the time when a user last logged into a game, game environment, game server, or the like. In some embodiments, table 2700 may store a user's login name, which may differ from their screen name. The login name may be used to identify the user when the user first logs in. The screen name may be used within a particular game to identify the user or the users character within that game. As will be appreciated, login names or screen names may be used for various other purposes.

Referring to FIG. 28, a diagram of an example 'game records' table 2800 according to some embodiments is shown. Game records table 2800 may store records of games played, such as records of the participants, scores, results, and so on. Game record ID field 2802 may store an identifier, (e.g., a unique identifier) of a particular instance of a game that has been played. For example, this might be a particular instance of the game 'Frog Hunt III', that was played at 11:05 p.m. on Aug. 4, 2024. Game ID field 2804 may store an indication of the game title or type of game of which the present record is an instance. For example, game ID field 2804 may indicate that the present game was Frog Hunt III. Start time field 2806 may store an indication of the time when the game started. End time field 2808 may store an indication of the time when the game ended. Participant ID(s) field 2810 may store an indication of the participants in a game. Participants may be individual users, teams, or any other type of participant, in some embodiments. Score field 2812 may store an indication of the score achieved in a game. If there are multiple participants that were each scored separately, then a score may be recorded for each of the participants. Winner field 2814 may store an indication of the winner of the game, if applicable. This may be a team, a user, or even a side in a game (e.g., the Werewolves won against the Vampires). Highest level achieved field 2816 may store an indication of the highest level that was achieved in a game. The level might include a particular board, particular screen, particular boss, a particular difficulty level, a particular environment, or any other notion of a level. Location(s) played from field 2818 may include an indication of where a game was played from. This might be a geographical location, an IP address, a building, or any other indication of a location.

Referring to FIG. 29, a diagram of an example 'game activity logs' table 2900 according to some embodiments is shown. In various embodiments, game activity logs table may store activities, such as granular activities or specific activities, that occurred within a game. Such activities may include motions made, routes chosen, doors opened, villains destroyed, treasures captured, weapons used, messages sent, or any other activity that occurred within a game. In some embodiments, activities may include specific inputs made to a game, such as inputs made through a peripheral device. These inputs might include mouse motions, buttons pressed, or any other inputs. Inputs may include passive inputs, such as a heart rate measured for a player during a game. As will be appreciated, many other types of game activities may be recorded and are contemplated according to various embodiments.

Game activity ID field 2902 may include an identifier (e.g., a unique identifier) for a particular activity in a game. Game ID field 2904 may include an indication of a particular game title in which the activity occurred. In some embodiments, field 2904 may include an indication of a particular instance of a game in which an activity occurred. Participant ID field 2906 may include an indication of a participant or player in a game that performed the activity. Start time field 2908 may include an indication of the time when the activity was started or initiated. This time may represent, e.g., a time when a mouse movement was initiated, a time when a character started down a particular road, a time when an attack was ordered, a time when a particular mouse button was pressed, a time when a particular head motion was initiated, etc. End time field 2910 may include an indication of the time when the activity was completed. For example, a mouse movement was completed, an attack was repelled, a bullet hit its mark, etc. Note that, for example, end time 2910 may be mere fractions of a second after start time 2908. This may occur for example when very quick or granular activities are being recorded. However, in some embodiments, an activity may take a longer amount of time.

Game State field 2912 may store an indication of a game state or situation at the time that the activity took place. A game state might include a level within a game, a screen within a game, a location within a virtual world of a game, a health status of a character, an inventory of the possessions of a character, a state of a character (e.g., invisible, e.g., temporarily incapacitated) a location of one or more villains or opponents, a set of playing cards held in a character's hand (e.g., in a poker game), an amount of money or other currency possessed by a player, an amount of money in a pot or kitty (e.g., as in poker), an amount of money remaining with some other game entity (e.g., with the bank in Monopoly), an indication of whose turn it is, a position or location of game pieces or game tokens, an indication of which moves are currently available (e.g., in chess the en passant move is available), an indication of which cards remain in a deck (e.g., in Monopoly® which chance cards are remaining, e.g., in Blackjack, which cards remain in the shoe), or any other aspect of a game state. In some embodiments, a game state may be stored in such detail as to allow the re-creation of the game from that state. Activity field 2914 may include an indication of the activity that was undertaken. Example activities include: shoot; move left; switch to laser weapon; draw 3 cards; e4xd5 (e.g., in chess), etc.

Referring to FIG. 30, a diagram of an example 'active game states' table 3000 according to some embodiments is shown. In various embodiments, active game states table 3000 may store the states of games that are in progress. Storing the states of games that are in progress may allow the central controller 110, a game server, or other entity to conduct a game, to render scenes from a game, to receive inputs from players in the game, to update a game to a succeeding state, to continue a game that has been stopped, to introduce a player back into a game after a connection has been lost, to arbitrate a game, or to perform any other desirable function. In various embodiments, table 3000 may store some or all information that is similar to information which is stored in field 2912. Game state ID field 3002 may store an identifier (e.g., a unique identifier) of a game state. Game ID field 3004 may store an indication of, or an identifier for, a game title that is being played. Game record ID field 3006 may store an indication of a game record (e.g., from game records table 2800) corresponding to a game for which the present state is an active game state, or a game state. For example, the present game State may be the state of a game that has been recorded in table 2800. Time remaining field 3008 may represent a time remaining in a game. For example, in a sports game this may represent the amount of time remaining on a game clock. In games where there are multiple periods (e.g., quarters or halves) this may represent the time remaining in the current period. In various embodiments, a stored game state may include an indication of the period that the game is in.

Level field 3010 may include an indication of the level where participants are at in the game. This may include a screen, a difficulty level, an environment, a villain, a boss, a game move number, a stage, or any other notion of level. In various embodiments, a game state might include separate information about two or more participants in the game. For example, each participant might have his or her own score, his or her own possessions, his or her own health status, etc. In some embodiments, table 3000 may have separate sets of fields for each participant. For example, each participant might have his or her own score field. Score fields 3012*a* and 3012*b* may include scores for a first and a second participant respectively (e.g., for participant 'a' and for participant 't'). Location fields 3014*a* and 3014*b* may include locations for a first and a second participant, respectively. Power field 3016*a* and 3016*b* may include power levels for a first and a second participant, respectively. Ammo field 3018*a* and 3018*b* may include amounts of ammunition possessed by a first and a second participant, respectively. As will be appreciated, a game may have more than two participants, in various embodiments. In such cases, table 3000 may include additional fields for the additional players. For example, table 3000 may include fields 3012*c*, 3014*c*, and so on. The aforementioned represent but some information that may characterize a game state. It will be appreciated that a game state might comprise one or more additional items of information. Further, different games may warrant different descriptions or fields representative of the game state. It is therefore contemplated, according to various and embodiments, that table 3000 may include additional or alternative fields as appropriate to characterizing a game state.

Referring to FIG. 31, a diagram of an example shared projects table 3100 according to some embodiments is shown. Shared projects table 3100 may store information pertinent to joint, team, shared and/or collaborative work products or projects. Projects may include shared documents, collaborative workspaces, etc. Table 3100 may include data about the work product itself (e.g., an in-progress document), identities of contributors or collaborators to a project, a record of project states over time, historical snapshots of the project, goals for the project, checklist for the project, dependencies of different components of the project, or any other aspect of the project. Project ID field 3102 may store an identifier, (e.g., a unique identifier) for a project (e.g., for a shared project). Project type field 3104 may include an indication of the type of project. Example project types may include text document, spreadsheet, presentation deck, whiteboard, architectural design, paintings, sculptures, drawings, virtual visual arrangements of interiors, music, or any other project type. Participants field 3106 may store an indication of participants in the project. Participants may include contributors, collaborators, reviewers, or other stakeholders. Data field 3108 may include data about the work product. For example, if the project is to construct a text document, then field 3108 may include the text that has been generated so far. If the project is to create an advertising flyer, then field 3108 may include the text copy and the images that are to appear on the flyer. As will be appreciated, the data may take many other forms, and the form of the data may depend on the nature of the project.

Referring to FIG. 32, a diagram of an example of a 'shared project contributions' table 3200 according to some embodiments is shown. Shared project contributions table 3200 may record the individual contributions made by participants in shared projects. Contribution ID field 3202 may include an identifier (e.g., a unique identifier) of a contribution made to a project. Project ID field 3204 may include an indication of a project to which the contribution was made. The indication may be, for example, a project identifier that cross references to table 3100. Participant ID field 3206 may include an indication of the participant or participants who made a particular contribution. Time of contribution field 3208 may store an indication of the time at which a contribution was made. Contribution type field 3210 may store an indication of the type of contribution that was made. A contribution may take various forms, in various embodiments. A contribution might add directly to the final work product. For example the contribution may be a paragraph in a text document. The contribution may be an idea or direction. The contribution may be feedback on a suggestion made by someone else. The contribution may be feedback on an existing work product. The contribution may be a datapoint that a contributor has researched which informs the direction of the project. The contribution may take the form of a message that is exchanged in a chat or messaging area. A contribution may be a rating of the quality of the content created to that point. A contribution may be made in any applicable fashion or form. In various embodiments, contribution type field 3210 may store a place or location to which the contribution was made (e.g., "main document", "chat window"). In various embodiments, field 3210 may store the nature of the contribution. The nature of the contribution may be, for example, 'background research', 'work product', 'suggestion', 'vote', 'expert opinion', 'edit', 'correction', 'design', and so on. Contribution content field 3212 may store the content or substance of the contribution. For example, if the contribution was for the user to write part of a document, then field 3212 may store the text of what the user wrote. If the contribution was an image, then field 3212 may store the image or a link to the image. If the contribution was a suggestion, field 3212 may store the text of the suggestion. As will be appreciated, various embodiments contemplate a contribution may be stored in other forms.

Referring to FIG. 33, a diagram of an example of advertisement table 3300 according to some embodiments is shown. Advertisement table 3300 may include information about one or more advertisements, promotions, coupons, or other marketing material, or other material. In various embodiments, an advertisement may be presented to a user. An advertisement may be presented to a user in various modalities, such as in a visual form, in audio form, in tactile form, or in any other applicable form. An advertisement may be presented via a combination of modalities, such as via visual and audio formats. In various embodiments, an advertisement may be presented to a user via one or more peripheral devices. For example, an advertisement may be displayed on a display screen built into a mouse. In another example, the advertisement is a message spelled out by sequentially lighting up individual keys of a user's keyboard. In various embodiments, an advertisement may be presented to a user via one or more user devices. Advertisement table 3300 may store the content of an advertisement, instructions for how to present the advertisement, instructions for what circumstances the advertisement should be presented under, or any other information about the advertisement. Advertisement ID field 3302 may store an identifier (e.g., a unique identifier) for an advertisement. Advertiser field 3304 may store an indication of an advertiser that is promoting the advertisement. For example, the advertiser may be a company with products to sell.

Ad server or agency field 3306 may store an indication of an ad server, an advertising agency, or other intermediary that distributed the ad. Target audience demographics field 3308 may include information about a desired target audience. Such information may include demographic information, e.g., age, race, religion, gender, location, marital status, income, etc. A target audience may also be specified in terms of one or more preferences (e.g., favorite pastimes, e.g., favorite types of vacations, e.g., favorite brand of soap, e.g., political party, etc.). A target audience may also be specified in terms of historical purchases, or other historical behaviors. In some embodiments, a target audience may be specified in terms of video game preferences. Such preferences may be readily available, for example, to a game server. Various environments contemplate that a target audience may be specified in any suitable form, and/or based on any suitable information available. Ad trigger field 3310 may store an indication of what events or circumstances should trigger the presentation of an ad to a user. Events may include an initiation of gameplay by the user, a change in a user's performance while playing a game (e.g., a users rate of play slows down 10%), a certain level being achieved in a game, a certain score being achieved in a game, or any other situation that occurs in a game. Triggers for presenting advertisements may include ambient factors, such as the temperature reaching a certain level, the noise level exceeding a certain threshold, pollution levels reaching a certain level, humidity reaching a certain level, or any other ambient factors. Triggers may include times of day, e.g., the time is 4 PM. Various embodiments contemplate that any suitable trigger for an advertisement may be used.

In various embodiments, limits field 3312 may store limits or constraints on when an ad may or must be presented, or under what circumstances an ad may be presented. For example, a limit may specify that no more than one thousand ads per day are to be presented across all users. As another example, a limit may specify that a maximum of two of the same advertisements may be presented to a given user. As another example, a constraint may specify that an ad should not be presented between the hours of 11 p.m. and 8 a.m. Another constraint may specify that an ad should not be presented when a mouse is in use (e.g., the ad may be intended for presentation on the mouse, and it may be more likely that the ad is seen if the user is not already using the mouse for something else). Various embodiments contemplate that any suitable constraints on the presentation of an advertisement may be specified. Presenting devices field 3314 may indicate which types of devices (e.g., which types of peripheral devices, e.g., which types of user devices), and/or which combination of types of devices, should be used for presenting an advertisement. Example presenting devices may include: a keyboard; a mouse; a PC with mouse; a tablet; a headset; a presentation remote; an article of digital clothing; smart glasses; a smartphone; or any other device; or any other device combination. Modality(ies) field 3316 may indicate the modalities with which an advertisement may or must be presented. Example modalities may include video; tactile; video and LED; image and tactile; heating, or any other modality or combination of modalities. In various embodiments, when an advertisement is presented, it is presented simultaneously using multiple modalities. For example, a video of a roller coaster may be displayed while a mouse simultaneously rumbles. As another example, an image of a relaxing ocean resort may be presented while a speaker simultaneously outputs a cacophony of horns honking (as if to say, "get away from the noise"). Ad content field 3318 may store the actual content of an advertisement. Such content may include video data, audio data, tactile data, instructions for activating lights built into peripheral devices or user devices, instructions for activating heating elements, instructions for releasing fragrances, or any other content or instructions.

Referring to FIG. 34, a diagram of an example of 'advertisement presentation log' table 3400 according to some embodiments is shown. Advertisement presentation log

3400 may store a log of which ads were presented to which users and when, in various embodiments. Advertisement presentation ID field 3402 may store an identifier (e.g., a unique identifier) of an instance when an ad was presented to a user. Advertisement ID field 3404 may store an indication of which advertisement was presented. User ID field 3406 may store an indication of the user to whom the ad was presented. Presentation device field 3408 may store an indication of one or more devices (e.g., user devices, e.g., peripheral devices) through which the ad was presented. For example, field 3408 may store an indication of a mouse on which a video was presented. For example, field 3408 may store an indication of a keyboard and a speaker through which an ad was presented (e.g., using two different modalities simultaneously). Time field 3410 may store an indication of when the ad was presented. User response field 3412 may store an indication of how the user responded to the ad. Example responses might include, the user clicked on the ad, the user opened the ad, the user viewed the ad, the user responded with their email address, the user made a purchase as a result of the ad, the user forwarded the ad, the user requested more information, the user agreed to receive product updates via email, the user's heart rate increased after viewing the ad, the user took a recommendation made in the ad, the user had no response to the ad, or any other response.

Referring to FIG. 35, a diagram of an example of 'AI models' Table 3500 according to some embodiments is shown. As used herein, "AI" stands for artificial intelligence. An AI model may include any machine learning model, any computer model, or any other model that is used to make one or more predictions, classifications, groupings, visualizations, or other interpretations from input data. As used herein, an "AI module" may include a module, program, application, set of computer instructions, computer logic, and/or computer hardware (e.g., CPU's, GPU's, tensor processing units) that instantiates an AI model. For example, the AI module may train an AI model and make predictions using the AI model. AI Models Table 3500 may store the current 'best fit' model for making some prediction, etc. In the case of a linear model, table 3500 may store the 'best fit' values of the slope and intercept. In various embodiments, as new data comes in, the models can be updated in order to fit the new data as well.

For example, central controller 110 may wish to estimate a user's skill level at a video game based on just a few minutes of play (this may allow the central controller, for example, to adjust the difficulty of the game). Initially, the central controller may gather data about users' actions within the first few minutes of the video game, as well as the final score achieved by the users in the game. Based on this set of data, the central controller may train a model that predicts a user's final score in a game based on the user's actions in the first few minutes of the game. The predicted final score may be used as a proxy for the user's skill level. As another example, a central controller may wish to determine a user's receptivity to an advertisement based on the motions of the user's head while the user views the advertisement. Initially, the central controller 110 may gather data from users who watch an advertisement and subsequently either click the advertisement or ignore the advertisement. The central controller may record users' head motions while they watch the advertisement. The central controller may then train a model to predict, based on the head motions, the chance that the user will click the advertisement. This may allow the central controller, for example, to cut short the presentation of an ad if it is clear that the user is not receptive to the ad.

AI Model ID field 3502 may store an identifier (e.g., a unique identifier) for an AI model. Model type field 3504 may store an indication of the type of model. Example model types may include 'linear regression', '2nd degree polynomial regression', 'neural network', deep learning, backpropagation, and so on. Model types may be specified in terms of any desired degree of specificity (e.g., the number of layers in a neural network, the type of neurons, the values of different hyperparameters, etc.). 'X' data source field 3506 may store information about the input data that goes into the model. Field 3506 may indicate the source of the data, the location of the data, or may store the data itself, for example. Example input data may include game scores after the first five minutes of play for game gm14821, or the content of team messages passed for game gm94813. 'Y' data source field 3508 may store information about the data that is intended to be predicted by the model. This may also be data that is used to train the model, to validate the model, or to test the model. Field 3508 may indicate the source of the data, the location of the data, or may store the data itself, for example. Example output data may include final game scores for game gm14821, or final team scores for game gm94813. For example, a team's final score may be predicted based on the content of the messages that are being passed back and forth between team members. This may help to determine whether a team can improve its methods of communication.

Parameter Values field 3510 may store the values of one or more parameters that have been learned by the model, or which have otherwise been set for the model. Examples of parameters may include a slope, an intercept, or coefficients for a best fit polynomial. Accuracy field 3512 may store an indication of the accuracy of the model. The accuracy may be determined based on test data, for example. As will be appreciated, accuracy may be measured in a variety of ways. Accuracy may be measured in terms of a percentage of correct predictions, a root mean squared error, a sensitivity, a selectivity, a true positive rate, a true negative rate, or in any other suitable fashion. Last update field 3514 may store an indication of when the model was last updated. In various embodiments, the model may be retrained or otherwise updated from time to time (e.g., periodically, e.g., every day, etc.). New data that has been gathered may be used to retrain the model or to update the model. This may allow the model to adjust for changing trends or conditions. Update trigger field 3516 may store an indication of what would trigger a retraining or other update of the model. In some embodiments, a retraining is triggered by a date or time. For example, a model is retrained every day at midnight. In some embodiments, the model is retrained when a certain amount of new data has been gathered since the last retraining. For example, a model may be retrained or otherwise updated every time 1000 new data points are gathered. Various other triggers may be used for retraining or updating a model, in various embodiments. In various embodiments, a person may manually trigger the retraining of a model.

Referring to FIG. 36, a diagram of an example authentication table 3600 according to some embodiments is shown. Authentication table 3600 may store user data, such as biometric data, that can be used to authenticate the user the next time it is presented. In various embodiments, table 3600 may store multiple items of user data, such as multiple items of biometric data. Different applications may call for different types or different combinations of user data. For example, a very sensitive application may require a user to authenticate himself using three different points of data, such as fingerprint, voiceprint, and retinal scan. A less sensitive application may require only a single point of data for a user to authenticate himself. Authentication ID field 3602 may store an identifier (e.g., a unique identifier) that identifies the authentication data. User ID field 3604 may store an indication or identifier for a user, i.e., the user to whom the data belongs. Image(s) field 3606 may store an image of the user. These may be images of a user's eye, ear, overall face, veins, etc. Fingerprint images field 3608 may store fingerprint data for the user, such as images of the user's fingerprint. Retinal scans field 3610 may store one or more retinal or iris scans for the user. Voiceprint field 3612 may store voice data, voiceprint data, voice recordings, or any other signatures of a user's voice. In various embodiments, other types of data may be stored for a user. These may include other types of biometric data, such as DNA, facial recognition, keystroke data (e.g., a series of keystrokes and associated timestamps), electrocardiogram readings, brainwave data, location data, walking gait, shape of ear, or any other type of data. In various embodiments, data that is personal to a user and/or likely to be known only by the user may be stored. For example, the name of the user's first pet, or the user's favorite ice cream may be stored.

In various embodiments, when a user is to be authenticated, the user presents information, and the information presented is compared to user information on file in table 3600. If there is a sufficient match, then it may be concluded that the user is in fact who he claims to be. In one embodiment, after a user is authenticated, the central controller 110 looks up the user in employee table 5000 (or in some embodiments user table 700) to verify that the user is clear to work with objects in a particular location. For example, one user might be cleared to use a particular chemical, but is not allowed into a room because a different chemical is present which the user is not cleared to handle. So even though the user is authenticated, they may not have the right credentials as a user for the chemical in that particular location. Examples of things that may require a level of authentication include radioactive elements, hazardous chemicals, dangerous machinery, government contracts, encryption keys, weapons, company sensitive information such as financials or secret projects, personnel information such as salary data, confined space entry, etc.

Referring to FIG. 37, a diagram of an example privileges table 3700 according to some embodiments is shown. Privileges table 3700 may store one or more privileges that are available to a user, together with criteria that must be met for the user to receive such privileges. For example, one privilege may allow a user to read a document, and the user may be required to provide a single datapoint to prove his identity (i.e., to authenticate himself). As another example, a privilege may allow a user to delete a document, and the user may be required to provide three data points to prove his identity. The different number of data points required by different privileges may reflect the potential harm that might come about from misuse of a privilege. For example, deleting a document may cause more harm than can be caused merely by reading the document. Privilege ID field 3702 may store an identifier (e.g., a unique identifier) of a privilege that may be granted to a user. Privilege field 3704 may store an indication of the privilege that is to be granted. 'Points of authentication required' field 3706 may store an indication of the amount of authenticating or identifying information that would be required of a user in order to receive the privilege. In various embodiments, the amount of authenticating information required may be specified in terms of the number of data points required. For example, if two data points are required, then the user must provide two separate items of information, such as a retinal scan and a fingerprint. In some embodiments, some data points may carry more weight than others in terms of authenticating a user. For example, a retinal scan may be worth three points, whereas a fingerprint may be worth only two points. In this case, a user may satisfy an authentication requirement by using any combination of information whose combined point value meets or exceeds a required threshold. As will be appreciated, a user may be required to meet any suitable set of criteria in order to be granted a privilege. In one embodiment, the number of authentication points required may vary by the job title of a user, for example, a senior safety manager may require less authentication than a lower-level user.

Authentication

In various embodiments, various applications can be enhanced with authentication protocols performed by a peripheral, user device 107a, central controller 110, and/or other device. Information and cryptographic protocols can be used in communications with other users and other devices to facilitate the creation of secure communications, transfers of money, authentication of identity, and authentication of credentials. Peripheral devices could be provided to a user who needs access to sensitive areas of a company, or to sensitive information. The peripheral might be issued by the company and come with encryption and decryption keys securely stored in a data storage device of the peripheral. In various embodiments, encryption is an encoding protocol used for authenticating information to and from the peripheral device. Provided the encryption key has not been compromised, if the central controller can decrypt the encrypted communication, it is known to be authentic. Alternatively, the cryptographic technique of "one-way functions" may be used to ensure communication integrity. As used herein, a one-way function is one that outputs a unique representation of an input such that a given output is likely only to have come from its corresponding input, and such that the input can not be readily deduced from the output. Thus, the term one-way function includes hashes, message authenticity codes (MACs—keyed one-way functions), cyclic redundancy checks (CRCs), and other techniques well known to those skilled in the art. See, for example, Bruce Schneier, "Applied Cryptography," Wiley, 1996, incorporated herein by reference. As a matter of convenience, the term "hash" will be understood to represent any of the aforementioned or other one-way functions throughout this discussion.

Tamper Evidence/Resistance

One or more databases according to various embodiments could be stored within a secure environment, such as within a secure enterprise or off-premises datacenter within locked doors and 24/7 security guards, or in a cloud computing environment managed by a third party storage/compute provider such as Google® Cloud or Amazon® Web Services. These databases could be further secured with encryption software that would render them unreadable to anyone without access to the secure decryption keys. Encryption services are commonly offered by cloud database storage services. Security could be used to protect all databases according to various embodiments, or it could be applied only to select databases—such as for the storage of user passwords, financial information, or personal information. An alternative or additional form of security could be the use of tamper evident or tamper resistant enclosures for storage devices containing databases. For example, a dedicated computer processor (e.g., processor 605) may have all of its components—including its associated memory, CPU and clock housed in a tamper-resistant and/or tamper-evident enclosure to prevent and reveal, respectively, tampering with any of these components. Tamper-evident enclosures include thermoset wraps which, upon inspection, can reveal any attempt to physically open the structure. Tamper-resistant structures may electronically destroy the memory contents of data should a player try to physically open the structure.

Devices and Interactions

Figure 38:
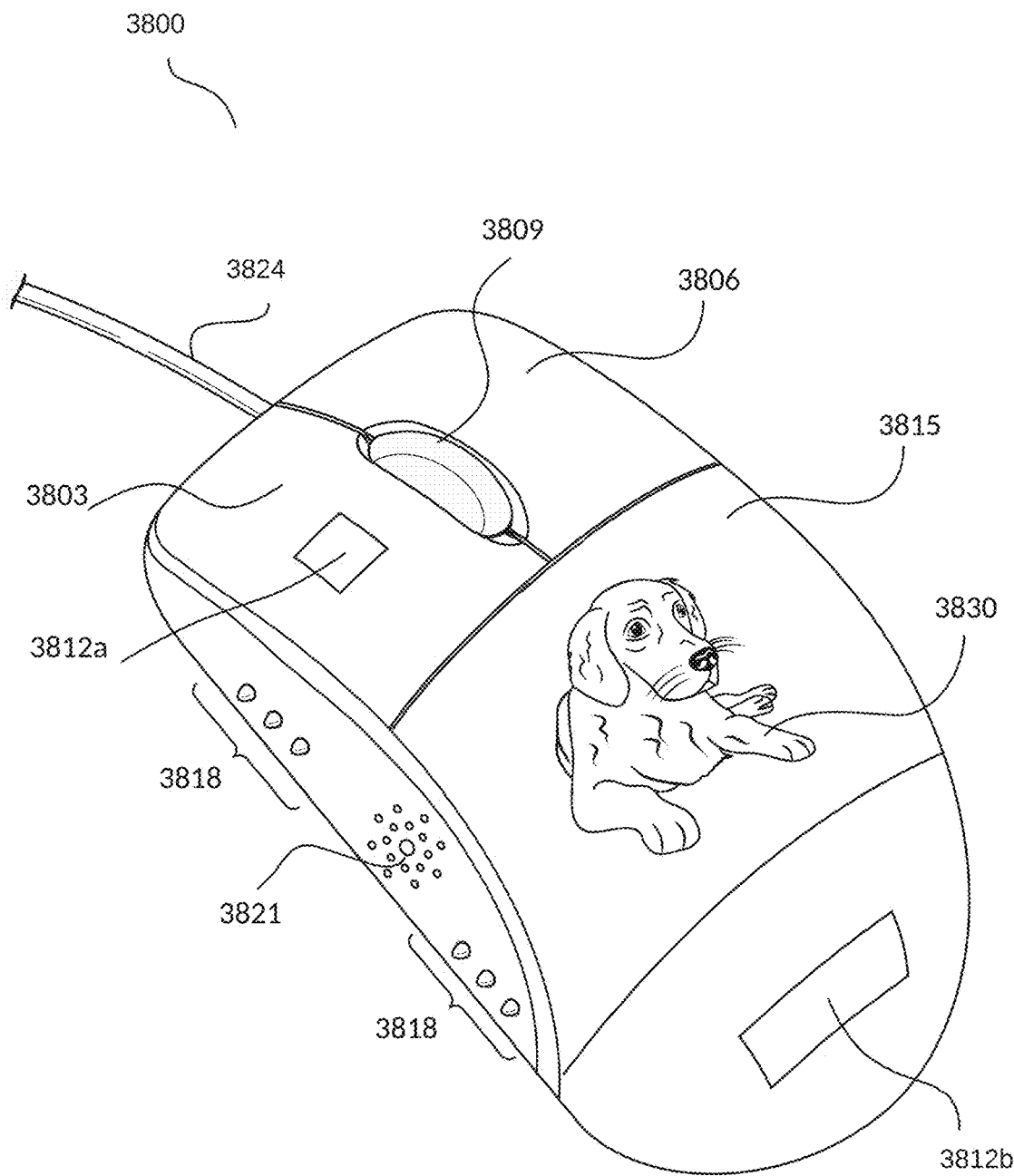
FIG. 38 is a computer mouse consistent with at least some embodiments described herein.

With reference to FIG. 38, a computer mouse 3800 according to some embodiments is shown. The mouse has various components, including left button 3803, right button 3806, scroll wheel 3809, sensors 3812a and 3812b, screen 3815, lights 3818a and 3818b, speaker 3821, and cord 3824. In various embodiments, hardware described herein (e.g., mouse 3800) may contain more or fewer components, different arrangements of components, different component appearances, different form factors, or any other variation. For example, in various embodiments, mouse 3800 may have a third button (e.g., a center button), may lack a cord (e.g., mouse 3800 may be a wireless mouse), may have more or fewer sensors, may have the screen in a different location, or may exhibit any other variation. In various embodiments, screen 3815 may be a display screen, touch screen, or any other screen. Screen 3815 may be a curved display using LCD, LED, mini-LED, TFT, CRT, DLP, or OLED technology or any other display technology that can render pixels over a flat or curved surface, or any other display technology. Screen 3815 may be covered by a chemically tempered glass or glass strengthened in other ways, e.g., Gorilla® Glass®, or covered with any other materials to stand up to the wear and tear of repeated touch and reduce scratches, cracks, or other damage. One use of a display screen 3815 is to allow images or video, such as dog image 3830, to be displayed to a user. Such an image could be retrieved from user table 700 (e.g., field 726) by central controller 110. Images displayed to a user could include game updates, game tips, game inventory lists, advertisements, promotional offers, maps, work productivity tips, images of other players or co-workers, educational images, sports scores and/or highlights, stock prices, news headlines, and the like. In some embodiments, display screen 3815 displays a live video connection with another user which may result in a greater feeling of connection between the two users. Sensors 3812a and 3812b may be contact sensors, touch sensors, proximity sensors, heat sensors, fingerprint readers, moisture sensors, or any other sensors. Sensors 3812a and 3812b need not be sensors of the same type. Sensors 3812a and/or 3218b may be used to sense when a hand is on the mouse, and when to turn display 3830 off and on.

Figure 39:
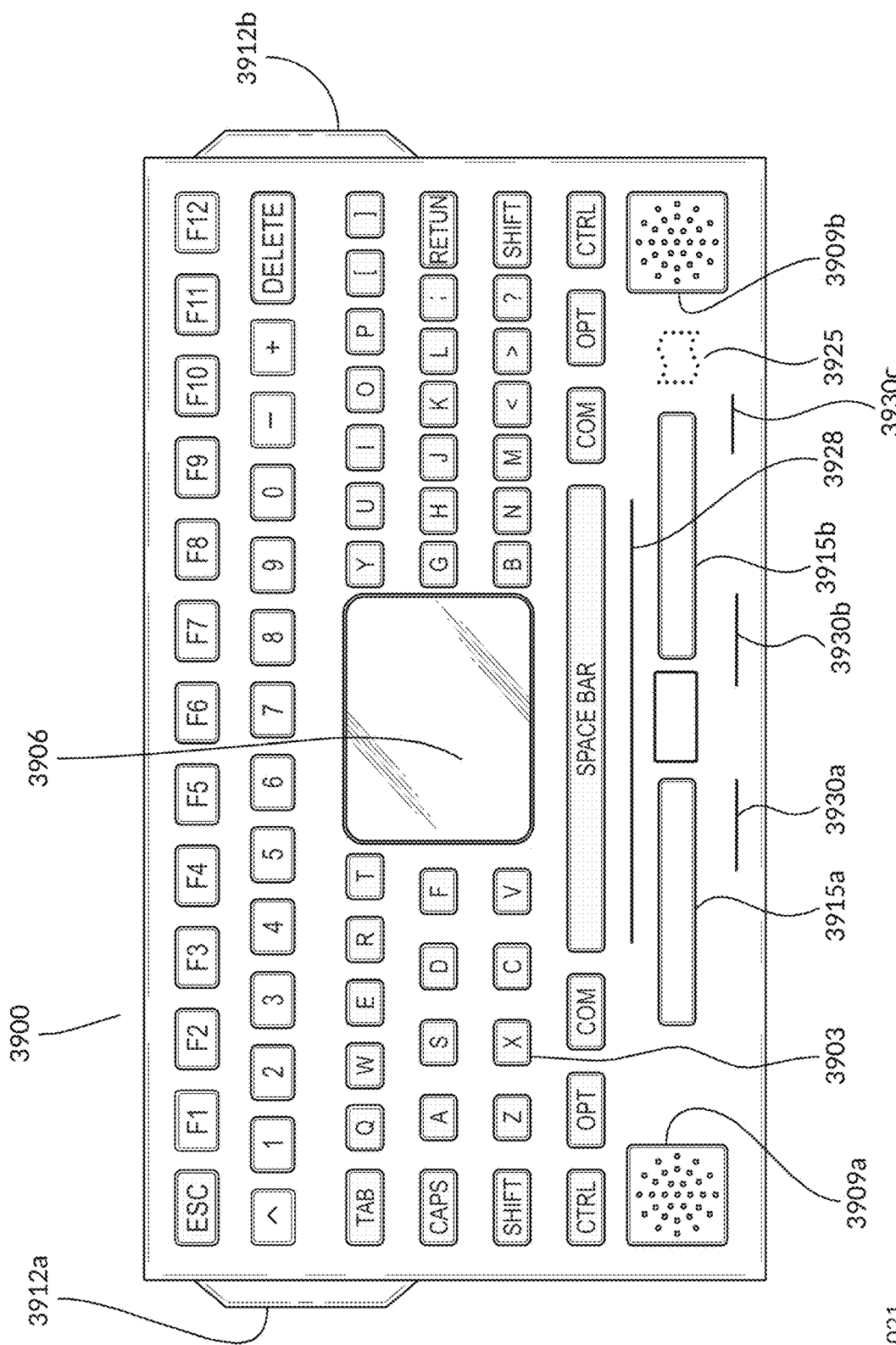
FIG. 39 is a computer keyboard consistent with at least some embodiments described herein.

With reference to FIG. 39, a computer keyboard 3900 according to some embodiments is shown. The keyboard has various components, including keys 3903, a screen 3906, speakers 3909a and 3909b, lights 3912a and 3912b, sensors 3915a and 3915b, microphone 3920, optical fibers 3928, 3930a, 3930b, and 3930c, and memory and processor 3925. In various embodiments, the keyboard is wireless. In some embodiments, the keyboard 3900 may connect to a user device, e.g., user device 106b (or other device), via a cord (not shown). Keyboard 3900 could be used by a user to provide input to a user device or to central controller 110, or to receive outputs from a user device or from central controller 110. Keys 3903 can be pressed in order to generate a signal indicating the character, number, symbol, or function button selected. It is understood that there may be many such keys 3903 within keyboard 3900, and that more or fewer keys 3903 may be used in some embodiments. Keys 3903 may be physical keys made of plastic. In some embodiments, keys 3903 are virtual keys or physical keys with display screens on top that can be programmed to display characters on top of the key which can be updated (e.g., updated at any time). Screen 3906 may include any component or device for conveying visual information, such as to a user. Screen 3906 may include a display screen and/or a touch screen. Screen 3906 may include a CRT screen, LCD screen, plasma screen, LED screen, mini-LED screen, OLED screen, TFT screen, DLP screen, laser projection screen, virtual retinal display, or any other screen, and it may be covered by a chemically tempered glass or glass strengthened in other ways, e.g., Gorilla® Glass®, or covered with any other materials to stand up to the wear and tear of repeated touch—and reduce scratches, cracks, or other damage. In some embodiments, displayed visual information can include game tips, game inventory contents, images or other game characters such as teammates or enemy characters, maps, game achievements, messages from one or more other game players, advertisements, promotions, coupons, codes, passwords, secondary messaging screens, presentation slides, data from a presentation, images of other callers on a virtual call, text transcriptions of another user, sports scores and/or highlights, stock quotes, news headlines, etc. In some embodiments, two players are using a keyboard 3900 with both keyboards connected through central controller 110. In these embodiments, one player can type a message using keys 3903 with the output of that typing appearing on screen 3906 of the other player. In some embodiments screen 3906 displays video content, such as a clip from a game in which one user scored a record high number of points, or a message from a company CEO. In some embodiments, light sources such as lasers, LED diodes, or other light sources, can be used to light up optical fibers 3928, 3930a, 3930b, and 3930c with a choice of colors; in some embodiments, the colors controlled by central controller 110 for the keyboards of various players in a game, or various participants in a meeting, can be synchronized, or used to transmit information among players or participants, e.g. when players or participants are available, unavailable, away for a time, in "do not disturb" mode, or any other status update that is desired.

Speakers 3909a and 3909b can broadcast sounds and audio related to games, background music, game character noises, game noises, game environmental sounds, sound files sent from another player, etc. In some embodiments, two game players can speak to each other through microphone 3920, with the sound being transmitted through microphone 3920 to memory and processor 3925 and then to central controller 110 to speakers 3915a and 3915b on the other player's keyboard 3900. Lights 3912a and 3912b can illuminate all or part of a room. In some embodiments, suitable lighting technology could include LED, fluorescent, or incandescent. In various embodiments, lights 3912a and 3912b can serve as an alerting system to get the attention of a user such as a game player or a virtual meeting attendee by flashing or gradually increasing the light's intensity. In some embodiments, one user can send a request signal to memory and processor 3920 to flash the lights 3915a and 3915b of the other users keyboard 3900. Sensors 3915a and 3915b may include mechanical sensors, optical sensors, photo sensors, magnetic sensors, biometric sensors, or any other sensors. A sensor may generate one or more electrical signals to represent a state of a sensor, a change in state of the sensor, or any other aspect of the sensor. For example, a contact sensor may generate a "1" (e.g., a binary one, e.g., a "high" voltage) when there is contact between two surfaces, and a "0" (e.g., a binary "0", e.g., a "low" voltage) when there is not contact between the two surfaces. A sensor may be coupled to a mechanical or physical object, and may thereby sense displacement, rotations, or other perturbations of the object. In this way, for example, a sensor may detect when a surface has been touched, when a surface has been occluded, or when any other perturbation has occurred. In various embodiments, sensors 3915a and 3915b may be coupled to memory and processor 3925, and may thereby pass information on to central controller 110 or to a room controller.

Microphone 3920 can pick up audible signals from a user as well as environmental audio from the surroundings of the user. In one embodiment, microphone 3920 is connected to memory and processor 3925. Memory and processor 3925 allows for the storage of data and processing of data. In one embodiment, memory and processor 3925 is connected to central controller 110 and can send messages to other users, receive files such as documents or presentations, store digital currencies or financial data, store employee ID numbers, store passwords, store cryptographic keys, store photos, store video, and store biometric values from the keypad and store them for processing. In various embodiments, memory and processor 3925 can communicate via wired or wireless network with central controller 110 and house controller 6305. Memory and processor 3925 may include memory such as non-volatile memory storage. In some embodiments, this storage capacity could be used to store software, user images, business files (e.g. documents, spreadsheets, presentations, instruction manuals), books (e.g., print, audio), financial data (e.g. credit card information, bank account information), digital currency (e.g., Bitcoin™), cryptographic keys, user biometrics, user passwords, names of user friends, user contact information (e.g., phone number, address, email, messaging ID, social media handles), health data (e.g. blood pressure, height, weight, cholesterol level, allergies, medicines currently being taken, age, treatments completed), security clearance levels, message logs, GPS location logs, and the like.

Various embodiments contemplate the use of diffusing fiber optics, such as optical fiber 3928 or shorter strand optical fibers 3930a, 3930b, and 3930c. These may include optical glass fibers where a light source, such as a laser, LED light, or other source is applied at one end and emitted continuously along the length of the fiber. As a consequence, the entire fiber may appear to light up. Optical fibers may be bent and otherwise formed into two or three dimensional configurations. Furthermore, light sources of different or time varying colors may be applied to the end of the optical fiber. As a result, optical fibers present an opportunity to display information such as a current state (e.g., green when someone is available and red when unavailable), or provide diverse and/or visually entertaining lighting configurations.

Figure 40:
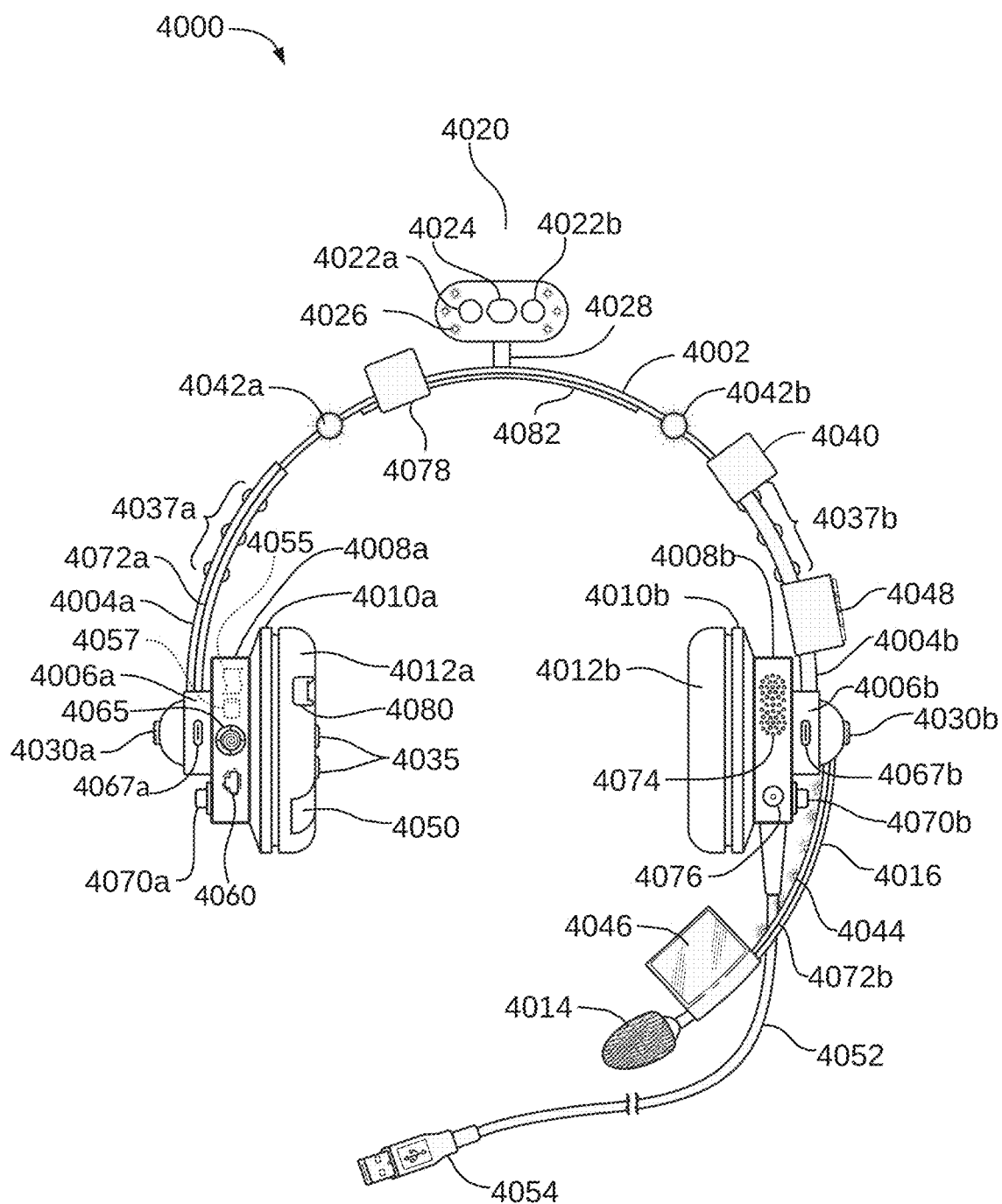
FIG. 40 is a headset consistent with at least some embodiments described herein.

With reference to FIG. 40, a headset 4000 according to some embodiments is shown. Headband 4002 may serve as a structural element, connecting portions of the headset that are situated on either side of the user's head. The headband may also rest on the user's head. Further, the headband may serve as a conduit for power lines, signal lines, communication lines, optical lines, or any other communication or connectivity between attached parts of the headset. Headband 4002 may include slidable components 4004a and 4004b (e.g., "sliders"), which may allow a user to alter the size of the headband to adjust the fit of the headset. Slidable component 4004a may attach to base 4006a and slidable component 4004b may attach to base 4006b. Right base 4006a and left base 4006b connect into slidable components 4004a and 4004b, and connect to housing 4008a and 4008b. In various embodiments, one or both of the left and right housings may comprise other electronics or other components, such as a processor 4055, data storage 4057, network port 4060, heating element 4065, or any other components. The left and right speakers 4010a and 4010b may broadcast sound into the users left and right ears, respectively. Right cushion 4012a may substantially cover right speaker 4010a, thereby enclosing the right speaker. Right speaker cushion 4012a may be padded along its circumference to surround a user's right ear, and provide a comfortable contact surface for the user. Right speaker cushion 4012a may include perforations or other transmissive elements to allow sound from the left speaker to pass through to the user's ear. Left speaker cushion 4012b may have analogous construction and function for the user's left ear.

In various embodiments, one of right speaker cushion 4012a or left speaker cushion 4012b includes one or more tactile dots 4035. A tactile dot may include a small elevated or protruding portion designed to make contact with the user's skin when the headset 4000 is worn. This could allow for embodiments in which processor 4055 could direct a haptic signal to alert a user via tactile dots 4035, or direct heat via heating element 4065, or provide a puff of air. As the headset may have a similar appearance from the front and from the back, a tactile dot (when felt on the appropriate side) may also serve as a confirmation to the user that the headset is facing in the proper direction. A microphone 4014 together with microphone boom 4016 may extend from base 4006b, placing the microphone in a position where it may be proximate to a user's mouth. Headset 4000 may include one or more camera units 4020. Two forward-facing cameras 4022a and 4022b are shown atop the headband 4002. In some embodiments, two such cameras may provide stereoscopic capability. An additional camera (e.g., a backward facing camera) (not shown) may lie behind camera unit 4020 and face in the opposite direction. Camera unit 4020 may also include a sensor 4024 such as a rangefinder or light sensor. Sensor 4024 may be disposed next to forward facing camera 4022a. In some embodiments, sensor 4024 may be a laser rangefinder. The rangefinder may allow the headset to determine distances to surrounding objects or features. In one embodiment, sensor 4024 includes night vision capability which can provide data to processor 4055, which can in some embodiments direct the user in gameplay to avoid danger, capture enemies, or perform other enhanced maneuvers. Camera unit 4020 may include one or more lights 4026 which can help to illuminate objects captured by forward facing cameras 4022a-b.

Buttons 4030a and 4030b, may be available to receive user inputs. Exemplary user inputs might include instructions to change the volume, instructions to activate or deactivate a camera, instructions to mute or unmute the user, or any other instructions or any other inputs. In various embodiments, headset 4000 may include one or more additional input components. In some embodiments, an extendible stalk 4028 is included to allow the camera unit 4020 to be raised to a higher level, which could allow for sampling of air quality at a higher level, for example. In some embodiments, extendible stalk 4028 may be bendable, allowing a user to position camera unit 4020 at various angles.

In various embodiments, headset 4000 may include one or more attachment structures 4037a and 4037b consisting of connector points for motion sensors, motion detectors, accelerometers, gyroscopes, and/or rangefinders. Attachment structures 4037a and 4037b may be electrically connected with processor 4055 to allow for flow of data between them. Attachment structures 4037a and 4037b could include one or more points at which a user could clip on an attachable sensor 4040. In some embodiments, standard size structures could enable the use of many available attachable sensors, enabling users to customize their headset with just the types of attachable sensors that they need for a particular function. For example, a firefighter might select several types of gas sensors to be worn on the headset, or even attach a sensor for a particular type of gas prior to entering a burning building suspected of containing that gas. In another embodiment, the attachment structures 4037a and 4037b could be located on other portions of headset 4000 such as on speakers 4010a-b or on bases 4006a-b. The attachable sensors 4040 may be used to detect a user's head motions, such as nods of the head or shaking of the head. The sensors may be used for other purposes, too. In some embodiments, a user may take a sensor from attachment structures 4037a or 4037b and clip it to their clothing (or to another user's clothing) and then later return the sensor to attachment structures 4037a or 4037b.

In various embodiments, instead of forward facing cameras 4022a-b (or instead of a backward facing camera), headset 4000 may include a 360-degree camera on top of headband 4002 within camera unit 4020. This may allow for image capture from all directions around the user. In some embodiments, microphone boom lights 4044 may be capable of illuminating the user, such as the user's face or skin or head or other body part, or the user's clothing, or the user's accessories, or some other aspect of the user. In other embodiments, headband lights 4042a and 4042b may be disposed on headband 4002, facing away from a prospective user. Such lights might have visibility to other users, for example. When activated, such lights might signal that the user has accomplished something noteworthy, that it is the user's turn to speak, that the user possesses some rank or office, or the lights may have some other significance, some aesthetic value, or some other purpose.

Display 4046 may be attached to microphone boom 4016. In various embodiments, display 4046 faces inwards towards a prospective user. This may allow a user to view graphical information that is displayed through his headset. In various embodiments, display 4046 faces outwards. In various embodiments, display 4046 is two-sided and may thereby display images both to the user and to other observers. In various embodiments, an inward facing display and an outward facing display need not be part of the same component, but rather may comprise two or more separate components. Headband display 4048 may be disposed on headband 4002, e.g., facing away from a prospective user, and may thereby display images to other observers.

Cushion sensor 4050 may be disposed on right cushion 4012a. When the headset is in use, cushion sensor 4050 may be in contact with a user's skin. The sensor may be used to determine a user's skin hydration, skin conductivity, body temperature, heart rate, or any other vital sign of the user, or any other signature of the user. In various embodiments, additional sensors may be present, such as on left cushion 4012b. Cushion sensor 4050 may be used as a haptic for feedback to the user, to impart some sensory input, which may be a buzzing, a warm spot, or any other sensory information. In various embodiments, additional sensors may be present, such as on left cushion 4012b. Cable 4052 may carry power to headset 4000. Cable 4052 may also carry signals (e.g., electronic signals, e.g., audio signals, e.g., video signals) to and from the headset 4000. Cable 4052 may terminate with connector 4054. In some embodiments, connector 4054 is a USB connector.

Terminals 4067a and 4067b may lead into speaker bases 4006a and 4006b, and may serve as an attachment point for electronic media, such as for USB thumb drives, for USB cables, or for any other type of media or cable. Terminals 4067a-b may be a means for charging headset 4000 (e.g., if headset 4000 is wireless). data storage 455 may comprise non-volatile memory storage. In some embodiments, this storage capacity could be used to store software, user images, business files (e.g. documents, spreadsheets, presentations, instruction manuals), books (e.g. print, audio), financial data (e.g. credit card information, bank account information), digital currency (e.g., Bitcoin™), cryptographic keys, user biometrics, user passwords, names of user friends, user contact information (e.g. phone number, address, email, messaging ID, social media handles), health data (e.g. blood pressure, height, weight, cholesterol level, allergies, medicines currently being taken, age, treatments completed), security clearance levels, message logs, GPS location logs, current or historical environmental data (e.g. humidity level, air pressure, temperature, ozone level, smoke level, CO2 level, CO level, chemical vapors), and the like. In various embodiments, headset 4000 includes a Bluetooth® antenna (e.g., an 8898016 series GSM antenna) (not shown). In various embodiments, headset 4000 may include any other type of antenna. In various embodiments, headset 4000 includes an earbud (not shown), which may be a component that fits in the ear (e.g., for efficient sound transmission).

Headset 4000 may also include accelerometers 4070a and 4070b which are capable of detecting the orientation of headset 4000 in all directions and the velocity of headset 4000. Such accelerometers might be used for detecting the direction of gaze of a user, speed of walking, nodding of the users head, etc. Optical fibers 4072a and 4072b are a thin strand of diffusing optical fiber. These may include optical glass fibers where a light source, such as a laser, LED light, or other source is applied at one end and emitted continuously along the length of the fiber. As a consequence, the entire fiber may appear to light up. Optical fibers may be bent and otherwise formed into two or three dimensional configurations. Furthermore, light sources of different or time varying colors may be applied to the end of the optical fiber. As a result, optical fibers present an opportunity to display information such as a current state (e.g., red when a user is in an environment with low oxygen levels), or provide diverse and/or visually entertaining lighting configurations. In some embodiments, headset 4000 includes outward speakers 4074 which can generate a sound hearable by other users. A projector 4076 could be used to project information in front of a user. In some embodiments, projector 4076 may project text from a machine instruction manual onto a wall in front of the user. In some embodiments, a smell generator 4078 is capable of generating smells which may be used to alert the user or to calm down the user. Vibration generator 4080 may be used to generate vibrations that a user feels on the surface of cushion 4012a. Piezoelectric sensor 4082 may be attached to headband 4002 so as to detect bending of headband 4002 (e.g. detecting when a user removes or puts on a headset).

In some embodiments, a heads up display ("HUD") (not shown) and/or "helmet mounted display" ("HMD") (not shown) is included in headset 4000 and used to display various data and information to the wearer. In some embodiments, HUD and/or HMD capability may be incorporated into projector 4076. The HUD and/or HMD can use various technologies, including a collimator to make the image appear at an effective optical infinity, project an image on a facemask or windshield, or "draw" the image directly on the retina of the user. Some advantages of a HUD and/or HMD include allowing the user to check on various important data points while not changing their visual focus, which might be beneficial when used in aircraft and automobile embodiments. Other applications could include military settings, for motorcyclists, etc. A HUD and/or HMD may display important operational information in industrial settings, such as ambient temperatures, oxygen levels, a timer, the presence of toxic elements, or any other information or data that is needed. A HUD and/or HMD may display status information of another user, such as their heart rate, respiration rate, blood alcohol level, etc. A HUD and/or HMD may display environmental information of another user, such as oxygen level, temperature, location, presence of dangerous gasses, etc. A HUD and/or HMD may also display important information to a gamer, such as health levels, shield strength, remaining ammunition, opponent statistics, or any other relevant information. In some embodiments, a HUD and/or HMD may comprise text output such as instruction steps for fixing a machine, or text instructions for a student who is struggling with a math problem, or recipe instructions for a user baking a cake, etc. In some embodiments, a HUD and/or HMD can be utilized to present augmented reality ("AR") images, or virtual reality ("VR") images to the wearer. In some embodiments, a HUD and/or HMD can be used to enhance night vision, enabling the user to be more effective in industrial settings where light is low, or in gaming scenarios where night vision can aid in game play.

In some embodiments, headset 4000 may be constructed in such a way that the earpieces fit inside the ears rather than cover the ears. In these embodiments, headset 4000 is lighter and less cumbersome, and certain features, sensors, etc. are relocated. In embodiments that fit inside the ears, there is more situational awareness that is possible; this may be important in various industrial scenarios in which process noises, alerts, and emergency notifications need to be monitored for safety and/or productivity.

In various embodiments, headset 4000 may facilitate the ability to sense smoke and alert users to stop smoking. In some embodiments, sensors may be used to detect smoke and alert the user. A user may want to try and stop smoking cigarettes and need some coaching from headset 4000. A smoke sensor may be attached to connector point 4037*a-b* by the user or as displayed in attachable sensor example 4040. When a user lights a cigarette and smoke emits, an attachable sensor 4040 may detect the smoke, provide the information to processor 4055 and provide an alert to the user reminding them to stop smoking. This alert from the processor may be in the form of a vibration from vibration generator 4080, an audible alert saying, 'please stop smoking, it is bad for you' in speakers 4010*a-b*, or in any other forms of feedback (e.g. buzz, beep, chirp). Boom lights 4044 may display a color or pattern (e.g. red blinking) and/or display 4046 may provide an image to distract the user and remind the user to stop smoking (e.g. a video showing someone suffering from lung disease or a picture of their family). The alerts may be selected in advance by the user on a device (e.g., on a user device, peripheral device, personal computer, phone, etc.), loaded using network port 4060 and stored locally in data storage 4057.

In various embodiments, headset 4000 may facilitate the ability to sense smoke and provide safety warnings, with sensors used to detect smoke and alert the user or others around them. A user may be working in a warehouse or industrial setting in building 6802 with flammable substances. If a flammable substance ignites, the headset 4000 may detect the smoke and alert the user more quickly than human senses are possible. A smoke sensor may be attached to connector point 4037*a-b* by the user or as displayed in attachable sensor 4040. If a flammable substance ignites in an area away from the user, attachable sensor 4040 may detect the smoke, provide the information to processor 4055 and provide an alert to exit the area immediately. This alert from the processor may be in the form of a vibration from vibration generator 4080, an audible alert saying, 'smoke detected, please exit immediately and call 9-1-1' in speakers 4010*a-b*, lights 4042*a-b* flashing red to alert others around the user to evacuate and take the individual, boom lights 4044 on microphone boom 4016 may display a color or pattern (e.g. blinking red) and/or display 4046 may provide an image to alert the user to exit (e.g. a floor plan and path to the exit the room and building). Likewise, optical fibers 4072*a-b* may light up in orange for immediate visual alerts to others or emergency workers. The outward speaker 4074 may provide a high pitched burst of beeps to indicate the need to evacuate or a verbal warning that 'smoke has been detected, please exit immediately'. Attachable sensor 4040 may detect the type of smoke (e.g. chemical, wood, plastic) based on information stored in data storage 4057 and interpreted by processor 4055. If the smoke detected is from a chemical fire, communications to company safety teams may occur through internal satellite, Bluetooth® or other communications mechanisms within headset 4000 and housing 4008*a-b* to alert them to the type of fire for improved response and specific location. Projector 4076 may display a message on the wall indicating that 'smoke has been detected and it is a chemical fire—exit immediately— proceed to the wash station'. Also, the projector 4076 may display a map of building 6802 with the nearest exit or provide on display 4046.

In various embodiments, headset 4000 may facilitate the ability to sense various gases (e.g. natural gas, carbon monoxide, sulfur, chlorine) and provide safety warnings. In some embodiments, sensors (e.g. natural gas, carbon monoxide, sulfur) may be used to detect odors or gas composition (e.g. odorless carbon monoxide) and alert the user. A user may be working in their living room where a gas fireplace is located. During the day, the pilot light may go out, but the gas remains on due to a faulty fireplace gas sensor. The user's senses become saturated to a point they no longer smell the gas posing a danger to her family. The headset 4000 may detect the natural gas and alert the user more quickly than human senses are possible. A natural gas sensor may be attached to connector point 4037*a-b* by the user or as displayed in attachable sensor 4040. Attachable sensor 4040 may detect the natural gas, provide the information to processor 4055 and provide an alert to the user to exit the house immediately or open the windows and doors. This alert from the processor may be in the form of a headset vibration with vibration generator 4080, an audible alert saying, 'natural gas detected, please exit immediately and call 9-1-1' in speaker 4010*a-b* and/or outward speaker 4074, boom lights 4044 may display a color or pattern (e.g. blinking red) and/or display 4046 may provide an image to alert the user to exit (e.g. a floor plan and path to the exit the room and home). The attachable sensor 4040 may be used to detect the type of gas as well (e.g. natural gas, carbon monoxide, non-lethal sulfur, chlorine) based on information saved in data storage 4057 and interpreted by processor 4055. The headset 4000 may alert the fire department, other emergency agencies or family members with headsets through the communications mechanisms (e.g. antenna, satellite, Bluetooth®, GPS) within housing 4008*a-b* about the gas and composition and location of the user for more rapid response. Likewise, a research and development employee in building 6800 biohazard room 6870 may be working on an experiment to make chlorine gas. Instead of adding small amounts of concentrated hydrochloric acid to the potassium permanganate solution, the researcher adds too much hydrochloric acid, creating an unstoppable reaction and creating too much lethal chlorine gas. The headset 4000 may immediately detect elevated levels of chlorine gas through the attachable sensor 4040 based on values in data storage 4057 and interpreted by processor 4055 and immediately alerts the employee, safety teams, public emergency works and other employees. This alert sent from processor 4055 may be in the form of a buzz from cushion sensor 4050, an audible alert in speaker 4010*a-b* saying, 'chlorine gas detected, please exit immediately and call 9-1-1', boom lights 4044 or headband lights 4042*a-b* may display a color or pattern (e.g. blinking and solid red variation) and/or display 4046 may provide an image to alert the user to exit (e.g. a floor plan and path to the nearest exit the room). Headset 4000 may alert the fire department, other emergency agencies, local safety team members or employees in close proximity with headsets through the internal communications (e.g. antenna, satellite, Bluetooth, GPS) within housing 4008*a-b* about the chlorine gas for more rapid and accurate response (e.g. correct equipment to combat the chlorine gas). Alerts (e.g. chlorine gas detected in room 6870) may also be displayed on building 6802 walls using projectors 6850*a-f* and lights 6808*a-g* (e.g. red flashing) along with evacuation notices from speakers 6850*a-e*.

In various embodiments, headset 4000 may facilitate the ability for a user to progress through a checklist (e.g. recipe). In various embodiments, forward facing cameras 4022*a-b* may be able to detect steps on a checklist and assist the user. A user may store a recipe (e.g. pasta fagioli soup) in data storage 4057 using an electronic device (e.g. computer, phone, tablet) through network port 4060. This recipe may be interpreted by processor 4055 and stored in data storage 4057 with a unique name (e.g. pasta fagioli soup) for later retrieval. The user may access the recipe by speaking into microphone 4014 to request retrieval of the pasta fagioli soup using a voice command (e.g. 'retrieve pasta fagioli recipe'). As the user is preparing the soup, the forward facing camera 4022*a-b* on extendible stalk 4028 may capture the movements and steps and communicate with processor 4055. The processor may determine that the user has skipped adding a dash of tabasco sauce from the recipe and informs the user through speaker 4010*a-b* that a step was missed and tells the user the ingredient that was left out (e.g. tabasco). Likewise, display 4046 or projector 4076 may also show the steps of the recipe and indicate they are completed (e.g. crossing through the step, checking off the step). If a step is missed or performed out of order or incorrectly as determined by forward facing camera 4022*a-b* and processor 4055, the headset 4000 may provide alerts such as vibrations from the vibration generator 4080, notices on display 4046 (e.g. 'stop—a step was missed in the recipe'), boom lights 4044 may display yellow, outward speaker 4074 or speaker 4010*a-b* may provide verbal warnings (e.g. 'review steps or ingredients') of missed steps or missing ingredients. Likewise, a user may decide to by-pass the warning or message if they do not want to include the ingredient by pressing the button 4030*a-b* indicating to processor 4055 to skip the step or ingredient.

In various embodiments, headset 4000 may facilitate the ability to detect steps on a checklist and assist the user. A pilot or company may input the pre-flight checklist for all aircraft in the headset 4000 and save in data storage 4057 from an electronic device (e.g. computer, phone, digital tablet) through the network port 4060. The pilot, using microphone 4014, may request retrieval of the pre-flight checklist using a voice command (e.g. 'load pre-flight checklist for MD-11'). The pre-flight checklist may be shown on display 4046 as a reminder to the pilot along with scrolling capabilities. As the pilot is performing the pre-flight check, the forward facing camera 4022*a-b* may capture the movements and steps of the pilot during the pre-flight activities and communicate those with processor 4055. The accelerometer 4070*a-b* may detect that the head movement and focus did not occur on an element of the plane referenced in the checklist. The processor detects that the pilot may have skipped checking the flaps on the right wing and may inform the pilot through speaker 4010*a-b* (e.g. check right wing flaps), vibration to the pilot from vibration generator 4080 to alert the pilot of a missed step, colors on microphone boom lights 4044 (e.g. solid red) and/or communication to the flight control team through communication mechanisms (e.g. Bluetooth, satellite, cellular) that a step was missed. The flight control team may communicate directly to the pilot through the headset 40000 asking her to recheck the pre-flight steps or inform the captain. Likewise, display 4046 may also show the pre-flight checklist and indicate the completed (e.g. crossing through the step, checking off the step) or missing (e.g. highlighting in bold and red) steps.

In various embodiments, headset 4000 may facilitate the ability to coach a user through steps and provide analysis. There may be situations where repeating a step is needed for ongoing improvement and coaching analysis is needed. A new basketball player may have to shoot thousands of free throws to improve their performance. Coaching after every shot may not be appropriate. The headset 4000 with cameras 4022*a-b* may record each free throw taken by the player during practice. After every 50 shots, processor 4055 may perform an analysis of all shots and provide a coaching summary. The analysis may be in the form of written comments on display 4046 (e.g. 45% shots made, too many dribbles before shooting, not enough arch on the ball, too long of a delay before shooting), highlights of good and poor shots displayed on a wall with projector 4076 for review by the player, verbal feedback in speaker 4010*a-b* providing steps for improvement or encouragement (e.g. 'good shot'). Likewise, so as to not interrupt the player, feedback may be given to the coach or others watching. Headband lights 4042*a-b* may display green when processor 4055 determines the technique in shooting was performed well or red when improvements are needed. The coach observing the player may immediately see the lights and determine if they should stop the player and provide more coaching or encouragement.

In various embodiments, headset 4000 may facilitate the ability to coach or provide feedback to users regarding verification of performed steps. In some embodiments, a user may need to understand what steps of a process were missed for training purposes, but interruption during the process is not desired. A factory worker may be required to assemble small components on a computer board. The user may have been trained and now the employer needs to verify they can successfully complete the steps. The user wearing a headset 4000 begins to assemble the computer board. The forward facing cameras 4022*a-b* may record each step of assembly along with the duration of each step and communicate this information to processor 4055 and data storage 4057. Once the assembly is completed, processor 4055 may review the steps for accuracy and time and inform the user. The feedback may be through display 4046 or projector 4076 on a wall that a step was missed and/or the time to complete specific steps took too long (e.g. step 3 took 30 seconds and only 15 seconds is allocated). The user may make the necessary corrections and perform the steps again with headset 4000 until there are no missed assembly steps and the time to perform the steps are within an acceptable range. Likewise, when all steps are performed correctly and within an acceptable time, headband lights 4042*a-b*, lights 4026 or optical fibers 4072*a-b* may light up (e.g. solid green) to indicate to the supervisor that there are no issues. The factory worker may also get notification through boom lights 4044 (e.g. green) or display 4046 (e.g. "OK—great work") that there are no performance issues.

In various embodiments, headset 4000 may facilitate the ability to capture records of completing checklist items for later recall. In some embodiments, there may be situations where a user needs to recall specific actions performed as proof that there were no deficiencies. In a manufacturing room 6885 where chemical cleaning occurs on parts, it may be necessary to provide evidence that a part was cleaned according to specific instructions and steps to defend the company's actions in court or appease an upset customer. Using headset 4000, forward facing cameras 4022*a-b* may record the actions of a user cleaning parts in the chemical room with acid tanks 6885. The forward facing cameras record the specific part by reading the part measurements, barcode or image. The processor 4055 compares measurements or images to stored parts in data storage 4057 to retrieve the checklist or procedures for the specific part. While the user is cleaning the part, the forward facing cameras capture the video of the item, date, time, and procedures performed according to the documented checklist. This information may be stored in data storage 4057 for uploading to company databases from network port 4060 or other communications capabilities in housing 4008*a-b* (e.g. Bluetooth®, satellite, USB connection). In some embodiments, the information stored in data storage 4057 may be used as an audit trail which can be provided to company auditors, regulators, safety inspectors, etc. In various embodiments, a company may use information stored in data storage 4057 to prove in court that a part number was cleaned properly. The company may retrieve the part number and actions that were performed on the part to defend themselves in court. Likewise, they may retrieve all video of the part cleaning process to defend their standard operating procedure.

In various embodiments, headset 4000 may facilitate the ability to include a checklist with criteria that can be verified by eye gaze/head/body orientation. In some embodiments there may be situations where assembly line workers are needed to visually inspect items for quality control. An automobile manufacturer may require a visual inspection of final painted vehicles for scratches or paint flaws. The employee with a headset 4000 and forward facing cameras 4022*a-b* may inspect the automobiles coming off the assembly line. Accelerometers 4070*a-b* may be used to monitor eye gaze time and head movements to validate that a user is actually looking at the exterior of the automobile for defects and not in other locations. If the camera or accelerometer detects the user gazing in a direction other than the automobile, vibration from vibration generator 4080 may occur to alert the user to pay attention, a tone in speaker 4010*a-b* may occur (e.g. short chirping sound), headband lights 4042*a-b* may flash orange giving the supervisor and opportunity to coach the employee to pay more attention or the display 4046 may show a message to the worker to look in the direction of the automobile. Boom lights 4044 may also blink in red to alert the worker to pay attention.

In various embodiments, headset 4000 may provide an opportunity for another person to observe an action such as in industrial settings, construction, healthcare, fast food and the like without physically being in the room. In healthcare environments where highly contagious or seriously ill people require limited contact, it may be necessary for other medical professionals to assess the patient through the eyes of only one person in the room. A person suffering from meningitis may have a doctor with headset 4000 evaluate their condition while other physicians observe in remote locations. As this is a highly contagious disease, other doctors may want to evaluate them without entering the room. The forward facing cameras 4022*a-b* may record in the direction the physician is looking at the patient. The physician may dictate through microphone 4014 to turn on lights 4026 so she can evaluate the dilation of the eyes. A doctor watching in a remote location through the eyes of the on-site physician may notice a slow dilation response and ask the doctor in the room to perform a different alertness assessment. The physician may decide to prescribe a new drug and speak into microphone 4014 and show the dosage and drug interactions on display 4046 before writing the prescription. Later, the physician may want to perform a new evaluation technique but needs to see the exact process. Projector 4076 displays on the wall behind the patient the steps and video of the procedure before the doctor performs the evaluation. In some embodiments, evaluation of hearing may take place by having the physician request audible sounds be delivered from outward speaker 4074 so the patient can respond (e.g. hold up your hand if you hear a tone). The overall evaluation may be recorded by cameras 4022*a-b* and stored in data storage 4057 for future reference and training of interns.

In various embodiments, headsets may facilitate good cleaning practices. Office cleaning may become more important to remove germs and create a safe work environment. In some embodiments, maintenance personnel with headset 4000 may be instructed to spray the desk, wait for 30 seconds and wipe until dry, spending a minimum of 2 minutes per desk to ensure a safe work environment. During cleaning, forward facing cameras 4022*a-b* may collect the desk cleaning activities of the maintenance worker, send a record to processor 4055 for evaluation against standards and store the results in data storage 4057. The processor determines that in one situation cleaning spray was not applied and the speaker 4010*a-b* may alert the user to reclean the desk and apply a cleaning solution. The processor may also determine that desks are only being cleaned an average of 1 minute 30 seconds, not the required 2 minutes. Cushion sensor 4050 may provide a haptic response to the worker (e.g. buzz), while display 4046 reminds the worker with a message to clean each desk for 2 minutes and to redo the cleaning, and microphone boom lights flash in multi-colors indicating the worker should reclean the surface. In some embodiments, this information may be sent from data storage 4057 by internal communications (e.g. Bluetooth®, satellite, cellular) in housing 4008*a-b* to the company facility and maintenance team databases for evaluation. This information may be reviewed with the cleaning company for improvement and compliance. Likewise, when employees approach their desk each day and don a headset 4000, the piezoelectric sensor 4082 may recognize the person is putting on a headset. Forward facing camera 4022*a-b* or GPS in the housing 4008*a-b* recognizes the specific desk and location. In some embodiments, processor 4055 may retrieve data from the company database and provide information regarding the cleaning status to display 4046 (e.g. all cleaned) and/or microphone boom lights 4044 (e.g. display solid green for cleaned desk or red for unclean desk) to the employee. Likewise, the employee may be presented with a brief video on display 4046 showing successful cleaning the night before indicating it is safe to sit and begin work.

Figure 41A:
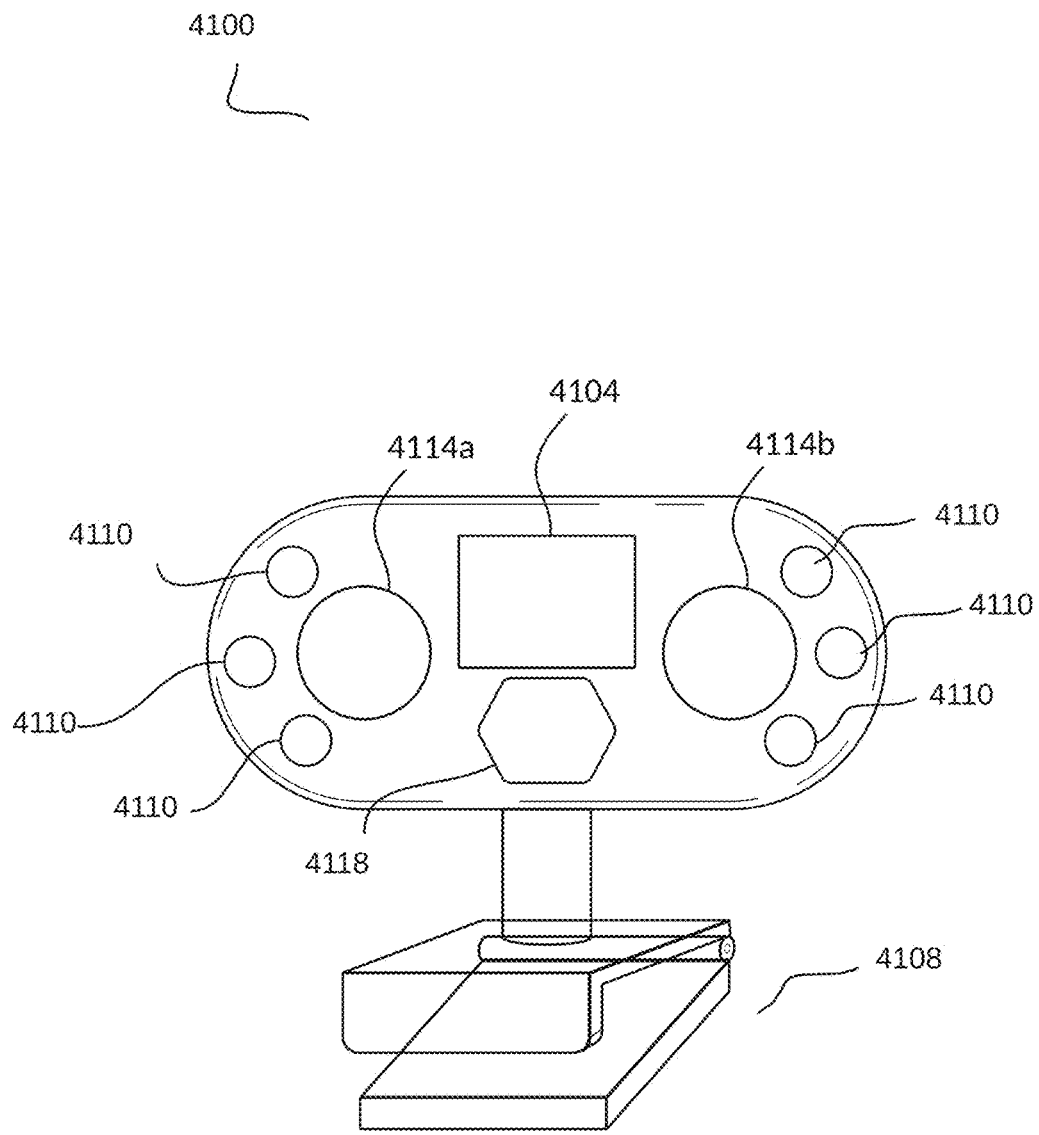
FIG. 41A and FIG. 41B depict a camera unit consistent with at least some embodiments described herein.

With reference to FIG. 41A, a camera unit 4100 according to some embodiments is shown with a front facing view of the camera unit. Two front-facing cameras, 4114*a* and 4114*b* may provide camera unit 4100 with extra depth perception, or may serve any other purpose. Screen 4104 may show images or video, such as what one or both of the front-facing cameras is currently capturing. Base 4108 may enable attachment to another device, such as to a computer monitor or a headset. Lights 4110 may indicate a status of the camera (e.g., 'filming' or 'not filming'), may provide ambient background lighting, or may serve any other function. Camera unit 4100 may also include a sensor 4118, such as a rangefinder or light sensor.

Figure 41B:
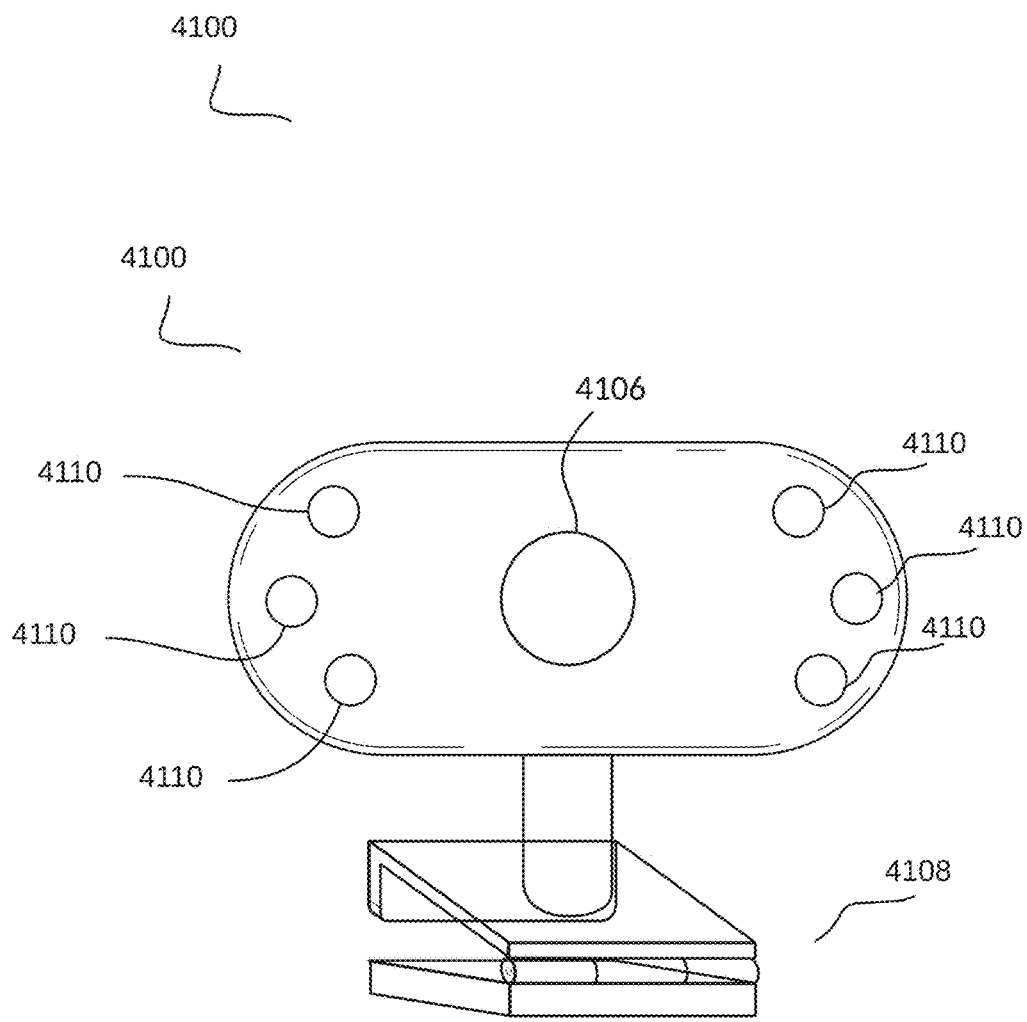

With reference to FIG. 41B, a camera unit 4100 according to some embodiments is shown with a rear facing view of the camera unit. Rear-facing camera 4106 may capture activity behind the camera unit 4100. Lights 4110 may indicate a status of the camera (e.g., 'filming' or 'not filming'), may provide ambient background lighting, or may serve any other function. Base 4108 may enable attachment to another device, such as to a computer monitor or a headset.

Figure 42:
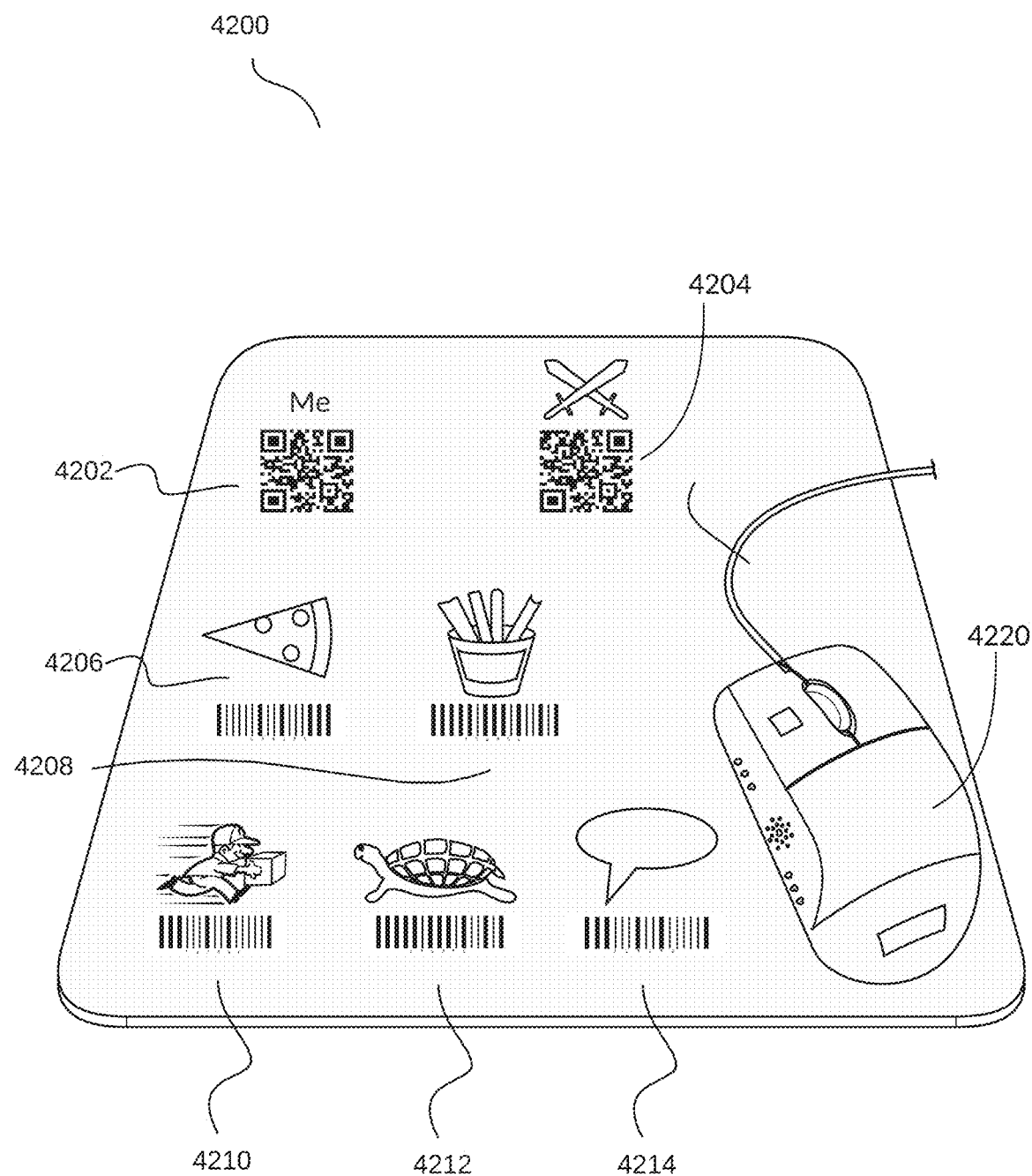
FIG. 42 is a mouse pad consistent with at least some embodiments described herein.

With reference to FIG. 42, a mouse pad 4200 according to some embodiments is shown. In various embodiments, mouse pad 4200 may provide a means to input commands to a mouse or headset. The mouse pad may include one or more barcodes, such as traditional barcodes or two-dimensional barcodes. Each barcode may be associated with an input, a command, an instruction, or the like. Barcode 4202 may serve as an authenticator for the user. For example, the barcode 4202 may encode a unique password for the user. Barcode 4204 may serve as an authenticator for the user in a particular context, such as for playing a particular video game. As will be appreciated, barcodes may be used to authenticate a user in other contexts. Barcodes 4206 and 4208 may serve as instructions to order food, e.g., particular items of food associated with each barcode. For example, barcode 4206 may be used to order pizza, while barcode 4208 is used to order French fries. As will be appreciated, barcodes could be used for ordering other items. Barcodes 4210 and 4212 may be used to modify parameters of a headset's functionality. For example, bar code 4210 may be used to increase the resolution of a headset camera, while bar code 4212 may be used to decrease the audio quality rate. As will be appreciated, barcodes could be used for other types of modifications to mouse or headset parameters. Barcode 4214 may be used to create a message, such as a text message that will be sent to another user. In various embodiments, the barcode may trigger a predefined message, such as, "How's it going?" In various embodiments, the barcode may place the mouse or headset in a receptive mode, after which the mouse of headset will accept verbal dictation and transcribe a text message. In various environments, barcodes may be used for various other instructions, and for various other purposes.

In various embodiments, a headset 400 (not shown) includes functionality of a barcode reader, and is thereby able to read and interpret instructions represented by a barcode. For example, headset 4000 may include a camera, laser, light, or other optical element in order to read barcodes. In various embodiments, a mouse pad may incorporate or embed instructions using other means. For example, a mouse pad may incorporate RFID chips, NFC chips, proximity chips, or the like, which may trigger an instruction for the headset when the headset is nearby. In various embodiments, form factors besides a mouse pad may incorporate barcodes, proximity chips, or any other device for triggering instructions. In various embodiments, peripheral devices other than a mouse may detect and/or respond to barcodes, proximity chips, or the like.

Figure 43:
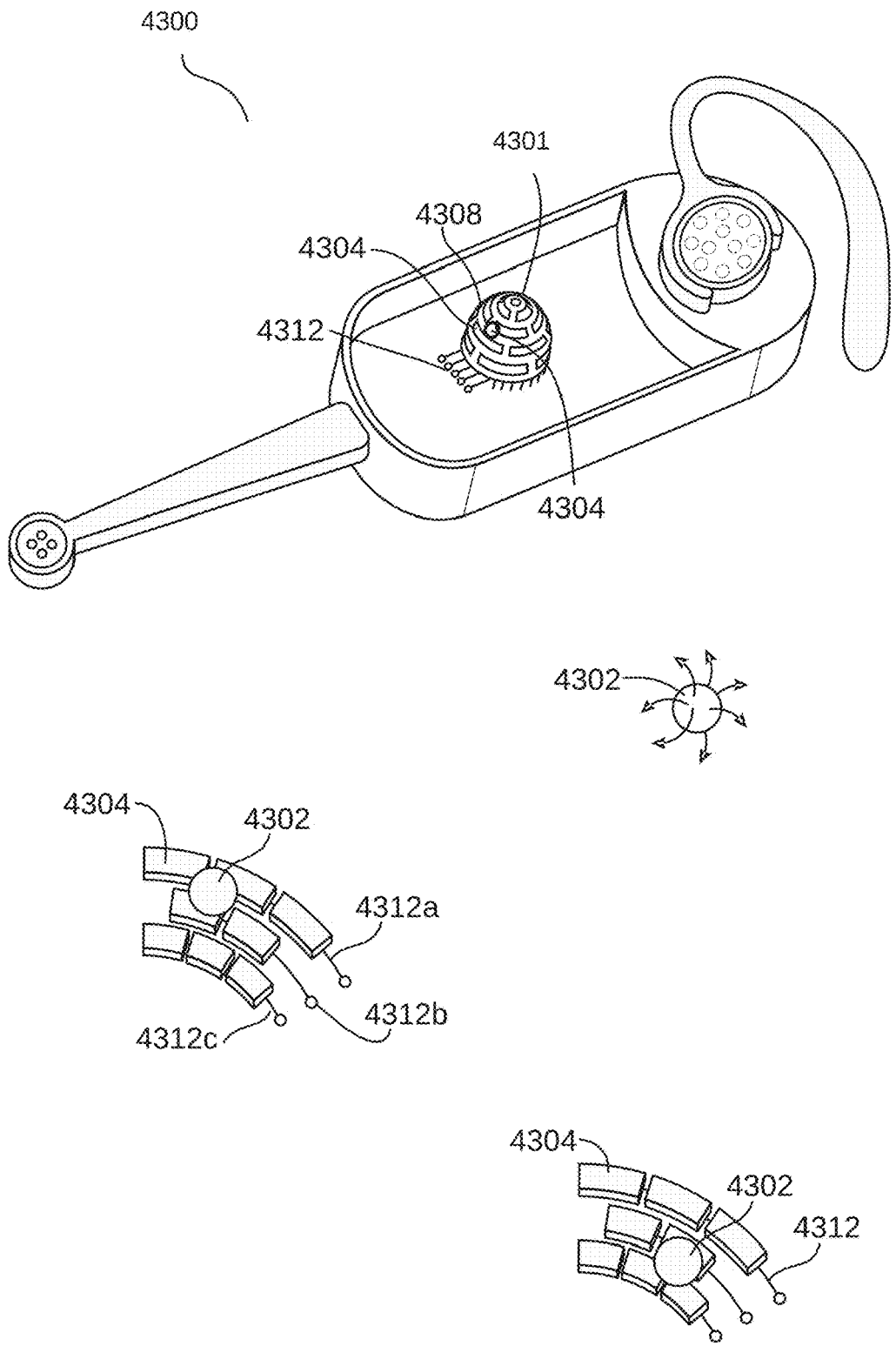
FIG. 43 is a headset with motion sensor consistent with at least some embodiments described herein.

With reference to FIG. 43, a headset 4300 with motion sensor 4301 according to some embodiments is shown. Motion sensor 4301 comprises a capsule 4308, which may be substantially spherical in shape. Multiple fixed conductors 4304 line the inside of capsule 4308. A movable conductor 4302 is free to move about inside the capsule. Movable conductor 4302 may be substantially spherical in shape. Fixed conductors 4304 may be in electrical communication with one of a plurality of wires 4312 (e.g., with wires 4312*a*, 4312*b*, and 4312*c*). In various embodiments, adjacent wires (e.g., 4312*a* and 4312*b*) are of opposite polarities (e.g., one is grounded while the other is connected to the positive supply voltage). When movable conductor 4302 bridges the gap between two fixed conductors on adjacent wires (e.g., between wires 4312*a* and 4312*b*), a circuit is completed.

The circuit completion can be detected by a logic gate bridging the two particular wires that are now in electrical communication. For example, an "AND" gate is connected at one input to the positive voltage supply (e.g., via wire 4312*a*), and at the other input (e.g., via wire 4312*b*), through a resistor, to ground. Normally, with only one input connected to the positive voltage supply (i.e., to logic "1"), the AND gate will output a "0" signal. However, when movable conductor 4302 bridges the two wires connecting to the respective inputs of the AND gate, both inputs will now be logically positive, and the AND gate will output a "1" signal. Depending on which AND gate outputs a logical "1" at any given time, it may be determined which two wires are being bridged by the movable conductor 4302. In various embodiments, other methods (e.g., other logic gates, etc.) may be used to determine which wires are bridged at any given time.

By sequentially detecting which wires are being bridged, a trajectory (or some information about a trajectory) of movable conductor 4302 may be inferred. Since movable conductor 4302 is under the influence of gravity, it may thereby be inferred how the headset has moved so as to change the relative location of movable conductor 4302 within capsule 4308. For example, if movable conductor 4302 is detected bridging wires 4312*a* and 4312*b*, it may be inferred that such wires are closest to the physical ground at the moment. In various embodiments, headset 4300 may contain multiple capsules, each with wires in different orientations relative to one another. In this way, for example, more precise positioning information may be obtained.

In various embodiments, repeatedly sampled position information from one or more sensors such as sensor 4301 may be differentiated to obtain velocity information, and may be twice differentiated to obtain acceleration information.

As will be appreciated, sensor 4301 represents a method of obtaining motion data according to some embodiments, but any suitable sensor or sensors may be used in various embodiments.

Motion sensor 4301 and other motion sensors may be found in U.S. Pat. No. 8,315,876, entitled "Headset wearer identity authentication with voice print or speech recognition" to Reuss issued Nov. 20, 2012, at columns 7-9, which is hereby incorporated by reference.

Figure 44:
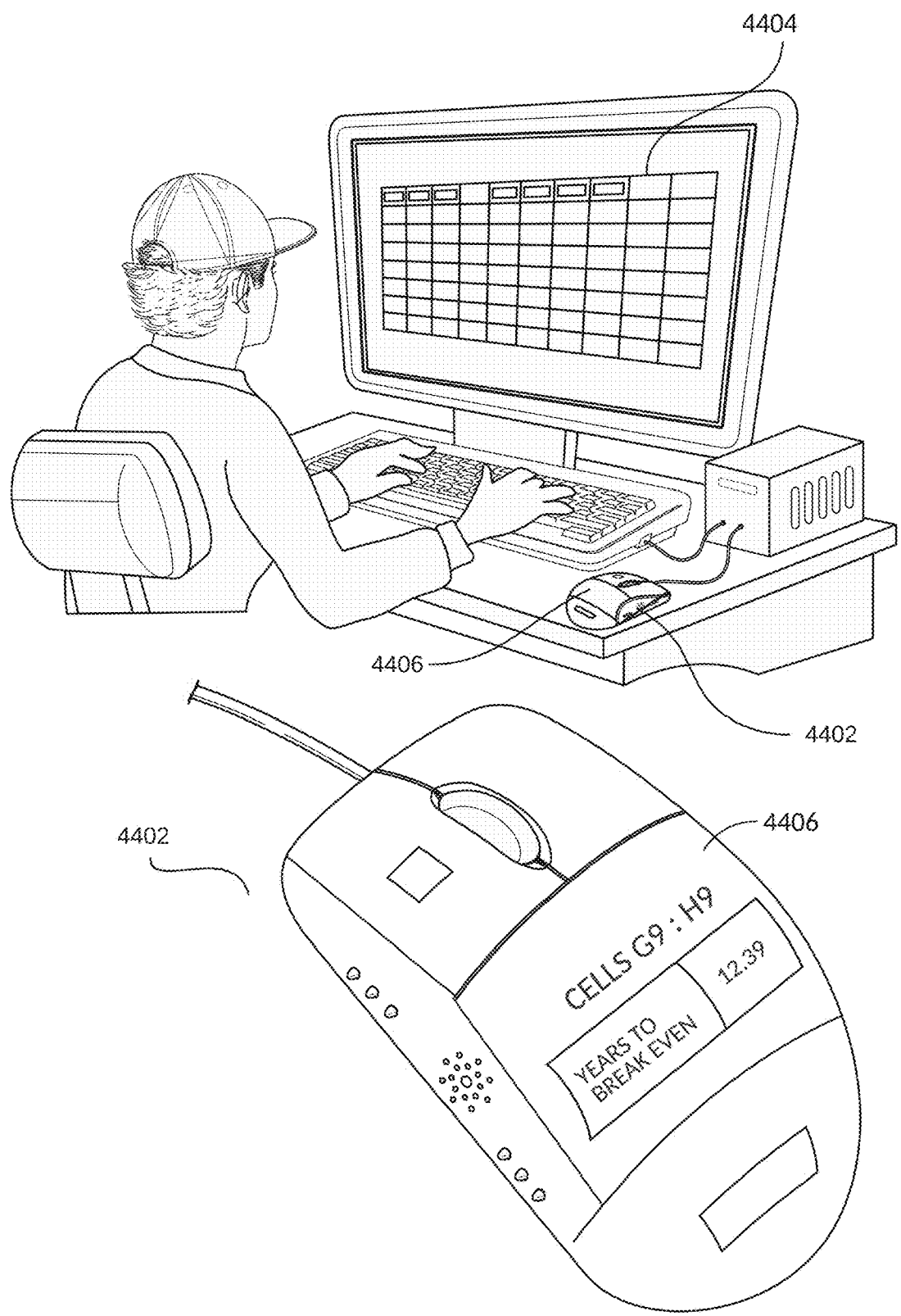
FIG. 44 is a mouse with displayed information consistent with at least some embodiments described herein.

With reference to FIG. 44, a mouse 4402 used in cooperation with a computer application 4404 according to some embodiments is shown. Note that the same mouse 4402 is shown in both a proportionate view, and an exploded view for added clarity. As depicted, a user at a user device is interacting with a spreadsheet program. The user may wish to monitor the contents of a particular group of cells in the spreadsheet program, even while the user interacts with other, distant cells. Under normal circumstances, the user might not be able to keep both of (1) the monitored cells and (2) the cells with which he is currently interacting, on the same screen. Thus, the user has configured his mouse to display the monitored group of cells. The user may now save time by modifying the distant cells and watching the impact of such modifications on the monitored cells (shown on his mouse at 4406), without having to constantly move back and forth on the computer monitor. In some embodiments, a headset 4000 may be used to gather information about what spreadsheet cells a user is looking at.

Figure 45:
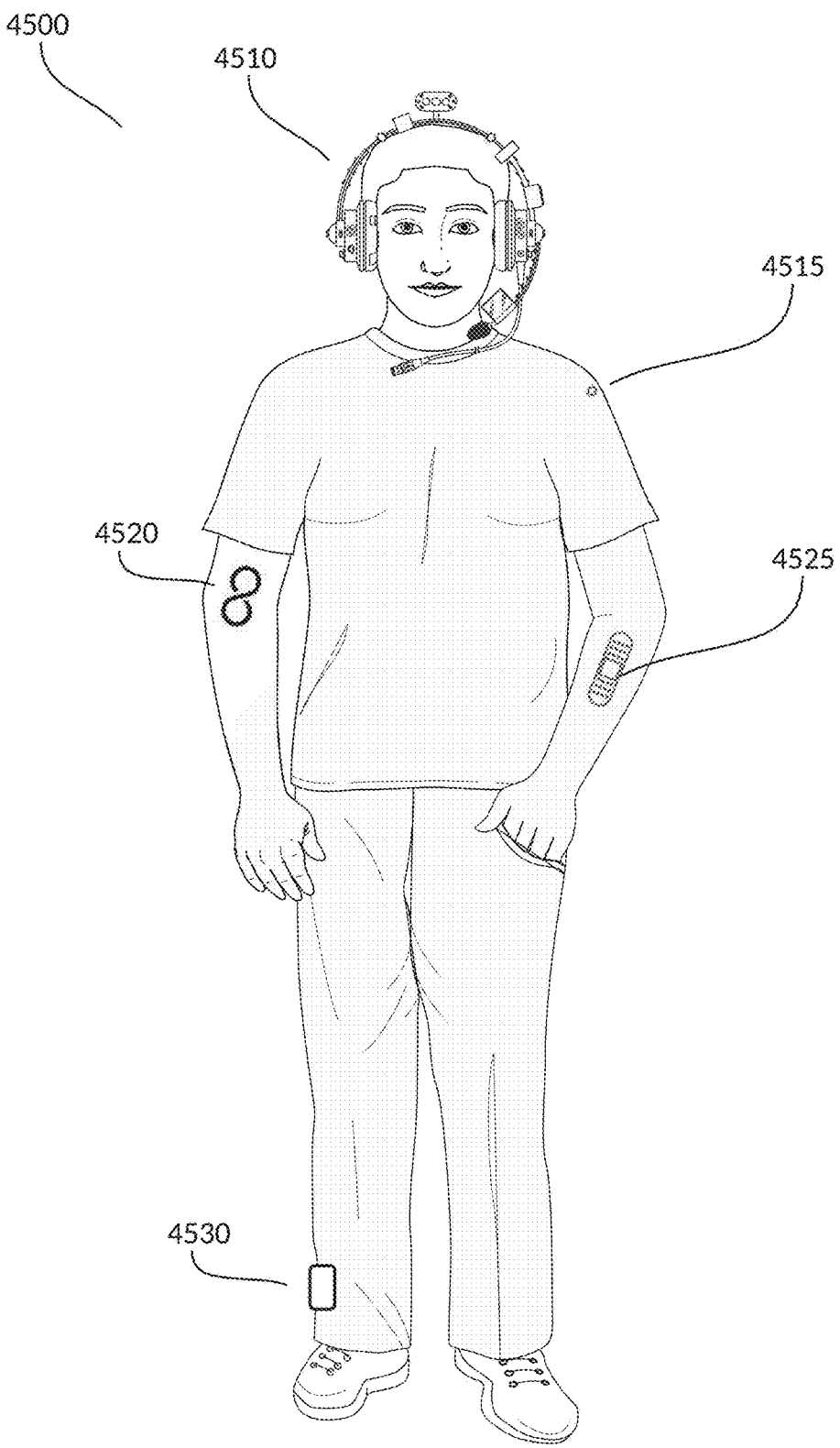
FIG. 45 is a person wearing a headset consistent with at least some embodiments described herein.

With reference to FIG. 45, person 4500 has a wearable light 4515, skin sensor 4525 and wearable sensor 4530 attached. Tattoo symbol 4520 is also an image on the skin of user 4500 that uniquely identifies the person to the tattoo. User is also wearing headset 4510 which may include any of the functionality of headset 4000 of FIG. 40 or of any other headset described herein. Wearable light 4515 may be used to communicate with headset 4510 and display a blinking or solid light to aid in illuminating a path, alerting others (e.g. emergencies, approaching from a distance) or alerting the user (e.g. obstructions, health emergencies, biometric awareness). Skin sensor 4525 may detect biometric data (e.g. hydration levels, glucose levels, sodium levels, pulse or other elemental levels detectable through the skin) and communicate to the user through headset 4510 or wearable light 4515 when levels are not acceptable or within a given range. Skin sensor 4525 may also detect environmental conditions as well (e.g. pollen levels, air quality, UV exposure levels) and communicate to the user through headset 4510 or wearable light 4515. High levels of pollen on a walking path may be detected through the skin sensor and communicated to the users headset for adjustments to the route. Wearable sensor 4530 may capture movement of the user (e.g. number of steps, stride length, force of step, pace, stride width) and communicate to the user through headset 4510. As a user walks or runs, the wearable sensor may collect the stride length and communicate to the user through the headset informing them to increase or decrease their stride. A user with headset 4510 may use a camera to capture the tattoo symbol 4520 that is adhered to the skin. The headset 4510 may verify that the captured image belongs to the user and authenticate them for access to established functions (e.g. buildings, rooms, accounts, payments, devices). Other users with headsets may scan the tattoo symbol for purposes of authenticating the user. An administrative assistant with headset 4510 may need to unlock a door for the user to grant building access. The administrative assistant may scan the tattoo symbol 4520 to confirm the identity and allow access.

Figure 46:
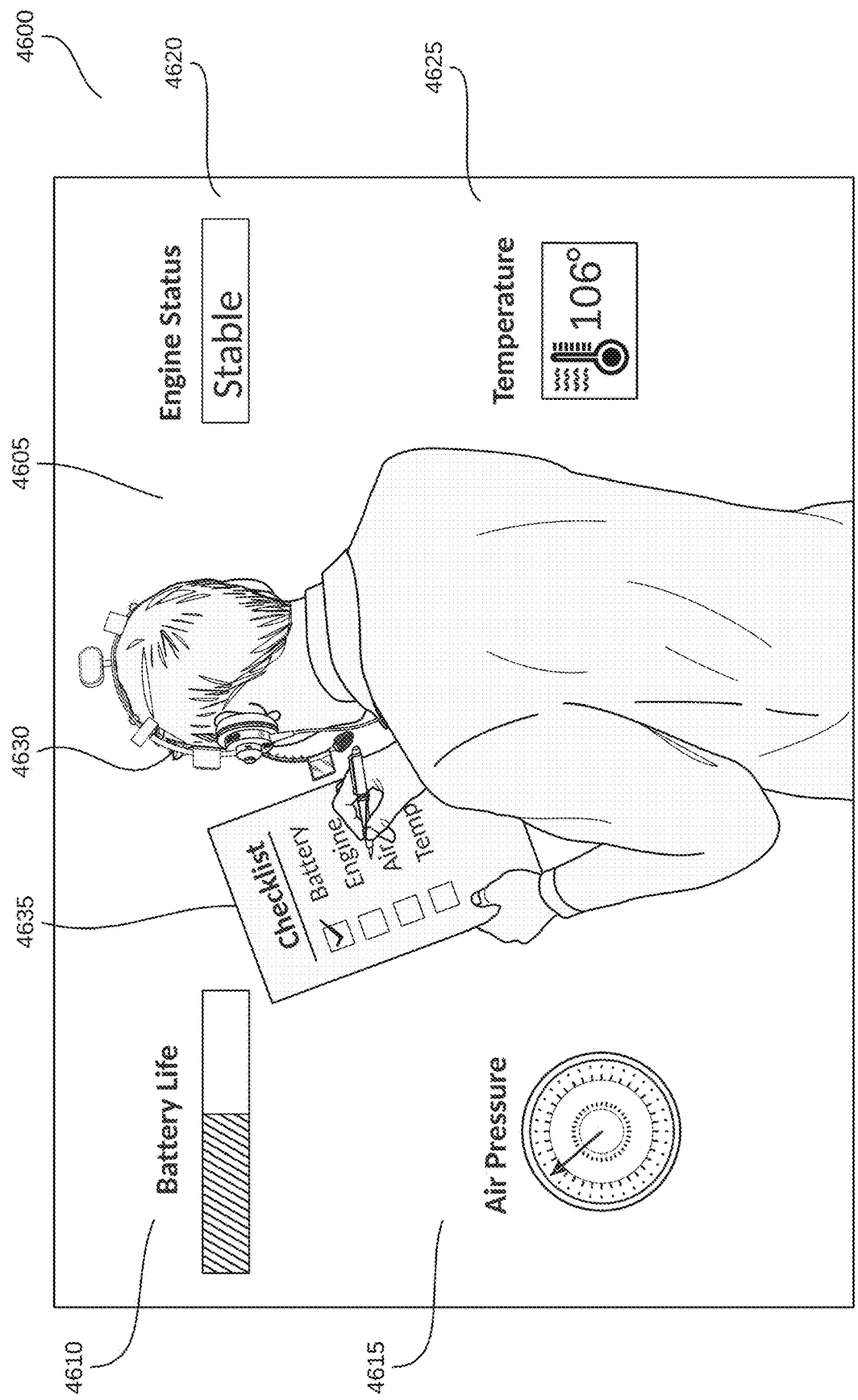
FIG. 46 is a person performing a status review process consistent with at least some embodiments described herein.

With reference to FIG. 46, a status review 4600 is shown in which a user is checking the status of various outputs from a machine. In various embodiments, headset 4630 (which may be similar to headset 4000) may facilitate the ability to detect steps on a checklist and assist the user.

In some embodiments, a user such as a machine technician is tasked with completing a checklist 4635 of items relating to status indicators of status board 4605. Status board includes indicator of battery life 4610, air pressure 4615, engine status 4620, and temperature 4625. Many more or fewer status indicators may be included on status board 4605. In some embodiments, status indicators are located on or near various machines so that the user may have to walk around in order to read the current status and mark them off as checked on checklist 4635. In some embodiments, supervisory personnel may wish to ensure that the user is diligently checking all required status indicators rather than simply checking them all off without looking at them in order to quickly complete checklist 4635, which could result in critical status updates not being identified—which could create dangerous conditions for employees or expensive breakdowns of machinery and result in halted machine output.

In various embodiments, a user headset 4630 may track the head movements of the user with accelerometers and a processor (not shown) compares the expected head movement with the actual movement. For example, once the user checks off that he has read the battery life 4610 indicator, the processor of headset 4630 may expect to see the user turn his head to the right in order to read the next status on checklist 4635 which is engine status 4620. If the user in fact makes no movement of his head to the right, the processor may send a signal to central controller 110 to alert a supervisor who can intervene to see if there is a problem with the employee completing the checklist 4635.

In some embodiments, central controller 110 may receive a video feed from the users headset 4630 and direct the user to view particular machine status indicators, obviating the need for a checklist document to be created as the video feed from the user could be read by central controller 110 to determine the status indicator values.

Figure 47:
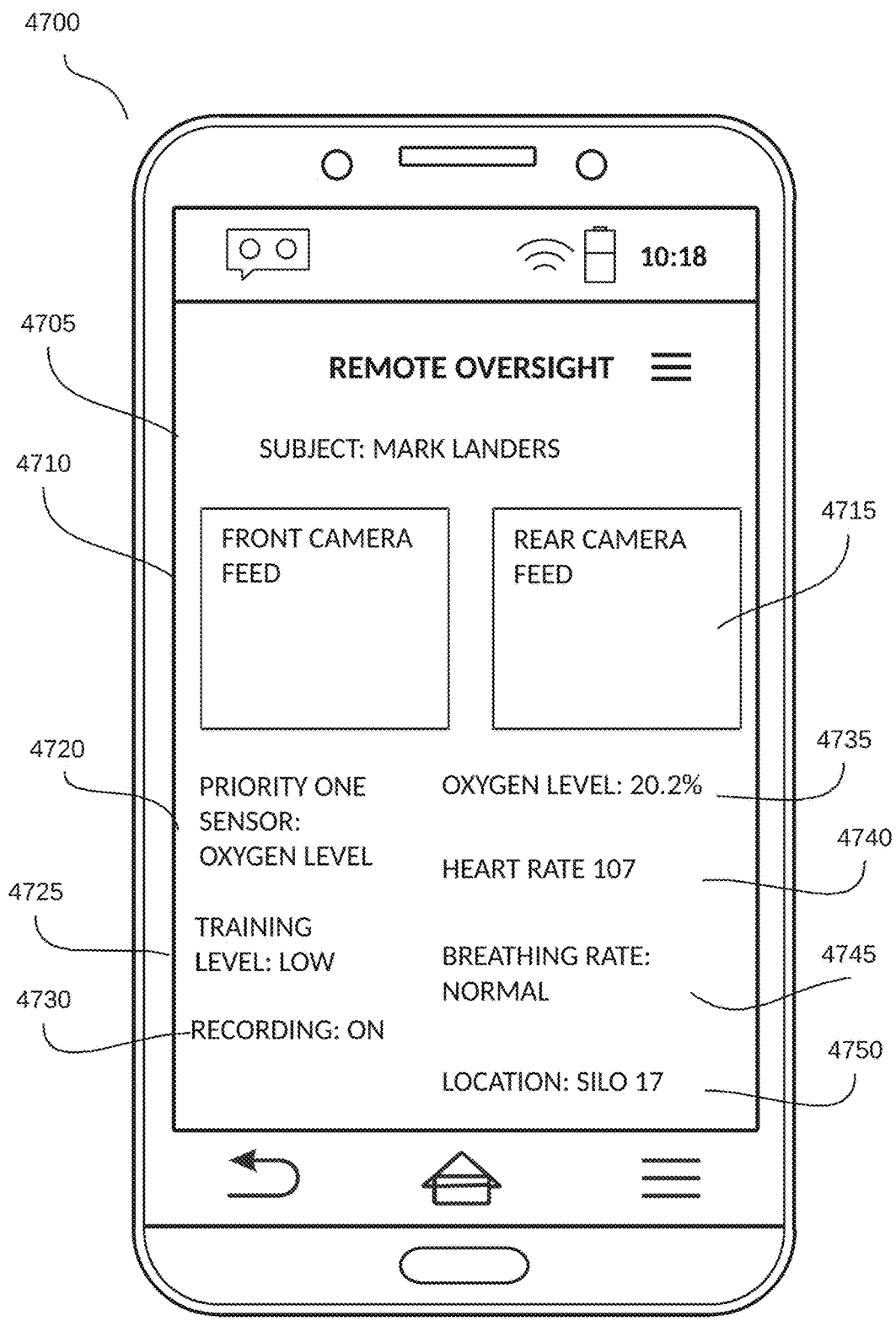
FIG. 47 is a screen from an app for interacting with a peripheral device consistent with at least some embodiments described herein.

With reference to FIG. 47, a screen 4700 from an app for interacting with a remote subject according to some embodiments is shown. In various embodiments, the app provides data and enables communication between a remote subject 4705 named Mark Landers who is wearing a headset and an observer providing oversight. In some embodiments, the subject 4705 is working in an industrial area on the repair or maintenance of a machine, with app 4700 facilitating an oversight function by a more senior observer who can provide feedback and keep an eye on the vital signs of subject 4705 and the environment of the subject. As depicted, front camera feed 4710 and rear camera feed 4715 show camera feeds from cameras in the headset of subject 4705. In some embodiments, the app may show information about subject 4705, such as a detected heart rate 4740, a breathing rate 4745, and a location 4750 (e.g. the subject is currently in silo number 17). In some embodiments, environmental data is shown, such as an oxygen level reading 4735 of 20.2%. In some embodiments, a training level 4725 indicates how well the subject has been trained in the activity that he is currently performing. An observer may also be able to select whether or not an observing session is being recorded 4730 or not. Various embodiments contemplate that any other peripheral usage data, or any other input data from a peripheral device, may be shown, may be shown over time, or may be shown in any other fashion.

In various embodiments, the app allows an observer to configure one or more parameters of a headset. In some embodiments, the app may allow an observer to select one of the sensors worn by subject 4705 to be the priority one sensor 4720, in this case the observer has selected oxygen level as the top priority.

Figure 48:
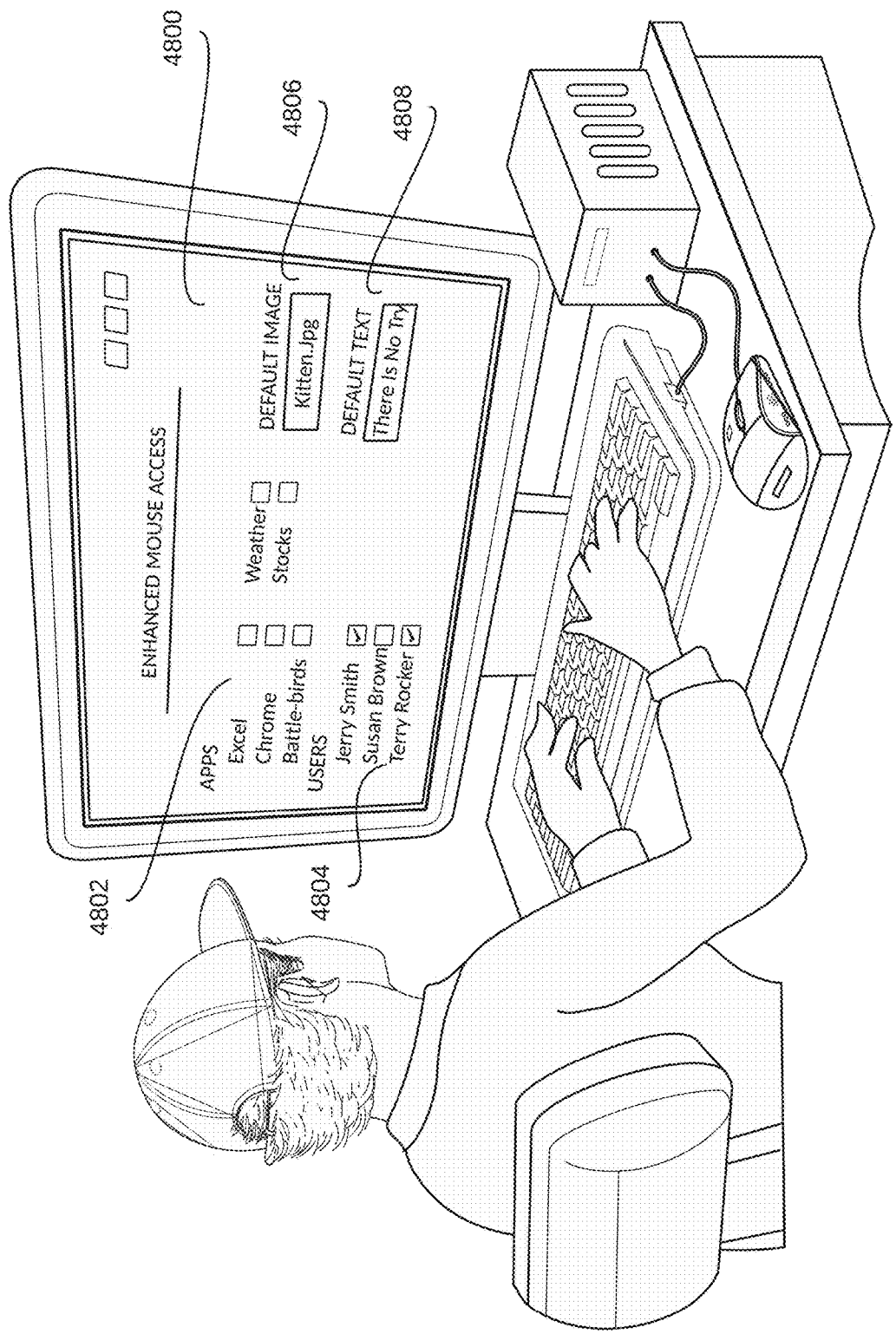
FIG. 48 is a screen for configuring a peripheral device consistent with at least some embodiments described herein.

With reference to FIG. 48, a screen 4800 for configuring a peripheral device according to some embodiments is shown. The screen may represent a screen in an app. The screen may be an output or rendering from a peripheral device. For example, a mouse may output text or graphics to a computer monitor (e.g., via a direct connection; e.g., via a user device to which the mouse is connected). The screen may be from a set-up wizard for a peripheral. Various embodiments contemplate that the user may configure a peripheral device in any suitable or applicable fashion. At 4802, the user may configure which apps will have "enhanced mouse access". Example apps include "Excel", "Chrome", "Battle-birds", etc. However, one or more alternative or additional apps may appear in various embodiments. Selected apps may interact with the mouse in non-standard, non-traditional, enhanced, etc. ways. In various embodiments, such apps may have the ability to display information on a display screen of the mouse itself. In various embodiments, such apps may have the ability to send signals, alerts or warnings to the mouse, such as by causing lights on the mouse to shine, such as by causing lights on the mouse to change colors, such as by broadcasting a tone to the mouse, such as by causing the mouse to rumble, or in any other fashion. In various embodiments, a selected app may allow a mouse to move a mouse pointer in a custom fashion, such as by following lines in the app, moving stepwise from cell to cell in a spreadsheet app, or in any other fashion.

At 4804, the user may select one or more other users or parties that may be associated with the mouse. These users may have the ability to send messages to the mouse, receive messages from the mouse, take control of the mouse, alter the function of the mouse, be on the same team as the owner of the mouse, combine inputs of the mouse with inputs from their own mouse or peripheral, or have any other relationship or any other association with the mouse. In various embodiments, for each user selected, the user may configure individual abilities or privileges (e.g., such as with a sub-menu for each selected user). At 4806, the user may designate a default image for the mouse (e.g., to be displayed on a display screen of the mouse). At 4808, the user may indicate default text that is to appear on the mouse. In various embodiments, a user may configure one or more other aspects of the mouse. In various embodiments, a user may configure special key combinations (e.g., hotkeys; e.g., short cuts) on the mouse, and match them to what the effects will be in the corresponding app. In various embodiments, parameters for configuration may be presented in any suitable order or arrangement. There may be multiple screens, multiple windows, multiple tabs, selections that become visible when scrolling down a page, etc. While screen 4800 has been depicted with respect to a mouse, various embodiments contemplate that similar screens could be used for other peripheral devices.

Figure 49:
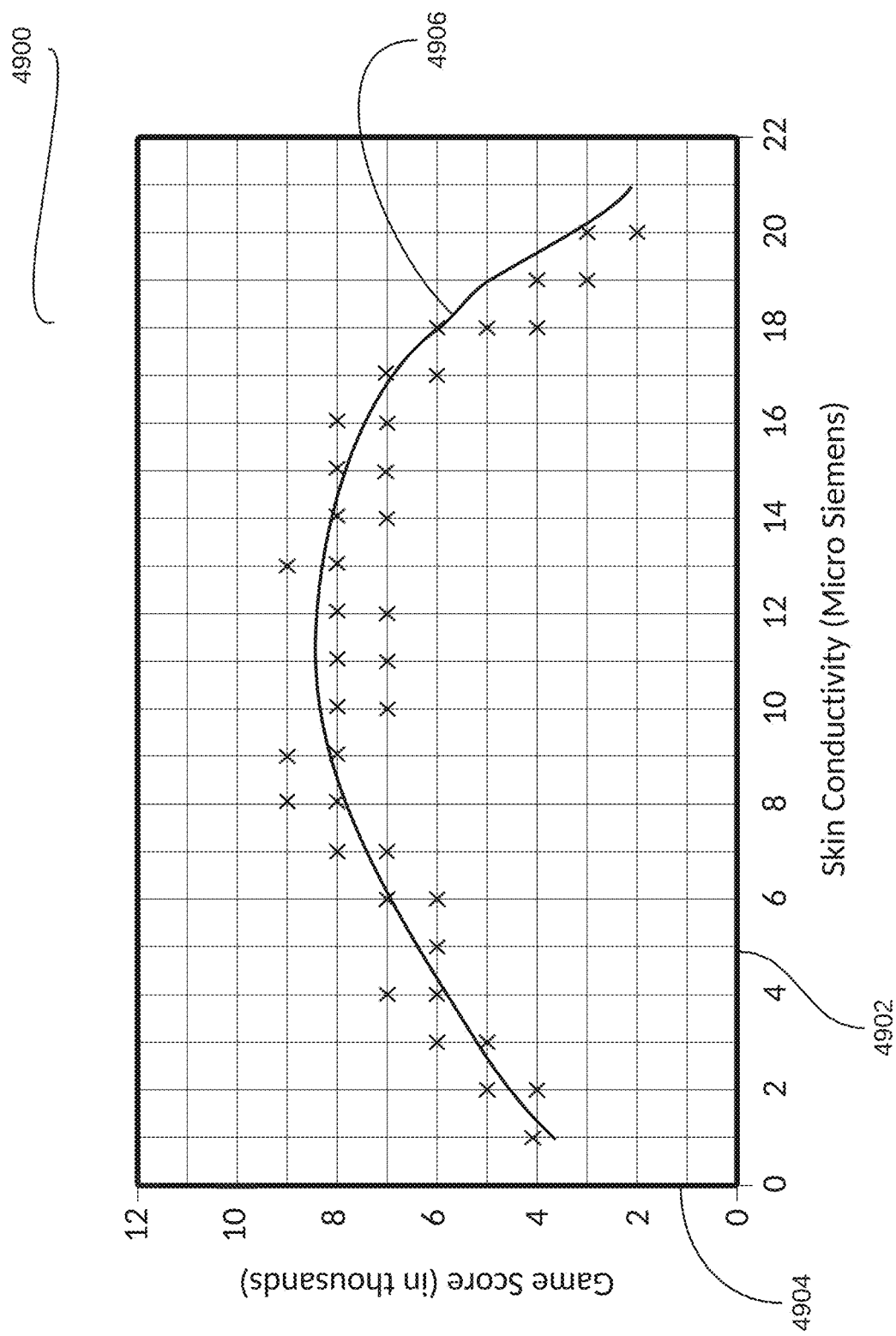
FIG. 49 is a plot of a derived machine learning model consistent with at least some embodiments described herein.

With reference to FIG. 49, a plot 4900 of a derived machine learning model according to some embodiments is shown. For the indicated model, data has been gathered relating a measured skin conductivity of a user (represented on the 'X' axis 4902) to the users score in a game (represented on the 'Y' axis 4904). Each marker in the plot represents a single data point. Using the individual data points, a machine learning program has derived a best-fit model, represented by the continuous curve 4906. The machine learning model seeks to predict a game score based on the skin conductivity, even where no data has been gathered for similar skin conductivities. In various embodiments, any suitable machine learning, artificial intelligence, or other algorithm may be used to derive a model from data. Any suitable cost or benefit function may be used, such as one that seeks to minimize a mean squared error between the model's prediction, and the measured values of the data. In various embodiments, more or less data may be used. Higher dimensional data may be used. Other types of data may be used. Other types of predictions may be made or sought.

Methods

Figure 85:
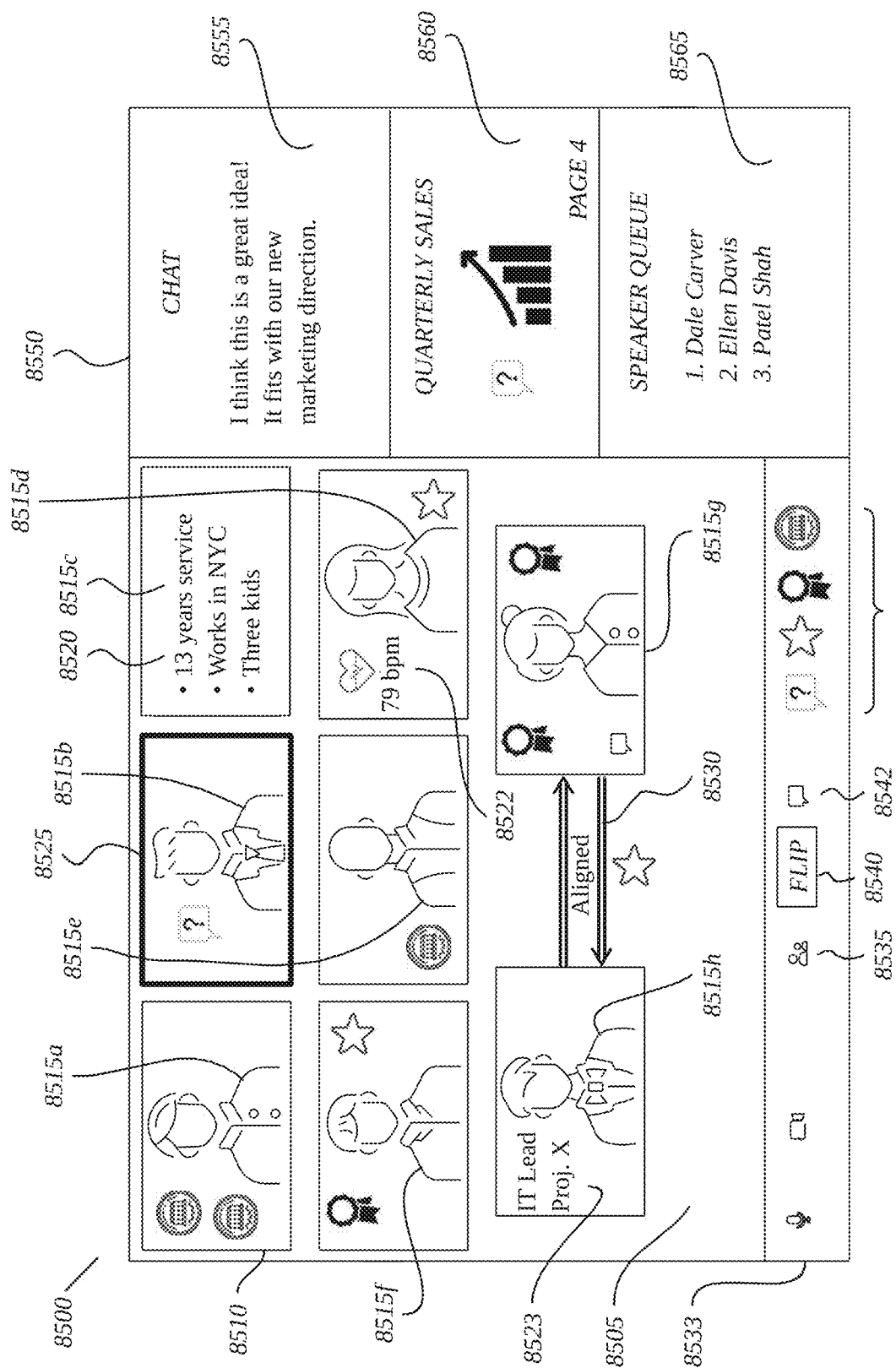
FIG. 85 is a user interface for a virtual meeting consistent with at least some embodiments described herein.
Figure 86A:
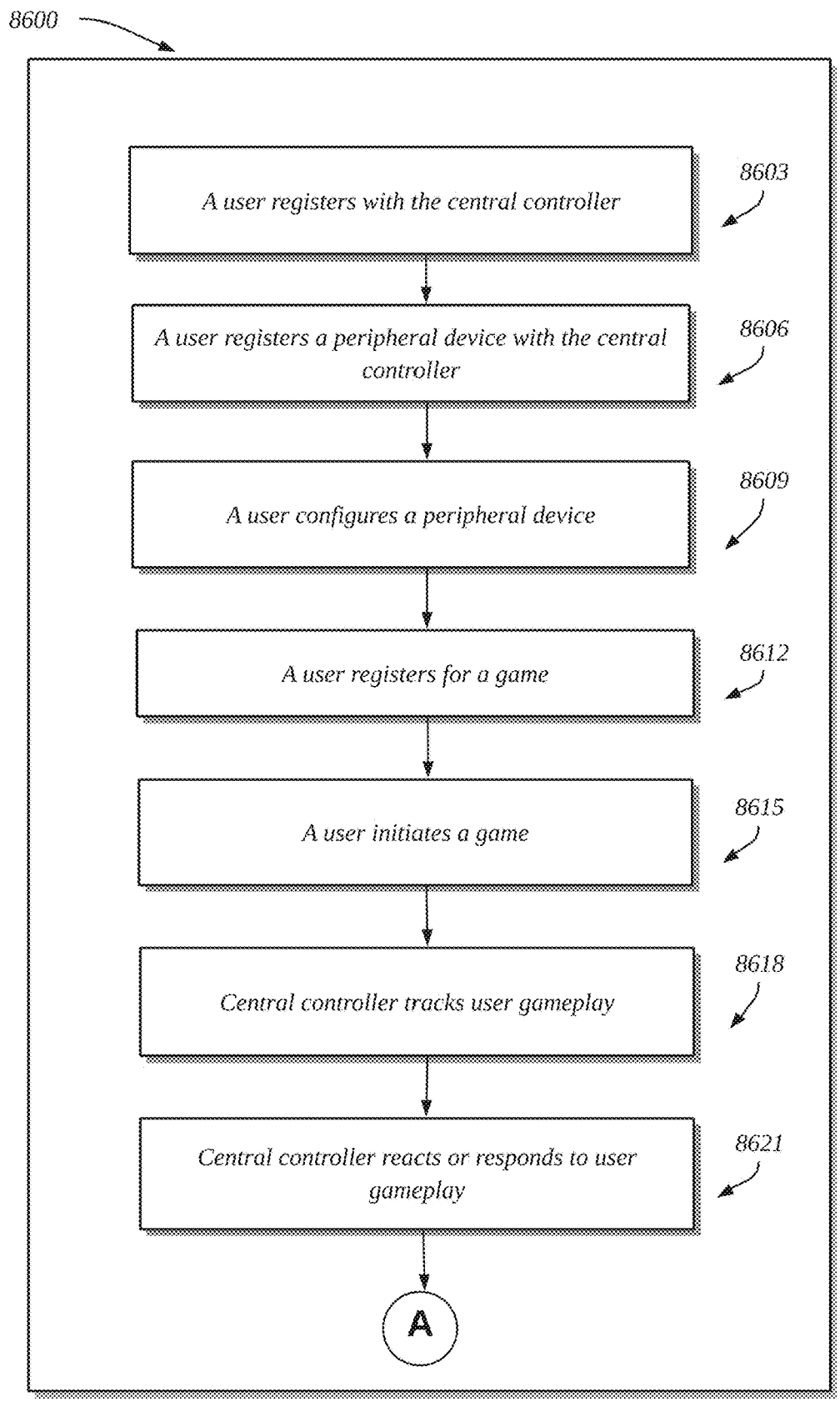
FIG. 86A, FIG. 86B, and FIG. 86C, together show a diagram of a process flow consistent with at least some embodiments described herein.
Figure 86B:
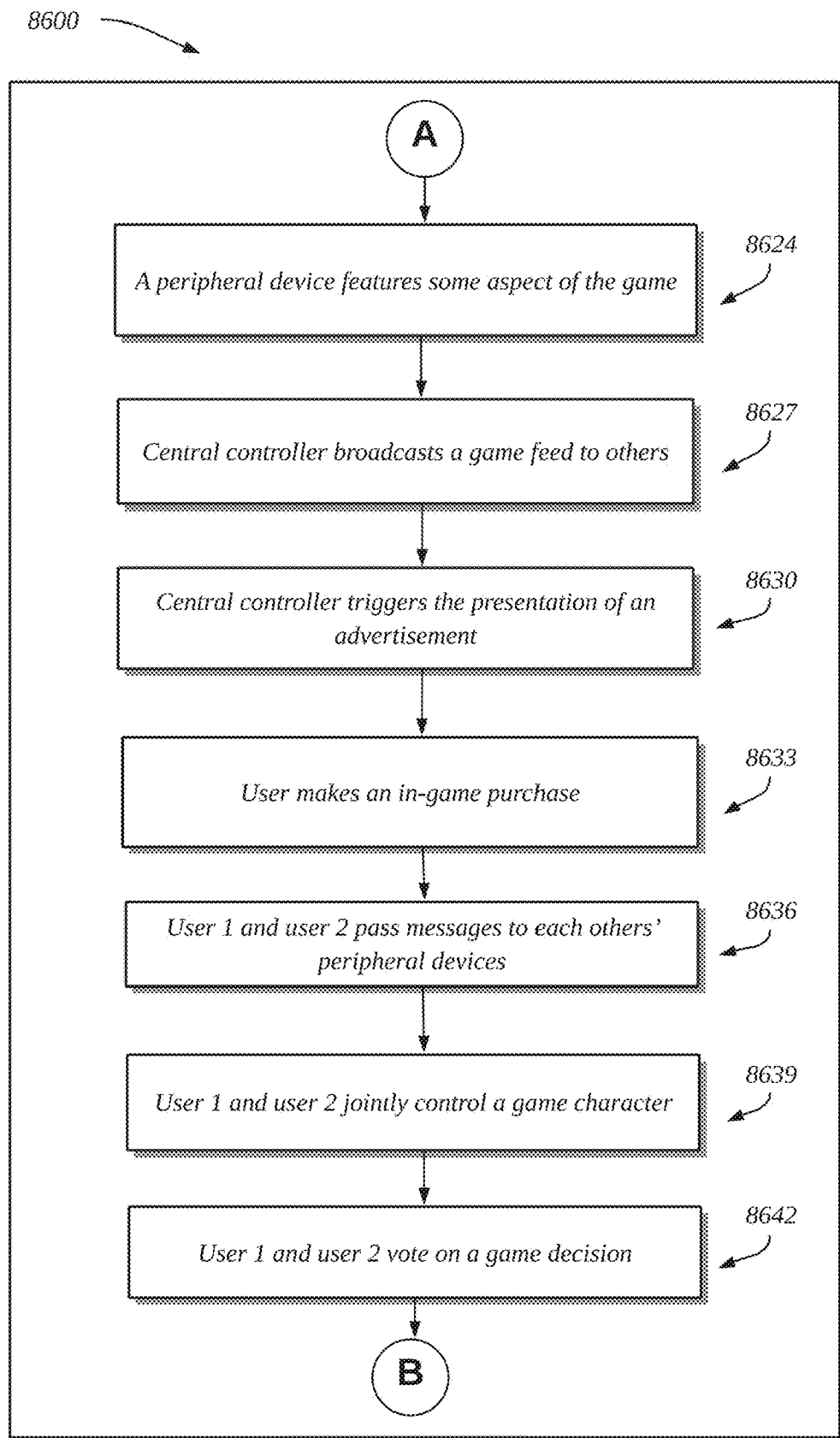
Figure 86C:
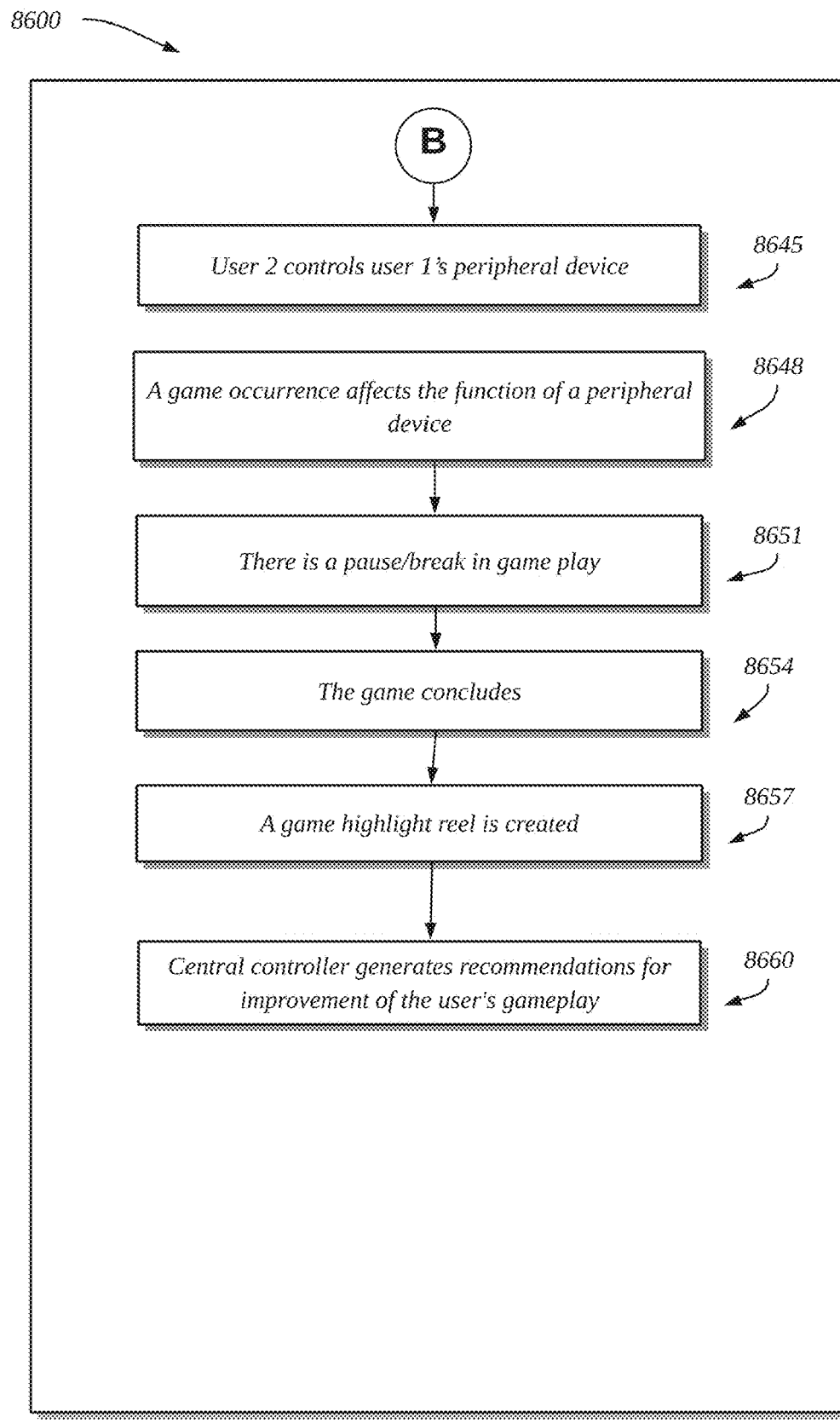

Referring now to FIGS. 86A, 86B, and 86C, a flow diagram of a method 8600 according to some embodiments is shown. In some embodiments, the method 8600 may be performed and/or implemented by and/or otherwise associated with one or more specialized and/or specially-programmed devices and/or computers (e.g., the resource devices 102*a-n*, the user devices 106*a-n*, the peripheral devices 107*a-n* and 107*p-z*, the third-party device 108, the and/or the central controller 110), computer terminals, computer servers, computer systems and/or networks, and/or any combinations thereof. In some embodiments, the method 8600 may cause an electronic device, such as the central controller 110 to perform certain steps and/or commands and/or may cause an outputting and/or management of input/output data via one or more graphical interfaces such as the interfaces depicted in FIGS. 67 and 85.

The process diagrams and flow diagrams described herein do not necessarily imply a fixed order to any depicted actions, steps, and/or procedures, and embodiments may generally be performed in any order that is practicable unless otherwise and specifically noted. While the order of actions, steps, and/or procedures described herein is generally not fixed, in some embodiments, actions, steps, and/or procedures may be specifically performed in the order listed, depicted, and/or described and/or may be performed in response to any previously listed, depicted, and/or described action, step, and/or procedure. Any of the processes and methods described herein may be performed and/or facilitated by hardware, software (including microcode), firmware, or any combination thereof. For example, a storage medium (e.g., a hard disk, Random Access Memory (RAM) device, cache memory device, Universal Serial Bus (USB) mass storage device, and/or Digital Video Disk (DVD); e.g., the data storage devices 215, 345, 445, 515, 615) may store thereon instructions that when executed by a machine (such as a computerized processor) result in performance according to any one or more of the embodiments described herein. According to some embodiments, the method 8600 may comprise various functional modules, routines, and/or procedures, such as one or more AI-based algorithm executions.

Games

A process 8600 for conducting a game with a user participating in the game is now described according to some embodiments. At step 8603, a user may register with the central controller 110, according to some embodiments. The user may access the central controller 110 by visiting a website associated with the central controller, by utilizing an app that communicates with the central controller 110, by engaging in an interactive chat with the central controller (e.g., with a chatbot associated with the central controller), by speaking with a human representative of the central controller (e.g., over the phone) or in any other fashion. The aforementioned means of accessing the central controller may be utilized at step 8603 and/or during any other step and/or in conjunction with any other embodiments. Using the example of a website, the user may type into one or more text entry boxes, check one or more boxes, adjust one or more slider bars, or provide information via any other means. Using an example of an app, a user may supply information by entering text, speaking text, transferring stored information from a smartphone, or in any other fashion. As will be appreciated, the user may supply information in any suitable fashion, such as in a way that is consistent with the means of accessing the central controller 110. The user may provide such information as a name, password, preferred nickname, contact information, address, email address, phone number, demographic information, birthdate, age, occupation, income level, marital status, home ownership status, citizenship, gender, race, number of children, or any other information. The user may provide financial account information, such as a credit card number, debit card number, bank account number, checking account number, PayPal account identifier, Venmo account identifier or any other financial account information.

In some embodiments, the user may create or establish a financial account with the central controller 110. The user may accomplish this, for example, by transferring funds from an external account (e.g., from a Venmo® account) to the central controller 110, at which point the transferred funds may create a positive balance for the user in the new account. In some embodiments, the user may provide information about one or more preferences. Preferences may relate to one or more activities, such as playing games, learning, professional development, interacting with others, participating in meetings, or doing any other activities. In the context of a game, for example, preferences may include a preferred game, a preferred time to play, a preferred character, a preferred avatar, a preferred game configuration, or any other preferences. In the context of learning, preferences may include a preferred learning format (e.g., lecture or textbook or tutorial, etc.; e.g., visual versus aural; e.g., spaced sessions versus single crash course; etc.), a subject of interest, a current knowledge level, an expertise level in prerequisite fields, or any other preferences. In various embodiments, a user may provide preferences as to desired products or services. These preferences may, for example, guide the central controller in communicating advertisements or other promotions to the user. In various embodiments, preferences may include preferences regarding any field or activity.

The central controller 110 may store user information and user preferences, such as in user table 700, user game profiles table 2700, and/or in any other table or data structure. In various embodiments, a user may provide biometric or other identifying or other authenticating information to the central controller 110. Such information may include, photographs of the user, fingerprints, voiceprints, retinal scans, typing patterns, or any other information. When a user subsequently interacts with the central controller 110, the user may supply such information a second time, at which point the central controller may compare the new information to the existing information on file to make sure that the current user is the same user that registered previously. Biometric or other authenticating information may be stored by the central controller in a table, such as in authentication table 3600. Further details on how biometrics can be used for authentication can be found in U.S. Pat. No. 7,212,655, entitled "Fingerprint verification system" to Tumey, et al. issued May 1, 2007, at columns 4-7, which is hereby incorporated by reference.

At step 8606, a user may register a peripheral device with the central controller 110, according to some embodiments. Through the process of registering a peripheral device, the central controller may be made aware of the presence of the peripheral device, the fact that the peripheral device belongs to (or is otherwise associated with) the user, and the capabilities of the peripheral device. The user may also provide to the central controller one or more permissions as to how the central controller may interact with the peripheral device. The user may provide any other information pertinent to a peripheral device. In various embodiments, registering a peripheral device may be performed partly or fully automatically (e.g., the peripheral device may upload information about its capabilities automatically to the central controller 110). The user may provide information about the peripheral itself, such as type, the manufacturer, the model, the brand, the year of manufacture, etc. The user may provide specifications for the peripheral. These specifications may indicate what buttons, keys, wheels, dials, sensors, cameras, or other components the peripheral possesses. Specifications may include the quantities of various components (e.g., a mouse may have two or three buttons; e.g., a mouse may have one, two, or more LED lights; e.g., a camera peripheral may have one, two, three, etc., cameras). Specifications may include the capabilities of a given component. For example, a specification may indicate the resolution of a camera, the sensitivity of a mouse button, the size of a display screen, or any other capability, or any other functionality.

In various embodiments, the central controller 110 may obtain one or more specifications automatically. For example, once given information about the model of a peripheral, the central controller may access a stored table or other data structure that associates peripheral models with peripheral specifications. In various embodiments, information about a peripheral may be stored in a table, such as in peripheral device table 1000. Any information stored in peripheral device table 1000 may be obtained from a user, may be obtained automatically from a peripheral, or may be obtained in any other fashion. In various environments, a user may provide the central controller with guidelines, permissions, or the like for interacting with the peripheral device. Permissions may include permissions for monitoring inputs received at the peripheral device. Inputs may include active inputs, such as button presses, key presses, touches, mouse motions, text entered, intentional voice commands, or any other active inputs. Inputs may include passive inputs (e.g., inputs supplied unconsciously or passively by the user), such as a camera image, a camera feed (e.g., a camera feed of the user), an audio feed, a biometric, a heart rate, a breathing rate, a skin temperature, a pressure (e.g., a resting hand pressure), a glucose level, a metabolite level, or any other passive input.

In some embodiments, separate permissions may be granted for separate types of inputs. In some embodiments, a global permission may be granted for all types of inputs. In some embodiments, a global permission may be granted while certain exceptions are also noted (e.g., the central controller is permitted to monitor all inputs except for heart rate). In various embodiments, permissions may pertain to how the central controller may use the information (e.g., the information can be used for adjusting the difficulty but not for selecting advertisements). In various embodiments, permissions may pertain to how long the central controller can store the information (e.g., the central controller is permitted to store information only for 24 hours). In various embodiments, permissions may pertain to what other entities may access the information (e.g., only that user's doctor may access the information). In various environments, the user may grant permissions to the central controller to output at or via the peripheral.

The user may indicate what components of the peripheral device may be used for output. For example, a mouse might have a display and a heating element. The user may grant permission to output text on the display, but not to activate the heating element. With reference to a given component, the user may indicate the manner in which an output can be made. For example, the user may indicate that a speaker may output at no more than 30 decibels, a text message on a screen may be no more than 50 characters, or any other restriction. The user may indicate when the central controller 110 may output via the peripheral (e.g., only during weekends; e.g., only between 9 p.m. and 11 p.m.). The user may indicate circumstances under which an output may be made on a peripheral. For example an output may be made only when a user is playing a particular type of game. This may ensure, for example, that the user is not bombarded with messages when he is trying to work.

In various embodiments, a user may indicate what other users or what other entities may originate a message or content that is output on the peripheral. For example, the user may have a group of friends or teammates that are granted permission to send messages that are then output on the user's peripheral device. A user may also grant permission to a content provider, an advertiser, a celebrity, or any other entity desired by the user. In various embodiments, a user may indicate what other users or entities may activate components of a peripheral device, such as triggering a heating element. In various embodiments, a user may grant permissions for one or more other users to take control of the peripheral device. Permission may be granted to take full control, or partial control. When a second user takes control of a first user's peripheral device, the second user may cause the peripheral device to transmit one or more signals (e.g., signals that control the movements or actions of a game character; e.g., signals that control the progression of slides in a slide presentation; e.g., signals that control the position of a cursor on a display screen).

It may be desirable to allow a second user to control the peripheral device of a first user under various circumstances. For instance, the second user may be demonstrating a technique for controlling a game character. As another example, the second user may be indicating a particular place on a display screen to which he wishes to call the attention of the first user (e.g., to a particular cell in a spreadsheet). In various embodiments, a user may indicate times and/or circumstances under which another user may take control of his peripheral device. For example, another user may only control a given user's peripheral device when they are on the same team playing a video game. Permissions for another user or a third-party to control a peripheral device may be stored in a table, such as in peripheral configuration table 1100 (e.g. in field 1110). Aforementioned steps (e.g., granting of permission) have been described in conjunction with a registration process. However, it will be appreciated that in various embodiments, the aforementioned steps may be performed at any suitable time and/or may be updated at any suitable time. For example, at any given time a user may update a list of other users that are permitted to control the users peripheral device. In various embodiments, a registration process may include more or fewer steps or items than the aforementioned.

At step 8609, a user may configure a peripheral device, according to some embodiments. The user may configure such aspects as the operation of the peripheral device, what key sequences will accomplish what actions, the appearance of the device, and restrictions or parental controls that are placed on the device. With regard to the operation of the peripheral device, the user may configure one or more operating variables. These may include variables governing a mouse speed, a mouse acceleration, the sensitivity of one or more buttons or keys (e.g., on a mouse or keyboard), the resolution at which video will be recorded by a camera, the amount of noise cancellation to be used in a microphone, or any other operating characteristic. Operating characteristics may be stored in a table, such as in peripheral configuration table 1100. In various embodiments, a user may configure input sequences, such as key sequences (e.g., shortcut key sequences). These sequences may involve any user input or combination of user inputs. Sequences may involve keys, scroll wheels, touch pads, mouse motions, head motions (as with a headset), hand motions (e.g., as captured by a camera) or any other user input. The user may specify such sequences using explicit descriptions (e.g., by specifying text descriptions in the user interface of a program or app, such as "left mouse button—right mouse button"), by checking boxes in an app (e.g., where each box corresponds to a user input), by actually performing the user input sequence one or more times (e.g., on the actual peripheral), or in any other fashion. For a given input sequence, a user may specify one or more associated actions. Actions may include, for example, "reload", "shoot five times", "copy formula" (e.g., in a spreadsheet), send a particular message to another user, or any other action. In various embodiments, an action may be an action of the peripheral itself. For example, pressing the right mouse button three times may be equivalent to the action of physically moving the mouse three feet to the right.

In various embodiments, a user may specify a sequence of actions that corresponds to an input sequence. For example, if the user scrolls a mouse wheel up and then down quickly, then a game character will reload and shoot five times in a row. A sequence of actions triggered by a user input may be referred to as a "macro". A macro may allow a user to accomplish a relatively cumbersome or complex maneuver with minimal input required. In some embodiments, a peripheral device (or other device) may record a user's actions or activities in a live scenario (e.g., as the user is playing a live video game; e.g., as the user is editing a document). The recording may include multiple individual inputs by the user (e.g., multiple mouse movements, multiple key presses, etc.). These multiple inputs by the user may be consolidated into a macro. Thus in the future, for example, the user may repeat a similar set of multiple inputs, but now using a shortcut input. Configuration of user input sequences may be stored in a table, such as in table "mapping of user input to an action/message" 2600.

In various embodiments, a user may configure the appearance of a peripheral device. The appearance may include a default or background image that will appear on the device (e.g., on a screen of the device). The appearance may include a color or intensity of one or more lights on the peripheral device. For example, LED lights on a keyboard may be configured to shine in blue light by default. The appearance may include a dynamic setting. For example, a display screen on a peripheral may show a short video clip over and over, or lights may cycle between several colors. An appearance may include a physical configuration. For example, a camera is configured to point in a particular direction, a keyboard is configured to tilt at a certain angle, or any other physical configuration. As will be appreciated, various embodiments contemplate other configurations of an appearance of a peripheral device. In various embodiments, a user may configure a "footprint" or other marker of a peripheral device. For example, the user may configure a mouse pointer as it appears on a user device (e.g., on a personal computer). In various embodiments, a configuration of an appearance may be stored in a table, such as in "peripheral configuration table" 1100. In various embodiments, a user may configure restrictions, locks, parental controls, or other safeguards on the use of a peripheral.

Restrictions may refer to certain programs, apps, web pages, Facebook® pages, video games, or other content. When an attempt is made to use a peripheral in conjunction with restricted content, the functionality of the peripheral may be reduced or eliminated. For example, if a user attempts to click on a link on a particular web page (e.g., a web page with restricted content), then the users mouse button may not register the user's click. In various embodiments, restrictions may pertain to the motion or other usage of the peripheral device itself. A restriction may dictate that a peripheral device cannot be moved at more than a certain velocity, cannot be moved more than a certain distance, cannot be in continuous motion for more than some predetermined amount of time, cannot output sound above a particular volume, cannot flash lights at a particular range of frequencies (e.g., at 5 to 30 hertz), or any other restriction. Such restrictions may, for example, seek to avoid injury or other harm to the user of the peripheral, or to the surrounding environment. For example, a parent may wish to avoid having a child shake a peripheral too violently while in the vicinity of a fragile crystal chandelier. In various embodiments, a peripheral may identify its current user. For example, the peripheral may identify whether an adult in a house is using a peripheral, or whether a child in a house is using the peripheral. A peripheral may explicitly ask for identification (or some means of ascertaining identification, such as a password unique to each user), or the peripheral may identify a user in some other fashion (e.g., via a biometric signature, via a usage pattern, or in any other fashion).

In various embodiments, a peripheral may require authentication for a user to use the peripheral. For example, the peripheral may require a password, fingerprint, voiceprint or other authentication. In various embodiments, restrictions or parental controls may apply to individual users. For example, only the child in a particular house is restricted from accessing certain web content or video games. In this way, after identifying a user, a peripheral may implement or enforce restrictions only if such restrictions apply to the identified user. In various embodiments, a peripheral device may not function at all with one or more users (e.g., with any user other than its owner). This may, for example, discourage someone from taking or stealing another user's peripheral. In various embodiments, a user designates restricted content by checking boxes corresponding to the content (e.g., boxes next to a description or image of the content), by providing links or domain names for the restricted content, by designating a category of content (e.g., all content rated as "violent" by a third-party rating agency; e.g., all content rated R or higher) or in any other fashion. A user may designate one or more users to which restrictions apply by entering names or other identifying information for such users, by checking a box corresponding to the user, or in any other fashion. In various embodiments, a user may set up restrictions using an app (e.g., an app associated with the central controller 110), program, web page, or in any other fashion.

At step 8612, a user may register for a game, according to some embodiments. The user may identify a game title, a time to play, a game level, a league or other desired level of competition (e.g., an amateur league), a mission, a starting point, a stadium or arena (e.g., for a sports game), a time limit on the game, one or more peripheral devices he will be using (e.g., mouse and keyboard; e.g., game console controller), a user device he will be using (e.g., a personal computer; e.g., a game console; e.g., an Xbox), a character, a set of resources (e.g., an amount of ammunition to start with; e.g., a weapon to start with), a privacy level (e.g., whether or not the game can be shown to others; e.g., the categories of people who can view the game play), or any other item pertinent to the game. In various embodiments, a user may sign a consent form permitting one or more aspects of the user's game, character, likeness, gameplay, etc. to be shown, shared, broadcast or otherwise made available to others. In various embodiments, a user may pay an entry fee for a game. The user may pay in any suitable fashion, such as using cash, game currency, pledges of cash, commitments to do one or more tasks (e.g., to visit a sponsors website), or in any other form.

In various embodiments, a user may register one or more team members, one or more opponents, one or more judges, one or more audience members, or any other participant(s). For example, the user may provide names, screen names, or any other identifying information for the other participants. In various embodiments, a user may designate a team identifier (e.g., a team name). One or more other users may then register and indicate that they are to be part of that team. Similarly, in various embodiments, a user may designate a game. Subsequently, one or more other users may then register and indicate that to are to be part of that game. Various embodiments contemplate that multiple participants may register for the same team or same game in any suitable fashion. In various embodiments, user information provided when registering with the central controller, when registering for a game, or provided at any other time or in any other fashion, may be stored in one or more tables such as in "user game profiles" table 2700. In various embodiments, when a user has registered for a game, the user may be provided with messages, teasers, reminders, or any other previews of the game. In various embodiments, a peripheral device may show a timer or clock that counts down the time remaining until the game starts. In various embodiments, a peripheral device may change colors as game time approaches. For example, the peripheral device might change from displaying a green color to displaying a red color when there are less than five minutes remaining until game time. In various embodiments, a peripheral may sound an alarm when a game is about to start.

In the lead-up to a game (or at any other time) a user may take a tutorial. The tutorial may explain how to play a game, how to efficiently play a game, how to execute one or more actions during a game, how to use a peripheral effectively during a game, or may cover any other task or subject. In various embodiments, one or more components of a peripheral will attempt to draw a user's attention during a tutorial. For example, a key or a button may blink, light up, or change color. In another example, a button may heat up or create a haptic sensation. The intention may be for the user to press or actuate whatever component is drawing attention. For example, if the tutorial is teaching a user to press a series of buttons in succession, then the buttons may light up in the order of which they should be pressed. Once the user presses a first button that has been lit, the first button may go off and a second button may light up indicating that it too should be pressed. In various environments, a tutorial uses a combination of text or visual instruction, in conjunction with hands-on actuation of peripheral device components by the user. The text or visual instruction may be delivered via a user device, via a peripheral device (e.g., via the same peripheral device that the user is actuating), or via any other means.

At step 8615, a user may initiate a game, according to some embodiments. In various embodiments, the game starts based on a predetermined schedule (e.g., the game was scheduled to start at 3 p.m., and does in fact start at 3 p.m.). In various embodiments, the user manually initiates gameplay (e.g., by clicking "start", etc.). When a user begins playing, any team members, opponents, judges, referees, audience members, sponsors, or other participants may also commence their participation in the game. In various embodiments, a user may join a game that has been initiated by another user. For example, the user may join as a teammate to the initiating user or as some other participant.

At step 8618, the central controller 110 may track user gameplay, according to some embodiments. The central controller 110 may track one or more of: peripheral device use; game moves, decisions, tactics, and/or strategies; vital readings (e.g., heart rate, blood pressure, etc.); team interactions; ambient conditions (e.g., dog barking in the background; local weather); or any other information. In various embodiments, the central controller 110 may track peripheral device activity or use. This may include button presses, key presses, clicks, double clicks, mouse motions, head motions, hand motions, motions of any other body part, directions moved, directions turned, speed moved, distance moved, wheels turned (e.g., scroll wheels turned), swipes (e.g., on a trackpad), voice commands spoken, text commands entered, messages sent, or any other peripheral device interaction, or any combination of such interactions. The peripheral device activity may be stored in a table, such as in 'peripheral activity log' table 2200. Each activity or action of the peripheral device may receive a timestamp (e.g., see fields 2206 and 2208). In this way, for example, peripheral device activity may be associated with other circumstances that were transpiring at the same time. For example, a click of a mouse button can be associated with a particular game state that was in effect at the same time, and thus it may be ascertainable what a user was trying to accomplish with the click of the mouse (e.g., the user was trying to pick up a medicine bag in the game).

Peripheral device activities may be stored in terms of raw signals received from the peripheral device (e.g., bit streams), higher-level interpretations of signals received from the peripheral device (e.g., left button clicked), or in any other suitable fashion. In various embodiments, two or more actions of a peripheral device may be grouped or combined and stored as a single aggregate action. For example, a series of small mouse movements may be stored as an aggregate movement which is the vector sum of the small mouse movements. In various embodiments, the central controller may track vital readings or other biometric readings. Readings may include heart rate, breathing rate, brain waves, skin conductivity, body temperature, glucose levels, other metabolite levels, muscle tension, pupil dilation, breath oxygen levels, or any other readings. These may be tracked, for example, through sensors in a peripheral device. Vital readings may also be tracked indirectly, such as via video feed (e.g., heart rate may be discerned from a video feed based on minute fluctuations in skin coloration with each heartbeat). Vital readings or biometrics may be tracked using any suitable technique.

In some embodiments, the vital readings of a first user may be broadcast to one or more other users. This may add a level of excitement or strategy to the game. For example, one player may be able to discern or infer when another player is tense, and may factor that knowledge into a decision as to whether to press an attack or not. In various embodiments, the central controller 110 may track ambient conditions surrounding gameplay. These may include room temperature, humidity, noise levels, lighting, local weather, or any other conditions. The central controller may track particular sounds or types of sounds, such as a dog barking in the background, a horn honking, a doorbell ringing, a phone ringing, a tea kettle sounding off, or any other type of sound. In various embodiments, ambient conditions may be correlated to a user's gameplay. For example, the central controller 110 may determine that the user tends to perform better in colder temperatures. Therefore, ambient conditions may be used to make predictions about a user's game performance, or to recommend to a user that he seek more favorable ambient conditions (e.g., by turning on the air conditioning). In various embodiments, ambient conditions may be detected using one or more sensors of a peripheral device, using a local weather service, or via any other means.

In various embodiments, the central controller 110 may track game moves, decisions, tactics, strategies, or other game occurrences. Such a occurrences may include a weapon chosen by a user, a road chosen by a user, a path chosen, a door chosen, a disguise chosen, a vehicle chosen, a defense chosen, a chess move made, a bet made, a card played, a card discarded, a battle formation used, a choice of which player will covered which other player (e.g., in a combat scenario, which player will protect the back of which other player), a choice of close combat versus distant combat, or any other game choice made by a player or team of players. In various embodiments, the central controller may track decisions made by referees, judges, audience members, or any other participants. In various embodiments, the central controller 110 may track team interactions. The central controller may track text messages, messages, voice messages, voice conversations, or other signals transmitted between team members. The central controller may track resources passed between player characters (e.g., ammunition or medical supplies transferred). The central controller may track the relative positioning of player characters. The central controller may track any other aspect of team interaction. In various embodiments, the central controller 110 may utilize an aspect of a user's gameplay to identify the user. For example, the user may have a unique pattern of moving a mouse or hitting a keyboard. In some embodiments, a user may be subsequently authenticated or identified based on the aspect of the user's gameplay.

At step 8621, the central controller 110 may react or respond to user gameplay, according to some embodiments. In various embodiments, the central controller may adjust one or more aspects of the game (e.g., difficulty level) based on user gameplay. The central controller may increase difficulty level if the user is scoring highly relative to other users, or relative to the current users prior scores at the same game. The central controller may decrease difficulty level if the user is scoring poorly relative to other users, is dying quickly, or is otherwise performing poorly. In various embodiments, if a user is primarily or overly reliant on one resource (e.g., on one particular weapon or vehicle), or on a small group of resources, then the central controller 110 may steer the game in such a way that the one resource (or small group of resources) is no longer as useful. For example, if the user has been relying on a motorcycle as transportation, then the central controller may steer the game such that the user has to navigate a swamp area where other vehicles (e.g., a canoe) may be preferable to a motorcycle. This may incentivize the user to become acquainted with other resources and/or other aspects of the game. In various embodiments, the central controller 110 may steer a game towards circumstances, situations, environments, etc., with which the player may have had relatively little (or no) experience. This may encourage the player to gain experience with other aspects of the game.

In various embodiments, elements of ambient conditions may be incorporated into a game itself. For example, if the central controller 110 detects a dog barking in the background, then a dog might also appear within a game. In various embodiments, the central controller 110 may advise or tell the user of an action to take based on observations of the user's gameplay. If the central controller has detected low metabolite levels (e.g., low sugar or low protein) with the user, the central controller may advise the user to eat and/or to quit. In various embodiments, the central controller may infer user health status from game play. In various embodiments, one or more vital signs (e.g., blood pressure) may be obtained directly or indirectly from sensors. In various embodiments, the central controller may utilize user actions as an indicator of health state or status. If a user's game performance has declined, then this may be indicative of health problems (e.g., dehydration, fatigue, infection, heart attack, stroke, etc.). In various embodiments, game performance may be measured in terms of points scored, points scored per unit of time, opponents neutralized, levels achieved, objectives achieved, time lasted, skill level of opponents beaten, or in terms of any other factor.

A decline in game performance may be defined as a reduced performance during a given time interval (e.g., the last 15 minutes, today, the most recent seven days) versus game performance in a prior time interval (e.g., the 15-minute period ending 15 minutes ago; e.g., the 15-minute period ending one hour ago; e.g., the 15-minute period ending this time yesterday; e.g., the day before yesterday; the seven-day period ending seven days ago; etc.). In various embodiments, the central controller may monitor for a decline of a certain amount (e.g., at least 10%) before conclusively determining that performance has declined. In various embodiments, a player's performance may be compared to that of other players (such as to that of other players of a similar skill level, such as to that of other players with a similar amount of experience, such as to all other players). If a player's performance is significantly worse than that of other players (e.g., 20% or more worse), then the central controller 110 may infer a health problem.

In various embodiments, improvements in a player's performance may be used to infer positive changes in health status (e.g., that the user is better rested; e.g., that the user has overcome an illness; etc.). In various embodiments, the central controller 110 may combine data on vital signs with data on player performance in order to infer health status. For example, an increased body temperature coupled with a decline in performance may serve as a signal of illness in the player. In various embodiments, the central controller 110 may initiate recording and/or broadcasting of user gameplay based sensor readings from a peripheral. Such sensor readings may include readings of vital signs. The central controller may also initiate recording and/or broadcasting based on inferred vital signs. This may allow the central controller, for example, to detect a level of excitement with the user, and initiate recording when the user is excited. The central controller may thereby capture footage that is more likely to be exciting, interesting, memorable, or otherwise noteworthy. In various embodiments, the central controller 110 may initiate recording when a user's heart rate exceeds a certain level. The level may be an absolute heart rate (e.g., one hundred beats per minute) or a relative heart rate (e.g., 20% above a user's baseline heart rate). In various embodiments, the central controller may initiate recording in response to a change in skin conductivity, blood pressure, skin coloration, breath oxygen levels, or in response to any other change in a user's vital signs.

In various embodiments, the central controller 110 may stop or pause recording when a user's vital sign or vital signs have fallen below a certain threshold or have declined by predetermined relative amount. In various embodiments, the central controller 110 may start recording or broadcasting when vital signs have fallen below a certain threshold (or decreased by a certain relative amount). The central controller may stop or pause recording when vital signs have increased above a certain threshold. In various embodiments, the central controller 110 may use a combination of sensor readings (e.g., of user vital signs) and user gameplay as a determinant of when to commence or terminate recording. For example, if the user's heart rate increases by 10% and the number of clicks per minute has increased by 20%, then the central controller may commence recording. In various embodiments, the central controller may track sensor inputs or other inputs from other users or participants, such as from audience members. These inputs may be used to determine when to start or stop recording or broadcasting. For example, the central controller may detect excitement levels in an audience member, and may thereby decide to record the ensuing gameplay action, as it may have a high chance of being interesting.

At step 8624, a peripheral device may feature some aspect of the game, according to some embodiments. In various embodiments, a peripheral device may feature, convey, or otherwise indicate some aspect of the game. A peripheral may explicitly display information, such as an amount of ammunition remaining with a player, a number of damage points sustained by a player, a set of coordinates detailing a player's location in a game, the number of opponent characters within a particular radius of the player's character, or any other game information. The information may be displayed using alphanumeric characters, bar graphs, graphs, or using any other means of presentation. In various embodiments, game information may be conveyed by a peripheral indirectly. In various embodiments, the color of a component of a peripheral (e.g., of an LED) may vary based on the health of the player's game character. For instance, if the game character is at full strength, the LED may be green, while if the game character is one hit away from dying, then the LED may be red. In various embodiments, the LED may show a range of colors between red and green (e.g., each color within the range having a different mixture of red and green), to convey intermediate health statuses of the game character.

In various embodiments, a peripheral device may convey game information using a level of sound (e.g., louder sounds convey poorer health statuses of the game character), using a volume of sound, using a pitch of sound, using a tempo (e.g., which can be varied from slow to fast), using vibrations, using a level of heat, using a level of electric shock, or via any other means. In various embodiments, a peripheral device may display or otherwise convey an attribute of another player, such as an attribute of another player's gameplay or a vital sign of another player. For example, a peripheral device may display the heart rate of another player. As another example, the color of a component of a peripheral device may cycle in sync with the breathing cycle of another player (e.g., the LED varies from orange on an inhale to yellow on an exhale then back to orange on the next inhale, and so on).

At step 8627, the central controller 110 may broadcast a game feed to others, according to some embodiments. For example, the feed may be broadcast via Twitch, via another streaming platform, via television broadcast, or via any other means. In various embodiments, part or all of a feed may be broadcast to a peripheral device, such as a peripheral device of an observing user. A feed may seek to mimic or replicate the experience of the playing user with the observing user. For example, if the playing user is receiving haptic feedback in his mouse, then similar haptic feedback may be broadcast to an observing user's mouse.

At step 8630, the central controller 110 may trigger the presentation of an advertisement, according to some embodiments. In various embodiments, step 8630 may include the presentation of a promotion, infomercial, white paper, coupon, or any other similar content, or any other content. The advertisement may be triggered based on one or more factors, including: events in the game; detected user gameplay; sensor inputs; detected user vital signs; stored user preferences; ambient conditions; or based on any other factors. For example, upon detection of low glucose levels, an ad for a candy bar may be triggered. The advertisement may be presented to the user in various ways. the advertisement may appear within the gaming environment itself, such as on an in-game billboard. The advertisement may appear in a separate area on a screen, such as on the screen of a user device. The advertisement may appear as an overlay on top of the game graphics. The advertisement may temporarily interrupt gameplay, and may, e.g., appear full screen. In various embodiments, an advertisement may appear in full or in part on a peripheral device. For example, an advertisement may appear on a display screen of a mouse or of a keyboard. In various embodiments, a company's colors may be displayed with lights on a peripheral device. For example, LED Lights on a mouse may shine in the red white and blue of the Pepsi logo when a Pepsi advertisement is featured. In various embodiments, a peripheral device may broadcast sound, vibrations, haptic feedback, or other sensory information in association with an advertisement. For example, in conjunction with an advertisement for potato chips, a mouse may rumble as if to mimic the crunching of a potato chip.

At step 8633, the user makes an in-game purchase, according to some embodiments. The user may purchase a game resource (e.g., a weapon, vehicle, treasure, etc.), an avatar, an aesthetic (e.g., a background image; e.g., a dwelling; e.g., a landscape), a game shortcut (e.g., a quick way to a higher-level or to a different screen; e.g., a quick way to bypass an obstacle), a health enhancement for a game character, a revival of a dead character, a special capability (e.g., invisibility to other players, e.g., flight), or any other item pertinent to a game. In various embodiments, the user may purchase an item external to a game, such as an item that has been advertised to the user (e.g., a pizza from a local restaurant). In various embodiments, the user may make a purchase using a financial account, such as a financial account previously registered or created with the central controller 110. In various embodiments, prior to completing a purchase, the user may be required to authenticate himself. To authenticate himself, a user may enter a password, supply a biometric, and/or supply a pattern of inputs (e.g., mouse movements, e.g., keystrokes) that serve as a unique signature of the user. In various embodiments, an amount of authentication may increase with the size of the purchase. For example, one biometric identifier may be required for a purchase under $10, but two biometric identifiers may be required for a purchase over $10.

At step 8636, User 1 and user 2 pass messages to each other's peripheral devices, according to some embodiments. In various embodiments, a message may include words, sentences, and the like, e.g., as with traditional written or verbal communication. A message may include text and/or spoken words (e.g., recorded voice, e.g., synthesized voice). In various embodiments, a message may include images, emojis, videos, or any other graphic or moving graphic. In various embodiments, a message may include sounds, sound effects (e.g., a drum roll; e.g., a well-known exclamation uttered by a cartoon character) or any other audio. In various embodiments, a message may include other sensory outputs. A message may include instructions to heat a heating element, instructions for generating haptic sensations, instructions for increasing or decreasing the resistance of a button or scroll wheel or other actuator, instructions for releasing scents or perfumes or other olfactory stimulants, or instructions for inducing any other sensation. For example, user 1 may wish to send a message to user 2 with text "you are on fire!" and with instructions to increase the temperature of a heating element in user 2's mouse. The message may generate increased impact for user 2 because the message is experienced in multiple sensory modalities (e.g., visual and tactile).

In various embodiments, a user may explicitly type or speak a message. In various embodiments, a user may employ a sequence of inputs (e.g., a shortcut sequence) to generate a message. The central controller 110 may recognize a shortcut sequence and translate the sequence using one or more tables, such as "mapping of user input to an action/message" table 2600 and "generic actions/messages" table 2500. In various embodiments, a user may receive an alert at his peripheral device that he has received a message. The user may then read or otherwise perceive the message at a later time. The alert may comprise a tone, a changing color of a component of the peripheral device, or any other suitable alert. In various embodiments, a message may include an identifier, name, etc., for an intended recipient. In various embodiments, a message may include an indication of a peripheral device and/or a type of peripheral device that is the intended conveyor of the message. In various embodiments, a message may include an indication of a combination of devices that are the intended conveyors of the message. For example, a message may include instructions for the message to be conveyed using a mouse with a display screen and any peripheral device or user device with a speaker. In various embodiments, a message may be broadcast to multiple recipients, such as to all members of a gaming team. The message may be presented to different recipients in different ways. For example the recipients might have different peripheral devices, or different models of peripheral devices. In various embodiments, a message may contain instructions for conveying the message that specify a device-dependent method of conveyance. For example, if a recipient has a mouse with LED lights, then the LED lights are to turn purple. However, if a recipient has a mouse with no LED lights, then the recipient's computer monitor is to turn purple.

At step 8639, User 1 and user 2 jointly control a game character, according to some embodiments. In various embodiments, user 1 may control one capability of the game character while user 2 controls another capability of the game character. Different capabilities of the same game character may include: moving, using a weapon, firing a weapon, aiming a weapon, using individual body parts (e.g., arms versus legs; e.g., arms for punching versus legs for kicking), looking in a particular direction, navigating, casting a spell, grabbing or procuring an item of interest (e.g., treasure, e.g., medical supplies), building (e.g., building a barricade), breaking, solving (e.g., solving an in-game puzzle), signaling, sending a message, sending a text message, sending a spoken message, receiving a message, interpreting a message, or any other capability. For example, user 1 may control the movement of a character, while user 2 may control shooting enemy characters with a weapon. For example, user 1 may control the arms of a character, while user 2 may control the legs of a character. For example, user 1 may control the movement of a character, while user 2 communicates with other characters. In various embodiments, user 1 and user 2 jointly control a vehicle (e.g., spaceship, tank, boat, submarine, robot, mech robot), animal (e.g., horse, elephant), mythical creature (e.g., dragon, zombie), monster, platoon, army, battalion, or any other game entity. For example, user 1 may control the navigation of a spaceship, while user 2 may control shooting enemy spaceships.

In operation, the central controller 110 may receive inputs from each of user 1 and user 2. The central controller may interpret each input differently, even if they are coming from similar peripheral devices. For example, inputs from user 1 may be interpreted as control signals for a character's legs, while inputs from user 2 are interpreted as control signals for a character's arms. Prior to a game (e.g., during registration), two or more users may indicate an intent to control the same character. The users may then collectively select what aspect of the character each will control. For example, each user may check a box next to some aspect of a character that they intend to control. Subsequently, the central controller may interpret control signals from the respective users as controlling only those aspects of the character for which to respectively signed up. In various embodiments, one or more users may indicate an intent to control the same character at some other time, such as after a game has started. In various embodiments, inputs from two or more users may be combined or aggregated in some way to control the same character, and even to control the same aspect(s) of the same character. For example, the motion of a character may be determined as the sum of the control signals from the respective users. For example, if both user 1 and user 2 attempt to move the character to the right, then the character may in fact move right. However, if user 1 and user 2 attempt to move the character in opposite directions, then the character may not move at all. In various embodiments, control signals from two or more users may be combined in different ways in order to determine an action of a character. For example, the control signal of one user may take priority over the control signal of another user when there is conflict, or the control signal of one user may be weighted more heavily than the control signal of another user. In various embodiments, more than two users may jointly control a game character, vehicle, animal, or any other game entity.

At step 8642, User 1 and user 2 vote on a game decision, according to some embodiments. A game decision may include any action that can be taken in a game. A game decision may include a route to take, a weapon to use, a vehicle to use, a place to aim, a shield to use, a message to send, a signal to send, an evasive action to take, a card to play, a chess piece to move, a size of a bet, a decision to fold (e.g., in poker), an alliance to make, a risk to attempt, a bench player to use (e.g., in a sports game), an item to purchase (e.g., a map to purchase in a game) or any other game decision. In various embodiments, when a decision is to be made, the central controller may explicitly present the available choices to all relevant users (e.g., via menu). Users may then have the opportunity to make their choice, and the choice with the plurality or majority of the vote may be implemented. In various embodiments, decisions are not presented explicitly. Instead, users may signal their desired actions (e.g., using standard game inputs), and the central controller may implement the action corresponding to majority or plurality of received signals. As will be appreciated, various other methods may be used for voting on an action in a game and such methods are contemplated according to various embodiments. In various embodiments, the votes of different users may be weighted differently. For example, the vote of user 1 may count 40%, while the votes for each of users 2, 3 and 4 may count for 20%. A candidate action which wins the weighted majority or weighted plurality of the vote may then be implemented.

At step 8645, user 2 controls user 1's peripheral device, according to some embodiments. There may be various reasons for user 2 to control the peripheral device of user 1. User 2 may be demonstrating a technique, tactic, strategy, etc., for user 1. User 2 may configure the peripheral device of user 1 in a particular way, perhaps in a way that user 1 was not able to accomplish on his own. The peripheral device belonging to user 1 may have more capabilities than does the peripheral device belonging to user 2. Accordingly, user 2 may need to "borrow" the capabilities of user 1's peripheral device in order to execute a maneuver, or perform some other task (e.g., in order to instruct or control user 2's own character). User 2 may take control of the peripheral device of user 1 for any other conceivable reason. In various embodiments, to control the peripheral device of user 1, user 2 (e.g., a peripheral device of user 2, e.g., a user device of user 2) may transmit control signals over a local network, such as a network on which both user 1's peripheral and user 2's peripheral reside. In various embodiments, control signals may be sent over the internet or over some other network, and may be routed through one or more other devices or entities (e.g., through the central controller 110). In various embodiments, the peripheral device of user 1 may include a module, such as a software module, whose inputs are control signals received from user 2 (or from some other user), and whose outputs are standard component outputs that would be generated through direct use of the peripheral device of user 1. For example, a control signal received from user 2 may be translated by the software module into instructions to move a mouse pointer for some defined distance and in some defined direction.

In various embodiments, the peripheral device of user 1 may include a module, such as a software module, whose inputs are control signals received from user 2 (or from some other user), and whose outputs become inputs into the peripheral device of user 1 and/or into components of the peripheral device of user 1. For example, the output of the software module may be treated as an input signal into a mouse button, as an input signal to a sensor on the peripheral device of user 1, or as an input signal to the entire mouse. The output of the software module would thereby mimic, for example, the pressing of a mouse button on the peripheral device of user 1, or the moving of the peripheral device of user 1. In various embodiments, the software module may store a table mapping inputs (e.g., control signals received from user 2), to output signals for: (a) transmission to a user device; or (b) use as inputs to components of the peripheral device of user 1. In various embodiments, the software module may translate inputs received from another user into outputs using any other algorithm or in any other fashion.

In various embodiments, a control signal received from user 2 can be used directly (e.g., can be directly transmitted to the user device of user 1; e.g., can be directly used for controlling a game character of user 1), without modification. The peripheral device of user 1 would then be simply relaying the control signal received from user 2. In various embodiments, a hardware module or any other module or processor may be used for translating received control signals into signals usable by (or on behalf of) the peripheral device of user 1. In various embodiments, user 2 must have permission before he can control the peripheral device of user 1. User 1 may explicitly put user 2 on a list of users with permissions. User 1 may grant permissions to a category of users (e.g., to a game team) to which user 2 belongs. User 1 may grant permission in real time, such as by indicating a desire to pass control of a peripheral to user 2 in the present moment. In various embodiments, permissions may be temporary, such as a lasting a fixed amount of time, lasting until a particular event (e.g., until the current screen is cleared), lasting until to are withdrawn (e.g., by user 1), or until any other suitable situation. In various embodiments, user 1 may signal a desire to regain control of his peripheral device and/or to stop allowing user 2 to control his peripheral device. For example, user 1 may enter a particular sequence of inputs that restore control of the peripheral device to user 2.

At step 8648, a game occurrence affects the function of a peripheral device, according to some embodiments. A game occurrence may include a negative occurrence, such as being hit by a weapon, by a strike, or by some other attack. A game occurrence may include crashing, falling into a ravine, driving off a road, hitting an obstacle, tripping, being injured, sustaining damage, dying, or any other mishap. A game occurrence may include losing points, losing resources, proceeding down a wrong path, losing a character's ability or abilities, or any other occurrence. A game occurrence may include striking out in a baseball game, having an opponent score points, having a goal scored upon you (e.g., in soccer or hockey), having a touchdown scored upon you, having a team player get injured, having a team player foul out, or any other occurrence. A game occurrence may include losing a hand of poker, losing a certain amount of chips, losing material in a chess game, losing a game, losing a match, losing a skirmish, losing a battle, or any other game occurrence.

The functionality of a peripheral device may be degraded in various ways, in various embodiments. A component of the peripheral device may cease to function. For example, a button of a mouse or a key on a keyboard may cease to register input. An output component may cease to function. For example, an LED on a mouse may cease to emit light. A display screen may go dark. A speaker may stop outputting sound. In various embodiments, a component of a peripheral device may partially lose functionality. For example, a speaker may lose the ability to output sounds above a particular frequency. A display screen may lose the ability to output color but retain the ability to output black and white. As another example, a display screen may lose the ability to output graphics but may retain the ability to output text. In various embodiments, the peripheral may lose sensitivity to inputs. A button or key may require more pressure to activate. A button or key may not register some proportion or percentage of inputs. For example, a mouse button may not register every second click. Thus, in order to accomplish a single click, a player would have to press the mouse button twice. A microphone may require a higher level of incident sound in order to correctly interpret the sound (e.g., in order to correctly interpret a voice command). A camera may require more incident light in order to capture a quality image or video feed. Various embodiments contemplate that a peripheral may lose sensitivity to inputs in other ways.

In various embodiments, one or more categories of inputs may be blocked or disabled. A mouse motion in one direction (e.g., directly to the "East") may not register. (However, a user may compensate by moving the mouse first "Northeast" and then "Southeast"). In various embodiments, a sensor may be blocked or disabled. Thus, for example, the teammate of a user may be unable to ascertain the user's heart rate. Voice inputs may be disabled. Arrow keys may be disabled while text keys retain their function. Any other category of inputs may be blocked or disabled, according to some embodiments. In various embodiments, a peripheral device may generate outputs that are uncomfortable, distracting, and/or painful. For example, LED lights on a mouse may shine at full brightness, or may blink very rapidly. A heating element may become uncomfortably hot. A speaker might output a screeching sound. In various embodiments, a peripheral device may be degraded temporarily, for a predetermined amount of time (e.g., for 5 minutes) after which full functionality may be restored. In various embodiments, functionality returns gradually over some period of time. For example, functionality may return in a linear fashion over a period of 5 minutes. In various embodiments, full functionality may not necessarily be restored. In various embodiments, a peripheral device may return asymptotically to full functionality. In various embodiments, functionality is permanently effected (e.g., until the end of a game). In various embodiments, functionality may be improved or restored only upon the occurrence of some other game event (e.g., a positive game event for the player; e.g., the player successfully lands a shot on his opponent; e.g., the player finds a green ruby in the game).

At step 8651, there is a pause/break in game play, according to some embodiments. In various embodiments, a player desires to stop playing, such as to temporarily stop playing. Perhaps the player needs to get a drink or take a phone call. A player may take one or more actions to indicate he is taking a break. A player may turn over his mouse, flip over his keyboard, place his camera face-down, or otherwise position a peripheral in an orientation or configuration where it would not normally be used or would not normally function. The peripheral may then detect its own orientation, and signal to the central controller 110 that the user is taking a break. In various embodiments, when a user takes a break, the central controller takes note of a lack of input from the user (e.g., from a peripheral device of the user), and infers that the user is taking a break. When a user takes a break, the central controller 110 may pause gameplay, may inform other participants that the player has taken a break, may protect the player's character from attacks, may pause a game clock, or may take any other suitable action.

At step 8654, the game concludes, according to some embodiments. The central controller 110 may thereupon tally up scores, determine performances, determine winners, determine losers, determine prizes, determine any records achieved, determine any personal records achieved, or take any other action. The central controller 110 may award a prize to a user. A prize may include recognition, free games, game resources, game skins, character skins, avatars, music downloads, access to digital content, cash, sponsor merchandise, merchandise, promotional codes, coupons, promotions, or any other prize. In various embodiments, a peripheral device of the user may assume an altered state or appearance in recognition of a user's achievement in a game. For example, LEDs on a user's mouse may turn purple, a speaker might play a triumphant melody, a mouse may vibrate, or any other change may transpire. In various embodiments, user achievements may be broadcast to others. For example, the central controller 110 may broadcast a message to a user's friends or teammates detailing the achievements of the user.

At step 8657, a game highlight reel is created, according to some embodiments. The highlight reel may include a condensed or consolidated recording of gameplay that has transpired. The highlight reel may include sequences with high action, battle sequences, sequences where a player neutralized an opponent, sequences where a player sustained damage, sequences where a player scored points, or any other sequences. A highlight reel may include recorded graphics recorded audio, recorded communications from players, or any other recorded aspect of a game. In various embodiments, the highlight reel contains sufficient information to recreate a game, but does not necessarily record a game in full pixel-by-pixel detail. The highlight reel may store game sequences in compressed format. In various embodiments, a highlight reel may include sequences where a peripheral device has recorded sensor inputs meeting certain criteria. For example, a highlight reel may include all sequences where a player's heart rate was above 120. As another example, a highlight reel may include the 1% of the game where the users measured skin conductivity was the highest.

In various embodiments, a highlight reel may incorporate or recreate sensory feedback, such as sensory feedback to mimic what occurred in the game. For example, when a user's friend watches the highlight reel, the user's friend may have the opportunity to feel haptic feedback in his mouse just as the user felt during the actual game play. Thus, in various embodiments, a highlight reel may contain not only visual content, but also tactile content, audio content, and/or content for any other sensory modality, modality, or any combination of modalities. Further details on how haptic feedback may be generated can be found in U.S. Pat. No. 7,808,488, entitled "Method and Apparatus for Providing Tactile Sensations" to Martin, et al. issued Oct. 5, 2010, at columns 3-6, which is hereby incorporated by reference. In various embodiments, the central controller 110 may notify one or more other users about the existence of a highlight reel, e.g., by sending them the file, a link to the file, by sending an alert to their peripheral device, or in any other fashion.

At step 8660, the central controller 110 generates recommendations for improvement of the user's gameplay, according to some embodiments. In various embodiments, the central controller 110 may analyze the user's gameplay using an artificial intelligence or other computer program. The artificial intelligence may recreate game states that occurred when the user played, and decide what it would have done in such game states. If these decisions diverge from what the user actually decided, then the central controller may inform the player of the recommendations of the artificial intelligence, or otherwise note such game states. If the artificial intelligence agrees with what the user did, then the central controller may indicate approval to the user. In various embodiments, a user may have the opportunity to replay a game, or part of a game, from a point where the user did not perform optimally or did not make a good decision. This may allow the user to practice areas where his skill level might need Improvement. In various embodiments, the central controller 110 may compare a user's decisions in a game to the decisions of other players (e.g., to skillful or professional players; e.g., to all other players) made at a similar juncture, or in a similar situation, in the game. If the users decisions diverge from those of one or more other players, then the central controller may recommend to the user that he should have made a decision more like that of one or more other players, or the central controller may at least make the user aware of what decisions were made by other players.

Storage Devices

Referring to FIG. 71A, FIG. 71B, FIG. 71C, FIG. 71D, and FIG. 71E, perspective diagrams of exemplary data storage devices 7140a-e according to some embodiments are shown. The data storage devices 7140a-e may, for example, be utilized to store instructions and/or data such as: data in the data tables of FIGS. 7-37, 50-62, 64-66, 70, 73-78, 87-88, and 95-97; instructions for AI algorithms; instructions for facilitating a meeting; instructions for facilitating game play; instructions for optimizing emissions of a meeting; and/or any other instructions. In some embodiments, instructions stored on the data storage devices 7140a-e may, when executed by a processor, cause the implementation of and/or facilitate the methods: 7900 of FIGS. 79A-C; 8600 of FIGS. 86A-C; 9800 of FIG. 98; 9900 of FIG. 99; 10000 of FIG. 100; 10100 of FIG. 101; 10200 of FIGS. 102A-B, and/or portions thereof, and/or any other methods described herein.

According to some embodiments, the first data storage device 7140a may comprise one or more various types of internal and/or external hard drives. The first data storage device 7140a may, for example, comprise a data storage medium 7146 that is read, interrogated, and/or otherwise communicatively coupled to and/or via a disk reading device 7148. In some embodiments, the first data storage device 7140a and/or the data storage medium 7146 may be configured to store information utilizing one or more magnetic, inductive, and/or optical means (e.g., magnetic, inductive, and/or optical-encoding). The data storage medium 7146, depicted as a first data storage medium 7146a for example (e.g., breakout cross-section "A"), may comprise one or more of a polymer layer 7146a-1, a magnetic data storage layer 7146a-2, a non-magnetic layer 7146a-3, a magnetic base layer 7146a-4, a contact layer 7146a-5, and/or a substrate layer 7146a-6. According to some embodiments, a magnetic read head 7148a may be coupled and/or disposed to read data from the magnetic data storage layer 7146a-2.

In some embodiments, the data storage medium 7146, depicted as a second data storage medium 7146b for example (e.g., breakout cross-section "B"), may comprise a plurality of data points 7146b-2 disposed with the second data storage medium 7146b. The data points 7146b-2 may, in some embodiments, be read and/or otherwise interfaced with via a laser-enabled read head 7148b disposed and/or coupled to direct a laser beam through the second data storage medium 7146b. In some embodiments, the second data storage device 7140b may comprise a CD, CD-ROM, DVD, Blu-Ray™ Disc, and/or other type of optically-encoded disk and/or other storage medium that is or becomes known or practicable. In some embodiments, the third data storage device 7140c may comprise a USB keyfob, dongle, and/or other type of flash memory data storage device that is or becomes known or practicable. In some embodiments, the fourth data storage device 7140d may comprise RAM of any type, quantity, and/or configuration that is or becomes practicable and/or desirable. In some embodiments, the fourth data storage device 7140*d* may comprise an off-chip cache such as a Level 2 (L2) cache memory device. According to some embodiments, the fifth data storage device 7140*e* may comprise an on-chip memory device such as a Level 1 (L1) cache memory device.

The data storage devices 7140*a*-*e* may generally store program instructions, code, and/or modules that, when executed by a processing device, cause a particular machine to function in accordance with one or more embodiments described herein. The data storage devices 7140*a*-*e* depicted in FIG. 71A, FIG. 71B, FIG. 71C, FIG. 71D, and FIG. 71E are representative of a class and/or subset of computer-readable media that are defined herein as "computer-readable memory" (e.g., non-transitory memory devices as opposed to transmission devices or media).

Figure 72:
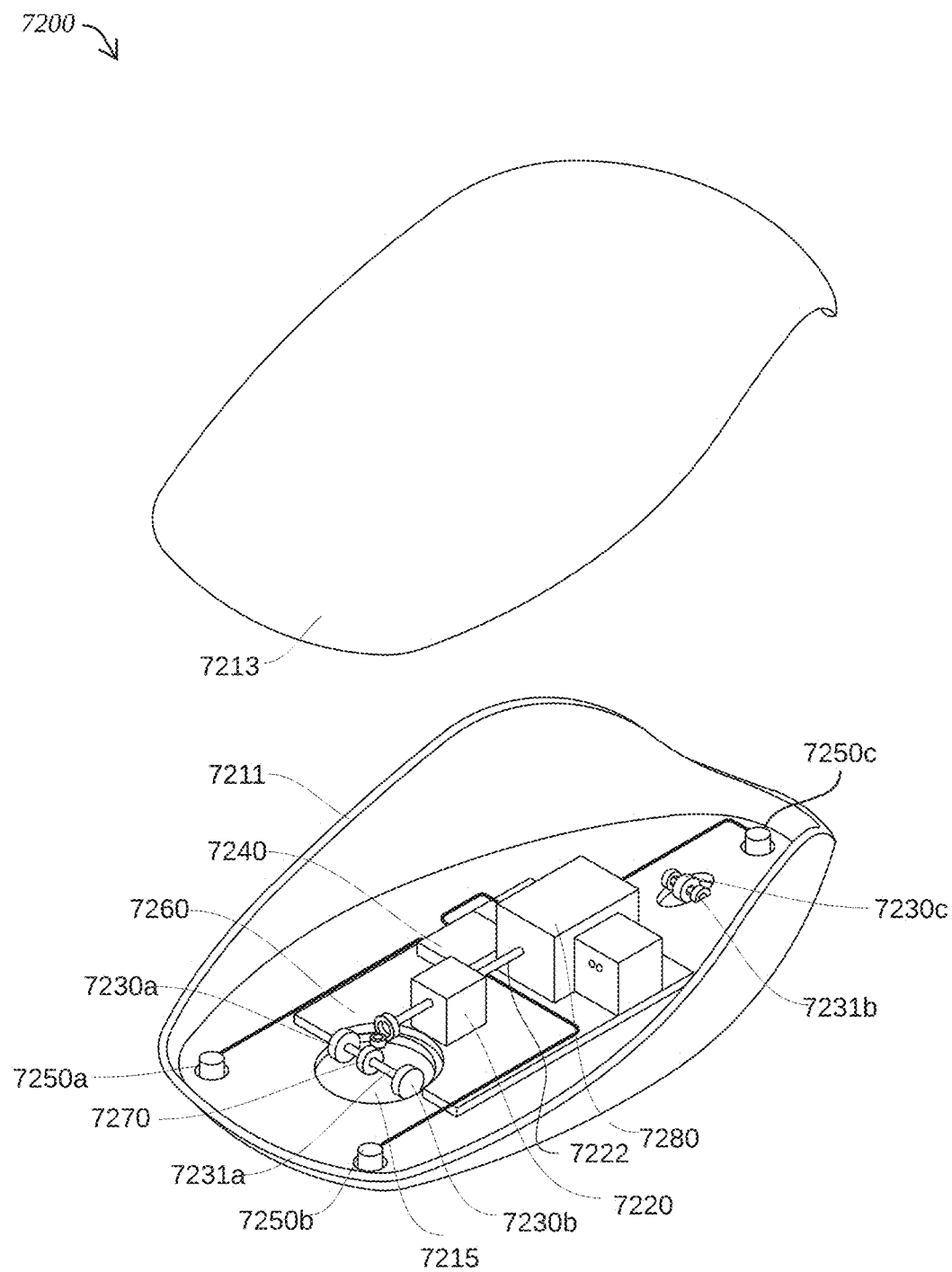
FIG. 72 is a block diagram of a peripheral (mouse) consistent with at least some embodiments described herein.

With reference to FIG. 72, a prior art illustration of the internal workings of one example of a computer mouse 7200 is shown. Further details can be seen in published patent US 2011/0291931 published Dec. 1, 2011, incorporated by reference herein.

Mouse 7200 includes cover 7211 and outer cover 7213. Sensing mechanisms of mouse 7200 act via through hole 7215 which accommodates corresponding wheels 7230*a*-*c*. Driver module 7220 can be an electric motor that includes shaft 7222 connected to gear 7270. Driver module 7220 provides driving force to the movement of gears 7270 by the shaft 7222 to drive movement of axle 7231*a* and the wheels 7230*a* and 7230*b*. Wheels 7230*a*-*c* are exposed from the bottom surface of cover 7211. Wheels 7230*a* and 7230*b* are mounted on axle 7231*a* and are exposed through hole 7215. Wheel 7230*c* is rotatably mounted on another axle 7231*b*. Axle 7231*a* is rotatably mounted within another end of cover 7211.

Control module 7240 transmits a command signal to an alarm to output a warning signal and is connected to driver module 7220. Sensors 7250*a*-*c* can accurately sense and maintain the position of the mouse to keep it from falling off the desktop. Sensors 7250*a*-*c* radiate continuous sensing light to the desktop or other plane and then receive reflected light from different reflective surfaces and can record transmission time of the reflected light. Circuit board 7260 is mounted within the main body. Gears 7270 engage with each other to drive wheels 7230*a* and 7230*b*. Cleaning device 7280 can clean dust on the movement path of the mouse.

Mouse Usage

In various embodiments, it may be useful to measure the utilization of a peripheral device. In various embodiments, a peripheral device utilization is measured without reference to any applications (e.g., without reference to user device applications to which the peripheral device utilization is directed, such as to excel or to a video game). In various embodiments, it may be determined when a user's effectiveness in utilizing a peripheral device has declined. In various embodiments, it may be determined when a user's utilization of a peripheral device has the potential to be adverse or harmful to a user (e.g., by keeping the user up late at night, e.g., by impacting the user's health, etc.). In various embodiments, a determination of the effectiveness of the user's utilization of the peripheral device, or the potential for harm to a user may be determined by monitoring or comparing utilization of a peripheral device over time. In various embodiments, utilization of a peripheral device may be monitored for any suitable purpose.

In measuring the utilization of a peripheral device, one or more types of inputs may be measured. The types of inputs may include: presses of a button; releases of a button; clicks of a button; single clicks of a button; double clicks of a button (e.g., two clicks of the button happening in rapid succession); clicks of a right button; clicks of a left button; clicks of a central button; individual interactions with a scroll wheel; degree to which a scroll wheel is turned; direction in which a scroll wheel is turned; movements of the device itself (e.g., movements of the entire mouse); direction of movement of the device; velocity of movement of the device; acceleration of movement of the device; sub-threshold inputs (e.g., pressure placed on a button that was insufficiently strong to register as a click); clicks coupled with motions of the entire device (e.g., drags); or any other types of inputs, or any combination of inputs. In various embodiments, utilization may be measured with passive inputs, such as with inputs detected at one or more sensors but not consciously made by a user. Utilization may measure such inputs as: pressure sensed on a peripheral device (e.g., resting hand pressure); heat sensed at a device (e.g., the heat of a user's hand); a metabolite level of a user; a skin conductivity of a user; a brainwave of a user; an image of a user; an image of part of a user (e.g., of the user's hands; e.g., of the user's face), or any other inputs, or any combination of inputs.

In various embodiments, combinations of inputs may provide a useful measure of utilization. With respect to a mouse, a user who is effectively using the mouse may direct a mouse pointer from a first location to a second location using a motion that is substantially a straight line. In contrast, for example, a user who is not effectively using the mouse may move the mouse pointer in the wrong direction (e.g., in a direction that is 10 degrees off from the direction of the second location with respect to the first location), or may overshoot the second location. Because the user is not being economical with his mouse motions, changes in direction of the mouse motion may be more prevalent with the user. In various embodiments, a metric of utilization may be based on some statistic of inputs measured over some period of time and/or per unit of time. A metric may include the number of inputs measured over some period of time. For example, the number of button clicks measured during a one minute interval. In various embodiments, a metric may include the aggregate of inputs measured over some period of time. For example, the total distance moved by a mouse in one minute, or the total number of degrees that a scroll wheel has turned in 1 minute. In various embodiments, a metric may include the proportion of one type of input to another type of input. For example, a metric may measure what proportion of button clicks on a mouse were left button clicks versus right button clicks.

In various embodiments, a metric may measure the proportion of time during which a user's hand was in contact with a peripheral. In various embodiments, a metric measures the proportion of sub-threshold clicks to actual clicks. If this metric increases over time, it may suggest, for example, that the user is tiring out and not concentrating on pressing a button hard enough. In various embodiments, a metric measures: (a) the aggregate absolute changes in direction of a mouse's movement divided by (b) the total absolute distance moved by the mouse, all within some unit of time (e.g., one minute). To use a simple example, suppose in one minute a mouse moves 3 inches to a user's right, then 0.5 inches to the user's left, then 2 inches directly away from a user. The mouse has changed directions twice, first by 180 degrees, then by 90 degrees, for an aggregate change in direction of 270 degrees. The mouse has moved a total absolute distance of 5.5 inches (i.e., the absolute value of the distance of each motion is added up). The metric will then take the value of 270 degrees/5.5 inches, or approximately 49 degrees per inch. In various embodiments, this metric may be computed at different time intervals. If the size of the metric is increasing from one time interval to the next, it may be indicative that the user is becoming tired and less efficient with his mouth movements.

In some cases, there may be other explanations for a changing metric. For example, a particular encounter in a video game may require a rapid series of short mouse movements in different directions. However, in various embodiments, by computing a metric over a relatively long time interval (e.g., over 10 minutes), or by computing the metric over many different intervals (e.g., over 20 1-minute intervals), the significance of other explanatory factors can be reduced, smoothed out, or otherwise accounted for. For example, where a metric is computed over many time intervals, values that represent significant outliers can be discarded as probably occurring as a result of other explanatory factors (e.g., not due to the users fatigue).

Adjustable Mouse Parameters

In various embodiments, in response to utilization metrics (e.g., to values of a utilization metric; e.g., to changes in the value of a utilization metric over time), one or more parameters of a peripheral may be adjusted. Parameters that may be adjusted include: a sensitivity to clicks, a sensitivity to button presses, a color of a light (e.g., an LED), a brightness of a light, a background color of a display screen, a sensitivity of a touch screen, an image shown on a display screen, a rate at which a light blinks, a volume of audio output, a mapping of detected motion to reported motion (e.g., a mouse may detect 2 inches of mouse displacement but report only 1 inch of displacement; e.g., a mouse may detect a user hand speed of 6 feet per second, but report a speed of only two feet per second; e.g., a mouse may detect a 30 degree turn of a scroll wheel, but report only a 10 degree turn of the wheel, etc.), or any other parameter.

In various embodiments, a parameter may include whether or not a mouse registers an input at all (e.g., whether or not the mouse will register a right click at all). In various embodiments, a parameter may include whether or not a mouse registers any inputs at all. For example, a parameter may, upon assuming a given value, stop the mouse from functioning entirely.

Glass

Various embodiments contemplate the use of glass for such purposes as: coating substrates; display screens; touch screens; sensors; protective covers; glare reducers; fingerprint readers, or fingerprint reducers (such as so-called oleophobic screens and/or coatings); or for any other purpose. In various embodiments the Gorilla® Glass® line of glass products developed by Corning Inc. may be suitable for one or more purposes. The Gorilla® Glass® line includes such products as Gorilla® Glass™ 3, Gorilla® Glass™ 5, Gorilla® Glass™ 6, and others. Gorilla® Glass™ may provide such advantages as scratch resistance, impact damage resistance, resistance to damage even after drops from high places, resistance to damage after multiple impacts, resistance to damage from sharp objects, retained strength after impacts, high surface quality, optical purity and high light transmission, thinness, and/or lightness. Glass may be used as a flat or 2D panel, or in curved or 3D shapes to embed displays and other functionality in various surfaces and devices. Some exemplary types of glass are described in U.S. Pat. No. RE47,837, entitled "Crack and scratch resistant glass and enclosures made therefrom" to Barefoot, et al., issued Feb. 4, 2020, the entirety of which is incorporated by reference herein for all purposes. One glass formulation described by the patent includes: "an alkali aluminosilicate glass having the composition: 66.4 mol % $SiO_2$; 10.3 mol % $Al_2O_3$; 0.60 mol % $B_2O_3$; 4.0 mol % $Na_2O$; 2.10 mol % $K_2O$; 5.76 mol % MgO; 0.58 mol % CaO; 0.01 mol % $ZrO_2$; 0.21 mol % $SnO_2$; and 0.007 mol % $Fe_2O_3$". However, it will be appreciated that various embodiments contemplate that other suitable glass formulations could likewise be used. Other glass products that may be used include Dragontrail™ from Asahi™ and Xensation™ from Schott™.

It will be appreciated that various embodiments contemplate the use of other materials besides glass. Such materials may include, for example, plastics, thermoplastics, engineered thermoplastics, thermoset materials, ceramics, polymers, fused silica, sapphire crystal, corundum, quartz, metals, liquid metal, various coatings, or any other suitable material.

Diffusing Fiber Optics

Various embodiments contemplate the use of diffusing fiber optics. These may include optical glass fibers where a light source, such as a laser, LED light, or other source is applied at one end and emitted continuously along the length of the fiber. As a consequence the entire fiber may appear to light up. Optical fibers may be bent and otherwise formed into two or three dimensional configurations. Furthermore, light sources of different or time varying colors may be applied to the end of the optical fiber. As a result, optical fibers present an opportunity to display information such as a current state (e.g., green when someone is available and red when unavailable), or provide diverse and/or visually entertaining lighting configurations.

Diffusing fiber optics are described in U.S. Pat. No. 8,805,141, entitled "Optical fiber illumination systems and methods" to Fewkes, et al., issued Aug. 12, 2014, the entirety of which is incorporated by reference herein for all purposes.

Terms

As used herein, a "meeting" may refer to a gathering of two or more people to achieve a function or purpose.

A "company" may be a for profit or not for profit company. It could also be a small group of people who have a shared purpose, such as a club. The company could have full or part time employees located at one or more physical locations and/or virtual workers.

A "meeting owner" may refer to a person (or persons) responsible for managing the meeting. It could be the speaker, a facilitator, or even a person not present at the meeting (physically or virtually) who is responsible for elements of the meeting. There could also be multiple meeting owners for a given meeting.

A "meeting participant" may refer to an individual or team who attends one or more meetings. In some embodiments, a meeting participant could be a software agent that acts on behalf of the person. In various embodiments, the terms "meeting participant" and "meeting attendee" may be used interchangeably.

An "Admin/Coordinator" may refer to an individual or individuals who play a role in setting up or coordinating a meeting, but may not participate in the meeting itself.

A "baton" may refer to a task, obligation, or other item that may be fulfilled in portions or parts (e.g., in sequential parts). The task may be assigned to a person or a team. Upon fulfilling their portion of the task, the person or team may hand the task over to another person or team, thereby "passing the baton". Such a task may be handed from one person to another—across meetings, across time, and/or across an organization. The task may ultimately reach completion following contributions from multiple people or teams. In various embodiments, a baton is first created in a meeting (e.g., as a task that results from a decision or direction arrived at in a meeting).

An "intelligent chair" may refer to a chair capable of performing logical operations (e.g., via a built-in processor or electronics), capable of sensing inputs (e.g., gestures of its occupants; e.g., voice commands of its occupants; e.g., pulse or other biometrics of its occupants), capable of sensing its own location, capable of outputting information (e.g., providing messages to its occupant), capable of adjusting its own configuration (e.g., height; e.g., rigidness; e.g., temperature of the backrest), capable of communicating (e.g., with a central controller), and/or capable of any other action or functionality.

As used herein, an "SME" may refer to a subject matter expert, i.e., a person with expertise or specialized knowledge in a particular area, such as finance, marketing, operations, legal, technology, a particular subdomain, such as the European market, server technology, intellectual property, or in any other area.

As used herein, a "Meeting Participant Device" or the like may refer to a device that allows meeting participants to send and receive messages before, during, and after meetings. A Meeting Participant Device may also allow meeting participants to take surveys about meetings, provide feedback for meetings and/or to engage in any other activity related to meetings. A meeting participant device may include: Smartphones (such as an Apple™ iPhone™ 11 Pro or Android™ device such as Google®™ Pixel 4™ and OnePlus™ 7 Pro); IP enabled desk phone; Laptops (MacBook Pro™, MacBook Air™, HP™ Spectre x360™, Google®™ Pixelbook Go™, Dell™ XPS 13™); Desktop computers (Apple™ iMac SKIM, Microsoft®™ Surface Studio 2™ Dell™ Inspiron 5680™); Tablets (Apple™ iPad™ Pro 12.9, Samsung™ Galaxy™ Tab S6, iPad™ Air, Microsoft®™ Surface Pro™); Watches (Samsung™ Galaxy™ Watch, Apple™ Watch 5, Fossil™ Spor™, TicWatch™ E2, Fitbit™ Versa 2™); Eyeglasses (Iristick.Z1 Premium™ Vuzix Blade™, Everysight Raptor™ Solos™ Amazon®™ Echo™ Frames); Wearables (watch, headphones, microphone); Digital assistant devices (such as Amazon®™ Alexa™ enabled devices, Google®™ Assistant™, Apple™ Siri™); and/or any other suitable device.

In various embodiments, a Meeting Participant Device may include a peripheral device, such as a device stored in table 1000. In various embodiments, a Meeting Participant Device may include a user device, such as a device stored in table 900.

As used herein, a "Meeting Owner Device" or the like may refer to a device that helps or facilitates a meeting owner in managing meetings. It could include the same or similar technology as described with respect to the Meeting Participant Device above.

Central Controllers

In various embodiments, central controller 110 may be one or more servers located at the headquarters of a company, a set of distributed servers at multiple locations throughout the company, or processing/storage capability located in a cloud environment—either on premise or with a third party vendor such as Amazon®™ Web Services™ Google®™ Cloud Platform™, or Microsoft®™ Azure™.

The central controller 110 may be a central point of processing, taking input from one or more of the devices herein, such as a room controller or participant device. The central controller may have processing and storage capability along with the appropriate management software as described herein. Output from the central controller could go to room controllers, room video screens, participant devices, executive dashboards, etc.

In various embodiments, the central controller may include software, programs, modules, or the like, including: an operating system; communications software, such as software to manage phone calls, video calls, and texting with meeting owners and meeting participants; an artificial intelligence (AI) module; and/or any other software.

In various embodiments, central controller 110 may communicate with one or more devices, peripherals, controllers (e.g., house controller 8305 (FIG. 83); e.g., equipment controllers, such as blinds controllers); items of equipment (e.g., AV equipment); items of furniture (e.g., intelligent chairs); resource devices (e.g., weather service providers; e.g., mapping service providers); third-party devices; data sources; and/or with any other entity.

In various embodiments, the central controller 110 may communicate with: room controllers; display screens; meeting owner devices/participant devices, which can include processing capability, screens, communication capability, etc.; headsets; keyboards; mice (Key Connection Battery Free Wireless Optical Mouse & a USB 2' Wired Pad, Logitech®; Wireless Marathon™ Mouse M705 with 3-Year Battery Life); presentation controllers; chairs; executive dashboards; audio systems; microphones; lighting systems; security systems (door locks, etc.); environmental controls (HVAC, blinds, window opacity); Bluetooth® location beacons or other indoor location systems, or any other entity.

In various embodiments, the central controller 110 may communicate with data sources containing data related to: human resources; presentations; weather; equipment status; calendars; traffic congestion; road conditions; road closures; or to any other area.

In various embodiments, the central controller may communicate with another entity directly, via one or more intermediaries, via a network, and/or or in any other suitable fashion. For example, the central controller may communicate with an item of AV equipment in a given room using a room controller for the room as an intermediary.

Embodiments

Referring to FIG. 50, a diagram of an example 'employees' table 5000 according to some embodiments is shown.

Employees table 5000 may store information about one or more employees at a company, organization, or other entity. In various embodiments, table 5000 may store information about employees, contractors, consultants, part-time workers, customers, vendors, and/or about any people of interest. In various embodiments, employees table 5000 may store similar, analogous, supplementary, and/or complementary information to that of users table 700. In various embodiments, employees table 5000 and users table 700 may be used interchangeably and/or one table may be used in place of the other.

Employee identifier field 5002 may store an identifier (e.g., a unique identifier) for an employee. Name field 5004 may store an employee name. Start date field 5006 may store a start date, such as an employee's first day of work. Employee level field 5008 may store an employee's level within the company, which may correspond to an employee's rank, title, seniority, responsibility level, or any other suitable measure.

Supervisor field 5010 may indicate the ID number of an employee's supervisor, manager, boss, project manager, advisor, mentor, or other overseeing authority. As will be appreciated, an employee may have more than one supervisor.

Office/cube location field 5012 may indicate the location of an employee's place of work. This may be, for example, the place that an employee spends the majority or the plurality of her time. This may be the place where an employee goes when not interacting with others. This may be the place where an employee has a desk, computer, file cabinet, or other furniture or electronics or the like. In various embodiments, an employee may work remotely, and the location 5012 may correspond to an employee's home address, virtual address, online handle, etc. In various embodiments, multiple locations may be listed for an employee, such as if an employee has multiple offices. In various embodiments, a location may indicate a room number, a cube number, a floor in a building, an address, and or any other pertinent item of information.

In various embodiments, knowledge of an employee's location may assist the central controller 110 with planning meetings that are reachable by an employee within a reasonable amount of time. It may also assist the central controller 110 with summoning employees to nearby meetings if their opinion or expertise is needed. Of course, knowledge of an employee's location may be useful in other situations as well.

Subject matter expertise field 5014 may store information about an employee's expertise. For example, an employee may have expertise with a particular area of technology, with a particular legal matter, with legal regulations, with a particular product, with a particular methodology or process, with customer preferences, with a particular market (e.g., with the market conditions of a particular country), with financial methods, with financials for a given project, or in any other area. In various embodiments, multiple areas of expertise may be listed for a given employee. In various embodiments, subject matter expertise field 5014 may assist the central controller 110 with ensuring that a meeting has an attendee with a particular area of expertise. For example, a meeting about launching a product in a particular country may benefit from the presence of someone with expertise about market conditions in that country. As will be appreciated, subject matter expertise field 5014 could be used for other situations as well.

Personality field 5016 may store information about an employee's personality. In various embodiments, information is stored about an employee's personality as exhibited within meetings. In various embodiments, information is stored about an employee's personality as exhibited in other venues or situations. In various embodiments, it may be desirable to form meetings with employees of certain personalities and/or to balance or optimize personalities within a meeting. For example, if one employee tends to be very gregarious, it may be desirable to balance the employee's personality with another employee who is focused and who could be there to keep a meeting on track. In various embodiments, it may be desirable to avoid forming meetings with two or more clashing personality types within them. For example, it may be desirable to avoid forming a meeting with two (or with too many) employees that have a confrontational personality. As will be appreciated, personality field 5016 may be used for other situations as well.

Security level field 5018 may store information about an employee's security level. This may represent, for example, an employee's ability to access sensitive information. An employee's security level may be represented numerically, qualitatively (e.g., "high" or "low"), with titles, with clearance levels, or in any other suitable fashion. In various embodiments, security level field 5018 may assist the central controller 110 in constructing meetings with attendees that have permission to view potentially sensitive information that may arise during such meetings.

Security credentials field 5020 may store information about credentials that an employee may present in order to authenticate themselves (e.g., to verify their identities). For example, field 5020 may store an employee's password. An employee may be required to present this password in order to prove their identity and/or to access secure information. Field 5020 may store other types of information such as biometric information, voiceprint data, fingerprint data, retinal scan data, or any other biometric information, or any other information that may be used to verify an employee's identity and/or access levels.

Temperature preferences field 5021 may store an employee's temperature preferences, such as an employee's preferred room temperature. This preference may be useful in calculating heating energy (or cooling energy), and/or any associated emissions that may be required to maintain a room at an employee's preferred room temperature. Employee temperature preferences may influence the temperature at which an employee's office is kept, the temperature at which a meeting room hosting the employee is kept, or any other applicable temperature.

Preferences

In various embodiments, meeting owners and meeting participants could register their preferences with the central controller relating to the management and execution of meetings. Example preferences of meeting participants may include:

I only want to attend meetings with fewer than 10 people.
I do not want to attend any alignment meetings.
I prefer morning to afternoon meetings.
I do not want to attend a meeting if a particular person will be attending (or not attending).
I don't like to attend meetings outside of my building or floor.
I don't attend meetings that require travel which generates carbon output.
Gestures that invoke action can be set as a preference. Tap my watch three times to put me on mute.
Nodding during a meeting can indicate that I agree with a statement.
Food preference for meetings. I only eat vegetarian meals.
My personal mental and physical well-being at a given time.

Example preferences of meeting owners may include:
I don't want to run any meetings in room 805.
I prefer a "U" shaped layout of desks in the room.
I prefer to have a five minute break each hour.
I prefer the lights to be dimmed 50% while I am presenting.
I never want food to be ordered from a particular vendor.
I want a maximum of 25 attendees at my Monday meetings.
I need to be able to specify camera focus by meeting type. For example, in a meeting at which a decision is being made I want the camera to be on the key decision makers for at least 80% of the time.
My personal mental and physical well-being at a given time.

Example preferences or conditions of the central controller may include:

There are certain days on which meetings cannot be scheduled.

For a given room, certain levels of management have preferential access to those rooms.

Preferences field 5022 may store an employee's preferences, such as an employee's preferences with respect to meetings. Such preferences may detail an employee's preferred meeting location or locations, preferred amenities at a meeting location (e.g., whiteboards), preferred characteristics of a meeting location (e.g., location has north-facing windows; e.g., the location has circular conference tables), room layouts (e.g. U-shaped desk arrangements), etc. Preferences field 5022 may include an employee's preferred meeting times, preferred meeting dates, preferred meeting types (e.g., innovation meetings), preferred meeting sizes (e.g., fewer than ten people), or any other preferences.

Preferred standard device configurations field 5024 may store information about how an employee would like a device configured. The device may be a device that is used in a meeting. The device may include, for example, a smartphone, a laptop, a tablet, a projector, a presentation remote, a coffee maker, or any other device. Exemplary preferences may include a preferred method of showing meeting attendees (e.g., show only the speaker on a screen; e.g., show all attendees on screen at once), a preferred method of broadcasting the words spoken in a meeting (e.g., via audio; e.g., via a transcript), a preferred method of alerting the employee when his input is required (e.g., via flashing screen; e.g., via a tone), a preferred method of alerting the employee when the meeting is starting, a preferred method of alerting the employee when a particular topic arises, a preferred method of showing the results of an in-meeting survey (e.g., via a bar graph; e.g., via numerical indicators for each available choice), or any other preferences.

Email field 5026 may store an employee's email address. In various embodiments, a company email address may be stored for an employee. In various embodiments, a personal email address may be stored for an employee. In various embodiments, any other email address or addresses may be stored for an employee.

Phone field 5028 may store an employee's phone number. In various embodiments, a company phone number may be stored for an employee. In various embodiments, a personal phone number may be stored for an employee. In various embodiments, any other phone number or numbers may be stored for an employee.

In various embodiments, any other contact information for an employee may be stored. Such contact information may include a Slack™ handle, a Twitter® handle, a LinkedIn® handle, a Facebook® username, a handle on a social media site, a handle within a messaging app, a postal address, or any other contact information.

In various embodiments, storing an employee's contact information may allow the central controller 110 to send a meeting invite to an employee, to send reminders to an employee of an impending meeting, to check in on an employee who has not appeared for a meeting, to remind employees to submit meeting registration information (e.g., a purpose or agenda), to send rewards to employees (e.g., to send an electronic gift card to an employee), or to communicate with an employee for any other purpose.

Referring to FIG. 51, a diagram of an example 'meetings' table 5100 according to some embodiments is shown. In various embodiments, a meeting may entail a group or gathering of people, who may get together for some period of time. People may gather in person, or via some conferencing or communications technology, such as telephone, video conferencing, telepresence, zoom calls, virtual worlds, or the like. Meetings (e.g., hybrid meetings) may include some people who gather in person, and some people who participate from remote locations (e.g., some people who are not present in the same room), and may therefore participate via a communications technology. Where a person is not physically proximate to other meeting attendees, that person may be referred to as a 'virtual' attendee, or the like.

Further details on how meetings may occur via conferencing can be found in U.S. Pat. No. 6,330,022, entitled "DIGITAL PROCESSING APPARATUS AND METHOD TO SUPPORT VIDEO CONFERENCING IN VARIABLE CONTEXTS" to Doree Seligmann, issued Dec. 11, 2011, at columns 3-6, which is hereby incorporated by reference.

A meeting may serve as an opportunity for people to share information, work through problems, provide status updates, provide feedback to one another, share expertise, collaborate on building or developing something, or may serve any other purpose.

In various embodiments, a meeting may refer to a single-event or session, such as a gathering that occurs from 2:00 PM to 3:00 PM on Apr. 5, 2025. In various embodiments, a meeting may refer to a series of events or sessions, such as to a series of ten sessions that occur weekly on Monday at 10:00 AM. The series of sessions may be related (e.g., they may all pertain to the same project, may involve the same people, may all have the same or related topics, etc.). As such, in various embodiments, the series of sessions may be referred to collectively as a meeting. Meetings may also include educational sessions like a Monday 2 PM weekly Physics class offered by a university for a semester.

Meeting identifier field 5102 may store an identifier (e.g., a unique identifier) for a meeting.

Meeting name field 5104 may store a name for a meeting. A meeting name may be descriptive of the subject of a meeting, the attendees in the meeting (e.g., a meeting called 'IT Roundtable' may comprise members of the IT department), or any other aspect of the meeting, or may have nothing to do with the meeting, in various embodiments.

Meeting owner field 5106 may store an indication of a meeting owner (e.g., an employee ID; e.g., an employee name). A meeting owner may be an individual or a group of individuals who run a meeting, create a meeting, organize a meeting, manage a meeting, schedule a meeting, send out invites for a meeting, and/or who play any other role in the meeting, or who have any other relationship to the meeting.

Meeting type field 5108 may store an indication of a meeting type. Exemplary meeting types include learning; innovation; commitment; and alignment meetings. A meeting type may serve as a means of classifying or categorizing meetings. In various embodiments, central controller 110 may analyze characteristics of a meeting of a certain type and determine whether such characteristics are normal for meetings of that type. For example, the central controller may determine that a scheduled innovation meeting has more people invited then would be recommended for innovation meetings in general.

In various embodiments, central controller 110 may analyze the relative frequency of different types of meetings throughout a company. The central controller may recommend more or fewer of certain types of meetings if the number of a given type of meeting is out of proportion to what may be considered healthy for a company. In various embodiments, meeting types may be used for various other purposes.

Level field 5110 may store a level of a meeting. The level may represent the level of the intended attendees for the meeting. For example, the meeting may be an executive-level meeting if it is intended to be a high-level briefing just for executives. In various embodiments, prospective attendees with ranks or titles that do not match the level of the meeting (e.g., a prospective attendee's rank is too low) may be excluded from attending the meeting. In various embodiments, meetings of a first-level may take priority over meetings of a second level (e.g., of a lower level). Thus, for example, meetings of the first level may be granted access to a conference room before meetings of a second level when meeting times overlap. In various embodiments, meeting levels may be used for other purposes as well.

Location field 5112 may store a location of a meeting. The location may include a building designation, a campus designation, an office location, or any other location information. In various embodiments, if a meeting is to be held virtually, then no information may be stored in this field.

Room identifier field 5114 may store an identifier of a room in which a meeting is scheduled to occur. The room may be a physical room, such as a conference room or auditorium. The room may be a virtual room, such as a video chat room, chat room, message board, Zoom® call meeting, WebEx® call meeting, or the like. In some embodiments, a meeting owner or central controller 110 may switch the room location of a meeting, with the record stored in the room identifier field updated to reflect the new room.

Start date field 5116 may store the start date of a meeting. In various embodiments, the start date may simply represent the date of a solitary meeting. In various embodiments, the start date may represent the first in a series of sessions (e.g., where a meeting is recurring).

Time field 5118 may store a time of a meeting, such as a start time. If the meeting comprises multiple sessions, the start time may represent the start time of each session. In embodiments with offices in different time zones, time field may be expressed in GMT.

Duration field 5119 may store a duration of a meeting, such as a duration specified in minutes, or in any other suitable units or fashion. The duration may represent the duration of a single session (e.g., of a recurring meeting).

Frequency field 5120 may store a frequency of a meeting. The field may indicate, for example, that a meeting occurs daily, weekly, monthly, bi-weekly, annually, every other Thursday, or according to any other pattern.

End date field 5122 may store the end date of a meeting. For meetings with multiple sessions, this may represent the date of the last session. In various embodiments, this may be the same as the start date.

Phone number field 5124 may store a phone number that is used to gain access to a meeting (e.g., to the audio of a meeting; e.g., to the video of a meeting; e.g., to slides of a meeting; e.g., to any other aspect of a meeting). In various embodiments, phone number field 5124 or a similar type field may store a phone number, URL link, weblink, conference identifier, login ID, or any other information that may be pertinent to access a meeting.

Tags field 5126 may store one or more tags associated with a meeting. The tags may be indicative of meeting purpose, meeting content, or any other aspect of the meeting. Tags may allow for prospective attendees to find meetings of interest. Tags may allow for comparison of meetings (e.g., of meetings with similar tags), such as to ascertain relative performance of similar meetings. Tags may serve other purposes in various embodiments.

'Project number or cost center association' field 5128 may store an indication of a project and/or cost center with which a meeting is associated. Field 5128 may thereby allow tracking of the overall number of meetings that occur related to a particular project. Field 5128 may allow tallying of costs associated with meetings related to a particular cost center. Field 5128 may allow for various other tracking and/or statistics for related meetings. As will be appreciated, meetings may be associated with other aspects of an organization, such as with a department, team, initiative, goal, or the like.

Ratings field 5130 may store an indication of a meeting's rating. A rating may be expressed in any suitable scale, such as a numerical rating, a qualitative rating, a quantitative rating, a descriptive rating, a rating on a color scale, etc. A rating may represent one or more aspects of a meeting, such as the importance of the meeting, the effectiveness of the meeting, the clarity of the meeting, the efficiency of the meeting, the engagement of a meeting, the purpose of the meeting, the amount of fun to be had in the meeting, or any other aspect of the meeting. A rating may represent an aggregate of ratings or feedback provided by multiple attendees. A rating may represent a rating of a single session, a rating of a group of sessions (e.g., an average rating of a group of sessions), a rating of a most recent session, or any other part of a meeting.

In various embodiments, ratings may be used for various purposes. A rating may allow prospective attendees to decide which meetings to attend. A rating may allow an organization to work to improve meetings (e.g., the way meetings are run). A rating may aid an organization in deciding whether to keep a meeting, cancel a meeting, change the frequency of a meeting, change the attendees of a meeting, or change any other aspect of a meeting. A rating may allow an organization to identify meeting facilitators who run good meetings. A rating may be used for any other purpose, in various embodiments.

Priority field 5132 may store a priority of a meeting. A priority may be represented using any suitable scale, as will be appreciated. The priority of a meeting may serve various purposes, and various embodiments. A company employee who is invited to two conflicting meetings may attend the meeting with higher priority. If two meetings wish to use the same room at the same time, the meeting with higher priority may be granted access to the room. A meeting priority may help determine whether a meeting should be cancelled in certain situations (e.g., if there is inclement weather). Employees may be given less leeway in declining invites to meetings with high priority versus those meetings with low priority. As will be appreciated, the priority of a meeting may be used for various other purposes.

Related meetings field 5134 may store an indication of one or more related meetings. Related meetings may include meetings that relate to the same projects, meetings that are on the same topic, meetings that generate assets used by the present meeting (e.g., meetings that generate ideas to be evaluated in the present meeting; e.g., meetings that generate knowledge used in the present meeting), meetings that have one or more attendees in common, meetings that use assets generated in the present meeting, meetings run by the same meeting owner, meetings that occur in the same location, meetings that occur at the same time, meetings that occur at an approximate time, or meetings with any other relationship to the present meeting. Any given meeting may have no related meetings, one related meeting, or more than one related meeting, in various embodiments.

In various embodiments, table 5100, or some other table, may store an indication of meeting connection types. This may include an indication of types of devices that may be used to participate in a meeting (e.g., mobile, audio only, video, wearable). This may include an indication of types of connections that may be used to participate in the meeting (e.g., Wi-Fi®, WAN, 3rd party provider).

Referring to FIG. 52, a diagram of an example 'Meeting attendees' table 5200 according to some embodiments is shown. Meeting attendees table 5200 may store information about who attended a meeting (and/or who is expected to attend).

Meeting identifier field 5202 may store an indication of the meeting in question. Date field 5203 may store an indication of the date of the meeting or of a particular session of the meeting. In some cases, an attendee might attend one session of a meeting (e.g., of a recurring meeting) and not attend another session of the meeting.

Attendee identifier field 5204 may store an indication of one particular attendee of a corresponding meeting. As will be appreciated, table 5200 may include multiple records related to the same meeting. Each record may correspond to a different attendee of the meeting.

Role field 5206 may store a role of the attendee at the meeting. Exemplary roles may include meeting owner, facilitator, leader, note keeper, subject matter expert, or any other role or function. In various embodiments, a role may be 'interested participant' or the like, which may refer to a non-meeting participant, such as a CEO, CIO, VP/Director of Meetings, or Project Sponsor. In various embodiments, a role may be 'central controller administrator', 'central controller report administrator', or the like, which may refer to a participant that performs or oversees one or more functions of the central controller as it pertains to the meeting. In various embodiments, a role may be 'meeting room and equipment administrator' or the like, which may refer to a participant that oversees operations of the meeting room, such as ensuring that projectors and AV equipment are running properly.

An attendee with no particular role may simply be listed as attendee, or may be designated in any other suitable fashion.

Manner field 5208 may store an indication of the manner in which the attendee participated in the meeting. For example, an attendee may participate in person, via video conference, via web conference, via phone, or via any other manner of participation.

Referring to FIG. 53, a diagram of an example 'Meeting engagement' table 5300 according to some embodiments is shown. Meeting engagement table 5300 may store information about attendees' engagement in a meeting. Storing engagement levels may be useful, in some embodiments, for seeking to alter and improve meetings where engagement levels are not optimal. Engagement may refer to one or more behaviors of an attendee as described herein. Such behaviors may include paying attention, focusing, making contributions to a discussion, performing a role (e.g., keeping notes), staying on topic, building upon the ideas of others, interacting with others in the meeting, or to any other behavior of interest. In some embodiments, headset 4000 may provide data that informs the determining of an engagement level (e.g. detection of head drooping down, eyes closing, snoring sounds).

Meeting identifier field 5302 may store an indication of the meeting for which engagement is tracked. Date field 5304 may store the date of the meeting or of a session of the meeting. This may also be the date for which engagement was recorded.

Time field 5306 may store an indication of the time when the engagement was recorded, measured, noted, observed, reported, and/or any other pertinent time. For example, engagement may be observed over a five minute interval, and time field 5306 may store the time when the interval finishes (or the time when the interval starts, in some embodiments). In various embodiments, time field 5306 may store the entire interval over which the engagement was recorded. In various embodiments, an attendee's engagement may be measured multiple times during the same meeting or session, such as with the use of surveys delivered at various times throughout a meeting. In such cases, it may be useful to look at changes in engagement level over time. For example, if an attendee's engagement has decreased during a meeting, then the attendee may be sent an alert to pay attention, may be provided with a cup of coffee, or may otherwise be encouraged to increase his engagement level. In one embodiment, if engagement levels are low for a particular meeting, central controller 110 may send an instruction to the company catering facilities to send a pot of coffee to the room in which the meeting is occurring.

Attendee identifier field 5308 may store an indication of the attendee for whom engagement is measured.

Engagement level field 5310 may store an indication of the attendee's level of engagement. This may be stored in any suitable fashion, such as with a numerical level, a qualitative level, quantitative level, etc. In various embodiments, an engagement level may refer to a quantity of engagement, such as a number of comments made during a discussion. In various embodiments, an engagement level may refer to a quality of behavior, such as the relevance or value of comments made during a discussion. In various embodiments, an engagement level may refer to some combination of quality and quantity of a behavior. An engagement level may refer to any suitable measure or metric of an attendee's behavior in a meeting, in various embodiments.

In various embodiments, an engagement level may be connected to a biometric reading. The biometric may correlate to a person's visible behaviors or emotional state within a meeting. In various embodiments, for example, an engagement level may be a heart rate. A low heart rate may be presumed to correlate to low engagement levels. In various embodiments, field 5310 may store a biometric reading, such as a heart rate, breathing rate, measure of skin conductivity, or any other suitable biometric reading.

Engagement indicator(s) field 5312 may store an indication of one or more indicators used to determine an engagement level. Indicators may include biometrics as described above. Exemplary indicators include signals derived from voice, such as rapid speech, tremors, cadence, volume, etc. Exemplary indicators may include posture. For example, when a person is sitting in their chair or leaning forward, they may be presumed to be engaged with the meeting. Exemplary indicators may be obtained through eye tracking. Such indicators may include eye movement, direction of gaze, eye position, pupil dilation, focus, drooping of eyelids, etc. For example, if someone's eyes are just staring out into space, it may be presumed that they are not engaged with the meeting. As will be appreciated, many other engagement indicators are possible.

Burnout risk field 5314 may store an indication of an attendee's burnout risk. Burnout may refer to a significant or lasting decline in morale, productivity, or other metric on the part of an attendee. It may be desirable to anticipate a burnout before it happens, as it may then be possible to prevent the burnout (e.g., by giving the attendee additional vacation days, by giving the attendee less work, etc.). A burnout risk may be stored in any suitable fashion, such as on a "high", "medium", "low" scale, on a numerical scale, or in any other fashion.

A burnout risk may be inferred via one or more indicators. Burnout indicators field 5316 may store one or more indicators used to assess or detect an attendee's burnout risk. Exemplary indicators may include use of a loud voice, which may portend a high burnout risk. Exemplary indicators may include steady engagement, which may portend a low burnout risk. Burnout risk may also be inferred based on how often an attendee declines invites to meetings (e.g., an attendee might decline 67% of meeting invites). A high rate of declining invites might indicate that the attendee is overworked or is simply no longer interested in making productive contributions, and may therefore be burning out. An exemplary indicator might be a degree to which an attendee's calendar is full. For example, an attendee with a calendar that is 95% full may represent a medium risk of burnout. In various embodiments, multiple indicators may be used in combination to form a more holistic picture of an employee's burnout risk. For example, an employee's rate of declining meeting invites may be used in conjunction with the employee's calendar utilization to determine an employee's burnout risk.

Referring to FIGS. 54*a* and 54*b*, a diagram of an example 'Meeting feedback' table 5400 according to some embodiments is shown. Note that meeting feedback table 5400 extends across FIGS. 54*a* and 54*b*. Thus, for example, data in the first record under field 5420 (in FIG. 54*b*) is part of the same record as is data in the first record under field 5402 (in FIG. 54*a*).

Meeting feedback table 5400 may store feedback provided about a meeting. The feedback may come from meeting attendees, meeting observers, from recipients of a meeting's assets, from contributors to a meeting, from a meeting owner, from management, from facilities management, or from any other parties to a meeting or from anyone else.

Meeting feedback may also be generated via automatic and/or computational means. For example, the central controller 110 may process an audio recording of the meeting and determine such things as the number of different people who spoke, the degree to which people were talking over one another, or any other suitable metric. In some embodiments, meeting feedback may be provided by a user via headset 4000, such as by providing a verbal message of support for another meeting attendee.

In various embodiments, meeting feedback may be stored in aggregate form, such as the average of the feedback provided by multiple individuals, or such as the aggregate of feedback provided across different sessions of a meeting. In various embodiments, feedback may be stored at a granular level, such as at the level of individuals.

Meeting feedback may be useful for making changes and or improvements to meetings, such as by allowing prospective attendees to decide which meetings to attend, or for any other purpose.

Meeting feedback can be expressed in any suitable scale, such as a numerical rating, a qualitative rating, a quantitative rating, a descriptive rating, a rating on a color scale, etc.

In various embodiments, feedback may be provided along a number of dimensions, subjects, categories, or the like. Search dimensions may cover different aspects of the meeting. In some embodiments, feedback could be provided regarding room layout, air conditioning noise levels, food and beverage quality, lighting levels, and the like.

Meeting identifier field 5402 may store an indication of the meeting for which feedback is tracked. Effectiveness of facilitation field 5404 may store an indication of effectiveness with which the meeting was facilitated. Other feedback may be stored in such fields as: 'Meeting Energy Level' field 5406; Did the Meeting Stay on Track?' field 5408; Did the Meeting Start/End on Time?' field 5410; 'Room Comfort' field 5412; 'Presentation Quality' field 5414;

'Food Quality' field 5418; 'Room lighting' field 5420; 'Clarity of purpose' field 5422; Projector quality' field 5424; 'Ambient noise levels' field 5426; 'Strength of Wi-Fi® Signal' field 5428; 'Room cleanliness' field 5430; and 'view from the room' field 5432 where the field labels themselves may be explanatory of the type of feedback stored in such fields.

'Overall rating' field 5416 may store an overall rating for a meeting. The overall rating may be provided directly by a user or by multiple users. The overall rating may be computationally derived from feedback provided along other dimensions described herein (e.g., the overall rating may be an average of feedback metrics for effectiveness of facilitation, meeting energy level, etc.). The overall rating may be determined in any other suitable fashion.

Other feedback may be related to such questions as: Were meeting participants encouraged to provide their opinions?; Was candor encouraged?; Was the speaker's voice loud enough?; Was the speaker understandable?; Did the meeting owner know how to use the technology in the room?

In various embodiments, the central controller 110 may inform the meeting owner during or after the meeting that clarity is low (or may provide some other feedback to the meeting owner or to any other participant). Feedback could be private to the meeting owner, or it could be made available to everyone in the room, or just to management.

In various embodiments, feedback about the meeting owner goes to the meeting owners boss (or to any other person with authority over the meeting owner, or to any other person).

In various embodiments, feedback about the meeting may be used as a tag for the meeting. The tag may be used in searching, for example.

In various embodiments, other feedback may relate to meeting content (presentation, agenda, meeting assets, etc.), and may address such questions as: Was the content organized efficiently?; Was the content clear and concise?; Was the content appropriate for the audience? For example, was the presentation too technical for an executive level meeting?

In various embodiments, other feedback may relate to presentation material and slide content, and may address such questions as: How long did the presenter spend on each slide?; Were the slides presented too quickly?; Were some slides skipped?; What type of slides result in short or long durations?; How long did the presenter spend on slides related to the meeting purpose or agenda?; Did the presenter finish the presentation within the allotted time?; Were there too many words on each slide?; Did the presentation include acronyms?; Was there jargon in the presentation?; Were graphs, figures, and technical materials interpretable and readable?; Which slides in meeting participants return to review? The answers to these questions could be used to tag low clarity scores to particular material, presentations, or individual slides.

In various embodiments, other feedback may relate to technology, and may address such questions as: Was all room equipment working throughout the meeting?; Did external factors (home Wi-Fi®, ISP provider, energy provider disruption) contribute to poor use of technology?; Was equipment missing from the room (for example chairs, projectors, markers, cables, flip charts, etc.)?

In various embodiments, other feedback may relate to room setup, and may address such questions as: Was the room difficult to locate?; Were participants able to locate bathrooms?; Was the room A/C or heating set appropriately for the meeting?; Was the room clean?; Were all chairs and tables available per the system configuration?; Was the screen visible to all participants?; Were the lights working?; Was the room unlocked?; Was the room occupied?; Was food/beverage delivered on-time and of high quality?

Referring to FIG. 55, a diagram of an example 'Meeting participation/Attendance/Ratings' table 5500 according to some embodiments is shown. Meeting participation/Attendance/Ratings table 5500 may store information about attendees' participation, attendance, ratings received from others, and/or other information pertaining to a person's attendance at a meeting. Information stored in table 5500 may be useful for trying to improve individual attendees' performances in meetings. For example, if an attendee is habitually late for meetings, then the attendee may be provided with extra reminders prior to meetings. Information stored in table 5500 may also be useful for planning or configuring meetings. For example, if it is known that many attendees had to travel far to get to a meeting, then similar meetings in the future may be held in a more convenient location. Information stored in table 5500 may be used for any other suitable purpose.

Meeting identifier field 5502 may store an indication of the meeting in question. Date field 5504 may store an indication of the date of the meeting or of a particular session of the meeting. In some cases, an attendee might attend one session of a meeting (e.g., of a recurring meeting) and not attend another session of the meeting.

Employee identifier field 5506 may store an indication of one particular employee or attendee of a corresponding meeting. Role field 5508 may store a role of the attendee at the meeting as described above with respect to field 5206. 'Confirmed/Declined meeting' field 5510 may store an indication of whether the employee confirmed his or her participation in the meeting or declined to participate in the meeting. In various embodiments, field 5510 may indicate that the employee actually attended the meeting, or did not actually attend the meeting.

'Time arrived' field 5512 may indicate when an employee arrived at a meeting. This may represent a physical arrival time, or a time when the employee signed into a meeting being held via conferencing technology, and/or this may represent any other suitable time.

'Time departed' field 5514 may indicate when an employee departed from a meeting (e.g., physically departed; e.g., signed out of a virtual meeting; etc.).

'Travel time to meeting location' field 5516 may indicate an amount of time that was required for the employee to travel to a meeting. The travel time may be the time it actually took the employee to reach the meeting. The travel time may be a time that would generally be expected (e.g., a travel time of the average person at an average walking pace; e.g., a travel time of the average driver at an average driving speed; etc.). In various embodiments, the travel time may assume the employee started at his office or his usual location. In various embodiments, the travel time may account for the employee's actual location prior to the meeting, even if this was not his usual location. For example, the travel time may account for the fact that the employee was just attending another meeting and was coming from the location of the other meeting.

'Travel time from meeting location' field 5518 may indicate an amount of time that was required for the employee to travel from a meeting to his next destination. Similar considerations may come into play with field 5518 as do with field 5516. Namely, for example, travel times may represent actual or average travel times, destinations may represent actual or typical destinations, etc.

'Employee rating by others' field 5520 may represent a rating that was given to an employee by others (e.g., by other attendees of the meeting). The rating may reflect an employee's participation level, an employee's contribution to the meeting, an employee's value to the meeting, and/or any other suitable metric.

Referring to FIG. 56, a diagram of an example 'Employee calendars' table 5600 according to some embodiments is shown. Table 5600 may store information about employees' scheduled appointments, meetings, lunches, training sessions, or any other time that an employee has blocked off. In various embodiments, table 5600 may store work-related appointments. In various embodiments, table 5600 may store other appointments, such as an employee's personal appointments. Table 5600 may be useful for determining who should attend meetings. For example, given two possible attendees, the central controller may invite the employee with more free time available on his calendar. Table 5600 may also be used to determine whether an employee's time is being used efficiently, to determine an employee's transit time from one appointment to another, in the nature of meetings with which employees are involved, or in any other fashion.

Employee identifier field 5602 may store an indication of an employee. Meeting identifier field 5604 may store an indication of a meeting. If the appointment is not a meeting, there may be no identifier listed. Subject field 5606 may store a subject, summary, explanation, or other description of the appointment. For example, field 5606 may store the subject of a meeting if the appointment is for a meeting, or it may describe a 'Doctor call' if the appointment is for the employee to speak to his doctor.

Category field 5608 may store a category of the appointment. Exemplary categories may include 'Meeting' for appointments that are meetings, 'Personal' for appointments that are not work related (e.g., for an appointment to attend a child's soccer game), 'Individual' for appointments to spend time working alone, or any other category of appointment. In various embodiments, categories are input by employees (e.g., by employees who create appointments; e.g., by meeting organizers; e.g., by employees conducting a manual review of calendars). In various embodiments, a category is determined programmatically, such as by classifying the subject of an appointment into the most closely fitting category.

Date field 5610 may store the date of the appointment. Start time field 5612 may store the start time of the appointment. Duration field 5614 may store the duration of the appointment. In various embodiments, a separate or alternate field may store an end time of the appointment.

'Company/personal' field 5616 may store another means of classifying the appointment. In this case, the appointment may be classified as either company (e.g., work-related), or personal (not work-related).

Referring to FIG. 57, a diagram of an example 'Projects' table 5700 according to some embodiments is shown. Table 5700 may store information about projects, initiatives, or other endeavors being undertaken by an organization. Tracking projects at an organization may be useful for various reasons. An organization may wish to see how many meetings are linked to a particular project. The organization may then, for example, decide whether there are too few or too many meetings associated with the project. The organization may also allocate a cost or a charge to the project associated with running the meeting. The organization may thereby, for example, see whether a project is overstepping its budget in light of the number of meetings it is requiring.

Project ID field 5702 may store an identifier (e.g., a unique identifier) for a project. Name field 5704 may store a name associated with a project. 'Summary' field 5706 may store a summary description of the project.

Exemplary projects may include a project to switch all employees' desktop computers to using the Linux™ operating system; a project to allow employees to work remotely from the office in a manner that maximizes data security; a project to launch a new app; a project to obtain up-to-date bids from suppliers of the organization. As will be appreciated, any other suitable project is contemplated.

Start date field 5708 may store a start date of the project. Priority field 5710 may store a priority of the project. Expected duration field 5712 may store an expected duration of the project.

Percent completion field 5714 may store the percentage of a project that has been completed. Various embodiments contemplate that other metrics of a project completion may be used, such as number of milestones met, percent of budget spent, quantity of resources used, or any other metric of project completion.

Budget field 5716 may store a budget of the project.

Personnel requirements field 5718 may store personnel requirements of the project. In various embodiments, personnel requirements may be expressed in terms of the number of people required and/or in terms of the percentage of a given person's time (e.g., of a given workday) which would be devoted to a project. For example, a personnel requirement of '10 people at 75% time' may indicate that the project will require 10 people, and that each of the 10 people will be utilizing 75% of their time on the project. In various embodiments, personnel requirements may be specified in additional terms. For example, personnel requirements may indicate the departments from which personnel may be drawn, the number of personnel with a given expertise that will be required (e.g., the number of personnel with java expertise), the number of personnel with a given title that will be required (e.g., the number of project managers), or any other requirements for personnel.

Referring to FIG. 58, table 5800 may store information about employees or other people involved in projects. In various embodiments, table 5800 may store information about key personnel involved in projects. In some embodiments, table 5800 may include information beyond employees, such as contractors, vendors, trainers, safety inspectors, or regulators who may be involved in the project (e.g. a laser safety trainer).

Project ID field 5802 may store an identifier of a project. Employee ID field 5804 may store an indication of an employee who is somehow involved or associated with the project. Role field 5806 may store an indication of an employee's role within a project. Exemplary roles may include: project manager; lead developer; communications strategist; procurement specialist; or any other role, or any other function, or any other association to a project.

Referring to FIG. 59, a diagram of an example 'Projects milestones' table 5900 according to some embodiments is shown. Table 5900 may store information about project milestones, phases, goals, segments, accomplishments or other components of a project.

Project ID field 5902 may store an identifier of a project. Milestone ID field 5904 may store an identifier (e.g., a unique identifier) of a milestone.

Sequence number field 5906 may store a sequence number representing where the present milestone falls in relation to other milestones within the project. For example, the first milestone to be accomplished in a project may receive a sequence number of 1, the second milestone to be accomplished in a project may receive a sequence number of 2, and so on. As will be appreciated, sequence numbers may be designated in any other suitable fashion, such as with roman numerals, with letters of the alphabet, by counting up, by counting down, or in any other manner. In various embodiments, field 5906 (or another field) may also store an indication of the total number of milestones in a project, or of the highest sequence number in the projects. For example, a sequence number may be stored as "3 of 8", indicating that the milestone is the third milestone out of eight milestones in the project. In various embodiments, it may be intended that some milestones be completed in parallel. Exemplary milestones to be completed in parallel may be designated "3A", "3B", etc., or may use any other suitable designation.

Summary field 5908 may store a summary or other description of the milestone. Exemplary summaries include: draft request for proposal; implement pilot with legal group; stress test; review all vendor proposals; or any other summary or description.

Due date field 5910 may store a date when the milestone is due for completion. Percent complete field 5912 may store an indication of what percentage (or fraction) of a milestone has been completed.

Approver(s) field 5914 may store an indication of one or more people who have the authority or ability to approve that a milestone has been completed. For example, an approver might be a project manager, a vice president of a division overseeing a project, a person with expertise in the technology used to accomplish the milestone, or any other suitable approver. Violations field 5916 may store an indication of one or more violations that have occurred on a project.

Referring to FIG. 60, a diagram of an example 'Assets' table 6000 according to some embodiments is shown. Assets may include encapsulated or distilled knowledge, roadmaps, decisions, ideas, explanations, plans, processing fees, recipes, or any other information. Assets may be generated within meetings (e.g., a meeting may result in decisions). Assets may be generated for meetings (e.g., presentation decks). Assets may be generated in any other fashion or for any other purpose.

Figure 68:
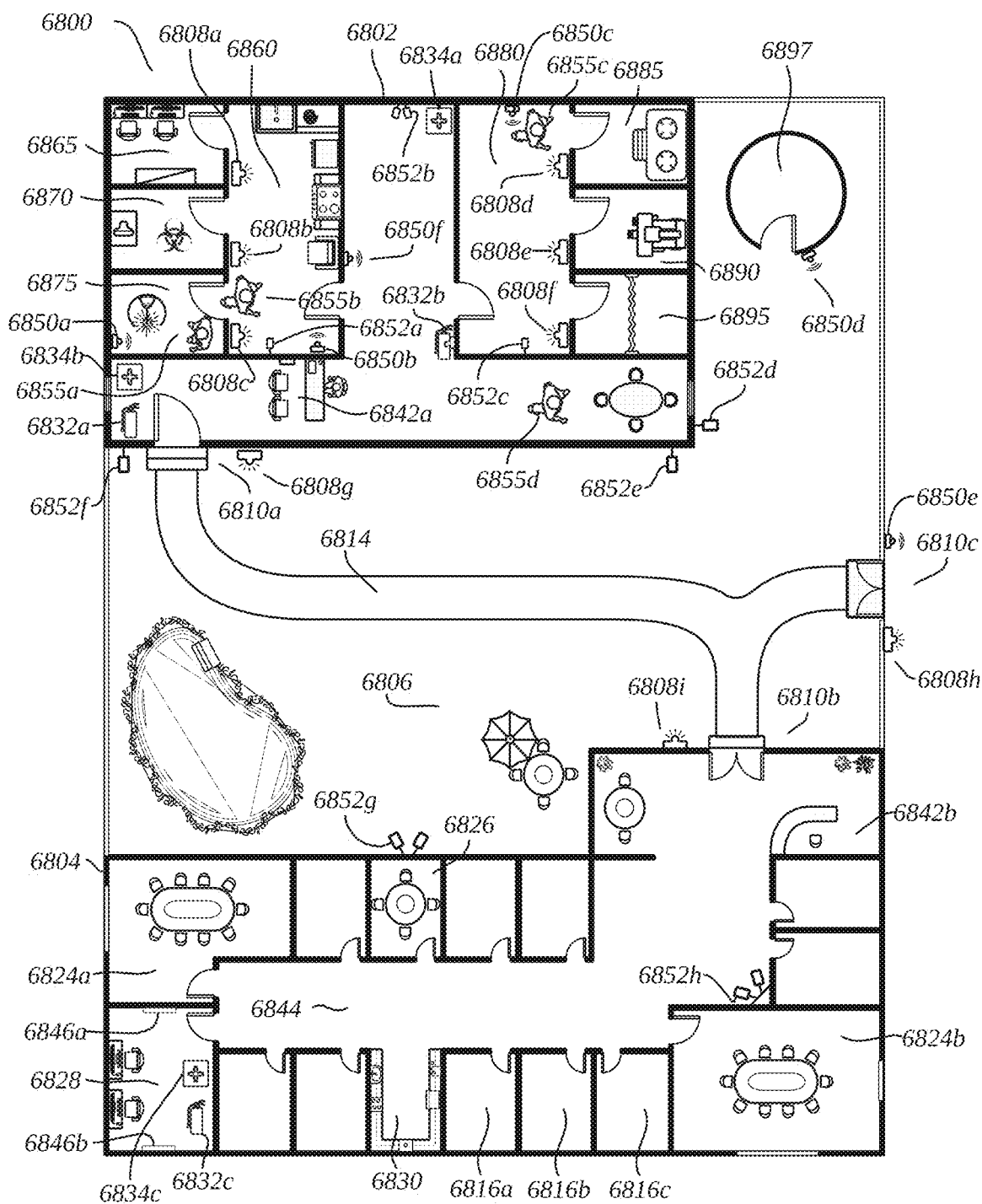
FIG. 68 is a map of a campus with buildings consistent with at least some embodiments described herein.

In various embodiments, an asset may include information for improving company operations, or meetings themselves. In various embodiments, an asset may include a map, an office map, a campus map, or the like. An exemplary map 6300 is depicted in FIG. 68. For example, a map may assist in planning for meetings by allowing for selection of meeting locations that minimize participant travel times to the meeting, or match the meeting to the nearest available location with the appropriate capacity or necessary technology.

Table 6000 may store information about assets. Table 6000 may be useful for a number of reasons, such as allowing an employee to search for an educational deck, allowing an employee to find a summary of a meeting that he missed, allowing employees to act in accordance with decisions that have been made, allowing employees to review what had been written on a whiteboard, etc.

In various embodiments, table 6000 may be used in addition to, instead of, and/or in combination with asset library table 1900.

Asset ID field 6002 may store an identifier (e.g., a unique identifier) of an asset. Asset type field 6004 may store an indication of an asset type. Exemplary asset types may be: a presentation deck; notes; meeting minutes; decisions made; meeting summary; action items; photo of whiteboard, or any other asset type. Exemplary asset types may include drawings, renderings, illustrations, mock-ups, etc. For example, an asset might include a draft of a new company logo, a brand image, a mock-up of a user interface for a new product, plans for a new office layout, etc. Exemplary asset types may include videos, such as training videos, promotional videos, etc.

In various embodiments, an asset may include a presentation or presentation template formatted for a particular meeting type or audience (e.g., formatted for executives, members of the board of directors, a project sponsor, a team meeting, a one-on-one, etc.).

In various embodiments, an asset may include a progress report, progress tracker, indication of accomplishments, indication of milestones, etc. For example, an asset may include a Scrum Board, Kanban Board, etc.

In various embodiments, assets may be divided or classified into other types or categories. In various embodiments, an asset may have multiple classifications, types, categories, etc.

Meeting ID field 6006 may store an identifier of a meeting with which an asset is associated. For example, if the asset is a deck, the meeting may be the meeting where the deck was used. If the asset is a decision, the meeting may be the meeting where the decision was made.

Creation date field 6008 may store a date when an asset was created. In various embodiments, one or more dates when the asset was modified (e.g., the date of the most recent modification) may also be stored.

Author field 6010 may store the author or authors of an asset. In various embodiments, authors may include contributors to an asset. For example, if an asset is a photo of a whiteboard, then the authors may include everyone who was at the meeting where the whiteboard was populated.

Version field 6012 may store the version of an asset. In various embodiments, an asset may undergo one or more updates, revisions, or other modifications. Thus, for example, the version number may represent the version or iteration of the asset following some number of modifications. At times, it may be useful for an employee to search through older versions of an asset, perhaps to see what the original thinking behind an idea was before it got removed or changed.

Tags field 6014 may store one or more tags associated with an asset. Tags may provide explanatory information about the asset, indicate an author of an asset, indicate the reliability of the asset, indicate the finality of the asset, indicate the state of the asset, indicate the manner in which the asset was generated, indicate feedback about an asset, or provide any other information pertinent to an asset. Exemplary tags include: rated 8/10; author eid204920; computer transcription; needs VP confirmation; short-term items; all items approved by legal; medium quality.

Keywords field 6016 may store one or more keywords or other words, numbers, phrases, or symbols associated with an asset. Keywords may be excerpted from an asset. For example, keywords may be taken from the title of the asset. Keywords may be words that describe the subject or the nature of the asset but are not necessarily literally in the asset. Keywords may be any other suitable words. In various embodiments, keywords may serve as a means by which an employee can locate an asset of interest. For example, if an employee wants to learn more about a certain topic, then the employee may search for assets where the keywords describe the topic. Exemplary sets of keywords include: mission statement, vision, market impact, value prop, customer segments, breakeven, technology roadmap, fiber cables, cloud, personnel, resources, European market, SWOT analysis.

Rating field 6018 may store one or more ratings for the asset. Ratings may represent the utility of the asset, the quality of the asset, the importance of the asset, and/or any other aspect of the asset, and/or any combination of aspects of the asset.

Asset data field 6020 may represent the data comprising the asset itself. For example, if the asset is a deck, then data field 6020 may store the actual PowerPoint file data for the deck. If the asset is a photograph, then data field 6020 may store an actual JPEG file of the photograph. In various embodiments, table 6000 may store a link or reference to an asset, rather than the asset data itself (e.g., the asset may be stored in a separate location and table 6000 may store a link or reference to such location).

Presentation Materials

Many company presentations include a deck such as a Microsoft® PowerPoint™ presentation that is emailed to participants and projected for meeting participants to view and discuss during a meeting. Presentation materials can also include videos, white papers, technical documents, instruction manuals, checklists, etc. These presentation materials, however, are often stored on local computers that are not searchable by other individuals.

Various embodiments bring the content of all presentation materials into the central controller 110 (or stored in a cloud provider in a way that is accessible by the central controller) so that they are available to any meeting owner, participant, or employee of the company. A central store of all presentations could include access to historical presentations.

Referring to FIG. 61, a diagram of an example 'Presentations' table 6100 according to some embodiments is shown. Presentations may include decks (e.g., PowerPoint™ decks, Apple® keynote decks, Google® slide decks, etc.). Presentations may include other types of files, such as PDF files, Microsoft® Word™ documents, multimedia files, or any other type of file or any other type of information.

Table 6100 may store information about presentations. Table 6100 may be useful for a number of reasons, such as allowing an employee to search for a particular presentation, a presentation on a topic of interest, the latest in a series of presentations, highly rated presentations, etc. Table 6100 may also allow, for example, comparison of different attributes of a presentation (e.g., number of slides; e.g., number of tables; etc.), in order to ascertain what attributes of a presentation improve the presentation's effectiveness. Table 6100 may also allow a user to search through presentation decks on a particular topic so that he or she can use material from those decks to aid in the creation of a new presentation deck. Table 6100 may be used for various other purposes as well.

In various embodiments, table 6100 may be used in addition to, instead of, and/or in combination with meeting assets table 6000. In various embodiments, a presentation is a type of asset.

Asset ID field 6102 may store an identifier of an asset, where, in this case, the asset is a presentation. Number of slides field 6104 may store the number of slides. Number of words field 6106 may store the number of words in the presentation. In various embodiments, a density of words per slide may be computed from fields 6104 and 6106 (e.g., by dividing the number of words described in 6106 by the number of slides described in 6104).

Size of the file field 6108 may store the size of a file that represents the presentation (e.g., the size of a PowerPoint file comprising the presentation). Presentation software version field 6110 may store the software, software version, application, program, or the like used for a presentation (e.g., Microsoft® PowerPoint™ for Mac® version 16.35; Keynote™ 11.0; Google® slides).

Number of graphics field 6112 may store the number of graphics used in the presentation. Graphics may include pictures, charts, graphs, tables, maps, animations, illustrations, word clouds, or any other graphic, or any other information.

Number and type of tags field 6114 may store an indication of the number and/or types of tags associated with a presentation. Tags may include descriptive tags, which may describe the nature, subject matter or content of the presentation (e.g., to aid in searching for the presentation), or a portion thereof. Tags may include ratings tags, which may evaluate the presentation, or a portion thereof, along one or more dimensions (e.g., quality, clarity, relevance, reliability, currency, etc.). In various embodiments, a tag may apply to the presentation as a whole. In various embodiments, a tag may apply to a portion of the presentation, such as to an individual slide, an individual graphic, a group of slides, a group of graphics, a section of the presentation, or to any other portion of the presentation. With tags, an employee may be able to search for the "financials" portion of a presentation on the "Mainframe architecture" project, for example.

Number of times presented field 6116 may store an indication of the number of times the presentation has been presented (e.g., the number of meetings in which the deck has been featured).

Template used field 6118 may store an indication of a template that was used in creating the presentation. In various embodiments, it may be desirable that presentations on certain topics or for certain purposes follow a specific format. This format may be dictated by a template. For example, a project evaluation committee may wish that all proposals for new projects follow a set format that is dictated by a "Project proposal" template. As another example, it may be desirable that all presentations that are seeking to educate the audience follow a particular format that has been found conducive to learning. Such presentations may follow a "Learning template". The presence of templates may also assist the creator of a presentation in creating the presentation more rapidly.

In various embodiments, there may be multiple templates available for creating a certain type of presentation. For example, there may be multiple types of business plan templates. Those specific template children may depend on the nature of the business plan, the preferences of the presentation creator, or on any other factor. Example templates depicted for field 6118 include: learning template #3; business plan template #8; financials template #3.

Time to create presentation field 6120 may store an indication of the time it took to create the presentation. In various embodiments, this may be an indicator of the quality of a presentation. In various embodiments, a company may wish to make it easier or more efficient to create presentations, and therefore may wish to track how long it took to make every presentation and watch for decreases in creation time over time.

Key points field 6122 may store key points that are in the presentation. These may represent key insights, takeaways, summaries, topics, decisions made, or any other key points, or any other points. Field 6122 may allow employees to search for presentations covering points of interest to them.

Take away summary included field 6124 may indicate whether or not the presentation includes a take away summary. In various embodiments, it may be desirable to encourage presenters to include a take away summary, so the presence of such a summary may be tracked. In various embodiments, an employee with limited time may wish to search for presentations with takeaway summaries and read such summaries rather than reading the entire presentation. A takeaway summary may be used in other embodiments as well.

Security level field 6126 may indicate a security level of the presentation. The level may be expressed in terms of a minimum title or rank an employee must have in order to access the presentation. Example security levels include: general; manager+; VP+. Security levels may be expressed in other terms or scales as well. For example, security levels may be specified in terms such as "general", "sensitive", "secret", "top secret", or using any other scale or terminology.

In various embodiments, portions of a presentation may have their own security levels. For example, the first slide in a presentation may be available for general consumption at the company, whereas another slide may have a higher security level and be accessible only to managers and above. In various embodiments, security levels may apply to individual slides, groups of slides, sections of a presentation, individual graphics, groups of graphics, and/or any other portion or subset of a presentation.

Presentation creation date field 6130 may store the date the presentation was created. In various embodiments, this or another field may store the date of the last revision of the presentation.

Presentation rating field 6132 may store an indication of a rating given to the presentation. A rating may be expressed in any suitable scale (e.g., quantitative, qualitative, etc.). A rating may represent one or more aspects of a presentation, such as the importance of the presentation, the effectiveness of the presentation, the clarity of the presentation, or any other aspect of the presentation. A rating may represent an aggregate of ratings or feedback provided by multiple people. A rating may represent any other suitable statistic.

Acronyms field 6134 may store an indication of acronyms used in the presentation. The field may include an explanation or expansion of the acronym(s). In various embodiments, this may provide a convenient means for uninitiated readers to see what the acronyms mean. In various embodiments, acronyms may be tracked by a company with the desire to reduce the use of acronyms within presentations. Example acronyms include: DCE—data communications equipment; IMAP—internet message access protocol, FCE—frame check sequence.

Tags field 6136 may store one or more tags associated with a presentation. Tags may provide explanatory information about the presentation, indicate an author of the presentation, indicate the reliability of the presentation, indicate the finality of the presentation, indicate the state of the presentation, indicate the manner in which the presentation was generated, indicate feedback about an presentation, or provide any other information pertinent to an presentation. Exemplary tags include: pr75660791, pr71427249 (i.e., this presentation is associated with project IDs pr75660791 and pr71427249), DCE, learning; business plan, market assessment; Projections, financials, pr96358600.

Referring to FIG. 62, a diagram of an example 'Presentation Components' table 6200 according to some embodiments is shown. Presentations may include decks (e.g., PowerPoint decks, Apple Keynote decks, Google® slide decks, etc.). Presentations may include other types of files, such as PDF files, Microsoft® Word documents, multimedia files, or any other type of file or any other type of information. A component of a presentation could be a subset of the content of the presentation.

Table 6200 may store information about components of presentations, such as a particular page of a PowerPoint™ presentation or a chart from a pdf document. Presentation components could also include portions of a video or audio file. Table 6200 may be useful for a number of reasons, such as allowing meeting participants to rate particular components of a presentation, such as by providing a numeric rating for each of three important slides from a presentation as opposed to an overall rating for the presentation. Table 6200 may also allow a user to identify the highest rated sales chart from a large library of presentations, and to use that sales chart at a sales team Town hall presentation. Table 6200 may be used for various other purposes as well.

In various embodiments, table 6200 may be used in addition to, instead of, and/or in combination with meeting presentation table 6100. In various embodiments, a presentation component is a type of asset.

Asset ID field 6202 may store an identifier of an asset, where, in one embodiment, the asset is a presentation. Component ID field 6204 identifies a component of an asset, such as a single slide page from a presentation. In this example, the presentation is the asset and the component is the slide page. Each identified asset may contain many components identified by component ID 6204.

Component type field 6206 may store an indication of the component being identified. For example, a component type might be PowerPoint™ slide 7, a graphic file from a Keynote™ presentation, a section of a presentation that discusses benefits of a new software package for the finance department, a two-minute audio clip from a 30-minute CEO all hands presentation, etc.

Average rating field 6208 may store one or more ratings for the component ID. Ratings may represent the utility of the component, the quality of the component, the importance of the component, and/or any other aspect of the component, and/or any combination of aspects of the component. Ratings could be aggregated numerical ratings one a scale of one to ten, such as ratings of 7.5 or 8.2. Ratings could be provided by meeting attendees who attended one or more meetings in which the component was presented, providing a rating after review of the component via a user device in communication with central controller 110.

Ratings associated with presentation components could be useful in identifying employees who produce high quality assets. For example, a component with a high rating can be traced through component ID field 6204 to the corresponding meeting asset ID field 6202 and then, through presentation assets table 6000, to author field 6010 to determine the identity of the author or the presentation from which the component was a part.

Figure 63A:
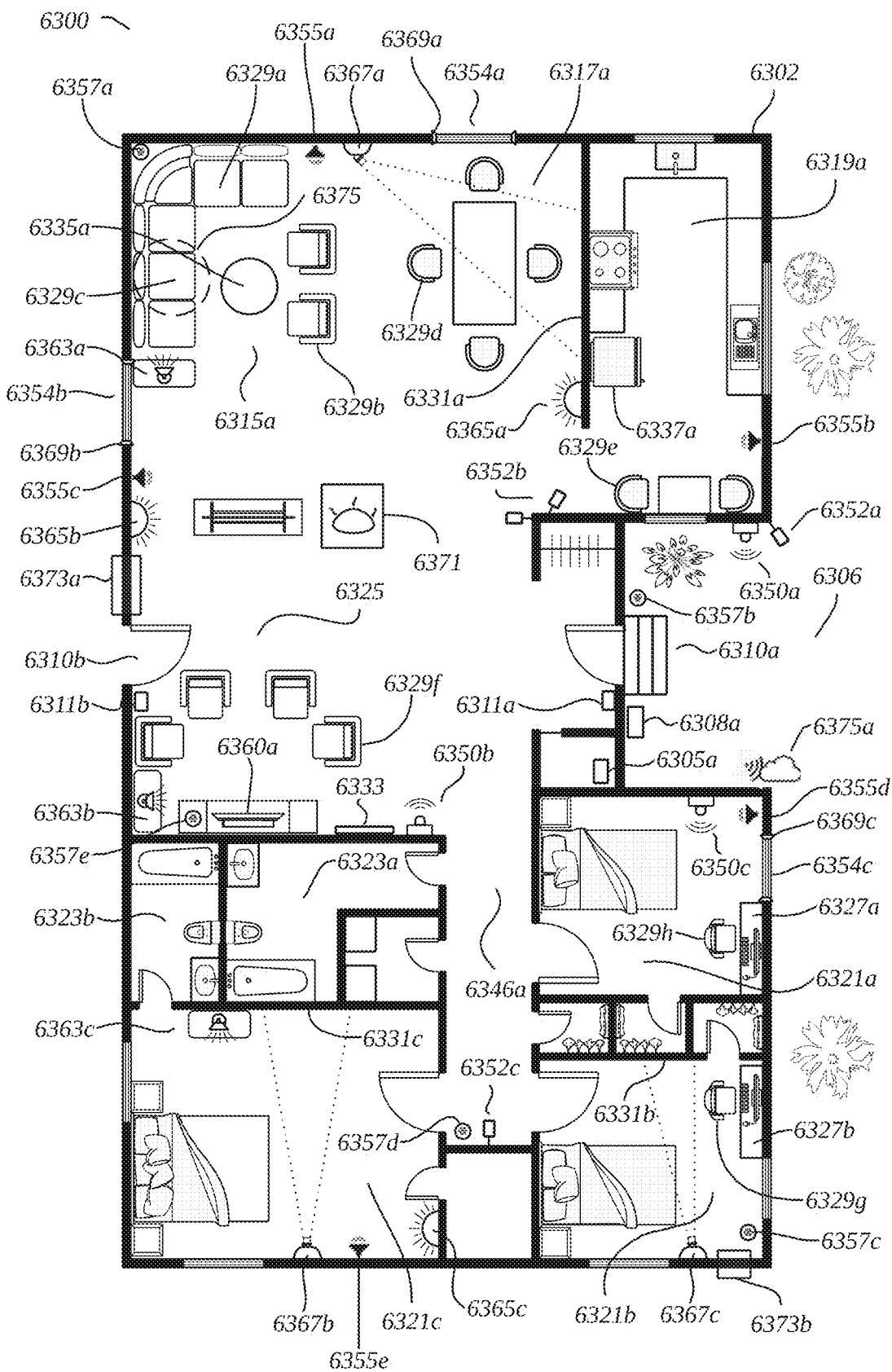
FIGS. 63A and 63B together are a map of two houses consistent with at least some embodiments described herein.
Figure 63B:
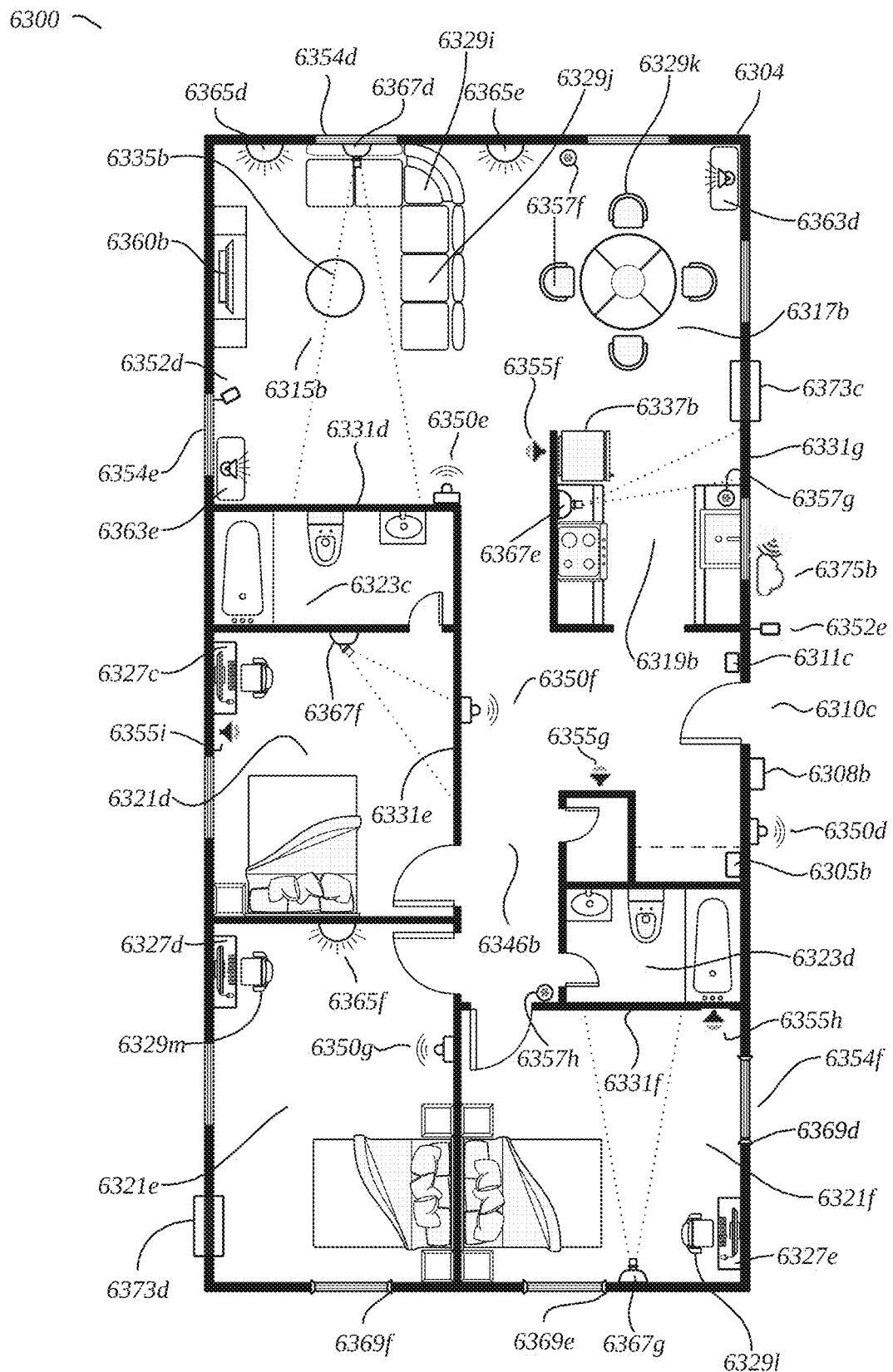

With reference to FIGS. 63A and 63B, a depiction of an example map 6300 according to some embodiments is shown. The map may represent houses, apartments, dorm rooms, or the like. In various embodiments, the map may represent a map of any building, set of buildings, or other environment. This floor plan view of two houses is intended to illustrate some of the devices that may be usefully controlled in a house in order to improve the fun, productivity, clarity, collaboration, connectivity, engagement, safety, or other factors. In some embodiments, devices within various rooms of a house are under the control of a house controller which may use wired or wireless connections to send commands or requests of each of the devices in the house. This allows people to employ user devices or peripheral devices to communicate with the house controller in order to command various devices in the house, and to receive information back from one or more of these devices in the house. It will be understood that this layout 6300 of two houses is for illustrative purposes only, and that any other shape or layout of houses could employ the same technologies and techniques. The depicted houses include various devices and represent one exemplary arrangement of devices. However, various embodiments contemplate that any suitable arrangement of devices, and any suitable quantity of devices (e.g., quantity of chairs; e.g., quantity of cameras) may likewise be used.

Map 6300 depicts two houses 6302 and 6304 with an outdoor area 6306. In one example, houses 6302 and 6304 may be located next to each other, with outdoor area 6306 being located between the two houses. As depicted in map 6300, houses 6302 and 6304 each have only one floor. However in various embodiments, houses with multiple floors may be depicted. In some embodiments, devices within the map 6300 are under the control of a central controller 110 which may use wired or wireless connections to send commands or requests to various devices and locations in one or more of the houses. This allows game players, computer users, and virtual call participants to employ peripherals (e.g. game consoles, headsets, mice, keyboards) or user devices (e.g. smartphone, smart watch) to communicate with central controller 110 in order to command various devices throughout one or more locations. It will be understood that this layout of houses is for illustrative purposes only, and that any other shape or layout of houses could employ the same technologies and techniques.

The depicted map view includes various devices and represents one exemplary arrangement of rooms, walls, furniture, and devices. However, various embodiments contemplate that any suitable arrangement of rooms, walls, furniture, and devices, and any suitable quantity of devices (e.g., quantity of chairs; e.g., quantity of cameras) may likewise be used.

House 6302 has main entrance 6310a and backyard entrance 6310b. House 6304 has entrance 6310c. The outdoor area 6306 may comprise a front yard, backyard, porch, balcony, swimming pool, etc. In various embodiments, the outdoor area 6306 may be fenced-off.

Inside houses 6302 and 6304 are depicted various rooms, including living rooms, dining rooms, kitchens, offices, bedrooms, bathrooms, game rooms, etc. Various embodiments contemplate that houses may include other types of rooms even if not explicitly depicted (e.g., exercise areas, roof areas, balconies, basements, atrium space, storage space, etc.).

House 6302 includes hallway 6346a, and house 6304 includes hallway 6346b. Map 6300 depicts various cameras, such as camera 6352b which observes the outdoor area 6306, and camera 6352a which observes hallway area 6346a. Inside houses 6302 and 6304 are depicted various windows. It will be appreciated that map 6300 depicts an arrangement of rooms according to some embodiments, but that various embodiments apply to any applicable arrangement of rooms.

House controller 6305 may be configured to manage devices throughout houses 6302 and 6304, communicating with those devices via wired or wireless signals. In some embodiments, house controller 6305 may also send a signal to one or more room lights 6363 to go dark or lower their intensity in order to make other lights or displays more visible. Additionally, house controller 6305 may send a signal to shade controller 6369 instructing it to lower the shade for one or more windows in a house as a way to make a game experience more immersive.

Identification readers 6308a and 6308b are positioned at the entry points 6310a and 6310c, respectively, and serve to identify people and allow/deny access as they attempt to move through the entry points. For example, identification readers can be RFID readers to scan a badge, a camera to identify the person via face recognition, a scanner to identify a person by a carried user device, a microphone for voice recognition, or other identification technology. Identification readers 6308a and 6308b may communicate with headsets worn by users in order to receive identifying information. In some embodiments, a user authenticates himself using his headset in communication with an identification reader. In some embodiments, identification readers 6308a-b transmit data about people entering or leaving house 6302 and 6304 and transmit data to house controller 6305 or directly to central controller 110, e.g. for the purposes of communicating with game players in a house within a house or with other houses in order to enhance game play.

Access controls 6311a, 6311b, and 6311c can lock or unlock a door leading into houses 6302 and 6304. Such controls could be used, for example, to enable a game player to remotely allow access to a house to join one or more other players in a game. In some embodiments, a user authenticates himself at an access control point using biometrics transmitted from his headset (e.g. spoken passwords, voiceprint, fingerprint, iris scan).

Various rooms and locations throughout houses 6302 and 6304 could include Living Rooms 6315, Dining Rooms 6317, Kitchens 6319, Bedrooms 6321, Bathrooms 6323, Game Areas 6325, Desks 6327, Chairs 6329, Walls 6331, Smart Boards 6333, Tables 6335, Refrigerators 6337, etc.

Living rooms 6315a and 6315b can serve as spaces for families to gather, and for game activities that require more than one player. Dining rooms 6317a and 6317b may primarily be a place for meals, though it can also serve as another place to play games as well. Kitchens 6319a and 6319b can hold food and beverage products as well as devices for game play. For example, kitchens 6319a-b could include a refrigerator, oven, stove, sink, coffee maker, hot water dispenser, microwave oven, hot plate, toaster, and the like. Devices within kitchens 631a-b could be controlled by house controllers 6305a-b. In some embodiments, a coffee maker could be instructed to turn on ten minutes before the first game of each day, so that coffee is ready when game participants walk into living room 6315a. Bedrooms 6321a, 6321b, 6321c, 6321d, 6321e, and 6321f can also host game sessions. In some embodiments, a number of players may play a shared or collaborative game in which they each occupy separate bedrooms but communicate and play a game through house controller 6305a-b or via central controller 110. Bathrooms 6323a, 6323b, 6323c, and 6323d may have communication devices such as speakers 6355 or room lights 6363 that can provide messages to players such as a warning that game play is going to resume in five minutes.

Game area 6325 is adjacent to living room 6315a, and in some embodiments serves as a dedicated game play area.

Houses 6302 and 6304 are also shown including objects that can support or enhance activities with a house (e.g. game play, video conference calls). Desks 6327a, 6327b, 6327c, 6327d, and 6327e can hold user devices and peripheral devices. For example, desk 6327c might have a computer, keyboard, headset, and mouse on its surface. Chairs 6329a, 6329b, 6329c, 6329d, 6329e, 6329f, 6329g, 6329h, 6329i, 6329j, 6329k, 6329l, and 6329m can also be used for many purposes, including game play or virtual calls. Chairs 6329a-m can provide seating for a game participant. In some embodiments, chairs 6329a-m could include input and output sensors, powered wheels, tilt sensors, display screens, speakers, location detection technology (e.g., GPS), and the like. In some embodiments, house controller 6305 can send and receive messages from chairs 6329a-m. For example, the location detection technology of chair 6329g could send a signal to house controller 6305a every hour, allowing for inventory control of chair 6329g which would allow central controller 110 to know when chairs had been moved within a house. In other embodiments, chairs 6329a-m include built-in buttons for game inputs, voting, messaging, volume control, temperature control, etc. Walls 6331a, 6331b, 6331c, 6331d, 6331e, 6331f, and 6331g can be used as a surface on which projectors 6367a-g may project images, video, messages, etc.

Smart board 6333 can capture ideas, drawings, lists, and other information, and in some embodiments transmit them to house controller 6305a for storage or processing, or transmit the data directly to central controller 110 for storage or processing. In some embodiments, information from smart board 6333 may be used to update data tables in house controller 6305a or central controller 110 such as user game preferences, messaging between game players, game character strategies, etc.

Tables 6335a and 6335b can provide a surface on which game players can place devices (e.g. laptop computers, smartphones) as well as peripherals (e.g. mouse, keyboard, game controller, headset). In one embodiment, speakers 6355 and microphones 6357 (which could be combined into a speakerphone) may be built into one or more tables 6335a-b. In some embodiments, tables 6335a-b include built-in touch sensitive displays (not shown) which allow game participants to enter information and view data being presented on the table surface. In some embodiments, tables 6335a and 6335b can communicate with peripheral devices such as a headset, mouse, keyboard, etc.

Refrigerators 6337a and 6337b can hold food and beverages for consumption by gaming participants. In one embodiment, refrigerator 6337a has a locking mechanism which is controlled via communications with house controller 6305a or central controller 110. In this embodiment, a game player could reward another game player via a user device by sending an instruction to house controller 6305a to send a signal to refrigerator 6337a to unlock so that the rewarded game participant could take out a snack item. In some embodiments, refrigerators 6337a-b are configured as a vending machine in which instructions can be sent from house controllers 6305a-b to vend one or more products for gaming participants.

Motion sensors 6350a, 6350b, 6350c, 6350d, 6350e, 6350f, and 6350g may be positioned throughout map 6300. In some embodiments, motion sensors 6350a-g capture movements of occupants throughout map 6300 and transmit the data to central controller 110 for storage or processing, e.g., for the purposes of locating users, identifying users, assessing engagement and energy level in a meeting, etc. In some embodiments, motion sensors 6350*a-g* may transmit data directly to central controller 110. In various embodiments, motion sensors 6350*a-g* capture data about people entering or leaving map 6300 and transmit data to house controllers 6305*a-b* or directly to central controller 110 (e.g. for the purposes of knowing where other users are). In some embodiments, motion sensors 6350*a-g* can be set for a low resolution mode in which only coarse movement may be detected. For example, only movements of large objects may be detectable, such as the movement of one or more people, while movements of smaller objects such as dogs or cats are not detected. In various embodiments, the resolution of motion sensors 6350*a-g* may vary by location in the house, by time of day, day or the week, or altered based on events such as the detection of a fire in which case the motion sensors 6350*a-g* may immediately switch to high resolution mode. In various embodiments, the resolution of motion sensors 6350*a-g* may be stored in a database at house controller 6305 or central controller 110. In some embodiments, peripheral devices such as a headset with built-in or attached motion sensors may communicate directly with central controller 110 or house controller 6305 in order to provide motion detection data from wherever the headset wearing user is located.

Cameras 6352*a*, 6352*b*, 6352*c*, 6352*d*, and 6352*e* may be configured to record video or still images of locations throughout map 6300. In some embodiments, Cameras 6352*a-e* capture a video signal that is transmitted to house controllers 6305*a-b* via a wired or wireless connection for storage or processing. In some embodiments, house controllers 6305*a-b* may then transmit the video to central controller 110. In other embodiments, any of cameras 6352*a-e* send a video feed directly to central controller 110. In one embodiment, a game player might bring up the video feed from one or more of cameras 6352*a-e* in order to keep track of the location of other game players. Such a video feed, for example, could allow a first player in bedroom 6321*b* to see a feed from camera 6352*e* to identify that a second game player had gone back to house 6304 and would thus not be likely to return to the game in the next two minutes. In some embodiments, cameras 6352*a-e* can be set by users for low resolution mode in which fewer pixels of detail are captured. For example, the resolution of a single image or frame of video captured might range from a high or ten million pixels to a low of 100 pixels. Low resolution modes may be useful when a user needs more privacy or anonymity, but still wants to convey basic information to other users. For example, a user might select a resolution mode of 1,000 pixels per image in order to convey that a group of people are playing video games in living room area 6315*a*, but at that resolution it may not be possible to identify any of the people in the image. In some embodiments, peripheral devices such as a headset with one or more cameras may communicate directly with central controller 110 or house controller 6305 in order to provide camera images or video from wherever the headset wearing user is located.

Windows 6354*a*, 6354*b*, 6354*c*, 6354*d*, 6354*e*, and 6354*f* can include dynamic tinting technology. In some embodiments, examples include electrochromic glass, photochromic glass, thermochromic glass, suspended-particle, micro-blind, and polymer-dispersed liquid-crystal devices. Windows 6354*a-f* can have an associated direction. For example, window 6354*b* may be facing west while window 6354*c* may be facing east. Knowing the direction in which windows are facing can be helpful in those embodiments in which sun angle may be used to determine optimum times during the day for viewing of screens during a game, or for knowing during which time frame sunlight might be expected to be in the eyes of game players in a particular room.

Speakers 6355*a*, 6355*b*, 6355*c*, 6355*d*, 6355*e*, 6355*f*, 6355*g*, 6355*h*, and 6355*i* can broadcast sounds and audio related to games, messages, background music, etc. In various embodiments, a first game player could hear comments during a game from a second user at another location. In one embodiment, game audio follows a user as she walks through house 6302. For example, she might start a game in bedroom 6321*b*, and then walk toward kitchen 6319*a*, passing motion sensor 6350*b* which then tracks her movement and sends a command to speaker 6355*b* to relay the current game audio via that speaker. She may then move into living room 6315*a* where again she is tracked by motion sensor 6350*b*, which results in game audio being transmitted to speaker 6355*a* and stopped in speaker 6355*b*. In this way, the player is able to move about the house while continuing to keep up with audio (such as audio messages from teammates) while being away from her computer in bedroom 6321*b*. In other embodiments, video from a users game may be displayed on screens or projected on walls as the user moves through a house as tracked by motion sensors. In some embodiments, peripheral devices such as a headset with speakers may communicate directly with central controller 110 or house controller 6305 in order to receive audio signals that may be played back to the user via the user's headset speakers as the user walks throughout a house.

Microphones 6357*a*, 6357*b*, 6357*c*, 6357*d*, 6357*e*, 6357*f*, 6357*g*, and 6357*h* allow for audio throughout houses 6302 and 6304 to be picked up and transmitted to house controllers 6305*a-b* or central controller 110. In various embodiments, users may issue verbal commands that are received via microphones 6357*a-h*. In some embodiments, microphones 6357*a-h* may have a range of available sensitivities, allowing a user to select a sensitivity level that might be lower in order to capture some louder sounds, but not pick up quieter sounds like conversations that a user would like to keep private. Such sensitivity settings may be stored with house controller 6305 or central controller 110. In some embodiments, peripheral devices such as a headset with one or more microphones may communicate directly with central controller 110 or house controller 6305 in order to provide verbal commands.

Displays 6360*a* and 6360*b* are devices that can provide a video/audio signal. In some embodiments, this is a computer monitor or a large flat screen television that can display a game. In other embodiments, displays 6360*a-b* indicate messages for a first user from a second user, game highlight reels, and the like.

Room lights 6363*a*, 6363*b*, 6363*c*, 6363*d*, and 6363*e* are devices that provide light to rooms in houses 6302 and 6304. Room lights 6363*a-e* could include lamps, ceiling lights, outdoor lights, ring lights, etc. In some embodiments, suitable lighting technology could include LED, fluorescent, or incandescent. In various embodiments, lights 6363*a-e* can provide a continuum of lighting power under the control of house controller 6305 or from a user device.

Color lighting devices 6365*a*, 6365*b*, 6365*c*, 6365*d*, 6365*e*, 6365*f* are capable of generating light of many colors that could illuminate all or part of a room. For example, a game player could decide that a game had reached a tension moment and that red lighting in living room 6315*a* would enhance the experience of the game session. The game player then sends a color change request with a user device (such as a smartphone) that transmits the request to house controller 6305a which then sends a signal to color lighting device 6365a and 6365b which then begin to output red light for living room 6315a. In some embodiments, peripheral devices such as a headset with color lighting capability may communicate directly with central controller 110 or house controller 6305 in order to provide lighting changes via a user's headset that may be seen by the user as well as other users who are nearby.

Projectors 6367a, 6367b, 6367c, 6367d, 6367e, 6367f, and 6367g can display information (e.g. video, photos, game screens, virtual call participants, messaging) on a wall, ceiling, floor, table, window shade, outside wall, or other surface on which light can be projected. In some embodiments, projectors 6367a-g can provide messages to game players, such as words of encouragement from another team member. In other embodiments, projectors 6367a-g can provide supplemental game data (e.g. number of lives left, distance to a goal, number of points earned) which can act as a second screen of information in addition to a main screen display 6360 on which a game is being played. In some embodiments a user can control one of projectors 6367a-g to generate a spotlight 6375 in order to highlight a user; for example, a user could direct house controller 6305a to cause projector 6367a to generate spotlight 6367 illuminating seat 6329c during a game play session with another player announcing (in the style of introducing a prizefighter) saying "and now, coming in at five years experience in Castle Crusade, with three Ultimate Battle Victories, in the green shirt, Gary!" In some embodiments, generating a spotlight 6375 can be synced with actions of speakers 6355a and 6355c, display 6360, color lighting device 6365a and 6365b, and smell generator 6371 for added effect. Projectors 6387a-g can project images on walls 6331a-f or display 6360 for presentations, movies, still images, or entertainment. In some embodiments, peripheral devices such as a headset with projector may communicate directly with central controller 110 or house controller 6305 in order to receive projection video which can be projected from the headset's projector.

Shade controllers 6369a, 6369b, 6369c, 6369d, 6369e, and 6369f can be used to drive motors which can raise or lower shades in front of windows. In one embodiment, a game player can reduce the amount of natural light in the room by sending a request, via a user device (e.g. a smartphone) to a house controller 6305 which then relays the command to shade controller 6369 to lower the shade to reduce the amount of sunlight getting into a room.

Smell generator 6371 can generate a variety of different smells that can change the mood of the room using digital sense technology in which scents are pushed out into the room. In some embodiments, scent generation technology employs storage modules containing scents which are then disbursed based on signals from a user. An example commercially available smell generator is the SmXT1™ from SensoryCo® of Thousand Palms, Calif. Research has shown that smells have an effect on people. For example, certain smells are known to calm people (e.g. rosemary, lavender, jasmine, vanilla, lemon, cinnamon). In one embodiment, a game player may decide that team members are too agitated, and send a request to house controller 6305 to generate one or more smells known to calm people, with house controller 6305 then sending a request on to smell generator 6371 to release the desired smells.

Air conditioning units 6373a, 6373b, 6373c, and 6373d can adjust the temperature of the room, heating or cooling as necessary. In some embodiments, air conditioning units 6373a-d can also manage the humidity level of the room.

House controllers 6305a-b could send signals to air conditioning units 6373a-d based upon requests received from central controller 110. In other embodiments, game players can use a user device to communicate a request for a temperature change to either house controller 6305 or directly to air conditioning unit 6373.

Weather sensors 6375a and 6375b can detect environmental data such as temperature, humidity, rainfall intensity, cloud cover, wind speed, wind direction, barometric pressure, visibility, and the like. This data may be transmitted to house controller 6305 or to central controller 110 so that it can be made available to user devices and peripheral devices. For example, weather sensor 6375a may detect heavy rainfall at house 6302 and send this information to house controller 6305a and central controller 110, where it can be provided on a display screen of a mouse to another user who is in another state or country.

In some embodiments, map 6300 may be stored with central controller 110, and could thus be sent to user devices as a way to help users know where game play is taking place. For example, a game player in living room 6315a may be finishing a game that ends at 3:00 PM, and wants to know how long it will take to get to their next game which begins at 3:00 PM in living room 6315b. By downloading map 6300 from central controller 110, the user can clearly see the location of the game session and estimate how long it will take to walk to that location. With that in mind, the game participant may leave living room 6315a extra early given that it may be a long walk to living room 6315b. In one embodiment, central controller 110 draws a path on map 6300 from living room 6315a to living room 6315b to make it easier for the user to identify how to get to that room. In some embodiments, alternate routes may be shown on map 6300. For example, there may be two paths to get to a game room, but only one path passes by kitchen 6319b where a user can get some coffee on the way to the game. In some embodiments, users have preferences stored with the central controller 110, such as a preference to drink coffee between 8:00 AM and 10:00 AM. In this example, central controller 110 may create a gaming path for a user that includes a stopping point at a kitchen when a user is attending meetings in the 8:00 AM to 10:00 AM timeframe.

In various embodiments, central controller 110 may estimate how long it will take for a user to get from one game play location to another. For example, after determining a path to take, central controller 110 may calculate the distance and then multiply this distance by the users walking speed to estimate how long of a walk it is from one location to another. In some embodiments, a path between two game locations may employ one or more different modes of transportation which have different estimated speeds. For example, a user might walk for part of the path and then drive during another part of the path. In some embodiments, the speed of one mode may depend on the time of day or other factors. For example, getting from a game location in one building to a game location in another building may require a drive across town. That might take 10 minutes during off-peak times, but could take 30 minutes when there is traffic or bad weather. Central controller 110 can retrieve traffic information and weather data to help create a more accurate estimate of game player travel time in such cases.

In various embodiments, individuals in the same house 6302 may want to play a game in different rooms. A parent in game area 6325 initiates a request for play through a peripheral (e.g. mouse, keyboard, headset) by using an established key combination for an individual in room 6321c. The request is sent to room controller 6305a or central controller 110 which transmits the request to the requested participant's enabled peripheral. The enabled peripheral may light up, vibrate, make a sound or display an image based on the preference the player has established for the requester. The requested player recognizes the alert and confirms or denies the request on the peripheral device by initiating the desired input (e.g. mouse click, movement, verbal command) or verbal command through one of microphones 6357*a-d* with the response is transmitted through room controller 6305*a* or central controller 110. In the same manner a request is sent to a peripheral, room 6321*c* with color lighting capabilities 6365*c* could light up in red to alert the individual that a request for play was initiated. Projector 6367*b* in room 6321*c* could also show a game avatar or player name on the wall of the requestor to alert the individual that play is requested.

In various embodiments, individuals in different homes 6302 and 6304 may want to play a game. A first user in house 6302 and room 6321*c* initiates a request for a game play session with a second user through a peripheral (e.g. mouse, keyboard, headset) by using an established key combination. The request is sent to room controller 6305*a* or central controller 110 which then transmits the request to the second user (who is currently in room 6321*f*) via room controller 6305*b* or central controller 110 to the peripheral device. The second user's mouse may light up, vibrate, make a sound, or display an image based on the preference the second user has established for the first user. The second user recognizes the alert and confirms or denies the request on the peripheral device by initiating the desired input (e.g. mouse click, movement, verbal input). The response is transmitted through room controller 6305*b* and/or central controller 110 to the first user's home controller 6305*a* or central controller 110. In the same manner a request is sent to a peripheral device, room 6321*c*, with color lighting capabilities 6365*c* which could light up in red to alert the second user that a request for play was initiated. Projector 6367*b* in room 6321*c* could also project on the walls the game avatar or player name of the second user to alert the individual that play from another person was requested. Likewise, either player in house 6302 or 6304 may confirm or deny the request by providing a verbal command (e.g. ok, wait 5 minutes) to the first user using microphones 6357*a-h* and the response delivered via speakers 6355*a-i*.

In some embodiments, headset 4000 from house 6300 may help a parent incentivize a child to take out the trash to earn game points, food or allowance as a way to reward their completion of a chore. In one embodiment, a parent in kitchen 6319*b* may alert a child in room 6321*f* that it is time to take out the trash. The parent may initiate the communication through a headset 4000 by using an established command saved in data storage 4057 and selecting button 4030*a-b* or verbal request for the child through microphone 4014 (e.g. 'take out the trash'). The request is sent to house controller 6305*b* or central controller 110 which transmits the request to the child's headset 4000. The headset may light up, vibrate, make a sound or display a message based on the preference that the child has established for requests received from the headsets. The child may collect the garbage from house 6300 and take it to the garbage can. This activity is recorded on the child's headset 4000 through forward facing camera 4022*a-b*. When completed, the child may transmit the video to the parent's headset 4000 for viewing on display 4046. When confirmed, the parent may recognize completion of the task by selecting a pre-established reward saved in data storage 4055 with button 4030*a-b*. The reward may be in the form of increased game time, game tokens, pizza or allowance money to the child. The child's headset may display the reward on display 4046 from preferred rewards stored in the data storage 4057 for use. The response communication between headsets may be sent to home controller 6305*b* or central controller 110 and transmitted to the parent's and child's headset for alerts. The requests and responses could also be provided to speaker 6355*b* in kitchen 6319*a* or displayed on walls in rooms 6319*b* and 6321*f* from projectors 6367*g* or 6367*e*.

In some embodiments, as chores are completed, sounds may be emitted from headset 4000 or other devices from house 6300 as a way to create excitement. A child is given a checklist of chores by the parent (e.g. clean room, fold laundry, feed the dog) and may be loaded on the child's headset 4000 through network port 4060. As the child performs the chore, camera 4022*a-b* may recognize the activity through processor 4055 and begin to play lively and fun music for the child through speaker 4010*a-b* or outward speaker 4074 as a way to motivate them and create a more pleasant experience. As the chore is completed, the headset may communicate with home controller 6305*b* or central controller 110 and begin to a play chimes, bells or provide words of encouragement (e.g. 'great job, keep it up') in speakers 6355*a-i* or celebratory images (e.g. balloons, 'great work', emojis) displayed on house 6300 walls 6331*d-f* from projectors 6367*a-g*.

In some embodiments, headset 4000 in house 6300 may facilitate the use of a countdown timer to motivate a person to complete a task. For example, the child is given a checklist of chores by the parent (e.g. clean room, fold laundry, feed the dog) and are pre-established on the child's headset 4000 that must be completed within 30 minutes. As the child performs the chore, camera 4022*a-b* recognizes the activity through processor 4055 and begins to display the countdown timer on the walls using projectors 6367*a-g* (e.g. 'time remaining 28:52'). As the time gets closer to completion, a clock sound may also be played in speakers 6355*a-i* or 4010*a-b* to provide increased excitement to complete the chores on time. The headset may communicate with home controller 6305*b* or central controller 110 to facilitate alerts, sounds and displays to headset 4000 and other peripheral devices.

In various embodiments, headset 4000 from house 6300 may facilitate the display of the lost and assignment of chores to a team (e.g. a collective group of children in a home) as a way to encourage cooperation in completing tasks. A team may be given a checklist of chores by the parent (e.g. clean the kitchen, fold laundry, feed the dog, take out the garbage) and stored on each child's headset 4000 and data storage 4057. This list may be provided on display 4046 of each child's headset or on smartboard 6333 or walls 6331*d-f* from projectors 6367*a-g*. User 1 may scroll through the list and use microphone 4014 to indicate they will clean the kitchen. Display 4046, smartboard 6333 or walls 6331*d-f* from projectors 6367*a-g* may be updated to show that the chore is no longer available for selection by the other children. User 2 indicates they will take the chores of folding laundry and feeding the dog and may select those from smartboard 6333. Display 4046, smart board 6333 or walls 6331*d-f* from projectors 6367*a-g* may be updated to show the remaining chore (e.g. take out the garbage. User 3 may select button 4030*a-b* and choose the final chore, take out the garbage. Display 4046, smartboard 6333 or walls 6331*d-f* from projectors 6367*a-g* may update to indicate all chores have been selected and users assigned. The headset may communicate with home controller 6305*a* or central controller 110 to facilitate alerts, sounds and displays to headset 4000 and other peripheral devices.

Gamification

In some embodiments, headset 4000 in house 6300 may be used as an extension of a virtual game for collecting and using objects. A user playing a computer game in room 6325 with headset 4000 may decide to select his house 6300 as an extra space for virtual play with button 4030a-b or in the game. As the user walks through room 6315a, headset 4000 projector 4076 may display pictures of gold stars on wall 6331a that must be captured to earn points. The user may approach the wall and touch the gold stars. Camera 4022a-b may record the activity and send it to house controller 6305a and central controller 110 for communication to the virtual game for collecting points. In a similar manner, the user may wish to use items in the home as shields to defend themselves in a game. The user stores the plate image in the data storage 4055 as an item to be used in game play using camera 4022a-b. As a war game is taking place, the user may walk to the kitchen 6319a, open the cabinet and grab a dinner plate. The camera 4022a-b may notice the user holding the plate. As other players shoot at the user in the game, the plate is used as a virtual shield deflecting the weapon. Likewise, in many games, virtual players may perform tasks or collect items to gain energy. The user playing a game notices they are running low on fuel. The user with headset 4000 may walk to kitchen 6319a and open refrigerator 6337a. The user may pour a glass of orange juice and take a drink. Camera 4022a-b records the activity and sends to house controller 6305a and central controller 110 for communication to the virtual game which may increase the fuel level for the user.

In various embodiments, headset 4000 in house 6300 may be used by a parent to incentivize a child to take out the trash in order to earn game points or unlock game rewards. In some embodiments, a parent in kitchen 6319b may alert a child that it is time to pick up the toys in room 6325. The parent may initiate the communication through headset 4000 by using an established command saved in data storage 4057 and selecting button 4030a-b or verbal request for the child through microphone 4014 (e.g. 'pick up toys'). The request is sent to house controller 6305a or central controller 110 which transmits the request to the child's headset device 4000. The headset may light up on boom lights 4044 (e.g. blue), vibrate using the vibration generator 4080, make a beep sound in speaker 4010a-b, or show a text message on display 4046 (e.g. 'pick up toys'). The child may begin to pick up the toys from room 6325. This activity may be recorded on the child's headset 4000 through forward facing camera 4022a-b. When the toys are picked up, processor 4055 may recognize this and communicate with house controller 6305a or central controller 110 to the child's favorite game. The child may be rewarded by their favorite game with extra play time, extra avatar lives or more game tokens to be used to unlock other game rewards, providing motivation to complete the chore and a way to make an unpleasant task fun.

Schoolwork

In some embodiments, headset 9000 in house 6300 may be used to observe a child doing homework as a way to check progress and provide assistance by a parent, teacher, tutor, mentor or other person skilled in the subject. A child with headset 9000 may try to complete multiplication problems in room 6321f. Camera 9090 may be pointed toward the homework to observe the child solving the math problem. A parent sitting at work with headset 4000 and projector 4076 may display the video of the child completing their math homework on the wall. As the child works the multiplication problem, the parent notices the child is not performing the right calculation and is getting frustrated. The parent may speak to the child using microphone 4014 giving helpful tips to complete the math problem. The child listens to the parent through speaker 4012a-b and makes the necessary corrections. In some embodiments where there are multiple children doing homework, the parent with headset 4000 may speak into microphone 4014 and ask the 4055 processor to move the display 4046 and projector 4076 to the next child. This may be in the form of stating the child's name or a general command such as 'next person'. The parent may also ask for one child's homework to be displayed on the wall from projector 4076 while a different child's homework is presented on display 4046 allowing for the parent to observe and assist both children at the same time.

Homework problems can be projected on walls, speak out loud and the software tells the child if they got the answer correct.

In various embodiments, headset 4000 camera shows you the workbook page your child is working on.

In various embodiments, headset 4000 allows a tutor to speak to a child and walk them through a tricky problem (e.g., as described above).

In some embodiments, headset 9000 in house 6300 may improve the performance of an individual through recording and playback. Headset 9000 records an assignment of a student preparing for a public speech on Abraham Lincoln in room 6321d. The student desires to practice the speech for review and feedback. Camera 9090 is pointed to the students face and the speech is delivered. Headset 9000 with processor 9055 and storage 9057 record the speech. The student initiates playback of the speech and watches the performance on display 9046. The child may want to display the playback speech on wall 6331e from projector 6367f from house controller 6305b and central controller 110. The processor in housing 9008 interprets the speech and offers helpful suggestions (e.g., slow down at minutes 1-2, look into the camera, use more inflections) through speakers and display 9046 or on wall 6331f from projector 6367g. The student makes the adjustments and delivers the speech again. This time, flawlessly. The boom lights 9044 display flashing green and display 9046 display a congratulatory comment (e.g. 'great delivery, you are ready'). The speaker 6355h may play a song and provide congratulatory comments.

In some embodiments, using headset 4000 in house 6300, a parent may want to verify that their child is completing a musical homework such as doing scales with a piano. The child may use headset 4000 to capture video and audio and store it for later review by a parent on data storage 9057. In some embodiments, students playing musical instruments may be expected to practice daily for a set period of time. If the parent is not in the room, it may be difficult to confirm that the practice actually took place. In various embodiments, using headset 4000, the child begins playing scales on the piano. Camera 4022a-b and microphone 4014 record the practice and save it on data storage 4057. When the parent arrives home from work, they inquire with the child about their piano practice and ask to see the video and hear the audio. The student shares the video from headset 4000 by selecting button 4030a-b and transmitting to the parent's headset 4000 through house controller 6305b and central controller 110. The parent may request the video playback be shown on display 4046 to observe the practice or wall 6331d from projector 6367d.

In some embodiments, a child may want to learn to draw polygons. Headset 4000 can use projector 4076 to project an outline of a shape which the child can trace. Camera 4022*a-b* can take pictures of the child's work and along with processor 4055 determine how well the child was able to trace the shape. Headset 4000 can provide feedback through the projecting words or pictures to indicate performance or by providing spoken feedback via headset speakers 4010*a-b*, or by providing other forms of feedback such as tones, music, or other projected images such as stars, flashing lights, trophies, or any other type of reinforcing image.

In some embodiments, headset 4000 can track and record the time a child spends on homework questions, and provide the data to a teacher. In various embodiments, headset 4000 has one or more lesson plans stored in a data storage device, such as a list of ten math questions along with the answers. When the child requests initiation of the math lesson, headset 4000 projects the first of the ten math questions onto a wall in front of the child. The child works out an answer and speaks the answer into microphone 4014, with processor 4055 determining whether or not the answer was correct. If the answer was correct, projector 4076 displays the second math question and calculates how much time elapsed between the projection of the first question and the projection of the second math question. The data can be summarized in various ways, including the set of problems that take the longest to complete, or the set of problems that have the highest number of incorrect answers by a class, which can be used by a teacher to focus extra help in the areas most needed.

In various embodiments, the walls of a house could be used to create immersive educational games. In some embodiments, one or more wall mounted projectors 4076 project regional geographic maps on one or more walls of the house. Central controller 110 may then identify a target city such as Tokyo, and audio in headset 4000 tells the child through speaker 4010*a* to "find Tokyo." The child wearing headset 4000 then walks through the house looking for Tokyo on one of the walls. When the child touches the spot on the wall which shows Tokyo, it can be confirmed by camera 4020 of headset 4000, and that confirmation can be sent to central controller 110 for storage. In some embodiments, when she touches Tokyo happy sounds are produced, or a song is saved to headset 4000 for later listening. In some embodiments, central controller 110 asks the child to answer more complicated questions such as requesting that the child locate the city in Japan with the largest population, find the southernmost country, find a large mountain range, find the city that was buried in ash from the explosion of Mount Vesuvius, or find the cities (in order) that served as the capital of the United States.

In some embodiments, a parent may want to push a reminder or alert to a child or another person—such as reminding a child to stop playing games before bedtime, telling them to come to dinner, or limiting play time. In one embodiment, a parent in kitchen 6319*a* needs to alert a child in room 6321*b* that it is time for dinner. The parent initiates the communication through a peripheral (e.g. mouse, keyboard, headset) by using an established key command or verbal request for the child through microphone 6357*a*. The parent enters the communication request in the peripheral device or preselects a common command (e.g. 'Stop playing', 'Bedtime', 'Time for dinner', 'Do your homework'). The request is sent to house controller 6305*a* or central controller 110 which transmits the request to the child's peripheral device. The peripheral device may light up, vibrate, make a sound or display a message based on the preference that the child has established for requests received in room 6321*b*. The child may respond to the request with pre-selected responses (e.g. 'OK', 'In a few minutes', 'No', 'Already done') or enter their own response in the peripheral device or through microphone 6357*c*. The response is sent to home controller 6305*a* or central controller 110 and transmitted to the parent's peripheral device for alerting. The response could also be provided to speaker 6355*b* in kitchen 6319*a*.

In various embodiments, an individual or system may want to push communications to a person or house without the need for a response. For example, a parent in house 6304 may want to provide the teenagers coming home from school a chore list or schedule for the evening. The parent may use their peripheral device (e.g. mouse, keyboard, headset) to push the chore list to the teenagers. When a child enters house 6302 and is detected by identification reader 6308*b*, projector 6367*e* in kitchen 6319*b* displays the chore list or evening schedule for the teenager(s) identified by the identification reader. In another example, a family in house 6302 may subscribe to news or weather applications for alerts. In the case of weather alerts, house controller 6305*a* and central controller 110 are informed of an impending thunderstorm, such as by receiving information from weather sensor 6375*a*. House controller 6305*a* may push update information and messages to peripheral devices, projectors 6367*a-c*, speakers 6355*a-d*, tables 6335*a*, smart board 6333, changing light colors for alerts to color lighting 6365*a-c*, or room lights 6363*a-c*. In another example, communication within the home to various individuals may be set-up to be personalized for each person's daily routine. Using peripheral devices, player 1 in room 6321*c* may establish their wake-up time as 0600. At 0600, the light 6363*c* may begin to slowly illuminate, projector 6367*b* displays a sunrise over a serine beach on the wall, and speaker 6355*e* plays sounds of the ocean. Player 2 in room 6321*a* may want a loud sound from speaker 6355*d* to sound at 0600. Lastly, the parents in 6321*b* may want the house filled with the smell of freshly baked cinnamon rolls from smell generator 6371 to get the family enticed to get out of bed at 0600.

There are times when parents need to be alerted of the activities of their children. In various embodiments, parents and children with connected devices (e.g. mouse, keyboard, headset) can establish parameters (e.g. purchase limits, types of purchases) when a push alert can be sent to the child. An example may be for online game purchases. In home 6302, a child may wish to purchase ancillary add-ons for a game, costing the child a significant amount of money. A child in room 6321*b* may initiate a payment via a peripheral device (e.g. mouse, keyboard, headset), which the device communicates to home controller 6305*a* which in turn alerts the parent's peripheral device. Display 6360*a*, table 6335*a*, and smart board 6333 may also display a message(s) of the requested purchase. Speakers 6355*a-e* may also provide an audible alert (e.g. cash register sound) for the payment request approval. The parent can initiate approval or denial via the enabled user device, via verbal approval through a microphone 6357*a-e*, or indicate approval by selecting a response displayed on table 6335*a* or smart board 6333. The response is sent to the home controller 6305*a* and/or central controller 110. The child is informed of the parent's decision via the peripheral device, audible alert, via speaker 6355*e*, color lighting device 6365*c* (e.g. it displays red if denied and green if approved) or lights 6363*c* (e.g. flashing for denied and solid for approved). If approved the purchase can take place, otherwise it is blocked. In a similar manner, certain games or content with explicit ratings may be prohibited by the parent. The connected devices may be configured to block content. If a child attempts to access this content or game, the parent's peripheral device provides as audible message (e.g. 'non-approved access'), or a message is provided via speakers 6355*a-e*, or an alert is displayed on table 6335*a* or smart board 6333 (e.g. 'non-approved access for room 6321*c*' or child 'Karen') is received via home controller 6305*a* or central controller 110 for approval or denial. The parent is informed and can take appropriate action. In the case of denial, access to the content is prohibited and the device(s) may also be locked until reset by the parent.

In various embodiments, multiple people may work in the same electronic document updating content, or a team of players may want to control various aspects of a game or game avatar at the same time. For example, player 1 in house 6302 in game area 6325 initiates play of a game with player 2 in house 6304 in living room 6315*b*. Player 3 is located in house 6304 in room 6321*f*. Each player selects a portion of the game or game avatar that they want to control using their peripheral device (e.g. mouse, keyboard, headset). The selected portion is transmitted to the other players via house controller 6305*a-b* or central controller 110. Player 1 selects the movement of the game avatar (e.g. the legs), player 2 selects the weapons to be used by the game avatar (e.g. guns, arrows, rocket) and player 3 selects the terrain (e.g. desert, forest, ocean floor) to be used and the environmental conditions (e.g. hot, humid, cold, overcast, rainy). During the game each player's peripheral device is alerted via house controller 6305*a-b* and/or central controller 110 of the selections made. Player 1 may choose to move the avatar faster through the terrain and player 3 may hear (through speakers 6355*h*) faster footsteps of the game avatar, creating excitement in the game. Player 3 may decide to change the environmental conditions by moving the game avatar to the desert using their peripheral device. In this case, house controller 6305*b* and/or central controller 110 receive a signal from the peripheral device of the environmental change. House central controller 6305*b* and/or central controller 110 inform players in home 6302 and 6304 of the change via house controller 6305*a-b*. House controllers 6305*a-b* communicate with the air conditioning units 6373*a* and 6373*c* and turn up the heat in game area 6325 for player 1 and living room 6315*b* for player 2 to mimic hotter desert conditions while the game is played. In addition, shade controller 6369*b* and color lighting 6365*b* are notified of desert conditions via home controller 6305*a* and/or central controller 110. The shade controller 6369*b* opens the blinds and the color lighting devices 6365*b* illuminate more light for player 1. Windows 6354*a-b* for player 1 may also become more transparent—allowing more light if the game is being played during sunny conditions. Player 2 in living room 6315*b* may have pictures and videos of desert conditions projected on the walls with projector 6367*d* making game play more realistic in the room. Desert sounds (e.g. wind blowing, rattlesnakes, vultures flying) may also be heard from speaker 6355*f* for player 2 in living room 6315*b*. In a similar manner, player 2 may choose to use a rocket to launch the game avatar weapon from their peripheral device during the game. When this happens the house controller 6305*b* or central controller 110 receives the message and transmits it to player 1 in house 6302 via house controller 6305*a* and central controller 110. Game area 6325 for player 1 with speakers 6355*a-c* may make a launching and exploding sound. A flash of light to mimic an explosion (e.g. red, orange, bright white) may be generated from color lighting device 6365*a*. For player 3, the speaker 6355*h* in room 6321*f* may also make a launching and explosion sound. There may be a desire for players to be virtually present in the room with another player. In the case of multiple players, player 1 in game area 6325 may request virtual access to player 2's living room 6315*b* using peripheral devices. If player 2 accepts the request using their peripheral device, the image of player 1 collected from camera 6352*b* is sent through house controller 6305*a-b* and central controller 110 to player 2's projector 6367*d*. The image of player 1 is displayed on wall 6331*d* of player 2 in living room 6315*b*. In another embodiment, player 1 may want to impede the game progress of player 2 by inhibiting his peripheral device. Player 1 may have achieved a certain level during the game which gives him the ability to request/take control of another player's peripheral device. Player 1 sends a command through their peripheral device for device control through house controller 6305*a* and central controller 110. Player 2 receives the command from central controller 110 through house controller 6305*b*. Player 1 may begin to control the movement, speed, color, sounds, and images of player 2's game character for a period of time during game play. In addition, player 1 may also control elements of house 6304 during this time by, for example, adjusting the color of a room with color lighting device 6365*d*, sounds from speakers 6355*f*, brightness of light 6363*e* and video/image on the walls with projector 6367*d*. Furthermore, refrigerator 6337*b* may be locked by player 1 to prevent snacking during play and interruption of the game. This interaction of players through control and collaboration provides a more socially connected gaming experience for players 1-3.

In various embodiments, members of a family or friends may want to recognize someone for an accomplishment or an act of kindness. For example, family members eating dinner in house 6302 dining room 6317*a* may want to recognize a child who just received an award at school. The parent was notified by the school on their peripheral device (e.g. mouse, keyboard, headset). The parent may select the child to be recognized on their peripheral device or other devices such as the table 6335*a* or smartboard 6333. Once all family members are seated in chairs 6329*d*, the parent prompts the initiation of child's recognition via the house controller 6305*a* or central controller 110 using peripheral devices. At this point, camera 6352*b* recognizes where the child to be recognized is sitting, and projector 6367*a* points to the child and illuminates a spot light on the child. Speakers 6355*a-c* begin to play celebration music, the child's favorite scent (e.g. birthday cake, pizza, popcorn) begins to emit from smell generator 6371 and the room lights up with varying colors (e.g. red, blue, pink) by color lighting device 6365*a*. In some embodiments, a child's peripheral device (e.g. mouse, keyboard, headset) may light up or provide an audio message congratulating a child on his or her achievements. In some embodiments, central controller 110 stores packaged offerings of celebratory messages with coordinated signals to speakers, displays, projectors, smell generators, and peripheral device screens for many occasions. For example, a birthday package offering might include music to be played via speakers, a virtual birthday cake on a display, customizable text messages for projection, and cake smells directed to smell generators.

In one embodiment, player 1 in house 6304 room 6321*d* wants to play a game with his friend (player 2) in house 6302. In this example, player 2 is not yet at home. Player 1 notices that not only is his friend (player 2) not online, but has not yet entered house 6302. This information is determined from one or more of identification device 6308*a*, motion sensor 6350*a*, and camera 6352*a*. House controller 6305*a* relays this information to central controller 110 which then sends the information to player 1 in house 6304 via house controller 6305*b*. Since identification device 6308*a* (or motion sensor 6350*a* or camera 6352*a*) has not identified player 2 as entering house 6304, this information can be sent to played. Once player 2 enters house 6302 and the identification reader 6308*a* (or other devices) is alerted, this information is sent via house controller 6305*a* and central controller 110 to house 6304 via house controller 6305*b*. Player 1 may be alerted that his friend has arrived home through his peripheral device, speaker 6355*h* (via a verbal alert that friend is home) or projector 6367*g* (e.g. projecting a picture of player 1). Play may once again be initiated.

There may be times when a game player wants to prepare house 6302 for game play in advance of actually being in the house. In some embodiments, for example, a player is at school and decides that they want to play immediately when they arrive home, but need the home conditions to be ready. The player may use their peripheral device while away from the home (e.g. mouse, keyboard, headset) to initiate the settings and conditions of house 6302 prior to entering the home. The settings and activation of devices occurs through house controller 6305*a* (if near the range of the home) or central controller 110 with authentication of the player's peripheral device. The player may wish to set the temperature of the house to 70 degrees at 2:00 pm using air conditioner 6373*a*. The room lights 6363*a-b* may be set in living room 6315*a* and brought to a low illumination level when the player is recognized as entering house 6302 using identification reader 6308*a* or camera 6352*a*. Furthermore, if the player enjoys a cup of hot coffee prior to game play he may set a coffee machine (not shown) in kitchen 6319*a* to prepare a cup of coffee upon identification of entry in house 6302. The player may also enjoy a fresh smell of the forest in house 6302 during game play and the smell generator 6371 may produce this scent just prior to the players arrival at house 6302, with the arrival time estimated based on a GPS signal from the player's headset and a calculation of the distance yet to be traveled and the current speed of the player. Display 6360*a* may also be set to turn on when the player enters house 6302 and is identified by identification reader 6308*a* or camera 6352*a*. The player's friend may be in house 6304 living room 6315*b*. House controller 6305*a* or central controller 110 receives confirmation of the entry of the player in house 6302 and initiates activation of camera 6352*d* to display the video and image of the player's friend on the smart board 6333 or display 6360*a* of house 6302 to immediately engage in conversation and play when the home is entered. These embodiments allow for pre-setting of conditions for day and time based on the preferences of the player(s) and provide for nearly immediate play and communication once the home is entered making for a superior gaming experience.

Referring to FIG. 73, a diagram of an example 'Sensor resolution rules' table 7300 according to some embodiments is shown. Sensor resolution rules table 7300 may store information about sensors. Sensors may include standalone sensors (e.g., cameras, microphones, etc.) and/or sensors in peripherals. Table 7300 may describe rules for what a given sensors resolution should be, depending on the circumstances. For example, depending on what user is detectable by a sensor, the sensor's resolution may change (e.g., to protect the privacy or identity of the user).

Sensor identifier field 7302 may store an identifier (e.g., a unique identifier) for a particular sensor (e.g., for a sensor in house 6300). Sensor type field 7304 may store an indication of a type of the sensor (e.g., camera, microphone, motion sensor, etc.). Sensor location field 7306 may store an indication of a location of the sensor (e.g., an indication of a room, surface, wall, etc.).

Authorized user field 7308 may store an indication of a user who will receive sensor data, view sensor data, view some result or transformation of sensor data, and/or who will otherwise be privy to sensor data. In various embodiments, this may be a first user who monitors the home of a second user so that the first user may be alerted when the second user is available to play a game or otherwise connect.

Subject field 7310 may store an indication of a user who is the subject of a sensor. A subject may be a person detected by the sensor, a person who triggers a sensor, a person identifiable by sensor data, and/or anyone who contributes to the generation of sensor data. In various embodiments, subject field 7310 may include animals, objects (e.g., readable documents; e.g., valuables), and/or other items.

In various embodiments, fields 7308, 7310 may define situations or circumstances that impact the configuration (i.e., resolution) at which a sensor will be set. For instance, it may be desirable to set the resolution of a sensor depending on who is viewing sensor data. A sensor might be set at a higher resolution if a more trusted individual is viewing the data, and at a lower-resolution if a less trustworthy individual is viewing the data. It may also be desirable to set the resolution of a sensor depending on who is the subject of the sensor. For example, if a child is walking in front of a camera, it may be desirable to set the camera at lower resolution to protect the child's identity. Also, if valuables are being carried in front of a camera, it may be desirable to set the camera at a lower resolution so as not to encourage theft.

In various embodiments, there may also be certain time periods when it is preferable to, e.g., reduce the resolution of a sensor (e.g., at night when occupants of a home may be in pajamas).

Fields 7308, 7310 define circumstances that impact sensor configuration, according to some embodiment. However, it will be appreciated that various embodiments contemplate other possible criteria or circumstances that may impact sensor configuration. For example, environmental conditions (e.g., ambient light levels; e.g., ambient noise levels) may make it desirable to alter a sensors resolution. For example, in conditions of low lighting, a sensor's light sensitivity may be increased.

Resolution field 7312 may store an indication of a resolution of a sensor. Thus, for example, sensor sid900437, a camera listed in table 7300, is to be set at a resolution of 480p if footage from the camera will be visible to authorized user u905598 (field 7308), and if a subject of the footage will be user u755419.

Sample rate field 7314 may store an indication of a sample rate of a sensor. Example rates may be expressed in terms of frames per second (e.g., with a camera sensor), kHz (e.g., with a microphone), Hz (e.g., with a motion sensor), or in terms of any other units. In various embodiments, a higher sample rate may correspond to better detection, better recognition, etc.

Sensitivity field 7316 may store an indication of a sensitivity of a sensor. A sensitivity may refer to a minimum level of input that can be detected. For example, in the case of a camera (or other light sensor), a sensitivity may refer to a minimum level of ambient lighting required for some given level of performance (e.g., for a 70% recognition rate). A camera may also use a standard measure of sensitivity, such as an ISO number. In the case of a microphone, a sensitivity might refer to a minimum sound volume that can be detected, and may be measured in decibels, for example. In the case of a motion sensor, a sensitivity might refer to a minimum weight of a subject or object that can be detected, and may be measured in pounds, for example. In various embodiments, a sensitivity may take any suitable meaning, and may have any suitable units.

Although fields 7312, 7314, and 7316 represent some parameters of a sensor that may be adjusted, various embodiments contemplate that other parameters of a sensor may also be adjusted.

In various embodiments, circumstances and configurations (e.g., resolutions) specified in table 7300 may be defined by a user (e.g., by the owner of a particular sensor; e.g., by the owner of the property where the sensor is located). In various embodiments, there may exist default circumstances and configurations that may be overridden, if desired, by a user.

Referring to FIG. 74, a diagram of an example 'Sensor resolution log' table 7400 according to some embodiments is shown. Sensor resolution log table 7400 may store information about current and historical sensor configurations (e.g., sensor resolutions, sensor sample rates, and sensor sensitivities). Table 7400 may also store information about what triggered a change in a sensor's configuration.

Sensor identifier field 7402 may store an identifier (e.g., a unique identifier) for a particular sensor. Sensor trigger field 7404 may store an indication of a trigger that caused a sensor configuration to change. In various embodiments, the trigger is what led to the configuration subsequently listed (i.e., in fields 7406, 7408, and 7410). As described with respect to FIG. 73, a trigger may represent a new circumstance, which means that some rule listed in table 7300 now applies, whereas the rule did not apply before the trigger. Thus, a trigger may include the appearance or disappearance of a particular subject (e.g., a subject specified in field 7310), a newfound presence of an authorized user (e.g., an authorized user specified in field 7308; e.g., a user who can view sensor data), the commencement of a new time period, and/or any other event or occurrence. Other triggers may include commencement of an activity by a subject (e.g., commencement of gameplay; e.g., commencement of eating). In various embodiments, a sensor configuration may be initiated manually. For instance, a user decides to increase the resolution of a camera in his home in order to better share his gaming experience with a friend. In various embodiments, a sensor configuration may revert to default, e.g., because some predetermined period of time has elapsed since the sensor was last reconfigured. Various embodiments contemplate that any other suitable trigger may change the configuration of a sensor.

Updated resolution field 7406, updated sample rate field 7408, and updated sensitivity rate field 7410 may store, respectively, an updated sensor resolution, an updated sensor sample rate, and an updated sensor sensitivity, following the occurrence of a trigger.

Configuration duration field 7412 may store an indication of the time period (e.g., start and end times) during which the configuration was in effect. If the configuration is currently in effect, field 7412 may store only a start time.

Referring to FIG. 64, a diagram of an example room table 6400 according to some embodiments is shown. In various embodiments, a room may entail a physical location in which people gather to conduct a meeting, presentation, lecture, class, seminar, government hearing, etc. The room may be physical, or it could be virtual such as an online meeting via some conferencing or communications technology, such as telephone, video conferencing, telepresence, zoom calls, virtual worlds, or the like. Room ID could also refer to a location such as a walking trail of a corporate campus in which a 'walking meeting' was to take place. In another embodiment, a room could be a place within a local park, or a particular table at a local restaurant. Rooms may be temporary in nature, such as the use of an employee office to host occasional meetings. Rooms (e.g., hybrid meetings) may include some people who gather in person, and some people who participate from remote locations (e.g., some people who are not present in the same room), and may therefore participate via a communications technology. Where a person is not physically proximate to other meeting attendees, that person may be referred to as a 'virtual' attendee, or the like. A meeting may serve as an opportunity for people to share information, work through problems, provide status updates, provide feedback to one another, share expertise, collaborate on building or developing something, or may serve any other purpose.

In various embodiments, a room could be part of a group of several meetings that are all used by a single meeting. For example, one meeting might be split over two rooms in different countries so as to avoid too much travel between locations for a meeting.

Room identifier field 6402 may store an identifier of a room in which a meeting is scheduled to occur. The room may be a physical room, such as a conference room or auditorium. The room may be a virtual room, such as a video chat room, chat room, message board, Zoom call meeting, WebEx call meeting, or the like. In some embodiments, a meeting owner or central controller 110 may switch the room location of a meeting, with the record stored in room ID field 6402 updated to reflect the new room.

Address field 6404 may store an address associated with the room. For example, a room may be located at 456 Gold Street in New York, N.Y. While this may provide only a high-level designation of the location of a particular room, in some embodiments this information is helpful to employees or contractors who are visiting a meeting location for the first time and need to know how to find the building itself first.

Building field 6406 may store the name of a building within a group of buildings that host meetings. For example, this field might store 'Building 1' to indicate that of the eight buildings in a corporate campus, this meeting room is located in Building 1.

Floor 6408 may store an indication of the floor on which the room is located. Room number 6410 field may store a number associated with the room, such as room '486'. Such room numbers might be added to stored floor plan maps of a company building, allowing meeting attendees to quickly associate the room number of a meeting with a particular location on a digital map that might be sent to their user device such as a smartphone prior to the start of a meeting.

Room name field 6412 may store a name for a room. A meeting room may be descriptive of the location, such as the 'Casey Auditorium', so as to make it easier for meeting participants to quickly understand where the meeting room is located.

Room area field 6414 may store the square footage of the room. In some embodiments this may allow central controller 110 to approximate the number of people that may comfortably fit within the room.

Room height field 6416 may store the height of the room. This could be an average height, or a range of the highest to lowest points in the room. For example, a room might be '10 feet' high or '8 to 12 feet' high.

Capacity field 6418 may store a capacity limit of the room, such as a capacity of 300 people. In one embodiment, this capacity level is determined by the central controller based on data from room area field 6414.

Energy usage field 6420 may store an amount of energy used to heat or cool the room. This could be a daily average derived from annual totals, or it could be based on actual energy use by day. Energy use would generally be more for larger rooms, such as the '34,000 BTU' requirement for room ID 'rm703'. Energy usage data stored in this field may be updated as weather changes occur (e.g. a cold snap may expect to increase energy requirements by 20% in order to achieve a comfortable room temperature) or if new air conditioning equipment is installed.

Sun exposure field 6422 may store the effect of window sizes and sun angles on the room. For example, 'rm486' may have 'high direct' sunlight at certain hours of the day which may cause room temperatures to rise at that time.

Temperature control field 6424 may store the level of control which users have over room temperatures. In some cases, users may have no control at all, which may make the room less desirable for hosting meetings when outdoor temperatures are very high or very low.

Room setup field 6426 may store the way in which the room is typically set up. For example, the room may be set up in 'classroom/lecture' style—which may be good for presenters providing educational materials, though that style may be less effective for brainstorming.

Tables field 6428 may store the number and type of tables in the room. For example, a room may have '6 rectangular tables' which are 'movable'. In some embodiments this may be an ideal set up for meetings in which participants need to break up into small groups at some point during the meeting.

Number of chairs present field 6430 may store the number of chairs that are supposed to be present in the room. This information is useful when trying to find a room for a particular number of participants. In various embodiments, the chairs are peripheral devices which are in communication with central controller 110, and the chairs may update their room location (determined via GPS or other location system) so that that central controller 110 may update the number of chairs in a room with current and updated information.

Last cleaned date/time field 6432 may store the date at which the room was last cleaned. In various embodiments, central controller 110 could send a request for facilities personnel to clean up a room when it has been more than five hours since the last cleaning.

AV status field 6434 may store an indication of whether or not the AV system is working or is in need of repair. For example, this field may store that 'rm799' is currently experiencing 'flicker on the screen'. This status could prompt central controller 110 to send a signal to AV technicians to schedule a servicing call for this room location.

AV configuration field 6436 may store a meeting type that is most appropriate for a particular room. For example, 'rm703' has an AV configuration of 'Learning', indicating that in some embodiments AV equipment in the room can support learning meetings in which one person is generally giving a presentation or lecture to a relatively large number of users. For example, the room may be equipped with a handheld microphone and flip charts.

AV quality field 6438 may store an average quality level of the AV equipment in the room. For example, a room might have an AV quality score of 5 out of 10 based on quality scores of the projector and the speakers in the room. In some embodiments, AV quality scores may come from users answering survey questions to gather feedback on the level of AV quality. In one embodiment, a meeting survey could include questions relating to AV equipment and forward the users answers to central controller 110 where they can be aggregated into an average score for storage in field AV quality 6438 of room table 6400.

Acoustics ratings field 6440 may store an average score representing the acoustic quality of the room. This might be useful to users looking for a room in which music is being played as part of a meeting, or users in an educational setting looking for a meeting room in which to practice a musical instrument.

Whiteboard status field 6442 may store the current condition of one or more whiteboards in a room. For example, whiteboard status might be 'fair, some permanent marks' or 'good, 3 markers left'. This could allow a user looking to book a meeting room for a brainstorming session to avoid rooms with whiteboards that are in poor condition. Many meeting rooms do not include whiteboards as part of the cleaning rotation, and thus marks left on the boards tend to become very hard to wipe off as they age. This can be very frustrating to a meeting facilitator who might walk into a room a few minutes before the scheduled start time, only to realize that the whiteboards are almost impossible to use in the current condition.

Catering availability field 6444 may store an indication of whether or not the meeting room can have catering service for meals, snacks, beverages, deserts, coffee, etc. In various embodiments, catering availability may include the ability to select from an approved set of local restaurants who deliver to the meeting room and have a corporate account with the company. Catering availability could also include information regarding the hours during which catering is available, or indicate what employee level is required in order to make a catering order.

Wheelchair accessibility field 6446 may store an indication of whether or not the room is accessible to users in wheelchairs. In some embodiments, this includes a description of what the access looks like, such as a description of ramps, their materials, and the angle of the ramp. In other embodiments, this field could also store other accessibility information such as whether or not there are places in the room to store the wheelchair or if there are desks in the room that can accommodate a wheelchair.

Referring to FIG. 65, a diagram of an example room peripheral table 6500 according to some embodiments is shown. A meeting room may contain one or more user peripherals, at different locations throughout the room. For example, meeting participants may use headsets, keyboards, presentation remote controllers, projectors, and chairs during a meeting. While some of these peripheral devices are removed by users at the end of the meeting, other peripherals may be left behind.

In various embodiments, peripherals, or other equipment may include video equipment, microphones, phones, display panels, chairs (intelligent and non-intelligent), and tables.

Room identifier field 6502 may store an identifier of a room in which a meeting is scheduled to occur. The room may be a physical room, such as a conference room or auditorium. The room may be a hybrid room, such as a physical room with some participants joining via video chat room, chat room, message board, Zoom® call meeting, WebEx® call meeting, or the like.

Peripheral ID field 6504 may store an identifier of each peripheral currently in the room. Location in room field 6506 may store the location of a peripheral within a meeting room. The location may be determined, for example, by a peripheral device locating itself via GPS or other suitable locating technology and then transmitting this location back to central controller 110. For example, the peripheral may be identified as in the 'corner of the far right wall' or in the 'center of the north wall.' In other embodiments, the location data is presented on a digital map so that the exact location in the room is immediately clear. In various embodiments, this peripheral location data may be provided to a user looking for that peripheral. For example, a meeting participant could be sent a digital map onto her user device for display of the map.

In various embodiments, peripheral or equipment models may be stored.

In various embodiments, training videos for using peripherals or equipment of a room or of any other part of system 100 may exist. Videos may be stored, e.g., in asset library table 1900, or in any other location.

Referring to FIG. 66, a diagram of an example vendor database table 6600 according to some embodiments is shown. In one embodiment, vendor database table 6600 service calls easier by storing vendor information that can be sent out to user devices through central controller 110.

Vendor ID field 6602 may store a unique identifier for each stored vendor. In some embodiments, these stored vendors are all company approved vendors that are known to perform a specific service. Name field 6604 may store the name of the vendor, such as 'Machine Cleaning Express' or 'Swift Copy Repair'. In some embodiments, vendors might include vendors supplying services for a meeting room such as supplying equipment, chairs, tables, cameras, lights, office supplies, training, etc. In some embodiments, vendors may offer services mediated by a remote person who delivers the services through a headset 400 worn by an employee of the company, potentially decreasing the costs of vendor services.

Category field 6606 may store the type of service provided by the vendor. These categories could include 'cleaning', 'printing', 'repair', etc. Price field 6608 may store an average cost per hour for the service. This could be used by central controller 110 to generate total service cost estimates.

Min time field 6610 may store a minimum amount of time for a particular service call. For example, 'Machine Cleaners Express' requires 90 minutes per service call.

Ratings field 6614 may store a numeric or level rating for the vendor, such as '4.5' on a five point scale. In some embodiments such ratings could be generated by user feedback through a user device connected to central controller 110 and then aggregated and stored in ratings field 6614. Stored ratings could also be stored and presented individually, so that ratings data for a vendor includes many comments from users of the service. Website field 6616 and phone field 6618 may store contact information for vendors so that requests can be placed or followed up on.

Figure 67:
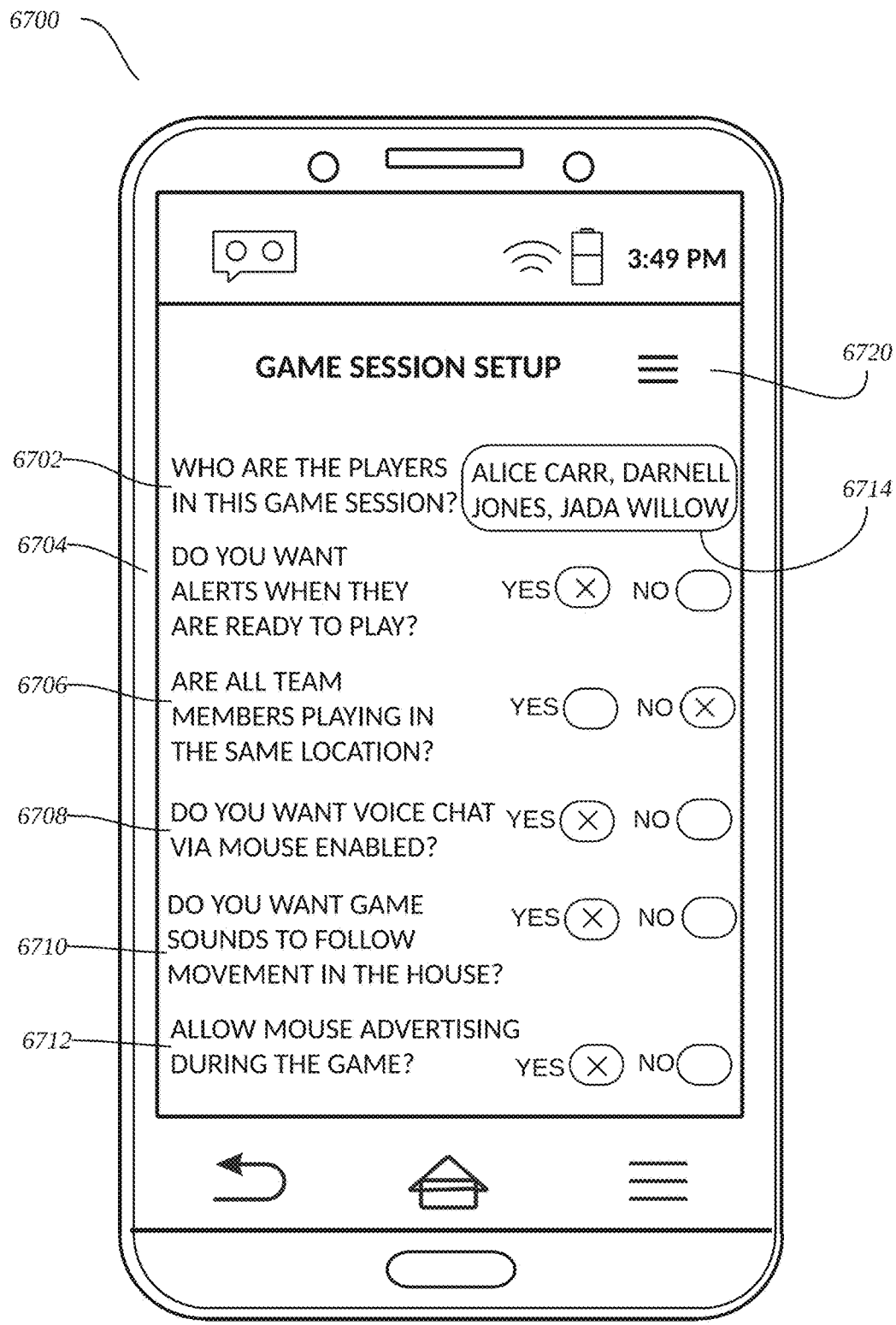
FIG. 67 is a user interface of an example user device consistent with at least some embodiments described herein.

FIG. 67 illustrates a graphical user interface which may be presented to a game player. FIG. 67 illustrates a respective graphical user interface (GUI) as it may be output on a peripheral device, mobile device, or any other device (e.g. on a mobile smart phone) The GUI may comprise several tabs or screens, as illustrated in FIG. 67.

In accordance with some embodiments, the GUI may be made available via a software application operable to receive and output information in accordance with embodiments described herein. It should be noted that many variations on such graphical user interfaces may be implemented (e.g., menus and arrangements of elements may be modified, additional graphics and functionality may be added). The graphical user interface of FIG. 67 is presented in simplified form in order to focus on particular embodiments being described.

With reference to FIG. 67, a screen 6700 from an app used by game players according to some embodiments is shown. The depicted screen shows app game session setup functionality that can be employed by a user to set up parameters and functionality for a group gaming session. In some embodiments, the setup data is provided via central controller 110 to one or more game platforms. In FIG. 67, the app is in a mode whereby users can answer questions in order to define the parameters of a game session. However various embodiments contemplate that an app may interact with other team members or other game players, including peripheral devices used by game players (e.g. headsets, mice, cameras).

In some embodiments, the user may select from a menu 6720 which displays one or more different modes of the software. In some embodiments, modes include 'game session setup', 'game selection', 'feedback to team members', 'request for game tips/coaching', 'feedback for advertisements, etc.

The app may show questions for a game team leader, such 'who are the players in this game session?' 6702. In this example, answers have been provided at 6714. Other questions may include, 'do you want alerts when they are ready to play?' 6704 (e.g. do you want a light on your mouse to light up when all players are determined to be ready to play), 'are all team members playing in the same location?' 6706 (e.g. will communication channels need to be set up between one or more of the players), 'do you want voice chat via mouse enabled?' 6708 (e.g. will players want to chat amongst the team members using voice capabilities in their mouse), 'do you want game sounds to follow movement in the house?' 6710 (e.g. will players need to be tracked via sensors in their house so that nearby speakers can provide ongoing game sounds as they move from one location in a house to another) and a question about whether the game team leader wants to 'allow mouse advertising during the game?' 6712. In these examples, yes/no answers are provided by the game team leader. For example, this game team leader has indicated that she wanted voice chat via mouse enabled 6708. In various embodiments, game session setup may include responses for a moment in time, provided once during a game, provided at a few fixed times during the game, or variations thereof. As will be understood, there are many different questions that might be asked of a game team leader or other game participants. In one embodiment, central controller 110 stores a list of potential questions, and game team leaders can pick from this list of questions in setting up the game session. In some embodiments, feedback may be requested from team members such as 'did you enjoy the game session?', 'would you like to see more games from this publisher?', 'are there other game players that you think should be invited to the next game?', etc. Feedback from users could also be more open-ended by giving them a chance to make any kind of comment. For example, a player might indicate that they are 'confused', 'distracted', 'not having fun playing on this game territory', 'feel like their voice is not heard when it comes to game strategy decisions', etc. In other embodiments, the app could solicit suggestions from players. Players might indicate that they have suggestions via the app, such as by suggesting that 'the game is too complex', 'we should take a break now', 'we need a new game strategy', 'we should be playing in the same location rather than connecting virtually', etc. In some embodiments, users of the app can cast votes during a game or add notes to voting results. In other embodiments, users provide summary evaluations at the conclusion of a game, such as a one to five star rating of a game, or a one to five star rating of whether or not the game session was fun. Additional general comments could be provided by users at the conclusion of the game, such as an evaluation of the success of the game session, or an indication of whether the game team leader encouraged team members to speak.

In some embodiments, the app could provide notifications to users as to game location changes, time changes, player changes, cancellations, etc. Various embodiments contemplate that any other feedback data, or any other input data from a peripheral device, may be shown, may be shown over time, or may be shown in any other fashion.

In various embodiments, the device running the app (e.g., a smartphone or tablet), may communicate directly with central controller 110 and directly with peripheral devices (e.g., via Bluetooth®; e.g., via local wireless network), or may communicate with the corresponding peripheral devices through one or more intermediary devices (e.g., through the central controller 110; e.g., through the user device), or in any other fashion.

With reference to FIG. 68, a depiction of an example map 6800 according to some embodiments is shown. The map may represent a map of a campus, an office building complex, a set of office buildings, or the like. In various embodiments, the map may represent a map of any building, set of buildings, or other environment.

Map 6800 depicts two buildings 6802 and 6804 with an outdoor area 6806 between them. As depicted in map 6800, buildings 6802 and 6804 each have only one floor. However, in various embodiments, buildings with multiple floors may be depicted. In some embodiments, devices depicted within the map 6800 are under the control of a central controller 110 which may use wired or wireless connections to send commands or requests to various devices and locations within the campus. This allows meeting owners, facilitators, participants, and observers to employ user devices (such as a smartphone) to communicate with central controller 110 in order to command various devices throughout the campus. It will be understood that this layout of a company or educational campus is for illustrative purposes only, and that any other shape or layout of a campus could employ the same technologies and techniques.

The depicted campus layout view includes various devices and represents one exemplary arrangement of rooms, paths, and devices. However, various embodiments contemplate that any suitable arrangement of rooms, paths, and devices, and any suitable quantity of devices (e.g., quantity of chairs; e.g., quantity of cameras) may likewise be used.

In various embodiments, building 6802 represents a factory, laboratory, research laboratory, fabrication facility, experimental facility, sensing facility, monitoring facility, communications facility, storage facility, and/or any other industrial or scientific facility. Building 6802 may include one or more areas where safety and/or intellectual property and/or property are of concern. Building 6802 may include machinery or equipment of a potentially dangerous nature (e.g., saws, lathes, lasers, industrial robots, etc.). Building 6802 may include irritants that may cause damage to organs/tissues (e.g. liver, heart, brain, stomach, eye, skin, nose, ears, lung) and/or dangerous chemicals, such as hydrofluoric acid. Building 6802 may include radioactive materials, radiation, biological hazards, pathogens, etc. Building 6802 may include controlled substances, such as opioids, drugs, drug precursors, etc. Building 6802 may include weaponizable materials. Building 6802 may include potentially hazardous gases, such as carbon monoxide, hydrogen, nitrogen, etc. Building 6802 may include objects or environments at extreme temperatures (e.g., furnaces, e.g., cryogenic storage), which may be potentially hazardous. Building 6802 may include sharp objects. Building 6802 may include dangerous heights, unguarded platforms, or other falling hazards. Building 6802 may include flammable, combustible, and/or explosive objects or materials. Building 6802 may include electrical components or equipment with dangerous voltage and/or current levels. Building 6802 may include high magnetic fields. Building 6802 may include vapors, breathing hazards (e.g., asbestos), etc. Building 6802 may include confined and/or unventilated areas. Building 6802 may include vats or liquids that present drowning or suffocation hazards. Building 6802 may include fragile, delicate, and/or otherwise sensitive items, such as clean rooms. Building 6802 may include sensitive plans, records (e.g., medical records), data, plans for controlled items (e.g., for rocket technology), and/or any other sensitive materials. Building 6802 may include commodities, valuables, and/or other items of value, such as currency, platinum, silver, computer chips, laptops, etc.

For these reasons, and/or for any other suitable reasons, it may be desirable to restrict or control access to building 6802 and/or to any rooms or portions thereof. Where access is granted, it may be desirable to monitor and or limit individuals to whom access is granted. It may be desirable to monitor and/or restrict what items go into building 6802 and/or what comes out of building 6802. For example, users may be forbidden from bringing in backpacks or other items that can conceal objects. It may be desirable to monitor and record occurrences at the building, such as equipment usage, what items were brought in, what items were brought out, who went in, who came out, what someone did while inside, environmental conditions (e.g., temperature, oxygen levels, gas levels, humidity levels, etc.), whether any safety hazards are present, when the most recent cleaning has occurred, what accidents or near accidents have occurred, and/or any other event or situation at building 6802. In various embodiments, it may be desirable to monitor areas outside and/or surrounding building 6802 (e.g., silo 6897, building 6804).

Building 6802 may include multiple tiers or levels of access control. For example, entry into a given room may require separate authorization, even if a user has already been authorized to enter the building and/or a separate room. Individual items of equipment (e.g., machines, computing devices) may require authorization for use. Viewing an item (e.g., a document, a piece of equipment) may require separate authorization. Authorization may be enforced through physical mechanisms, such as doors or barriers with locks (e.g., with electronic door locks). Authorization may be enforced by altering availability of a device or item of equipment. For example, a device may not be turned on unless a user is authorized to work with the equipment. Authorization may also require multiple steps, multiple factors, and/or repeated or continuous renewal. For example, a user's identity must be confirmed through three independent methods before a user is allowed to access a room. As another example, a user must re-verify his identity every 10 minutes in order to continue using a software program. In some embodiments, a user may be continuously authenticated with multiple streams of identifying information produced as the user goes through the day. In some embodiments, every time that a user speaks, headset 4000 verifies the voiceprint and stores an indication of whether or not the voiceprint matched that store with central controller 110. In some embodiments, cameras 6852*a-h* may take images of a user and determine whether or not an employee badge is worn, and if the badge corresponds to the user associated with the headset. In such embodiments, this continuous authentication enables a central controller 110 to pick up on the identity information that is constantly shed by users throughout the day. In various embodiments, each user output used in an authentication protocol may be transmitted to central controller 110 via a separate communication channel and/or processed with a separate processor of headset 4000.

In various embodiments, headset 4000, another peripheral, another device, and/or any device located within or proximate to building 6802 may facilitate logging, monitoring, restricting access, granting access, and or any other process described herein.

Building 6802 has entrance 6810*a* and building 6804 has entrance 6810*b*. The outdoor area 6806 has entrance 6810*c*. In various embodiments, 6810*c* is the only means of entry (e.g., permitted means of entry) into the campus from the outside. For example, the outdoor area 6806 may be otherwise fenced-off.

Entrances 6310*a*, 6310*b*, and 6310*c* may be connected via a walking path 6814. In various embodiments, the path may be available for various modes of transportation, such as walking, skating, scooter, bicycle, golf cart, etc.

Inside buildings 6802 and 6804 are depicted various rooms, including such offices as 6816*a*, 6816*b*, and 6816*c*; including such conference rooms as 6824*a* and 6824*b*; small conference room 6826; and including kitchen 6830. Various embodiments contemplate that buildings may include other types of rooms even if not explicitly depicted (e.g., gyms, cafeterias, roof areas, training rooms, restrooms, closets and storage areas, atrium space, etc.).

Building 6802 includes reception area 6842*a*, and building 6804 includes reception area 6842*b*. In some embodiments, users (e.g. employees, contractors, vendors, visitors, emergency responder, auditors) may be provided with a headset 4000 when entering a reception area, with the headset assigned to the user and registered with central controller 110 for tracking during the day. In some embodiments, users leaving a building may be required to return headsets 4000 to personnel in reception areas 6842*a-b*, with those headsets 4000 containing records of what that user looked at, where they went (e.g. GPS data), what other users they interacted with, etc.

Building 6804 includes hallway 6844. Map 6800 depicts various cameras, such as camera 6852*g* which observes the outdoor area 6806, and camera 6352*h* which observes hallway area 6844.

Inside building 6802 is depicted a research and development area 6860, which contains a government security clearance room 6865, a pathogen lab 6870, and a laser facility 6875. In some embodiments, each of these rooms requires authorization to enter given the safety or secrecy issues involved with entry into the room. There is also depicted a manufacturing area 6880, which contains acid tanks 6885, grinding machine 6890, and clean room 6895. In some embodiments, each of these rooms similarly requires authorization to enter.

Inside building 6804 is depicted a control room 6828 that may be used to house safety personnel, which in some embodiments may be called upon to provide safety training and/or respond to unclean conditions, unsafe conditions, safety hazards, failed authorization attempts, emergencies, etc. in building 6802. In some embodiments, employees can employ a user device (e.g. a smartphone) to provide emergency requests to control room 6828 via central controller 110. In some embodiments, central controller 110 may use images of rooms, facilities, etc. to automatically detect unsafe conditions and alert control room personnel, security personnel, etc. Control room 6828 may include displays 6846*a* and 6846*b* which may display still image or video feeds from one or more of cameras 6852*a-h*, allowing personnel in control room 6828 to monitor activities in building 6802 and 6804. In some embodiments, one or more users 6855*a-d* are wearing headsets 4000 and sending video feeds from a camera of headset 4000 to central controller 110 which in turn provides that video feed to control room 6828 for display on displays 6846*a-b*. In some embodiments, an audio feed from headsets 4000 of one or more users 6855*a-d* may be transmitted to central controller 110 for use by control room 6828, such as for assessing a safety situation near one or more users.

In various embodiments, central controller 110 may detect automatically if an area has hazardous or dangerous conditions, and may thereupon automatically alert the control room 6828, summon crew to the area, and/or take some other action. For example, the central controller may scan video feeds from a particular area (e.g. via a video feed from a user headset 4000) and identify water or hazardous liquids on the floor of a room. In some embodiments, if there has been no cleaning crew in the last 24 hours, for example, then the central controller may summon the cleaning crew to that area.

It will be appreciated that map 6800 depicts an arrangement of rooms according to some embodiments, but that various embodiments apply to any applicable arrangement of rooms.

Motion sensors 6850*a*, 6850*b*, 6850*c*, 6850*d*, 6850*e*, and 6850*f* may be positioned throughout map 6800. In some embodiments, motion sensors 6850*a-f* capture movements of users 6855*a-d* throughout map 6800 and transmit the data to central controller 110 for storage or processing, e.g., for the purposes of locating employees, identifying employees, authenticating employees, etc. In some embodiments, motion sensors 6850*a-f* may transmit data directly to central controller 110. In some embodiments, motion sensors 6850*a-f* capture data about users entering or leaving building 6802 or 6804 and transmit data to a room controller or directly to central controller 110, e.g. for the purposes of maintaining consistent safety protocols.

Cameras 6852*a*, 6852*b*, 6852*c*, 6852*d*, 6852*e*, 6852*f*, 6852*g* and 6852*h* may be configured to record video or still images of locations throughout campus 6800. In some embodiments, cameras 6852*a-h* capture a video signal that is transmitted to a room controller via a wired or wireless connection for storage or processing. In some embodiments, the room controller may then transmit the video to central controller 110. In other embodiments, any of cameras 6852*a-h* send a video feed directly to central controller 110. In some embodiments, cameras 6852*a-h* may be used in authentication protocols, or to determine whether or not an employee (or contractor or vendor) is in an area that they are not authorized to enter. In some embodiments, a meeting owner might bring up the video feed from one or more of cameras 6852*a-h* during a break in a meeting so that the meeting owner could keep an eye on meeting participants who left the meeting room during a break. Such a video feed, for example, could allow a meeting owner in conference room 6824*d* to see a feed from camera 6852*a* to identify that a meeting participant had gone back to building 6802 during the break and was currently standing in hallway 6846*a* and would thus not be likely to return to the meeting in the next two minutes.

User identification readers 6808*a*, 6808*b*, 6808*c*, 6808*d*, 6808*e*, 6808*f*, 6808*g*, 6808*h*, and 6808*i* are positioned at the entry points 6810*a-c* and at key access points to restricted areas in industrial building 6802 and serve to identify employees and allow/deny access as they attempt to move through the entry points. For example, user identification readers can be NFC and/or RFID readers to scan an employee badge, a camera to identify the user via face recognition, a scanner to identify a user by a carried user device, a microphone for voice recognition, or other user identification technology. In some embodiments, user identification readers 6808*a-i* transmit data about user entering or leaving campus 6800 and transmit data to a room controller or directly to central controller 110, e.g. for the purposes of maintaining access to secure rooms. User identification readers 6808*a-i* can allow or deny access to individual employees by validating their inclusion in tables stored with central controller 110 that contain the lists of employees properly trained to handle the equipment in the general R&D and Manufacturing areas, or in another embodiment, that contain lists of employees that are approved to work on certain projects or work in certain rooms (e.g. laser facility 6875). In various embodiments, user identification readers may grant or deny access to areas of access restricted based on ITAR requirements (e.g. via user identification reader 6808*a*), pathogen lab 6870 (e.g. via user identification reader 6808*b*), laser facility 6875 (e.g. via user identification reader 6808*c*), or areas restricted for any other reason. In various embodiments, these may grant or deny access to areas restricted based on HF acid training levels when a user attempts to access acid tanks 6885 (e.g. via user identification reader 6808*d*), safe industrial grinder operation levels when a user attempts to access grinding machine 6890 (e.g. via user identification reader 6808*e*), clean room training level (e.g., via user identification reader 6808*f*), confined space entry training when attempting to access silo 6897, or areas restricted for any other reason.

In some embodiments, map 6800 may be stored with central controller 110, and could thus be sent to user devices as a way to help users know where restricted rooms are, and to determine a path out of a room if a safety issue requires the user to leave the room. In some embodiments, motions sensors 6850*a-f* can be used to track and guide employees in their regular duties or in emergency situations. For example, in one embodiment motion sensor 6850*d* by silo 6897 can update main a database record stored with central controller 110 when an employee enters the confined space, and personnel can communicate via the employee's headset to help them find their way, keep track of time, complete their tasks safely, or accomplish anything else. In some embodiments, the headset can be used to track levels of oxygen, or dangerous gases, or extreme heat or cold, or any other environmental variable, to ensure the employee is safe or warn the employee if conditions become unsafe. In various embodiments, headset 4000 can be used to track the alertness, movements, eyes, or any other aspect of the employee's behavior, and warn if and when an employee begins acting in a way that may indicate they are losing focus, getting drowsy, not getting enough oxygen, or exhibiting any other signs of degraded performance.

Figure 69:
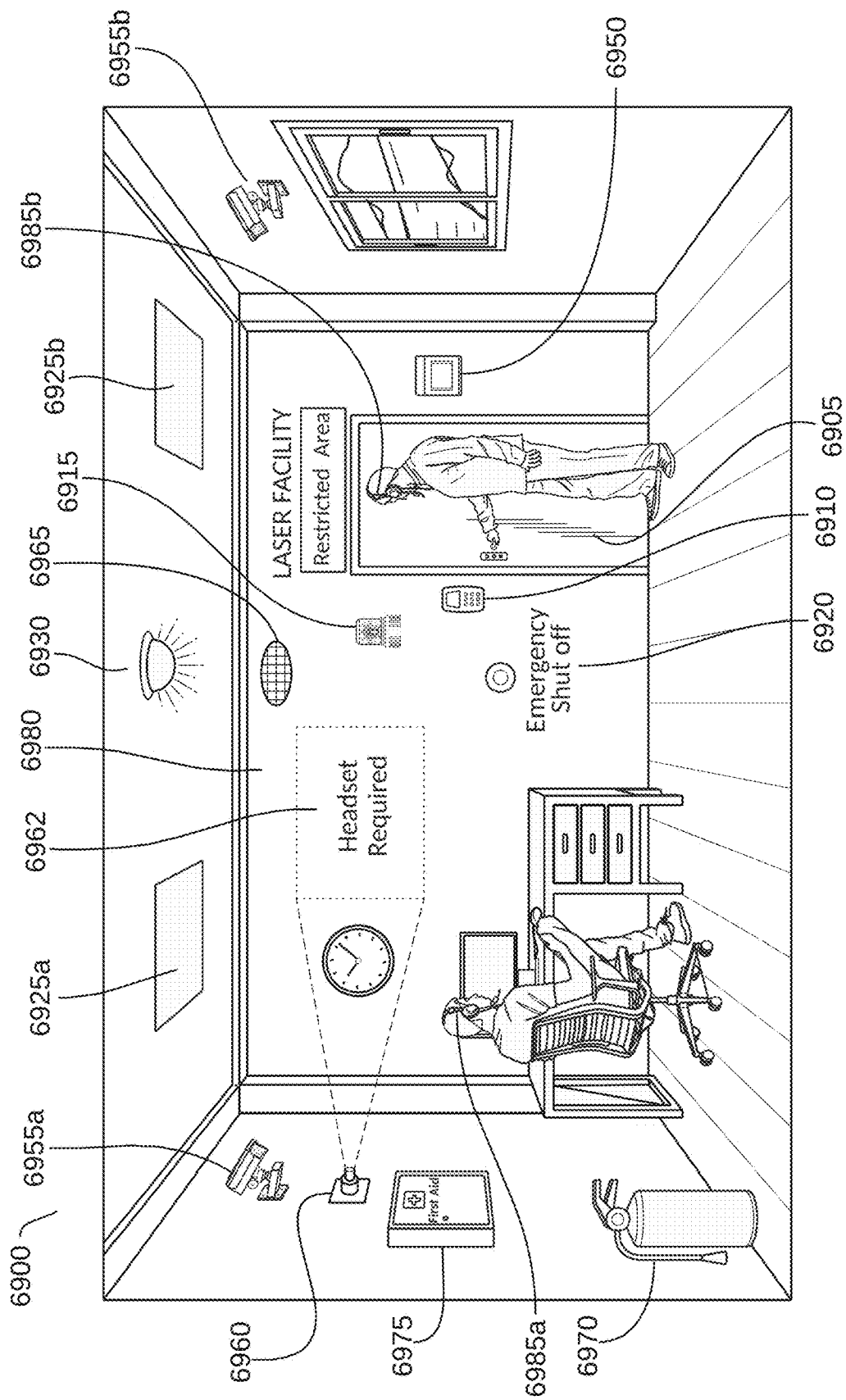
FIG. 69 is a representation of a door access control area consistent with at least some embodiments described herein.
Figure 71A:
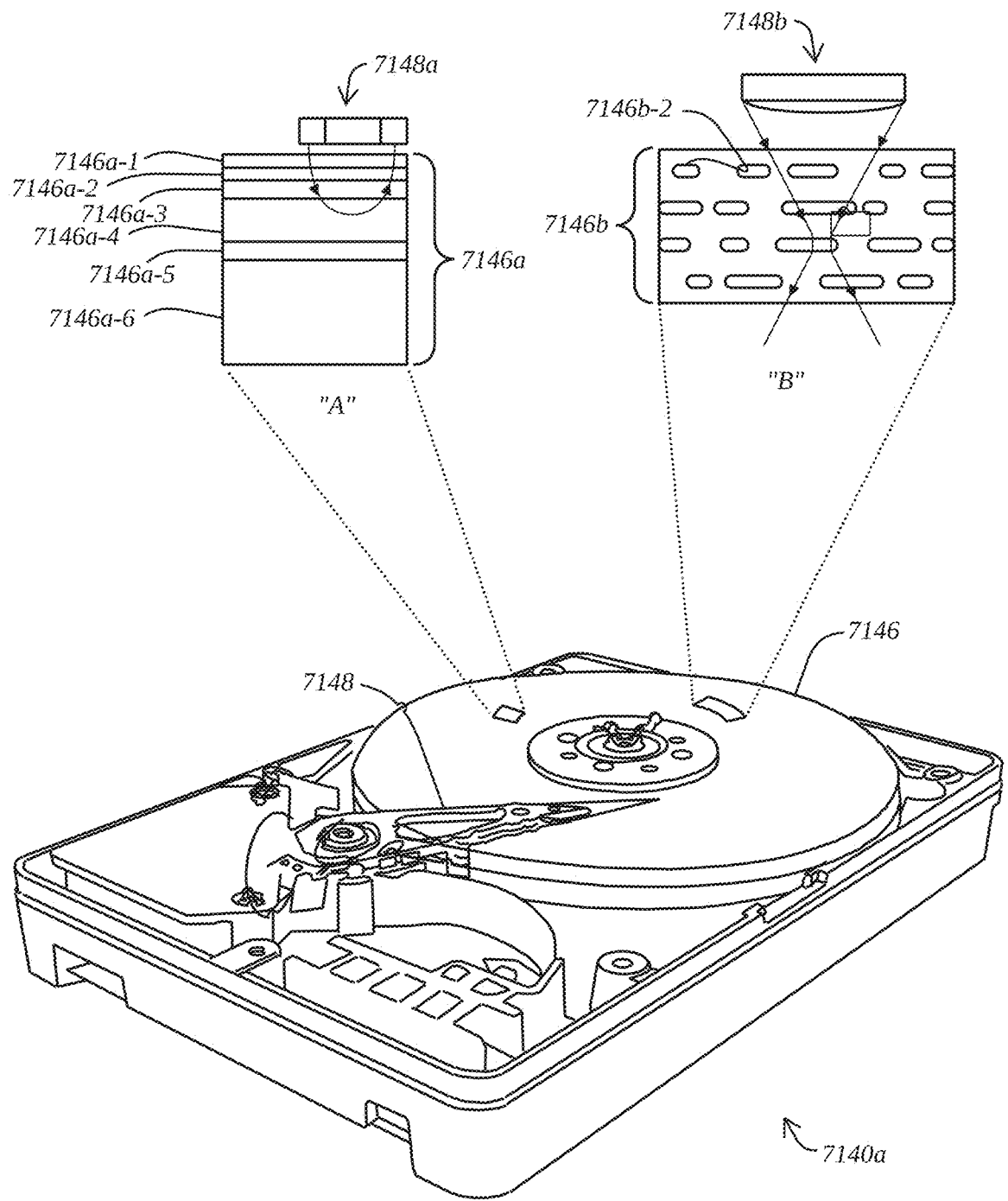
FIG. 71A, FIG. 71B, FIG. 71C, FIG. 71D, and FIG. 71E are perspective diagrams of exemplary data storage devices consistent with at least some embodiments described herein.
Figure 71B:
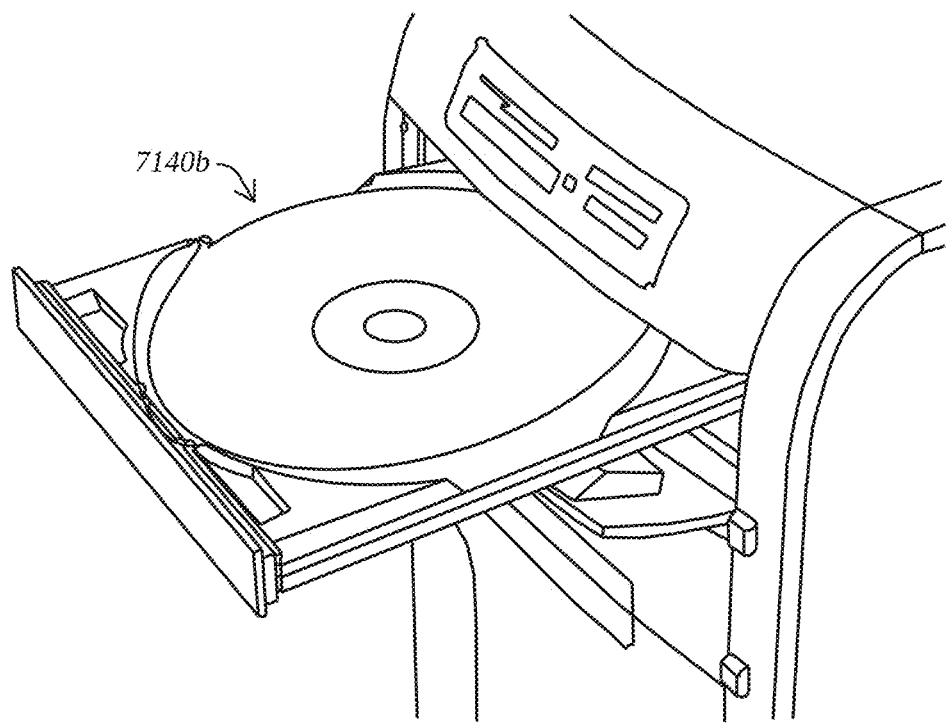
Figure 71C:
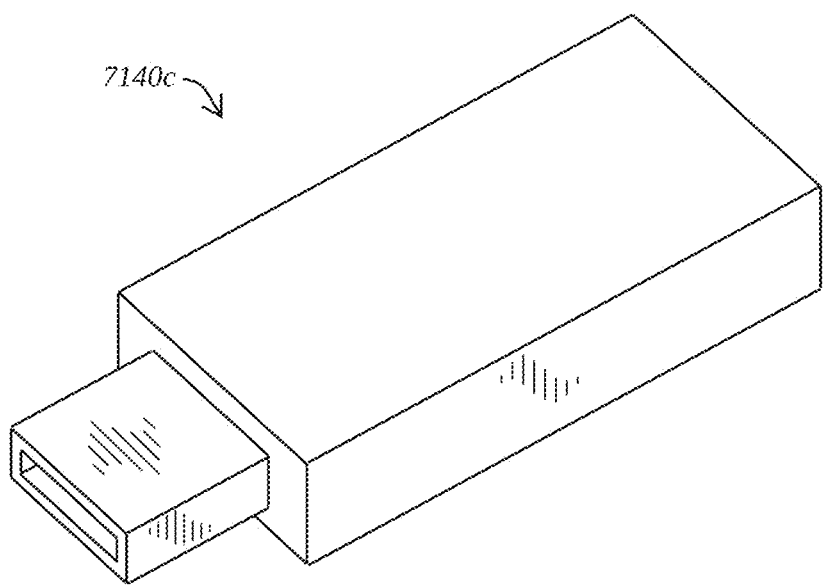
Figure 71D:
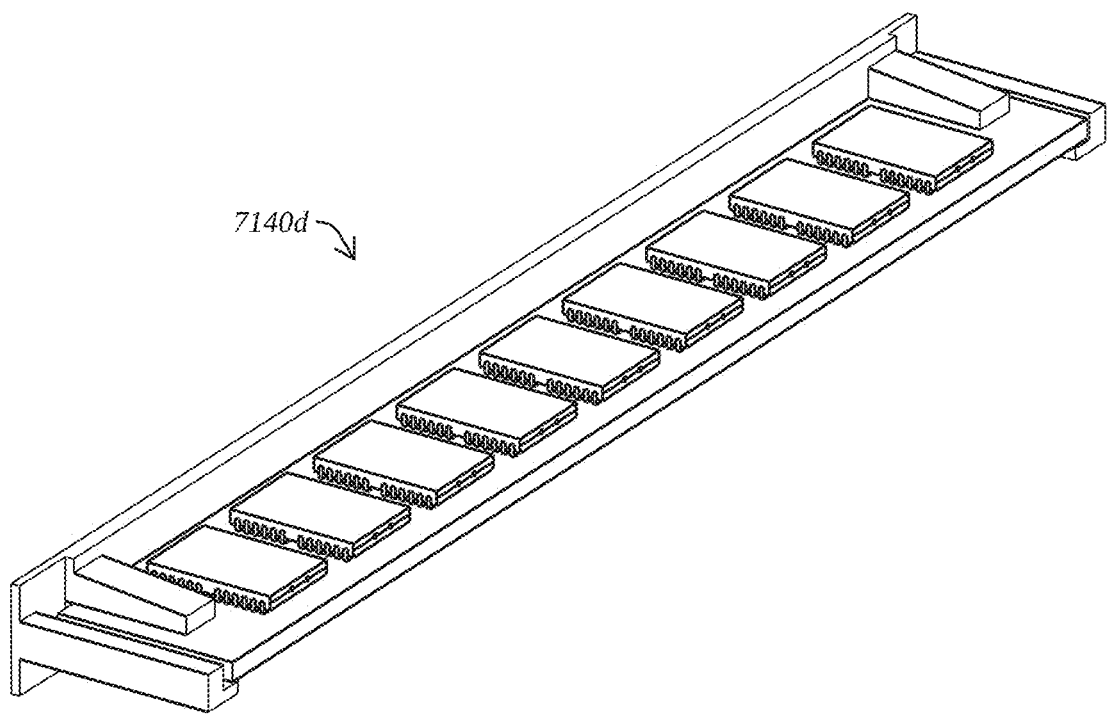
Figure 71E:
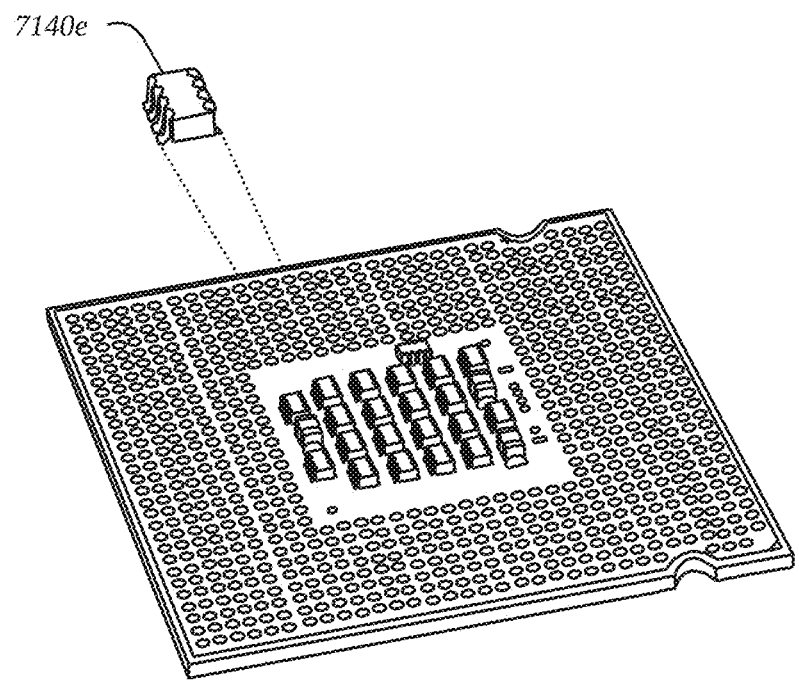

Referring to FIG. 69, a three-dimensional representation of a door access control area 6900 according to some embodiments is shown. In some embodiments, door access control area 6900 includes a door 6905 which may lead into a restricted area which may be dangerous for untrained or unsupervised personnel. Door 6905 may be secured in various ways, including having a lock, being made of strong materials such as metal, having messaging capability with a central controller 110 to alert others to an attempted door access without authorization, etc. In some embodiments, door 6905 has associated with it an access control 6910 such as a numeric keypad on which a user must type a numeric code in order to unlock door 6905. In some embodiments, a siren 6915 provides information about equipment on the other side of door 6905, such as by flashing the lights of siren 6915 if the laser in the restricted room is currently active and therefore may pose a risk to anyone entering the restricted room. In some embodiments, an emergency shut off button 6920 is located near door 6905, allowing a user to shut off equipment in the restricted room without having to gain access to the restricted room.

The depicted room includes lights 6925*a* and 6925*b*, which allow for illumination of door access control area 6900. In some embodiments, these lights may be under the control of central controller 110 and can be turned on or off as a way to communicate with users within (or near) door access control area 6900. For example, central controller 110 may direct lights 6925*a-b* to flash on and off when a user has entered an incorrect numeric code into access control 6910. Such flashing of lights could alert others to approach the user to determine if they need help or to determine if the user is authorized to access door 6905. Color lighting device 6930 may provide additional communication options. In some embodiments, color lighting device 6930 generates a red light which illuminates door access control area 6900 while the laser is currently active. In some embodiments, the depicted room may also include safety equipment such as a fire extinguisher 6970 and first aid kit 6975. In case of an emergency, central controller 110 might direct users to the location of such safety equipment. In some embodiments, central controller 110 directs all color lighting devices to display a green color if that room contains safety equipment.

In some embodiments, the depicted room may also include devices that may be used in the process of authenticating a user in order to determine if the user may gain entrance through door 6905. In some embodiments, motion sensor 6950 captures movements of occupants in door access control area 6900 and transmits the data to central controller 110 for storage or processing, e.g., for the purposes of locating users attempting to open door 6905 or identifying users nearby who may be able to assist in authenticating access to door 6905. In various embodiments, motion sensor 6950 captures data about people entering or leaving door 6905 and transmits data to room controllers or directly to central controller 110. In some embodiments, motion sensor 6950 can be set for a low resolution mode in which only coarse movements may be detected. For example, only movements of large objects may be detectable, such as the movement of one or more people, while movements of smaller objects such as boxes or carts are not detected. Cameras 6955*a* and 6955*b* may capture images or video of door access control area 6900. In some embodiments, cameras 6955*a-b* may be under the direction of central controller 110 and may thus be activated when a user attempts to authenticate himself in order to access door 6905. In some embodiments, central controller 110 receives images from cameras 6955*a-b* when a user requests authentication to door 6905, and compares those images to stored images of the user in order to determine a degree of match as part of the authentication process. In various embodiments, cameras 6955*a-b* may be movable, allowing them to be pointed at a particular user, or to zoom in on a particular part of the user such as a face, eye, lips, hands, fingers, hair, tattoos, jewelry, clothing, employee badge, materials with text visible, etc. Central controller 110 may then use one or more of these targets of cameras 6955*a-b* (e.g. a tattoo and a wedding band) as an input to the authentication process. Projector 6960 may display a message on wall 6980 such as message 6962 "Headset Required." In some embodiments, message 6962 may be incorporated into an authentication process, such as by asking a user seeking access to door 6905 to type the year he was born into a keypad of access control 6910. In some embodiments, speaker 6965 may be used to provide messages to a user seeking access to door 6905. In some embodiments, such messages could include instructions to the user, such as asking the user to turn and face camera 6955*b* during an authentication procedure.

In various embodiments, one or both of headsets 6985*a* and 6985*b* may be used in an authentication protocol in order for a user to gain access to door 6905. In some embodiments, a user seeking to gain access to door 6905 may be required to be wearing a headset 6985*b*. His headset 6985*b* could wirelessly transmit data to access control 6910 or central controller 110, using headset elements like a microphone (e.g. capturing a voiceprint of a spoken password), camera (e.g. capturing an image of his iris for biometric authentication), storage device (e.g. a stored password or cryptographic keys), accelerometer (e.g. identifying characteristics of the user's walking gait), brainwave sensor (e.g. determining an EEG signal), etc. Central controller 110 could also incorporate challenge/reply protocols into the authentication process, asking the user a question via a speaker of headset 6985*b* such as "what is the name of the meeting that you attended at 10:00 AM this morning?" In some embodiments, headset 6985*a* of another user within door access control area 6900 may be used in an authentication protocol. In some embodiments, a second user wearing headset 6985*a* is asked by central controller 110 to yell out a four digit number (e.g. provided by central controller via a speaker of headset 6985) so that a microphone of headset 6985*b* of a user seeking access to door 6905 picks up the four digit number and relays it back to central controller 110. In this way, the user with headset 6985*b* can authenticate that they are within yelling range of another user at the company. A camera of headset 6985*a* may also provide images to central controller 110 of the user attempting to gain access to door 6905.

Referring to FIG. 70, a diagram of an example videos library database table 7000 according to some embodiments is shown. There are many opportunities for using video to help employees complete work in an efficient and safe manner. In this table, video content is stored for delivery across a range of communication channels of the company. In some embodiments, Video ID field 7002 may store a unique identifier associated with a piece of video content. Content summary field 7004 may store a brief description of the video content, such as training video' or 'instruction manual'.

Referring to FIG. 76, a diagram of an example local weather log database table 7600 according to some embodiments is shown. There are many opportunities for using weather data in order to enhance game play, improve the sense of connection between players, improve emotional connectedness during virtual calls, etc. In this table, weather data is stored for use by peripheral devices and user devices.

Location field 7602 may store an address of a user at which weather data is recorded.

Date field 7604 may store an indication of the date on which the weather data was recorded, while time field 7606 may store the time at which the weather data was recorded. Temperature field 7608 indicates the temperature in Fahrenheit at this location 7602, humidity field 7610 stores the percent humidity, and wind speed field 7612 may store the current wind speed in miles per hour.

The type of precipitation field 7614 may store types of precipitation such as rain, snow, hail, etc. Each form of precipitation may store an associated precipitation rate in precipitation rate field 7616, such as 0.15 inches per hour of rainfall or 0.46 inches per hour of snow. Light level field 7618 stores the number of lux, while cloud cover field 7620 provides a percentage of the sky that is covered by clouds.

In various embodiments, weather data could be entered by a user, received from a weather sensor such as weather sensor 6375*a* of FIG. 63A, or received from government weather data agencies such as the National Weather Service. Weather data may be updated on a regular schedule, updated upon request of a user, or updated upon a triggering event such as when a user is detected to be walking into a house.

Referring to FIG. 77, a diagram of an example audio/video cues table 7700 according to some embodiments is shown. In various embodiments, a broadcast audio or video file is transmitted to a user in a way that allows devices in the users home or office to provide supplementary content that makes the broadcast content more entertaining, informative, and fun.

Asset ID field 7702 may uniquely identify audio or video content. Asset type field 7704 may store an indication of the kind of media that is being broadcast, such as a movie, television episode, audio book, and the like. Trigger ID field 7706 uniquely identifies one or more triggers associated with asset 7702, the trigger generating commands that drive user devices to generate additional content. The time field 7708 may store the time at which a trigger is engaged. For example, a trigger might engage at '00:36' minutes into the delivery of audio/visual content. Target output device field 7710 stores the output device (e.g. a color lighting device, speakers, projector) that will be instructed to deliver additional content. Output field 7712 stores an indication of the additional content, such as 'blue lighting' or the 'sound of a thunderstorm.' Duration field 7714 stores an indication of the length of the additional content, such as '90 seconds' in the example of the 'blue lighting' scenario. In various embodiments, the additional content delivered to the user through devices in their house or office adds many creative options for the enhancement of standard broadcast content such as television shows or movies. In some embodiments, a user listening to a murder mystery audio book may encounter a trigger which is associated with a particular paragraph of the audio book which triggers a speaker down the hall from the user to play the sounds of footsteps approaching which makes the content being read more exciting.

Figure 78:

Referring to FIG. 78, a diagram of an example live action cues table 7800 according to some embodiments is shown. In various embodiments, a live content stream (e.g. a game environment, a sporting event, a streaming channel) is transmitted to a user in a way that allows devices in the users home or office to provide supplementary content that makes live content more entertaining, informative, and fun.

Live content identifier field 7802 may uniquely identify audio or video content. Live content type field 7804 may store an indication of the kind of media that is being delivered, such as a game environment, streamer channel, sporting event, and the like. Trigger ID field 7806 uniquely identifies one or more triggers associated with live content 7802, the trigger generating commands that drive user devices to generate additional content. The trigger field 7808 may store a condition which, if satisfied, triggers the serving of additional content to a user. For example, a trigger might engage during a sporting event when the 'home team scores a touchdown.' Target output device field 7810 stores the output device (e.g. a color lighting device, speakers, projector) that will be instructed to deliver any additional content triggered. Output field 7812 stores an indication of the additional content, such as 'lighting decreases 75%' or the 'sound file of team song.' Duration field 7814 stores an indication of the length of the additional content, such as 'until game character is out of dark zone'. In various embodiments, the additional content delivered to the user through devices in their house or office adds many creative options for the enhancement of live content such as game environments or sporting events. In some embodiments, a user watching a football game may encounter a trigger when the home team scores a touchdown, with a sound file of the home team song playing for 90 seconds from the user's speakers.

Process Steps According to Some Embodiments

Turning now to FIG. 79, illustrated therein is an example process 7900 for conducting a meeting, which is now described according to some embodiments. In some embodiments, the process 7900 may be performed and/or implemented by and/or otherwise associated with one or more specialized and/or specially-programmed computers (e.g., the processor 605 of FIG. 6). It should be noted, with respect to process 7900 and all other processes described herein, that not all steps described with respect to the process are necessary in all embodiments, that the steps may be performed in a different order in some embodiments and that additional or substitute steps may be utilized in some embodiments.

Registering/Applying for a Meeting

At step 7903, a user may set up a meeting, according to some embodiments.

In setting up a meeting, the meeting owner might have to register the meeting or apply for the meeting with the central controller 110. This can provide a gating element which requires meeting owners to provide key information prior to the meeting being set up so that standards can be applied. For example, a meeting purpose might be required before having the ability to send out meeting invitations.

In various embodiments, the Meeting Owner (or Meeting Admin) could be required to apply to the central controller 110 to get approval for setting up a meeting. Without the approval, the central controller could prevent meeting invites from being sent out, not allocate a room for the meeting, not allow the meeting to be displayed on a calendar, etc. This process could be thought of as applying for a meeting license. To get a meeting license, the meeting might have to include one or more of the following: a purpose, an agenda, a designated meeting owner, a digital copy of all information being presented, an identification of the meeting type, an objective, a definition of success, one or more required attendees, evidence that the presentation has already been rehearsed, etc. Permitting may require Meeting Owner to apply a predefined number of points from a meeting point bank—e.g., different amounts of meeting points can be allocated to different employees, roles, expertise, levels once per given time period, with higher levels (e.g., VPs) being allocated more points (and accordingly being able to hold more meetings or meetings with more/higher 'value' attendees). Meeting points could also be earned, won, etc.

In various embodiments, the central controller 110 could also review the requested number of people in a meeting and compare that to the size of rooms available for that time slot. If a large enough room is not available, the central controller could make a recommendation to break the meeting into two separate groups to accommodate the available meeting size.

In various embodiments, the central controller could have a maximum budget for the meeting and determine an estimated cost of a requested meeting by using a calculation of the dollar cost per person invited per hour (obtained from HR salary data stored at the central controller or retrieved from HR data storage) multiplied by the number of people invited and multiplied by the length of the meeting in hours (including transportation time if appropriate). Such an embodiment would make the cost of meetings more immediately apparent to meeting organizers, and would impose greater fiscal responsibility in order to reduce the number of meetings that quickly grow in the number of attendees as interested—though perhaps not necessary—people join the meeting. In this embodiment, a meeting owner might be able to get budget approval for a meeting with ten participants and get that meeting on the calendar, but have requests for additional attendees approved only as long as the meeting budget is not exceeded. In various embodiments, the central controller could deny a meeting based on the projected costs, but offer to send an override request to the CEO with the meeting purpose to give the CEO a chance to allow the meeting because the achievement of that purpose would be so impactful in generating business value and shareholder value. Further, the central controller could allocate meeting costs to various departments by determining the cost for each attendee based on the time attended in the meeting.

In various embodiments, requesting a meeting could also require registering any projects(s) that the meeting is associated with. For example, a decision-making meeting might register one or more previously held brainstorming sessions which generated ideas that would serve as good fuel for the decision making session. Additionally, the meeting owner might be required to register any other meetings that will be held in the future that will be related to this meeting.

In various embodiments, meeting requests could require the meeting owner to tag elements associated with the meeting. For example, the meeting could be tagged with "Project X" if that is the main topic of the meeting. It might also be tagged with "Budget Decision" if the output will include a budget allocation amount. Another type of required tag could relate to whether or not legal representation is required at the meeting.

In various embodiments, when a meeting is requested, the meeting owner could be provided with meeting content/format/tips related to the type of meeting that they are trying to set up.

At step 7906, a user may determine meeting parameters, according to some embodiments.

Meeting Configurations

The central controller 110 may offer a number of standard configurations of equipment and software that will make it easier to configure a room.

In various embodiments, a meeting participant or meeting owner can set standard virtual meeting configurations. For example, there could be three standard packages available. Configuration #1 may include microphone type, camera to be used, volume levels, screens to be shared, multiple screen devices and background scenes to be used. Configuration #2 may include only audio/phone usage. Configuration #3 may include any combination of recognized devices to be used. Once settings are established, they may be controlled by voice activation or selection on any mobile or connected device.

In various embodiments, meeting owners can provide delegates with access to meeting set-up types (e.g. Admins).

In various embodiments, a meeting owner assigns participants to meeting room chairs (intelligent and non-intelligent chairs). Intelligent chairs can pre-set the chair configuration based on the person sitting in the chair (height, lumbar, temperature).

In various embodiments, the central controller 110 automatically determines a more appropriate meeting place based on the meeting acceptance (in-person or virtual) to make the most efficient use of the asset (room size, participant role/title and equipment needed to satisfy the meeting purpose).

In various embodiments, a meeting presenter can practice in advance and the central controller 110 uses historical data to rate a presentation and the presenter in advance.

Meeting Right-Sizing

Many large companies experience meetings that start out fairly small and manageable, but then rapidly grow in size as people jump in—sometimes without even knowing the purpose of the meeting. Many employees are not familiar with how large meetings should be, and that the size of the meeting might need to vary significantly based on the type of meeting.

Agenda

In various embodiments, the central controller 110 could understand the appropriate number of agenda topics for a meeting type and recommend adjustments to the agenda. For example, in a decision-making meeting, if the agenda includes a significant number of topics for a 1-hour meeting, the central controller could suggest removing some of the decisions needed and moving them to a new meeting.

Participants

In various embodiments, the central controller 110 could recommend a range for the number of meeting invitees based upon the meeting type, agenda, and purpose. If a meeting owner exceeds the suggested number of invitees, the central controller can prompt the meeting owner to reduce the number of invitees.

Dynamic Right-Sizing During Meetings

Based upon the agenda, the central controller 110 can allow virtual participants to leave the meeting after portions of the meeting relevant to them have finished. A scrolling timeline GUI could be displayed, showing different portions of a meeting as the meeting progresses; e.g., with icons/avatars for attendees currently in, previously in, or expected to join for different sections/portions. Additionally, the central controller can identify portions of the meeting that contain confidential information and pause the participation of individuals without the appropriate permission to view that information.

Recurring Meetings

In various embodiments, the central controller 110 can prompt owners of recurring meetings to adjust the frequency or duration of meetings to right-size meetings over time. The central controller can also prompt owners of recurring meetings whether invitees should still be participating as time goes on. The central controller can auto select time slots based on attendee list calendars, preferences, and/or historical data—e.g., higher measured level of attentiveness/interaction for one or more attendees at different times of day, days of week, etc.

Room Availability

Based upon the availability of larger meeting rooms, the central controller may prompt a meeting owner to reduce the number of participants or break the meeting into smaller meetings. Meetings that require more people than a room can accommodate, the central controller could recommend which participants should be present in the meeting room and those that should be virtual only. For example, if a decision-making meeting is taking place and three decision makers are key to achieving the goals, they should be identified as being physically present in the meeting room. The other participants should only be invited to attend virtually.

Learning Algorithm

Over time, the central controller 110 may begin to collect information regarding the meeting type, agenda items, duration, number of participants, occurrences, time of day, logistics (building location, time zones, travel requirements, weather), health of employees (mental and physical fitness, for example the central controller could recommend smaller meetings during the peak of flu season) and meeting results to provide more informed right-sizing recommendations. In other words, an Artificial Intelligence (AI) module may be trained utilizing a set of attendee data from historical meetings to predict expected metrics for upcoming meetings and suggest meeting characteristics that maximize desired metrics.

Meeting Participant Recommendations

At step 7909, the central controller 110 may suggest attendees, according to some embodiments. The central controller could take the agenda and purpose of the meeting and identify appropriate candidate meeting participants who could build toward those goals. In various embodiments, the central controller may take any other aspect of a meeting into account when suggesting or inviting attendees.

In various embodiments, given a meeting type (e.g., innovation, commitment, alignment, learning), the central controller may determine a good or suitable person for this type of meeting. In various embodiments, the central controller may refer to Meetings table 5100, which may store information about prior meetings, to find one or more meetings of a similar type to the meeting under consideration (or to find one or more meetings sharing any other feature in common with the meeting under consideration). In various embodiments, the central controller may refer to Meeting Participation/Attendance/Ratings table 5500 to determine a given employee's rating (e.g., as rated by others) for prior meetings.

In various embodiments, the central controller may refer to Employees table 5000 to find employees with particular subject matter expertise, to find employees at a particular level, and/or to find employees with particular personalities. Thus, for example, an employee can be matched to the level of the meeting (e.g., only an executive level employee will be invited to an executive level meeting). An individual contributor level meeting may, on the other hand, admit a broader swath of employees.

In various embodiments, if the meeting is about Project X then the central controller could recommend someone who has extensive experience with Project X to attend the meeting. The central controller may refer to meetings table 5100 (field 5128) to find the project to which a meeting relates. The central controller may recommend attendees who had attended other meetings related to Project X. The central controller may also refer to project personnel table 5800 to find and recommend employees associated with Project X.

The meeting owner, prior to setting up the meeting, could be required to identify one or more functional areas that will be critical to making the meeting a success, preferably tagging the meeting with those functional areas.

In various embodiments, the central controller 110 recommends meeting invites based on the ratings of the individuals to be invited (e.g., as indicated in Meeting Participation/Attendance/Ratings table 5500). For example, if this is an innovation meeting, the central controller can recommend participants that were given a high rating on innovation for the functional area they represent. In various embodiments, the central controller may find individuals or meeting owners with high engagement scores (e.g., as indicated in Meeting Engagement table 5300) involved in innovation, commitment, learning, or alignment meetings based on the relevant meeting tags (e.g., as indicated in Meetings table 5100, at field 5108).

In various embodiments, the central controller may find individuals named as inventors on patent applications and/or applications in different classifications, fields, technology areas that may be applicable to the meeting/project.

In various embodiments, the meeting owner in a meeting could request that the central controller 110 open up a video call with an employee who is going to be handed a baton as a result of the meeting discussions.

Cognitive Diversity

Having a diverse group of meeting participants can lead to better meeting outcomes, but it can be difficult to identify the right people to represent the right type of diversity. Employees can have a variety of backgrounds, experiences, personality types, and ways of thinking (cognitive types). These frameworks shape how individuals participate in meetings and interact with other members of the meeting. In various embodiments, the central controller 110 could improve meeting staffing by identifying employees' cognitive frameworks, suggesting appropriate mixes of these cognitive frameworks.

Identifying Cognitive Types

The central controller could identify employees' cognitive type through employee self-assessments, cognitive assessments or personality inventories (e.g., MMPI, "big 5," or MBTI) conducted during hiring processes, or inductively through a learning algorithm of meeting data.

High Performance Meetings

Over time, the central controller 110 could learn which combinations of cognitive types are likely to perform better together in different types of meetings. High performance meetings can be assessed by measurements such as post-meeting participant ratings, by meeting engagement data, or by meeting asset generation. For example, the central controller could learn over time that innovation meetings produce ideas when individuals with certain cognitive types are included in the meeting.

Suggesting Invitees to Create Diversity

The central controller 110 could flag meetings with homogenous cognitive types and suggest additional meeting invitees to meeting owners to create cognitive diversity. Individual employees vary in their risk tolerance, numeracy, and other forms of cognitive biases. Meetings sometimes suffer from too many individuals of one type or not enough individuals of another type. The central controller can suggest to meeting owners that individuals be invited to a meeting to help balance cognitive types. For example, a decision-making meeting may include too few or too many risk tolerant employees. The central controller can prompt the meeting owner to increase or decrease risk aversion by inviting additional employees.

Optimization

At step 7912, the central controller 110 may optimize use of resources, according to some embodiments.

In order to maximize the business value from meetings, the central controller 110 can create optimal allocations of people, rooms, and technology in order to maximize Enterprise business value. The central controller could have information stored including the goals of the enterprise, a division, a team, or a particular initiative. For example, if two teams requested the same room for an afternoon meeting, the team working on a higher valued project could be allocated that room.

In various embodiments, the central controller can balance requests and preferences to optimize the allocation of meeting rooms and meeting participants/owners.

In various embodiments, the central controller could allocate meeting participants to particular meetings based on the skill set of the meeting participant.

In the case of a meeting participant being booked for multiple meetings at the same time, the central controller could provide the meeting participant with the meeting priority. For example, a subject matter expert is invited to three meetings at the same time. Based on the enterprise goals and priorities, the central controller could inform the subject matter expert which meeting is the highest priority for attendance.

In the case of multiple key meeting participants being asked to attend multiple meetings at the same time, the central controller 110 could optimize participants so all meetings are covered. For example, 5 subject matter experts are invited to 3 meetings taking place at the same time. The central controller could inform the subject matter experts which meeting they should attend so all meetings are covered.

At step 7915, the central controller 110 may send meeting invitations, according to some embodiments. Meeting invites may be sent to an employee's email address or to some other contact address of an employee (e.g., as stored in table 5000).

Automatic Meeting Scheduling

The central controller 110 could trigger the scheduling of a meeting, if a condition is met based upon data from an external source. The central controller could suggest meeting invitees relevant to the event. For example, an extreme event such as an increase in service tickets or a hurricane could trigger the scheduling of a meeting.

At step 7918, the central controller 110 may ensure proper pre-work/assets are generated (e.g., agenda), according to some embodiments.

Locking Functionality

In various embodiments, one or more privileges, access privileges, abilities, or the like may be withheld, blocked or otherwise made unavailable to an employee (e.g., a meeting owner; e.g., a meeting attendee). The blocking or withholding of a privilege may serve the purpose of encouraging some action or behavior on the part of the employee, after which the employee would regain the privilege. For example, a meeting organizer is locked out of a conference room until the meeting organizer provides a satisfactory agenda for the meeting. This may encourage the organizer to put more thought into the planning of his meeting.

In various embodiments, locking may entail: Locking access to the room; Preventing a meeting from showing up on your calendar; Video meeting software applications could be prevented from launching.

In various embodiments, locking may occur until a purpose is provided. In various embodiments, locking may occur until a decision is made. In various embodiments, locking may occur if the meeting contains confidential information and individuals without clearance are invited or in attendance. In various embodiments, locking may occur if the meeting tag (identifying strategy, feature, commitment, etc.) is no longer valid. For example, a tag of "Project X" might result in a lockout if that project has already been cancelled.

In various embodiments, locking may occur until the description of the asset generated is provided.

In various embodiments, locking may occur if the budget established by Finance for a project or overall meetings is exceeded.

In various embodiments, a meeting owner and/or participants could be provided with a code that unlocks something.

In various embodiments, different meeting locations can be locked down (prevented from use) based on environmental considerations such as outside temperature (e.g., too costly to cool a particular room during the summer, so don't let it be booked when temperature is too high) and/or all physical meeting rooms (or based on room size threshold) may be locked down based on communicable disease statistics such as season flu rate.

In various embodiments, during flu season, the central controller could direct a camera to determine the distances between meeting participants, and provide a warning (or end the meeting) if the distance was not conforming to social distancing protocols stored at the central controller.

At step 7921, the central controller 110 may remind a user of a meeting's impending start, according to some embodiments.

In various embodiments, a peripheral associated with a user may display information about an upcoming meeting. Such information may include: a time until meeting start; a meeting location; an expected travel time required to reach the meeting; weather to expect on the way to a meeting; something that must be brought to a meeting (e.g., a handout); something that should be brought to a meeting (e.g., an umbrella); or any other information about an upcoming meeting. In various embodiments, a peripheral may remind a user about an upcoming meeting in other ways, such as by providing an audio reminder, by vibrating, by changing its own functionality (e.g., a mouse pointer may temporarily move more slowly to remind a user that a meeting is coming up), or in any other fashion.

In various embodiments, the central controller may send a reminder to a user on a user's personal device (e.g., phone; e.g., watch). The central controller may text, send a voice message, or contact the user in any other fashion.

in various embodiments, the central controller may remind the user to perform some other task or errand on the way to the meeting, or on the way back from the meeting. For example, the central controller may remind the user to stop by Frank's office on the way to a meeting in order to get a quick update on Frank's project.

At step 7924, the central controller 110 may track users coming to the meeting, according to some embodiments.

On the Way to a Meeting

Meetings are often delayed when one or more participants do not reach the meeting room by the designated start time, and this can cause frustration.

Estimating Time of Arrival

The central controller 110 could estimate the time of arrival for participants from global positioning data and/or Bluetooth® location beacons and/or other forms of indoor positioning systems. The central controller could display these times of arrival to the meeting owner.

Finding the Meeting

The central controller could provide meeting attendees with a building map indicating the location of the meeting room and walking directions to the room based upon Bluetooth® beacons or other indoor positioning systems. The central controller could also assist meeting participants in finding nearby bathroom locations or the locations of water fountains, vending machines, or coffee machines.

Late Important Participants

The central controller could prompt the meeting owner to delay the start of the meeting if key members of the meeting are running late.

Late Participants Messaging

Late participants could record a short video or text message that goes to the meeting owner. Exemplary messages may include: I'm getting coffee/tea now; I ran into someone in the hallway and will be delayed by five minutes; I will not be able to attend; I will now attend virtually instead of physically.

Catching Up Late Arrivals

The central controller 110 could send to late arrivals a transcript or portions of a presentation that they missed, via their phones, laptops, or other connected devices.

Pre-Meeting Evaluation

At step 7927, the central controller 110 may send out pre-meeting evaluation, according to some embodiments.

Meeting agendas and presentations are often planned far in advance of the meeting itself. Providing meeting owners with information collected from attendees in advance of the meeting allows meeting owners and presenters flexibility to tailor the meeting to changing circumstances.

Pre-Meeting Status Update

The central controller could elicit responses from attendees prior to the meeting by sending a poll or other form of text, asking how they feel prior to the meeting. Exemplary responses may include: Excited!; Dreading it; Apathetic; Sick; a choice from among emojis; and/or a choice of food and/or beverage.

At step 7930, the central controller 110 may set the room/meeting environment based on the evaluation, according to some embodiments.

Dynamic Response

Based upon these responses, the central controller can alter the physical environment of the room, order different food and beverage items, and alter the meeting owner about the status of attendees. The room can use this information, for example, to decide whether to: Request responses from participants; Order snacks/candy; Play more soothing music; Reduce/increase the number of slides; Change the scheduled duration of the meeting; Set chairs to massage mode; Turn the lights down/up; or to make any other decision.

Based on the type of meeting, agenda and the responses sent to the meeting organizer, the central controller 110 can provide coaching or performance tips to individual participants, via text or video or any other medium. For example, if there is an innovation meeting where the meeting participant is dreading the meeting, the central controller may text the individual to take deep breaths, think with an open mind, and not be judgmental. If there is a learning meeting where the meeting participant is excited, the central controller may advise the individual to use the opportunity to ask more questions for learning and share your energy.

In various embodiments, there may be attendee-specific rewards for attending, achieving and/or meeting goals. Rewards may be allocated/awarded by the meeting organizer and/or system.

At step 7933, the central controller 110 may start the meeting, according to some embodiments. Users may then join the meeting, according to some embodiments.

During the Meeting

Continuing with step 7933, the central controller manages the flow of the meeting, according to some embodiments.

Textual Feedback (Teleprompter)

In various embodiments, a presenter may receive feedback, such as from the central controller 110. Feedback may be provided before meeting (e.g., during a practice meeting), during a meeting, and/or after meeting Presenters will sometimes use devices such as teleprompters to help them to remember the concepts that they are trying to get across. In various embodiments, a teleprompter may show textual feedback to a presenter. Feedback may specify, for example, if the presenter is speaking in a monotone, if the presenter is speaking too fast, if the presenter is not pausing, or any other feedback.

In various embodiments, a teleprompter may act in a "smart" fashion and adapt to the circumstances of a meeting. In various embodiments, some items are removed from the agenda if the meeting is running long. In various embodiments, the teleprompter provides speed/cadence queues.

In various embodiments, a presenter may receive feedback from a wearable device. For example, a presenter's watch may vibrate if the presenter is speaking too quickly.

Request an Extension

In various embodiments, a meeting owner or other attendee or other party may desire to extend the duration of a meeting. The requester may be asked to provide a reason for the extension. the requester may be provided with a list of possible reasons to select from.

In various embodiments, a VIP meeting owner gets precedence (e.g., gets access to a conference room, even if this would conflict with another meeting set to occur in that conference room).

In various embodiments, if a project is of high importance, the central controller may be more likely to grant the request.

In various embodiments, a request may be granted, but the meeting may be moved to another room. In various embodiments, a request may be granted, and the next meeting scheduled for the current room may be moved to another room.

Deadline and Timeline Indications

Companies often impose deadlines for actions taken to complete work. In the context of meetings, those deadlines can take a number of forms and can have a number of implications.

In various embodiments, there could be deadlines associated with actions for a particular meeting, like the need to get through an agenda by a certain time, or a goal of making three decisions before the end of the meeting. Based upon the meeting agenda, the central controller 110 can prompt the meeting owner if the current pace will result in the meeting failing to achieve its agenda items or achieve a particular objective If meeting participants do not achieve an objective in the time allotted, the central controller could:
  End the meeting
  End all instances of this meeting
  Move participants to a "lesser room"
  Shorten (or lengthen) the time allocated to the meeting
  Require the meeting owner to reapply for additional meeting time.
  Restrict the meeting owner from reapplying for additional time or from scheduling meetings without prior approval.

Room Engagement Biometric Measurements

At step 7936, the central controller 110 tracks engagement, according to some embodiments.

In various embodiments, one or more of the following signs, signals, or behaviors may be tracked: Eye tracking; Yawning; Screen time/distraction; Posture; Rolling eyes; Facial expression; Heart rate; Breathing Rate; Number of overlapping voices; Galvanic skin response; Sweat or metabolite response; Participation rates by individual.

In various embodiments, the central controller 110 may take one or more actions to encourage increased participation. For example, if Frank has not said anything, the central controller may ping him with a reminder or have him type an idea to be displayed to the room.

In various embodiments, there may be a range of "ping styles" based on the MBTI of a participant, based on such aspects of personality as introversion/extroversion levels, or based on other personality characteristics. In various embodiments, a participant may choose their preferred ping style.

In various embodiments, one or more devices or technologies may be used to track behaviors and/or to encourage behavioral modification.

In various embodiments, a mobile phone or wearable device (watch) is used for collection of biometric feedback during the meeting to the central controller and for meeting owner awareness. Real-time information to include; heart rate, breathing rate, and blood pressure. Analysis of data from all attendees alerts the meeting owner for appropriate action. This includes: tension (resulting from higher heart and breathing rates), boredom from lowering heart rates during the meeting and overall engagement with a combination of increased rates within limits.

In various embodiments, there exists wireless headphones with an accelerometer that detects head movement for communicating to the central controller and meeting owner. Downward movement includes boredom and lack of engagement. Nodding up and down can indicate voting/agreement by participants. Custom analytics of head movements based on attendee—e.g., cultural differences in head movements may be auto-translated into expressive chat text, status, metrics, etc.

In various embodiments, virtual meetings display meeting participants in the configuration of the room for a more true representation of being in the room. For example, if the meeting is taking place in a horseshoe room known by the central controller 110, the video of each person in each chair around the table should be displayed. This may provide advantages over conventional views where you get a single view of a table. This can create a more engaged virtual participant.

Various embodiments may include custom or even fanciful virtual room configurations and/or locations.

Individual Performance Indicators

At step 7939, the central controller 110 tracks contributions to a meeting, according to some embodiments.

In various embodiments, the central controller could measure the voice volume of individual speakers and/or speaking time to coach individuals via prompts (send a message to you to tone it down a bit or to let others speak). The central controller could analyze speech patterns to tell individuals whether they are lucid or coherent and inform speakers whether they are not quite as coherent as usual.

At step 7942, the central controller 110 manages room devices, according to some embodiments. This may include air conditioners, video players, projectors, and/or any other devices.

At step 7945, the central controller 110 alters a room to increase productivity, according to some embodiments. Alterations may include alterations to room ambiance, such as lighting, background music, aromas, images showing on screens, images projected on walls, etc. In various embodiments, alterations may include bringing something new into the room, such as refreshments, balloons, flowers, etc. In various embodiments, the central controller may make any other suitable alterations to a room.

Color Management

Color can be used for many purposes in improving meeting performance. Colors can be used to:
- Identify meeting type. For example, a learning meeting could be identified as green, an innovation meeting could be orange and a color allocated to any meeting.
- Highlight culture (e.g., to proudly display company colors; e.g., to show support for a group, a cause, a holiday, etc., represented by the color)
- The central controller could use various inputs to determine whether or not the participants are aligned, and then color the room green, for example, if there is good perceived alignment from these non-verbal signals:
  - Arms crossed
  - Eye rolling
  - Nodding/Head shaking
  - People leaning toward or away from other participants
  - People getting out of their chairs
  - People pushing themselves away from the table
  - People pounding their fists on a table
- Reflect the mood/morale of people in the room
- Reflect the level of confusion
- Identify whether or not the meeting is off topic or on topic
  - For example, when the meeting is going off topic the room controller could send a signal to lights in the room to cast a red light in the room as a reminder to participants that time may be being wasted.
- Indicate whether meeting participants are bored Dynamic and Personalized Aroma Therapy The central controller 110 can both detect and output smells to meeting participants as a way to better manage meetings. The central controller could be in communication with a diffuser that alters the smell of a room.

If a meeting participant brings food into the room, the central controller could detect the strength of the smell and send a signal to the meeting owner that they may want to remove the items because it could be a distraction.

When the central controller receives an indication that a meeting is getting more tense, it could release smells that are known to calm people—and even personalize those smells based on the participant by releasing smells from their chair or from a headset.

During innovation meetings, the central controller could release smells associated with particular memories or experiences to evoke particular emotions.

Food/Beverage Systems

Getting food delivered during a meeting can be a very tedious process. Tracking down the food selections of participants, getting order changes, tracking down people who never provided a food selection, or having to call in additional orders when unexpected participants are added to the meeting at the last minute.

Various embodiments provide for vendor selection. The central controller 110 can have a list of company approved food providers, such as a list of ten restaurants that are approved to deliver lunches. When a meeting owner sets up a meeting, they select one of these ten vendors to deliver lunch. The central Controller can track preferred food/drink vendors with menu selections along with preferences of each participant. If the meeting owner wants to have food, they select the vendor and food is pre-ordered.

Various embodiments provide for default menu item selections. The central controller 110 can have default menu selection items that are pre-loaded from the preferred food/beverage vendors. The administrator uploads and maintains the menu items that are made available to the meeting participants when food/beverages are being supplied. When participants accept an in-person meeting where food is served from an authorized vendor, the participant is presented with the available menu items for selection and this information saved by the central controller.

Various embodiments provide for participant menu preferences. The central controller maintains the menu preferences for each individual in the company for the approved food/beverage vendors. This can be based on previous orders from the vendor or pre-selected by each meeting participant or individual in the company. For example, a participant might indicate that their default order is the spinach salad with chicken from Restaurant "A", but it is the grilled chicken sandwich with avocado for Restaurant "B". In that way, any meeting which has identified the caterer as Restaurant "B" will create an order for the chicken sandwich with avocado for that participant unless the participant selects something else in advance.

Various embodiments provide for an ordering process. Once a meeting participant confirms attendance where food will be served, participants select their menu item or their default menu preference is used. The central controller aggregates the orders from all meeting attendees and places the order for delivery to the food vendor. Participant "A" confirms attendance to a meeting and is presented with the food vendor menu, they select an available option and the central controller saves the selection. Participant "B" confirms attendance to a meeting and is presented with the food vendor menu, but elects to use the default menu item previously saved. For those participants that did not select a menu item or have a previously saved preference for the vendor, the central controller will make an informed decision based on previous orders from other vendors. For example, always orders salads, is a vegetarian, or is lactose intolerant as examples. At the appropriate time, based on lead times of the food vendor, the central controller places the order with the food vendor.

Various embodiments provide for default meeting type food/beverage selections. The central controller 110 could store defaults for some meeting types. For example, any meeting designated as an Innovation Meeting might have a default order of coffee and a plate of chocolate to keep the energy high. For Learning meetings before 10 AM, the default might be fruit/bagels/coffee, while Alignment meetings after 3 PM might always get light sandwiches and chips/pretzels.

At step 7948, side conversations happen via peripherals or other devices, according to some embodiments.

In various embodiments, it may be desirable to allow side conversations to occur during a meeting, such as in technology-mediated fashion. With side conversations, employees may have the opportunity to clarify points of confusion, or take care of other urgent business without interrupting the meeting. In various embodiments, side conversations may be used to further the objectives of the meeting, such as to allow a subset of meeting participants to resolve a question that is holding up a meeting decision. In various embodiments, side conversations may allow an attendee to send words or symbols of encouragement to another attendee.

In various embodiments, side conversations may occur via messaging between peripherals (e.g., headsets, keyboards, mice) or other devices. For example, a first attendee may send a "thumbs up" emoji to a second attendee, where the emoji appears on the mouse of the second attendee. Where conversations happen non-verbally, such conversations may transpire without disturbing the main flow of the meeting, in various embodiments.

In various embodiments, the central controller 110 may create a whitelist of one or more people (e.g., of all people) in a meeting, and/or of one or more people in a particular breakout session. An employee's peripheral device may thereupon permit incoming messages from other peripheral devices belonging to the people on the whitelist. In various embodiments, the central controller 110 may permit communication between attendees' devices during certain times (e.g., during a breakout session, e.g., during a meeting), and may prevent such communication at other times.

In various embodiments, the central controller may store the content of a side conversation. In various embodiments, if there are questions or points of confusion evident from a side conversation, the central controller may bring these points to the attention of the meeting owner, a presenter, or of any other party.

At step 7951, the central controller 110 manages breakout groups, according to some embodiments.

In various embodiments, a meeting may be divided into breakout groups. Breakout groups may allow more people to participate. Breakout groups may allow multiple questions or problems to be addressed in parallel. Breakout groups may allow people to get to know one another and a more close-knit environment. Breakout groups may serve any other purpose.

In various embodiments, the central controller 110 may determine breakout groups. Breakout groups may be determined randomly, in a manner that brings together people who do not often speak to each other, in a manner that creates an optimal mix of expertise in each group, in a manner that creates an optimal mix of personality in each group, or in any other fashion. In various embodiments, breakout groups may be predefined.

In various embodiments, an employee's peripheral device, or any other device, may inform the employee as to which breakout group the employee has been assigned to. In various embodiments, a breakout group may be associated with a color, and an employee's peripheral device may assume or otherwise output the color in order to communicate to the employee his breakout group.

In various embodiments, a peripheral device may indicate to an employee how much time remains in the breakout session, and/or that the breakout session has ended.

In various embodiments, communications to employees during breakout sessions may occur in any fashion, such as via loudspeaker, in-room signage, text messaging, or via any other fashion.

Voting, Consensus and Decision Rules

At step 7954, decisions are made, according to some embodiments.

During meetings, participants often use rules, such as voting or consensus-taking, to make decisions, change the agenda of meetings, or end meetings. These processes are often conducted informally and are not recorded for review. The central controller could facilitate voting, gauging opinions, or forming a consensus.

The central controller 110 may allow the meeting owner to create a rule for decision making, such as majority vote, poll or consensus, and determining which meeting participants are allowed to vote.

The central controller may allow the votes of some participants to be weighted more/less heavily than others. This could reflect their seniority at the company, or a level of technical expertise, domain expertise, functional expertise, or a level of knowledge such as having decades of experience working at the company and understanding the underlying business at a deep level.

The central controller may share a poll with meeting participants.

The central controller may display the aggregated anonymized opinion of participants on decision or topic.

The central controller may display the individual opinion of participants on a decision or topic.

The central controller may require individuals to provide a rationale for a vote either through preconfigured answers or open-ended responses.

The central controller 110 may display a summary of rationales. For example, the central controller could identify through text analysis the top three factors that were cited by those voting in favor.

The central controller may use a decision rule to change, add or alter the agenda, purpose or deliverable of the meeting.

The central controller may facilitate voting to end the meeting or extend the time of the meeting.

The central controller may match meeting participants who share similar or dissimilar opinions on a topic for a breakout session.

The central controller may record votes and polls to allow review.

The central controller may determine over time which employees have a track record of success/accuracy in voting in polls or who votes for decisions that result in good outcomes through an artificial intelligence module.

The central controller may allow for dynamic decision rules which weights participants' votes based upon prior performance as determined by an artificial intelligence module.

The meeting owner could add a tag to a presentation slide which would trigger the central controller to initiate a voting protocol while that slide was presented to the meeting participants.

In various embodiments, votes are mediated by peripherals. Meeting attendees may vote on a decision using peripherals. For example, a screen on a mouse displays a question that is up for a vote. An attendee can then click the left mouse button to vote yes, and the right mouse button to vote no. Results and decisions may also be shown on peripherals. For example, after a user has cast her vote, the screen shows the number of attendees voting yes and the number of attendees voting no.

At step 7957, the central controller 110 tracks assets, according to some embodiments.

In various embodiments, the central controller 110 solicits, tracks, stores, and/or manages assets associated with meetings. Assets may be stored in a table such as table 6000.

The central controller may maintain a set of rules or logic detailing which assets are normally associated with which meetings and/or with which types of meetings. For example, a rule may specify that a list of ideas is one asset that is generated from an innovation meeting. Another rule may specify that a list of decisions is an asset of a decision meeting. Another rule may specify that a deck is an asset of a learning meeting.

If the central controller does not receive one or more assets expected from a meeting, then the central controller may solicit the assets from the meeting owner, from the meeting note taker come out from the meeting organizer, from imaging presenter, from a meeting attendee, or from any other party. The central controller may solicit such assets via email, text message, or via any other fashion.

In various embodiments, if the central controller does not receive one or more assets expected from a meeting (e.g., within a predetermined time after the end of the meeting; e.g., within a predetermined time of the start of the meeting; e.g., within a predetermined time before the meeting starts), then the central controller may take some action (e.g., enforcement action). In various embodiments, the central controller may revoke a privilege of a meeting owner or other responsible person. For example, the meeting owner may lose access to the most sought-after conference room. As another, the meeting owner may be denied access to the conference room for his own meeting until he provides the requested asset. As another example, the central controller may inform the supervisor of the meeting owner. Are there enforcement actions may be undertaken by the central controller, in various embodiments.

Rewards, Recognition, and Gamification

At step 7960, the central controller 110 oversees provisions of rewards and/or recognition, according to some embodiments.

While management can't always be in every meeting, various embodiments can provide ways for management to provide rewards and/or recognition to people or teams that have achieved certain levels of achievement.

In various embodiments, the following may be tracked: Participation rate in meetings; Engagement levels in meetings; Leading of meetings; Questions asked; Assets recorded; Ratings received from meeting owner or other participants; Post-meeting deliverables and/or deadlines (met or missed); Meeting notes typed up; Demonstrated engagement levels with meeting materials such as reading time or annotations; Tagging of presentation slides.

In various embodiments, reward/recognition may be provided in the form of:
  Promotions
  Role changes
    The central controller begins to identify those highly regarded in the organization for different meeting types. For example, a meeting owner who received good scores for running Innovation Meetings might be chosen to run more Innovation sessions, or to be a trainer of people running or attending Innovation meetings.
  Salary increase
    Central controller aggregates meeting participant scores and informs their manager when salary increases are taking place.
  Bonuses
  Meeting room/time slot preferences
    Top meeting owners/participants get preferred status for best rooms, meeting times, other assets
  Additional allocation of meeting 'points' (for scheduling/permitting meetings, etc.)
  Name displayed on room video screens
  A recipient's peripheral device changes its appearance.
    E.g., an employee's mouse glows purple as a sign of recognition. An employee's peripheral may change in any other fashion, such as by playing audio (e.g., by playing a melody, by beeping), by vibrating, or in any other fashion.
  Identify a person as one of the following:
    Top meeting owner
    Top participant
  In various embodiments, certain stats may be tracked related to performance:
    Baseball card stats for meetings or people or rooms
    Perfect attendance or on time, or finish on time, or develop good assets, reach good decisions, feed good outputs, as inputs to next meeting After the Meeting In various embodiments, the central controller 110 asks whether or not you attended the meeting.

In various embodiments, the central controller requests notes and vote(s) from you (and perhaps others), including ratings on the room and equipment itself and other configured items established by the meeting owner.

In various embodiments, the central controller provides your meeting engagement score (participant or owner) and leadership improvement data.

In various embodiments, the central controller 110 can identify people with higher engagement scores for coaching sessions.

In various embodiments, the central controller asks if the meeting should be posted for later viewing by others.

Sustainability

At step 7963, the central controller 110 scores a meeting on sustainability, according to some embodiments. Some contributions to sustainability may include: environmental soundness, reduced meeting handouts (physical), increased remote participation, etc.

Many companies are now working diligently to respect and preserve the environment via Corporate Social Responsibility (CSR) focus and goals. These CSR goals and initiatives are key in improving and maintaining a company's reputation, maintaining economic viability and ability to successfully recruit the next generation of knowledge workers. Various embodiments can help to do that. For example, companies may take the following thinking into consideration:
  Making virtual participation more effective allows for fewer participants having to travel for meetings, reducing car exhaust and airplane emissions.
  With smaller meetings, smaller meeting rooms can be chosen that require less air conditioning.
  Carbon dioxide elimination/Green score/Corporate Social Responsibility score by meeting and individual—participants that are remote and choose to use virtual meetings are given a CO2 elimination/green score.
    These scores can be broadcast throughout the company.
    These scores can be highlighted in corporate communications or on a company website.
  Not printing content and making all presentations, notes, feedback and follow-up available electronically, can generate a green score by participants/meeting/organization.
  Brainstorming sessions can be done regarding making environmental improvements, with the results of those sessions quickly made available to others throughout the enterprise, and the effectiveness of those suggestions tracked and evaluated.
  The company heating/cooling system could get data from the central controller in order to optimize temperatures.

When engagement levels start to drop, experiment with changes in temperature to see what changes help to bring engagement levels up.

When the central controller knows that a meeting room is not being used, the air conditioning can be turned off. It can also be turned back on just before the start of the next meeting in that room. At 3 PM if the last meeting is done, the AC should go off and the door should be closed.

When the central controller knows a meeting participant is attending a meeting in person, the air conditioning or heating temperature should be adjusted in the attendee's office to reflect that they are not in their office.

Room blinds should be controlled to minimize energy requirements.

Headsets equipped with temperature, environmental and light sensors, along with cameras and microphones, could collect data from each user in a meeting room. This data could be sent to the central controller and communication in the room controller to adjust the environmental elements or provide feedback for adjustments. The dynamic changes could help to conserve power and contribute to a positive CSR score.

CSR scores could be broadcast throughout the company's headsets for education and awareness purposes.

Headsets may facilitate heating/cooling adjustments. Headsets could collect the body temperature of each person. If the temperature increases beyond a particular threshold, the central controller could communicate with the in-room controller or central HVAC system to start the air conditioning. Likewise, if the body temperatures are too cold, the central controller could communicate with the in-room controller or central HVAC system to stop the air conditioning and possibly turn on the heat.

Headsets with cameras could detect the number of people in a meeting room. If the number of people in the room is significantly less than the accommodating size (e.g. 2 people sitting in a 20 person conference room), the HVAC system is not adjusted and conserves power. This could mimic the environmental control behavior of the central controller when a room is not in use and encourage the use of other rooms or virtual meetings.

Room blinds could be controlled to minimize energy requirements. If the headset senses light shining on a presentation panel or the room is becoming too hot, the in-room controller could obtain information from the central controller and close the blinds. Likewise, if the room becomes too dark on a sunny day, the in-room controller could obtain information from the central controller and automatically open the blinds letting in light, thus reducing the need to turn on lights.

In various embodiments, headsets may facilitate maintenance. With respect to office equipment and furniture, the headsets (cameras) could notice that chairs are missing from the room and notify the facilities department via the central controller that chairs are missing and could be brought to the conference room. This could occur for any missing asset that is not registered with the central controller for the associated room (e.g. trash cans, markers).

With respect to maintaining office cleanliness, the headsets (cameras) could notice that the trash can is full of lunch from a previous meeting or that there are crumbs on the floor and the cleaning crew could be dispatched to clean the room via the central controller. In addition, if the trash can is not full or the room is clean, the cleaning crew could be notified to not access the room and save on maintenance and power costs.

In various embodiments, the central controller 110 could have access to the organization's environmental Corporate Social Responsibility (CSR) goals and targets. These are preloaded into the central controller. When meetings are scheduled, the central controller informs the meeting lead and participant of the meetings CSR target score based on the overall organization goals. When team members elect to participate remotely or not print documents related to the meeting these are components that generate a CSR meeting score. This score can be maintained real-time by the central controller and used to monitor and update in real-time the CSR score to target goal. This score can be promoted on both internal sites for employee awareness and external sites for customer viewing. For example, meeting owner "A" schedules a meeting with 10 people in location ABC. 5 people are remote, 3 work from home and 2 are co-located in location ABC. The meeting owner is provided with the CSR target goal of 25%. If 3 of the 5 remote attendees elect to not fly to location or rent a car or stay in a hotel in location ABC, the meeting receives a positive contribution to the CSR goal. When 2 people decide to fly to the meeting, they receive a negative contribution to the CSR goal since they are contributing to more carbon dioxide emissions, renting fossil fuel vehicles and staying in hotels that use more energy. Likewise, the 3 people that work from home and do not drive to the office contribute positively to the CSR goal. The 2 co-located meeting participants in location ABC receive a score as well since they drive to the office daily and consume utilities at their place of employment. Furthermore, as attendees see the meeting CSR score in advance of the meeting and make alternative choices in travel and attendance, the score adjusts. As more people elect to attend in person, the score begins to deteriorate. If people begin to print copies of a presentation, the network printers communicate to the central controller and the CSR score begins to deteriorate as well. As more people attend in person, the AC/Heating costs begin to increase and again, this contributes negatively to the CSR score. Upon completion of the meeting, the final CSR score is provided to all attendees and the central controller maintains the ongoing analytics of all meetings for full reporting by the organization.

Even when meetings are not taking place in a physical room, the room itself could be contributing to a negative CSR score. Rooms require heat and cooling even when no one is in the workplace. The meeting controller should be aware of all meetings and proactively adjust the heating and cooling of each room. For example, the meeting controller knows a meeting is taking place in conference room "A" from 8:00 AM-9:00 AM. The meeting room controller should alert the heating and cooling system to adjust the temperature to 76 degrees Fahrenheit at 7:45 AM. Also, the meeting room controller should also notice that another meeting is taking place from 9:00 AM-10:00 AM in the same room and hence should maintain the temperature. If however, there is no meeting scheduled from 9:00 AM-11:00 AM, the central controller should inform the heating and cooling system to turn off the system until the next scheduled meeting. When temperatures are adjusted to match the use of the room, the CSR score is positively impacted since less energy is used.

Since the central controller 110 also knows which individuals are attending the meeting in person, if the individual has an office, the heating and cooling system should be adjusted in the office to conserve energy. For example, person "A", who sits in an office, elects to attend a meeting in conference room "B" in person at 8:00 AM. At 7:55 AM, or whenever the time to travel begins for the individual, the central controller informs the heating and cooling system to adjust the temperature for an unoccupied room. In this case, it could be set to 80 degrees Fahrenheit. Since the office is not occupied during the meeting time, less energy is spent heating and cooling the office. This contributes positively to the overall CSR target score and the central controller maintains this information for use by the organization.

As temperature conditions in the room are impacted by sun through windows, the central controller should interface with the window blind system accordingly. For example, in the winter, the central controller could interface with the local weather system to determine that it will be sunny and 45 degrees Fahrenheit outside and that the room windows face the south. In this case, in order to use solar energy, the blinds of the meeting room should be opened by the central controller to provide heat and hence use less energy sources. Likewise, in the summer, with a temperature of 90 degrees Fahrenheit, this same southern facing conference room should have the blinds closed to conserve cooling energy. This data should be provided by the central controller to the overall CSR target goals for the organization. The central controller could integrate to sites to calculate the CSR savings/Green savings by not flying or driving. Since the central controller knows where the meeting participant is located and where the meeting is taking place they can determine the distance between the locations and calculate the savings. For example, the central controller knows the meeting is taking place at 50 Main Street in Memphis, Tenn. An individual in Denver, Colo. elects to participate remotely and not travel. The central controller can access a third party site to calculate the CO2 emissions saved thus the positive contribution to the CSR target. In addition, a person in a suburb of Memphis decides to participate remotely and not drive to the meeting. The central controller can access third party mapping software and determine the driving distance and access a third party site to calculate the CO2 emission saved. This information is collected by the central controller and provided to the organization for CSR reporting.

Keyboards

Figure 80:
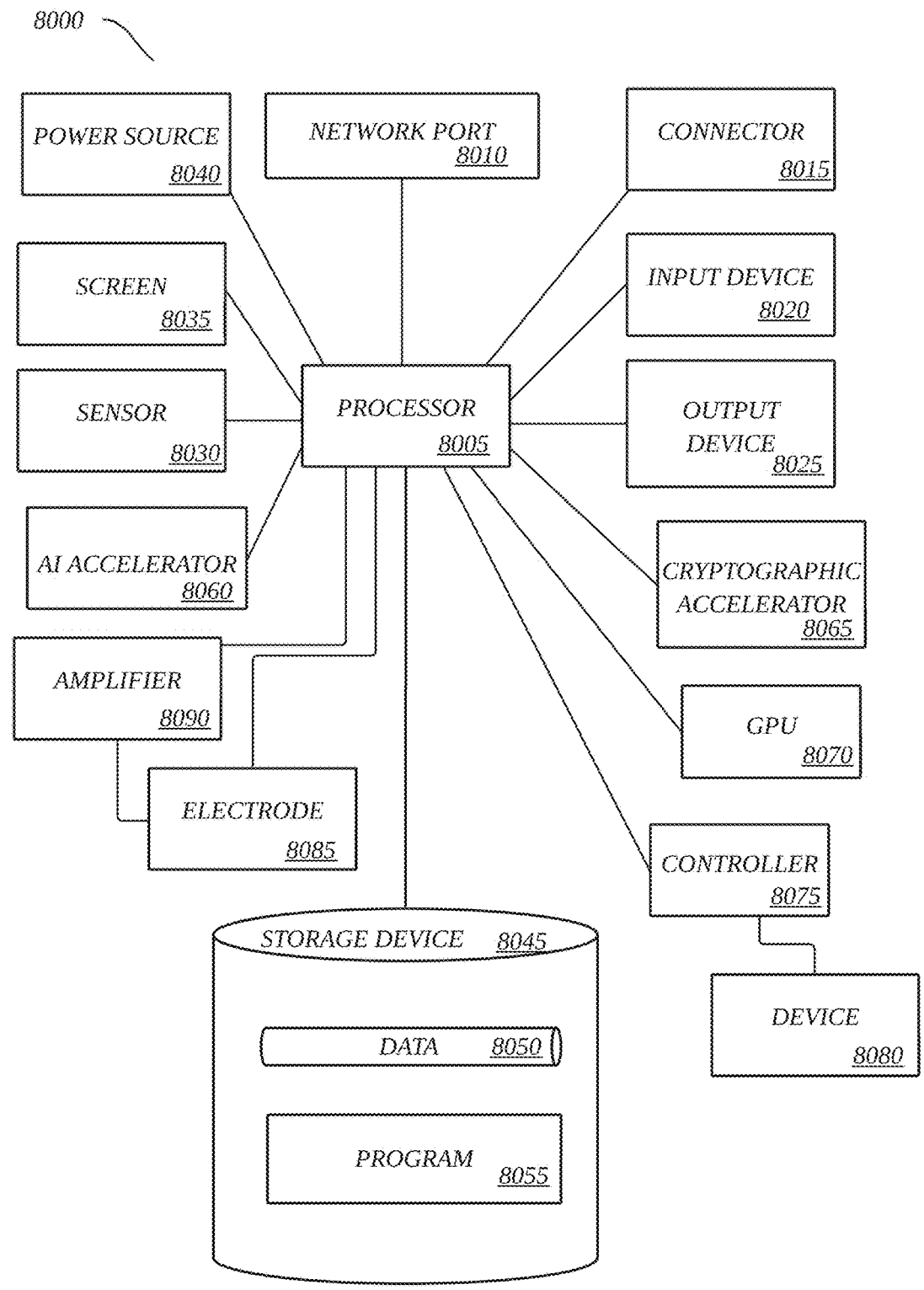
FIG. 80 is a block diagram of a peripheral (headset) consistent with at least some embodiments described herein.

Turning now to FIG. 80, a block diagram of a headset device 8000 according to some embodiments is shown. In various embodiments, a headset device may be worn on a user's head which receives inputs and provides outputs.

Headset device 8000 may include various components. Headset device 8000 may include a processor 8005, network port 8010, connector 8015, input device 8020, output device 8025, sensor 8030, screen 8035, power source 8040, storage device 8045, AI accelerator 8060, cryptographic accelerator 8065, and GPU (graphics processing unit) 8070. Storage device 8045 may store data 8050 and program 8055. A number of components for headset device 8000 depicted in FIG. 80 have analogous components in user device 106*a* depicted in FIG. 3 (e.g., processor 8005 may be analogous to processor 305) and in peripheral device 107*a* depicted in FIG. 4 (e.g. sensor 8030 may be analogous to sensor 430), and so such components need not be described again in detail. However, it will be appreciated that any given user device or peripheral device and any given headset device may use different technologies, different manufacturers, different arrangements, etc., even for analogous components. For example, a particular user device may comprise a 20-inch LCD display screen, whereas a headset device may comprise a 2-inch OLED display screen. It will also be appreciated that data 8050 need not necessarily comprise the same (or even similar) data as does data 350 or data 450, and program 8055 need not necessarily comprise the same (or even similar) data or instructions as does program 355 or program 455. Input device 8020 may include audio input that may be provided by a user which results in a command sent to network port 8010.

In various embodiments, analogous components in different devices (and/or in different variations of a device) may use a similar and/or analogous numbering scheme. For example, reference numerals for like components may differ only in the "hundreds" or "thousands" digits, but may have similar trailing digits. For example, processor 305 in FIG. 3 and processor 405 in FIG. 4 may be analogous components, and have the same last two digits in their respective reference numerals. In various embodiments, where components in different figures have similar and/or analogous numbering schemes, such components may have similar and/or analogous functions and/or construction. In various embodiments, however, analogous numbering schemes do not necessarily imply analogous functions and/or construction.

In various embodiments, connector 8015 may include any component capable of interfacing with a connection port (e.g., with connection port 315). For example, connector 8015 may physically complement connection port 315. Thus, for example, headset device 8000 may be physically connected to a user device via the connector 8015 fitting into the connection port 315 of the user device. The interfacing may occur via plugging, latching, magnetic coupling, or via any other mechanism. In various embodiments, a headset device may have a connection port while a user device has a connector. Various embodiments contemplate that a user device and a headset device may interface with one another via any suitable mechanism. In various embodiments, a user device and a headset device may interface via a wireless connection (e.g., via Bluetooth®, Wi-Fi®, or via any other means).

AI accelerator 8060 may include any component or device used to accelerate AI applications and calculations. AI accelerator 8060 may use data collected by sensor 8030 and/or input device 8020 to use as input into various AI algorithms to learn and predict outcomes. AI accelerator 8060 may use storage device 8045 for both input and result data used in AI algorithms and calculations.

In various embodiments, AI accelerator 8060 can send a signal back to user device 106*a* upon making a prediction, determination, or suggestion. For example, if a user is playing a game and it is determined by AI accelerator 8060 that the user is performing poorly a signal can be sent back to user device 106*a* to adjust the difficulty to a more appropriate level. It may also track a user's learning curve and be able to predict when the user will require a harder level.

In various embodiments, AI accelerator 8060 can use multifaceted data collected by sensor 8030 as input to induce actions. The AI accelerator can use this information, for example, to: trigger recording of the current game session when a user shows excitement through speech or skin response, induce a vibration in the headset if the user is showing signs of being distracted or sleepy, etc.

In various embodiments, AI accelerator 8060 may combine data from various sources including sensor 8030 and input device 8020 with its own data calculated and/or stored on storage device 8045 over a long period of time to learn behaviors, tendencies, idiosyncrasies and use them for various purposes. For example, the AI accelerator may determine that the person using headset 8000 currently is not the approved user based on movement patterns, ambient sound, voiceprint, fingerprint, etc. and prevent unauthorized access of headset 8000. The AI accelerator may find concerning medical conditions through heart rate sensor, temperature, movement patterns and notify the user to seek medical attention. The accelerator may determine the users learning capabilities and knowledge base to determine complexity settings on future games, applications, templates, etc.

Cryptographic accelerator 8065 may include any component or device used to perform cryptographic operations. Cryptographic accelerator 8065 may use data collected by various sources including but not limited to sensor 8030 and/or input device 8020 to use as input into various cryptographic algorithms to verify user identity, as a seed for encryption, or to gather data necessary for decryption. Cryptographic accelerator 8065 may use storage device 8045 for both input and result data used in cryptographic algorithms.

In various embodiments, cryptographic accelerator 8065 will encrypt data to ensure privacy and security. The data stored in storage device 8055 may be encrypted before being written to the device so that the data can only be usable if passed back through 8065 on output. For example, a user may want to store sensitive information on the storage device on headset 8000 so that they can easily authenticate themselves to any attached user device 106*a*. Using the cryptographic accelerator to encrypt the data ensures that only the given user can decrypt and use that data. In some embodiments, cryptographic accelerator 8065 includes multifactor authentication capability so that headset 8000 may be used in remote authentication protocols.

In various embodiments, cryptographic accelerator 8065 will encrypt signals to ensure privacy and security. Signals sent to user device 106*a* through connector 8015 and connection port 315 can be encrypted so that only a paired user device can understand the signals. Signals may also be encrypted by the cryptographic accelerator and sent directly via network port 8010 to another peripheral device 107*a* via that device's network port 410. For example, a user may use a microphone on their headset to record speech for private communications and that data can pass through cryptographic accelerator 8065 and be encrypted before being transmitted. The destination device can decrypt using its cryptographic accelerator using shared keys ensuring no other party could listen in.

GPU (graphics processing unit) 8070 may include any component or device used to manipulate and alter memory to accelerate the creation of images in a frame buffer intended for output on one or more display devices. GPU 8070 may use data collected by various sources including but not limited to sensor 8030 or from the attached user device via connector 8015 to use in graphics processing. GPU 8070 may use storage device 8045 for reading and writing image data.

In various embodiments, GPU 8070 will create image data that will be displayed on screen 8035 or output device 8025. For example, a user is playing a game and GPU 8070 can be used to process data and display the data on a keyboard display (output device 8025), and can assist in processing graphics data.

In some embodiments, headset device 8000 includes controller 8075 which can manage multiple devices 8080 in order to reduce the computational load on processor 8005.

In some embodiments, storage device 8045 may store financial data (e.g. credit card numbers, bank account numbers, passwords, digital currencies, coupons), medical data, work performance data, media (e.g. movies, songs, books, audio books, photos, instruction manuals, educational materials, training materials, presentations, art, software applications, advertisements), etc. In various embodiments, users may be required to authenticate themselves to headset 8000 before gaining access to data stored in storage device 8045.

Figure 81:
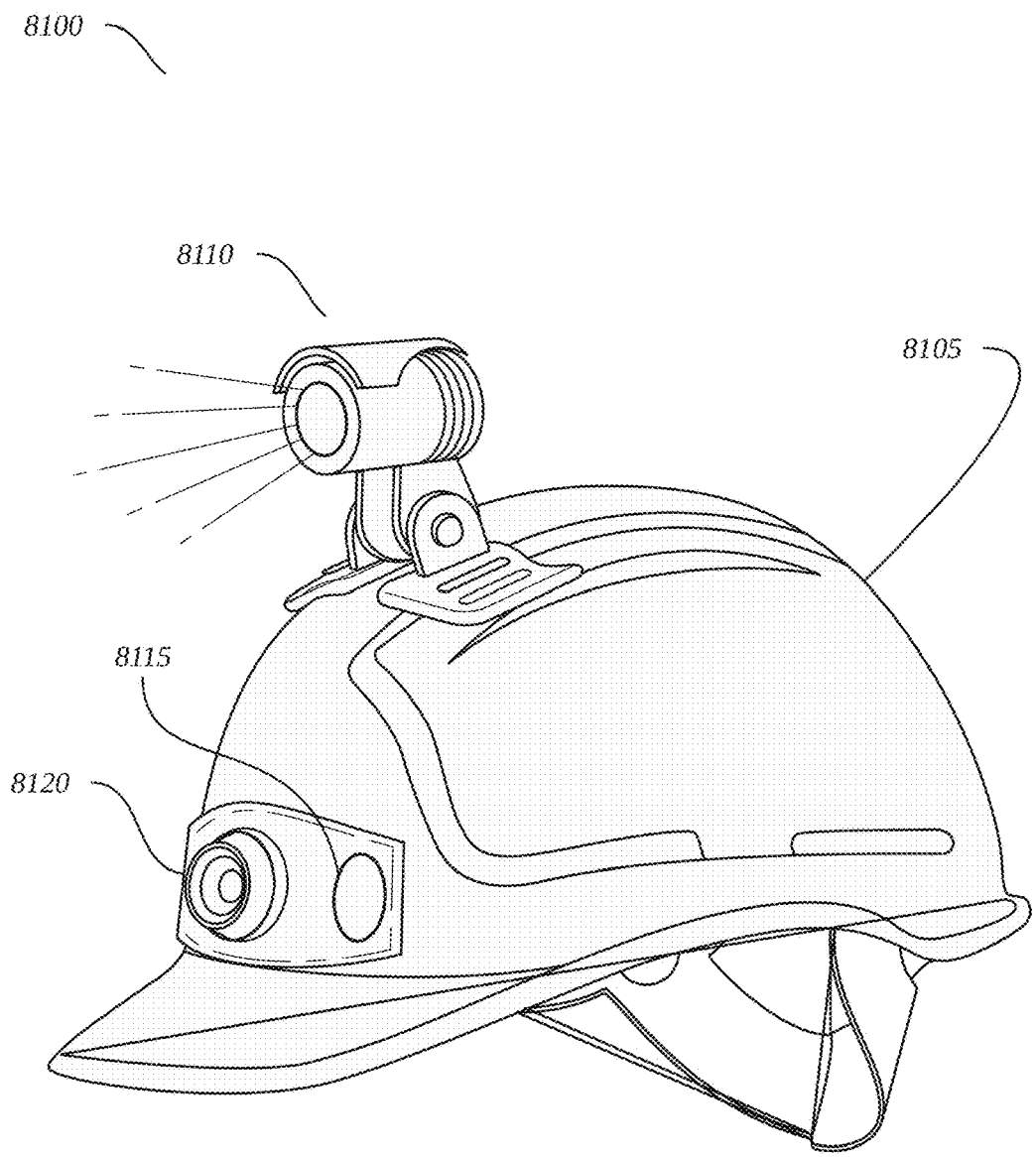
FIG. 81 is a hardhat consistent with at least some embodiments.

With reference to FIG. 81 there is shown an illustration of a hardhat 8100. The hardhat 8105 may contain a camera 8110 with lights and microphone, a sensor 8115 (e.g. gas, environmental, light, pollution, range) and projector 8120 to assist a worker in an environment or profession needing additional protection (e.g. construction, miner). Hardhat 8105 may include any of the functionality of headset 4000 of FIG. 40 or of any other headset described herein. A miner wearing hardhat 8105 may enter a mine, well below ground. Sensor 8115 may notice the light dissipating and communicate with the hardhat to turn on camera 8110 with a light for better visibility. The camera 8110 may also detect objects in a dim lit space (e.g. shovel, cart, boulders) and alert the miner of the upcoming obstacle. While working in the mine, levels of carbon monoxide may increase. Sensor 8115 may detect carbon monoxide levels are not acceptable and alerts the miner through the hardhat using camera 8115 lights (e.g. red strobe light) and communication to the safety monitoring team on ground level. While in the mine, the miner may encounter a broken draw bar gear connecting the cars. The miner requests through headset 8105 a video of how to repair the gear from the maintenance team. The maintenance team may deliver the repair video to the miner through the headset and projects on the wall using projector 8120. Camera 8110 may also capture images of all workers in the area and compare to the safety protocols established by the company. Any violations may be communicated to the miner headsets.

Figure 82:
FIG. 82 is an employee wearing a headset consistent with at least some embodiments described herein.

With reference to FIG. 82 there is shown an illustration of a repair 8200. Office worker is attempting to repair broken machine 8215. Office worker is wearing headset 8210 which may include any of the functionality of headset 4000 of FIG. 40 or of any other headset described herein. The office worker is needing assistance to repair the broken machine 8215 and uses headset 8210 to request an experienced technician from the manufacturer provide instructions remotely. The office worker speaks into the microphone and initiates a request and video feed to the technician while looking at broken machine 8215. The technician joins with their headset and observes the broken machine and guides the office worker through the steps needed to repair the machine. Likewise, the office worker with headset 8215 may request a video be shown on the display (e.g. a training video on how to fix the particular problem) to assist in fixing the broken machine 8215 independent of another person. The office worker may also request internal assistance from other workers who are more familiar with fixing the broken machine 8215 (e.g. an administrative assistant) using headset 8210. The office worker requests through the headset a display of all internal company employees with experience fixing the broken machine type. A list is provided on the headset display and the office worker selects an individual. Communication from the headsets is established with the other company employee and assistance is provided to fix the machine in a manner similar to the manufacturer representative.

Keyboard Output Examples

In various embodiments, a keyboard is used to output information to a user. The keyboard could contain its own internal processor. Output from the keyboard could take many forms.

In various embodiments, the height of keys serves as an output. The height of individual keys (depressed, neutral or raised) could be controlled as an output.

In various embodiments, a keyboard contains a digital display screen. This could be a small rectangular area on the surface of the keyboard which does not interfere with the activity of the user's fingers while using the keyboard. This display area could be black and white or color, and would be able to display images or text to the player. This display would receive signals from the user device or alternately from the central controller, or even directly from other peripheral devices.

In various embodiments, the screen could be touch-enabled so that the user could select from elements displayed on this digital display screen. The screen could be capable of scrolling text or images, enabling a user to see (and pick from) a list of inventory items, for example. The screen could be mounted so that it could be flipped up by the user, allowing for a different angle of viewing. The keyboard display could also be detachable but still controllable by software and processors within the mouse.

In various embodiments, a keyboard may include lights. Small lights could be incorporated into the keyboard or its keys, allowing for basic functionality like alerting a user that a friend was currently playing a game. A series of lights could be used to indicate the number of wins that a player has achieved in a row. Simple lights could function as a relatively low-cost communication device. These lights could be incorporated into any surface of the keyboard, including the bottom of the keyboard. In some embodiments, lights are placed within the keyboard and can be visible through a semi-opaque layer such as thin plastic. The lights could be directed to flash as a way to get the attention of a user.

In various embodiments, a keyboard may render output in the form of colors. Colors may be available for display or configuration by the user. The display of colors could be on the screen, keys, keyboard, adjusted by the trackball or scroll wheel (e.g., of a connected mouse; e.g., of the keyboard), or varied by the sensory information collected. The intensity of lights and colors may also be modified by the inputs and other available outputs (games, sensory data or other player connected devices).

In various embodiments, a keyboard may render outputs in the form of motion. This could be motion of the keyboard moving forwards, backwards, tilting, vibrating, pulsating, or otherwise moving. Movements may be driven by games, other players or actions created by the user. Motion may also be delivered in the form of forces against the hand, fingers or wrist. The keyboard device and keys could become more firm or softer based on the input from other users, games, applications, or from the keyboard's own user. The sensitivity of the keys could adjust dynamically.

In various embodiments, a keyboard may render outputs in the form of sound. The keyboard could include a speaker utilizing a diaphragm, non-diaphragm, or digital speaker. The speaker could be capable of producing telephony tones, ping tones, voice, music, ultrasonic, or other audio type. The speaker enclosure could be located in the body or bezel of the keyboard.

In various embodiments, a keyboard may render outputs in the form of temperature (or temperature changes). There could be a small area on the surface of the keyboard keys or in the keyboard bezel which contains heating or cooling elements. These elements could be electrical, infrared lights, or other heating and cooling technology. These elements could output a steady temperature, pulsating, or increase or decrease in patterns.

In various embodiments, a keyboard may render outputs in the form of transcutaneous electrical nerve stimulation (TENs). The keyboard could contain electrodes for transcutaneous electrical nerve stimulation. These electrodes could be located in the keys or the areas corresponding with areas used by fingertips or by the palm of the hand. These electrodes could also be located in an ergonomic device such as a wrist rest.

In various embodiments, a keyboard may render outputs in the form of scents, smells, or odors. A keyboard may include a scent machine (odor wicking or scent diffuser). The keyboard could contain an air scent machine, either a scent wicking device or a scent diffusing device. This air scent machine could be located in the body or bezel of the keyboard.

Referring to FIG. 87, a diagram of an example 'game character with independently controllable elements' table 8700 according to some embodiments is shown. Table 8700 may store an indication of a game character that is controlled by two or more users. In some embodiments, a game character (e.g. fighting character, dancer, animal, object) may have controllable elements in a game (e.g. velocity of movements, direction of movements, weapon selection, armor selection, acceleration, braking, size of bets, type of game skin, strategic decisions, communications) which may be allocated to multiple players to control. For example, a car racing game may have three independent elements (e.g. steering, accelerating, and braking) shared among three players, each of whom controls one of the elements during game play, requiring a significant amount of coordination among the three players and adding a new element to game play.

Game character ID field 8702 may include an identifier (e.g., a unique identifier) for a particular game character. In some embodiments, a game character can be an object such as a car or boat, or a collection of game protocols that may be separated into two or more pieces such as poker actions and bet sizing. Independently controllable elements field 8704 may include an identification of two or more elements (e.g., aim, trigger pulls, and movement) for a particular game character ID 8702. In some embodiments, each element is controlled by a single player, with the player's peripheral device providing input for the independently controllable element selected or assigned to the player. Each of these three input streams is assembled by central controller 110 so that the game character has all controllable elements in place to control the game character. In various embodiments, one or more players may be assigned (or choose) to provide input for two or more of the independently controllable elements. Time of control field 8706 may store the length of the game play session in which independently controllable elements are controlled by players. In some embodiments, this is a fixed amount of time like '5 minutes', though triggers (e.g. 'until game ends', 'duration of tournament') could also serve as an end point for the play session.

Referring to FIG. 88, a diagram of an example 'user control' table 8800 according to some embodiments is shown. Table 8800 may store an indication of a user who has lost control of a peripheral device to another user. In some embodiments, a player using a peripheral device (e.g. mouse, keyboard, game console controller) to control an element in a game (e.g. a game character, one side of a chess game, a car) may lose that control at some point during the game. In some embodiments, loss of control may result from a player losing a battle, falling into a trap, not scoring enough points, teammates voting to take away the player's control, etc.

Peripheral ID field 8802 may include an identifier (e.g., a unique identifier) for a particular peripheral device of a user. User ID normally in control field 8804 may include an identifier (e.g., a unique identifier) for a particular user who is normally in control of peripheral 8802. In some embodiments, this may be the owner of the peripheral device 8802, or the current user holding peripheral device 8802. User ID taking over control field 8806 may include an identifier (e.g., a unique identifier) for a particular user who is taking over control of peripheral 8802. In some embodiments, this may be an opponent of the user normally in control 8804, or a teammate of the user normally in control. End time of user taking over control field 8808 may store the date and time at which control of the peripheral reverts back to the user ID normally in control of the peripheral. In other embodiments, control may revert back upon a game result (e.g. the user taking control loses a battle), a payment by the user normally in control (e.g. points, digital currency, money), the end of a game session, etc.

Figure 90:
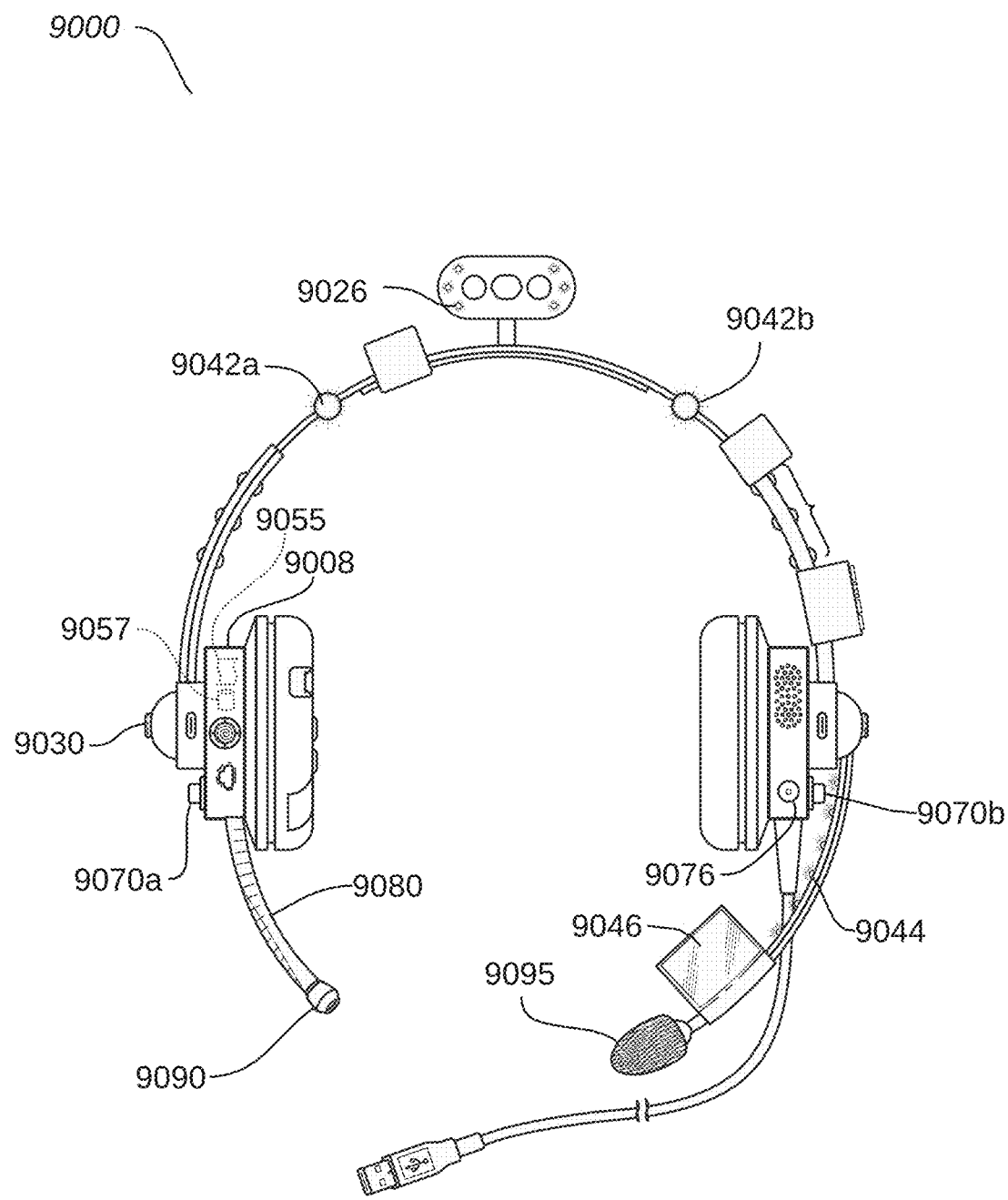
FIGS. 90 through 91 are headsets consistent with at least some embodiments described herein.

With reference to FIG. 90, a headset 9000 according to some embodiments is shown. Headset 9000 includes a camera 9090 attached to a bendable stalk 9080 which attaches camera 9090 to housing 9008. In various embodiments, bendable stalk 9080 allows a user to position camera 9080 to capture video or still images from many angles. In some embodiments, bendable stalk 9080 may be made from a material that is capable of bending, though it retains its position once bent. In various embodiments, camera 9090 may be aimed at an object in front of the user, aimed at another user, aimed at the user's face (e.g. to capture distances between eyes, ears, nose and mouth for biometric calculations), aimed at one of the user's eyes (e.g. to capture an image of the user's iris for a biometric calculation), aimed at the user's lips (e.g. to capture lip movements to help other user's understand what the user is saying), aimed at a tattoo of the user (e.g. to transmit a photo of the tattoo to central controller 110 to aid in identifying or authenticating the user), aimed at clothing or jewelry of the user, aimed at the hair of the user, aimed at the skin of the user's neck (e.g. to determine an approximate age of the user), aimed at written text, aimed at tools required to fix an object (e.g. copy machine), aimed at a pet (e.g. to aid in identifying or authenticating the user), aimed at the users clothing, aimed at an aspect of the environment around the user which identifies the user's current location (e.g. street signs, a name plaque on a building, a recognizable building facade), etc. In some embodiments, lights 9042a, 9042b, 9044, and/or 9026 may be illuminated by headset 9000 in order to provide better lighting conditions for camera 9090. In some embodiments, camera 9090 includes one or more lights that may be directed at the object camera 9090 is pointed at. In some embodiments, headset 9000 includes microphone 9095.

In some embodiments, bendable stalk 9080 includes one or more motors which are under control of central controller 110 so that central controller 110 may "look around" the user. Such motors may also enable headset 9000 to maintain a video feed associated with a fixed object in the field of view even when the user turns her head.

In other embodiments, video captured by camera 9090 may be output via display screen 9046 and/or projector 9076, allowing the user to see what camera 9090 is pointed at. In some embodiments, headset 9000 uses data from accelerometers 9070a and 9070b in order to determine the position of the user's head, and uses that head position to better identify where the user is looking.

In various embodiments, headset 9000 may facilitate observing a path for safety where a user is walking, running, or biking. Active users oftentimes walk, run or bike in areas where paths are worn or items are obstructing the path, causing potential safety hazards through tripping and falling. Headset 9000 with camera 9090 on a bendable stalk 9080 may assist the user. A biker may be riding on a path that has broken asphalt and potholes. Camera 9090 with the bendable stalk 9080 may be adjusted by the biker to focus slightly forward and downward on the path, allowing the biker to observe and pay attention to other surroundings (e.g. walkers, scenery, animals). While the biker is observing a walker with a dog coming in his direction, camera 9090 may detect a pothole on the path. The headset may notify the biker through the speaker (e.g. buzz) alerting him that a pothole or object is approaching and to stay alert. Likewise, display 9046 may show the pothole to provide a more clear indication of the object in front of the biker.

In various embodiments, headset 9000 may watch children while a user is working. There may be times where a parent needs an extra set of eyes to watch children while working. While on conference call, a remote home worker may wear headset 9000 with camera 9090. A baby is sitting in a seat next to the parent and the parent focuses camera 9090 with the bendable stalk 9080 on the baby. While the parent is watching a computer monitor on a conference call and working, camera 9090 may be focused on the baby. During the conference call, the camera detects the baby waking and moving, signifying to the parent that they are wanting attention. Display 9046 alerts the parent to take a break and address the baby's needs by showing a video of the baby. Likewise, boom lights 9044 may blink yellow to indicate that the parent needs to tend to the baby.

In various embodiments, headset 9000 may facilitate the fixing of something while observing another function. There are times when a user needs to focus on one task but observe the effects of their actions. For example, an exterior light on a home has stopped working and the homeowner suspects a blown fuse that needs reset. Wearing headset 9000, the homeowner may open the electrical panel and point camera 9090 with bendable stalk 9080 towards the exterior light that is not working. Lights 9042a-b may illuminate the electrical panel so the homeowner can see the panel switches. While resetting each electrical switch, camera 9090 may detect when the exterior light comes back on. As the light turns on, a message may be heard by the homeowner in the speaker (e.g. 'fixed') or display 9046 may show the video of the light coming on collected by camera 9090. These alerts may allow the homeowner to stay focused on resetting the electrical panel while being informed of the task completion using the camera 9090 on bendable stalk 9080.

In various embodiments, headset 9000 may facilitate lip reading from a distance. Individuals with hearing impairments rely on lip reading, but this requires the individual to be in close proximity to the person speaking in order to see their lips. Headset 9000 with camera 9090 may help provide a closer image of a person's lips to aid in lip reading. In some embodiments, a user with headset 9000 may attend a conference and attempt to listen to a keynote speaker on stage and take notes. The user may adjust camera 9090 with bendable stalk 9080 toward the stage, focusing on the keynote speakers lips. The keynote speakers lips may be magnified and projected on display 9046, allowing a clearer view and ability for the user to read the lips. This feature provides enhanced opportunities for hearing impaired individuals.

In various embodiments, headset 9000 may assist in gathering health assessments. Health assessments of individuals entering the country are oftentimes random. In some embodiments, temperature checks for international travelers at arriving airports are random. An airport worker with headset 9000 and camera 9090 on a bendable stalk 9080, may point the camera to the arriving passenger passageway. As passengers enter, the camera 9090 with a thermal sensor may detect the temperature of each person. If a passenger has an elevated temperature, projector 9076 may display the image of the person and a message on a wall for them to step to the side for evaluation, an image of the person may show on display 9046 prompting the attendant to approach the passenger or a sound may be played in the speaker to alert the attendant of needed action (e.g. detain passenger). Likewise, as in various embodiments, camera 9090 may detect other passenger biometric data to validate against no-fly lists and potential threats.

In various embodiments, headset 9000 may assist a user in recalling names and details. It is common for people to forget names and details of individuals, especially if their interactions are limited. Headset 9090 may assist users in this situation. In some embodiments, a salesperson may have met a person and had a brief conversation at a conference. The salesperson with camera 9090 may collect this conversation and images of the person they are interacting with and store them in the data storage 9057 within housing 9008. Months later, at a different conference, the same individual approaches the salesperson. Camera 9090 on the bendable stalk 9080 is pointed to the crowd and recognizes the person from data storage 9057 in headset 9000. The camera display 9046 may provide the image, video or text of the earlier conversation to assist the salesperson in recalling specifics. Likewise, the speakers in headset 9000 may also provide the name of the approaching individual and any stored details. As the user approaches, the salesperson is equipped with information to re-engage the individual and not create an awkward moment of re-introductions.

In various embodiments, headset 9000 may facilitate checklists and checklist completion for technicians. Checklists are provided for many professionals as reminders to complete tasks and provide repetitive service. FIG. 46 represents an automobile technician wearing a headset 4630 using a checklist 4635 to assess the key functions of an automobile (e.g. battery life 4610, air pressure 4615, engine status 4620 and temperature 4625). Camera 9090 on bendable stalk 9080 may be pointed toward the checklist 4635. As the technician observes the battery life indicator in the automobile, camera 9090 may record the technician completing the task and checking it off the list. If the technician skips a step on the checklist or fails to mark it off, the camera 9090 may recognize this missed step and inform the technician through audio alerts on the speaker, boom lights 9044 (e.g. red flashing) or comments on display 9046 (e.g. missed steps). Furthermore, if the camera detects an unacceptable level on the automobile or display wall, the technician may also be informed. Camera 9090 may detect that air pressure 4615 is too low. While the technician completes this step from checklist 4635, the headset 4630 through display 9046 or speakers may inform the technician that further evaluation is needed to correct.

Figure 91:
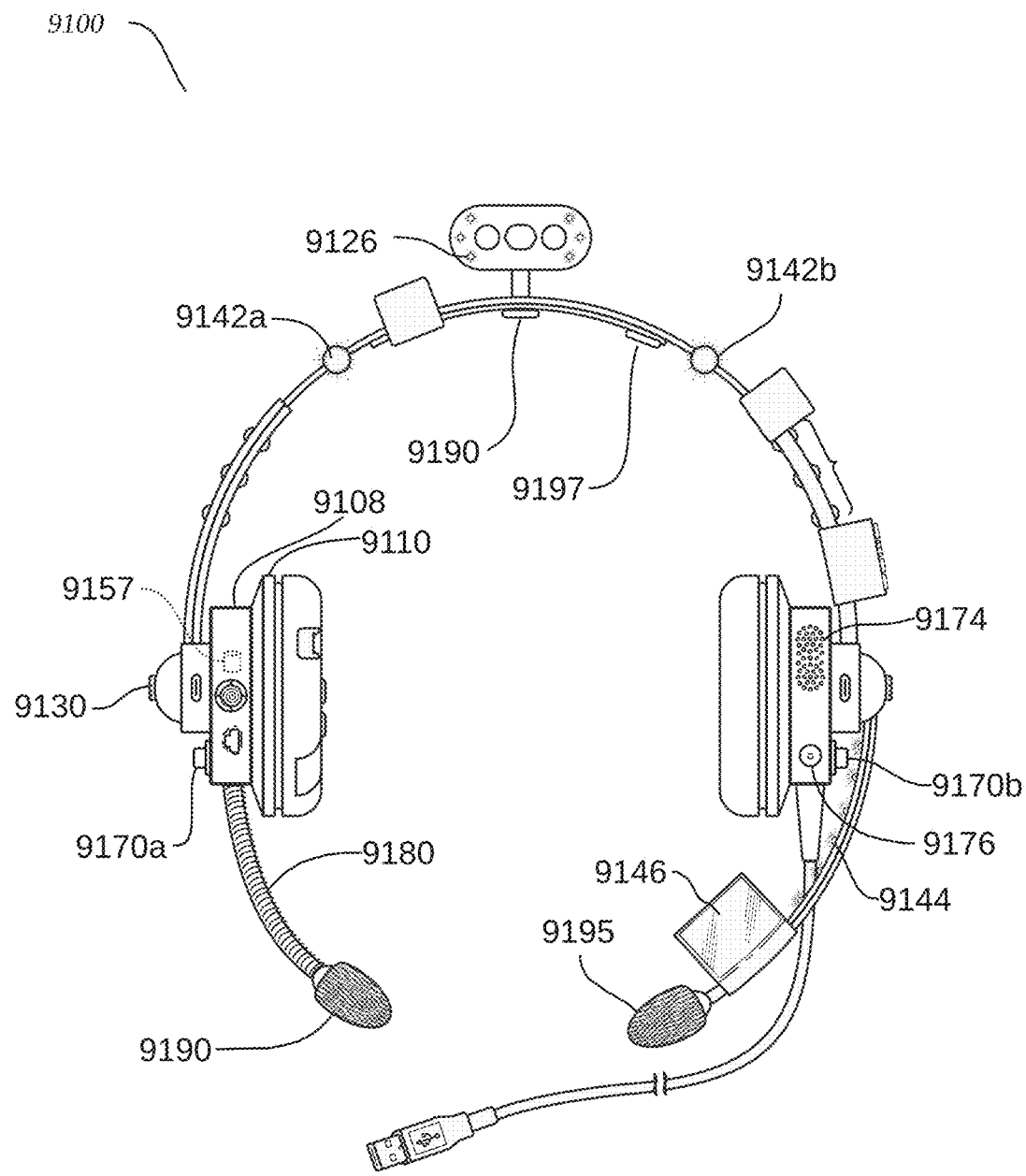

With reference to FIG. 91, a headset 9100 according to some embodiments is shown. Headset 9100 includes a directional microphone 9190 attached to a bendable stalk 9180 which attaches directional microphone 9190 to housing 9108. In various embodiments, bendable stalk 9180 allows a user to position microphone 9180 to capture audio from different positions. In some embodiments, bendable stalk 9180 may be made from a material that is capable of bending, though it retains its position once bent. In various embodiments, directional microphone 9190 may be moved toward or away from the users mouth. In some embodiments, detachable microphone 9190 and bendable stalk may be removed from headset 9100 and attached to another person or object.

In some embodiments, bendable stalk 9180 includes one or more motors which are under control of central controller 110 so that central controller 110 may move the directional microphone 9190 in the direction of an object of interest, such as another user.

In other embodiments, audio captured by directional microphone 9190 may be output via speaker 9174, allowing other nearby users to hear what microphone 9180 is picking up. In some embodiments, headset 9100 uses data from accelerometers 9170a and 9170b in order to determine the position of the user's head, and uses that head position to better identify where the user is looking.

In some embodiments, headset 9100 may facilitate including a user without a headset in a conversation. There may be situations where a user of a headset 9100 needs to share a microphone with a different user. In some embodiments, a manager is engaged in a conversation with a support person regarding a computer system outage using headset 9100 and microphone 9195. A developer enters the manager's office to engage in the conversation but does not have a headset. The manager points the directional microphone 9190 on bendable stalk 9180 to the developer to engage in the conversation. When the bendable stalk is pointed to the developer, the speaker 9174 begins to project the conversation so the developer can hear as well. Likewise, the manager may engage button 9130 to activate the speaker 9174 or directional microphone 9190 allowing another person to engage in the conversation.

In some embodiments, headset 9100 may facilitate listening in on background conversations as a casual listener. There may be a need to listen to other conversations in the background to provide input. People often do this naturally, or multi-task, but it distracts from the primary conversation they are engaged in. In some embodiments, headset 9100 can act as a second set of ears to listen and assist the user in responding. In some embodiments, a user is participating on a virtual conference call to address an emergency computer outage using headset 9100 and microphone 9195. At the same time, during a meeting in a physical room, the user is expected to participate when asked a question by those physically present in the room. At the beginning of the physical meeting the user points directional microphone 9190 on bendable stalk 9180 toward the other attendees in the conference room. When directional microphone 9190 receives the name of the user being spoken or keywords that were stored in a storage device on camera 9100, the headset alerts the user to participate. This alert may be in the form of a tone in the headset speaker (e.g. beep), displayed on the headset (e.g. you are needed) or by bringing the volume down on the emergency call. This adjustment in volume and alerts allows a user to participate in a primary conversation but be alerted to switch to a different conversation when notified. Likewise, when the particular conversation in the conference room ends, the user can select a button to return the volume to the initial level for the emergency call addressing the computer outage.

In some embodiments, headset 9100 may facilitate detecting key words, names or phrases to automatically amplify volume or provide an audible alert. Oftentimes users participate in conversations but are not actively engaged for a variety of reasons (e.g. lack of interest, not relevant at the moment, distracted with other tasks). Headset 9100 may amplify the volume in speaker 9110 when a user needs to engage. In various embodiments, at the end of a meeting, a user with a headset 9100 may be in a room with others discussing dates and times for the next meeting. The user happens to be taking notes, reading email or texts or planning their next day's activities and not paying attention. The directional microphone 9190 with bendable stalk 9180 may be pointed toward individuals in the physical room to follow the conversation, allowing the user to focus on other tasks. As the directional microphone 9190 receives the person's name being spoken or keyword (e.g. calendar, schedule, time) mentioned, as previously saved in data storage 9157, the speaker volume may automatically amplify or play a beeping sound, prompting the user to pay more close attention to the conversation.

In various embodiments, headset 9100 may assist people with hearing impairments. Oftentimes people with hearing impairments need users to speak louder, but this can be frustrating to continually ask people. Directional microphone 9190 with bendable stalk 9180 may point to the person or room with individuals to pick up the conversations and amplify them in the headphone speaker 9110. In addition, accelerometer 9170-*a-b* may detect motion and direction of the head and directional microphone 9190 hone in on the person speaking, providing more clarity for the hearing impaired person.

In various embodiments, headset 9100 may detect a nearby speaker and project their voice to the audience in a conference call. There are times when a speaker in a physical conference room cannot be heard. The headset 9100 may be used to project their voice to the audience. For example, user 1 with a headset is in a physical conference room with many people. User 2 is sitting next to user 1 in the conference room but has forgotten to bring their headset. As user 2 is speaking, others on the conference call or in the physical conference room may begin to complain that they cannot hear user 2's comments and ask them to speak up. User 1, with headset 9100, points microphone 9190 on bendable stalk 9180 to user 2 sitting next to them. The headset and directional microphone may begin to detect and amplify the voice of user 2 to others on the conference call and in the physical conference room through the speakers in the room.

In various embodiments, headset 9100 may facilitate detection of sounds (e.g. kids playing, vehicles in proximity, people/things approaching) requiring a user response. There are embodiments where non-verbal sounds around a user need to be monitored for a response. For example, a jogger with a headset 9100 and directional microphone 9190 on bendable stalk 9180 may be jogging in the park on a dark path. A different jogger with a dog approaches them from behind. Directional microphone 9190 is pointed behind the user and may detect the dog and jogger approaching. The display 9146 may indicate an approaching person through text, speaker 9110 may provide an alert (e.g. 'caution, object approaching' or beep) or boom lights 9144 may turn yellow indicating someone is approaching from behind. These indicators may provide the user with a sense of increased safety and help them not to be startled when someone approaches from behind.

In various embodiments, headset 9100 may include one or more electrodes (e.g., two electrodes 9197 and 9198). These may be conductors and may be fashioned from metal or some other conducting material. Electrodes may help to detect electrical potentials at different points on a users head, and may thereby allow detection of brainwaves (e.g., EEG signals).

Figure 93:
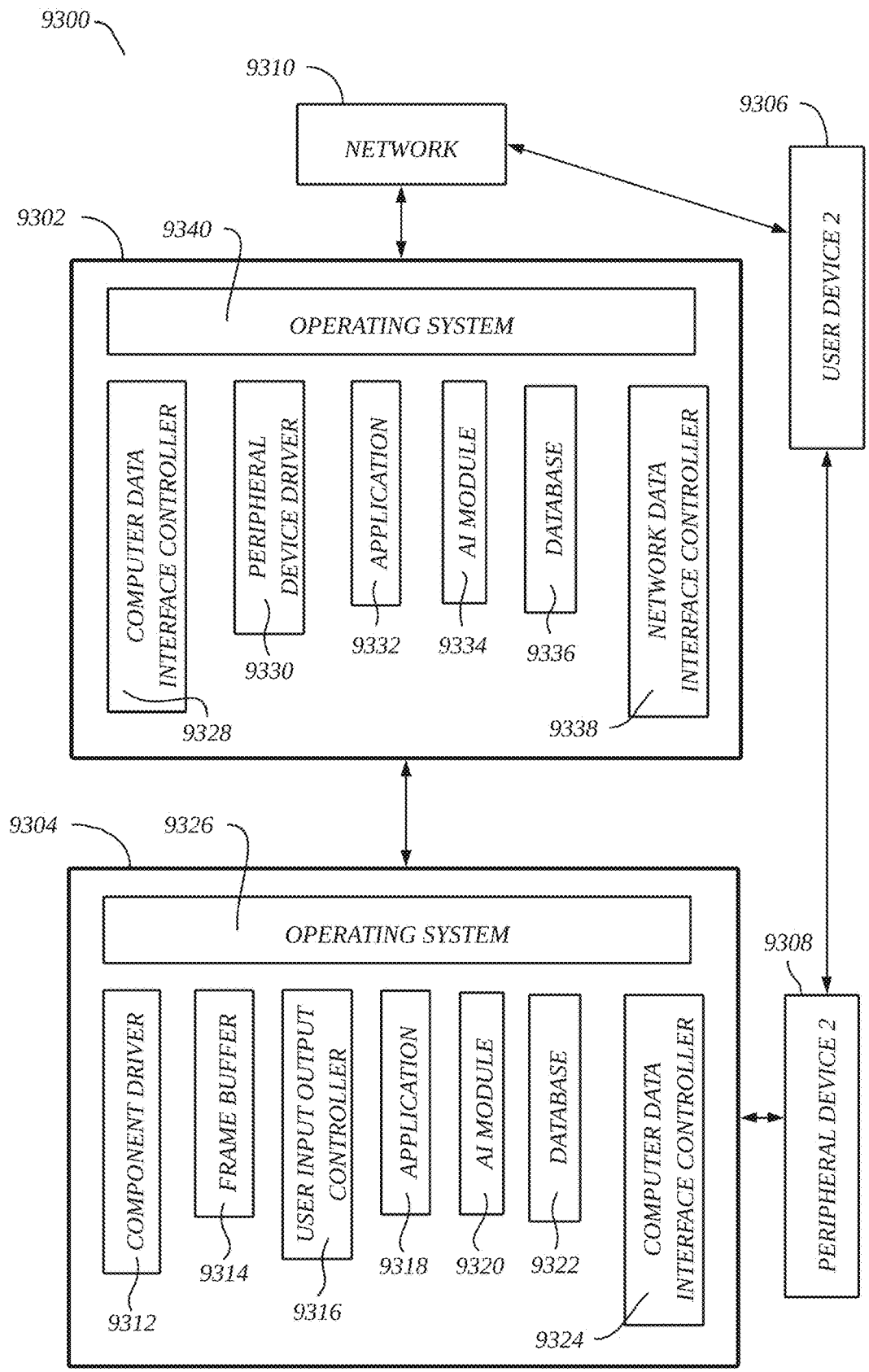
FIG. 93 is a block diagram of a system consistent with at least some embodiments described herein.

Turning now to FIG. 93, a block diagram of a system 9300, including devices with software modules, is shown according to some embodiments. System 9300 includes a first user device 9302 (e.g., a personal computer; e.g., a laptop computer), a first peripheral device 9304 (e.g., a mouse, e.g., a keyboard; e.g., a headset), a second user device 9306, and a second peripheral device 9308 (e.g., a headset). One or more of devices 9302, 9304, and 9306 may be connected to a network, e.g., network 9310. Also, the first peripheral device 9304 may be in communication with the first user device 9302 (e.g., via a cable; e.g., via Wi-Fi® connection), and the second peripheral device 9308 may be in communication with the second user device 9302. Also, the first peripheral device 9304 may be in communication with the second peripheral device 9308 as will be appreciated, the depicted devices represent some exemplary devices, and system 9300 may include more or fewer devices, in various embodiments. Also, various embodiments contemplate that any combination of devices may be in communication with one another.

In various embodiments, a message is sent from the first peripheral device 9304 to the second peripheral device 9308. For example, the message may be a congratulatory message being sent from the owner of peripheral device 9304 to the owner of peripheral device 9308. The message may have any other form or purpose, and various embodiments.

The message originating from peripheral device 9304 may be transmitted via user device 9302, network 9310, and user device 9306 before reaching peripheral device 9308. At peripheral device 9308, the message may be output to a user in some fashion (e.g., a text message may be displayed on a screen of peripheral device 9308; e.g., an audible message may be broadcast from a speaker of a headset). In various embodiments, the message originating from peripheral device 9304 may be transmitted via network 9310, and via user device 9306 before reaching peripheral device 9308. In various embodiments, the message originating from peripheral device 9304 may be transmitted directly to peripheral device 9308 (e.g., if peripheral device 9304 and peripheral device 9308 are in direct communication).

In various embodiments, as a message is conveyed, the form of the message may change at different points along its trajectory. The message may be represented in different ways, using different technologies, using different compression algorithms, using different coding mechanisms, using different levels of encryption, etc. For example, when originally created, the message may have the form of electrical impulses read from a mouse button (e.g., impulses representing the pressing of the button). However, within the peripheral device 9304, the electrical impulses may be interpreted as discrete bits, and these bits, in turn, interpreted as alphanumeric messages. Later, when the message is transmitted from the user device 9302 to the network, the messages may be modulated into an electromagnetic wave and transmitted wirelessly.

Various embodiments include one or more modules (e.g., software modules) within devices 9304, 9302, 9306, and 9308. In various embodiments, such modules may contribute to the operation of the respective devices. In various embodiments, such modules may also interpret, encode, decode, or otherwise transform a message. The message may then be passed along to another module.

Modules may include programs (e.g., program 9455), logic, computer instructions, bit-code, or the like that may be stored in memory (e.g., in storage device 9445) and executed by a device component (e.g., by processor 9405). Separate modules may represent separate programs that can be run more or less independently of one another and/or with some well-defined interface (e.g., API) between the programs.

Operating system 9326 may be a module that is capable of interfacing with other modules and/or with hardware on the peripheral device 9304. Thus, in various embodiments, operating system 9326 may serve as a bridge through which a first module may communicate with a second module. Further, operating system 9326 may coordinate the operation of other modules (e.g., by allocating time slices to other modules on a processor, such as processor 9405). Further, operating system 9326 may provide and/or coordinate access to common resources used by various modules. For example, operating system 9326 may coordinate access to memory (e.g., random access memory) shared by other modules. Exemplary operating systems may include Embedded Linux™, Windows® Mobile Operating System, RTLinux™, Windows® CE, FreeRTOS, etc.

Component driver 9312 may serve as an interface between the operating system and an individual hardware component. As depicted, peripheral device 9304 includes one component driver 9312, but various embodiments contemplate that there may be multiple component drivers (e.g., one component driver for each component of the device). A component driver may translate higher level instructions provided by the operating system 9326 into lower-level instructions that can be understood by hardware components (e.g., into instructions that specify hardware addresses, pin numbers on chips, voltage levels for each pin, etc.). A component driver may also translate low level signals provided by the component driver into higher level signals or instructions understandable to the operating system.

Frame buffer 9314 may store a bitmap that drives a display (e.g., screen 9435). When another module (e.g., application 9318) wishes to output an image to a user, the module may generate a bitmap representative of the image. The bitmap may then be transmitted to the frame buffer (e.g., via the operating system 9326). The corresponding image may then appear on the display. If another module (e.g., application 9318) wishes to output a video to a user, the module may generate a sequence of bitmaps representative of sequential frames of the video. These may then be transmitted to the frame buffer for display one after the other. In various embodiments, the frame buffer may be capable of storing multiple images at once (e.g., multiple frames of a video), and may thereby ensure that video playback is smooth even if there are irregularities in transmitting the video bitmaps to the frame buffer.

User input/output controller 9316 may serve as an interface between the operation system 9326 and various input and output devices on the peripheral. As depicted, peripheral device 9304 includes one user input/output controller 9316, but various embodiments contemplate that there may be multiple user input/output controllers (e.g., one controller for each input device and output device on the peripheral). A user input/output controller provides an interface that allows other modules (e.g. application 9318) to retrieve data or messages from an input device (e.g. the left button was clicked). The user input/output controller also provides an interface that allows other modules (e.g. application 9318) to send data or commands to an output device (e.g. vibrate the peripheral). The data or messages sent via this controller may be modified so as to translate module level data and commands into ones compatible with the input and output devices.

Application 9318 may be any computer code run in the operating system 9326 that runs algorithms, processes data, communicates with various components, and/or sends messages. As depicted, peripheral device 9304 includes one application 9318, but various embodiments contemplate that there may be multiple applications (e.g. one application to send messages to peripheral device 9308 and another that plays a video on screen 9435). Applications may be run independently but may share resources (e.g. two applications running may both use database 9322 to read and store data).

AI Module 9320 may process various data input sources (e.g. input device 9420) to learn and predict user behavior. The AI Module may apply various heuristics and algorithms to parse the input data to construct and update models that can predict future input (e.g. predict when the next mouse click will come) or prepare a custom output (e.g., Display a congratulatory message on screen 9435 when a user completes a new level in a game). The module may use database 9322 to read saved models, create new models, and update existing ones that are stored on storage device 9445.

Database 9322 may serve as an interface to structured data on storage device 9445. The database module provides an abstraction to other modules to allow high level read and write requests for data without knowledge of how the data is formatted on disk. As depicted, Peripheral device 9304 includes one database 9322, but various embodiments contemplate that there may be multiple databases (e.g., one storing click history and another an AI model). The database may store data in any format (e.g. relational database) and may be stored in multiple files and locations on storage device 9445. A database may also access remote data, either on user device 9302 or in the cloud via network 9310. The database may restrict access to data to certain modules or users and not allow unauthorized access.

Computer data interface controller 9324 may serve as an interface between the peripheral 9304 and the attached user device 9302 or peripheral device 9308. The interface controller allows messages and data packets to be sent in both directions. When another module (e.g., application 9318) wishes to send a message to a remote device, the module would use the API provided by the computer data interface controller 9324 to do so. The interface controller collects messages and data packets received by the peripheral and transmits them via operating system 9326 to the module that made the request or that is necessary to process them.

User device 9302 may include one or more modules, e.g., operating system 9340, computer data interface controller 9328, peripheral device driver 9330, application 9333, AI module 9334, database 9336, and network interface controller 9338. In various embodiments, user device 9302 may contain more or fewer modules, and may contain more or fewer instances of a given module (e.g., the user device may contain multiple application modules).

Operating system 9340 may have an analogous function on user device 9302 as does operating system 9326 on peripheral device 9304. Exemplary operating systems include Apple® macOS, Microsoft® Windows™, and Linux™.

Computer data interface controller 9328 may serve as an interface between the user device 9302 and the peripheral device 9304. Computer data interface controller 9328 may have an analogous function to computer data interface controller 9324 in the peripheral device 9304.

Peripheral device driver 9330 may translate unique or proprietary signals from the peripheral device 9304 into standard commands or instructions understood by the operating system 9340. The peripheral device driver may also store a current state of the peripheral device (e.g., a mouse position). Peripheral states or instructions may be passed to operating system 9340 as needed, e.g., to direct progress in application 9332.

In various embodiments, peripheral device driver 9330 may translate messages from an application or other module into commands or signals intended for the peripheral device 9304. Such signals may direct the peripheral device to take some action, such as displaying text, displaying an image, activating an LED light, turning off an LED light, disabling a component of the peripheral device (e.g., disabling the left mouse button), enabling a component of the peripheral device, altering the function of the peripheral device, and/or any other action.

Application 9332 may include any program, application, or the like. Application 9332 may have an analogous function to application 9318 on the peripheral device 9304. In various embodiments, application 9332 may include a user-facing application, such as a spreadsheet program, a video game, a word processing application, a slide program, a music player, a web browser, or any other application.

AI module 9334 and database 9336 may have analogous functions to AI module 9320 and database 9322, respectively, on the peripheral device 9304.

Network interface controller 9338 may serve as an interface between the user device 9302 and the network 9310. In various embodiments, network interface controller 9338 may serve as an interface to one or more external devices. The interface controller 9338 may allow messages and data packets to be sent in both directions (e.g., both to and from user device 9302). When another module (e.g., application 9332) wishes to send a message over network 9310 and/or to a remote device, the module may use an API provided by the network data interface controller 9338 to do so. The interface controller 9338 may collect messages and data packets received by the user device and transmit them via operating system 9340 to the module that made the request or that is necessary to process them.

Although not shown explicitly, user device 9302, peripheral device 9304, central controller 110, and/or any other device may include such modules as: a text to speech translation module; a language translation module; a face recognition module; and/or any suitable module.

Although not shown explicitly, user device 9306 may have a similar set of modules as does user device 9302. Although not shown explicitly, peripheral device 9308 may have a similar set of modules as does peripheral device 9304.

Figure 94:
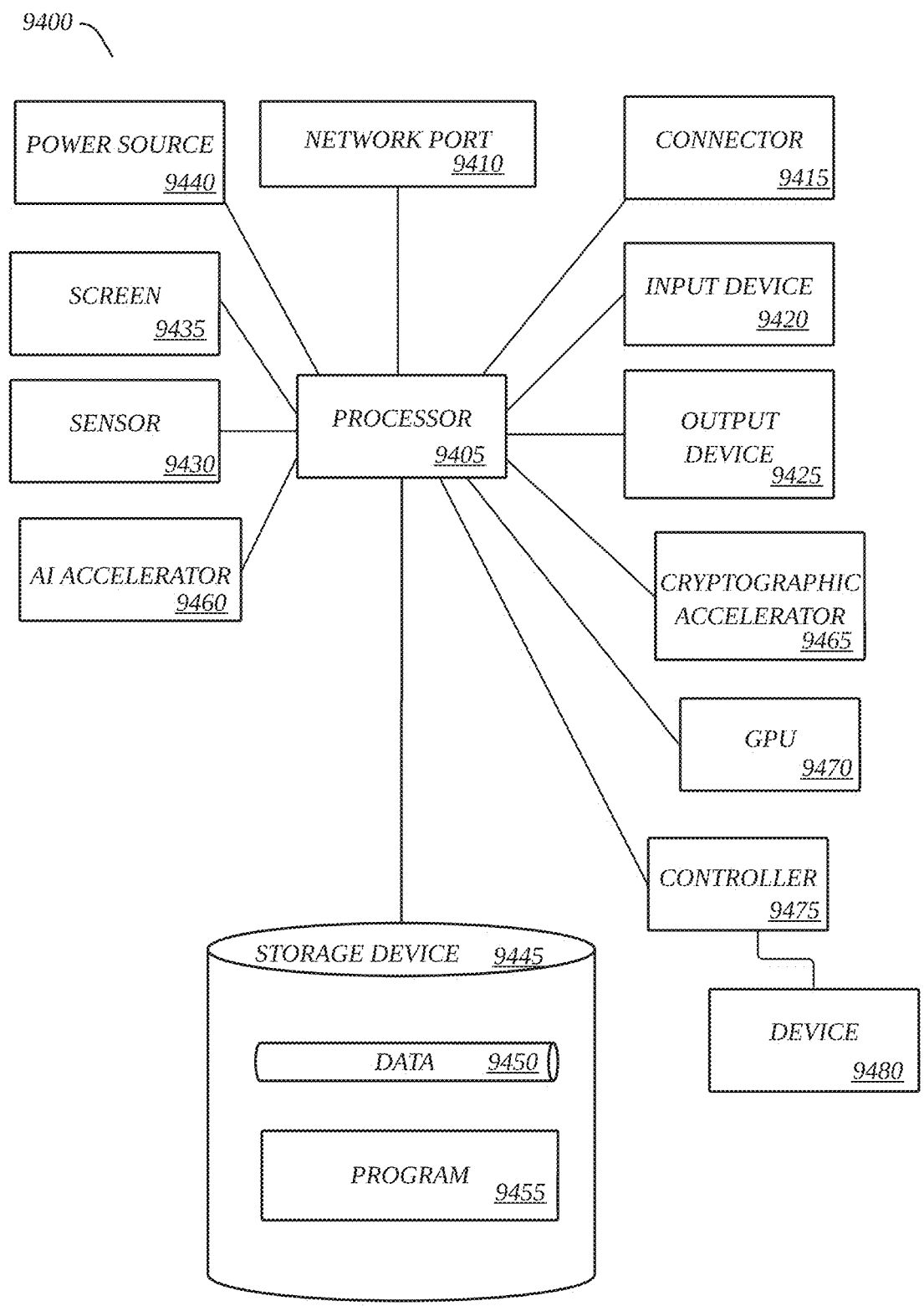
FIG. 94 is a block diagram of a peripheral consistent with at least some embodiments described herein.

Turning now to FIG. 94, a block diagram of a mouse device 9400 according to some embodiments is shown. In various embodiments, a mouse device may be a mechanical, optical, laser, gyroscopic or any other peripheral device that translates physical movements into a digital signal.

Mouse device 9400 may include various components. Mouse device 9400 may include a processor 9405, network port 9410, connector 9415, input device 9420, output device 9425, sensor 9430, screen 9435, power source 9440, storage device 9445, AI accelerator 9460, cryptographic accelerator 9465, and GPU (graphics processing unit) 9470. Storage device 9445 may store data 9450 and program 9455. A number of components for mouse device 9400 depicted in FIG. 94 have analogous components in user device 106a depicted in FIG. 3 (e.g., processor 9405 may be analogous to processor 305) and in peripheral device 107a depicted in FIG. 4 (e.g. sensor 9430 may be analogous to sensor 430), and so such components need not be described again in detail. However, it will be appreciated that any given user device or peripheral device and any given mouse device may use different technologies, different manufacturers, different arrangements, etc., even for analogous components. For example, a particular user device may comprise a 20-inch LCD display screen, whereas a mouse device may comprise a 1-inch OLED display screen. It will also be appreciated that data 9450 need not necessarily comprise the same (or even similar) data as does data 350 or data 450, and program 9455 need not necessarily comprise the same (or even similar) data or instructions as does program 355 or program 455.

In various embodiments, connector 9415 may include any component capable of interfacing with a connection port (e.g., with connection port 315). For example, connector 9415 may physically complement connection port 315. Thus, for example, mouse device 9400 may be physically connected to a user device via the connector 9415 fitting into the connection port 315 of the user device. The interfacing may occur via plugging, latching, magnetic coupling, or via any other mechanism. In various embodiments, a mouse device may have a connection port while a user device has a connector. Various embodiments contemplate that a user device and a mouse device may interface with one another via any suitable mechanism. In various embodiments, a user device and a mouse device may interface via a wireless connection (e.g., via Bluetooth®, Wi-Fi®, or via any other means).

AI accelerator 9460 may include any component or device used to accelerate AI applications and calculations. AI accelerator 9460 may use data collected by sensor 9430 and/or input device 9420 to use as input into various AI algorithms to learn and predict outcomes. AI accelerator 9460 may use storage device 9445 for both input and result data used in AI algorithms and calculations.

In various embodiments, AI accelerator 9460 can send a signal back to user device 106a upon making a prediction, determination, or suggestion. For example, if a user is playing a game and it is determined by AI accelerator 9460 that the user is performing poorly a signal can be sent back to user device 106a to adjust the difficulty to a more appropriate level. It may also track a user's learning curve and be able to predict when the user will require a harder level.

In various embodiments, AI accelerator 9460 can use multifaceted data collected by sensor 9430 as input to induce actions. The accelerator can use this information, for example, to: trigger recording of the current game session when a user shows excitement through speech or skin response, induce a vibration in the mouse if the user is showing signs of being distracted or sleepy, etc.

In various embodiments, AI accelerator 9460 may combine data from various sources including sensor 9430 and input device 9420 with its own data calculated and/or stored on storage device 9445 over a long period of time to learn behaviors, tendencies, idiosyncrasies and use them for various purposes. For example, the AI accelerator may determine that the person using the mouse currently is not the approved user based on movement patterns, ambient sound, pressure applied to buttons, etc. and lock the computer to prevent unauthorized access. The accelerator may find concerning medical conditions through heart rate sensor, temperature, movement patterns and notify the user to seek medical attention. The accelerator may determine the users learning capabilities and knowledge base to determine complexity settings on future games, applications, templates, etc.

Cryptographic accelerator 9465 may include any component or device used to perform cryptographic operations. Cryptographic accelerator 9465 may use data collected by various sources including but not limited to sensor 9430 and/or input device 9420 to use as input into various cryptographic algorithms to verify user identity, as a seed for encryption, or to gather data necessary for decryption. Cryptographic accelerator 9465 may use storage device 9445 for both input and result data used in cryptographic algorithms.

In various embodiments, cryptographic accelerator 9465 will encrypt data to ensure privacy and security. The data stored in storage device 9455 may be encrypted before being written to the device so that the data can only be usable if passed back through 9465 on output. For example, a user may want to store sensitive information on the storage device on the mouse so that they can easily authenticate themselves to any attached user device 106*a*. Using the cryptographic accelerator to encrypt the data ensures that only the given user can decrypt and use that data.

In various embodiments, cryptographic accelerator 9465 will encrypt signals to ensure privacy and security. Signals sent to user device 106*a* through connector 9415 and connection port 315 can be encrypted so that only a paired user device can understand the signals. Signals may also be encrypted by the cryptographic accelerator and sent directly via network port 9410 to another peripheral device 107*a* via that device's network port 410. For example, a user may use a microphone on their mouse to record speech for private communications and that data can pass through cryptographic accelerator 9465 and be encrypted before being transmitted. The destination device can decrypt using its cryptographic accelerator using shared keys ensuring no other party could listen in.

GPU (graphics processing unit) 9470 may include any component or device used to manipulate and alter memory to accelerate the creation of images in a frame buffer intended for output on one or more display devices. GPU 9470 may use data collected by various sources including but not limited to sensor 9430 or from the attached user device via connector 9415 to use in graphics processing. GPU 9470 may use storage device 9445 for reading and writing image data.

In various embodiments, GPU 9470 will create image data that will be displayed on screen 9435 or output device 9425. For example, a user is playing a game and GPU 9470 can be used to process data and display the data on mouse display (output device 9425), and can assist in processing graphics data.

In some embodiments, mouse device 9400 includes controller 9475 which can manage one or more devices 9480 in order to reduce the computational load on processor 9405.

Referring to FIG. 95, a diagram of an example 'Peripheral component types' table 9500 according to some embodiments is shown. Peripheral component types table 9500 may store information about types of components that may be used in peripherals. Such components may include hardware output devices like LED lights, display screen, speakers, etc. Such components may include sensors and input devices, like pressure sensors, conduction sensors, motion sensors, galvanic skin conductance sensors, etc.

Component type identifier field 9502 may store an identifier (e.g., a unique identifier) for a particular type of component. Component description field 9504 may store a description of the component. This may indicate (e.g., in human-readable format) what the component does, what the function of the component is, what type of output is provided by the component, what type of input can be received by the component, what is the sensitivity of the component, what is the range of the component's abilities, and/or any other aspect of the component. For example, a component description may identify the component as an LED light, and may indicate the color and maximum brightness of the LED light.

Manufacturer field 9506 may store an indication of the component's manufacturer. Model field 9508 may store an indication of the component model. This may be a part number, brand, or any other model description.

In various embodiments, information in table 9500 may be useful for tracking down component specifications and/or for instructions for communicating with a component.

Referring to FIG. 96, a diagram of an example 'Peripheral component address table' table 9600 according to some embodiments is shown. Peripheral component address table 9600 may store information about particular components that are used in particular peripheral devices. By providing a component address, table 9600 may allow a processor 9405 and/or component driver 9312 to direct instructions to a component and/or to interpret the origination of signals coming from the component.

Component identifier field 9602 may store an identifier (e.g., a unique identifier) for a particular component (e.g., for a particular LED light on a particular mouse). Component type field 9604 may store an indication of the component type (e.g., by reference to a component type listed in table 9500). Reference name field 9606 may store a description of the component, which may include an indication of the component's location on or within a peripheral device. Exemplary reference names include "Left light #1", "right LED #2", "Front speaker", and "Top left pressure sensor". For example, if there are two LED lights on the left side of a mouse, and two LED lights on the right side of a mouse, then a reference name of "Left light #1" may uniquely identify a component's location from among the four LED lights on the mouse.

Address field 9608 may store an address of the component. This may represent a hardware address and/or an address on a signal bus where a component can be reached.

Referring to FIG. 97, a diagram of an example 'Peripheral component signal' table 9700 according to some embodiments is shown. Peripheral component signal table 9700 may store an indication of what signal is needed (e.g., at the bit level) to achieve a desired result with respect to a type of component. For example, what signal is needed to turn on an LED light. Table 9700 may also indicate how to interpret incoming signals. For example, table 9700 may indicate that a particular signal from a particular button component means that a user has pressed the button.

Signal identifier field 9702 may store an identifier (e.g., a unique identifier) for a particular signal. Component type field 9704 may store an indication of the component type for which the signal applies.

Incoming/Outgoing field 9706 may store an indication of whether a signal is outgoing (e.g., will serve as an instruction to the component), or is incoming (e.g., will serve as a message from the component). Description field 9708 may store a description of the signal. The description may indicate what the signal will accomplish and/or what is meant by the signal. Exemplary descriptions of outgoing signals include "turn the light on" (e.g., an instruction for an LED component), "Turn the light on dim", and "tone at 440 Hz for 0.5 seconds" (e.g., an instruction for a speaker component).

Signal field 9710 may store an actual signal to be transmitted to a component (in the case of an outgoing signal), or a signal that will be received from a component (in the case of an incoming signal). As depicted, each signal is an 8-bit binary signal. However, various embodiments contemplate that a signal could take any suitable form. In the case of an outgoing signal, when a component receives the signal, the component should accomplish what is indicated in the description fields 9708. In the case of an incoming signal, when the signal is received (e.g., by component driver 9312), then the signal may be interpreted as having the meaning given in description field 9708.

In various embodiments, a complete instruction for a component includes a component address (field 9608) coupled with a signal (field 9710). This would allow a signal to reach the intended component, (e.g., as opposed to other available components). The component could then carry out a function as instructed by the signal.

Figure 98A:
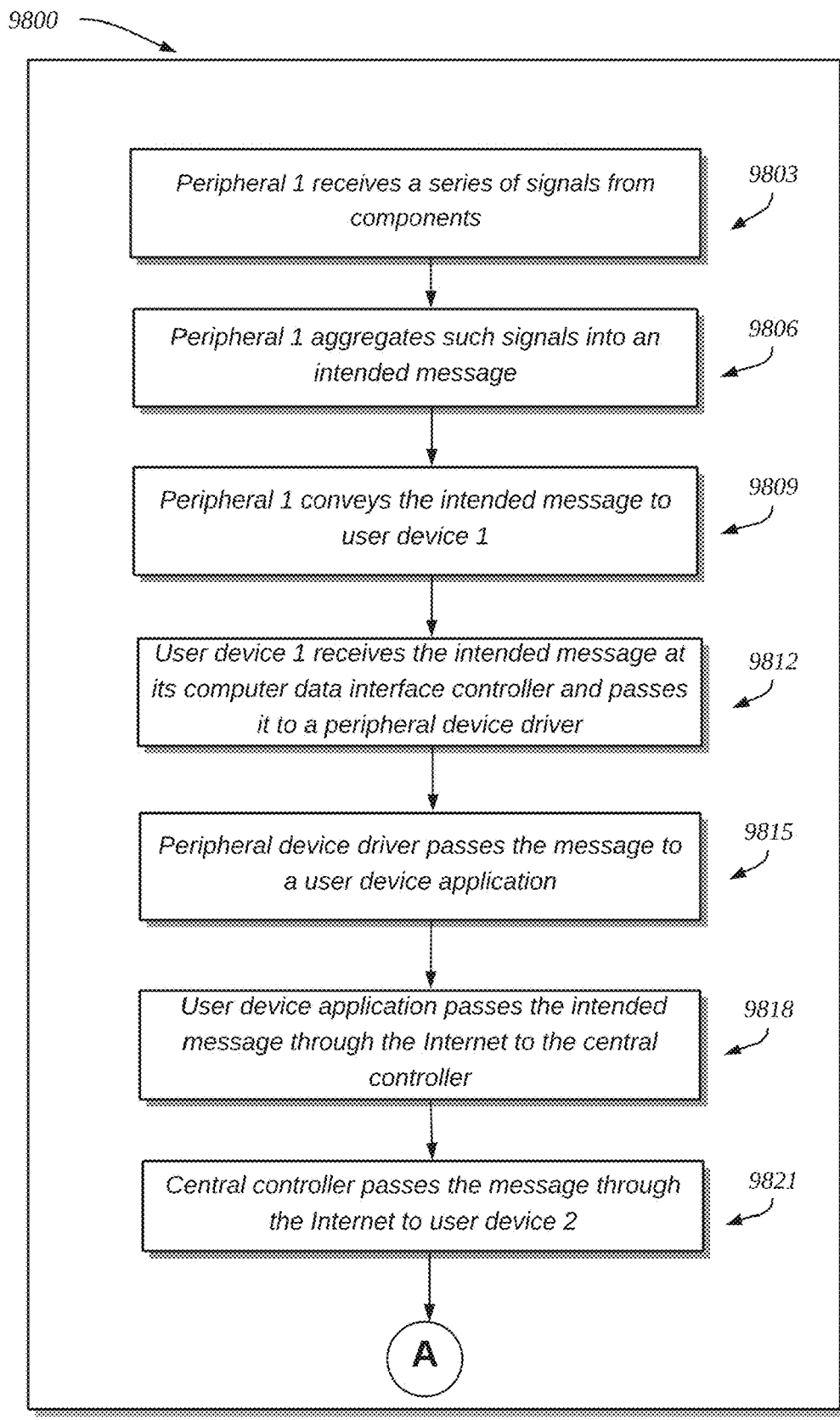
FIG. 98A and FIG. 98B together show a diagram of a process flow consistent with at least some embodiments described herein.
Figure 98B:
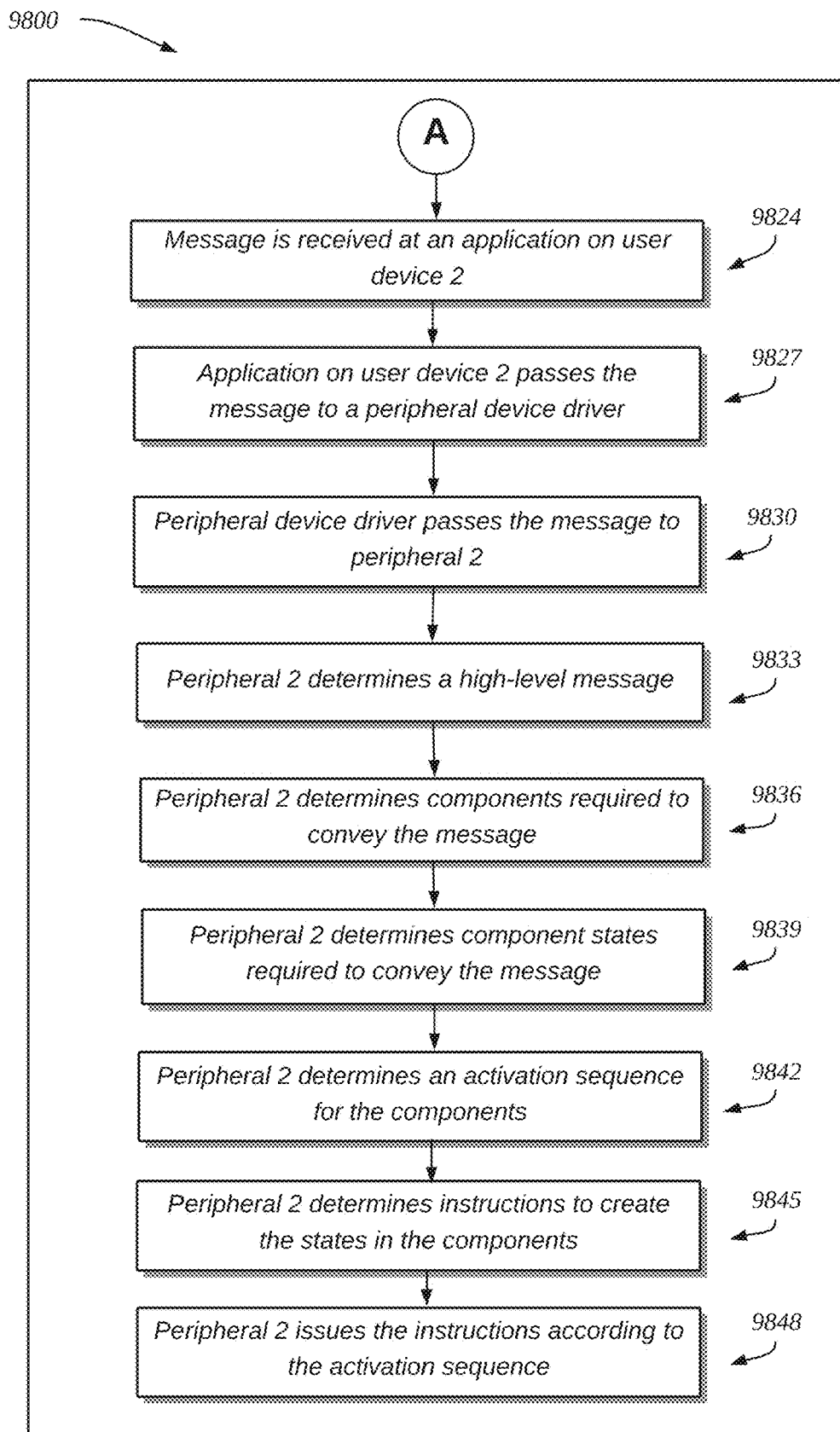

Referring now to FIG. 98, a flow diagram of a method 9800 according to some embodiments is shown. Method 9800 details, according to some embodiments, the trajectory of a message entered by a first user into a first peripheral ("peripheral 1") 9304 as it travels to a second peripheral ("peripheral 2") 9308 where it is conveyed to a second user. En route, the message may travel through a first user device ("user device 1") 9302, and a second user device ("user device 2") 9306. For the purposes of the present example, the message transmitted is a text message with the text "Good going!". However, various embodiments contemplate that any message may be used, including a message in the form of an image, video, vibration, series of movements, etc.

At step 9803, peripheral 1 receives a series of signals from components. These may be components of the peripheral device such as input device 9420 and/or device 9480. Exemplary signals originate from button clicks (e.g., button clicks by a user), key presses, scrolls of a mouse wheel, movements of a mouse, etc.

Initially, signals may be received at component driver module 9312. As the signals are incoming signals (i.e., incoming from components), table 9700 may be used to interpret the meaning of such signals (e.g., "click of the right mouse button"). In various embodiments, signals are received at 'user input output controller' 9316. In various embodiments, signals received at component driver module 9312 are then passed to 'user input output controller' 9316, e.g., by way of operating system 9326.

At step 9806 peripheral 1 aggregates such signals into an intended message. Thus far, peripheral 1 only recognizes the received signals as a collection of individual component activations (e.g., as a collection of clicks). At step 9806, peripheral 1 may determine an actual message (e.g., a human-interpretable message; e.g., a text message) that is represented by the component activations.

The component driver 9312 or the user inputs/output controller 9316 may pass its interpretation of the incoming signals to the application 9318. The application may then aggregate, combine, or otherwise determine a message intended by the signals. Application may reference 'Generic actions/messages' table 2500 or 'Mapping of user input to an action/message' table 2600 in database 9322, in order to determine an intended message. In various embodiments, the signals may represent characters or other elementary components of a message, in which case such elementary components need only be combined (e.g., individual characters are combined into a complete text message). In various embodiments, a message may be determined using any other data table, and/or in any other fashion.

In various embodiments, there may not necessarily be a precise correspondence between incoming signals and a message. For example, mouse movements (e.g., gestures) may be representative of words or concept in American Sign Language. However, the precise boundaries between a gesture representing one concept and a gesture representing another concept may not be clear. In such cases, AI module 9320 may be used to classify a mouse movement as representative of one concept versus another concept. In various embodiments, AI module 9320 may be used in other situations to classify signals into one intended meaning or another.

At step 9809 peripheral 1 conveys the intended message to user device 1. Once application 9318 has determined the intended message, the application may pass the message to the computer data interface controller 9324. The message may then be encoded and transmitted to user device 1 (e.g., via USB, via firewire, via Wi-Fi®, etc.)

At step 9812 user device 1 receives the intended message at its computer data interface controller 9328. The received message may then be passed to peripheral device driver 9330, which may need to transform the message from a format understood by the peripheral device 9304 into a format understood by user device 9302 (e.g., by the operating system 9340 of user device 9302).

At step 9815 the peripheral device driver passes the message to a user device application (e.g., application 9332). In various embodiments, in accordance with the present example, application 9332 may be a messaging application that works in coordination with peripheral device 9304. The messaging application may maintain a running transcript of messages that have been passed back and forth to peripheral device 9304. In this way, for example, a user may scroll up through the application to see old messages in the conversation. However, in various environments, application 9332 on the user device may serve only as a relayer of messages.

At step 9818 the user device application passes the intended message through the Internet to the central controller 110. Application 9332 may initially pass the message to the network data interface controller 9338, where it may then be encoded for transmission over network 9310. In various embodiments, application 9332 may include an intended recipient and/or recipient address along with the message.

At step 9821 the central controller passes the message through the Internet to user device 2 (e.g., to user device 9306). In various embodiments, the central controller 110 may also log the message (e.g., store the message in a data table such as 'Peripheral message log' table 2400).

At step 9824 the message is received at an application on user device 2. The message may initially arrive at a network data interface controller of 'user device 2' 9306 before being decoded and passed to the application.

At step 9827 the application on user device 2 passes the message to a peripheral device driver.

At step 9830 the peripheral device driver passes the message to peripheral 2. In various embodiments, the peripheral device driver may pass the message by way of a computer data interface controller. Peripheral 2 may receive the message at its own computer data interface controller, where the message may be decoded and then passed to an application on peripheral 2.

At step 9833 peripheral 2 determines a high-level message. In various embodiments, a high-level message may be determined in an application. Example messages may include, display the text "Good going!", create a "wave" of green LEDs, output an audio jingle with the notes "C-C-G-G-A-A-G", etc.

At step 9836 peripheral 2 determines components required to convey the message. For example, if a message includes text or images, then a display screen, an LCD display, or any other suitable display may be used to convey the message. In various embodiments, if a message is text, then the message may be conveyed by depressing or lighting keys on a keyboard peripheral. If the message involves lights (e.g., sequences of light activation), then LEDs may be used to convey the message. If the message involves audio, then a speaker may be used to convey the message. In various embodiments, a message may be intended for more than one modality, in which case multiple components may be required.

Peripheral 2 may determine available components with reference to a database table, e.g., to table 9600. Table 9600 may also include component locations, so that peripheral 2 may determine the geometrically appropriate component required to convey a message (e.g., peripheral 2 may determine which is the frontmost LED as required by a message). In various embodiments, the application on peripheral 2 may determine the required components.

At step 9839 peripheral 2 determines component states required to convey the message. Component states may include whether a component is on or off, the intensity of an output from a component, the color of an output, the degree of depression of a key, and/or any other state. Exemplary component states include a light is green, a light is red, a light is dim, the "x" key is depressed by 1 mm, etc. In various embodiments, the application on peripheral 2 may determine the required component states.

At step 9842 peripheral 2 determines an activation sequence for the components. An activation sequence may specify which component will activate first, which will activate second, and so on. In various embodiments, an activation sequence may specify a duration of activation. In various embodiments, two or more components may be activated simultaneously and/or for overlapping periods. In one example, an LED goes on for five seconds, then a haptic sensor starts vibrating, etc. In various embodiments, the application on peripheral 2 may determine the activation sequence.

At step 9845 peripheral 2 determines instructions to create the states in the components. In various embodiments, determining instructions may entail determining component addresses and determining signals to transmit to the components. In various embodiments, component addresses may be obtained by reference to a database table, such as to table 9600 (e.g., field 9608). In various embodiments, signals may be obtained by reference to a database table, such as to table 9700 (e.g., field 9710). Since such signals will be part of instructions to a component, such signals may be listed as "outgoing" at field 9706. A complete instruction may be assembled from the address and from the signal to be sent to that address. For example, given an 8-bit address of "10010101", and an 8-bit signal of "11101110", a complete instruction may read "1001010111101110". In various embodiments, instructions may be determined in an application, in a user input/output controller and/or in a component driver of peripheral 2.

At step 9848 peripheral 2 issues the instructions according to the activation sequence. The instructions determined at step 9845 may be sequentially transmitted (e.g., at appropriate times) to the various components of peripheral 2. The instructions may be transmitted by a user input/output controller and/or by a component driver of peripheral 2. In various embodiments, an application may govern the timing of when instructions are issued. With instructions thus issued to a peripheral's components, the message may finally be related to the second user. E.g., user 2 may see on his mouse's display screen the message, "Good going!".

Process 9800 need not merely relate to inputs intentionally provided by a first user, but may also relate to actions, situations, circumstances, etc. that are captured by peripheral 1, or by other sensors or devices. In various embodiments, one or more sensors on peripheral 1 (or one or more other sensors) may capture information about the first user (e.g., the first user's breathing rate) and/or about the first users environment. Sensor data may be aggregated or otherwise summarized. Such data may then be relayed ultimately to the second user's peripheral device, peripheral device 2. Peripheral device 2 may then determine how the data should be displayed, what components are needed, what states are needed, etc. User 2 may thereby, for example, receive passive and/or continuous communication from user 1, without the necessity of user 1 explicitly messaging user 2.

In various embodiments, a message transmitted (e.g., from peripheral 1 to peripheral 2) may include intentional inputs (e.g., inputs explicitly intended by user 1) as well as data passively captured about user 1 and/or user 1's environment. For example, if user 1 sends a "hello" text-based message to user 2, and user 1 is eating, the fact that user one is eating may be captured passively (e.g., using cameras) and the "hello" message may be rendered for user 2 on the image of a dinner plate.

Figure 99:
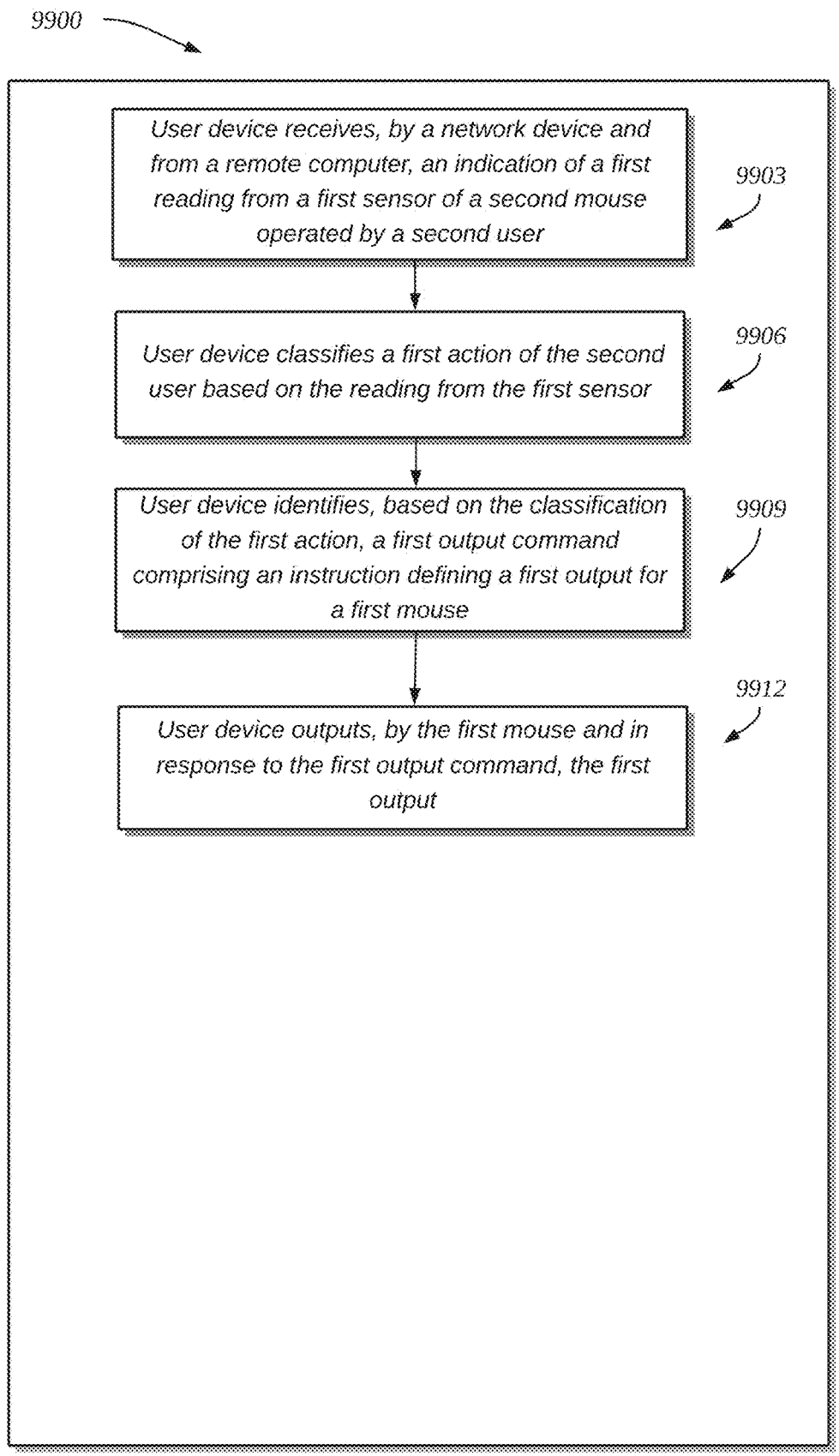
FIG. 99 is a diagram of a process flow consistent with at least some embodiments described herein.

Referring now to FIG. 99, a flow diagram of a method 9900 according to some embodiments is shown. In various embodiments, process 9900 may be performed by a user device (e.g., user device 106*a*) in communication with a peripheral device (e.g., peripheral device 107*a*).

In various embodiments, the peripheral device may be a first mouse operated by a first user. The first mouse may comprise an output component operable to generate human-perceptible output. The output component may include a light, speaker, or any other output component. The output component may be operable to generate human-perceptible output at varying intensities (e.g., varying brightness; e.g., varying volume).

In various embodiments, the user device may be a computer. The computer may comprise an electronic processing device (e.g., a processor). The computer may comprise a network device in communication with the electronic processing device. The computer may comprise a memory storing instructions that, when executed by the electronic processing device, may result in performance/execution of process 9900.

At step 9903, the user device may receive, by the network device and from a remote computer, an indication of a first reading from a first sensor of a second mouse operated by a second user (e.g., a friend of the first user). The first sensor may be a biometric device, which may capture heart activity, or any other activity.

At step 9906, the user device may classify a first action of the second user based on the reading from the first sensor. In various embodiments, the user device may thereby determine that the second user is available (e.g., to play a game).

At step 9909, the user device may identify, based on the classification of the first action, a first output command comprising an instruction defining a first output for the first mouse.

At step 9912, the user device may output, by the first mouse and in response to the first output command, the first output. In various embodiments, the output may be light (e.g., at some specified intensity; e.g., at some specified color).

In various embodiments, process 9900 may be performed by any suitable device, such as a user device of a first user, a user device of second user, a peripheral device of a first user, a peripheral device of a second user, the central controller 110, and/or any other device.

Mouse and Keyboard Logins

In some embodiments, a mouse and/or keyboard may log into a user computer by transmitting a signal representing mouse movement or a keyboard character (e.g. a space bar character) in order to wake up a user computer. At that point, one or more usernames and passwords may be passed from a mouse and/or keyboard in order to log into the user device. Once logged in, the mouse and/or keyboard may then get access to the operating system of the user computer in order to read or write data. In some embodiments, a mouse logs into a user computer on a scheduled basis (e.g. every 20 minutes) in order to gather information about the status of another user. For example, software on the user computer may request status updates stored at central controller 110 every time the user computer is woken up. If there are any new updates since the last query, that information is then transmitted to storage device 9445 of the user computer. In embodiments in which a mouse or keyboard autonomously logs into a user computer periodically in order to receive status updates relating to one or more other users, some functionality of the mouse may be disabled when a user is not present. For example, the xy positioning data generated by mouse movements may be disabled during these autonomous logins so that an unauthenticated person trying to use the mouse while it is logged into the user computer to get status updates will not be able to generate any xy data and will thus be unable to perform any actions with the user computer while it is activated by the autonomous logins.

Mouse and Keyboard Security

In some embodiments, a mouse may be used in a way that supplements the security of a user device. For example, passwords and cryptographic keys may be stored in storage device 9445, or within encryption chip 9465. These keys may be transmitted to a user device in order to wake up and/or login to the user device. In such embodiments, passwords stored within the mouse may be more secure than those stored in the memory of a user device because the operating system of the mouse will not be familiar to potential attackers seeking to obtain (e.g. via hacking) those passwords or cryptographic keys. In embodiments in which a mouse autonomously logs into a user computer periodically in order to receive status updates relating to one or more other users, some functionality of the mouse may be disabled when a user is not present. For example, the xy positioning data generated by mouse movements may be disabled during these autonomous logins so that an unauthenticated person trying to use the mouse while it is logged into the user computer to get status updates will not be able to generate any xy data and will thus be unable to perform any actions with the user computer while it is activated by the autonomous logins.|

Figure 83:
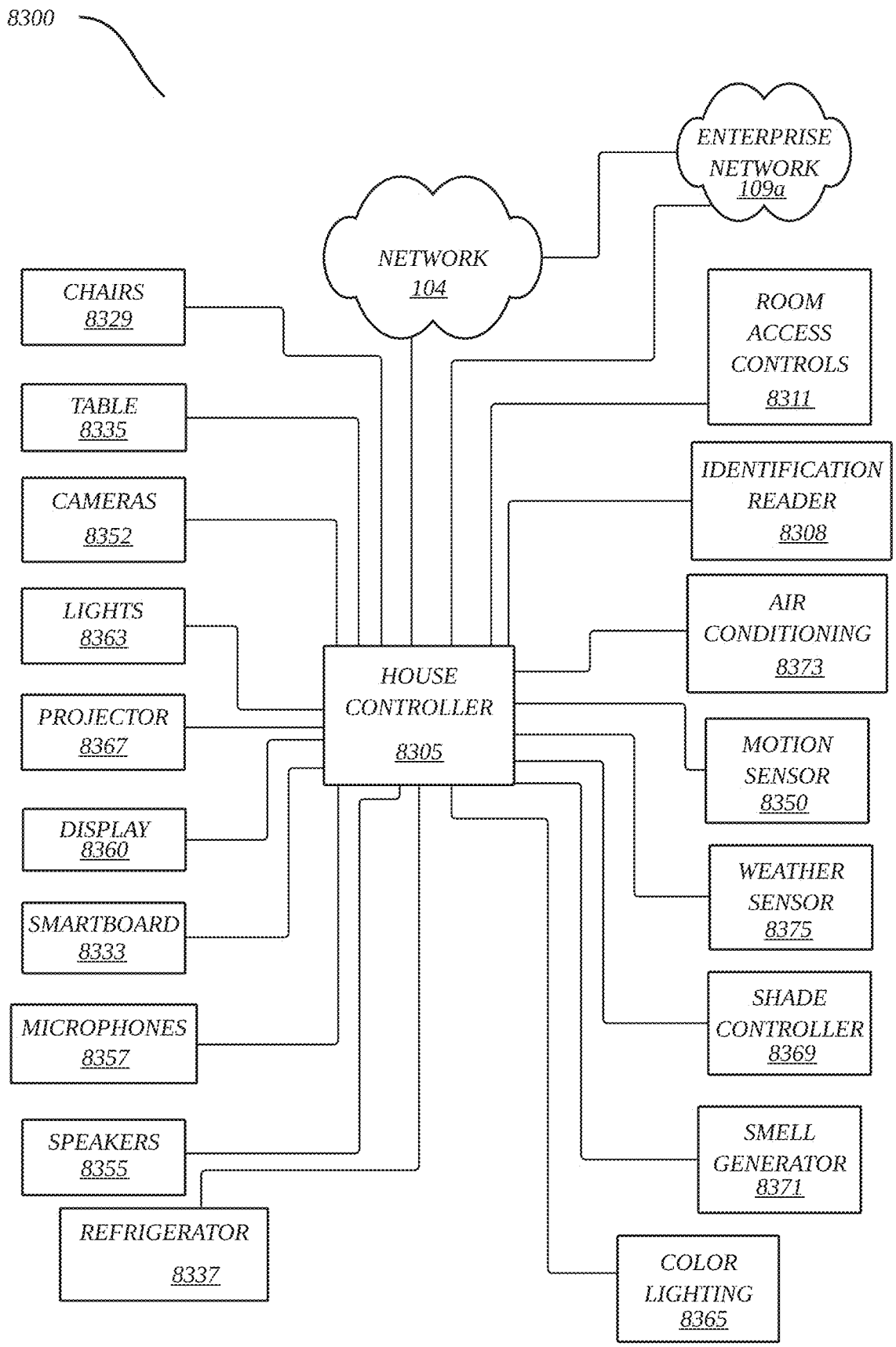
FIG. 83 is a block diagram of a system consistent with at least some embodiments described herein.

Referring to FIG. 83, a block diagram of a system 8300 according to some embodiments is shown. In some embodiments, the system 8300 may comprise a plurality of house devices in communication via house controller 8305 or with a network 104 or enterprise network 109*a*. According to some embodiments, system 8300 may comprise a plurality of house devices, and/or a central controller 110, In various embodiments, any or all of the house devices may be in communication with the network 104 and/or with one another via the network 104. House devices within system 8300 include devices that may be found within a house which help to ensure effective management and support of the house, including managing game playing by users. House devices include chairs 8329, tables 8335, cameras 8352, lights 8363, projectors 8367, displays 8360, smartboards 8333, microphones 8357, speakers 8355, refrigerators 8337, color lighting 8365, smell generator 8371, shade controllers 8369, weather sensors 8375, motion sensors 8350, air conditioning 8373, identification readers 8308, and room access controls 8311. House devices are explained more fully in FIGS. 63A and 63B.

Figure 84:
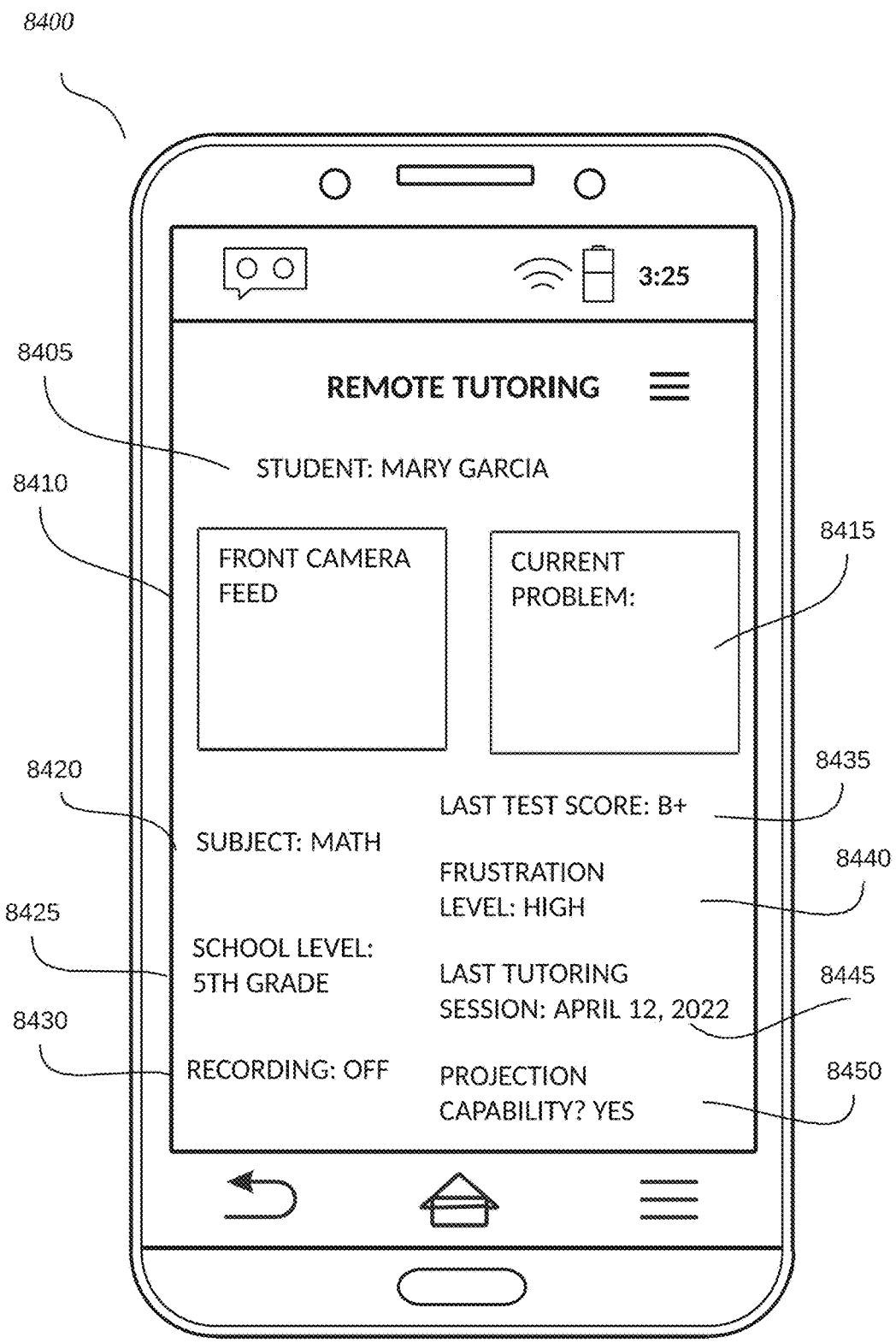
FIG. 84 is a user interface for a tutor receiving data from a headset consistent with at least some embodiments described herein.

With reference to FIG. 84, a screen 8400 from an app for interacting with a remote student according to some embodiments is shown. In various embodiments, the app provides data and enables communication between a remote student 8405 named Mary Garcia who is wearing a headset and a tutor providing guidance. In some embodiments, student 8405 is working on homework problems after returning home from school, with app 8400 facilitating guidance by a tutor who can provide feedback and suggestions while student 8405 is working on homework or having a supplemental tutoring session. As depicted, front camera feed 8410 may show video of what the student 8405 is currently seeing (e.g. a math workbook) and current problem 8415 indicates the specific problem that she is working on (e.g. solve for X: $3X+4=19$). In some embodiments, the app may show information about student 8405, such as a last test score 8435 (e.g. a B+), a current frustration level 8440 (e.g. high), and a date of their last tutoring session 8445 (e.g. Apr. 12, 2022). In some embodiments, one or more capabilities of the student's headset may be shown, such as indicating whether or not the student's headset can project onto a wall or table 8450. In some embodiments, a subject 8420 (e.g. math) indicates that the student is working on math problems. A school level 8425 may indicate the grade level of student 8405 (e.g. 5th grade). A tutor may also be able to select whether or not a tutoring session is being recorded 8430 or not. Various embodiments contemplate that any other peripheral usage data, or any other input data from a peripheral device, may be shown, may be shown over time, or may be shown in any other fashion.

In various embodiments, the app allows an observer to configure one or more parameters of a headset. In some embodiments, the app may allow a tutor to select one of the sensors worn by student 8405 to be shown in app 8400.

Call Platforms

With reference to FIG. 85, a display 8500 of call platform software from an app used by meeting participants according to some embodiments is shown. The depicted screen shows app functionality that can be employed by a user to participate in a virtual meeting in which participants may see each other during a virtual call. In some embodiments, data communication is managed through central controller 110 or network 104. In FIG. 85, the app may allow participants to join or leave the call at will, and various controls and features allow participants functionality during calls (e.g. sending text messages, displaying a presentation deck, being placed in a call queue, receiving additional information about other call participants, providing rewards to other participants, highlighting one or more participants). Various embodiments contemplate that an app may receive data from peripheral devices used by meeting participants (e.g. headsets, keyboard, mice, cameras, desktop or laptop computers).

FIG. 85 illustrates a respective graphical user interface (GUI) as it may be output on a peripheral device, mobile device, or any other device (e.g. on a mobile smart phone). The GUI may comprise several tabs or screens. The present invention allows for a greater variety of display options that make meetings more efficient, effective, and productive. Some embodiments can make calls more entertaining and help to bring up engagement levels and mitigate call fatigue. In accordance with some embodiments, the GUI may be made available via a software application operable to receive and output information in accordance with embodiments described herein. It should be noted that many variations on such graphical user interfaces may be implemented (e.g., menus and arrangements of elements may be modified, additional graphics and functionality may be added). The graphical user interface of FIG. 85 is presented in simplified form in order to focus on particular embodiments being described.

Display 8500 includes a GUI that represents callers in a single gallery view 8505. In this illustration, there are eight grid locations 8510 within the gallery view 8505, each of which contains one of callers 8515*a-h*. In this embodiment, a caller can see an image of other callers while verbally interacting with them. In some embodiments, the effectiveness of virtual meetings/calls is enhanced by allowing users to set a preferred grouping or ordering of gallery view 8505 based on a user's preferences—such as grouping caller images by hierarchy, job function, seniority, team, meeting role, etc. Call participants can take direct actions to manage the gallery view 8505 of participants on a call in a way that enhances the user's call experience. Call participants could be provided the ability to move the images of callers 8515*a-h* around during a call, ordering and placing the images in a way that is most beneficial to the user. For example, a user could click on caller image 8515*a-h* and drag that image to a new grid location 8510. A user could drag multiple gallery images to form a circle, with the new image locations stored in an image location field of a gallery database stored with the central controller or call platform software. This stored set of image locations forming a circle could be associated with a keyword such that the user could, upon the initiation of subsequent similar calls, type in the keyword to retrieve the desired locations and have the current gallery images placed into a circular arrangement. A user could also double click on a caller image to remove it, gray it out, make it black and white, make it more transparent, eliminate the background, or crop it (such as cropping to non-rectangles such as circles or ovals), or make the image smaller.

Caller images 8515*a-h* can include still photos of the user, a drawing of the user, a video stream of a user, etc. In one embodiment of the present invention, a user can create a cartoon character as a video call avatar that embodies elements of the user without revealing all of the details of the users face or clothing. For example, the user could be represented in the call as a less distinct cartoon character that provided a generic looking face and simplified arms and hands. The character could be animated and controlled by the user's headset (or a webcam of the user's computer detecting head movement). A user might create a cartoon character, but have his headset track movement of his head, eyes, and mouth. In this embodiment, when the user tilts his head to the left an accelerometer in his headset registers the movement and sends the movement data to the headset's processor and then to the call platform software which is in control of the user's animated avatar, tilting the avatars head to the left to mirror the head motion of the user. In this way, the user is able to communicate an essence of himself without requiring a full video stream. The user could also provide a verbal command to his headset processor to make his avatar nod, even though the user himself is not nodding.

One of the benefits to using an avatar is that it would require significantly less bandwidth to achieve (another way to reduce bandwidth used is to show a user in black and white or grayscale). The users headset processor could also use data from an inward looking video camera to capture movement of the user's eyes and mouth, with the processor managing to send signals to the central controller or directly to the call platform software to control the users avatar to reflect the actual facial movements of the user. In this way, the user is able to communicate some emotion via the user's avatar without using a full video feed.

While gallery views usually show just the face and name of the user, there is a lot of information about users that could be displayed as well. Such information could include what a call participant is thinking at that moment, which would allow for more informed and effective actions by the other call participants. Additional information could also include social information that could help other call participants get to know a user, or as an icebreaker at the start of a meeting. For example, the user might provide names of children and pets, favorite books, games played, sporting activities, and the like. In some embodiments, each caller has associated additional flip side information 8520 that can be seen by other callers by using a 'Flip' command 8540 to flip the caller image over to reveal the additional image on the back like looking at the reverse side of a baseball card. User image 8515*c* is illustrated as having been flipped to the back side, revealing that user 8515*c* has worked with the company for 13 years, currently works in New York City, and has three kids.

Alterations to the way in which call participants are displayed in the image gallery could be based on sensor data received and processed by the call platform software. In another embodiment, a user's heart rate could be displayed alongside a user image 8515. For example, the user's mouse (not shown) could be equipped with a heart rate sensor which sends a signal representing the user's heart rate 8522 to the call platform software (or central controller 110) in order to identify when a caller might be stressed. As illustrated, caller 8515*d* has an icon next to her caller image that indicates that her current heart rate is 79 beats per minute. In various embodiments, other biometric data (e.g. galvanic skin response) can be displayed alongside a user image. Supplemental background information 8523 could include information such as team affiliation, functional area, level, skill sets, past work/project history, names of their supervisors, etc. In the illustration, user 8515*h* has background information 8523 which indicated that he is an 'IT Lead' and is currently working on 'Project x'. The information could also include what the user is currently thinking (e.g. they want to respond to the last statement). In another example, a meeting owner could assign roles to call participants during the call, with those assigned roles appearing as supplemental information such as by adding a label of "note taker" below a call participants gallery view image. Supplemental information could include dynamic elements, such as showing a user's calendar information or current tasks that they are working on. Other dynamic supplemental information could include statistics around the meeting, such as the current average engagement level, percentage of agenda items completed, number of current participants, etc. This dynamic supplemental information could be about an individual, such as showing the user's current engagement level, talk time, number of tags placed, number of agenda items completed, badges received, etc.

In some embodiments, there are times on a call when a user would like to communicate with another call participant, but the number of participants makes that difficult to do without waiting for an opportunity to speak. In such embodiments, a user could communicate via a caller border 8525 around their caller image 8515*a-h* while on the call. For example, a user could double click on their caller image in order to have the caller border 8525 flash three times or change color in order to quickly get the attention of other call participants. In another example, the user could communicate by changing the color of their caller border 8525 to red if they would like to make a candid statement or green if they are feeling very in tune with the other participants. In the current illustration, caller 8515*b* has elected to make the frame of caller border 8525 bolder in order to indicate that he is waiting to say something important. In addition to changing the look of the user's gallery view image, the present invention can also allow a call participant to see the ways that call participants are connected, revealing information that could help to enhance the effectiveness of the meeting. For example, callers 8515*h* and 8515*g* have a visible alignment 8530 indication. This alignment could be determined by call platform software in conjunction with central controller 110. For example, central controller 110 could determine that these two callers are both working to move a particular company software application to the cloud. Alignment 8530 could also reflect meeting ratings stored with central controller 110, with two callers aligned if their ratings were more than 90% the same.

In some embodiments, call participants can use call functions 8533 to provide more information to other users, reveal more information about other users, provide rewards and ratings to other users, indicate that they have a question about another user, etc. With a set alignment button 8535, a user could identify two callers who seem to be aligned in some way and have that alignment 8530 made visible to other call participants. A 'flip' button 8540 could allow a user to flip a second user's image to reveal additional information about that second user. A note 8542 could allow a user to attach a note to a second user's grid location 8510 or caller image 8515. The note might be a question, a comment, a clarification, a drawing, etc. In some embodiments, callers have access to tags 8545 which can be placed onto grid locations 8510 associated with other users. For example, a user might show some appreciation for an insightful statement from caller image 8515*d* by dragging a star symbol into her grid location. This star might be visible only to caller 8515*d*, only to members of her functional group, or visible to all call participants. The star could remain for a fixed period of time (e.g. two minutes), remain as long as the call is in progress, disappear when caller 8515*d* clicks on it, disappear when caller 8515*d* stops speaking, etc. Other examples of tags being provided to other users in this illustration include two ribbon tags 8545 attached to caller 8515*g*, a star symbol attached to alignment 8530 and to caller 8515*f* and to caller 8515*d*, a question tag 8545 attached to caller 8515*b* indicating that another user has a question for him, and coin tags 8545 associated with caller 8515*a* (two coins) and one coin associated with caller 8515*e*. In the example of coins, these might be convertible into monetary benefits or might be exchangeable for digital assets like music or books. Such coins might encourage productivity and focus during calls as users seek to 'earn' coins with helpful comments, new ideas, good facilitation, etc. Many other suitable tags could be used for different purposes.

In other embodiments, modules area 8550 contains one or more software modules that could be selectable by users or established by meeting owners prior to a meeting. These modules can provide functionality which can enhance the effectiveness of a virtual call. For example, chat area 8555 allows call participants to chat with each other or to the group. A presentation module 8560 could show a thumbnail view of a presentation slide, which users could click on to enlarge it to full screen. Callers could also add comments or questions to a particular slide. In the illustrated example, a quarterly sales chart is shown on page 4 of the presentation. One caller is unclear about an aspect of the chart and adds a question symbol to alert the meeting owner or other callers that something is not clear. A speaker queue 8565 could allow callers to enter into a queue to speak during the call. In large meetings, it is common for one person to make a statement and for others to then want to verbally respond. But if there are many who want to respond, there is often a confusing time when multiple people are trying to respond at the same time, creating some chaos that is disruptive to the meeting.

The call platform software could determine a speaking queue by receiving requests from call participants who want to speak. As this queue is adjusted, the participants waiting to speak could be displayed in the gallery in speaking order. As the individual approaches their time to speak, the border 8525 on the gallery could begin to change colors or flash. In another example, the call platform software determines the order of the next five speakers and places a number from one to five as an overlay on top of each of the five participant's images, so the next participant due to speak has a number one on their image, the second has the number two, etc. In some embodiments, participants who want to speak could be presented with the ability to indicate how their contribution relates to elements of the conversation. An individual who wishes to speak could be presented with choices such as "I have the answer to your question"; "I agree"; "I want to offer an example;" "I'd like to highlight something that was just said"; "I want to offer a different opinion"; "I think that's not relevant;" "I want to summarize the discussion"; "I'd like transition or move on"; "I'd like to ask for a poll" "I'd like to ask for the feeling of the room" "I'd like to ask a question"; "I'd like us to take an action or make a decision." Participants could fill a short text box with information about what they are going to say. When individuals select an option to indicate how they want to contribute or input a description of what they want to say, the type of their contribution or their rationale could be visually indicated to others on the call.

In another embodiment, individuals could select from digital representations associated with contribution types known as "intenticons." Intenticons are abstract representations of intent similar to emojis or emoticons. The intenticon could be displayed next to the participant's name, could replace the participant's name, could be placed above, below, around or composited on top of the participant's image, or could replace the participant's image. Call participants who want to respond to a current speaker could enter text summarizing the nature of their response, allowing call platform software to merge one or more responses or bump up the priority of one or more responses. For example, two users might want to respond by pointing out a security issue brought up by the current speaker, in which case the call platform software picks only one of those responses to be made, sending a message to the other responder that their response was duplicative. Information about a potential responder's response could change the prioritization level, such as by a user who wants to bring up a potential regulatory issue with a previous statement.

In some embodiments, the meeting owner could allow participants to indicate which other participants they would like to hear next. For example, participants could reorder a visual queue containing the contributions or the names of participants in the speaking queue. For example, participants could click on other participants' images 8515a-h, grid locations 8510, or contributions to indicate. By indicating, the call platform could change the visual representation of the gallery view to highlight individuals that others think should talk next. A highlighted frame could appear around the user, or the user could be placed in a spotlight, for example. In other embodiments, individuals could upvote or downvote individuals in a speaking queue by clicking on a button indicating thumbs up/down, "speak next"/"don't speak next", or left mouse clicking or right mouse clicking, swiping left or swiping right. Individuals could remove themselves from the speaking queue. In one embodiment, the participant could click a "never mind" button. In another embodiment, a participant could remove oneself by right clicking on a visual representation of the queue and selecting an option to remove oneself. In various embodiments, a configuration may specify an order of speakers or presenters.

Exercise Reminders

As modern workers increasingly sit all day doing information work, they run the risk of developing health issues if they do not get up and take occasional breaks to stretch and move around. In various embodiments, when a meeting participant has been in a long meeting, the chair could send a signal to the room controller indicating how long it had been since that participant had stood up. If that amount of time is greater than 60 minutes, for example, the central controller could signal to the chair to output a series of three buzzes as a reminder for the participant to stand up. The central controller could also send a signal to the meeting owner that a ten-minute break is needed for the whole room, or even initiate the break automatically. The central controller could send signals to smart variable-height desks to automatically adjust from sitting to standing position as an undeniable prompt that participants should stand up. In various embodiments, if the central controller identifies a meeting participant who is in back to back meetings for four hours straight, it could send a signal to the participant device with verbal or text reminders to stretch, walk, take some deep breaths, hydrate, etc. In various embodiments, if a meeting participant is scheduled for four hours of meetings in a row, the central controller could send the participant alternate routes to walk to those meetings which would take more steps than a direct route. In various embodiments, for virtual meeting participants, the central controller can also send reminders to participants that they should take a break and walk outside or spend a few minutes doing stretching/exercising. These suggestions could be linked to heart rate readings from a mouse, slouching or head movements seen by a camera, a fidgeting signal from a chair, etc.

Mental Fitness

As employees perform more and more information-driven work, keeping their minds functioning well is more critical than ever. An employee who is tired, distracted, unable to focus, or perhaps even burned out will have a hard time performing complex analytical tasks. Research has shown, for example, that software developers need large blocks of uninterrupted time in order to write good software. If their minds are not sharp, significant business value can be lost. In various embodiments, the central controller reviews the meeting schedule of all knowledge workers in order to assess the impact that the schedule may have on the mental fitness of the employee. For example, when the central controller sees that an employee has back to back meetings for a six hour block on two consecutive days, the employee may receive direction in ways to reduce some of the stress associated with those meetings. Stress alleviation suggestions could include: Meditation; Exercise (e.g., light yoga, stretching); Healthy snacks; Naps; Fresh air; Focus on a hobby or something of personal interest; Calming videos or photos; Positive/encouraging messages from company leadership; or any other suggestions. The central controller reviews the meetings of the knowledge worker and compares them to other knowledge workers in similar roles to see if any are getting oversubscribed. For example, if certain key subject matter experts are being asked to attend significantly more innovation meetings than other subject matter experts, the central controller can alert the management team of possible overuse. In addition, the overused subject matter expert could be alerted by the central controller to consider delegating or rebalancing work in order to maintain a healthy lifestyle. In the converse, as an example, if a subject matter expert or key role (e.g. decision maker) individual is currently undersubscribed compared to others, the central controller can alert management or other meeting leads to put this person at the top of the list if they have a need for this expertise.

In various embodiments, the central controller 110 may review information collected about a meeting participant to look for signs that an employee may be heading toward burning out. Such signals could include the employee is: Using a loud voice in a meeting; Having a rapid heartbeat; Slouching or not being engaged with other participants; Interrupting other participants; Declining meetings at a more significant rate than most in similar roles; Significantly more out of office or absentees in a short period of time; Changes in level of meeting engagement; No breaks for lunch; or any other signals. In various embodiments, the central controller 110 can also monitor biometric information (such as heart rate, posture, voice, blood pressure) and compare the results to the entire organization to determine if the pattern is higher than expected. For example, if the individual on the verge of burnout shows that they are interrupting individuals using a loud voice more frequently than most, the central controller can alert the individual during the meeting to consider alternative approaches for engagement such as, taking a break, breathing deeply, meditating or any predetermined approaches deemed appropriate by the organization. If the data continue to support potential burnout, the central controller can inform the individuals management for intervention and coaching. In various embodiments, the central controller 110 can interrogate the calendars of individuals to determine if they are getting uninterrupted time for lunch during a specific time. For example, the central controller can look at an individual's calendar over a month time period. If the time slot between 11:30 AM-1:30 PM is consistently booked with meetings more than 50% of the time, the central controller can alert the individual to reconsider taking lunch breaks for healthy nutrition and also inform meeting leads that the use of lunch meetings could be excessive.

In various embodiments, the central controller 110 could also have the ability to look at the home calendar of employees so that it has an understanding of how busy they might be outside of work. For example, the central controller can look to see if exercise routines are typically scheduled on an individual's calendar. If so, and suddenly they begin to not appear, the central controller can provide reminders to the individual to reconsider adding exercise routines to their calendar to maintain a healthy lifestyle. Another example could be for the central controller to view events on an individual's calendar outside of normal work hours (pre-8:00 AM and post-5:00 PM) to determine if enough mental free time is being allocated for mental health. If calendars are continually booked with dinner events, children's events, continuing education or volunteer work without time for rest, this could be early signs of burnout. The central controller could remind the individual to schedule free time to focus on mental rest, prioritize activities and provide access to suggested readings or activities to promote mental wellbeing. In various embodiments, the central controller 110 can maintain analytics on the number of declined meetings that are typical in an organization and compare to an individual. If the number of declined meetings for the individual is higher than average, helpful information can be provided. For example, if the organization typically has 5% of their meetings declined and meeting participant "A" has an average of 25% of meetings declined, the central controller can prompt to individual to consider other alternatives to declining a meeting such as delegating, discussing with their manager any situation prompting them to decline meetings, or make use of mental and physical wellness activities for improvement. Many enterprise organizations have access to an array of mental and physical health content and individual health providers via the insurance companies that provide health benefits. The central controller could identify these individuals and direct them to their health insurance provider. This immediate intervention and access to a professional in the field of mental health via their insurance providers could help mitigate the health issues.

Virtual Audience Feedback

When presenting at a meeting which has a high percentage of virtual participants, it can sometimes be disconcerting for a presenter to speak in front of a largely empty room. In various embodiments, one or more video screens are positioned in front of the speaker to provide images of participants, and to guide the presenter to make head movements that will look natural to virtual participants. In various embodiments, color borders (or other indicia) may be used for VPs, or other key people. In various embodiments, three people (e.g., stand-in people) are set up before the call (can be dynamic based on what slide the presenter is on). The presenter can then practice presenting to these three people. In various embodiments, it is oftentimes important to know the roles or organizational level of individuals in a meeting to make sure that the presenter is responding appropriately. For example, if a Decision meeting is taking place, it is important to quickly be able to identify these individuals so you can speak more directly to them. The central controller could gather this information from the meeting presenter in advance. Once they join the meeting, their images could have a border in a different thickness, pattern or color to more easily identify them. Since they are the key members in this particular meeting, their images could display larger than others and be represented on the various display devices. If any of these individuals speak, the central controller could adjust the border to brighten in color, flash a particular pattern and gray out the images of others. This allows the presenter to quickly focus on the key participant speaking and make better eye contact.

In various embodiments, an audience (emoji style) is displayed to the presenter. In meeting settings it is important to connect with the audience and even more so in a virtual meeting. Each meeting attendee can provide an image of themselves or use an already approved picture via a corporate directory to the central controller. When the meeting begins, the individual images are presented on the various display devices. As emotions and biometric data is collected by the central controller, the emoji can change to reflect the state of the individual. If the audience is happy, the emojis change to provide the presenter immediate feedback. Conversely, if the central controller detects the audience is confused or frustrated, the emoji changes immediately to reflect the new state. This feedback allows the presenter to collect real time audience information and adjust their presentation accordingly. Furthermore, if a presenter needs to practice a presentation remotely in advance of the live presentation, the central controller can present a random set of emojis and images for the presenter to practice. In various embodiments, a real-time emoji dashboard is displayed to the presenter for selected reactions. The central controller should allow the meeting participants to provide emoji style feedback to the presenter in real time. For example, if a presenter is training an audience on a new product and some attendees are confused, others are happy and some are bored, the audience members can provide the appropriate emoji to the presenter. The central controller collects all emojis and displays them in dashboard format to the presenter. In this case, 10 confused emojis, 50 happy emojis and 2 bored emojis appear on the dashboard bar chart for interpretation by the presenter. They may elect to pause and review the slide showing 10 confused faces. In addition, the central controller could record the emotions on each slide, along with the participant, and inform the presenter. After the meeting, the presenter can address the reaction on each slide with those that had the issue/concern.

In various embodiments, feedback can be presented to the speaker/coordinator/organizer in a graphical form that privately (or publicly) parses out responses, statuses, etc., by attendee. The speaker can easily view, for example, who has provided an answer to a question (e.g., a poll) and who still needs to answer. In various embodiments, as presenters are speaking, a feeling thermometer dynamic dashboard is presented for review and real-time adjustments to their presentation. For example, the central controller could provide each participant with an opportunity to rate the presentation using a feeling thermometer based on any dimension the meeting owner selects. Is the presentation material clear? The participant can adjust the thermometer to indicate very clear to very unclear. The collective ratings of all thermometer scores is dynamically presented to the presenter for any needed adjustments. In addition, the pace at which a presentation is being delivered can also be measured and presented on the dashboard as well.

Virtual Producer

As meetings become more virtual, it may be increasingly important for meeting owners and meeting participants to maintain a natural look during meetings. The way that they are looking and the angle of the head will convey a lot of non-verbal information. In this embodiment, the central controller uses software to make suggestions to participants and to pick camera angles much like a producer would in a control room of a television news show which can do things like cut to the best camera angle or include a small video frame to support the point that the presenter is making. In various embodiments, there are three cameras (or some other number have cameras) and the system picks the best angle. For example, the central controller 110 identifies who is speaking and where they are in relation to the display you are using. When you look in the direction of the person speaking (virtually or not) the appropriate camera focuses the angle in the direction you are looking. In various embodiments, the system tells you how to turn when you are on video. For example: As a presenter to a virtual audience, you may need to turn your head to appear to speak to a larger audience and not give the appearance that you are staring at them. The central controller can track how long you are focused in one direction and prompt you to move your head and look in a different direction. This provides a more realistic view of the presentation to the audience and can put them at ease as well.

In various embodiments, the presenter talks with his/her hands, the camera should zoom out. The central controller 110 could determine if you are using your hands to speak more or illustrate a point. Your hands and arms may appear to come in to focus more often. In this case, the central controller could communicate with the camera to zoom out and pick up movements in a larger frame. Pan-Tilt-Zoom (PTZ) camera can be auto controlled by the system to meet production goals (e.g., zoom in to emphasize speaker as speaker volume or role increases). In various embodiments, a meeting lead can determine if other speakers are brought in to view or remain focused on them only. Example: if I am a lecture or in a town hall, I may only want the camera in me and not go to others. The meeting lead can interact with the central controller in advance of the meeting to determine if participants will be brought in to focus during the meeting. If the preference is to not allow the participant to be in focus, when they speak, the central controller will not display the individual, but camera focus will remain on the presenter/meeting lead. In various embodiments, the system may bring participants in or out of focus. When a speaker comes in to focus, the other participants gray out or turn to a different hue. This forces people to focus on the person speaking. For example, in interview situations, question/answer sessions or learning meetings, it is important that the vast majority of participants stay focused on a primary individual. When an individual begins to speak for a few seconds, they quickly come into focus while the others are displayed in a monochromatic display. In this case, the eyes of the participants are drawn to the speaker that remains in full color. In various embodiments, the system determines if focus is on the content displayed or the presenter. During a presentation, while the attendees may be listening and watching the presenter, they are interested in the presentation content as well. In advance of the presentation, the presenter can set a preference via the central controller to make the presentation deck the main focus and a small image of the presenter in the corner of the screen. The central controller could know when the presentation is complete and refocus on the presenter. If the presenter goes back to the slide presentation, the central controller can revert back to the original setting.

Eye Tracking

Tracking where participants are looking can be very helpful in evaluating presentations and estimating the level of meeting participant engagement. Various embodiments track where on a slide that participants are looking. This could provide an indication of the level of engagement of the audience. Various embodiments track where in the room participants are looking. Automatically identify potential distractions; prompt the meeting owner or a particular meeting participant to turn off TV, close window blind, etc. Various embodiments track which other participants a participant is looking at and when. For example, the central controller could track eye movements of people to determine if an issue exists. If multiple participants look over at someone working on a laptop/phone this may mean they are frustrated with this person because they are not engaged. The central controller could track eye movements of people coming and going from the room which may be an indication that a break is needed. If a meeting participant is routinely looking at another participant during a presentation, this could indicate they are not in agreement with the content and looking for affirmation from another participant. Various embodiments include tracking eye rolling or other visual cues of agreement or disagreement. For example, if eyes roll back or are simply staring, this could indicate they are in disagreement with the topic or person and inform the meeting owner.

Gesture Tracking

With cameras, GPS, and accelerometers, there are many physical gestures that can be tracked and sent to the central controller. Example gestures include: arms folded; holding up some number of fingers (e.g., as a show of support or objection to some proposition; e.g., a fist of five); hands clasped together or open; clapping; fist on chin; getting out of one's chair; pushing back from a table; stretching or fidgeting. Some gestures of possible interest may include head movement. In various embodiments, head movement can be an excellent way to provide data in a natural way that does not disrupt the flow of the meeting. Head movements could be picked up by a video camera, or determined from accelerometer data from a headset, for example. In various embodiments, virtual participants could indicate that they approve of a decision by nodding their head, with their headset or video camera sending the information to the room controller and then summarizing it for the meeting owner. Participants could also indicate a spectrum of agreement, such as by leaning their head way left to indicate strong disagreement, head in the center for neutrality, or head far to the right to indicate strong agreement. In various embodiments, virtual participants could enable muting of their connection by making a movement like quickly looking to the right. For example, when a dog starts to bark, it is natural for participants who are not muted to look in the direction of the dog or child making noise, which would automatically mute that person. They could be muted for a fixed period of time and then automatically be taken off mute, or the participant could be required to go back off mute when they are ready. Virtual participants could also make a gesture that would bring up a background to hide something. For example, a participant who had a small child run up behind them while on a video call could tip their head backward to bring up the background which would prevent others on the call from seeing the child.

Verbal Queues not Intended for Meeting Participants

There are times when meeting participants make soft comments that are not meant to be heard by the meeting participants or that are not understood by the participants. These verbal queues oftentimes indicate some other emotion from the meeting participant. The central controller could detect these verbal queues and use them to generate the meeting participants immediate reaction or emotion. For example, if a participant is listening to a presentation and does not agree with the content, they may make comments like, 'I don't agree, no way, that's absurd or some other short phrase, the central controller could pick this phrase up and use it to populate the meeting owner dashboard or other device recording/displaying their emotion.

Help that can be Provided by the Central Controller

In various embodiments, the central controller 110 may manage the type of connection made from a user device. The central controller may manage the connection with a view to achieving a stable connection while also giving the user the best experience possible. In various embodiments, if the central controller determines that a user device can only maintain a low bandwidth connection, the central controller may admit the user to a meeting as a virtual participant using only a low-bandwidth feed (such as an audio-only feed or a low-resolution video feed). On the other hand, if the user device can maintain a stable connection at high bandwidth, then the user may be admitted as a virtual participant using a high-bandwidth feed, such as via high-resolution video. In various embodiments, if a connection to a meeting participant is lost, the central controller may inform the meeting owner, the meeting presenter, and/or some other party. The central controller may attempt to re-establish a connection, perhaps a lower bandwidth connection. Once a connection is re-established, the central controller may again inform the meeting owner.

Central Controller Actions

In various embodiments, the central controller 110 may monitor a meeting or a room for problems, and may take corrective action. In various embodiments, the central controller 110 may take away the room if you have three people in an eight person room. It can then suggest other available rooms with the needed amenities and a simple 1 button acceptance or suggested change with notification to all participants. If there are technical issues in a room, the central controller 110 may take such actions as: Shut down room and turn off lights; Have video screens with shut down signal; Reschedule all meetings for other rooms; Notify facilities/IT personnel. If the room is not clean or has not been serviced, the central controller may arrange for food/beverage/trash removal. If a meeting has not been registered, the meeting may use a conference room on a "standby" status. That is, the room can be taken away (e.g., If the room is required by a meeting that was properly registered). If a person is absent from a meeting, or it is desirable to bring a particular person into a meeting, then the central controller may assist in locating the person. The central controller may take such actions as: Can ping them; Can break into a call or meeting room to contact the person; Can cause their chair to buzz or vibrate; Can buzz their headset; Can text them. In various embodiments, the central controller may perform a system self/pre-check prior to the meeting to make sure all devices are functioning (e.g. audio, video, Wi-Fi®, display, HVAC) and alert the responsible technical party and meeting organizer/owner. Meeting options to be provided if not resolved within 1 hour prior to the meeting.

Tagging the Presentation

Presentations contain valuable information but must be linked in a way to quickly and easily retrieve information at any point in time. The central controller could maintain access to all presentations and content along with the relevant tags. Tags may be used in various ways. These include: The main slide with the financials is tagged "financials"; Tag the slide which begins discussions around Project X; Tag slides as "optional" so they can be hidden when time is running low; Tag a presentation as "main microservices training deck"; Show who is a delegate for someone else; Tag for HR review later (and send meeting notes); Tag for legal review later (and send meeting notes). As an example, during an alignment meeting, a meeting owner is asked about the financials for project ABC which are not included in the current meeting presentation. The meeting owner asks the central controller to retrieve the financial information for project ABC. The central controller responds by sending the most recent financial slides for project ABC for display in the meeting.

Generating Meeting Notes/Minutes

While many meeting owners and meeting participants have the best of intentions when it comes to creating a set of meeting notes or minutes at the end of a meeting, all too often they are forgotten in the rush to get to the next meeting. A more efficient and automatic way to generate notes would allow for greater transparency into the output of the meeting. This is especially important for individuals who count on meeting notes to understand the action items that have been assigned to them. In various embodiments, meeting participants could dictate notes during or after the meeting. If a decision was made in a meeting, for example, the meeting owner could alert the room controller by getting its attention by saying a key word expression like "hey meeting vault" or "let the record reflect", and then announcing that "a decision was made to fully fund the third phase of Project X." The room controller would then send this audio recording to the central controller which would use speech to text software to generate a text note which is then stored in a record associated with the unique meeting identifier. Similar audio announcements by meeting participants throughout the meeting could then be assembled into a document and stored as part of that meeting record. Voice recognition and/or source identification (e.g. which device recorded the sound) can be utilized to identify each particular speaker and tag the notes/minutes with an identifier of the speaker. In various embodiments, the central controller listens to key phrases for diagnostic purposes such as items "you're on mute," "can you repeat that," "we lost you," "who is on the call," "can we take this offline," "sorry I'm late . . . " In various embodiments, cameras managed by the room controller could take images (or video) of walls during the meeting. A team that had done some brainstorming, for example, might have notes attached to the walls. In various embodiments, meeting notes could be appended to another set of meeting notes. In various embodiments, decisions from one meeting could be appended to decisions from another set of meeting notes.

Using Meeting Notes

While storing meeting notes is important, it may be desirable to make it easier for meeting participants to use those notes to enhance effectiveness and boost productivity. In various embodiments, the full corpus of all notes is stored at the central controller and fully searchable by keyword, unique meeting ID number, unique meeting owner ID, tags, etc. In various embodiments, less than the full corpus may be stored, and the corpus may be only partially searchable (e.g., some keywords may not be available for use in a search). In various embodiments, notes are sent to some portion of attendees, or everyone who attended or missed the meeting. In various embodiments, attendees are prompted for voting regarding the notes/minutes—e.g., attendees vote to indicate their approval that the notes/minutes represent a complete and/or accurate transcript of the meeting. In various embodiments, meeting notes are sent to people who expressed an interest in the notes (e.g. I work in legal and I want to see any set of notes that includes the words patent, trademark, or copyright). Various embodiments provide for automatic tracking of action items and notification to meeting participants upon resolution/escalation.

Meeting Assets and Batons

It may be desirable that meetings generate value for the business. The central controller 110 can provide transparency into whether meetings create value by recording the assets created during a meeting. Additionally, there may be task items generated during the meeting that need to be assigned to a person or team. These task items become a kind of "baton" which is handed from one person to another—across meetings, across time, and across the enterprise.

Recording Meeting Assets

Based upon the type of meeting, the central controller 110 can record and tag the asset created during the meeting. For example, in a decision meeting, the central controller could record that a decision was made and the reasoning. For innovation meetings, the central controller could record the ideas generated during the meeting.

Action Items

Some meetings generate action items, to-do items, or batons as an asset. The central controller 110 could record these actions items, the owner of these action items, and who created these action items. The central controller could alert employees of new action items. The central controller could provide these employees with a link to the meeting notes and presentation of the meeting that generated the action item, which would provide information and context to the action item.

Links Between Meetings

The central controller 110, based upon batons or other assets, could identify links between meetings. The central controller could identify duplicative, overlapping, or orphaned meetings. This can trigger actions based on meeting hierarchy—e.g., sub-meeting resolutions may trigger parent meetings to discuss/review resolutions/assets from sub-meetings.

Dormant Assets and Action Items

The central controller 110 could identify dormant assets or action items and flag them for review by their owners or schedule a new meeting.

Low Value Meetings

The central controller could flag meetings that produce few assets, result in dormant action items, or produce few assets relative to the expense of holding the meeting.

CEO (or Project Sponsor) Controls

Various embodiments provide a CEO (or other leader, or other authority, or other person) a chance to ask a challenge question in advance of a meeting based on the registered purpose of the meeting. For example, if the purpose of the meeting is to make a decision, the CEO can have an experienced and highly rated meeting facilitator ask a meeting owner (or some other attendee) exactly what they are trying to decide. The CEO may require that the meeting owner has to respond before the meeting, or deliver the output as soon as the meeting is done. In various embodiments, a CEO has the option to require an executive summary immediately after a meeting (e.g., within half an hour), on decision(s), assets generated, outcomes, and/or Other aspects of a meeting.

Request an Approval

In various embodiments, it may be desirable to obtain an approval, authorization, decision, vote, or any other kind of affirmation. It may be desirable to obtain such authorization during a meeting, as this may allow the meeting to proceed, for example, further agenda items that are contingent upon the approval. The approval may be required from someone who is not currently in the meeting. As such, it may be desirable to contact the potential approver. In various embodiments, the central controller 110 may set up a real-time video link from a meeting room to a potential approval. In various embodiments, the central controller 110 may email the decision maker with the data from the meeting to get an asynchronous decision. In various embodiments, the central controller 110 may message someone authorized to make a decision (or vote), e.g., if the main decision maker is not available.

Subject Matter Experts (SMES)

In various embodiments, it may be desirable to find someone with a particular expertise. The expert may be needed to provide input in a meeting, for example. For example, meeting participants may desire to find the closest available SME with an expertise of "Java". Categories of expertise/SMEs may include the following: Coding; Supply chain/logistics; Finance; Marketing/Sales; Operations; Strategy; Value stream mapping; Quality/Lean; HR; IT Architecture; Customer Experience and Core Business knowledge; Meeting facilitator by meeting type (e.g. an SME whose expertise is facilitating Innovation Meetings); and/or Any other area of expertise.

Employee Handheld/Wearable Devices

In various embodiments, an employee device, such as a handheld or wearable device (e.g., a user device of table 900 or a peripheral device of table 1000), may assist an employee with various aspects of a meeting. In various embodiments, an employee device may: Show the employee the location of your next meeting; Show the employee who is running the meeting; Show the employee who the participants will be; Let the employee vote/rate during meetings; Connect the employee via chat/video with someone you need temporarily in a meeting; Display the meeting purpose; Display the slides of the deck; Take a photo of the whiteboard and send it to the central controller for that meeting ID number; Take a photo of stickies which the central Controller can OCR and add to meeting notes; and/or may I assist with any other action.

Network/Communications

In various embodiments, the central controller 110 could play a role in managing communication flow throughout the enterprise. If there are dropped connections from participants (e.g., from participant devices) provide immediate notification to the meeting owner for appropriate action. In various embodiments, a meeting owner could initiate a communication link between two ongoing meetings. The central controller could also automatically create a video link between two ongoing meetings that had agendas that were overlapping. For example, two meetings that identified Project X as a main theme of the meeting could be automatically connected by the central controller. In various embodiments, when network bandwidth is constrained, the central controller could turn off the video feeds of current virtual participants and switch them to audio only. If there is failed video/audio, the central controller may provide immediate notification to the meeting owner and other participants. Communication channels could also be terminated by the central controller. For example, a side channel of texting between two different meetings could be stopped while key decisions are being made in those meetings. During a meeting, the meeting owner could ask the central controller to be immediately connected to an SME who had expertise in data security.

Ratings and Coaching

A potentially important part of improving the performance of meetings (and employees) and bringing greater focus and purpose to work is to gather data from employees and then provide assistance in making improvements. One way to gather such data is by having participants provide ratings, such as polling all meeting participants in a 20-person meeting to ask whether or not the meeting has been going off track. Additionally, the central controller 110 could gather similar data via hardware in the room. For example, during that same 20-person meeting the central controller could review data received from chairs in the room which indicate that engagement levels are probably very low. These ratings by machine and human can be combined, building on each other. The ratings can then be used as a guide to improving performance or rewarding superior performance. For example, someone who was using a lot of jargon in presentations could be directed to a class on clear writing skills, or they could be paired with someone who has historically received excellent scores on presentation clarity to act as a mentor or coach. In this way, the performance of employees can be seamlessly identified and acted upon, improving performance levels that will translate into enhanced performance for the entire enterprise.

The ratings produced according to various embodiments can also be used to tag content stored at the central controller. For example, ratings of individual slides in a PowerPoint deck could be stored on each page of that deck so that if future presenters use that deck they have an idea of where the trouble spots might be. Edits could also be made to the deck, either by employees or by software at the central controller. For example, the central controller could collect and maintain all ratings for slides that deal with delivering financial information. Those financial slides with a high rating are made available to anyone needing to develop and deliver a financial presentation. This continual feedback mechanism provides a seamless way to continually improve the performance of the individual (person preparing the presentation) and the enterprise. Less time is spent on failed presentations and relearning which presentations are best at delivering information and making those available to anyone in the enterprise. Furthermore, in addition to providing the highly rated presentation, the actual video presentation could be made available for viewing and replication. If a presenter earned a high rating for delivering the financial presentation, the content and actual video output of the presentation could be made available to anyone in the enterprise for improvement opportunities. In various embodiments, ratings may be used to tag content. Thus, for example, content may become searchable by rating. Content may be tagged before, during, or after the meeting. Tags and ratings me until some of the feedback described with respect to FIG. 54.

Feeling Thermometer

As a PowerPoint™ presentation is being presented, meeting participants could use a dial on their meeting participant device to indicate whether the material is clear. As a speaker is leading a discussion, meeting participants could use the same dial to indicate the level of engagement that they feel in the meeting. The output of such continuous rating capabilities could be provided in a visual form to the meeting owner, such as by providing that meeting owner with a video of the presentation with a score at the top right which summarizes the average engagement score as indicated by the participants.

Rating Participants

Participants can be rated by other participants on various meeting dimensions. These may include, contribution to the meeting, overall engagement and value as the role being represented. The central controller could collect all participant feedback data and make available to the participant, meeting owner and manager for coaching opportunities.

Dynamic Ratings and Coaching

During meetings, the central controller 110 could prompt presenters and participants for ratings. For example, the central controller could provide cues to the meeting owner or presenter to slow down or increase the speed of the meeting based upon time remaining. The central controller also could prompt individual participants to rate particular slides or parts of a presentation if it detects low levels of engagement based, for example, on eye tracking or chair accelerometers. Based upon ratings from prior meetings, the central controller could assign a "Meeting Coach" who can provide feedback at future instances of the meeting.

Signage in Room

Meetings often start with administrative tasks taking place and waste time getting to the true purpose of the meeting. Reinforcing relevant information at the start of a meeting can help to streamline the meeting time and set a positive tone in advance of the actual start. In various embodiments, signage (or some other room device) displays the meeting purpose (or says it out loud). In various embodiments, the central controller 110 knows the purpose of the meeting based on the meeting owner's input in the invitation. The central controller could display the purpose on all monitors in the meeting room and display devices accessing the meeting remotely. In various embodiments, signage (or some other room device) shows a meeting presentation. The central controller 110 can queue up the appropriate presentation based on the meeting owner input. As the meeting agenda is followed, each subsequent presentation can be queued as to not cause a delay in connecting a laptop and bringing up the presentation. In various embodiments, signage (or some other room device) shows people who have not yet arrived. Many meetings take enormous amounts of time taking attendance. The central controller can dynamically list those that have not joined the meeting either in person or virtually. Those attendees that have informed the meeting owner they will be late or not attend via the central controller can be displayed and also when their estimated arrival time will be. Those that actually attend can be sent to the meeting owner.

In various embodiments, signage (or some other room device) shows people who need to move to another meeting. Signage may give people their "connecting gates" for their next meeting. The central controller could provide proactive alerts to attendees requiring them to leave the meeting in order to make their next meeting on time. This can be displayed on the monitors or on personal devices. For example, if participant "A" needs to travel to another meeting and it takes 15 minutes of travel time, the central controller could provide a message to display that participant "A" needs to leave now in order to make the next meeting on time. Likewise, if participant "B" in the same meeting only needs 5 minutes of travel time, participant "B" could be altered 5 minutes prior to the start of the next meeting. In various embodiments, signage (or some other room device) shows people who are no longer required at this meeting. As meetings progress through the agenda, certain topics no longer require specific individuals in a meeting. Providing a visual indication of only those participants needed can help streamlining decisions and make everyone more productive. For example, if the first agenda topic takes 10 people in a meeting, but the second agenda item only needs 5 people, the central controller could notify those 5 they can now leave the meeting and display the message on the monitor and devices. In various embodiments, signage (or some other room device) shows a decision that was made last week which was relevant to the current meeting topic. Each agenda item/action item has a tag identified. As action items are resolved and decisions made, these can be displayed in advance of the meeting or throughout the tagged agenda items. For example, the central controller has access to all agenda items, action items and decisions and each has an associated tag. As the meeting progresses and topics in the agenda are covered, the central controller can display resolved action items and decisions relevant to the agenda topic and used in the discussions.

In various embodiments, the room knows what to say. Using meeting time to celebrate and communicate important information not directly related to the agenda items can be a way to reinforce key topics and focus on the people aspects of a company. In various embodiments, the room may display messages. The central controller can access HR information (birthdays, work anniversaries, promotions), third party external sites (traffic, weather alerts, local public safety information) and internal text or video messages from key leaders (CEOs, Project Sponsors, key executives). Example messages may pertain to: Promotions; Anniversaries; Birthdays; Company successes; Employee Recognition; CEO message; Traffic updates; "We just shipped the fifth plane with medical supplies"; "Did you know that . . . ?" In various embodiments, it may be desirable that messages take the right tone and be at the right time. The central controller knows each type of meeting taking place (informational, innovation, commitment and alignment). Based on the meeting type, the central controller displays meeting specific information on display devices and to attendees in advance. Innovation sessions should have lighter/more fun messages. On the other hand, commitment meetings might prevent all such messages. Learning meetings could feature pub quiz type messages. Alignment meetings may show messages indicating other people or groups that are coming into alignment. For example, a message may show four other teams in Atlanta are meeting about this same project (show a map of locations). In various embodiments, a message or view may be changed based on a particular tag (e.g. a participant may select a tag to show all microservices meetings). As another example, a participant may ask to see the top priorities for other orgs/ARTs/teams.

Audio/Video

In various embodiments, the central controller 110 may store audio and/or video of a meeting. The central controller may store the full audio and/or video of a meeting. In various embodiments, the central controller may store part of the audio or video of a meeting based on one or more factors. The central controller may store part of the audio or video of a meeting based on a request from participants (e.g. "please record the next two minutes while I describe my idea for improving collaboration") (e.g. "please clip the last two minutes of discussion"). The central controller may record any time loud voices are detected. The central controller may record any time the word "decision" or "action item" is heard. The central controller may record a random portion of the meeting. In various embodiments, a presentation has built in triggers on certain slides that initiate recording until the meeting owner moves to the next slide.

Other Hardware Devices

Various devices may enable, enhance and/or complement a meeting experience.

Virtual Reality

In various embodiments, virtual reality goggles may be used in a meeting. These may provide a more complete sense of being in a meeting and interacting with those around the wearer. In various embodiments, these may obviate the need for a camera, screens, rooms—instead, the meeting controller handles it all.

Headsets

As more and more meetings are held virtually, a greater number of meeting participants are not physically present in a room. Those participants are connecting via phone, or more commonly via video meeting services such as Zoom® or WebEx®. In these situations, it is common for participants to be wearing headsets. Connected into the central controller 110, this could allow a headset to help sense more information from meeting participants. The headset could contain any of the following sensors and connect to them the central controller: accelerometer, thermometer, heating and/or cooling device, camera, chemical diffuser, paired Wi-Fi® ring or smart watch, galvanic skin response sensors, sweat sensors, metabolite sensors, force feedback device. In various embodiments, an accelerometer is used to detect head movements, such as:

Detecting whether or not a meeting participant is currently nodding in agreement or shaking their head from side to side to indicate disagreement.

Detecting head movements along a continuum so that the participant can indicate strong agreement, agreement, neutrality, disagreement, or strong disagreement based on the position of their head in an arc from left to right.

Detecting whether a person is getting sleepy or bored by having their head leaned forward for a period of time.

If a head turns abruptly, this could indicate a distraction and mute the microphone automatically. When a dog enters or someone not a part of the meeting (a child), oftentimes people turn their head quickly to give them attention.

Detecting whether someone has been sitting for long periods to remind the wearer to take breaks and stand up.

Head movements coupled with other physical movements detected by the camera could be interpreted by the central controller. For example, if a participant's head turns down and their hands cup their face, this may be a sign of frustration. Fidgeting with a headset might be a sign of fatigue.

The central controller could interpret head movements and provide a visual overlay of these movements in video conferencing software. For instance, the central controller could interpret a head nod and overlay a "thumbs up" symbol. If the central controller detects an emotional reaction, it could overlay an emoji. These overlays could provide visual cues to meeting participants about the group's opinion at a given moment.

In various embodiments, a thermometer is used to measure the wearer's temperature and the ambient temperature of the room.

The central controller could record the wearer's temperature to determine if the wearer is healthy by comparing current temperature to a baseline measurement.

The central controller could determine if the individual is hot or cold and send a signal to environmental controls to change the temperature of the room.

The central controller could use temperature to determine fatigue or hunger and send a signal to the wearer or the meeting owner to schedule breaks and order food.

In various embodiments, a headset could contain a heating and/or cooling device to signal useful information to the wearer by change temperature, such as whether they are next in line to speak, whether a prediction is accurate ("hotter/colder" guessing), proximity in a virtual setting to the end of level or "boss", or signal time remaining or other countdown function. In various embodiments, the headset could have a camera that detects whether or not the users mouth is moving and then check with virtual meeting technology to determine whether or not that user is currently muted. If they are currently muted, the headset could send a signal to unmute the user after a period of time (such as 10 seconds), or it could trigger the virtual meeting technology to output a warning that it appears the user is talking but that they are currently muted. In various embodiments, the headset could contain a chemical diffuser to produce a scent. This diffuser could counteract a smell in the room, use aromatherapy to calm an individual, evoke a particular memory or experience, or evoke a particular physical place or environment. In various embodiments, the headset could be paired with a Wi-Fi® ring/smart watch which would set off an alarm in the headset when the user's hand approached their face. This could allow presenters to avoid distracting an audience by touching their face, or it could be used to remind participants not to touch their face when flu season is in full swing. In various embodiments, the headset could contain galvanic skin response sensors, sweat sensors, and/or metabolite sensors. The central controller could record the galvanic skin response or the rate of sweat or metabolite generation to determine whether the wearer is healthy by comparing the current measurement to a baseline measurement. The central controller could then signal to the meeting owner whether the meeting should continue or be rescheduled.

Force Feedback

One or more devices could employ force feedback. This could include hardware associated with the device which causes the device to buzz when prompted. In various embodiments, the presentation controller could be used for the meeting owner to contact a meeting participant verbally. For example, a meeting owner may need to ask a question specific to another person without others hearing in the room. They could speak the question in the presentation controller and it could be heard by the meeting participant to respond. Also, they could use the same capability to request the meeting participant to engage in the discussion.

Microphones

Microphones may have various uses in meetings. Meetings are routinely interrupted by background sounds from remote meeting attendees causing a break in the meeting cadence and lost productivity. By using pre-recorded sounds that invoke a response by the central controller, the microphone could be put on mute automatically. For example, if your dog's bark is pre-recorded, the central controller could be listening for a bark and when recognized, the microphone is automatically put on mute. Similarly, if a doorbell or a cell phone ring tone is recognized, the microphone is put on mute automatically. In various embodiments, microphones should be muted automatically if they are outside the range of the meeting or the person is no longer visible on the video screen. Remote workers take quick breaks from meetings to take care of other needs. For example, a parent's child may start screaming and need immediate attention. If the meeting controller recognizes the meeting participant has moved from the video screen or several feet from their display device, mute the microphone automatically. Another example may be where someone leaves the meeting to visit the restroom. In various embodiments, a microphone is always listening (e.g., for a participant to speak). For participants that are on mute, once they begin to speak, the microphone detects this and automatically takes them off mute. For example, there are many occasions where meeting participants place themselves on mute or are placed on mute. Oftentimes, they do not remember to take themselves off of mute and it forces them to repeat themselves and delay the meeting.

Presentation Controllers and Remote Control Devices

Presentation controllers, remote control devices, clickers, and the like, may be useful in meetings. In various embodiments, hardware/software added to these devices can be used to increase their functionality, especially by allowing for direct communication with the central Controller 110 or room controller. In various embodiments, a presentation controller and/or remote control device may include a Wi-Fi® transmitter/receiver (or Bluetooth®). This may allow the device to communicate with the central controller, a room controller, participant device, smartphones, screens, chairs, etc. Wi-Fi® data can also be used in determining the position of the device. In various embodiments, a presentation controller and/or remote control device may include a GPS or other positioning device. This may allow the central controller to determine where the presentation clicker is and whether it is moving. In various embodiments, a presentation controller and/or remote control device may include one or more accelerometers. By knowing the position of the device in three dimensions, it can be determined where the pointer is pointing within a room, which can allow for the presenter to obtain and exchange information with participants or devices within the room. In various embodiments, a presentation controller and/or remote control device may include a microphone. This could pick up voice commands from the meeting owner directed to the central controller or meeting controller to perform certain actions, such as recording a decision made during a meeting. In various embodiments, a presentation controller and/or remote control device may include a speaker. The speaker may be used to convey alerts or messages to a presenter. For example, the presentation controller may alert the user when one or more audience members are not paying attention. As another example, a member of the audience may ask a question or otherwise speak, and the presenter may hear the audience member through the remote control device. In various embodiments, messages intended for the audience (e.g., messages originating from the central controller, from the CEO, or from some other party), may be output through the speaker. As will be appreciated, a speaker may be used for various other purposes.

In various embodiments, a presentation controller and/or remote control device may include a force feedback. This could include hardware associated with the device which causes the device to buzz when prompted. In various embodiments, a presentation controller and/or remote control device may include a display screen. This could be touch enabled, and could show maps, meeting participant information, slide thumbnails, countdown clocks, videos, etc. In various embodiments, meeting participants need to quickly move between virtual meeting breakout rooms. In order to easily navigate between rooms, the attendee could touch the meeting room they need to attend and the central controller automatically puts them in the meeting room for participation. Furthermore, if attendees need to be assigned to a meeting breakout room, the meeting room owner could easily touch the person's picture and drag the icon to the appropriate room. This can be done individually or in bulk by clicking on multiple picture icons and dragging to the appropriate room. In various embodiments, a presentation controller and/or remote control device may include lighting, such as one or more lights capable of displaying different colors and capable of flashing to get the attention of the presenter. Presentation controllers and remote control devices may have one or more capabilities enabled, according to various embodiments. Capabilities may include alerting/communicating with other devices.

Capabilities may include responding to or interacting with an object being pointed at. A presenter (or other person) may point a presentation controller at people to get information about their mood. A presenter may point a presentation controller at a statistic on a slide to pull up additional info. A presenter may point a presentation controller at a chart on a slide to email it to someone. In various embodiments, a clicker vibrates when it is pointed at someone who is waiting to ask a question. In various embodiments, a clicker vibrates when it is pointed at someone who is confused. In various embodiments, Augmented Reality (AR), such as through smart glasses, highlights different attendees in different colors to identify different votes, answers, moods, status, participation levels, etc. In various embodiments, AR may highlight an attendee if the clicker is pointed at the attendee. In various embodiments, a presentation controller and/or remote control device may change colors. In various embodiments, the device can turn red to reflect stress levels of participants. The device can automatically cue up a coaching video on a room display screen based on the current stress level of the room. In various embodiments, voice recognition capabilities may be useful (e.g., as a capability of a presentation controller and/or remote control device) in that they allow for the presenter to perform tasks without having to type messages and without breaking the flow of the presentation. In various embodiments, voiced instructions could be used for jumping to particular slides For example, the presenter could tell the device to jump ahead to "slide 17". For example, the presenter could tell the device to jump ahead "five slides". For example, the presenter could tell the device to jump ahead "to the slide with the financials".

Managing a Meeting Break

Various Embodiments May Facilitate Efficient Meeting Breaks. In Various Embodiments, a Room Screen shows everyone's current location. This may allow a meeting owner to more easily round up late returnees from a break. In various embodiments, people can text in a reason for being late to return. In various embodiments, participants could vote to extend the break. In various embodiments, the central controller could recommend a shorter break. In various embodiments, a countdown clock is sent to participant devices. In various embodiments, a countdown clock is sent to kitchen screens. In various embodiments, lights can go up during a break.

Playing Videos

In various embodiments, one or more videos may be played during a meeting, during a meeting break, prior to a meeting, or after a meeting. Videos may have a number of uses. During a meeting, videos may help to calm people down, instruct people, inspire people, get people excited, get people in a particular state of mind, etc. In various embodiments, a background image or video is used to encourage a particular mood for a meeting. For a commitment meeting, a calming image may be used, e.g., a beach. Music may also be chosen to influence the mood. For an innovation meeting, there may be upbeat music. There may also be a varying background. In various embodiments, the tempo of music (e.g., in a video) may be used to influence the mood. For example, music gets faster as you get closer to the end of the meeting. A video of the CEO may get participants thinking about purpose (e.g., a purpose for the meeting). The video may play two minutes before the meeting. An innovation session may start with a video of what problem the session is trying to solve. Financial stats scroll by so you can see where the company needs help. A program increment (PI) planning meeting (i.e., a standard meeting used as part of the SAFe/Agile development framework) may begin with a video explaining the purpose of the meeting as one to align employees to a common mission and vision. In various embodiments, any other meeting type may begin with a video explaining the purpose of the meeting.

In various embodiments, a background video may show customers being served. Meeting participants may get the feeling, "I want to be part of that". In various embodiments, a cell phone (or other participant device) shows each participant a photo of a different customer. Virtual participants in a meeting may feel a kind of emotional distance to other participants as a result of the physical distance and/or separation. It may be desirable to break down the space between two physically distant people, i.e., to "connect them" more deeply. In various embodiments, participants may pick emojis to represent themselves. Emojis may represent a mood, a recent experience (e.g., emojis show the three cups of coffee that the participant has consumed), or some other aspect of the participant's life, or some other aspect of the participant. In various embodiments, some description (e.g., personal description) of a participant may appear on screen to better introduce the participant. For example, text underneath the participant's video feed may show for the participant: kids names, hobbies, recent business successes and/or a current position in a discussion of a commitment. Various embodiments may include a library of Subject Matter Expert videos in which these SMEs explain technical issues or answer questions related to their subject matter expertise. Videos may be stored, for example, in assets table 6000. SME videos may give people more confidence to make decisions because they have a deeper understanding of technical issues that may improve the decision quality. Videos may provide methodical injections of confidence builders. Videos may provide feedback from previous decisions. Videos may provide Agile software user story expertise. In various embodiments, an attendee has an opportunity to provide reasons that he is late for a virtual or physical meeting. In various embodiments, the meeting platform (e.g., Zoom) texts the attendee and gives him several options to choose from, such as: I will be five minutes late; Having trouble with my PC; I forgot, logging in now; I will not be there.

Enterprise Analytics

In various embodiments, analytics may help with recognizing patterns and making needed adjustments for efficiency and may contribute to the success of an enterprise. The central controller could collect some or all data related to meetings to train Artificial Intelligence (AI) modules related to individual and team performance, meeting materials and content, and meeting processes. Insights from these data could be made available to leadership or other interested parties through a dashboard or through ad hoc reports. An AI module may be trained utilizing meeting data to identify individual performance in leading and facilitating meetings, creating and delivering presentations, and contributing to meetings. Additionally, an AI module may be trained to optimize meeting size, staffing requirements, and the environment and physical layout of meetings. An AI module may be trained to identify meetings that are expensive, require large amounts of travel, or result in few assets generated. Some examples of meeting data that could be used as a training set for these and other AI modules include:

- Meeting size (number of participants, split out into physical and virtual)
- Meeting length (including allocations for travel time if appropriate)
- Number of meetings per day
- Meeting type
- Results accomplished
- Spawned action items or new meetings
- Time of day/week
- Purpose
- Presentation materials
- Participation rate Meetings linked to enterprise goals
Tagged meetings and assets
Cost of meeting
Number of meeting invites forwarded for attendance
Rating of meeting by participants
Biometric data (for example, average level of engagement as determined via a combination of data from cameras in the room and motion data tracked by headsets)
All other collected meeting information Some examples of data related to meeting participants/owners that could be used as a training set for these and other AI modules include:

Participant rating by meeting and aggregated over time
Meeting owners rating by meeting and aggregated over time
Ratings by seniority level. For example, do executives rate the meeting owner higher than their peers?
Time spent in meetings over a period of time
Number of meetings attended over time, by project and by enterprise goal
Sustainability score by participant, owner, department and enterprise
All other collected meeting information for participants and owners
Hardware utilized
Biometric data (for example, level of engagement of a particular meeting participant as determined via a combination of data from cameras in the room and motion data tracked by headsets).

In various embodiments, analytics may be used for generating reports, dashboards, overviews, analyses, or any other kind of summary, or any other view. Analytics may also be used for indexing, allowing for more efficient or more intelligent searches, or for any other purpose. In various embodiments, analyses may include:

An overview of meeting assets generated.
Reporting based on tags associated with meetings or presentation materials.
Find the decision that was made on whether or not we are going into the German market; find the materials generated (e.g. the Kepner Tregoe method of decision analysis, the Porter's 5 forces analysis, the macroenvironment analysis, the Strengths, Weaknesses, Opportunities and Threats (SWOT)) that supported the decision to go into the German market based on asset tagging.
Provide reporting for spikes in meetings. Provide reporting on the number of meetings on a certain day during a specific time period.
Ratings. Provide reports on ratings for meeting, meeting types, assets and individuals (meeting owners and participants)
System notices that the quality of meetings about Project X has decreased. This might then get a manager to audit the next meeting.
Central controller has a database of pre/post meeting questions requiring rating by participants and selected by the meeting owner.
Tables/chairs/layout (e.g. how many meeting rooms are "U" shaped, how many chairs does an average meeting room contain, etc.)/equipment type/equipment age
Rooms (physical and virtual)
  Tend to go well—based on ratings by participants and meeting owners
  Facilities issues—based on ratings from meeting participants and meeting owners, including functioning equipment and cleanliness.
  Do people stay awake, engagement and mental and physical fitness based on biometric data collected during the meeting.
  Do actions (audio, warnings, lighting, AC changes, etc.) generate effects? Provide reporting based on environmental changes and the impact to meeting results and biometric data collected.
  All other collected meeting information for meeting rooms The central controller 110 could collect all data related to headset communications and functions so that statistics and insights could be sent back to individuals and teams using a headset. The collected data could also be used to train Artificial Intelligence (AI) modules related to individual and team performance, meeting materials and content, meeting processes, business and social calls, in-game communications, athletic performance, and the like. Insights from these data could be made available to interested parties through a dashboard or through ad hoc reports. An AI module may be trained utilizing headset data to identify individual performance in leading and facilitating meetings, creating and delivering presentations, contributing to meetings, managing calls, athletic achievement, social achievement, and achieving success in a game. Additionally, an AI module may be trained to optimize meeting size, meeting effectiveness, and meeting communications. An AI module may be trained to identify meetings that are expensive, require large amounts of travel, or result in few assets generated.

In some embodiments, a CEO is interested in being more connected with those who work for her, and wants to be able to help a greater number of employees without spending all of her time attending meetings. The CEO could designate "office hours" which could be transmitted to a central controller, or saved into a data storage device of the headsets of all company employees. This would allow employees to connect seamlessly with the CEO, regardless of where they are or where the CEO is. The user's headset could include information via a video display of the headset (or via speakers) with information on whether or not the CEO was already in a call, and an indication of how many people might be currently in line to speak with her. The CEO could also use her headset to manage the priority of incoming calls, moving callers on hold up or down in priority. Users could also provide a short audio clip summarizing the reason for the call via a microphone of the users headset which can be made available to the CEO via a speaker of her headset, enabling more effective prioritization of calls.

In some embodiments, users could subscribe to audio channels by tag, such as a software architect subscribing to all current audio feeds tagged with "architecture."

Analytics regarding the performance of users on a call could also be provided to appropriate personnel at a company. Performance regarding call data could include speaking time, quality ratings from other participants, engagement levels of the user, etc. Input data could include call-related data, biometric inputs, user location, physical movements, volume and pitch of voice, direction of gaze, post-call 360s, tagging data, etc.

Predictive analytics could also be used to help users avoid making mistakes or saying the wrong thing. For example, if a user's headset pulse rate sensor indicates that the user may be agitated while on a call, the processor of the headset may put the user on mute until his pulse rate drops to a level which indicates he is going to be more level-headed. Instead of automatically being muted, the user might be given a verbal warning by the headset or he might be connected via a sub-channel with a coach who can help guide him toward improved performance.

The user headset could also make predictions, either via the processor of the headset or in conjunction with the central controller, predicting when people are not at their best by reviewing camera, microphone, accelerometer, and other sensor data. Predictions by the headset could include whether or not the user is in good health, is tired, is drunk, or whether he might need a boost of caffeine.

Some examples of data that could be used as a training set for these and other AI modules include health data (e.g., blood pressure, pulse rate, pupil dilation, breathing rate), athletic performance data (e.g., velocity, location), emotional data, environmental sensor data (e.g., pollution levels, noise levels).

Security

Maintaining a secure meeting environment may be important to an enterprise. It may be important that only those meeting participants and owners that have privileges to a meeting can actually join and participate. The central controller should maintain information about each person that is used as an additional layer of meeting security. Dimensions that can be used to authenticate a meeting owner and/or participant include:

Facial Recognition

Voiceprint

Various embodiments include a mouse that shows me that my opponent is someone that I have played against before. The mouse may also show prior moves or strategies of my opponent. Similar to how sports teams watch game videos to learn the playing style and strategies of other teams, the same approach may be used with peripherals. For example, Player 1 is invited to play a game with Player 2 or initiates play with Player 2 using a peripheral (e.g. mouse, keyboard). Player 1 requests through the peripheral 3800 to the network port 9410 the previous opening game moves or typical movements from Player 2's processor 9405 and storage device 9445. Player 1 receives the stored game information from Player 2 through the house controller 6305*a-b* and central controller 110 to her device for display on screen 3815. Examples of the information Player 1 receives on the peripheral from Player 2 at the start of the game is that they frequently move to the right in the map sequence, hide behind a building in a combat game, during a chess match make the move 1.e4 75% of the time. This information may be displayed on Player 1's screen 3815 in text form or image form (e.g. chess board showing the typical moves). In addition, Player 1 may receive the complete statistics of Player 2 for a game being played such as the number of lives lost, the type and number of weapons used, the number of chess moves before a win or loss, the amount of time spent playing the game over some time period (e.g. 3 hours of Fortnite® during the last 7 days). All of the information allows Player 1 to gain more insight to Player 2's strategy, strengths and weaknesses for the game being played.

Biometrics Used to Make Game Recommendations

In various embodiments, player biometric and game data is used to more closely match different games for each player. Mouse 3800 and AI accelerator 9460 for Player 1 may collect data over time from sensor 9430 and input device 9420 for use in making game recommendations. For example, Player 1 may play war type games and sensor 9430 detects an elevated heart rate and excessive sweating while at the same time hit rate of weapons decreases and movement of the avatar slows. The AI accelerator 9460 may determine that war games cause Player 1 frustration and do not promote their unique gaming skills. The processor 9405 takes the information collected from storage device 9445 and AI accelerator 9460 and communicates to house controller 6305*a-b*, central controller 110, and/or to various game manufactures. The stored information of Player 1 is used to provide recommendations for games that are less intense that may not cause the heart rate to increase, use less skill and accuracy in using weapons and make the player less frustrated. These game recommendations are sent through the network port 9410 or input device 9420 to the processor 9405 for display on output device 9425. Player 1 may want to switch or purchase the recommended game as a way to achieve a more satisfying experience.

Various embodiments include an adaptive mouse for visual impairment. There may be situations where a visually impaired person may need to have the mouse 3800 to adjust information delivery from output device 9425 to accommodate the impairment. For example, the user may indicate through mouse 3800 that he is visually impaired through input device 9420, and information about the impairment may then be stored in storage device 9445. When game play occurs, images and text that would typically display on screen 3815 may be enlarged based on the visually impaired information stored in 9445. In addition, text images that are typically displayed for non-visually impaired users may now also be audio generated and heard through speaker 3821 (e.g., a message displayed on screen 3815 reading 'Hey, this is Jim. Do you want to listen to my podcast?' may now be heard through speaker 3821 as well). Colors that may typically appear on lights 3818 for non-visually impaired people may now cause the mouse 3800, through output device 9425, to vibrate (e.g. a green light generates 1 vibration, a yellow light generates 2 vibrations, and red light generates 3 vibrations).

Customized Modes for Mouse/Keyboard

A visually or hearing impaired individual may need to enable, disable, modify default settings and store the information in a peripheral. This information may be used by gamers, streamers and other players to deliver and communicate information. For example, user 1 may be hearing impaired, with 50% hearing loss. Using mouse 3800, the user may indicate through input device 9420 that they have lost 50% of their hearing. This information is collected by the processor 9405 and stored in storage device 9445. When the user plays a game, listens to a streamer or podcast, the device may amplify the sound 100% through output device 9425 and speaker 3821 to assist the user in hearing better. In addition, words that may typically be heard in a game, podcast or by a streamer are now displayed on screen 9435 as an alternative form of communication to the user. Likewise, visually impaired individuals with stored data in storage device 9445 (e.g. 75% vision loss) may require that information delivered through screen 9435 is now magnified (e.g. from 100% to 125%) for easier viewing or delivered audibly through output device 9425 and speaker 3821.

Various embodiments include the ability to change the priority settings of the mouse, e.g., so that you can go from work settings to game settings. There may be situations where a peripheral (e.g. mouse) is used for both business and pleasure. A user at work may want fewer visual and audio signals to be sent to them as this can interrupt co-workers. However, when a peripheral is used at home to play a game, the user may want the full features of the visual and audio capabilities. The user may store the work mode preferences in storage device 9445 (e.g. limit audio output on speaker 3821 to only critical alerts, turn off visual alerts on screen 9435) or pleasure mode preferences (e.g. amplified audio of 125% output on speaker 3821, all visual alerts on screen 9435) through input device 9420. For example, at work, device 3800 may be placed into work mode by the user through input device 9420, indicating that the user is in work mode and work mode preferences stored in 9445 are utilized. When normal priority messages sent from the children are received through input device 9420 or network port 9410, these messages may not get displayed on screen 3815 or delivered through speaker 3821 since the preference does not allow this. However, if a critical alert message is received from the user's spouse, the mouse 3800 using work mode preferences now displays the message on screen 3815 and the message is played audibly through speaker 3821. Later in the evening, the user may play a game and indicate through mouse 3800 that they are in game mode and using game setting preferences stored in storage device 9445. When messages, alerts, game sounds and images are sent to the peripheral through input device 9420, these may be displayed on screen 3815 and heard through speaker 3821 since the game mode preferences may not disable these functions.

Authentication

In various embodiments, a user's pattern of interaction with a peripheral device may serve as a presumed unique identifier or authenticator of the user. In such embodiments, it may be assumed that different users interact differently with a peripheral device, and such differences can be discerned using an algorithm. For example, a user's interaction pattern with a peripheral device may be quantified in terms of one or more features. In a first example, when a user types the word "the" on a keyboard, the ratio of (1) the elapsed time between typing the "t" and the "h"; to (2) the elapsed time between typing the "h" and the "e", may serve as one feature. In another example, the absolute elapsed time between typing the "h" and the "e" may be another feature. In another example, the amount of pressure a user uses on a key (or on a button) may be another feature. In fact, there may exist a separate feature for each key or button. In another example, the top speed at which a user moves a mouse may be a feature. In another example, the average speed at which a user moves a mouse during the course of a motion may be a feature. In another example, the pressure a user exerts on a mouse button when the user is not clicking the button may be a feature.

For any given user, values for the aforementioned features, a subset thereof, or any other features, may be recorded and/or calculated based on historical usage data (e.g., based on three hours of usage).

When it is desirable to verify the identity of a user, or otherwise authenticate the user, a new sample of usage data may be obtained from the user. For example, the user may be asked to type a paragraph, or to perform a series of tasks on a website or app that involve clicking and moving a mouse. Usage features may be calculated from the newly obtained usage data. The new values of the usage features may be compared to the values of the usage features obtained from the users historical usage data. If the newly obtained values match the historical values (e.g., the sum of the absolute values of the differences is less than a predetermined amount), then the user may be considered verified.

In various embodiments, a classification algorithm may be used (e.g., a decision tree), to classify an unknown user by deciding which known users data is most closely matched by data newly obtained from the unknown user. As will be appreciated, various embodiments contemplate other ways in which the usage patterns of a peripheral device by a user may be used to authenticate the user.

In various embodiments, data passively obtained from users, such as via sensors (e.g., heart rate sensors) may also be used to create features, and/or to authenticate a user. In various embodiments, sensor data may be used in combination with usage data.

In various embodiments, usage patterns, features obtained from usage patterns, sensor data, and/or features obtained from sensor data may serve as a biometric.

In various embodiments, a biometric may serve as a way to identify or authenticate a user. In various embodiments, biometric may serve as a basis for responding to the user, adapting to the user, enhancing the user experience, or otherwise making a customization for the user. For example, a usage pattern may correlate to a skill level in a game, and the central controller may utilize the inferred skill level to adjust the difficulty of a game.

In various embodiments, certain activities may have legality, eligibility, regulatory, or other rules that vary from location to location. For example, gambling may be legal in one jurisdiction, but not in another jurisdiction. In various embodiments, a peripheral device may be used to authenticate a user's location, or some other aspect of the user, in order to comply with any applicable laws or regulations.

In various embodiments, a peripheral device includes a GPS sensor, a positioning sensor, or any other location sensor or determinant. When a user is contemplating a regulated activity, the peripheral device may transmit to the central controller, or to some other authority, an indication of the user's location. The user may then be granted permission to participate in the regulated activity based on whether or not the activity is permitted in the user's location.

In various embodiments, a peripheral device may be used as part of a process of multi-factor authentication. A user may initially be associated with a particular peripheral device (e.g., with a trusted peripheral device). For example, the user registers a trusted peripheral device in association with his name. Presumably, this peripheral device would henceforth be in the possession of the user. In various embodiments, when a user is attempting to authenticate himself for some reason, a temporary code, personal identification number (PIN), or the like may be sent to the same peripheral device. The user may then key in the same code (e.g., on some other device, such as on a personal computer) as part of the authentication process.

In various embodiments, as part of a multi-factor authentication process, a user is prompted to use a peripheral device. The user's unique pattern of usage may then serve as a confirmation of the user's identity.

The biometric data from the devices could be used for validating survey responses and embedded survey experiments. For example, whether a person actually took the survey and whether the individuals were confused or frustrated by particular survey questions. Additionally, the object of the survey could be to measure an individual's biometric responses when asked particular questions.

Online advertisers often pay per click or impression. These revenue systems are often spoofed by bots or other means. The devices according to various embodiments could be used to authenticate "true clicks" or "true impressions" by verifying that an actual person clicked or viewed the ad. In some embodiments, peripheral device (e.g. mouse, keyboard, headset) movements generated by a user may be transmitted to central controller 110 for correlation of their timing with any clicks on advertising. Clicks that are not associated with any peripheral movement would be deemed as illegitimate clicks. In other embodiments, cameras or sensors (e.g. motion sensors, microphones) may similarly send information to central controller 110 as corroborating data regarding verification of user mouse clicks on advertisements.

Many websites prohibit online reviews, posts, or comments which are posted by bots or other automated means. The devices according to various embodiments could be used to authenticate that online reviews, posts, or comments were made by an actual individual.

In various embodiments, peripheral devices may serve as a first or second check that a live user is providing information. Sensors built into peripheral devices, and vital signs or biometrics read from peripheral devices, may be used to verify that a live user is providing some information or instruction, such as a password, credit card number, review, post, game input, etc.

Advertisers often have difficulty in distinguishing between different users on shared devices and tracking individuals across multiple devices. The devices according to various embodiments could help advertisers disambiguate and track users, either because individuals sign into their devices, or because a user's "fist," or characteristic patterns of inputs could allow the central controller to identify particular individuals using a device or an individual across several devices.

Figure 89:
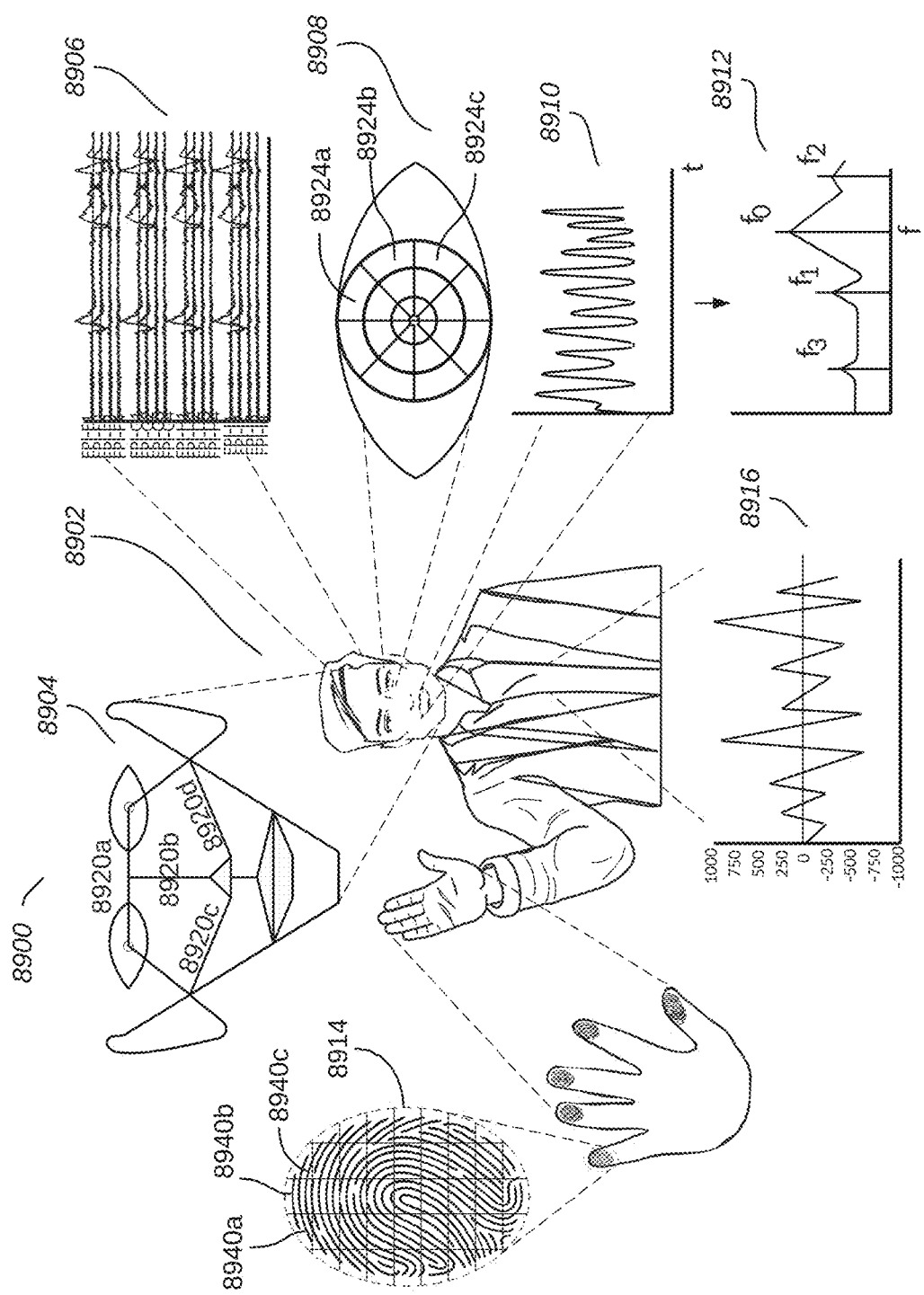
FIG. 89 is an illustration of an individual with biometric information consistent with at least some embodiments described herein.

Turning now to FIG. 89, a diagram of a person with associated biometric data 8900 according to some embodiments is shown.

The depicted biometric data is intended for illustrative purposes, and does not necessarily depict actual data read from an actual human being.

In FIG. 89, an individual 8902 has various types of associated biometric data. Further, a given type of biometric data may be associated with a given part of the body. Facial measurements 8904 are associated with the user's face. Electroencephalogram (EEG) data 8906 is associated with the user's head (i.e., with the brain). Iris and/or retinal data 8908 are associated with the user's eye(s). Voice data 8910 and 8912 is associated with the user's mouth. Fingerprint data 8914 are associated with the user's hand. Heart waveforms 8916, such as electrocardiogram (ECG/EKG), arterial pressure waves, etc. are associated with the user's heart. It will be noted, however, that associations between data and body parts are made for convenience and could be made in any suitable fashion. For example, voice data may just as well be associated with a user's lungs as with his mouth.

In various embodiments, biometric data is used to establish features and/or combinations of features that can be uniquely linked or tied to an individual. The following discussion represents some methods of extracting and using features according to some embodiments. However, it will be appreciated that other methods of extracting and features could be used and are contemplated by various embodiments herein.

With respect to facial measurements 8904, raw data may include an image of a face, such as an image captured by a video camera. The image may be processed (e.g., using edge detection, peak detection, etc.) to determine the location of "landmarks", such as the centers of eyes, the corners of lips, the tips of cheekbones, the bridge of a nose, etc. Distances may then be determined between various combinations of landmarks (e.g., between nearby landmarks). At 8904 are depicted various exemplary distances, including a distance between the centers of the eyes 8920*a*, a distance from the bridge of the nose to the tip of the nose 8920*b*, a distance from a first corner of the nose to a first cheekbone 8920*c*, and a distance from a second corner of the nose to a second cheekbone 8920*d*. In various embodiments, any suitable landmarks may be used, and any suitable distances may be used.

In various embodiments, to allow for different ranges from the subject at which an image may be captured, distances between landmarks may be normalized, such as by dividing all distances between landmarks by a particular distance (e.g., by the distance between the centers of the eyes 8920*a*). In such cases, all distances are effectively expressed as multiples of the particular distance (e.g., as multiples of distance 8920*a*). Normalized distances may then be used as the "X" input (i.e., a vector of inputs) to a classification algorithm, or other AI algorithm, or other algorithm.

Whereas some biometric markers remain relatively constant (e.g., fingerprints), EEG data can change in response to a users actions or to stimuli experienced.

Methods for classifying individuals based on EEG data are discussed in the paper "Exploring EEG based Authentication for imaginary and Nonimaginary tasks using Power Spectral Density Method", Tze Zhi Chin et al 2019 IOP Conf, Ser.: Mater, Sci, Eng, 557 012031, the entirety of which is incorporated herein for all purposes.

With respect to EEG data 8906, raw data may be determined from electrodes placed at two or more points on a user's head, In various embodiments, one of the electrodes is placed proximate to the motor cortex. In the "10-20 system", the electrode may correspond to the "O4" electrode.

A user is asked to imagine performing a task repeatedly, such as opening and closing his hand once every second for sixty seconds, where the seconds are marked with an audible tone (e.g., with a metronome), In various embodiments, any suitable task may be performed. In various embodiments, the task need not be repetitive.

As the user performs the imaginary task, a voltage differential is measured between two electrodes. An amplifier may be used to amplify the voltage differential. The voltage differential may be recorded as a function of time (e.g., using multiple samples; e.g., with a sample rate of 1024 Hz), thereby generating a time series waveform. In fact, voltage differentials may be recorded across multiple pairs of electrodes, thereby generating multiple waveforms (i.e., one waveform for each pair of electrodes). Graphic 8906 shows exemplary waveforms from 16 different pairs of electrodes.

The raw waveform(s) may be filtered to preserve only certain ranges of frequencies. Commonly recognized frequency bands with respect to EEG data include delta, theta, alpha, beta, and gamma frequency bands. In various embodiments, a bandpass filter (e.g., a Butterworth bandpass filter) is used to preserve the beta frequency band (from 13 to 30 Hz).

The spectral density of the filtered waveform is then estimated using Welch's method. Welch's method includes segmenting the filtered time-series into overlapping 1-second segments, applying a windowing function at each segment, transforming the results using a discrete Fourier transform, and computing the squared magnitudes of the transformed results, The squared magnitudes are then averaged across all the results (i.e., all the segments). At the end is a set of frequency "bins" and associated power measurements for each bin, i.e., a power spectral density. In various embodiments, other methods of computing a power spectral density may be used.

Features are then extracted from the power spectral density. In some embodiments, features include each of the:

mean (i.e., the mean power magnitude across all the frequency bins), median, mode, variance, standard deviation, minimum and maximum.

In some embodiments, features are the individual power levels for the respective frequency bins.

Once extracted, features then serve as an input to a K-nearest neighbor classification algorithm. In various embodiments where authentication of a user is desired, the feature vector (i.e., the "X" vector) must fall within a predetermined "distance" of the reference vector (i.e., the "Y" vector) for the user in order to make an affirmative authentication. In various embodiments, any other suitable algorithm may be used.

In various embodiments, rather than asking a user to perform a particular task, the headset or central controller 110 may observe a task that the user is performing and/or a stimuli that the user is experiencing. For example, the headset may observe (e.g., via a forward facing camera in the headset) that a user is looking at a particular piece of machinery. A waveform may be determined at the time of the task or stimuli, and this waveform may be compared to a reference waveform generated under similar conditions (e.g., when the user was performing a similar task, or experiencing similar stimuli).

In various embodiments, a classification algorithm (or other algorithm), seeks to determine not whether a subject corresponds to a particular individual, but rather whether a subject's mental state corresponds to a particular mental state (e.g., "alert", "drowsy", "drunk", etc.). For example, it may be desirable to assess whether an individual is in an alert mental state prior to entering a room containing dangerous equipment.

The process for classifying a mental state may proceed along similar lines, but where a reference signal is not necessarily derived from the subject being tested. Rather, a reference signal for an "alert" mental state may come from a different individual, or may represent an "average" signal from various individuals each of whom is known to be in an "alert" mental state.

Various embodiments seek to classify a mental state of "recognition" or "familiarity", in contrast to such states as "novelty" or "confusion". In such embodiments, a user may see or be shown a stimulus (such as a piece of lab equipment). After having experienced the stimulus (e.g., seen the object), the user's mental state may be classified as one of "recognition", or "novelty". It may thereby be determined whether or not the user has had prior experience with the stimulus (e.g., whether the user has seen the object before). In authentication embodiments, a user may be shown an object which the authentic user will likely recognize, but which an imposter likely will not. Then, based on the user's classified mental state, the users identity may be confirmed, or not.

With respect to iris and/or retinal data 8908, raw data may include an image of an iris or retina. The captured image may be divided into sectors. These sectors may be of standardized size and shape (e.g., a sector encompasses 45 degrees of arc and one third the radius of the image of interest, e.g., one third the radius of the iris). Exemplary sectors are depicted at 8924a, 8924b, and 8924c. Various embodiments contemplate, however, that more or fewer sectors could be used, and differently shaped sectors could be used.

For each sector, an overall grayscale metric may be determined. For example, a sector that is very light in color receives a metric of 0, while a sector that is very dark in color receives a metric of 1. In various embodiments, the grayscale metric may be determined by averaging the color across the whole sector (e.g., by taking an average value of all the constituent pixels falling within a sector).

In various embodiments, to allow for different illuminations at which an image might be captured, grayscale values for sectors may be normalized. For example, the brightest sector receives a value of 0, the darkest sector receives a value of 1, and grayscale values for other sectors are scaled so that their proportionate distances from the values of the brightest and darkest sectors remain the same.

Once sectors receive grayscale values, such values may then be used as the "X" input to a classification algorithm, etc.

With respect to voice data 8910, raw data may include pressure data sampled from a microphone (e.g., at 48 kHz), thereby generating the depicted time series waveform. The waveform may be transformed into the frequency domain, such as via a Fourier transform, thereby generating a frequency spectrum 8912. A peak detection algorithm may then be used to find peak frequencies (i.e., frequencies representing local maxima in the frequency spectrum), A predetermined number of the most strongly represented peak frequencies may be selected. For example, the 10 strongest peak frequencies may be selected. These may be sorted by amplitude, and then used as the "X" input to a classification algorithm, etc.

In various embodiments, when peak frequencies are detected, only fundamental frequencies are considered, and harmonic frequencies are eliminated from consideration. For example, if there are peaks detected at 440 Hz and at 880 Hz, the peak at 880 Hz may be eliminated from consideration.

In various embodiments, rather than detecting peak frequencies, amplitudes a1, a2, a3, etc. may be recorded for a set of predetermined frequencies f1, f2, f3, etc. The amplitudes may then be used as the "X" input to a classification algorithm, etc.

With respect to fingerprint data 8914, raw data may include an image of a fingerprint. The captured image may be divided into regions. These regions may be of standardized size and shape (e.g., a region is a square 0.5 millimeters on a side). Exemplary regions are depicted at 8940a, 8940b, and 8940c. For each region, an overall grayscale metric may be determined. And analysis may proceed as described above with respect to iris/retinal data 8908.

With respect to heart waveforms 8916, raw data may include, for example, an ECG waveform. A typical ECG waveform may include five standard segments, labeled P, Q, R, S, and T. Each has a biological significance (e.g., the P segment corresponds to contraction of the atrium). Each segment may have an associated duration and an associated amplitude. For example, the P segment may last 0.11 seconds and have an amplitude of 0.3 mV. In addition, since not all segments are contiguous, additional segments may be defined with combinations of letters (e.g., where ST represents the interval from the end of S to the beginning of T).

In various embodiments, the durations and amplitudes of the different standard segments may serve as features. Additionally, durations for the additional segments (e.g., for ST) may also serve as features. These features may then be used as the "X" input to a classification algorithm, etc.

Gestures

In various embodiments, it may be desirable to identify someone based on their gestures, such as by their head motions when they are wearing a headset. As such, it may be desirable to extract and/or utilize certain features of detected gestures as input to a machine learning model, algorithm, AI algorithm, and/or as input to any other algorithm. For example, the output of such an algorithm may be an identification of an individual (e.g., from among multiple possible individuals), or the closeness of fit between an input gesture and a reference gesture (e.g., an indication of confidence that a person is who he says he is). In various embodiments, gestures may be recorded and/or detected by means of motion sensors, accelerometers (e.g., accelerometers 4070a and 4070b), or the like.

In various embodiments, features of gestures may include one or more of: the distance moved in one direction (e.g., the distance of a head motion from top to bottom when someone is nodding his head); the number of reversals in direction per unit time (e.g., the speed with which someone shakes their head or nods their head); the maximum upward distance moved when compared to a neutral position (e.g., how far does someone lift their head during a head nod); the maximum downward distance moved when compared to a neutral position; the most commonly assumed position (e.g., how does someone commonly hold their head, whether it be straight, tilted slightly to the right, tilted forward, etc.); the amount of head motion associated with speaking; the amount of head motion associated with drinking; the amount of head motion exhibited when responding to a voice from behind the user (e.g., does the user turn his head to face the other person); and/or any other suitable features.

Productivity/Performance Enhancements

In various embodiments, a peripheral device measures the performance of an associated user device (e.g., the speed, processor load, or other performance characteristics). The peripheral device may determine such performance in various ways. In some embodiments, a user device informs the peripheral device of the current processor load, the current availability for inputs, or some other measure of performance. In various embodiments, a peripheral device may sense how frequently it is being polled by the user device for user inputs at the peripheral device, how frequently the user device is accepting messages from the peripheral device, how frequently the user device is sending signals back to the peripheral device, or any other indication of the performance of the user device. In various embodiments, a peripheral device may indirectly infer the performance of a user device. For example, if a user is repeating the same input motions at a peripheral device, it may be inferred that the user device has been slow to register such motions. For instance, a user may be trying to click a tab on a web browser, however the tab may be very slow to come up on the user device because the user device is occupied with some other process or is otherwise exhibiting poor performance characteristics. A peripheral device may infer poor performance of a user device if the user is making repetitive inputs or motions, if the user is employing exaggerated motions, if the user is waiting an unusually long time between motions (e.g., the user is waiting for the user device to register an earlier motion before making a new motion), if the users rate of typing has slowed down, or if the pattern of user inputs at the peripheral has changed in any other fashion.

In various embodiments, by providing insight into the performance of a user device, a peripheral device may assist in the pricing of a warranty or other service contract for the user device. For example, if the user device is exhibiting poor performance, a warranty may be priced more expensively than if the user device is exhibiting good performance characteristics. In various embodiments, peripheral devices may be used to suggest to a user that the user obtain professional assistance with improving the performance of the user device. In various embodiments, a peripheral device may trigger an application or other program that is designed to increase performance of a user device (e.g., a memory defragmenter).

In various embodiments, a peripheral device may adjust the data it sends to a user device based on the performance of the user device. For example, if the user device is exhibiting poor performance characteristics, then the peripheral device may limit data sent to the user device to only high-priority data. For example, the peripheral device may prioritize data on basic motions or other user inputs, but may refrain from sending data about the user's vital signs, ambient conditions, voice messages created by the user, or other types of data deemed to be of lesser priority. If performance characteristics of a user device later improve, then the peripheral device may send data or signals that had been previously held back.

In various embodiments, a peripheral device may be the property of a company, or other organization. In many organizations, peripheral devices are assigned to individuals. For example, an individual has his or her own desk, and peripheral devices reside more or less permanently at the desk. However, in situations where individuals do not work full-time, are not in the office full-time, are not at their desk frequently, or in other situations, a peripheral device may remain unused for a significant period of time.

In various embodiments, a company or organization may increase the utilization of peripheral devices by allowing such devices to be shared among different users. For example, users with complementary schedules (e.g., one user works mornings, and the other user works afternoons) could share the same peripheral device. This would allow a company or other organization to get by with fewer peripheral devices, or to permit greater usage of expensive peripheral devices.

In various embodiments, users may schedule time to use peripheral devices. When it is a given user's turn to use a device, the user's name, initials, or other identifying information may appear on the peripheral. In various embodiments, when it is a user's turn with a peripheral, only that user may activate the peripheral, such as with a password or a biometric.

In various embodiments, a peripheral may track its own usage. The peripheral may discover patterns of usage. For example, the peripheral may discover that it is never used on Wednesdays. Based on the pattern of usage, the peripheral may advertise its availability during times when it would otherwise be idle. For example, a peripheral may advertise its availability every Wednesday. A user in need of a peripheral during such idle times may sign up to use the peripheral at these times. Alternatively, a scheduler (e.g., the central controller) may assign peripherals to different users who are known to be in need at such times.

In various embodiments, a peripheral may provide instructions to a user as to where to leave the peripheral when a user is done with it (e.g., leave it on the conference table of the marketing department), so that the next assigned user can begin using the peripheral.

In various embodiments, a peripheral may be configurable to communicate with different user devices. A switch or other input device on the peripheral may allow the user to associate the peripheral with different user devices. For example, a user may place a switch on a keyboard in one position, after which the keyboard will direct keystrokes to a personal computer; the user may place the switch on the keyboard in another position, after which the keyboard will direct keystrokes to a tablet computer. The switch may be physical. In various embodiments, the switch is virtual, such as a picture of a switch on a touch screen.

In various embodiments, a peripheral device saves one or more inputs to the device. Such inputs may include key presses, button presses, wheel scrolls, motions, touches on a touchpad, turns of a trackball, or any other inputs. In various embodiments, a peripheral device may save sensor readings. Saved inputs may include timestamps or other metadata. Such data may allow the inputs to be placed in chronological order.

In various embodiments, a user may search through old inputs to a peripheral device. For example, a user may enter a sequence of inputs which he wishes to find from among historical inputs. In the case of a keyboard, a user may wish to search for a sequence of keystrokes, such as a word or a phrase. The user may key in such keystrokes into the keyboard. The keyboard may then display to the user (e.g., via a display screen) any matches to the user's search. The keyboard may display context, such as keystrokes that were entered before and after the particular keystrokes that are the subject of the search. In various embodiments, the keyboard may present search results in another fashion, such as by transmitting the results to a separate display device, by saving the results to a memory (e.g., to an attached USB thumb drive), or in any other fashion.

Where a user is able to search for inputs on a peripheral device, the search may effectively span across multiple applications and even across virtualized OS partitions. In other words, a single search may locate inputs that were directed to different applications, and even two different OS partitions.

In various embodiments, a peripheral device may track usage statistics. Such statistics may include number of buttons pressed, number of times a particular button was pressed, number of times a particular key was pressed, the distance a peripheral was moved, the number of different sessions during which a peripheral was used, the number of times a headset was put on, or any other usage statistic. Usage statistics may also be tracked by another device, such as a user device linked to a tracked peripheral device.

In various embodiments, an app may allow a user to view usage statistics. The app may communicate directly with a peripheral device, such as for the purposes of uploading usage statistics. In various embodiments, the app obtains usage statistics from the central controller, which in turn receives such statistics from a tracked peripheral device (e.g., directly, e.g., indirectly).

In various embodiments, a peripheral may track patterns of usage and associate such patterns with either productive or non-productive work. Examples of non-productive work may include playing video games, surfing the web, arranging photos, or any other activities. Initially, a peripheral may receive information about an app or program with which a user is interacting. Based on the type of app, the peripheral may classify whether such activity is productive or not. In various embodiments, a user may classify different apps or activities as productive or not, and may indicate such classifications to a peripheral device.

The peripheral device may then learn to recognize patterns of inputs associated with a productive activity, versus those associated with a non-productive activity. For example, in a game of solitaire, a peripheral device may learn to recognize the repetitive motions of dragging cards to different locations. A peripheral device may later classify a user's pattern of inputs without direct knowledge of the app to which such inputs are directed.

In various embodiments, if a peripheral device determines that a user is engaged in non-productive activities, the peripheral device may take one or more remedial actions. Actions may include: shutting off, reducing functionality, temporarily shutting off, alerting a user that he is engaged in a non-productive activity, or any other remedial action.

In various embodiments, video footage may be captured of a user typing. Video footage may be captured, for example, by a camera, such as by a camera peripheral device. The video footage may be used for improving auto suggestion, auto complete, computer generated text, or for any other tasks. Context clues from the video (e.g., derived from the video) may include speed, typing mistakes, deleted words, text that gets modified, and any other clues. These contextual clues or features may be used in combination with surrounding text in order to make new predictions (e.g., in order to predict the remaining words in a sentence). In various embodiments, contextual clues may be used for sentiment analysis. For example, if a user is typing in a very animated way, then a happy or excited sentiment may be inferred. In various embodiments, contextual clues are used in combination with the inferred meaning of the text in order to estimate a sentiment.

In various embodiments, a peripheral device may correct or otherwise alter user inputs. The peripheral device may make such corrections or alterations prior to transmitting the inputs to a user device. In various embodiments, a keyboard may correct typing inaccuracies before displaying, transmitting, or otherwise handling user inputs. For example, a user might type 'teh' and the keyboard outputs 'the' to the associated user device (e.g., computer).

In various embodiments, a peripheral device may make automatic corrections based on both a particular input (e.g., an erroneous input), and a user behavior (e.g., typing style). For example, one type of error may be common with a particular typing style. Thus, for example, if an error is detected, then the error may be corrected if it is known that the user employs that typing style. Identified errors or mistakes may be handled differently depending on whether the typing style is, for example, 'touch', 'chop-stick', 'looking at', 'anthropometry', etc.

In various embodiments, certain mistakes or errors may be more common with certain types of keyboards. For example, the relative key spacing on certain types of keyboards may make it more common for certain keys to be inadvertently interchanged. In various embodiments, an identified error may be corrected one way if a user has one type of keyboard, or another way if the user has another type of keyboard.

In various embodiments, a user's game performance, chess performance, productivity, etc., is predicted based on initial movements, initial activities, initial performances, and/or environmental queues. For example, the central controller may predict a user's ultimate score in a game based on his first five minutes of play. As another example, the central controller may predict a user's performance based on the ambient noise level. If it is predicted that the user will achieve a high performance, then the user may be encouraged to continue. However, if it is predicted that the user will achieve a poor performance, then the user may be advised to halt his activities (e.g., halt his game playing), seek to change his environment (e.g., move to a quieter place), or to take some other action (e.g., to take a deep breath).

In various embodiments, tracking performance on a game (or other task, e.g., typing speed) may be used to measure the effectiveness of vitamins, food, red bull, drugs, etc. For example, it may be desirable to market a product as a performance enhancer, or it may be desirable to ensure that a product does not have harmful side effects, which might manifest themselves as poor performance in a video game or other tasks. Thus, in various embodiments, players may be asked to document when they have ingested certain vitamins, food, drinks, or other items. The player's performance (e.g., game score) may then likewise be documented. In various embodiments, a player is asked to play a game or perform some other task both before and after ingesting a food, beverage, vitamin, drug, etc. In this way, the effects of the item ingested can be better discerned. In various embodiments, when a sufficient number of players have ingested an item and also performed a task, a conclusion may be drawn about the effects of the ingested item on the performance of the task.

Following an aforementioned experiment, for example, an energy drink manufacturer might advertise that after one drink, game performance is elevated for 2 hours, versus only 1 hour for the competition.

In various embodiments, a user's ingestion of an item may be documented in an automated fashion. For example, a pill bottle may communicate wirelessly with a user device, with the central controller, or with some other device. The pill bottle may automatically note when it has been opened, and transmit the time of opening to another device for documentation.

Functionality Enhancements

In various embodiments, a mouse or other peripheral may generate a collision alert. The alert may be generated when the mouse is in proximity to another item, when the mouse is heading in the direction of another item, or under some other suitable circumstance. It is not uncommon for a user to have a beverage (e.g., a hot beverage) on a desk with a peripheral. A collision detection alert may save the user from knocking over the beverage. In various embodiments, the alert may be in the form of a beep or some other audible sound. In various embodiments, a peripheral device will brake, such as by locking a wheel on the underside of the device.

In various embodiments, a mouse pointer may be configured to move in non-standard ways. For example, rather than moving in a continuous fashion that mirrors the motion of a mouse, a mouse pointer may follow an edge (e.g., of an application window), jump from one discreet location to another (e.g., from one text entry box to another), or take some other non-standard path. The configuration of mouse movement may be program or app dependent. For example, within the window of an app, the mouse pointer behaves one way, while outside the window of the app the mouse pointer behaves in another way.

In various embodiments, the motion of a mouse is projected from two dimensions into one dimension. The one dimension may correspond to some edge in an app, such as to the edge of a table, the edge of a row of cells (e.g., in a spreadsheet), the edge of a page, or to any other edge, or to any other one-dimensional object. Thus, for example, if a user moves the actual mouse perpendicular to the edge, then the mouse pointer does not move at all. On the other hand, if the mouse moves parallel to the edge, then the mouse pointer will move along the edge.

In various embodiments, a mouse pointer may move only between certain objects. For example, the mouse pointer moves only from one cell to another cell in a spreadsheet. As another example, a mouse pointer moves only between examples of a particular phrase (e.g., "increased revenue") in a text document. This may allow a user to quickly find and potentially edit all examples of a particular phrase or wording. In various embodiments, a mouse pointer moves only to instances of the letter "e". In various embodiments, a mouse pointer moves only to proper names. In various embodiments, a mouse pointer is configured to move only among instances of a particular category of words or other objects.

In various embodiments, a mouse pointer is configured to move from one text entry box to another. For example, if a user is filling in a form, each nudge of the mouse will automatically move the mouse pointer to the next box to fill in. The mouse may also auto-fill text entries based on stored information or based on deductions.

In various embodiments, a peripheral provides noise cancellation. A peripheral may receive an indication of ambient sounds, such as via its own microphone, or via signals from other devices. The peripheral may then emit its own sounds in such a way as to cancel the ambient sounds. For example, a peripheral device may emit sound waves that are of the same frequencies, but 180 degrees out of phase with the ambient sound waves. The peripheral device may further estimate the location of a user, such as via physical contact with the year, via a visual of the user (e.g., using a camera), via knowledge of a user's typical positioning with respect to the peripheral device, or in any other fashion. Having estimated the location of the user, the peripheral device may better generate sound waves that cancel the ambient sound waves at the location of the user.

Customization and Tailoring

In various embodiments, the outputs of a peripheral device (e.g., a mouse, keyboard, or headset) may be customized. Outputs may include beeps, tones, clicking sounds, pressing sounds, alerts, alerts to incoming messages, warning tones, lights, light blinks, or any other outputs. Customizations may include changing volume of a sound or other noise. For example, to avoid irritation, a user may wish to silence any audible outputs coming from a peripheral device. This may constitute a silence mode. In various embodiments, a volume of audio outputs may be set to any desired level.

In various embodiments, a particular melody, tune, jingle, tone, note, beat, rhythm, or other audio may be set for an output of a peripheral device. For example, a user may customize a sound that will be made by a mouse when there is an incoming message from another user. In various embodiments, a user may customize the sound of mouse clicks, scrolls of a mouse wheel, key presses on a keyboard, or any other sound. For example, a mouse click may assume the sound of a chime. In various embodiments, a user may customize any audible output that may be made by a peripheral device.

In various embodiments, sounds emanating or resulting from a peripheral device may be broadcast only by a headset. For example, the sound of a mouse click is broadcast only within a headset that a user is wearing. In this way, for example, sounds made by a peripheral device may avoid irritating other people in the vicinity.

In various embodiments, a user may purchase, download, and/or otherwise obtain sound effects for a peripheral device.

In various embodiments, the physical appearance and/or the physical structure of a peripheral device may be customizable. A user may have access to various component physical structures of a peripheral device. The user may have an opportunity to assemble the component structures in different configurations as desired by the user. For example, a user may have access to blocks, beams, rods, plates, or other physical structural components. These components may then snap together, bind together, screw together, join with hooks, or otherwise come together.

By assembling his or her own peripheral device, a user may customize the size of the device to best suit his hand size or hand orientation. A user may select components with a desired texture, hardness, weight, color, etc. A user may select components with a desired aesthetic. A user may also construct a peripheral device with an overall appealing shape.

In various embodiments, a user may add components that provide entertainment, distraction, or other appeal. For example, a user may build a fidget spinner into a mouse.

In various embodiments, inputs received at a peripheral device may be reflected or manifested in a game character, in a game environment, or in some other environment. Inputs received may include button presses, mouse motions, key presses, shakes of the head, nods of the head, scrolls of a wheel, touches on a touchpad or touch screen, or any other inputs. Inputs may include pressure used (e.g., to press a key or a button), speed (e.g., the speed of a mouse motion), or any manner of providing an input. Inputs may also include sensor readings, such as readings of a user's heart rate, breathing rate, metabolite levels, skin conductivity, etc. In various embodiments, features or derivative values may be computed based on inputs. For example, the rate at which keystrokes are made, the variation in time between mouse motions, the longest mouse motion in a given period of time, or any other value derived from inputs may be computed.

In various embodiments, inputs or derivatives of inputs may be translated into characteristics or attributes of a game character or game environments. Attributes may include the manner in which a character makes footsteps. For example, if a user's inputs are made with a relatively large amount of force (e.g., relative to the typical force used by a user), then the footfalls of a game character associated with the user may be more forceful. Attributes may include the footwear of a character, the attire of a character, the weight of a character, the speed at which a character moves, the facial expressions of a character, the breathing rate of a character, hairstyle of a character, or any other attribute of a character or a game environment.

In various embodiments, the weather in a game environment is dependent on user inputs. For example, if a user's heart rate is high, the clouds in the sky of a game environment may be moving quickly.

In various embodiments, a user may create custom mouse pointers. The user may create a mouse pointer that incorporates a favored picture (e.g., a picture of the user's dog), logo, or other graphic. In various embodiments, a user may send a custom mouse pointer to another user, such as by sending the mouse pointer to the other users mouse. The other user may then have the opportunity to view the mouse pointer, e.g., reflected on a screen of an associated user device. The user may then have the opportunity to continue using the mouse pointer, or to decline to use the mouse pointer.

In various embodiments, a mouse pointer may react to its environment. For example, if the mouse pointer is a dog, and the mouse pointer comes near to a word (e.g., in a text document) describing a food item, then the dog may lick its lips.

Multiple Modes

In various embodiments, a mouse (or other peripheral device) may be capable of operating in different modes or states. Each mode may utilize received inputs (e.g., mouse click, mouse movements, etc.) in different ways. In a first mode, a mouse may allow interaction with a local or internal application (e.g., with an application 9318 running on the mouse). If the application is a survey application, then, for example, different mouse inputs (e.g., left button versus right button) may correspond to different answers to a multiple choice question. If the application is a messaging application, then, for example, the scroll wheel of a mouse may allow the user to scroll through different pre-composed messages for selection and submission to a friend.

In a second mode, a mouse may function as a traditional mouse, and inputs received at the mouse may be passed to a user device, such as to control an application being run on the user device.

As a mouse may have a limited number of input components (e.g., buttons), it may be difficult for the mouse to operate a local or internal application and serve as a traditional mouse at the same time. If the mouse attempted both, then a given input provided by a user for one purpose (e.g., to answer a survey question on the mouse) could be inadvertently misinterpreted as being intended for another purpose (e.g., as a click within an application on a user device).

Thus, it may be advantageous that a mouse can switch between modes whereby in one mode user inputs are directed to an internal application, and in another mode the mouse is functioning traditionally. In various embodiments, a user may switch between modes using some predetermined input (e.g., three rapid clicks on the right mouse button). In various embodiments, a mouse may include a dedicated switch, toggle, or other component for switching between modes. In various embodiments, a mouse may be capable of operating in more than two modes.

Social Connectivity

Various embodiments provide for a quick and/or convenient way for a player to initiate a game. Various embodiments provide for a quick and/or convenient way for a player to initiate a game with a select group of other players (e.g., friends). Various embodiments provide for a quick and/or convenient way for a player to invite other players into a gaming environment, such as a private gaming environment, or such as a private game server.

In various embodiments, a player may use a sequence of keystrokes or button presses (such as a hotkey sequence) to initiate a game, invite players to a game, invite players into a gaming environment, etc. For example, a single click of a mouse by a player brings the player's friends into a private game server.

In various embodiments, two or more peripheral devices are configured to communicate with one another. The lines of communication may allow transmission of messages (e.g., chat messages, taunts, etc.), transmission of instructions, transmissions of alerts or notifications (e.g., your friend is about to start playing a game), and/or transmission of any other signals.

However, in various embodiments, it may be desirable for a given user to indicate that the user is unwilling or unavailable to receive communications at his peripheral device. For example, the user may be working, or may be away from his user device and associated peripheral device. In various embodiments, a peripheral device may be configured to receive communications only during certain times, such as only on weekends, only between 8 a.m. and 10 p.m., etc. In various embodiments, a peripheral device may be configured to not receive communications during particular hours. These may be, e.g., "Do not disturb" hours.

In various embodiments, a peripheral device can be manually set to be unavailable as for communication. For example, when a user steps away from a peripheral device, the user may manually set the peripheral device to be unavailable to receive communications. In various embodiments, a peripheral device may automatically detect when a user has stepped away from the peripheral device, or is no longer using the peripheral device for the time being. For example, if there has been more than five minutes of inactivity, then a peripheral device may automatically configure itself to stop receiving communications. When a user returns to a peripheral device, the peripheral device may detect the usage by the user, and may once again configure itself to receive communications.

In various embodiments, if a peripheral device is configured to not receive communications, the peripheral device may transmit an indication of such configuration to any other device that attempts to communicate with it. For example, if a second user tries to communicate with the peripheral device of a first user, the peripheral device of the first user may send an automatic message to the second user indicating that the first user is not available to receive communications.

In various embodiments, a peripheral device may receive communications, but may also indicate that the user is away or is otherwise not paying attention to such communications. In such cases, for example, any communications received at the peripheral device may be stored and revealed to the user once the user is again available to peruse or respond to communications.

In various embodiments, a document may include metadata describing the author or creator of some part of the document. The document may be a collaborative document in which there have been many contributors. Example documents may include a slideshow presentation, a PowerPoint presentation, a text document, a spreadsheet, or any other document. A user may click or otherwise select some portion of the document, such as a chart of financial data embedded within the document. The user may then be shown the creator of that part of the document. For example, the name of the creator may appear on the peripheral device of the user. In various embodiments, a user may click on a portion of the document and may thereupon become connected to the author of that part of the document. The connection may take the form of a communications channel between the peripheral devices of the initiating user and of the author.

Engagement

In various embodiments, it may be desirable to ascertain an engagement level of a user. This may measure the degree to which a user is focusing on or participating in a task, meeting, or other situation. In various embodiments, it may be desirable to ascertain an engagement level of a group of users, such as an audience of a lecture, participants in a meeting, players in a game, or some other group of users. If there is low measured engagement, it may be desirable to change course, such as changing the format of a meeting, allowing users to take a break, introducing exciting material, explicitly calling on one or more users, or making some other change.

In various embodiments, engagement may be measured in terms of inputs provided to a peripheral device. These may include button or key presses, motions, motions of the head, motions of a mouse, spoken words, eye contact (e.g., as determined using a camera), or any other inputs. Engagement may also be ascertained in terms of sensor readings, such as heart rate or skin conductivity. A level of engagement may be determined or calculated as a statistic of the inputs, such as an aggregate or summary of the inputs. For example, a level of engagement may be calculated as the number of mouse movements per minute, a number of head nods per minute, a number of words typed per minute, the percentage of time that eyes were directed to a camera, or as any other suitable statistic. As another example, engagement may be calculated as a heart rate plus five times the number of mouse movements per minute.

In various embodiments, some inputs may detract from a calculated engagement level. For example some movements of a peripheral device may be associated with distracted behavior (e.g., movements associated with playing a game while a meeting is in place). Thus, the more of such movements, the lower the perceived engagement level.

With respect to a group, an engagement level may be calculated as a mean or median of engagement levels for the individuals within the group. In various embodiments, an engagement level is calculated based on all the inputs received from the group. For example, a group is considered highly engaged if there are more than ten mouse movements amongst all the group members within a given time period. As will be appreciated, various embodiments contemplate other ways of calculating an engagement level.

Game Enhancements, Leveling the Playing Field

In various embodiments, a player may wish to celebrate, taunt, irritate, distract, or otherwise annoy another player. Ways in which one player can irritate another player include playing a sound in the other players headset. These may include the sound of a mosquito, bee, baby crying, siren, fingers on a chalkboard, Styrofoam™ bending, a shrieking wind, or any other irritating or distracting sound. In some embodiments, the sound may be controlled by one player who has won a battle or a round of a game, and they may be able to continue the sound for a certain period of time, while the receiving player cannot turn it off, or down.

In various embodiments, a player may pay for pre-packaged taunts. These may include pre-recorded phrases, sounds, images, videos, or other media that can be used to taunt or annoy another player. In other embodiments, these may also include phrases, sounds, images, videos, or other media that the player can record themselves. When triggered by a first player, the taunts may be delivered to a second player (e.g., with the intermediation of the central controller or some other intermediate device). In various embodiments, a taunt is communicated directly from a first user's peripheral device to a second user's peripheral device.

In various embodiments, a player may receive pre-packaged or recorded media in other ways, such as a reward for winning.

A first player may also irritate a second player by causing the second player's mouse to act in various ways. The second player's mouse cursor may write out "you suck", or some other taunting phrase or gesture. The mouse pointer itself may change to "you suck", "Player 1 rules," or to some other taunting phrase or gesture.

In various embodiments, random inputs or outputs may be added to a player's peripheral device as a way to irritate the player. For example, random motions may be introduced to a players mouse, or added to the intentional motions made by a player with a mouse; or the motions made by a player may be left-right swapped, or up-down swapped, or randomly magnified or scaled down, or randomly slowed down or sped up, or completely disabled for a period of time. Random keys may be pressed on a player's keyboard, or some keys may be disabled, or the entire keyboard may be disabled for a period of time. Random noise, or pre-recorded messages, music, or other sounds may be added to a player's audio feed so that the player has a harder time hearing and processing what is happening in a game. In other embodiments, a players display may be dimmed, flipped upside down or left-right flipped, or random colors or images may be introduced, or the display could be completely disabled for a period of time. As will be appreciated, other distracting or random inputs or outputs may be added to a player's peripheral device or to any device associated with a player.

In various embodiments, a player of a game may wish to be informed of choices or actions made by other players under similar circumstances to those currently facing the player (or under circumstances that the player had encountered). This may allow a player to learn from the decisions of other players, to become aware of what other players did, and/or to compare his own performance to that of other players. When a player reaches a particular game state, the central controller may recount other times that other players had been in similar states. The central controller may generate statistics as to what decision or what actions were made by the other players in the similar game states. The central controller may cause such statistics to be presented to the player. For example, a player may be informed that 60% of players took a left at a similar juncture in the game, with an average subsequent score of 234 points. On the other hand, 40% of players took a right with an average subsequent score of 251. In various embodiments, a player may wish to see decisions of only a subset of other players. This subset of other players may be, for example, the players friends, or top players.

Some Embodiments

In various embodiments, a user may receive offers of work, labor, jobs, or the like. Such offers may come via peripheral devices. For example, offers may be presented on the screen of peripheral devices. In various embodiments, the work offered may involve the use of such peripheral devices. For example, work may include editing documents, providing instruction on using a peripheral device (such as in the context of a particular application), controlling a video game character through a tricky sequence, answering a captcha question, assisting a handicapped user, or any other offer of work. In return for performing work, a user may receive payment, such as monetary payment, game currency, game privileges, or any other item of value or perceived value.

In various embodiments, the usage of peripheral devices may indicate the presence or absence of employees (or other individuals) at a company, or other organization. For example, if an employee's mouse is not used all day, it may be inferred that the employee was absent. Company-wide (or department-wide, etc.) data may be gathered automatically from peripherals to determine patterns of employee absence. Furthermore, peripheral devices may be capable of determining their own proximity to other peripheral devices. For example, a peripheral device may determine that it is near to another device because a wireless signal from the other device is relatively strong.

Proximity data, compared with usage data, may allow a company to determine a spatial pattern of absences among employees. This may, for example, represent the spread of an illness in a company. For example, it may be determined that 80% of employees within twenty feet of a given employee, were absent. Further, the presence or absence of employees may be tracked over time. In this way, a spatial pattern of absences may be correlated to a temporal pattern of absences. For example, it may be determined that, over a given five-day period, the number of absent employees has been increasing, and the distances of the desks of newly absent employees has been increasing relative to a fixed reference point (e.g., to the first employee in a company who was sick).

In various embodiments, peripheral devices may provide early warnings of contagious illness within a company. This may allow a company to take proactive actions to prevent further illness among its employees. This may, in turn, increase employee morale, reduce sick days, reduce insurance costs, or provide other benefits.

In various embodiments, peripheral devices may detect other signs of illness. Such signs may include sneezing (e.g., detected via a microphone), skin conductivity, or other vital signs, or other biometrics. Employees suspected of being ill may be allowed to leave early, may be given their own private offices, may be provided with a mask, etc.

In a gaming context, a player or a viewer may click on another players character and see what hardware that character is using. There may be a link to purchase the hardware. An avatar may wear a logo or other indicia indicating which hardware is currently controlling it.

In various embodiments, a teacher, professor, or other educator may wish to receive feedback about student engagement. Feedback may be particularly useful in the context of remote learning where a teacher may have less direct interaction with students. However, feedback may be useful in any context. In various embodiments, feedback may take the form of biometrics, vital signs, usage statistics, or other data gathered at students' peripheral devices.

In various embodiments, a heart rate is collected for the entire class and the average (or some other aggregate statistic) is sent to the teacher (e.g., to the teacher's mouse). The statistic could be displayed in different colors depending on the value of the statistic. For example, if the average heart rate is high, the teacher might see the color red on her mouse, whereas the teacher might see green if the average heart rate is low. It could display in a different color if elevated. Information about students' heart rates, or other vital signs, may allow a teacher to determine when students are anxious, confused, unfocused, etc. The feedback may allow a teacher to adjust the learning activity.

In various embodiments, an educator may receive information about whether or not students' hands are on their respective mice. If there is a lack of mouse movement among students (e.g., on average) then this may be indicative of a lack of engagement by students.

In various embodiments, rather than receiving continuous feedback about student engagement, a teacher may receive alerts if engagement data or engagement statistics satisfy certain criteria. For example, a teacher receives an alert if the average number of mouse motions per student per minute falls below 0.5. The alert may take the form of a colored output on the teacher's peripheral device (e.g., the teacher's mouse turns red), or it may take any other form.

In various embodiments, a teacher may cause the peripheral devices of one or more students to generate outputs. Such outputs may be designed to grab the attention of students, to encourage student engagement, to wake up students, or to accomplish any other purpose.

In various embodiments, a teacher may cause a student's peripheral to exhibit movements (e.g., a mouse may vibrate, keyboard keys may depress and elevate), to produce sounds, to show color, or to otherwise generate outputs. Such outputs may be designed to encourage student engagement.

In various embodiments, a teacher pushes a quiz to students. The quiz may be presented via a student's mouse or via some other peripheral device. Each student may receive a randomized quiz. For example, each student may receive different questions, or each student may receive the same questions but in different orders, or each student may receive the same questions with multiple choice answers in different orders. The randomization of quizzes may reduce the chance of collaboration among students. Three clicks by one student may be the right answer/response for that one student, and two clicks and a tracking ball move may be the right answer to the same question for another student.

Mouse Output Examples

In various embodiments, a mouse is used to output information to a user. The mouse could contain its own internal processor. Output from the mouse could take many forms. Because some of these embodiments could include relatively expensive components, the mouse could include hardening or an external case of some kind to protect the mouse.

In various embodiments, a mouse includes a display screen, such as a digital display screen. This could be a small rectangular area on the surface of the mouse which does not interfere with the activity of the user's fingers while using the mouse. This display area could be black and white or color, and would be able to display images or text to the player. This display would receive signals from the user device or alternately from the central controller, or even directly from other peripheral devices. The screen could be touch enabled so that the user could select from elements displayed on this digital display screen. The screen could be capable of scrolling text or images, enabling a user to see (and pick from) a list of inventory items, for example. The screen could be mounted so that it could be flipped up by the user, allowing for a different angle of viewing. The mouse display could also be detachable but still controllable by software and processors within the mouse.

In various embodiments, a mouse includes one or more lights. Lights (e.g., small lights) could be incorporated into the mouse, allowing for basic functionality like alerting a user that a friend was currently playing a game. A series of lights could be used to indicate the number of wins that a player has achieved in a row. Simple lights could function as a relatively low-cost communication device. These lights could be incorporated into any surface of the mouse, including the bottom of the mouse. In some embodiments, lights are placed within the mouse and can be visible through a semi-opaque layer such as thin plastic. The lights could be directed to flash as a way to get the attention of a user.

In various embodiments, a mouse may display or otherwise output one or more colors. Colors may be available for display or configuration by the user. The display of colors could be on the screen, mouse buttons, or on any other part of the mouse (or on keys of keyboard). In various embodiments, colors (e.g., color, intensity, color mix, etc.) may be adjusted by the trackball or scroll wheel, or varied by the sensory information collected. The intensity of lights and colors may also be modified by the inputs and other available outputs (games, sensory data or other player connected devices).

In various embodiments, a mouse may generate output in the form of motion. This could be motion of the device forwards, backwards, tilting, vibrating, pulsating, or other motions. Motions may be driven by games, other players, actions created by the user, or by any other cause. Motion may also be delivered in the form of forces against the hand, fingers or wrist. The mouse/keyboard device could become more firm or softer based on the input from other users, games, applications, or by the actual user of the mouse/keyboard.

In various embodiments, a glove may be a peripheral device. In various embodiments, a glove may be part of a peripheral device. For example, a glove may be attached to a mouse. A device attached to a mouse could allow for compression or pulsing of the hand for therapy purposes. The device could provide feedback to the user from other users by simulating compression and pulsing as well.

In various embodiments, a mouse may generate output in the form of sound. The mouse could include a speaker utilizing a diaphragm, non-diaphragm, or digital speaker. The speaker could be capable of producing telephony tones, ping tones, voice, music, ultrasonic, or other audio type. The speaker enclosure could be located in the body of the mouse.

In various embodiments, a mouse may generate output in the form of temperature. There could be an area (e.g., a small area) on the surface of the mouse or on keyboard keys which contains heating or cooling elements. These elements could be electrical, infrared lights, or other heating and cooling technology. These elements could output a steady temperature, pulsating, or increase or decrease in patterns.

In various embodiments, a mouse may generate output in the form of transcutaneous electrical nerve stimulation (TENs). The devices could contain electrodes for transcutaneous electrical nerve stimulation. These electrodes could be located in the surface of the mouse corresponding with areas used by fingertips or by the palm of the hand. These electrodes could also be located in a mousepad or in ergonomic devices such as a wrist rest.

In various embodiments, a mouse or other peripheral device may generate output in the form of smells, scents, or odors. A peripheral device may output scent via an air scent machine (odor wicking or scent diffuser). The devices could contain an air scent machine, either a scent wicking device or a scent diffusing device. This air scent machine could be located in the body of the mouse.

In various embodiments, a mouse may convey messages or other information using standard signals provided to a user device, thereby causing a mouse pointer to move on the user device in a desired way. For example, a mouse may cause a mouse pointer to trace out the word "Hello". In various embodiments, a mouse may cause a pointer to rapidly trace and retrace the same path, thereby creating the illusion of a continuous line, ark, or other shape. I.e., the mouse may cause the mouse pointer to move so quickly that the human eye is unable to discern the mouse pointer as its own distinct object, and sees instead the path traced out by the mouse pointer. In this way, a mouse may output text, stylized text, shapes (e.g., a heart shape), images, cartoons, animations, or any other output. An advantage of creating messages in this way is that such messages need not necessarily be application-specific. In other words, the mouse may cause a cursor to move along a particular trajectory regardless of the application at the forefront of the user device.

In various embodiments, a mouse may convey a message through interaction with an application on a user device. For example, a user device may have a keyboard app that allows a user to "type" alphanumeric keys by clicking on a corresponding area of a displayed keyboard. To convey a message, the mouse may automatically move the mouse pointer to appropriate keys and register a click on such keys, thereby causing the message to be typed out. For example, to convey the message "hello", the mouse may sequentially cause the cursor to visit and click on the "h", "e", "l", "l", and "o" keys.

In another example, a mouse may interact with a drawing application (e.g., with Microsoft® paint) to create shapes, drawings, etc., for a user to see.

In various embodiments, a mouse or other peripheral may store a script or other program that allows it to interact with an application in a particular way (e.g., so as to output a particular message).

In various embodiments, a mouse or other peripheral may have a message to convey to a user, but may require that the user be utilizing a particular application on the user device (e.g., the mouse may only be able to deliver the message through Microsoft® paint). In various embodiments, the mouse may detect when a user is using the appropriate application from the users mouse movements. The mouse may recognize certain emotions as indicative of use of a particular application. The mouse may then assume that such application is in use, and may then cause a message to be conveyed to the user with the aid of the application.

Software

The peripherals according to various embodiments may include processors, memory, and software to carry out embodiments described herein.

Mouse/Keyboard with Stored Value

Mice or keyboards according to various embodiments may become personalized, and could contain items of monetary value such as digital currencies, game rewards, physical items, coupons/discounts, character skins and inventory items, etc. It could also store the identity of the player (and the identity of her game characters), game preferences, names of team members, etc. Game highlight clips could also be stored for later viewing or uploading to a central controller. Access to the stored value/data could require the user to provide a voice print, password or fingerprint to gain access. The value could also be stored with a user device (or central controller) and accessed through a mouse or keyboard.

In various embodiments, users could store their identity for use across games, computers, and operating systems. For example, the mouse could store the player names and passwords associated with all of their favorite game characters. This would enable a player to take their mouse from their home and go to a friend's house to use it during game play there. The user device (e.g., game console) owned by their friend would then read in data from the users mouse, enabling that user to log in with any of their characters and have access to things like saved inventory items like a +5 sword or a magic healing portion. The user's mouse could display the items in inventory on a display screen of the mouse, allowing the user to touch an item to select it for use, with the mouse transmitting the selection to the user device, game controller, or central controller. The user could also have access to store preferences and customization for things like custom light patterns on their mouse. The user's mouse might also have stored game value that would allow a user to buy game skins during a game session at their friend's house.

Because the mouse or keyboard might include items of value, in some embodiments the user must provide a password in order to gain access to the mouse. For example, the user might have to enter a PIN number by touching digits that are displayed on the surface of the mouse, or enter a PIN into the user device which then uses that PIN to get access information from the central controller in order to get access to the value in the mouse. Items stored within the mouse or keyboard could be encrypted, with the user required to provide a decryption key in order to retrieve the item. In other embodiments, unique biometrics (such as an iris scan, fingerprint, heart rate, and the like) could be required in order to gain access to the value stored in the mouse. In one embodiment, the value is unlocked when a unique pace of mouse movements or keyboard pacing matches to those of the user.

In various embodiments, the mouse itself could store encryption/decryption keys for use by the user device, allowing the mouse to act like a secure dongle.

With payment transaction software and processors/storage within the mouse, various embodiments could enable users to make microtransactions in-game. For example, a user could provide a credit card number to the central controller and arrange to have $20 in value loaded onto the storage area of the users mouse. When the user is then playing a game, he could encounter an object like a Treasure Map that could be obtained for $1. The game controller sends the offer to the display screen of the user's mouse, and the user then touches an acceptance location and the $1 is taken out of the $20 in stored value and transferred to the game controller or central controller, after which the Treasure Map is added to the inventory items of the player, either in-game or within the user's mouse itself.

In various embodiments, micropayment transactions could also enable a user to rent game objects rather than buying them. For example, the user might want to obtain a rare game skin for his character in a game, but feels that the purchase price of $10 is too high. After rejecting the purchase, the game controller could send an offer to the user's mouse of a weekly rental period for the game character skin for $1/week. The user accepts the offer and $1 is transferred to the game controller or central controller and the character game skin is then enabled for that user. Each week the player pays $1 until cancelling the subscription. Alternatively, the subscription could be for a fixed period of time, or for a fixed period of game time. For example, the player could get ten hours of use of the game character skin for $1.

Another use for micropayment transactions is to allow a user to send small amounts of money to another player, transferring funds from the user's mouse to the central controller to the mouse of the other user. Such transactions could also be used to support game streamers by enabling simple and quick transfers of value to the streamer.

Some games have treasure chests that a user can elect to open, either by paying an amount of gold coins from the game or real money (such as a micropayment from stored value in the user's mouse) or by simply electing to open it. In one embodiment, the treasure chest requires a random selection from the user. For example, the player might pick a number between one and five (by pressing the number on the touch enabled display screen on the surface of the users mouse), with the Treasure Chest only opening if the player selected the number four.

In various embodiments, a mouse may reveal or unlock items in a game. For example, a player using a mouse may see hidden trap doors when hovering the mouse pointer over a particular region in the game area. A mouse may enable access to particular game levels or areas that may otherwise be inaccessible.

By creating a physical storage location within the mouse, the user could store items like a ring, sentimental items, currency, coins, mementos, etc. For example, the user could store a thumb drive within a locked portion of the mouse, with access requiring the use of a password or thumbprint to access.

Physical items could also be included in the mouse by the manufacturer, with the user able to access that item after achieving a goal such as using the mouse for ten hours, achieving a particular level of a particular game, identifying a list of favorite games, or the like. Once this goal had been achieved, the user device could send a signal to the mouse unlocking the compartment which held the manufacturer's object. To make the object more secure, the compartment could be designed such that attempting to break the compartment open would result in the functionality of the mouse being disabled or reduced in capability. Attempts to break open the compartment could also generate a signal sent to the user device which would then initiate a phone call to the user of the device and also trigger a camera to get video/photos of the mouse.

Gameplay could also unlock keys on a keyboard. For example, the user's keyboard could have three keys that are initially non-functional. They are enabled as the user completes certain goals. For example, the user might have a key unlocked when the user defeats ten opponents in a 24-hour period. This unlocked key could enable a user to open a communication link to game secrets that would improve their chances to win a particular game.

Another aspect of the user's identity is rating information about the user's ability to play a particular game, or a rating of the user's ability to function well on a team. For example, a users mouse might store an evaluation of the user's team skills, such as by storing a rating (provided by other players or determined algorithmically by one or more game controllers) of 9 on a 10 point scale. When the user uses his mouse to play in a new game, that new game can access the 9/10 rating from the user's mouse and use the rating to match the user with other players of a similar team rating level. Even though the user may have never played that particular game before, the user's team rating would allow the player to join a more experienced team than the users beginner's status would at first indicate.

Access to a mouse or keyboard could also be used by other parties to restrict game play. For example, a parent might set play time parameters for a mouse that would lock out a user when that user exceeds three hours of game play in a given day, or it could lock the player out between the hours of 3 PM and 6 PM on weekdays. The mouse or keyboard could also be restricted to certain types of game. For example, the mouse could be set to not operate in a third person shooter type of game.

Access to the mouse could also be restricted based on the condition of the user. For example, the user device or game controller might determine that, based on the mouse inputs currently being received, the user seems to be reacting slower than normal. This might be due to the player being tired or sick. If the player falls below a threshold amount, such as a reaction time of 90% or less of normal, then the mouse could be instructed to end current game play for a predetermined period of time, such as one hour. After that hour is up, the user would again have access to the mouse, but further checks of reaction time would be made. The mouse could also end game play if the user appeared to not be playing their best game. For example, a user playing three minute speed chess might have the game controller set to send the users current chess rating to be stored in the mouse, and when that rating falls by 100 points the mouse automatically ends game play for a period of time. A user playing poker might have access to the mouse and keyboard denied after the user most too much money or was playing in a way that was indicative of a player on tilt.

Stored value in a mouse could also be used to pay for items outside of a game environment. For example, a user at a coffee shop with a laptop computer and mouse could use value in the muse to pay for a coffee. In another embodiment, value stored in a mouse could be used to buy dinner via Seamless.

In various embodiments, value stored in a mouse could be locked up if the mouse was taken out of a designated geofenced area.

In various embodiments, stored value is associated with a mouse or with another peripheral. Value may take physical form, such as gold or currency physically locked inside of a mouse. Stored value may take other forms, such as cryptocurrency, electronic gift certificates, etc. In various embodiments, a user may perform certain actions on a peripheral in order to unlock, receive, or otherwise benefit from stored value. In various embodiments, a user must type in some predetermined number of words (e.g., one million words) to unlock value. In various embodiments, the words must be real words, not random key sequences. In various embodiments, a user must make a certain number of cumulative mouse motions in order to unlock value. For example, the user may move a mouse for one kilometer in order to unlock value.

In various embodiments, a mouse/keyboard or other peripheral device could respond to game conditions; in various embodiments, the mouse and keyboard may gain or lose functionality, or have altered functionality as a result of in-game development, and/or as a result of player actions during a game. In various embodiments, as a result of a player action, or an in-game development, a peripheral device becomes disabled for some period of time. For example, if, in a game, player one shoots the gun out of player two's hand, then player two's mouse may become disabled for thirty seconds. As another in-game example, if player one kills player two, player two's mouse and keyboard are disabled for five minutes. As another example, if a player takes damage in a game (e.g., in boxing), the player's mouse response lags or precision drops. As another example, if a player is drinking alcohol in a game (or while playing a game), mouse responsiveness becomes unpredictable, lags, or the keyboard begins to output more slowly or the wrong character now and then. Gamers would have the option of limiting this type of control to certain people.

In various embodiments, a player may pay to recover lost functionality of a peripheral device. The player may be able to pay to recover lost functionality immediately, or may pay to reduce the period of time for which functionality is lost. A player might pay the central controller, a game provider, or the person who caused the player to lose functionality in his peripheral device.

Mouse Extra Sensors Alter In-Game Character or Avatar or Actual Response from a Mouse-Keyboard A peripheral device (e.g., mouse, keyboard, etc.) may be equipped with various sensors that allow for collection of sensory data. This data could be used to alter the experience of the user(s) in both the virtual world (e.g. the game or virtual activity) and physical world (e.g. the physical mouse or keyboard).

In various embodiments, a mouse includes an accelerometer and/or another motion sensor. The sensor may be used to control the movement of objects in a game, including the movement of objects in three dimensions in a game. The sensor may also be used to control the movement of objects in other environments. In various embodiments, a user may provide an input to the sensor by positioning the mouse, such as positioning the mouse somewhere in 3-D space. A player in a game could use the accelerometer data to control the 3-D movement of objects either above, below, in front or behind the player. This is in contrast to the current 2-D dimensional play and movement. As an example, a player engaged in a combat game could pick up a flare and instead of using a 2-D enabled button or mouse control to launch the flare, the accelerometer equipped mouse could allow the user to move the mouse up to throw the flare up in the air or in the direction the mouse moves. This provides a more realistic experience for the game player.

In various embodiments, an accelerometer or other motion sensor may sense movement or momentum. For example, a user may move a mouse. In response, a character may move in the direction and pace of the mouse. Conventionally, movement of a character is controlled by static processing of buttons or joysticks to move the character in various directions within a game. In order to provide a more enhanced experience, the sensor-enabled mouse could be used to control the pace of movement and direction of the character. For example, if a character is running from the enemy, the mouse could be picked up and held with arms moving as if the user were running. The movement of the arms and pace of the arms could be reflected in the character and their movement. Once the arms stop moving, the character stops. If the user moves to the left, right, jumps up or lowers, the movement of the mouse in those directions could be reflected in the character as well.

In various embodiments, a user may move a mouse to perform a desired action in a game. Movements may include: the tap of the mouse on a surface; the tilting of the mouse to the left, right, front or back; quick movement to the left or right (front/back); or any other movements. Conventionally, mouse clicks or finger taps on a mouse may reflect some action that the user wants to occur on the screen. With a sensor-equipped mouse, the various unique movements of the user could reflect their specific choice in a game or any application setting. For example, as a card game player, the user may signal the dealer to deal another card by simply tapping the mouse; if the user wants to pass, they may quickly move the mouse to the right; or if the user wishes to fold and end the game, they may raise the back of their mouse. These movements could be configured to reflect actions particular to each game.

In various embodiments, a mouse may contain a tactile sensor. A tactile sensor may include galvanic sensors or other tactile sensors. The tactile sensor may be used, for example, to measure and adjust excitement level of the user. A tactile sensor may gather sensory information collected through the skin (e.g., temperature, pressure, moisture, metabolites, vibration).

Many games have predetermined levels and paths to successfully accomplish the game. Users either navigate successfully without much difficulty or fail repeatedly trying to accomplish a task. Measuring the relative excitement/intensity/frustration level (or lack thereof) may possibly make the game more fun. With the collection of sensory data in the mouse-keyboard, the tactile data collected could be used to alter the user experience and make the game more or less difficult. For example, a skilled game player may always navigate through a section of the game with little or no trouble. The tactile sensor is reading that the player's skin temperature, pulse rate and pressure applied to the mouse-keyboard are relatively consistent. In this case, to add to the excitement, the game could automatically introduce new and more challenging scenarios to raise the heart rate, force applied to the mouse-keyboard and overall temperature of the player. Conversely, if a novice player repeatedly fails in areas of the game and the tactile sensors are reading elevated levels, the game could provide on screen coaching to maneuver through the game or introduce easier levels to increase their skill.

In various embodiments, a tactile sensor may measure excitement levels in one player. Other players may then be apprised of the player's excitement level. In various embodiments, sensory information is collected through the skin (e.g., temperature, pressure, moisture, vibration information). Today, player information is either observed on screen or through audio queues. With the collection of tactile information from all players via mouse-keyboard, this information could be sent to each player's mouse-keyboard as another piece of data to enhance the experience and gain insight to their opponents reaction to the game. For example, a player may have an increased heart rate or elevated temperature during an intense battle. This information could be sent to an opponent's mouse-keyboard via lights/vibration during the game in order to adjust their playing style. If they are your enemy in the game, you may notice they are getting agitated and may wish to bring in other forces as they are nearing a point of failure. On the other hand, if the tactile sensory data provided indicates a teammate has increased sensory data and is reflected in your mouse/keyboard, you may wish to abandon your current task and go to assist.

In various embodiments, a tactile sensor may take measurements, which are then reflected in a user's avatar. In various embodiments, a tactile sensor may collect galvanic measure of temperature or moisture levels. Using galvanic measurements, the collected information could reflect in the in-game avatar. For example, if the sensor measures a person's temperature or moisture level (sweat) increasing, the in-game avatar could dynamically change to show the avatar sweating, face becoming red, facial expression of exhaustion, change of clothing to reflect body temperature (e.g., the avatar may wear lighter clothing), and/or the avatar may consume fluids. Conversely, if the sensor measures indicate a calm manner, the avatar could show a pleasant expression, casual stride or cooperative behavior.

In various embodiments a mouse or keyboard may include a biometric sensor. The sensor may determine a heart rate or other vital sign or other biometric measurement. The sensor reading may be incorporated into a game. In various embodiments, a finger sensor (or other sensor) collects the heart rate of the user. The heart rate of the player (user) is collected and provided to the other game players with sensor-enabled mice or keyboards. As the heart rate of the player is collected, the pulsing rate is sent to the other users in the form(s) of light pulses or actual vibration reflecting the exact heartbeat of the player. As a player enters an intense part of the game, or when the player loses the game, the players heart rate may increase. In various embodiments, this increase in heart rate may be seen in another's mouse-keyboard and/or felt via a corresponding vibration. This allows each player to feel more connected to the physical person, making the game appear more realistic.

In various embodiments a mouse or keyboard may include a force sensor. In various embodiments, the force sensor may allow force or pressure controlled movement of game/application items. Forces applied to a mouse-keyboard can be used to invoke actions in a game or application. For example, in a combat game with multiple weapon types, each may require a different level of force to pull a trigger. Instead of clicking a button or moving a joystick to fire a weapon, force applied to a mouse could be used. If one weapon is easier to shoot, the force needed on the mouse could be minimal, whereas larger, more complex weapons may require a higher degree of pressure and/or may require pressure from multiple locations on the mouse-keyboard (e.g. two fingers and the palm of your hand).

As a competitor, the player may wish to manipulate the play of their opponent. The game could allow the player to increase the mouse pressure making it more difficult for an opponent to engage a weapon, or require them to use multiple force actions on the mouse-keyboard to engage a weapon.

In various embodiments, an amount of force or pressure sensed may indicate tension/frustration on the part of a player. Such tension or frustration may be reflected in an avatar. Using forces applied to the mouse-keyboard could indicate frustration by the user. In this case, the in-game avatar could display an expression of frustration or the game could adjust to make elements of the game easier until the frustration level is reduced. If the mouse-keyboard are slammed on the table, this could reflect frustration and cause the avatar to slam their fist on an object or stomp on the ground in a game.

In various embodiments a mouse or keyboard may include one or more lights. In various embodiments, lights may adjust light to display activity, such as player activity. In various embodiments, data about player activity may be collected including player progress, opponent progress, availability, excitement level, rating, etc. Player (user) information may be collected in game or on device; opponent (other user) information may be collected in game or on device or via other connected devices.

Using information collected from multiple sources such as sensor equipped mouse-keyboard, external data sources like weather alerts, amber alerts, alarm systems, temperature sensors, gaming data from other opponents, player availability indicators (active indication versus calendar notification), the lights on a mouse-keyboard could be turned on, off, adjust brightness and patterns to reflect the specific event taking place. For example, if the player is engaged in a combat gaming scenario, the lights on a mouse-keyboard may display a rapid pulsing bright red color on the mouse or keyboard to indicate the battle is intense. On the other hand, if my doorbell rings, my mouse may suddenly reflect a bright green light indicating someone is at the door. These colors, patterns and brightness levels can be adjusted by the user.

Players often have teammates they frequently engage in games. When one player wants to play a game, they may wish to alert others of their availability or see another player's availability. For example, if one player is available to play a game, they may simply press a button on the mouse-keyboard that immediately lights up a green indicator on their friend's mouse-keyboard. This signals to their friend to join a game. Conversely, if for some reason a player is not able to play a game, they could hit a button on the mouse that indicates to others they are not available. This could be a green color or any other visual indicator.

In various embodiments a mouse or keyboard may include one or more audio output devices. In various embodiments, the audio output may be used to locate a misplaced device. In various embodiments, users desire the ability to find devices. As the mouse-keyboard becomes more customized devices that are carried from location to location, the opportunity to lose the device increases. Users may desire the ability to ping their device. For example, if a player takes their mouse to a friend's house to play a game and it is misplaced, the user can log in to their other electronic device and ping the mouse. The sound from the mouse-keyboard can be heard and the device located.

Game players or other users can send an audio signal to a mouse-keyboard. During a game, a user may send their friend or opponent a sound to distract them, encourage them or alert them. For example, if a person is playing a combat game and they ambush an opponent, they could send a loud sound to their opponent to scare them or distract them. Likewise, if during a game they see their teammate about to be attacked, they could alert them via a sound. Furthermore, at the end of a successful win, all team members' sounds could play various tones indicating success.

In various embodiments a mouse or keyboard may include a metabolite sensor. The metabolite sensor may collect or detect chemical content (e.g., potassium, sodium content).

Game players, when alerted to low levels of potassium or sodium (or any measured chemical level via the sensor), could have the game and avatar modified to indicate the response requested in the physical world. For example, if the sensor detects low levels of potassium, the game avatar may suddenly pick up a banana to eat or have it incorporated in the game to find and eat as another challenge. This may also remind the player to actually eat a food rich in potassium to resolve the deficiency. Likewise, other players that notice this activity may also be reminded to encourage the player to eat a food rich in potassium. In this regard, all players are observing and suggesting to each other to maintain good health habits.

In various embodiments, a mouse or keyboard may include an electroencephalogram (EEG) sensor. The EEG sensor may collect brainwave activity.

Game play invokes brain waves and can provide insight into the physical impacts of games on a players brain and also how to develop more challenging and intense games. A headband that measures brain waves could be used to collect this data and send the data to a central controller (possibly via a connected or associated mouse-keyboard) for analysis.

During a game, the EEG sensor could determine if you are having a headache and adjust the game to lessen the intensity. In addition, the brightness in the room, game, mouse-keyboard and any sensory controlled device in the room could be adjusted to lessen the impact on the brain and headache intensity.

During the game, if brain activity indicates stressful signals, the in-game avatar could dynamically change to indicate a potential issue by placing their hands on their head, taking a break or signaling to other players they are not feeling well. This could be an early indication to the player as well that a break from the game is needed.

During a game, if the brain signals are not very active, the game could dynamically change to introduce more complex or challenging activities to stimulate the brain.

In various embodiments a mouse or keyboard may include an electrocardiogram (EKG/ECG) sensor. The EKG/ECG may collect cardiac electrical waveforms. This may allow for game intensity to be measured and adjusted. As games become more complex or other players introduce activities that engage a player, the heart rate can be measured. If the heart rate increases, decreases or remains consistent, the game could be adjusted accordingly. For example, if a user is playing a soccer game and is constantly making goals while their heart rate remains constant, it may indicate the game is not challenging and could lead to boredom or switching the game. The game could introduce more challenging opponents or adjust the player skill and make it more difficult to score goals. Likewise, if the players heart rate is elevated for an extended period of time, the game difficulty could be adjusted to allow for recovery of the heart and a slowing of the heat rate.

In various embodiments a mouse or keyboard may include an electromyography (EMG) sensor. The EMG sensor may collect muscle response.

The mouse-keyboard could be equipped with an EMG sensor to measure muscle activity in the hands, fingers, wrists and arms. The user's muscle response to a game can be measured and game play adjusted. For example, if the EMG recognizes that the hand on the mouse demonstrated weak muscle activity, the sensitivity on the mouse-keyboard could change dynamically to not require such intense pressure to invoke a function during a game. If a user is shooting a weapon and requires pressing of a button, the button friction could change to make it easier if the EMG recognizes weak muscle response.

In various embodiments, players' skills may be ascertained based on EMG data. Adjustments may be made to level the playing field among different players. In order to create a more uniform play for games requiring teams, the EMG data collected from all players could be used to adjust the necessary mouse-keyboard settings, removing any advantage any player may have. For example, if a group of players are engaged in a team sport (e.g., football) and the passing, kicking and handoffs require a mouse-keyboard to be used with some level of muscle activity, those with stronger muscles may have an advantage. Adjusting each player's mouse-keyboard to be consistent so all players' intensity is the same, could provide a more balanced game.

In various embodiments, an EMG sensor in a mouse (or other peripheral) may detect if a player is leaning forward.

In various embodiments, a mouse or keyboard may include a proximity (IR-Infrared) sensor. The proximity (IR-Infrared) sensor may collect information indicative of obstacles or objects in the room.

In various embodiments, using proximity sensors in a mouse-keyboard device can alert the user of objects in the room. Oftentimes a user's back is facing a door making it difficult to see if someone walks in or is looking at the user's computer screen. The proximity sensor can provide the user with immediate information that someone is near them. This can be done by interfacing to the computer screen (or application), providing a message or visual indication of the actual object. The mouse-keyboard could vibrate or display a different color as well.

External Sensors Change In-Game Environment or Virtual Environment

The proliferation of external sensors allow for the data collected to be included as part of a user's in-game experience and reflect an indication of what is taking place in the real world.

In various embodiments, weather sensor data is reflected in a game. The game can collect real-time data from the various weather sources (such as the national weather service) for the physical location in which the player is playing the game. If the central controller receives data indicating rain in the area, the on-screen game environment could change to make it appear that it is raining or provide a sound mirroring the real weather events. In addition, if it is raining in the game environment, an in-game avatar could change to reflect that rain gear is worn. Another example could be tornado activity in the area. If this occurs, the game could alert the player by flashing lights on the player's mouse to get his attention. The player, who may be distracted by the game, could be instructed to take cover and look for a safe place. Likewise, a tornado could display on the screen and disrupt the players competitors.

The indication of thunder in real life could cause the mouse or keyboard of remote team members to vibrate to mirror the feeling of thunder. The same could be done if a snowstorm or heat wave is in the area and the temperature of the mouse or keyboard dynamically changes.

In various embodiments, garage door/doorbell data is reflected in a game. An increased number of garage doors are monitored and controlled electronically. This data could be displayed on the user's game screen or mouse display area as informational to the player/user. For example, as a teenager who is playing a game after school, they may want to be notified that the garage door/doorbell is being activated to determine who is home or to stop the game and focus on another activity (e.g., homework, chores, dinner).

In various embodiments, time of day can be mirrored in the sun/moon brightness on the mouse or keyboard. Based on the geographical location of the mouse, external sources such as the national weather service could provide the sunrise/sunset/cloudiness/moon brightness data. This information can be reflected in the mouse or keyboard display. For example, if the user is playing a game at 2 pm when the sun is bright, the keyboard backlighting could illuminate a bright sunny color. As time progresses and gets closer to dusk, the illumination in the keyboard backlighting could dynamically change to mirror the conditions outside—becoming less bright and softer in color. When sunset occurs and it is dark, depending on the brightness of the moon, the keyboard could adjust to reflect this intensity as well. A sun/moon could display on the mouse screen to match the ambient environment throughout the day.

In various embodiments, ambient sounds could change the in-game environment. Microphones on the users peripheral devices could detect sounds within the environment of the player to incorporate into the game environment. For example, if the bark of a dog was picked up by a microphone, the game controller could add a barking dog character into the game environment. Users could transmit a photo of the dog to the game controller so that a virtual representation of the user's dog can be seen in the game environment. In another embodiment, when a peripheral microphone picks up loud sounds, the game controller could create a sign in the game environment above the head of the user's game character which says "Currently in noisy environment."

In various embodiments, local news/events could be incorporated in the in-game environment. Items from a newsfeed (e.g., a feed of news that is local to the player's location) can be incorporated into a game. For example, an in-game billboard may display, "Congratulations to the Jonesville high school football team!!"

Sharing of Video Highlight Reels

When game players have success while playing a game, they sometimes want to brag about it to their friends, but that process can be clumsy and complicated. Various embodiments allow for players to quickly and easily capture video of game highlights and make them available in a variety of formats that make sharing them more fun and enjoyable. One or more peripherals can enable clipping, commenting, editing and display of short video clips. These clips could be video, streams of text, audio, animations, or computer simulations of the player successes.

When a user believes that they are about to execute gameplay—such as a game character about to attempt a dramatic leap across a ravine—that they feel might be of interest to their friends, the user could tip back the front of their mouse to initiate a signal to start a recording of gameplay at that moment. For example, the accelerometer in the mouse could identify that the mouse was tipped back and then send a signal to the user device (or central controller, or a game controller) requesting that a video be started at that moment. Once the leap across the ravine was successfully completed, the user could again tip back the mouse in order to send a signal indicating that the video recording should be stopped at that moment. The user device (or game controller) could then save the clip and send the clip to the central controller for storage in an account associated with the user unique identifier. There are many ways in which the user could initiate and terminate a gameplay clip. For example, the user might tap the mouse twice to begin recording and three times to end the recording. Another option would be for the user to say "record" into a microphone of the mouse, with software in the mouse capable of speech to text that can translate that verbal request into a 'start recording' signal to the user device or game controller. A physical or virtual button on the mouse could also be used to provide start and stop signals for the generation of gameplay clips.

The game controller could also start and stop video recording based on user biometrics. For example, gameplay could be recorded whenever a heart rate sensor of the user's mouse exceeded a particular number of beats per minute. In this way, the player does not have to initiate the creation of the gameplay clips, but rather the clips are recorded whenever the heart rate biometric indicates that the player is in an excited state.

Another way to generate start and stop times for gameplay clips could be via algorithms of the game software that predict that the user is about to do something exciting in the game. For example, the game software might begin to record gameplay whenever a user is involved in a sword fight with a more experienced opponent. After the sword fight was concluded, the game software could ask the user whether or not they wanted a clip of that sword fight to be sent to the users mouse for storage.

The user could also initiate a clip of gameplay to be recorded, but have the recording end within a particular period of time. For example, the user might set a preference stored in the mouse which indicates that clips should always end three minutes after initiation.

Rather than initiating a gameplay clip to be created as above, the user could initiate a streaming session by having the game software send all gameplay video directly to a video game streaming service such as Twitch. This initiation could be done via a series of taps on the mouse, verbal commands, biometric levels, or algorithmically by the game software.

Rather than creating video clips, the game software could be directed by the user to capture screenshots, audio files, maps of terrain traversed, a list of objects obtained, a list of enemies defeated, etc.

In various embodiments, the user initiates a video clip of his own face as seen through the front facing camera of the user device (e.g., user computer) during gameplay. For example, the user could send an initiation signal (such as taps on a mouse, or two quick blinks while facing the camera) to start a recording of the user's face while engaged in a particularly interesting or exciting activity in-game. Such a video could similarly be sent to the users mouse for storage, or be sent directly to the central controller for storage in the user's account. This user video could be combined with a clip of the gameplay associated with the game character, and saved as two side-by-side videos synchronized to capture the emotions of the player while showing the exciting gameplay that produced the emotions.

User clips stored in his account at the central controller could allow the user to build a video game highlight reel that could be sent to friends. Such video clips could be listed by game or chronologically. This could be combined with game statistics much like a baseball card. For example, for a game like Fortnite® the player might have several video clips as well as statistical information like the number of games played and the average success rate in those games. For players on teams, statistics and gameplay clips could be cross posted to teammates' pages.

One of the advantages of storage at a central controller is that the user can accumulate videos and statistics across all game platforms and game types.

Device-Assisted Discovery of Social Connections

More than ever, people are searching and engaging in various forms of social connection, both virtually and physically. The mouse and/or keyboard could be devices that applications use to alert a user when a connection is made. The mouse and/or keyboard could be devices that users use to indicate interest in an activity.

In various embodiments, applications alert a user via mouse-keyboard that a connection is made. As a user of an application, I may be interested in a topic or requesting recommendations. Once the request is sent in to various sites (e.g. Pinterest®, Nextdoor™, dating sites, local volunteer organizations, local interests (running club, chess club, gardening club), Ebay®), unless the user is routinely checking email, alerts may be missed. The mouse-keyboard could take these alerts and provide feedback that a connection or message has been made. Once notified, a simple mouse-keyboard movement could take a user instantly to the information. For example, a user is interested in getting a recommendation for the best appliance repair person in the area on Nextdoor™. After the request is submitted, the user resumes other activities using their mouse-keyboard. After some time, a recommendation is made. At that point, an alert is sent by Nextdoor™ to the user's mouse-keyboard. The mouse-keyboard could display a color, sound or skin display indicating that a message has been received.

In various embodiments, a user utilizes a mouse-keyboard to respond to connections. A user can respond to the mouse-keyboard indication that a connection is made in various ways. For example, once a user has indication that a message/connection is made via the mouse-keyboard, they can simply click the mouse (or press a key on the keyboard) and the message/action is immediately retrieved from the sending application. This not only provides immediate feedback to the sending application but makes a simple interaction between the user and the application thus creating efficiencies and improved experience. Likewise, in addition to retrieving messages in textual format, a user could open an audio or video channel to instantly connect to the application/other user. This could occur if a person is interested in playing a new game and is seeking an additional player. Once found and the device alerted, the person could communicate directly with the player to establish a time to play. If the response meets the user's needs or the connection is established, another simple click can turn off future alerts from the applications and end the communication.

In various embodiments, a mouse-keyboard assists in making or responding to in-game connections. An in-game player may want some immediate assistance from other players (already in the game or not) on the game overall or a particular section of the game. The user simply selects a mouse-keyboard action and a connection request is made to current and previous players. Once a player determines they want to connect (by selecting the action on the mouse-keyboard), the requesting player is notified on their mouse-keyboard. The connection is made by selecting the mouse-keyboard inputs and assistance is provided via a dedicated audio channel in-game, a textual message or video chat. Once either player decides to end the connection, a simple click on the mouse-keyboard is made.

In-Game Rewards Displayed on Socially-Enabled Peripherals

Game players sometimes gain abilities, levels, titles (like grandmaster, wizard), ratings, (such as a chess or backgammon rating) inventory items (like gold coins, weapons, ammunition, armor, potions, spells, extra lives, etc.) or other benefits achieved during game play. Players also accumulate statistics, such as win rates or accuracy rates. Many players like to show off such achievements, and to let their friends know how much they have achieved.

When a user achieves a level in the game, that level could be displayed on the surface of the user's mouse or keyboard. For example, a display area on the mouse could display that the user was a wizard who had achieved a level 50 of experience. This indication could be displayed whenever the player was using the mouse, or it could be displayed at all times. The user device or game controller could send a signal to the mouse of the achievement level and store it within storage media in the mouse. In another embodiment, the achievement level indication is displayed only when the mouse is not being used or does not have a hand on it. Pressure, temperature, or motion sensors built into the mouse could detect use and automatically turn off the ability level indication. The achievement level display could be an e-ink display which would reduce power consumption requirements.

An achievement level indication could change frequently during a game, such as when a chess player's rating moves up and down after a series of many blitz games with each lasting only a few minutes. The constantly updating rating could be displayed on the mouse display, or it could also be displayed on a keyboard according to various embodiments. For example, the keyboard could have back lighting for each individual key which is capable of causing keys to glow in an order determined by a signal from the user device or game controller. So if the user's new blitz chess rating was 2375, the "2" key would light up and then turn off, followed by the "3" key, then the "7" key, and then finally the "5" key.

Achievement level indicators could also be shared among multiple players. For example, a team of three users could have inventory items of all team members displayed on the mouse of each team member. For example, if player "A" has a Healing Potion, player "B" has a +5 Sword, and player "C" has 35 Gold Pieces, then each of these items would be listed on the display area of the three mice. So player "A" would see "Healing Potion, +5 Sword, and 35 Gold Pieces" displayed on his mouse. These items could be continuously displayed, with updates to the inventory items being sent from the game controller to the mouse whenever an item was added or used. Players could also trigger the display of the inventory items with the click of a button on the mouse, a verbal command to "show inventory", depressing a function key on the keyboard, or the like.

The mouse could also change its physical shape to reflect changing achievement levels. For example, in a first person shooter game the users mouse could extend out a small colored plastic plate at the top and bottom of the mouse when the user achieved victory over five opponents in the game. This would allow other users present to see at a glance that the player was doing well, and the extended plates could be positioned to not interfere with ongoing game control via the mouse.

Multiple Controllers, Single Cursor

Devices according to various embodiments could enable multiple users to control a single instance of software. The inputs of individual devices could be communicated to the central controller and then communicated from the central controller to the game controller or software. By allowing multiple users to input into a single piece of software, the devices could enable social game play.

For example, users could swap control of the inputs of a single character, avatar, vehicle, or other aspect of gameplay. Players could swap control voluntarily. Alternatively, the game controller could swap control probabilistically or based upon another dimension, such as relative skill at different aspects of a game, which player has had the least time of control, or which player generates the most excitement for non-controlling players.

Users could control a single input type for a composite character, avatar, vehicle, or other aspect of game play. For example, control of X,Y,Z movement, visual field, and weapon might be controlled by separate players. For example, a player might control the movement of a vehicle such as a ship, while another player might control its ability to shoot.

In various embodiments, one user controls a primary character or entity, and another user controls a sub-entity. For example, a first user controls a mothership, while a second user controls a space probe released by the mothership. As another example, one user controls a main character (e.g., a foot-soldier), while another user controls an assistant, such as a bird or drone that flies overhead and surveys the terrain.

In various embodiments, opponents may take control of one or more functions of input while the device owner might retain other aspects of input. For example, opponents might control the facial expressions of a character, while the device owner retains all other control over the character. As another example, opponents might control the communications (e.g., text or voice messaging) from a character, while the device owner retains all other control of the character. As another example, opponents might control the speed of a character's movement, while the device owner retains control over the direction of the character's movement.

In various embodiments, the central controller might average, select the most popular input, or otherwise combine the input of several users to control aspects of game play. For example, the character's direction of motion may be determined by the direction that was selected by a majority of users having input to the character's actions. As another example, the character's motion may be determined as the vector sum of inputs received from users controlling the character. In various embodiments, all users controlling a character or other game aspect have to agree on an input before some action is taken.

In various embodiments, aspects of control of a character or of other gameplay may not be explicitly communicated to a user. In other words, a user may not always know what effects his inputs will have on a character or on gameplay in general. For example, a user may not know that a particular key on his keyboard controls the speed of a character's trajectory. The user may be left to experiment in order to figure out the effects of his input on character actions or on other aspects of gameplay. In various embodiments, the effects of a particular key (or other input) may change without notice. A user may then be left to figure out what he is now controlling, and what he is no longer controlling.

In various embodiments, two or more users may play a game where one user serves as an instructor while the other user is a student. The instructor may be helping the student learn how to play the game, or to learn how to improve his game play. In various embodiments, the student may be allowed to control a character, vehicle, or other aspect of gameplay. However, when the instructor deems it appropriate, the instructor may assume control and guide the character, vehicle, or other aspect of gameplay. The instructor may thereby help the student with a tricky sequence, with a strategy that had not occurred to the student, with an improved set of motions, or with any other aspect of the game.

Mouse Voting

Teams playing games sometimes require decision making by the group, requiring some discussions between team members.

In various embodiments, game players needing to make a decision could conduct voting protocols through the mice of the players. In this embodiment, a team of five players registers their names with the game controller for communication to the user device and/or the central controller (which can associate the player names with the unique mouse identifiers associated with those player names). The five players then use their mice in gameplay and tap the surface of the mouse three times to initiate a voting protocol. For example, Player #3 might initiate the voting protocol in order to facilitate the group deciding whether or not to cast a spell that would build a bridge over a river. In this example, Player #3 taps her mouse three times quickly and a signal is sent to the user device and then on to the central controller. The central controller then sends a signal out to the mice of all five players, which displays on the surface of those five mice a yes/no option. Each of the five players taps once for 'yes', and twice for 'no'. This selection is communicated back to the central controller, and the option receiving the most votes is then communicated back to be displayed on the surface of each of the five mice.

Many voting protocols could be stored with the central controller, allowing options like giving users the ability to provide greater weights to the votes of more experienced players, or requiring unanimous consent or a two-thirds majority in order to make a decision.

Voting by users could be done anonymously, or the votes could be connected to their real name or game character name.

Mouse to Mouse Communication

Communication between players is very common in game environments, with players often texting each other or calling each other to communicate. This can sometimes be clumsy as players may have to take their hands off of the keyboard or mouse to initiate, manage, or end the communications.

In various embodiments, mice are enabled to communicate directly with each other. For example, a user could triple tap the surface of their mouse to initiate a communication channel with a particular friend, and then speak into a microphone contained within the mouse. That audio signal would then be transmitted to the user device and sent to the user device of the users friend, and finally sent to the friend's mouse for broadcast via an output speaker in the mouse. In this way, a pair of mice can communicate like a pair of hardwired walkie talkies.

The user could also store a list of the unique mouse identifiers of five of the users friends, and then initiate a mouse to mouse connection by tapping once on the user's mouse to be connected to the mouse of Friend #1, tapping twice on the mouse to initiate communication with the mouse of Friend #2, etc.

Communication could also be conducted through a microphone within the users keyboard in a similar manner. The user could say "Friend #3" into the microphone of the keyboard, which would then transmit the signal to the user device, which sends the signal to the user device of Friend #3, which then sends a signal to the speaker built into the keyboard of Friend #3, to thereby enable the direct communication from keyboard to keyboard.

Interactions with Streamers

Streaming platforms such as Twitch®, YouTube® Gaming, and Mixer™ now allow individuals to livestream video game sessions to audiences of thousands or even tens of thousands of fans. While fans can join chat streams with messages of encouragement, there is a need to allow fans to increase the level of interaction with streamers.

In various embodiments, fans of streamers can use their mice to vote for the actions that they want the streamers to take. For example, the streamer could send out a voting prompt to appear on the display screens of the mice of fans, asking them whether the streamer's game character should head North or South. Players then vote by touching the phrase "North" or "South" that is now displayed on their mouse. That signal would go to the user device and then to the central controller, and finally to the controller of the streaming platform to indicate to the streamer what action is requested by the fans.

In another embodiment, fans would be able to provide a direct input into the controls of one or more peripherals used by the streamer. For example, fans could provide input via their mice as to the direction and velocity with which to move over the next 60 seconds of gameplay, with the input from all of those mice combined by the central controller into a single aggregated direction and velocity with which the streamers game character would be moved for the next 60 seconds.

The ability to subscribe, re-subscribe, donate, or tip small amounts of money would also be facilitated in embodiments where a user's mouse stores value (such as currency) that can be transmitted to the streamer via the central controller.

The streamer could also enable loot boxes, raffles, and giveaways to users that appear on the display screen of a users mouse. The users mouse could glow red whenever the streamer was currently streaming.

The users mouse could include a streamers insignia or an image of his face on the display screen of a user's mouse.

A streamer could design a custom mouse that included design elements or colors associated with his brand. Such a mouse could include stored preferences including ways for the user to easily connect with the streamer.

Device Changing Shape

While many people work or play games with others remotely, there is a need for increasing the feeling of connection that can help bridge the distance gap.

In various embodiments, the mouse of a user is configured to have a look and feel evocative of a pair of lungs that reflect the actual breathing rate of a second remote user. The rate of breathing can be determined by receiving a breathing rate sensor value from the mouse (or other peripheral capable of determining breathing rate) from the second user, and replicating that breathing rate on the first user's mouse. The breathing effect could be generated by having a soft light glow on and off at a rate equal to the second user's breathing rate. Alternatively, the first user's mouse could have an internal mechanism that allows the mouse to expand on a cadence with the breathing rate. In these embodiments, the breathing rate of the first user could be reflected on the second user's mouse while the second users breathing rate could be reflected on the first user's mouse. In this way the two users would feel more connected even though they may be thousands of miles apart.

Another way in which the breathing effect could be embodied would be for some or all of the keys of the users keyboard to be directed to move up and down reflective of the breathing rate of the second user (and vice versa).

The ergonomic shape of peripherals could also change based on the needs of a user. For example, a keyboard could be directed by the user device to incline by a few degrees based on data generated by the user's camera.

Peripherals could also change shape when a user signals that the peripherals are being put away for storage or are being transported to another location. The altered form factor could make the peripherals less likely to sustain damage from being bumped or jostled.

Devices according to various embodiments could include a foldable form-factor in which the devices fold, hinge, or otherwise enclose themselves to protect the device during travel.

Mouse Actions

There are other ways in which a mouse can provide inputs beyond traditional two dimensional plane movements, clicking, and rolling wheels or trackballs.

In various embodiments, the user generates a signal from a mouse by tipping up the front of the mouse, but keeping the rear end of the mouse relatively stationary.

In various embodiments, a mouse may remain fixed or stationary and may interpret mere pressure from different sides as signals to move a mouse pointer. For example, if a person applies pressure to the right side of a stationary mouse (as if moving a mobile mouse to the left), the mouse pointer may move to the left.

A user mouse could also generate a unique signal by turning the mouse over. For example, a user could turn the mouse over to indicate that they were temporarily away from their keyboard, and then turn the mouse back over when they return to gameplay. The game controller could then relate that time away from the keyboard to the other players so that they know the user will be unresponsive during that time.

Connected Devices for Mobile Work

Individuals often use mobile computing devices, such as laptops, tablets, or phones, to conduct work outside of traditional office or home settings. These devices have built-in input devices, and detached keyboards and mice are accessory peripherals. The devices according to various embodiments could improve the functionality of these accessories.

Accessory keyboards and mice are frequently stolen or lost. To prevent theft, a device owner, for example, could set an alarm mode, allowing the owner to leave the device unattended. If the device is touched, the device could be set to produce a loud noise or flash bright colors. In an alarm mode, the device could be set to take a picture if it moved. If the device is connected with another computing device while in alarm mode, it could, for example, trigger the device to send its current GPS coordinates or the IP address of the device to the original owner. For example, to locate a lost device, an individual might enable a "lost device" mode that causes the device to produce a loud noise or cause the device to flash a bright light.

Devices could have additional functionality enabled by geofences or other location-context information, such as the ability to order items and process transactions. For example, a device might recognize that its owner is using it at a cafe and allow the device owner to order a coffee. Prior transactions in the same location might be stored in the memory of the devices for ease of reordering.

Charging devices can be challenging for mobile workers when electrical outlets are scarce or unavailable. Devices according to various embodiments might be able to charge wirelessly from other peripheral devices or from a mobile computing device.

Mobile workers often transport mice and keyboards in purses, backpacks, briefcases, and other bags without putting them in protective cases. Devices according to various embodiments could include a foldable form-factor in which the devices fold, hinge, or otherwise enclose themselves to protect the device during travel.

Parents Playing Games with Kids

Some parents enjoy playing computer games with their kids, but they feel like it would be a better experience if they could more fully participate in the gameplay experience.

One way to improve the shared experience of gameplay would be to have the game allow a single game character to be controlled by two players at the same time. In this way, a parent and child could play a game as one character rather than as competing characters.

Another example would be for the adult to be able to control a particular element of the game character that might be more complicated (like handling spell casting), while the child had the ability to control a simpler element of the game character (like the direction that the character walks). In various embodiments, two or more players controlling a single game character need not have any particular relationship to one another (e.g., such players need not have a parent-child relationship).

Dynamically Change Game Difficulty, Excitement Level, or Other Game Content

A key challenge for game creators is sustaining engagement and excitement over time, as well as balancing difficulty level. Players often lose interest in games over time. Games that are too difficult frustrate less skilled players, while games that are too easy frustrate more skilled players. Mice and keyboard devices according to various embodiments could facilitate a game controller dynamically changing in-game content to increase excitement, difficulty level, game play time, amount of money spent in-game, the amount of social interaction among players, or another goal of the game controller.

Mice and keyboard devices according to various embodiments could facilitate the onboarding of new players or users. An onboarding tutorial or help function could use the outputs of the devices to indicate to new players which mouse actions, key actions, and combinations of inputs control game actions. For example, a tutorial could use the visual outputs to light up keys in a sequence to demonstrate how to perform a complicated movement.

The mouse and keyboard of this device could be utilized to train an AI module that analyzes player input data to detect how a player responds to particular in-game stimuli. An AI module could then predict how the player would respond to different variations of in-game content, difficulty level, in-game loot, resource levels or other aspects of gameplay in order to elicit particular emotional responses, such as excitement or fear. Likewise, an AI module could predict how a player would respond to variation in game play to increase engagement, game play time, amount of money spent-in game, levels of social interaction among players, or another goal of the game controller. For example, a horror game might use an AI module trained on past player responses to stimuli, as measured through galvanic responses or heart rate changes, to dial in the appropriate level of fright for an individual player. For example, an AI module might detect that a player has reduced levels of game engagement and increase the likelihood of a player earning in-game loot boxes or other rewards in order to stimulate higher levels of engagement.

The mouse and keyboard of this device could be utilized to train an AI module that analyzes player skill level in order to dynamically vary the difficulty of the game. This AI module could be trained using device inputs, such as cursor speed or keystroke cadence, to detect patterns of game play by users of different skill levels and to predict skill level of the device owner. An AI module could detect the rate of learning for players and adjust game difficulty or skill level dynamically in response to skill acquisition.

In many games, dominant or popular strategies emerge ("the metagame" or "meta"), as players discover which strategies are likely to succeed and which strategies counter other strategies. An AI module could be trained to detect clusters of player behavior ("strategies") and analyze the relationship between strategy and in-game success. An AI module could then dynamically alter the difficulty of the game through managing in-game resources, non-player characters, or other aspects of game play, either dynamically during a game or by creating new levels, maps, or forms of game play that add novelty to the meta.

Because the game controller has information about all player actions, as well as perfect information about procedurally generated aspects of the game such as resources, non-player characters, and loot boxes, an AI module could predict when something exciting or interesting is likely to happen. Exciting or interesting elements could be players converging in the same area, a less skilled opponent beating a high skilled opponent, an improbable event happening, or another aspect of game play that has in the past elicited high levels of engagement, spikes in biometric data, social media shares or another aspect of excitement. If the AI module predicts that something interesting is likely to happen, it could visually indicate it to players. It could also automatically generate a clip (e.g., video clip) of the event and share it with players in-game, post it to social media, or share it on the internet. For example, because the game controller knows the locations and could predict likely paths of players, the controller could trigger a camera to capture the facial expressions of an individual likely to be in a line of fire or about to be ambushed. For example, the controller could message "watch out" to a player who is likely to crash in a racing game or "close call" to a player who escaped a predicted crash.

Digital Skins and Game Environment Synchronized with Physical Device

Mice and keyboards according to various embodiments can be customized through visual outputs, such as lights, screens, e-inks, and other visual outputs. These visual customizations can be controlled by the player, by the game controller, by the central controller or by other software. These visual outputs ("digital skins") can change dynamically while using a piece of software or may be set in a persistent output that lasts after the user has stopped using a piece of software.

In-game content that a player has earned, acquired or purchased can be displayed on the device in a manner similar to a trophy case. For example, the device might output visual representations of badges, trophies, interesting or valuable loot items, "season passes", skill trees, personalized in-game content, or other representation of the game.

Game play or in-game content can dynamically alter the outputs of these devices. The status of a player, current player performance, or the digital environment of the game, for example, might be dynamically displayed via visual output, tactile output, or other device outputs. Game play could for example change the appearance of the device. For example, if a player in an action game is being attacked or wounded, the device can display an output to show the direction of attack or whether the attack succeeded. Player performance might change the appearance of the device to indicate a streak of performance. For example, keys might light up one by one as the streak increases in length. Likewise, a "hot" or "cold" streak might result in the temperature of the device increasingly growing cold or hot to indicate the length of the streak. If a player, for example, was approaching the end of a level, suffering in the game, close to a boss, low on resources or running out of time to complete a task, the temperature of the device could change to indicate the situation to the player. A game for example could utilize device outputs such as lights as keys, puzzles, or other aspects of unlocking game functionality. For example, synchronizing lights on a keyboard or mouse with combinations of lights in a game could solve a puzzle or be used as a key to open a door. Likewise, a game set in a particular environment could display visual representations of that environment, such as trees or mountains, vibrate to indicate in-game terrain, or increase or decrease in temperature to match in-game environment. If a player, for example, is playing a game in a space or futuristic setting, the device can display stars and parallax movement.

Video game players often create "digital skins" for digital content by customizing the color, patterns, and visual textures of in-game content, such as the appearance of a digital character, vehicle, weapon, or other object. Various embodiments allow the player or the game to synchronize these digital skins to the device's visual output. These visual outputs could be displayed only during the game, or they could be displayed, like a trophy, when the player is not playing.

Individuals often customize the digital appearance of software ("themes"). The devices in this presentation could be customized in a similar manner as visual extensions of the software theme. Users often create different themes that dynamically transition over time of day or level of ambient light to diminish discomfort or to reduce the amount of blue light, which affects circadian rhythms and other biological clocks. The devices could also change visually according to time of day and ambient light to create a "light or day" mode and a "night and dark mode." The devices could alter levels of blue light over the course of day, or they could be used to increase exposure to blue light when users have insufficient exposure.

The devices could indicate whether software is being used, for example showing the logo of an application the device owner is using. For example, during a videoconference, the device could visually indicate that a call is ongoing or is being recorded.

Other software controllers could alter the outputs of the device. For example, while watching digital videos or listening to music, the title and creator of a song or video could be displayed. Likewise, album cover art or a clip of the music video could be displayed.

User Customizations

Game players often like to customize their gameplay experience. Various embodiments allow users to store information about desired customizations for use in customizing gameplay experiences. Customizations could be for digital actions/characters, or for physical changes.

Physical customization that a user might establish could include elements like the height of a chair, the springiness of keys on a keyboard, the tracking speed of a mouse, the angle of view of a camera, and the like.

Customization of a mouse could also include the location of display areas, size of the mouse, preferred color patterns, the weight of the mouse, etc.

Virtual customization could allow players to establish preferences for a wide range of enhancements. For example, the player might save a preference that when his mouse signals that he is away from the keyboard that the other players are alerted that he will return in ten minutes time. Customizations could also include a list of friends who are desired team members for a particular game. These players could automatically be added to a chat stream when that particular game was initiated.

Customizations could be stored in a peripheral device such as a mouse, in the user device, or at the central controller.

Status Updates Via Peripherals

With many players engaging in cooperative games from remote locations, knowing the status of another player in another location can be challenging. Is the player on a break? Does the player want to quit soon? Do they currently have a good internet connection? Getting answers to these questions can be time consuming and distract from player focus during ongoing games.

In various embodiments, a user identifies a number of other game players that he wants to get status updates from. For example, a user might identify three friends that he likes to play games with—Friend #1, Friend #2, and Friend #3. The identity of these friends is transmitted to the central controller. Periodically, status updates generated by the peripherals of these three players are sent to the central controller and then made available to the user on one of his peripherals. In one example, every five minutes the mouse of each of the three players checks for movement, sending a signal to the central controller if there is movement. If one or more of the three mice are moving (in this example that might be only Friend #2), the central controller sends a signal to the user device of the user which sends a signal to the user's mouse, storing an indication that Friend #2 now seems to be active. The users mouse might light up with a color associated with Friend #2, or an insignia associated with Friend #2 might be displayed on the users mouse, such as an icon for a wizard character that Friend #2 often uses in games. In this embodiment, it is easy for the user to know which of his friends are currently starting a game session. For example, a high school student might come home from school with the intent to play a game. He looks at his mouse to see if any of his friends are currently playing. If not, the user might begin to work on his homework while keeping an eye on his mouse, looking out for the telltale color which indicates gameplay is now underway.

In another embodiment, the user's mouse shows a constant indication of the status of the mice of all three friends. For example, the mouse may have a display area which is segmented into three locations, with each location lighting up when the corresponding friend is now using their mouse.

Player status can be much more than just an indication of whether or not the player is currently moving their mouse. It could also indicate whether or not the player was typing on their keyboard, moving in their chair, moving their headset, or moving/being in the field of view of a computer camera.

In another embodiment, players register a current status with the central controller. For example, a player might register that they are currently ready to begin a game with one of their friends. The central controller then sends a signal to the mice of those friends and displays a flashing light to inform that player that a friend is currently looking for a game. Similarly, a status of "I'll be ready to play at 3 PM" could be communicated to the other friends. A player might also send a status that they would like to talk with another player.

Users can also get information during gameplay about the status of remote players. For example, a player could tap three times on their mouse to initiate a signal to the central controller that they were currently on a break. The break status of the player is then sent to the user device of each of the other friends for display on their mice.

Communicating the status of a remote player could be done via the keyboard of a user by backlighting individual keys, For example, the "G" could be backlit when Gary is currently looking to begin a game.

The user's mouse could display a wide range of statuses for remote friends. In one embodiment, a user sees an indication for each friend of the current quality of their internet connection. A user's mouse could also indicate the type of game that a friend currently wants to play, or the top three games that the friend would like to play.

The user's mouse could also display information regarding inventory items, resources, or in-game statistics or remote friends.

Another status that could be of value to remote players is the engagement level or level of fatigue of a player. These could be used as a proxy for whether or not a player should not be relied upon during an upcoming period of complex gameplay.

Figure 101:
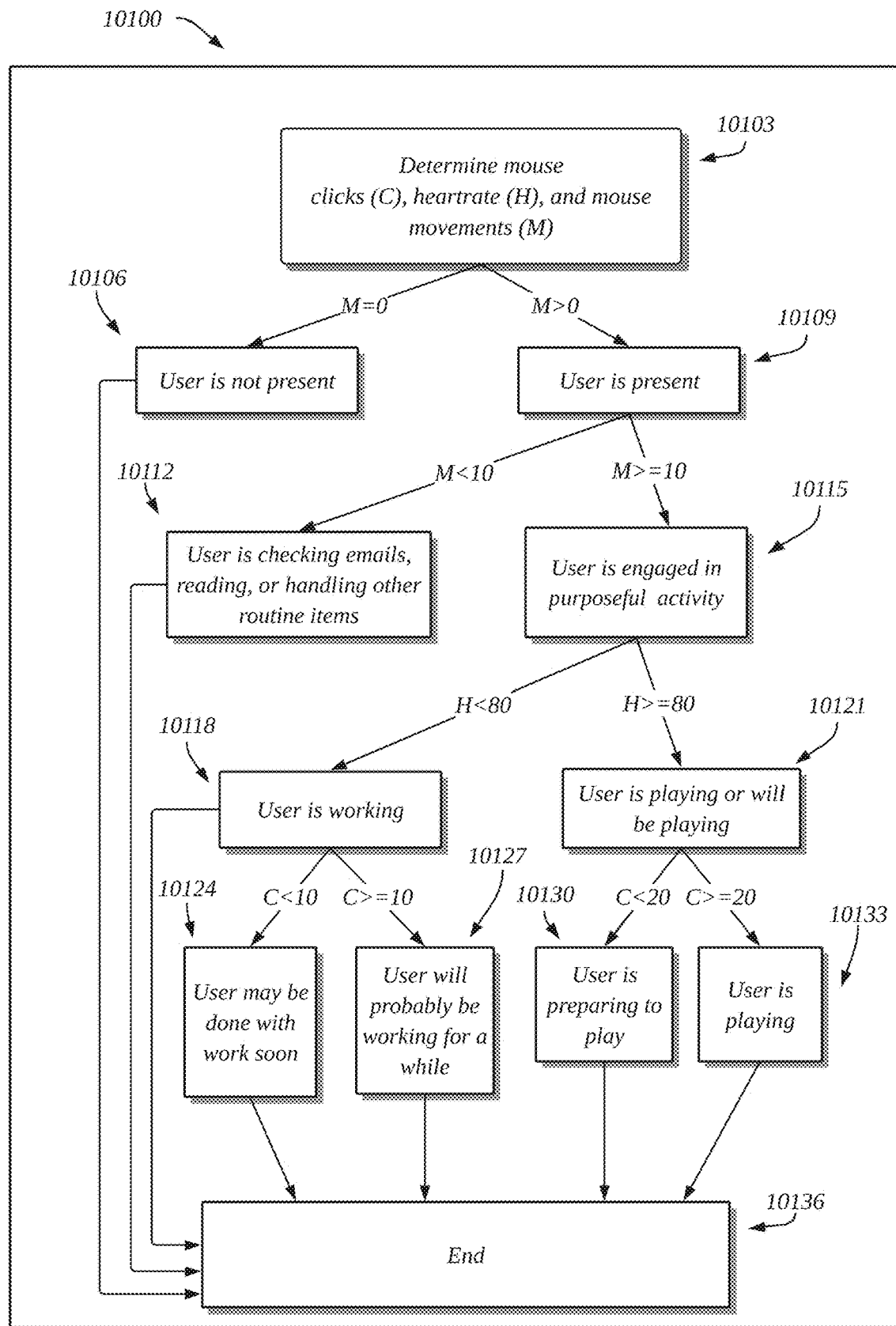
FIG. 101 is a diagram of a process flow consistent with at least some embodiments described herein.
Figure 102A:
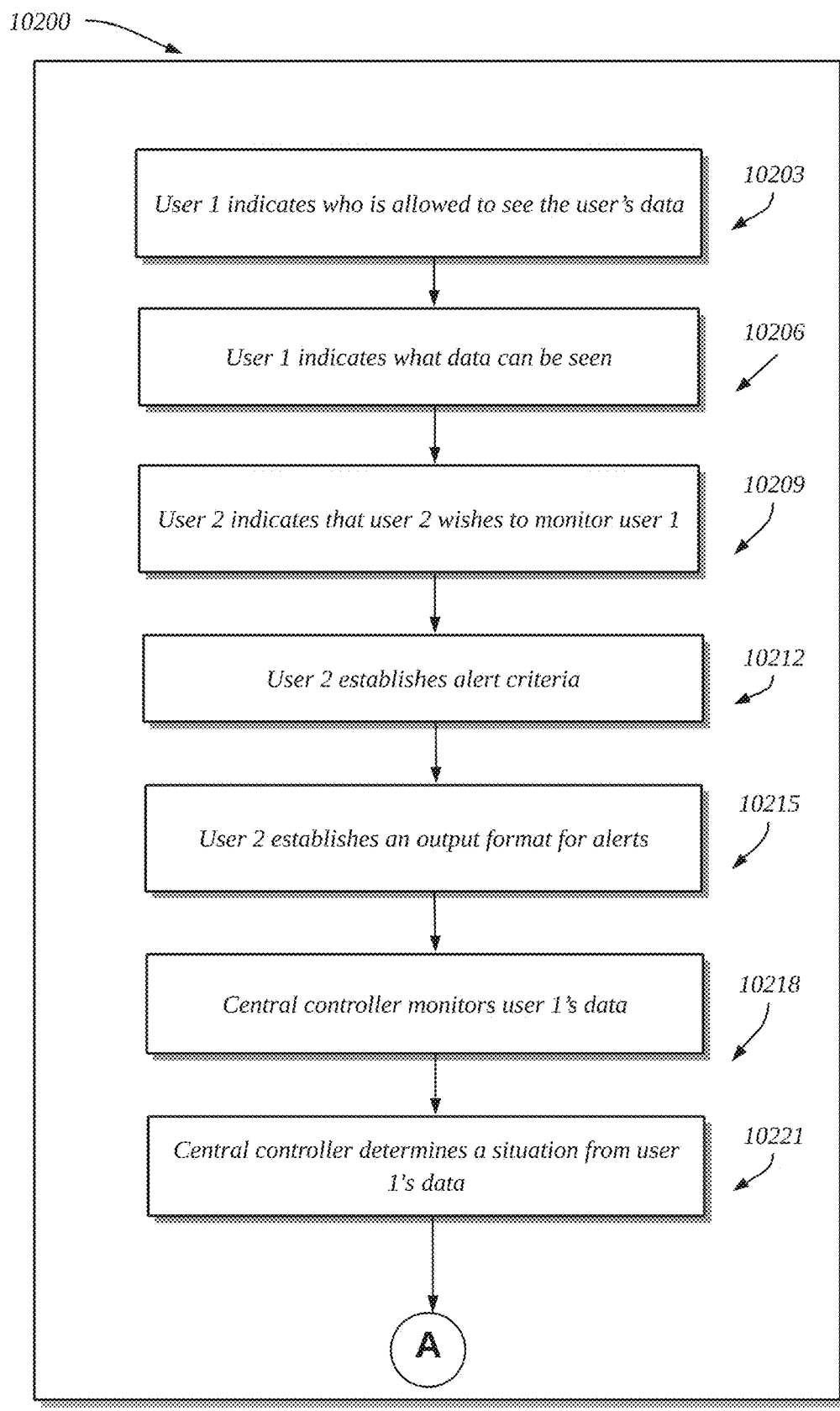
FIG. 102A and FIG. 102B, together show a diagram of a process flow consistent with at least some embodiments described herein.
Figure 102B:
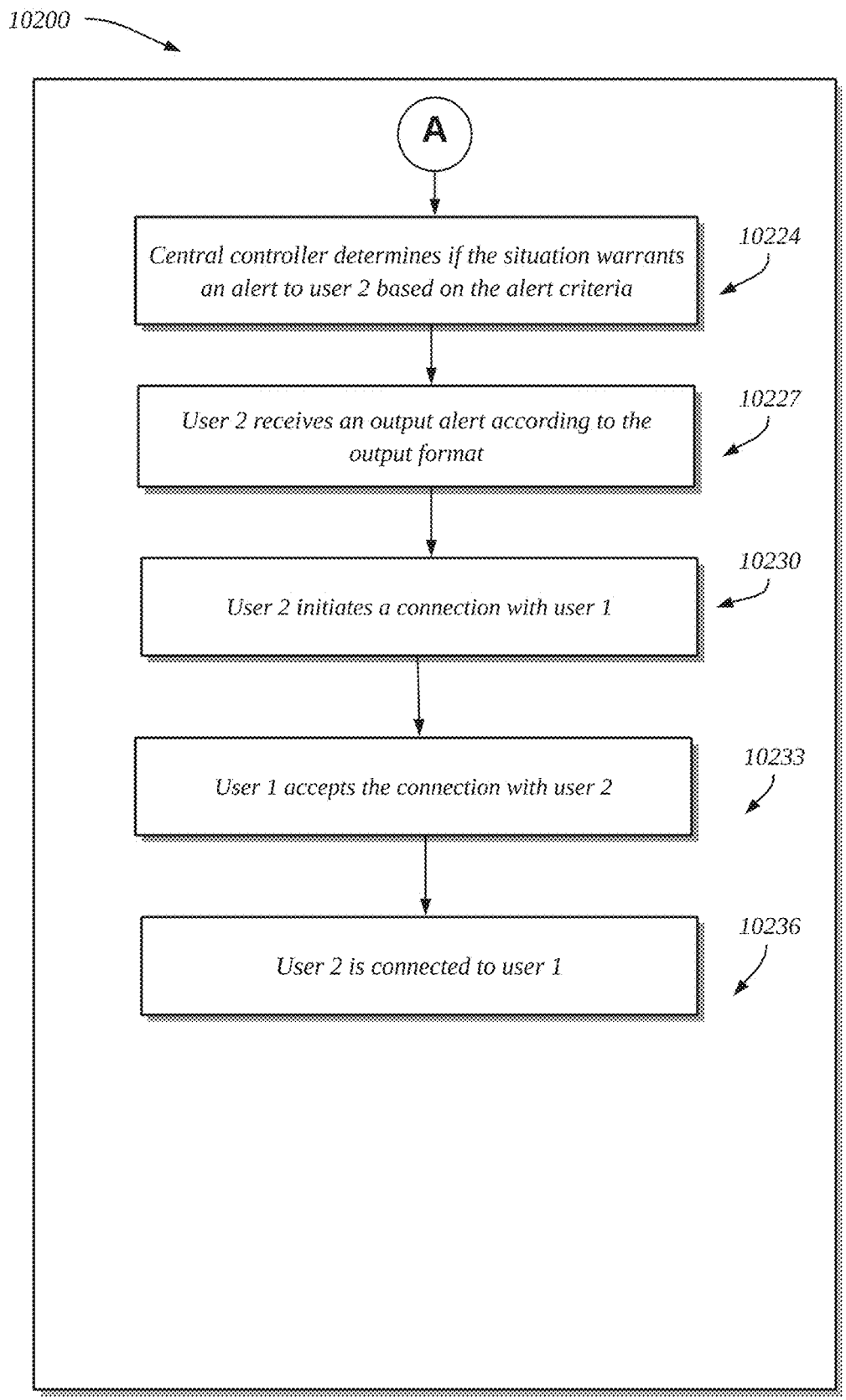

Referring now to FIG. 101, a flow diagram of a method 10100 according to some embodiments is shown. Method 10100 may be used to infer a user's intention based on the user's actions and/or based on sensor data gathered from the user. As used in the illustrative example, method 10100 seeks to determine a user's intention with regards to either doing work, or playing (e.g., playing an online video game). If it is determined that the user's intention is to play, for example, then the user's intention may be communicated to another, like-minded user (e.g., to the users friend), so that the two users may play a game together. On the other hand, if it is determined that the user's intention is to work, then such intentions may also be indicated to another user, but now with the purpose of tempering the other user's hopes of playing a game with the first user.

It will be appreciated that the illustrative example represents some types of inferences, but that other types of inferences may also be performed, in various embodiments. For example, various embodiments may seek to infer a user's mood, A user's intended purchase, a type of game that a user would like to play, a type of video that a user would like to watch, or anything else.

In various embodiments, FIG. 101 may represent a decision tree, such as is used in machine learning and artificial intelligence applications. The terminal nodes, or leaf nodes in the decision tree may represent an inferred user intention. Other nodes may branch in one direction or another based on the value of an input variable.

In the illustrative example depicted in FIG. 101, there are three input variables gathered from a user. These are: number of mouse movements in the last five minutes (represented by the variable "M"); number of clicks in the last five minutes (represented by the variable "C"); and heart rate (represented by the variable "H"). As will be appreciated, these represent exemplary inputs that may be gathered, and any other suitable inputs or combination of inputs may be used, in various embodiments. In various embodiments, other input variables may include: a number of keystrokes (e.g., at a keyboard); a number of mouse movements larger than five pixels; a number of turns of a mouse scroll wheel; a number of double clicks; a number of mouse drags; a number of different peripherals that have been used (e.g., 1 peripheral; e.g., 2 peripherals); and/or any other input variables.

Also, data may be gathered or tallied over other time windows (e.g., over time windows greater than or less than five minutes). In various embodiments, a decision tree may use more or less than three input variables. In various embodiments, any suitable classification algorithm may be used aside from a decision tree (e.g., a support vector machine, random forest, neural network, etc.). In various embodiments, any suitable algorithm may be used to discern or infer user intent.

For the purposes of the present example, the variable M may be understood to represent any mouse movement, however great or small, that would be sufficient to register a change in an x or y coordinate of a mouse pointer, and which is delimited by a pause (i.e., lack of movement) lasting at least 0.1 seconds. For the purposes of the present example, the variable C may be understood to represent any mouse click, whether left, right, or middle. For the purposes of the present example, the variable H may be understood to represent the users heart rate, in beats per minute, as measured over the preceding five-minute interval. However, as will be appreciated, any other suitable variable definitions could be used.

At block 10103, the values for variables M, C, and H are determined. Exemplary values might be 5, 11, and 77, respectively. The variable M is then compared to the predefined threshold of zero. If M is equal to zero, then it is inferred that the user is not present (block 10106). In other words, if there has been no mouse movement in the past five minutes, it may be inferred that the user is not present. Flow now stops (e.g., flow proceeds to "End" block 10136). If M is greater than 0, it is inferred that the user is present (block 10109).

At block 10109, M is compared to the predefined threshold of ten. If M is less than ten, it is inferred that the "User is checking emails, reading, or handling other routine items" (block 10112), and flow stops. If M is greater than or equal to ten, it is inferred that the "User is engaged in purposeful activity, block 10115.

At block 10115, the variable H is compared to the predefined threshold of eighty. If H is less than eighty, it is inferred that the "User is working, and flow proceeds to block 10118. If M is greater than or equal to eighty, it is inferred that the "User is playing or will be playing, and flow proceeds to block 10121. In this example, a higher heart rate is assumed to correlate to game playing or to the anticipation of game playing.

At block 10118, the variable C is compared to the predefined threshold of ten. If C is less than ten, it is inferred that the "User may be done with work soon" (block 10124), and flow stops. If C is greater than or equal to ten, it is inferred that the "User will probably be working for a while" (block 10127), and flow stops.

At block 10121, the variable C is compared to the predefined threshold of twenty. If C is less than twenty, it is inferred that the "User is preparing to play" (block 10130), and flow stops. If C is greater than or equal to twenty, it is inferred that the "User is playing" (block 10133), and flow stops.

One or more actions may then be taken (e.g., by central controller 110), based on the outcome of the decision tree. For example, if it is determined that the user is playing or will be playing, a light on a second user's mouse may turn green, suggesting that the second user would likely be successful in initiating a game with the first user (e.g., should the second user decide to issue a challenge to the first user). For example, if it is determined that the user is working but may be done with work soon, a yellow light on a second user's mouse may turn yellow, suggesting that the second user may be successful in initiating a game with the first user, at least if the second user waits a few more minutes. As will be appreciated, any suitable action may be taken resultant from an outcome of a decision tree.

Referring now to FIG. 102, a flow diagram of a method 10200 according to some embodiments is shown. Method 10200 may allow a user (user 2 in the present examples) to monitor the status and/or availability of other users (including user 1 in the present examples), so that user 2 may connect in some way with one of the monitored users (e.g., to play an online game together; e.g., to share in the experience of the other user; e.g., to exchange messages with the other user). In various embodiments, user 2 may see when another user is available (e.g., when user 1 is available), and may then challenge the other user to a game. In various embodiments, user 2 may see that another user (e.g., user 1) is having an interesting experience (e.g., seeing a nice sunset; e.g., having a good performance in a video game; etc.) and may wish to share in the experience with the other user. In various embodiments, user 2 may see that another user is available to have a conversation and may wish to open up a dialogue with the other user.

At step 10203, a user 1 indicates who is allowed to see the users data. In various embodiments, a user's status or availability (e.g., user 1's status or availability) will be broadcast to other users (e.g., to friends of the user). The user's status or availability may represent potentially sensitive information of the user. For example, a users status information may indicate that the user is not home, sleeping, out of town, etc. As such, a user may wish to limit which other users may see information about the user's status or availability. In various embodiments, a user may indicate other users through a GUI, e.g., through screen 4800.

In various embodiments, user 1 may indicate that another user (e.g., user 2) can see one type of data of user 1, and that still another user (e.g., user 3) can see another type of data of user 1. For example, user 2 is allowed to see when user 1 is available to play a game, while user 3 is allowed to see if user 1 is home or not. In this way, for example, less sensitive data can be made available to a wider set of users, and more sensitive data (e.g., data about whether user 1 is home or not) can be restricted to a narrower set of users (e.g., to more trusted users).

At step 10206, user 1 indicates what data about the user can be seen. In various embodiments, data may include raw data, such as sensor readings, video footage, audio recordings, mouse movement data, etc. In various embodiments, data may include inferred, deduced, or conclusory data. For example, data may include an identity of an individual in user 1's home (e.g., as deduced from video footage in user 1's home). Data may include an activity the user is involved in (e.g., eating, working, watching TV, etc.). Data about a user's activity may also represent inferred data, since it may rely on interpretation of video footage, mouse movements, or other raw data inputs.

In various embodiments, data about user 1 may include peripheral usage data, such as mouse movements, keyboard strokes, head motions captured by a headset, etc. Such data may be stored in, and/or obtained from peripheral activity log table 2200.

In various embodiments, data about user 1 may include data obtained from sensors at a user's peripheral device. Such data may be stored in, and/or obtained from peripheral sensing log table 2300. Data obtained from sensors may include a heart, a blood pressure, a skin conductivity, a metabolite level, and/or any other sensor data.

In various embodiments, data about user 1 may include user device usage data. Such data may be stored in, and/or obtained from user device state log table 2100. Data obtained about user device usage may include data about what applications a user was using, when the user was using such applications, what the user was doing with such applications (e.g., which websites the user was viewing using a browser; e.g., what type of document the user with editing using a word processing application), and/or any other user device usage data.

In various embodiments, data about user 1 may include data gathered from one or more devices (e.g., sensing devices; e.g., home automation devices; e.g., appliances) in the user's home. Such devices may include motion sensors, video cameras, thermal sensors, audio sensors, light sensors, and/or any other sensors. Exemplary sensors in a user's home are depicted in map 6300, according to various embodiments. In various embodiments, data about user 1 may include data gathered from one or home automation devices or appliances. For example, a thermostat may report data on when it was used, what settings it was placed at, when settings were changed, etc. As another example, a refrigerator may report when it was opened. As another example, a microwave oven may report when it was used and for how long. As another example, a closed circuit television camera may report video footage.

Data from home sensors and/or appliances may be stored in a table, such as in 'Home sensor and appliance logs' table 7500 of FIG. 75. With reference to FIG. 75, 'Appliance sensor reading ID' field 7502 may store an identifier (e.g., a unique identifier) of a reading or setting from a home sensor or appliance. Field 7504 may store an indication of a home sensor or appliance (e.g., an identifier or name for the appliance). Description field 7506 may store a description of the sensor, appliance, or component thereof (e.g., "refrigerator door"). Fields 7508 and 7510 may store, respectively, start and end times for when the reading was taken or received. Field 7512 may indicate the nature of the reading (e.g., that a door was opened). In various embodiments, field 7512 may store raw data, such as video footage from a camera.

User 1 may indicate what data can be seen by other users. The user may indicate what data can be seen by the central controller 110. The user may indicate, by user, or by group of users, which other users can see which items of data. For example, users in group a (e.g., a group as stored in user groups table 1500) can see raw motion sensor data from user 1's home. On the other hand, users in group b can only see inferred data about what room user 1 is in.

At step 10209 user 2 indicates that user 2 wishes to monitor user 1. User 2 may indicate that he wishes to monitor one or more other users as well. For example, user 2 may provide a list of friends that user 2 wishes to monitor. These may represent people with whom user 2 might wish to connect at some point (e.g., in order to play a game; e.g., in order to share an experience; etc.). As another example, user 2 may provide a list of co-workers that the user wishes to monitor. The user may wish to know when such coworkers are available, in case the user needs to talk to one of them.

In various embodiments, when user 2 indicates that he wishes to monitor user 1, the central controller 110 may verify that user 2 is among the people who are allowed to see user 1's data (e.g., as determined at step 10203; e.g., by verifying that user 2 is a member of a user group in table 1500 whose users are allowed to see user 1's data).

In various embodiments, user 2 may only wish to monitor user 1 at certain times of the day. For example, if user 1 is a prospective opponent of user 2 in an online video game, then user 1 may only wish to monitor user to during days or times when user one might want to play in a video game. Thus, for example, user 2 may wish to monitor user 1 only during evenings, because user 2 does not typically play video games in the mornings. On the other hand, user 2 may wish to make a different sort of connection with another user during the mornings (e.g., with a potential carpool buddy), and so user 2 may wish to monitor another user during the mornings.

Thus, in various embodiments, user 2 may specify not only another user that he wishes to monitor, but also dates and times during which user 2 wants to monitor the other user.

In various embodiments, user 2 may specify other circumstances for when he wishes to monitor user 1. For example, user 2 may specify that he only wishes to monitor user 1 when user 2 is at home. For example, if user 2 only please video games when he is at home, there may be little reason to monitor user 1 (a prospective video game opponent), when user 2 is not home. In various embodiments, user 2 may specify any suitable circumstances for when he wishes to monitor user 1 or any other user.

At step 10212 user 2 establishes alert criteria. Alert criteria may specify what data or situation about user one will trigger an alert to user 2. Example alert criteria may include one or more of: user 1 is home; user 1 has gone upstairs; user 1 has gone into a particular room (e.g., into the room and user ones house where user one typically plays video games); user 1 has just finished working; user 1 has just woken up; another member of user 1's household has just left the house; another member of user 1's household has just entered the house; user 1 looks bored; user 1 laughs; user 1 begin speaking; user 1 has just finished a phone conversation; it has started raining in the locale of user 1; and/or any other criteria.

At step 10215 user 2 establishes an output format for alerts. In various embodiments, and output format made detail the manner in which the alert will be conveyed to user 2.

The output format may include what device, devices, and/or device components will convey an alert. For example, a particular light on a mouse will be used to convey the alert (e.g., the third light from the front on a mouse). In various embodiments, user 2 may configure his mouse (or other peripheral device) so that different components (e.g., different lights) on the mouse correspond to different users that user 2 is monitoring. Thus, for example, when a particular light on his mouse goes on, user 2 may recognize automatically that his friend Bruce Gonzales is now home and possibly available to play a video game.

In various embodiments, other components besides a light may convey an alert. An alert may be generated using a haptic generator, an audio speaker, a heat generator, a display screen, a motor, an electric current generator. In various embodiments, alerts may be generated using components of a peripheral. In various embodiments, alerts may be generated using other devices. Other devices may include home alarms, televisions, cellular phones, phones, clock, smoke alarms, signage, digital picture frames, etc.

In various embodiments, an alert may be conveyed to a user via a user device (e.g., via a personal computer, tablet, etc.). For example, an app on a user device may flash a message to user 2 indicating that user 1 is at home in his gaming room.

In various embodiments, when user 2 establishes the output format of the alert, user 2 may specify the modality of the alert. The output format may include the modality of the alert. The modality may include one or more details about how the alert will be conveyed. Modality may include duration, intensity, and/or frequency of alert. For example, user 2 may specify that, as an alert, an LED light on his mouse will light up bright orange for 3 seconds, turn off for one second, light up bright orange for 3 seconds, turn off for 1 sec, and repeat the cycle for five minutes.

With respect to a light (e.g., an LED), an alert modality may specify a color, brightness, duration of turning on, duration of turning off, frequency of turning on and off, and any other pertinent parameter. A modality may specify that light is to alternate colors or cycle through colors.

In various embodiments, user 2 may establish different output formats corresponding to different users that user 2 is monitoring. For example, an LED light on user 2's mouse may show a blue light when user 2's friend Jack is available, and a purple light when user 2's friend Sam is available. In this way, for example time of the same component may be used to alert user 2 for multiple different monitored users.

With respect to a speaker or other audio generator, an alert modality may specify a frequency, a volume, a duration, or any other suitable parameter. In various embodiments, an alert may take the form of a pre-recorded audio message, song, jingle, or the like. For example, when user 2's friend Bob is available, a series of notes from a trumpet may play. When user 2's friend Suzy is available, a guitar riff may play.

Various embodiments contemplate that any other suitable modality may be used for presenting an alert.

At step 10218 the central controller 110 monitors user 1's data. The central controller may monitor data, readings, settings, usage statistics, etc. of any device, appliance or the like associated with user 1. The central controller may monitor readings from motion sensors, mouse movements, light levels, sounds, video footage, etc. The central controller may monitor use of a refrigerator, microwave, coffee maker, oven, stove, television, cable television, router, thermostat, window blind controller, etc.

In various embodiments, the central controller 110 monitors for the sounds of pets, sounds of doors opening or closing (e.g., room doors; e.g., a refrigerator door; e.g., a microwave door), the sound of footsteps, the sound of voices, the sound of a television, the sound of a phone conversation, or any other sound. For example, such sounds may allow the central controller to make an inference about user 1's availability to connect to user 2. For example, if the central controller detects the sound of a television, the central controller may infer that user 1 is engaging and leisure activities, and may therefore be available to connect with user 2 for an online video game.

In various embodiments, the central controller 110 may monitor Wi-Fi® signals within user 1's home. Wi-Fi® signals within a given location may change as a result of activity in the location. For example, a person walking between a Wi-Fi® source and a Wi-Fi® receiver may cause the strength of the received signal to temporarily change. It may thus be inferred that a person has walked past. Thus, in various embodiments, the central controller may use W-Fi signals to infer the availability of user 1, and/or to infer any other aspect of user 1.

In various embodiments, the central controller 110 may monitor a medical device associated with user 1. Exemplary medical devices may include an electrocardiogram (EKG), heart monitor, glucose monitors, scales, skin patches, ultrasounds, etc. In various embodiments, the central controller 110 may monitor data from a health or exercise monitoring device (e.g., from a Fitbit, treadmill, etc.).

In various embodiments, the central controller 110 may monitor data pertinent to user 1 that is not necessarily generated by user 1, or even generated at user 1's household. For example, knowing the location of user 1's house, the central controller may monitor the weather at user 1's location (e.g., using a public weather feed). In various embodiments, the central controller may monitor pollen count, the occurrence of local events (e.g., parades, softball games, etc.), traffic, crime statistics, or any other state of affairs that may impact user 1.

For example, if the central controller 110 determines that there is bad weather, or high pollen count in the vicinity of user 1, the central controller may infer that user one prefers to stay inside, and may thereby be potentially available to connect with user 2. On the other hand, if there is a local event going on, then the central controller may infer that user 1 may wish to go outside and attend the local event, and will therefore be unavailable to connect with user 2.

At step 10221 the central controller determines a situation from user 1's data. In various embodiments, using data gathered from or about user 1, the central controller 110 may infer, deduce, or otherwise determine a situation, a circumstance, an intent, and/or any other state of user 1. In various embodiments, the central controller may determine a current activity in which the user 1 is engaged (e.g., eating, sleeping, watching TV, playing a game, working, reading, speaking with a spouse, playing with children, doing chores, cooking, and/or any other activity). In various embodiments, the central controller may determine an intended activity of user 1 (e.g., an intention to eat, sleep, etc.). In various embodiments, the central controller may determine the state of user 1's environment (e.g. is user 1 hot, cold; e.g., is it noisy; e.g., is it rainy; e.g., is it bright outside). In various embodiments, the central controller may determine the state of user 1's health (e.g., is user 1 sick, injured, on medication, undergoing physical therapy, or in any other state of health). In various embodiments, the central controller may determine user 1's mood. In various embodiments, the central controller may determine user 1's location (e.g., room in the house; e.g., inside or outside the house; e.g., presence or absence from the house). In various embodiments, the central controller may determine any other aspect of user 1.

In various embodiments, user 1's mood May be determined from data from one or medical devices, such as from an EKG, Galvanic skin response (GSR) sensor, electroencephalogram (EEG), heart rate monitor, skin temperature sensor, Respiration sensor, Or any other sensor. Baseline correlations between mood and sensor data may be determined by capturing sensor data at times when the mood is known (e.g., when it is known that a user is happy because of a recent win in a game) and/or when the mood can be determined through other means (e.g., through analysis of facial expressions). When recognized sensor readings subsequently appear, these sensor readings can be used to determine a mood through the established baseline correlations. For example, high heart rate and high skin conductivity may correlate to a stressed mood.

In various embodiments, the central controller 110 may determine an aspect of another member of user 1's household. For example, the central controller may determine what room user 1's spouse is in. Knowing the circumstances of other members of user 1's household may have a bearing on user 1's ability to connect with user 2. For example, if there is another member of user 1's household in the same room as user 1, it may be inferred that user 1 is paying attention to the other member of the household, and may be unavailable to connect with user 2.

The following are some methods for determining a situation of user 1. If a motion sensor in a particular room detects motion, it may be inferred that user 1 is in that room. If an appliance in a given room reports usage (e.g., if a light in a given room is turned on) then it may also be inferred that user 1 is in that room. If certain types of appliances report usage (e.g., microwaves, refrigerators, stoves, etc.), then it may be inferred that user 1 is engaged in cooking and/or eating. Usage of other appliances may represent other activities (e.g., usage of a washer, dryer, or iron may indicate that a user is doing laundry). If audio of user 1 is recorded, user 1's mood may be inferred from tone of voice, pace of speaking, heaviness of footsteps, etc. If video of user 1 is recorded, user 1's mood may be determined from facial expressions. Video may also be used to infer an activity in which user 1 is engaged (e.g., through classification of captured video frames using a machine learning algorithm). As will be appreciated many methods are contemplated for inferring user 1's situation (e.g., using various algorithms; e.g., using various decision rules; e.g., using various sensors; e.g., using various data).

In various embodiments, a situation, circumstance, or other aspect of user 1 may be determined using methods described with respect to process 10100 (FIG. 101). For example, based on received data about user 1, a decision tree (or any other suitable algorithm) may be used to discern or infer an intent (or other circumstance) of user 1.

In various embodiments, data about user 1 is received from one or of: (a) a peripheral device of user 1, (b) a sensor in range of user 1; (c) an appliance; (d) a third-party data source (e.g., a weather service); and/or from any other suitable source. Such data may be transmitted to and/or aggregated on a peripheral device of user 1. The peripheral device of user 1 may then determine a situation of user 1. In various embodiments, such data may be transmitted to and/or aggregated on a user device of user 1. The user device of user 1 may then determine a situation of user 1. In various embodiments, such data may be transmitted to and/or aggregated on a peripheral device of user 2. The peripheral device of user 2 may then determine a situation of user 1. In various embodiments, such data may be transmitted to and/or aggregated on a user device of user 2. The user device of user 2 may then determine a situation of user 1.

In various embodiments, two or more devices in cooperation may determine a situation of user 1. In various embodiments, peripheral and user devices of user 1 may, in combination, determine a situation of user 1. In various embodiments, peripheral and user devices of user 2 may, in combination, determine a situation of user 1.

At step 10224 the central controller 110 determines if user 1's situation warrants an alert to user 2 based on the alert criteria. For example, if user 2 requested an alert when user 1 is in user 1's gaming room, and the central controller determines that user 1 is in user 1's gaming room, then the central controller may determine that an alert to user 2 is warranted.

At step 10227 user 2 receives an output alert according to the output format. For example, if user 2 has requested that an alert take the form of a particular audio jingle played from his mouse, then user 2's mouse may now play the jingle.

At step 10230 user 2 initiates a connection with user 1. User 2 may request to connect with user one in various ways. User 2 may click a button or otherwise activate a component on his mouse or other peripheral device that corresponds to user one. For example, if a particular light on user 2's mouse has been activated (e.g., lit up) to indicate the availability of user 1, then user 2 may press a mouse button near to (e.g., closest to) that light in order to initiate a connection with user 1. In various embodiments, user 2's mouse (or other peripheral) may instruct user 2 to click or press a particular button (e.g., "i" on a keyboard; e.g., the right mouse button) to initiate a connection. The connection may initiate, by default, with the other user who has triggered the most recent alert.

In various embodiments, user 2 may access a list of other users he is monitoring (e.g., available users he is monitoring), and select one such user (e.g., user 1) with whom to initiate a connection.

In various embodiments, a connection may be initiated automatically on behalf of user 2, such as when user 2 receives an alert related to user 1.

Various embodiments contemplate any other suitable method by which user 2 may initiate a connection with user 1.

At step 10233 user 1 accepts the connection with user 2. In various embodiments, user 1 receives a request to connect with user 2. For example, user 1 may receive a message on his mouse or other peripheral device. Use 1 may be asked to press a button or key, move his mouse, or take any other suitable action in order to accept the connection request from user 2.

In various embodiments, a connection may be initiated automatically between user 1 and user 2 even without an explicit acceptance on the part of user 1. Various embodiments contemplate any other suitable method by which user 1 may accept a connection with user 2.

At step 10236 user 2 is connected to user 1. In various embodiments, once connected, a peripheral device of user 2 may reflect (e.g., replicate; e.g., illustrate; e.g., represent) some aspect of the environment of user 1. A peripheral device of user 2 may reflect the local weather in the vicinity of user 1. For example, if it is raining at user 1's location, user 2's mouse may rumble to reflect the patterning of rain on a rooftop. If the sun is setting at user 1's location (e.g., user 1 and user 2 may be in different time zones), then user 2's mouse may turn orange and pink to represent the sunset. User 2's mouse may show an image or video of the sunset (e.g., as captured by a camera at user 1's house). User 2's mouse may show a rendering or animation of the sunset. In various embodiments, any representation of the weather at user 1's location may be shown on user 2's mouse (or other peripheral device).

As another example, if there are sounds at user 1's location (e.g., the sound of a dog barking; e.g., the sound of children laughing), then user 2's peripheral device may reflect the sounds, such as by outputting the sounds from a speaker in user 2's peripheral device. As another example, if it is hot at user 1's location, a heating element in user 2's mouse may activate and thereby allow user 2 to feel heat as well.

In various embodiments, if it is windy at user 1's location, then user 2's peripheral device may show (e.g., output on a display device) imagery evocative of the wind. Such imagery may include leaves being carried around in the wind, tree swaying, grass bending, an animal's fur being blown about, sand being stirred up, etc.

In various embodiments, once connected, a peripheral device of user 2 may reflect some aspect of user 1's vital signs. User 2's peripheral device may reflect a heartbeat of user 1. User 2's peripheral device may reflect the breathing of user 1.

In various embodiments, once connected, a peripheral device of user 2 may reflect some aspect of user 1's mood. User 2's peripheral device may reflect an anxiety level, confusion level, or any other aspect of user 1's mood. Other moods that may be reflected may include excitement, happiness, sadness, frustration, or any other mood.

In various embodiments, user 1's mood may be reflected using imagery, such as an emoji representative of the mood being depicted. For example, if user 1 is anxious, then an emoji with teeth chattering may be depicted on user 2's mouse. Mood may be reflected using color. For example, there can be depicted using progressively darker shades of red (e.g., for progressively increasing anger levels). Mood may be reflected using text. For example, user 2's mouse may show the text, "Jack is confused" (e.g., if user 1's name is Jack). As another example, a series of question marks may also represent confusion on the part of user 1.

One Player Effects Another Player's Peripherals

One of the advantages of connecting peripherals from one player to another is that the peripherals can be used to make a gameplay session feel more connected, and allow for greater creativity in how players interact with each other. Such enhanced connections can occur before a game, during a game, or after a game—and some aspects of the communication can last until an event happens (like losing a game) or even be more permanent.

Various embodiments allow one user to control aspects of another users game characters, game environments, or even the peripherals of the other user.

In various embodiments, a user is able to control elements of a second user's game character. For example, a first user might win a contest with the second user and earn the right to make an alteration to the second user's game character. The game controller could send a list of three potential game character changes to the first users mouse display area. For example, the first user might see "1) make character look like a baby; 2) make character look like a rabbit; 3) make character have big ears".

In various embodiments, a user is able to control elements of another user's game environment. For example, a first user could direct that a sign be put up in the second user's game environment mentioning what a skilled player the first user is.

In various embodiments, changes could be made to the room environment of a second user, such as by directing the second users user device to project an image onto the wall of the room in which the second user was sitting.

In various embodiments, a user is able to control peripherals of a second user.

In various embodiments, a first user can make changes to the mouse of a second user, such as by enabling a light to be lit green for the next ten minutes on the mouse of the second user.

In various embodiments, a first user can make changes to the keyboard of a second user. A first user could change the backlighting of the keyboard of a second user in a way that spells out words to the second user one letter at a time.

By allowing for communications between peripherals, the central controller can facilitate many cooperative and supporting behaviors between players. Such cooperation can enhance feelings of camaraderie during gameplay and make the human connection between players felt more strongly, even with remote players thousands of miles away.

At the end of a game, the central controller may facilitate such behaviors as shaking hands, patting each other on the back, nodding and/or smiling, allowing one player to place a dunce cap on another player, or any other behavior.

In various embodiments, the central controller may facilitate shaking hands.

Once play is complete (or a meeting is complete), individuals could select an on-screen player (meeting participant), press a button on the device to cause a vibration, color or slight movement (simulating the feel of a handshake) of the other person's mouse, indicating that a handshake is in order. The corresponding player (or meeting participant) could acknowledge this and perform a corresponding action on their device to reciprocate the gesture.

The device could also interface with the game and allow a player to select another player, invoke the handshake and the avatar simulate the handshake with the other player.

The device skin could change to show an outreached hand, simulating a handshake. The other person could reciprocate and when their device is invoked, both device skins could move (or render movement) simultaneously to simulate a handshake.

In various embodiments, the central controller may facilitate having players pat each other on the back.

Once play is complete (or a meeting is complete), individuals could select an on-screen player (meeting participant), press a button on the device or use the force sensor to cause a vibration, color or rapid pulse movement (simulating the feel of a pat on the back) on the other person's mouse, indicating a pat on the back. The corresponding player (or meeting participant) could acknowledge this and perform a corresponding action on their device to reciprocate the gesture.

The device could also interface with the game and allow a player to select another player, invoke the pat on the back action and the avatar simulate the pat on the other player.

The device skin could change to show an outreached hand, simulating a pat on the back. The other person could reciprocate and when their device is invoked, both device skins could move (or render movement) simultaneously to simulate a pat on the back.

In various embodiments, the central controller may facilitate having players nod and smile before exiting.

Once play is complete (or a meeting is complete), individuals could select an on-screen player (meeting participant), press a button on the device to cause a vibration, color (yellow representing a happy emotion) or slow/calming pulse movement in the device, indicating nod or smile. The corresponding player (or meeting participant) could acknowledge this and perform a corresponding action on their device to reciprocate the gesture.

The device could also interface with the game and allow a player to select another player to provide a response. The avatar could change and display a nod or smile to the other player(s).

The device skin could change to show a smiley face or a head that is nodding. The other person could reciprocate and when their device is invoked, both device skins could simultaneously move (or render movement) to show each are smiling or nodding.

Each player could also simply hit a button on the device which invokes an emoji on the screen representing a smile or nod.

In various embodiments, the central controller may facilitate having one player place a dunce cap upon the other player.

Once play is complete, and a game is lost, individuals could select the player that lost on screen, press a button on the device to cause a dunce cap to be placed on the head of the losing player.

The device skin for the losing player could change to show a dunce cap. Participants in the game could select the losing players avatar and place a unique dunce cap on them.

Each player could also simply hit a button on the device which invokes an emoji on the screen representing a dunce cap.

During a game, the central controller may facilitate such behaviors as indicating visual alignment, sharing positive verbal messages, and having other observers cheer players (e.g. voice overlay, text, images).

In various embodiments, the central controller may facilitate having players indicate visual alignment.

There may be times in a game (or meeting) where individuals want to demonstrate alignment using a visual cue and not a verbal remark for others to hear. For example, during a game, if a teammate is wanting to go to the left to search for the enemy, but does not want this to be made known to anyone else in the game, they can select the players to provide visual cues. The device is used to select a button/key and provide a pulsing color/vibration (or other visual cue, or other cue) to the selected player. If the player agrees, they select a button/key on the device and this is sent to the requesting players. The visual cue changes indicating acceptance. If they do not agree, the requesting player's color changes to a solid red color. The responses are displayed for a brief period of time before resetting.

The skins on the device can change indicating a need for alignment. For example, a person leading a meeting may need to get alignment on an issue after a discussion. Instead of verbally polling everyone, they simply invoke a button on their device, and each participant's device displays a thumbs up icon on the screen. If they agree, the participants press a corresponding button to accept or reject the alignment item.

In various embodiments, the central controller may facilitate the sharing of positive verbal messages.

The device could be used to deliver pre-recorded or unique messages to other game players or meeting participants. For example, if a person makes a good move in a game (or positive contribution in a meeting), the team players could select a device button/key that delivers a verbal message to the player either pre-recorded or recorded in real-time using the device. This could be in the form of a textual message (e.g. 'good job', 'great move') displayed only for the game character, displayed for all other players to see or an actual verbal message heard by the player in their headset.

In various embodiments, the central controller may facilitate having other observers cheer players (voice overlay, text, images, etc.).

The device could be used to deliver pre-recorded or unique messages to other game players from observers/virtual audience members. For example, if a person makes a good move in a game, the team players could select a device button/key that delivers a verbal message to the player either pre-recorded or recorded in real-time using the device. This could be in the form of a textual message (e.g. 'good job', 'great move') displayed only for the game character, displayed for all other players to see or an actual verbal message heard by the player in their headset.

Observers could use the device to display images and text to the player (meeting participants). For example, if someone contributes an innovative idea in a meeting, other participants could use their device to provide on-screen text or video saying, 'great idea' or send a device skin to the person showing an image of hands clapping.

Various embodiments contemplate audio cheering (such as in a game or by a third party not directly participating in a game). During a game, a player could send an audio message to another player or team cheering them on using a mouse or keyboard. Also, if a device owner is not engaged in the game (third party observer), they can still use their mouse-keyboard to send an audio cheer to an individual player or team. The device could also be used in a business context to cheer/motivate employees.

In various embodiments, the central controller may facilitate flirting. On social sites (e.g., dating sites, Facebook®, Twitter®) and in communication between individuals, a user could deliver flirting actions to another person using peripheral devices. In various embodiments, if a person wishes to give a wink, the receiving participant's device color flashes briefly and/or the device skin shows an eye winking. The receiving participant can elect to reciprocate, ignore or block the flirting by selecting a corresponding button/key on the device.

In various embodiments, if a person wishes to give a smile, the receiving participant's mouse color displays color and gets brighter or a skin is shown with a smiley face. The receiving participant can elect to reciprocate, ignore or block the flirting by selecting a corresponding button/key on the device.

In various embodiments, if a person wishes to give a kiss gesture, the receiving participant's mouse displays a hot red or the skin is shown with a pair of lips. The receiving participant can elect to reciprocate, ignore or block the flirting by selecting a corresponding button/key on the device.

In various embodiments, if a person wishes to pass a note/message, the receiving participant receives an alert on his mouse to check messages. A private message may be sent to an individual. The originator can record a message using the device or send a brief written message to the individual. The receiver's device could display a color to indicate they need to check their email message for a response. The skin on the receiver's device could change to display an envelope on the device as a reminder to check their messages. A brief text message could display on the device (e.g., 'meet me at 6 pm'). The receiver can confirm/reject by selecting a button/key on the device and have the sender notified on their device.

In various embodiments, if a person wishes to brush someone casually, the receiving participant's device could vibrate or change color indicating someone is wanting to meet them. In some embodiments, the shape of the keyboard could change based on another user indicating they are brushing up against you to get your attention. In some embodiments, the firmness of a key could change. For example, if a user wants to casually connect via brushing against you, the "E" on the keyboard could become significantly easier to press, thus getting your attention.

In various embodiments, one or more users may engage in a dance routine. In various embodiments, a multicolored display on a device may facilitate a dance routine.

Dancing is oftentimes a community activity. In various embodiments, peripheral devices can facilitate this. Those wanting to participate in dancing can modify the colors on their mouse and keyboard to be synchronized with the music and displayed for others to see.

In various embodiments, a peripheral device may feature a dance move as an image or "skin" of the device. If a user wants to display a dance move to others, they could select a dance move and have a static image displayed on their peripheral device or projected to another user's peripheral device. In addition to a static image, the display screen on the device could also display a video showing the dance move.

In various embodiments, a device may assist in showing or broadcasting a celebration dance. If a participant wins a game, they could use their device to select and show a winning dance to others. This could be in the form of displaying colors, presenting a dancing avatar or changing the skin of others to show a dance move in celebration of a win.

In various embodiments, a device may show, broadcast, or simulate laughter. In various embodiments, a device pulses to simulate a laugh. During a game/meeting, if an individual wants to show they are laughing without being heard, they could select a key/click combination on the selected devices of other users to begin the pulsating.

In various embodiments, a device color changes to represent a laugh. During a game/meeting, if an individual wants to show they are laughing without being heard, they could select a key/click combination on the selected devices of others and a color(s) display representing a laugh.

In various embodiments, a device skin changes showing a laughing face. During a game/meeting, if an individual wants to show they are laughing without being heard, they could select a key/click combination on the selected devices of other users to show a laughing face.

In various embodiments, an avatar changes to show someone laughing. During a game, if an individual wants to show they are laughing without being heard, they could select a key/click combination on the selected devices of others to make their avatar laugh.

In various embodiments, a peripheral device may facilitate praise. Using a peripheral device, a message could be displayed above the character and who sent it. The sending player selects the receiving player, the message and uses a button/key on the device to send. In comparison, this same approach could be used in a business setting for meeting participants.

In various embodiments, a specific quality is recognized in a person. For example, the phrase "good team player" is displayed above the player in the game or shown on the device skin.

In various embodiments, a specific skill is recognized in a person. For example, the phrase "great accuracy in shooting" is displayed above the player in the game or shown on the device skin.

Boasting

Part of gameplay often includes an element of playful boasting when one player defeats another player. This is normally good natured, and can enhance the competitive spirit of the players and spur greater efforts in improvement before returning to battle with greater skills next time. The device can be used to send and receive messages, images, colors and movement representing the various actions below.

A taunt may be brought about in various ways. When one player defeats another player in a game, the losing player may suffer one or more of the following taunts: (1) his game character shrinks in size; (2) he loses a weapon; (3) he starts to cry; (4) he has to bow to the winner; (5) his face gets distorted; (6) he gains weight; (7) he loses weight and becomes scrawny; (8) his mouse is less responsive for a period of time; (9) his Zoom background is swapped for something of the winning players choosing.

In various embodiments, when one player defeats another, the winning player's name is displayed on the losing player's mouse or keyboard (e.g., the keys of the winning player's first name rise up and cannot be used for 60 seconds). In various embodiments, something is projected onto the walls behind the losing player, like a skull and crossbones.

In various embodiments, a player may engage in trolling behavior. Such a player may seek to annoy or get a rise out of another player. In various embodiments, a player can clip something, add text or filters, and send it to the opponent. A player may cause an opponent's mouse to play classical music (or any other music type, or any other music). In various embodiments, a players character may be placed in various locations in the game for the opponent to discover. In various embodiments, a players character is allowed to follow an opponent's character. In various embodiments, a player is notified when a previous opponent is playing a game in order to join them in the same game. In various embodiments, a player can send short videos to another user's display device. In various embodiments, a player is able to control the movement or vibration of another person's mouse-keyboard.

In various embodiments, a player may engage in bullying behavior. In various embodiments, this type of behavior is permitted as part of the game. In various embodiments, while the behavior may be permitted, there may be efforts to identify and call out bullies.

In various embodiments, a player may get a virtual bully cap on their character. A player's audio channel or character may get a silly voice. In various embodiments, signs with taunting messages may appear in game (e.g., one player causes such signs to appear). In various embodiments, a player is permitted to 'trash talk' players and their skill or appearance. In various embodiments, a characters appearance changes to show the associated player as a bully for all to see and react. In various embodiments, a player's device begins to move or vibrate for a brief period of time (e.g., if such a player is being bullied). In various embodiments, a player's key functions are manipulated by an opposing player to disrupt their play briefly. These may be changing function or force, making it more difficult/easy to press a key.

Intentional Poor Performance

There are times in games that alternative objectives are being pursued by a player. For example, a player is trying to sabotage himself and/or his team. For example, the player is purposefully performing poorly. These behaviors can be made known to others in the game using peripheral devices.

In various embodiments, a players character slows in movement in an exaggerated way. The user is able to select clicks/buttons to control the avatar movement indicating they are not playing.

In various embodiments, a player's game skill (shooting, running, throwing, etc.) is reduced significantly. Other player devices could display the reduced accuracy of the player via changing colors, text on their respective displays or movement of their respective devices.

In various embodiments, text is presented to others that a player is not playing their best game, on purpose.

In various embodiments, text or images are presented to a player's team's display indicating the player's performance is degraded or the player is no longer playing to win.

In various embodiments, another player is able to control the use of the self-sabotaging player's device so they are not able to use it for a period of time, and cannot thereby cause the team to lose.

One Player Controls Another Player's Game Character

There are times in a game when one player may want to control another player's character using functions of a peripheral device, such as through buttons, clicks or movements.

In various embodiments, a first player could cause a second player's character to lie on the ground and take a nap on the ground. The first player could accomplish this by selecting the character and lifting the mouse to force the character to drop to the ground.

In various embodiments, a user could select a character and continually send messages not related to the game to display above the character, in the audio of others, or in visual display devices.

In various embodiments, text, images, colors or device movement is presented to other players indicating that a given player is not playing his best game or not playing to win. In this case, the other players could use the device to immobilize the given players character.

In various embodiments, the user could select a character and remove weapons or game attributes using the peripheral device. This may reduce the chance that the character's poor performance would hinder the team or allow an opposing player to gain an advantage.

Sharing Information

In various embodiments, it may be desirable to share information, such as a team logo, team flag, updates, minutes from most recent strategy sessions, etc. There are times in business settings that information needs to be shared quickly with people and using peripheral devices can facilitate this type of communication.

In embodiments involving a team logo or flag, the device could allow for members of a team to have a color, pattern, image or text to indicate the particular team they are associated with.

Various embodiments involved grouping employees. In certain business settings it is important to group individuals for tasks to complete. This is often done by self-selection. The meeting owner or lead could use enabled devices to group people automatically by color, image or text. Large groups of people could be grouped by having five mouse-keyboards light up red, five others light up yellow and five others light up blue. Likewise, the images on the device could each be different allowing another way to group individuals in smaller teams.

Various embodiments involve announcements. In various embodiments, employees and teams need and/or want to be kept informed. For example, the new CIO has selected a person for a promotion. This information could be quickly shared with people through peripheral devices by displaying the name, announcement or color. Another example may be in the case of important decisions. If a decision is made that impacts a team, instead of sending emails and waiting for people to see it, the sender of the announcement could send the information directly to the peripheral devices. The peripheral devices may each then show an image, text or color representing a signal for the peripheral device owners to check their email. This process may have advantages over texting, since with texting it is often cumbersome to obtain all phone numbers for large groups, and texting may also generate group chatter.

Various embodiments involve bringing all hands on deck. In cases where immediate action is necessary, emails and texts may be delayed, whereas peripheral devices can deliver quick information for action. For example, if a significant IT outage takes place, a message in the form of text, visual image, vibration or color can be sent to needed participants indicating there is a need to resolve the outage. The participants can respond immediately, affirming that they received the message using their peripheral devices.

In various embodiments, a user may shame or embarrass their own teammates or opponents. In such cases, an opponent's character may turn red; an opponent's character may change posture (e.g., with head turned down, with slouching, etc.); an opponent's character may provide blank stares to others; a skin on a device may change to match a character; an opponent's device color can change to red to show embarrassment; the force on the opponent's peripheral device lessens to indicate a collapse of the character; or any other indicator of embarrassment, or any other indicator may be put into effect.

Do not Disturb

In various embodiments, a user may indicate that he wants no interaction, wants to be left alone, does not want to be disturbed, or any similar sentiment. In various embodiments, a users avatar indicates this sentiment via a new color or persona, such as a bubble placed around them, which may be triggered by a peripheral device. In various embodiments, a user's avatar freezes and accepts no message or interaction.

Asking for Help

In various embodiments, a user wishes to ask for help. In various embodiments, the user may create an SOS alert. In various embodiments, there may be a physical, real world emergency and the player would like to let others know.

In various embodiments, a player/participant initiates a message (visual image, message, vibration or color) using the device to indicate help is needed.

In various embodiments, if a player's mood is declining or the player is depressed, the player may seek help from others via the device. In various embodiments, biometric data can be used to ascertain changes in a player's mood, and, if needed, may automatically send alerts to other users' devices.

In various embodiments, skins of opponents' or other players' devices display '9-1-1' messages with the name of the distressed player. In various embodiments, opponents' or other players' devices initiate 9-1-1 alerts. In various embodiments, on-screen messages are displayed to players to refocus attention on the emergency. In various embodiments, other players and opponents can change the appearance of a player's device indicating a medical image. In various embodiments, sensory data collected from the device indicates a physical problem and alerts others.

In various embodiments, a user may express his feelings towards interacting with others, such as to receiving taunts or to delivering taunts. The player may no longer want this type of interaction and may use a device to indicate this sentiment to others (e.g., via color, skin image or device motion). In various embodiments, the player may set his device to block taunts.

In various embodiments, a player may wish that other characters keep a certain distance away from the player's character. If other characters do not keep such a distance, the player may feel that the other characters are in the players space. A character may then be asked to move away from their opponent (e.g., from a character whose space they are occupying). In various embodiments, a character is given a force field so others cannot get within a certain distance.

In various embodiments, a player may desire help from a competitive standpoint (e.g., help at achieving a goal in a game). A players character may need backup in a game from teammates. A player may need advice in a game to accomplish a goal. In various embodiments, help may be solicited through changing colors, changing skins, or through any other mechanism applied to another player's peripheral device.

In various embodiments, a device's color can change indicating game play is correct after receiving input. In various embodiments, a device may display text or image indicating a player is close to completing the game or overtaking the opponent.

In various embodiments, a player may desire cooperative or coordinating help from other players. A players character may need backup in a game from teammates. The player's device may then display text to others with information about the game and where the player needs assistance. In various embodiments, a player's character needs advice in a game to accomplish a goal. Other players can send text or image assistance to complete the game. In various embodiments, sensor data collected can be used to provide assistance. If EKG or galvanic information indicates stress, other players are notified and may offer their assistance in the game (or meeting).

Game or Other Players can Change the Performance of Your Inputs Devices

In various embodiments, occurrences in a game, or instructions by other players may cause changes in the performance of a given player's device. Such changes may include: slowing a mouse velocity; adjusting the pressure on the mouse or keys required to invoke action on the device; altering or swapping the actions accomplished on a device by particular buttons or keys (e.g., the functions of the left mouse button and the right mouse button are swapped); randomly displaying colors and patterns on the device to distract a player or get their attention (as with a meeting participant); changing audio input by adding static, decreasing/increasing volume, adding random noises (e.g., animal noises, children, vehicle sounds, nature sounds, etc.); disabling button/key actions on a peripheral device (or any other device), or any other changes. Disabling button/key action on a device may include disabling the ability to fire a weapon or vote on a decision in a meeting for a period of time.

In various embodiments, a device may project a visual into a room or behind a player. The visual may show: a map of a game; in-game movements of one or more other players (e.g., of all players); banner of awards; messages; (e.g., text and pictures); colors, such as colors representing game intensity; player images; game title; and advertisements. In the context of a meeting, a device may project such visuals as meeting agendas, presentations, list of ideas, decisions, participant lists, to-do lists, and a virtual desktop.

Visual Customization and "Skins" for Education and Business

Various embodiments have applications in the world of business and education. For example, there are many ways in which a user's mouse or keyboard could be used to display performance indications, status, levels, ratings, etc.

Almost all companies offer awards to high performing employees or teams—such as public recognition at town hall meetings, or written praise in a company internal newsletter. In various embodiments, indications of employee achievements could be displayed on an employee's mouse. For example, when a user is designated as "Employee of the Month for June," those words could be transmitted to the employee's mouse and shown on a display screen for the entire month. Instead of displaying the words, the mouse could also be enabled to display a signature color which indicates that the employee was currently Employee of the Month (similar to the yellow jersey for the leader of the Tour de France). This would allow someone walking by the cube or office of the Employee of the Month to immediately see that status level, and it would be a psychological boost to the awardee while working at their desk. The employee's keyboard could also be configured to display an insignia reflecting that they are the current Employee of the Month, such as by enabling a special color backlight for the keys. Such an employee could bring the mouse and/or keyboard to meetings where other employees would have a chance to see the visual designations of the Employee of the Month status.

The employee's mouse could also display key metrics that are important for the employee to be aware of. For example, the employee's mouse could display a time signal indicating how long the employee had been working without a break. The keyboard could also make the keys harder to press as the length of time without a break increased. After a designated amount of time without a break, such as two hours, the keyboard itself could stop processing the employee's inputs until a break of at least ten minutes was taken.

The employee's mouse could also be enabled to show an indication that an employee was not engaged with work or was spending a large amount of time on websites or applications unrelated to work. For example, an insignia could appear on the mouse when the employee spent less than 50% of their time in the last hour using an application other than Microsoft® Word, Excel, or PowerPoint. The keyboard keys could also be made more difficult to depress when the employee was using particular websites.

Employers worry if remote workers are capable of functioning at a high level. They might be worried, for example, that remote workers are drinking alcohol during work hours. An AI module could be trained to determine whether employees are functioning within normal performance parameters. Such a module could be trained, for example, using a device owners' "fist," or their keystroke cadence, level of typing mistakes, and other aspects of typing that together create a pattern of baseline typing performance. An AI module could also be trained using biometric data from the device.

Notifications could also be done through a mouse or keyboard. For example, an employee's mouse could flash as a ten minute warning that a meeting was about to begin. Similarly, the keyboard backlighting could be made to flash when a meeting was fifteen minutes from the designated ending time.

In an educational context, teachers could create rewards for students such as virtual "stickers" or gold stars that can be displayed on a student's mouse. For example, a student might get a special Platinum Star when they finish reading ten books, with the Platinum Star being visible on the student's mouse. In another embodiment, the student's computer camera could display the Platinum Star in the upper right corner of any school video learning session for all call participants to see.

In a business meeting embodiment, the mouse display area could display a red color if the user is of a particular business group, such as a software developer. Alternatively, the mood of meeting participants could be reflected in the color of the keyboard backlights of their laptop computers in a meeting.

Social Devices for Education and Learning

Education, courses, training, examinations and other forms of learning increasingly use software, take place in digital environments or over videoconferencing, or utilize telepresence technologies. The devices according to various embodiments could enable improved measurement and feedback of learning and teaching outcomes, as well as provide coaching to students and teachers.

The devices could be used for verification of student identity and ensuring integrity for teaching, courses, and online examinations. Verifying that the correct individual is taking an exam and ensuring that individuals don't cut, copy, or paste material from outside of the exam into the exam software are challenges to replacing in-person exams with online exams. The devices could utilize biometric sensors or stored identity information to verify that the individual using the input device is the individual supposed to be taking the exam. Additionally, the device or central controller could lock functionality to cut, copy, or paste exam material into exams, or limit the ability to access non-exam software.

Devices according to various embodiments could be used for detecting plagiarism and other forms of cheating through one or more means. The devices could transmit a record of mouse clicks or a key log to the central controller, which would permit the automated comparison of the text of an assignment, paper, or exam against the input log. Additionally, an AI module could be trained based upon the inputs of the device that classify whether a given body of text was likely to have been produced by the device owner through classification of device owners' "fist" or unique cadence of keystrokes.

During classes, training, or exams, the central controller could detect whether the device owner is utilizing non-education software or whether the device owner is present in front of the computing device. The central controller could prompt the device owner to return to the educational software or could lock the functionality of the devices for non-education purposes during classes; until a task, assignment, or homework has been completed; or until the teacher permits a class break.

The devices could provide a real time measure of student engagement through an AI module that is trained using the devices inputs, such as biometric sensors. Using galvanic skin responses, heart rate or other biometric data, this AI module could detect whether the student is excited, apathetic, confused, stressed, or having some other emotional response to the learning material. Both level and type of engagement could be provided to either the student or the instructor through the visual output of the devices or through other means.

Such an AI module might be utilized in many ways. For example, an AI module could provide coaching to students about material they find difficult or frustrating. Or an AI module could detect material students find stimulating and give supplemental or additional course material. Additionally, an AI module could measure over time the effectiveness of different teaching strategies for teachers. The AI module could prompt teachers to alter ineffective teaching strategies, reinforce effective teaching strategies, or individualize strategies to different types of students. The AI module could track over time student responses to similar material to measure learning outcomes or to enable improved material presentation. An AI module could choose among multiple versions of teaching material to individualize learning to an individual student by dynamically matching versions with a student's learning history, or the module could offer another version if the AI module detects that student is not learning from a particular version.

The devices could be used to train an AI module that predicts the difficulty of learning material and would allow a teacher or educational software to "dial in" the difficulty of learning material to individualize learning content—either to decrease difficulty or increase difficulty.

The devices could be used to train an AI module that combines device inputs and sensor inputs to ascertain whether documents, presentations, or other material are challenging to read or comprehend. Such an AI module could be used to create an automated comprehension tool akin to "spell check" or "grammar check" that would prompt users of the comprehensibility of the document, presentation, or other material and suggest improvements.

The device could facilitate collaboration of multiple users by allowing individuals to quickly find where others' cursor or text input is located in a shared document, presentation, or other file. The device could communicate to the central controller whether an individual cursor or text input within a software program is located and then share that location with another user's computer. For example, the present system knows where an individual's cursor is located in a document, allowing another user to say "Take me there" and the other user's mouse cursor is taken to the same location.

The outputs of the devices according to various embodiments could be utilized for providing feedback to students in the form of visual, tactile, or audio feedback. These feedback can be controlled by the teacher, the central controller, the game or software controller, or an AI module. For example, a student could receive feedback, in the form of visual, vibration, or temperature changes, after they input an answer to the question. The teacher, software, central controller, or AI module could identify whether the question is correct and output a visual signal if correct (e.g., "yes", "thumbs up,").

Peripherals to Improve Onboarding, Software Training and Help Functions

Software users face the challenge of learning to control the functionality of software—whether as new users who are on-boarding or existing users seeking to improve their functional experience. The present devices allow for game or software creators to improve onboarding, learning tutorials, and help functions.

Figure 100:
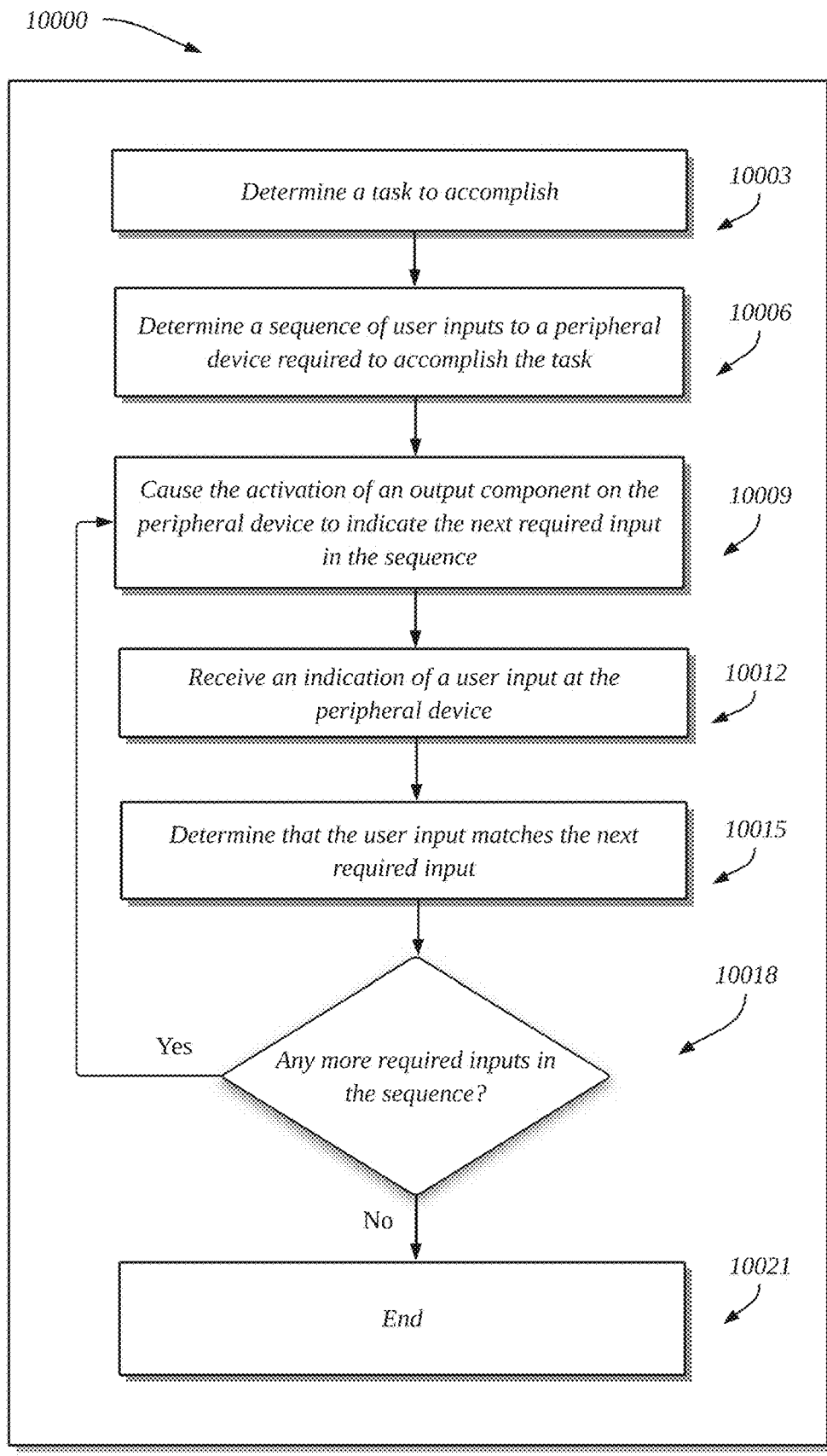
FIG. 100 is a diagram of a process flow consistent with at least some embodiments described herein.

Referring now to FIG. 100, a flow diagram of a method 10000 according to some embodiments is shown. In various embodiments, method 10000 may be used to train a user to accomplish a task. Method 10000 may be used to train a user to accomplish a task using a peripheral device. Method 10000 may be implemented by a peripheral device (e.g., peripheral device 107*a*), by a user device (e.g., by user device 106*b*; e.g., by a user device in communication with a peripheral device), by central controller 110, and/or by any other suitable combination of devices. For the purposes of the present example, user device 106*b* will implement the method while in communication with peripheral device

107a. However, it will be understood that the method need not only apply to this device combination.

At step 10003, user device 106b determines a task to accomplish. In some cases, a user may explicitly ask for help with accomplishing some task (e.g., with performing a mail-merge; e.g., with utilizing a particular attack sequence in a game). In some cases, a task may be predetermined as part of a lesson plan and/or a tutorial. A task may be determined in any other suitable fashion.

In various embodiments, an AI module could be trained using the inputs of the devices to detect when a user is struggling, confused, or unable to perform an input task. The module could then prompt the user with a tutorial, wizard, or help feature. The module could also infer what function the user was attempting to perform and demonstrate the input function by providing a visual, tactile, or audio output to help the user learn the correct combination of inputs. For example, in a game that requires simultaneously pressing keys to perform a move, the AI module could detect when a player is attempting to use that move but is not pressing the correct key combination. The game controller would then provide a visual output to show which keys to press.

An AI module could be trained using the inputs of the devices to detect when a user's performance using a piece of software has decreased or increased. This AI module could be used, for example, to detect whether a user is "rusty" due to taking a break from using the software and decrease the difficulty level of a game or education software; suggest a fresher tutorial; or use the devices' outputs to prompt the user with keys, mouse movements, shortcuts, or combos. The module could also prompt the user or lock the device if it detects a dramatic decline in performance.

At step 10006, user device 106b determines a sequence of user inputs to a peripheral device required to accomplish the task. Required input sequences may be determined from instructions, manuals, and/or specifications of a given application. In various embodiments, user device 106b may obtain such input sequences from central controller 110, from the creator of a software application, from a help menu associated with a software application, or through any other means. In various embodiments, one or more user devices may monitor use of a software application. The devices may learn (e.g., using an AI module) what inputs are necessary to accomplish a given task. These inputs may then be shared across user devices (e.g., through the intermediation of the central controller 110).

At step 10009, user device 106b causes the activation of an output component on the peripheral device to indicate the next required input in the sequence During onboarding, a tutorial could dynamically use the outputs of the device to indicate which keys, mouse clicks, or combination of inputs allow users to control certain functions. For example, keys could light up, vibrate, increase or decrease in height, change the temperature of keys to show a game player how to perform a certain move or combo. For example, in help features, these outputs could be used to show a user which combination of keys forms a shortcut for a particular function.

At step 10012, user device 106b receives an indication of a user input at the peripheral device. For instance, the user has pressed some keys, moved the mouse, clicked some buttons, or otherwise provided user inputs.

At step 10015, user device 106b determines that the user input matches the next required input. If the user input is the correct input required to accomplish the pertinent task, then user device 106b may determine that the user has made the correct input. If the user has not made the correct input, then user device 106b may wait for the correct input, may provide a hint to the user (e.g., in the form of a lit or depressed key, etc.), may display a message to the user (e.g., on peripheral device 107a; e.g., on user device 106b), or may take any other action.

At step 10018, user device 106b determines if there are any more required inputs in the sequence. If so, flow may proceed back to step 10009, only now with regards to the next required input. If there are no more required inputs in the sequence, then it may be determined that the user has successfully accomplished the required task, and flow may terminate (e.g., proceed to "End" block 10021). In various embodiments, the user may be given the opportunity to practice the task again (e.g., with fewer or no hints).

Video Game Analytics and Coaching

Video gaming analytics and video game coaching are increasingly popular with players seeking to improve their own performance. Devices according to various embodiments could facilitate the development of new measurements of gaming performance and enable new forms of AI-based coaching and performance improvement.

Devices according to various embodiments could combine mouse telemetry data, keystroke data, biometric data, and other forms of input data from the devices. These inputs could be communicated with the game controller, local software on the users computing device, or communicated with the central controller. By compositing input data with visual footage of gameplay, the device owner could review in depth what the player attempted to do in game with what the player actually did in game. The device, game controller, local software, or the central controller could measure the velocity of mouse cursor movement or key inputs during particular aspects of gameplay or to ascertain reaction times between in-game stimuli and player responses. For example, it could measure how quickly a player could bring a targeting reticle (such as a gunsight) on a target via mouse cursor velocity.

An AI module could be trained to identify whether a player is skilled at a game, as well as identify dimensions of skill related to a particular game. The module could allow a player to review their skill rating or the underlying dimensions of skill, or the module could provide automated feedback about which dimensions the player needs to improve. An AI module analyzing dimensions of skill for a particular game could be used to enable a leader, allowing a player to compare their skills with others. A leader board might also allow players to compare their performance in relation to the amount of money spent on in-game purchases.

An AI module could be trained to highlight particular kinds of clips for the player to review. This module could allow a player to see similar types of game situations and review performance data across these situations. The module could also flag clips with inflection points in the game for the player to review their decision making. The module could also allow a player to compare their gameplay with clips of more skilled players in similar game situations.

Utilizing biometric inputs from the devices, an AI module could be trained that analyzes physical and mental performance aspects of game play. For example, time of day, sleep deprivation, consumption of caffeine and performance enhancing substances, hunger, thirst, physical fatigue, length of games, length of gaming sessions, and other variables might affect individual performance. An AI module could identify factors affecting gameplay and allow the player to review these insights or provide automatic advice through on-screen prompts or through the output devices of the device. For example, the module might detect that a player performs poorly in a given match and the player had a slight hand tremor as measured by an EMG sensor or inferred from mouse or keyboard pressure. The AI module might prompt the player with a prompt to ask if they had consumed too much caffeine. The AI module might also allow players to optimize the scheduling of important matches or time gaming sessions to optimize performance by sharing insights with players.

The devices could enable the development of metrics regarding "general purpose" game skills. Rather than measuring performance within a single game software, the devices could enable tracking of player device inputs, player performance, and qualitative feedback from other plays across multiple games. The devices could communicate to the central controller, in addition to the game controller, which would permit the training of an AI module to measure general purpose gaming skills. These skills might be clustered by genre of game, for example, or they might be across all video games. The AI module could permit comparisons of players across different games to allow for rankings, leaderboards, a "pound for pound" best player, or other forms of public comparison. The module could also allow game designers to handicap games, allowing players with different levels of general purpose skills to compete on a level playing field. For example, players with low levels of dexterity or visual acuity due perhaps to age or other physical condition could compete with players with high levels of dexterity or visual acuity, with the game balancing the general purpose skills of both players.

In various embodiments, a given game may also be handicapped through adjustments to the capabilities of different player peripherals. If one player has a quicker reaction time than another player, then a delay may be added to any inputs provided by the first player to his peripheral device. For example, if the first player moves his mouse at time t, the mouse movement may only be transmitted at time t+50 milliseconds. Other adjustments that may be made to peripheral devices include adjusting sensitivity, adjusting pressure required to create an input, adjusting the resistance of buttons, keys or wheels, or any other adjustments. In various embodiments, adjustments may include enhancements or handicaps made to a peripheral device. For example, a game may be made more competitive by enhancing the weaker player's peripheral device, handicapping the stronger player's peripheral device, or some combination of both.

The inputs of the devices according to various embodiments could be trained to identify player skill at common roles within games dependent on team play. Using the devices' inputs, an AI module might identify clusters of player behavior to identify roles within teams and create an index of a players skill at performing those roles. An AI module might also identify which roles a player commonly fulfills, which they enjoy, and which they might be good at. The AI module could provide insight to the player about how to improve at a given role or make suggestions about how to better contribute to a team by changing roles.

Within games, players often identify a set of strategies that are more likely to result in winning, succeeding, or countering opponents' strategies. The set of commonly played strategies and how to respond to them is described by gamers as the "metagame" or the "meta." The inputs of the devices according to various embodiments could be used to train an AI module to identify the "meta" for a game. The inputs from individual devices and the game controller could be communicated to the central controller. The game controller could communicate with the central controller about the location of in-game resources, player spawn points, non-player characters or other game attributes. The central controller could contain a large dataset of individual players' inputs, which could be used to train an AI module which identifies clusters of individual player behavior (strategies), relationships between these clusters (which strategies are played together or against each other), and which clusters result in particular game outcomes. This AI module could also identify individual player preferences for strategies. This AI module could improve player performance in several ways. For example, the AI module could identify whether a player is utilizing a non-meta strategy, whether a strategy is weak or strong in a given meta, whether a player is utilizing the strategy correctly, whether a player is suited to particular strategies more than others, or which strategy to choose to counter common opponent strategies.

Players might improve their game play by reviewing the gameplay and performance metrics of better players. By synchronizing the history of skilled players' device inputs with visual clips, a player might be able to review how a more skilled player accomplished what they accomplished. An AI module might inform a player about the performance difference between their current skill level and more advanced levels and offer tips, tutorials or other forms of coaching about how to narrow specific performance gaps.

AI assisted coaching might occur in-game rather than after a match. An AI module could be trained that would provide guidance of a player's overall choice of strategies, highlight good or poor decision making at various points in the game, or analyze specific patterns of game play. An AI module could identify the meta of a given match, whether the player picked a correct strategy, or offer suggestions in light of the performance of an opponent. An AI module might review health and mental performance markers and make in-game suggestions to improve game play. For example, if the module detects elevated cortisol levels from metabolite sensors or an increase in sweat secretion from a sweat sensor, the module could provide feedback to the player to calm down, breathe, or relax. An AI module might utilize the device outputs, such as visual displays or tactile feedback, to provide prompts during gameplay.

Match-Making for Video Games

Video games utilize match-making systems to connect players together for gameplay. Matchmaking is integral to making adversarial, team games, or other forms of multi-player enjoyable. These systems often attempt to create matches between players of similar skill or level, while minimizing time spent queuing between matches as these systems attempt to create matches. The devices of the present system could enable pairing, creating teams, or making matches along other dimensions, such as level of engagement, excitement, or practice or educational value. The devices of the present system could also enable tracking of player skill, level, ability, across different games. From a players' perspective, the enjoyment of games is often associated with the "meta" of a game, or how common patterns of gameplay by players interact with other patterns of game play. The devices according to various embodiments could help identify a game's "meta" and utilize that information for improved matchmaking.

A player's skill level might vary with fatigue, health, time of day, amount of recent practice or gameplay and other factors. The inputs of the devices according to various embodiments could be utilized to train an AI module that calculates a relative skill level, based upon long-run player performance adjusted for fatigue, time of day and other factors. A matchmaking system could utilize these adjusted skill levels to create more balanced pairings, team making, and match making. For example, a player's skill might decline over a long gaming session, and the AI module adjusts the players skill level, the matchmaking system incorporates this adjusted skill level, and the system matches the player with increasingly lower level games.

Match making systems might create matches between players of different skill levels to allow weak players to practice and improve their game play. The inputs of the devices according to various embodiments could be utilized to train an AI module that identifies which types of pairings and matches are likely to result in skill transfer or improved game play, predicts which kinds of pairings would improve the skills of an individual player and create matches based upon the likelihood of players improving their skills. For example, the AI module could detect that a weaker player might benefit from playing more skilled or higher ranked players and create matches based upon the likelihood of improvement. For example, the AI module could detect whether a player is weak in a particular dimension of gameplay and create matches in which that player might be forced to use that dimension of gameplay more often than in other matches or where that player might observe other plays demonstrating that skill in that dimension.

Match making systems might match players to maximize enjoyment or another emotional response to the game. The devices according to various embodiments could be used to train an AI module that utilized biometric feedback and in-game telemetry data to identify matches or parts of matches that players enjoy, for example. The AI module could predict whether a potential match would likely elicit that emotional response and make matches that optimize the enjoyment of players. For example, an AI module might identify that users that spend money on in-game purchases enjoy utilizing those purchases or showing them off to other players and facilitate matches that allow the use of those in-game purchases.

Match making systems might create matches that alter common patterns of gameplay ("meta") to improve enjoyment. Within games, players often identify a set of strategies that are more likely to result in winning, succeeding, or countering opponents strategy. The inputs of the devices according to various embodiments could be used to train an AI module to identify the "meta" for a game. The inputs from individual devices and the game controller could be communicated to the central controller. The central controller could contain a large dataset of individual players' inputs, which could be used to train an AI module which identifies clusters of individual player behavior (strategies), relationships between these clusters' (which strategies are played together or against each other), and which clusters' result in particular game outcomes or player enjoyment. This AI module could also identify individual player preferences for strategies. Such an AI module could inform improved game play in many ways. For example, a matchmaking system might match players based upon the meta to facilitate competitive matches, or match players of weak strategies together to facilitate casual game play. Likewise, the AI module could communicate with the game controller to inform the strategies of non-player characters, locations of in-game resources, or other aspects of gameplay, either to counter player strategies or to facilitate player strategies.

Match making systems might match players to alter team play, to improve team performance, increase excitement level, and improve the skills of individual players. The inputs of the devices according to various embodiments could be trained to identify player skill at common roles within games dependent on team play. Using the devices' inputs, an AI module might identify clusters of player behavior to identify roles within teams and create an index of a player's skill at performing those roles. An AI module might also identify which roles a player commonly fulfills, which they enjoy, and which they might be good at if the player attempts to fulfill that role. An AI module might also be trained to identify how team composition affects team success, excitement level, or post-match ratings by players. A matchmaking system might incorporate these indexes in many ways—to form teams where individuals fill all roles, to balance the strength of teams, to increase excitement level for all players, by optimizing the composition of teams (for example, by having no players in a given role on either team), or to improve the excitement for players who spend more on the game. Likewise, the matchmaking system could create diverse game play experiences by allocating players to games which nudge players to try different roles or by allocating players to games where common sets of roles associated with the "meta" are unlikely to be played.

Match making systems could incorporate post-match feedback, in the form of player surveys or other methods for eliciting player feedback. This feedback could improve matchmaking in many ways, for example, by determining what kinds of matches players enjoyed, whether individuals were skilled teammates in team games, or individuals were abusive or bullying. The devices according to various embodiments could facilitate post-match feedback from other participants in many ways. For example, players could utilize lights on the devices to rate other players or the game could display questions, feeling thermometers or other survey tools on the devices through their visual outputs. For example, a player could control the temperature outputs of the devices to rate other players. Likewise, the devices' outputs could allow the device owner to observe how other players rated them. For example, post-match performance or feedback could be displayed through the device's visual outputs, the devices could change temperature, or they could use other outputs, such as vibration or sound. Players that receive negative feedback could be prompted to work on their skills or avoid certain behaviors. Feedback from other players about abusive or bullying behavior might lock the device owner's ability to participate in matches or disable the functionality of the device for a period of time.

Match making systems might incorporate information from player performance and/or ratings from other players across games. The devices according to various embodiments could allow tracking of player device inputs, player performance, and feedback from other players across multiple games. The devices could communicate device telemetry, biometrics, player feedback, and other information to the game controller and the central controller, and in turn the central controller could communicate this information to other game controllers. Match making systems might incorporate a measure of general video gaming skill, beyond skill in an individual game. For example, a system might incorporate information about player performance in analogous games or within the same genre of game. For example, a matchmaking system in a game dependent on visual acuity, hand-eye coordination, or reaction times might utilize a measurement of player performance drawn from other games to inform match making.

Social Peripherals for Art, Music, and Creativity

Creativity in the form of art and music could be facilitated by the mouse-keyboard. Many organizations and individuals collaborate to form paintings, sculptures, drawings, virtual visual arrangements of interiors and music. Collaborating virtually in these art forms, and allowing the mouse-keyboard to be a participant in the process could facilitate an enhanced experience and end product.

In various embodiments, a peripheral may facilitate music creation or listening.

In various embodiments, a mouse-keyboard acts as a conductor. With many people collaborating and using technology to create music, along with homeschooling, the mouse-keyboard could act as a conductor. For example, the user (e.g., conductor) could click the mouse to get the attention of the players, as if wielding a baton on the music stand. The user could establish beat patterns by using the mouse to conduct, set the beat rate using the touch control on the mouse, use the mouse to cut off the players/singers, use a visual metronome on the mouse or perform or utilize any other conductor related functions. These conductor motions could be displayed visually to the remote players/singers using the mouse-keyboard as the conductor without actually seeing the conductor and incurring a delay.

In various embodiments, such as where a mouse-keyboard has sensors, music could be streamed that matches a user's current physical mood. For example, if the EKG sensor in the mouse-keyboard indicates an elevated heart rate during a game, the user may want to have a soothing song or a more intense song to match the game play. These would be pulled from songs in the user's existing playlist.

In various embodiments, a painting is created using the mouse-keyboard as the brush and pallet. In various embodiments, a painting is created based on sensor activity. With all of the sensors in the mouse-keyboard, the mouse-keyboard could use the data to reflect the sensor activity in the creation of a piece of art. For example, if the user has elevated heart rate, blood pressure and brain waves, the mouse-keyboard may show vibrant colors and shapes to reflect the physical state the user is in at the moment the art is being created. The brush size could also reflect a more intense mood, making it larger as well.

In various embodiments, painting may be a cooperative activity. With multiple mouse-keyboard connected devices, users can contribute to a painting/drawing (or any other art form) by contributing their creativity to a piece of art. For example, one user may be skilled at drawing landscapes, while another is skilled at drawing figures; these can be done independently and brought together to form the final piece of art. Likewise, each may contribute simultaneously to the painting and control each other's pallet or brush to complete the piece.

Various embodiments contemplate sculpting using the mouse-keyboard as a chisel. With force sensors in the keyboard-mouse, virtual sculpting becomes a possibility. For example, if the virtual stone is displayed to the user, they can select a chisel and begin removing stone to create their masterpiece. The chisel force to remove the stone is controlled by the mouse-keyboard with the force sensor. If the force sensor recognizes a tighter grip or faster movement of the mouse, the chisel reflects a similar movement and more stone is removed. Likewise, if a smaller grip or shorter movements with the mouse are recognized, more detailed work is being done to the stone and less removed. The same approach could be used in collaborative sculpting as well.

Various embodiments contemplate molding and creating pottery using the mouse-keyboard. The force sensor equipped mouse-keyboard allows for a user to create a virtual sculpture. For example, the mouse-keyboard can be used to control the speed of the turning wheel and the force sensor on the mouse used to apply pressure and adjust the clay on the turning wheel. This activity allows the user to be in control of all aspects of the creation of the pottery piece.

Chatbot, User Experience, and Advertising

Companies routinely use behavioral insights to inform product design, increase customer satisfaction, customize product offerings, and improve the effectiveness of advertising. Many of these behavioral insights are drawn from imperfect metrics, such as ad clicks or cursor tracking, due to the difficulty of obtaining more direct measurements of individual engagement, mood, and attention. Various embodiments could allow for improved behavioral insights.

The devices according to various embodiments could allow an AI module to be trained that predicts the device owner's engagement level, mood, and level of alertness or attention. Mice or keyboards according to various embodiments could be equipped with sensors such as heart rate sensors, galvanic skin response sensors, sweat and metabolite sensors, or other biometric sensors. The data generated by these biometric sensors could be mouse telemetry data, mouse clicks, keystroke data, or other digital device inputs. The devices according to various embodiments could send biometric data to the owners computing device or an external server. An AI module could be trained using these inputs which would predict dimensions about the physical and mental state of the device user, such as engagement.

Player Performance and Segmented Advertising

In one embodiment, Player 1 in house 6302 may be playing a game using a mouse 3800 or keyboard 3900. Game play with mouse 3800 may involve using buttons 3803 and 3806, as well as scroll wheel 3809 as discussed with respect to FIG. 38. With respect to the block diagram of FIG. 94, processor 9405 determines that the click rate for Player 1 averages 100-120 clicks per minute. As the game progresses, the mouse processor 9405 determines that the click rate has reduced to 90 clicks per minute. The information collected by the mouse is sent to house controller 6305*a* and then to central controller 110 for transmission to advertisers. The advertiser may submit ads and messages to Player 1 related to caffeinated beverages on the mouse for display on screen 9435. This could be an image of the actual drink, company logo, a message indicating that play appears to be slowed and it is time for a refreshing beverage to improve performance, sounds of fizzing emitting from speakers 3821 or an option to purchase the drink through online ordering and payment using a special promotion and the mouse. The purchase may be completed by using sensor 9430 on the mouse to validate the user through a fingerprint, voice recognition or facial or retinal scan and apply Player 1's stored currency from storage device 9445 (e.g. digital currency, credit card payments, PayPal). Payment to the advertiser is submitted through house controller 6305*a* and central controller 110. In a similar manner, faster click rates by a user may allow the advertiser to push a congratulatory message or promotion (e.g. game clothing purchase, additional game add-ons) to the mouse on screen 9435, verbal message on speakers 3821 or display of various lights (e.g. flashing green, red and yellow) on lights 3821 or 3812*a-b*. As time progresses over hours and days, the AI accelerator 9460 may learn the various patterns of Player 1 (e.g. the second advertisement sent 30 minutes into game play has a higher rate of acceptance) and information to that effect is placed in storage device 9445. At the appropriate time, the storage device 9445 may submit the data to the network port 9410 for communication to the advertiser through house controller 6305*a* and central controller 110 for action. This specific player information may be used by advertisers to provide a more targeted message at the right time for the right player, which is the essence of segmented marketing. An AI module of user engagement could permit advertisers to target ads optimally to the user's mental and physical state and dynamically target ads based upon these states. For example, an advertiser might predict that their ad is more likely to be effective when users are alert or when users are hungry.

In various embodiments, an AI learns behavior of a player. A player in house 6302 may only eat two meals a day at around 7 am and 5 pm. Cameras 6352*a-b* may detect a user entering the kitchen, opening the refrigerator 6337*a* and determining the type of food and amount consumed. This information is collected by house controller 6305*a* and central controller 110. This information is sent to the peripheral device network port 9410 action performed with processor 9405 and stored in storage device 9445. As game play is progressing, Player 1 does not stop to eat by 6 pm. The AI Accelerator 9460, using information from storage device 9445, recognizes that the meal that Player 1 consumed at 7 am was less than in previous days. The output device 9425 receives a message from the processor 9405 to display on peripheral device 3800 or 3900 that it is time to stop and eat a meal. This message can be in the form of an image (e.g. slice of pizza) on screen 3815 or 3906, display on the wall with projectors 6367*a-c*, or any other display device in the enabled house, or a verbal message through speakers 3818, 3909*a-b* or 6355*a-e*.

The devices according to various embodiments could enable dynamic pricing of advertisements, for example, based upon what activity a device is being used for or based upon the individual users mental and physical states. For example, an ad placement might be less valuable if a user is typing, which indicates that they may not see the ad.

Various embodiments include targeted advertising based on user activity. There may be times when a user in house 6302 is highly engaged using a peripheral device 3800 or 3900 for a specific task based activity (e.g. typing a report or playing a game or simply watching a video). Advertisers may not get the attention of the user or not send the correct advertisement to the correct device for maximum exposure. For example, the peripheral device may collect the mouse movement/clicks/sensory data on 38003, 3806, 3809, or 3812*a-b* or keyboard actions from 3903, 3906, 3915*a-b* or 3920 to input device 9420. This information is sent to processor 9405 and placed in storage device 9445. An advertiser may want to push advertisements to a user and inquire with processor 9405 on the type of engagement (keys being used and rate, mouse being moved and actions) on which device. The processor 9405 sends the user data to house controller 6305*a* and central controller. The user may be heavily engaged in keyboard activities with typing. The advertiser determines that it may be best to delay the advertisement until the user has slowed typing. When the typing reaches an acceptable rate, indicating a potential break, the advertiser pushes the appropriate advertisement to the screen 3906 on the keyboard. This may be in the form of a product they have in the kitchen (drinks, snacks) or a reminder to take a break and watch a stretching video on screen 3906.

Online advertising could be displayed on the devices according to various embodiments. The visual outputs of these devices could be extensions of an ad displayed on another screen, or they could be standalone ads. Ads could use other outputs of the device. For example, an ad could depress or increase the height of keyboard keys to spell out a message or subtly indicate a brand name when a device owner mouses over an ad by the brand. Ads could use heating and cooling devices contained in the mouse to evoke weather or feelings associated with hot and cold temperatures. An ad for a hot sauce or a breath mint, for example, might cause the owner's device to heat or cool.

Advertisement and House Control Based on Sensory Information to User

An example of this may occur when a peripheral device 3800 or 3900 with sensor 9430 determines that a game players hands are cold in room 6321*c*. This may indicate the room temperature is at an unpleasant level and potentially degrade the players performance. The sensor collects the body temperature and communicates to processor 9405. Output device 9425 receives the signal and begins to warm slightly on the peripheral device 3800 or 3900 until the body temperature detected in sensor 9430 returns to an acceptable level. In addition, the sensor data collected by processor 9405 may be sent to house controller 6305*a* and central controller 110. The house controller communicates with air conditioning 6373*a* to increase the heat a few degrees in room 6321*c* to make the player more comfortable. In a similar manner, the sensor data from 9430 (e.g. cold body temperature), collected by processor 9405 and sent to the house controller 6305*a* and central controller 110 through network port 9410 may be communicated to advertisers indicating a player is cold while using a peripheral device. This may prompt the advertisers to send a targeted ad to a player through input 9425 to the peripheral device screen 3815 or 3906 showing a cup of hot chocolate or cup of fresh brewed coffee or a reminder to add the item to the grocery list through a simple mouse click on 3803 or 3806 or keystroke selection on keyboard 3903.

In Game Credits and Purchase

Many video games feature in-game ads and products. Watching ads while in-game could earn the device user value that could be stored on the device and used for in-game purchases. As an example, a player is playing their favorite military game. The peripheral devices may collect the intensity of play through sensor 9430 (e.g. elevated heart rate, sweat, click rate) and length of play for storing in 9445. This information is sent to the advertisers through the network port 9410. Advertisers may elect to show a quick clip of other military action games for viewing with a monetary value associated with them. If the user selects to watch the ad, processor 9405 collects this information and value and stores it in storage device 9445 for later use. Later in the game, the advertiser may promote a new jacket with the game insignia on screen 3815 and 3906 to the user. The user may elect to purchase the jacket with the peripheral device. The stored monetary value in the storage device 9445 from previously viewed ads may be used to purchase the jacket from the advertiser and complete the purchase.

Devices according to various embodiments could give content creators a new method for measuring engagement levels and emotional responses to digital content, such as videos, music, imagery, and games and other software. For example, telemetry data could show content creators that individuals watch videos in the background as they use their devices for other purposes. For example, advertisers conduct focus groups or conduct multiple forms of advertising to determine consumer effectiveness. Using peripheral devices with sensors 3915*a-b* and 3812*a-b*, advertisers may collect biometric data from users to measure engagement, responsiveness and overall effectiveness. For example, the peripheral device may collect the heart rate of an individual watching a sports car commercial at the beginning using sensors 3915*a-b* and 3812*a-b* or through device motion from input device 9420. During the first 10 seconds of the commercial the heart rate may decrease and device motion increases possibly indicating the commercial does not engage the consumer and they are bored with the product. However, during the final 30 seconds, the heart rate may increase and device motion decreases indicating a more captive consumer. In this case the sensor 9430 data is collected by processor 9405 and sent to storage device 9445 and network port 9410 for delivery to the advertiser. This feedback assists the advertiser in creating more effective ad campaigns.

Devices according to various embodiments could help improve the ability of chatbots and virtual assistants to provide context-specific responses to the peripheral device owner. Chatbots and virtual assistants utilize scripts and AI-generated responses to engage with users via text or voice. An AI module that utilizes the biometric data and other user data generated by the present device could detect the emotional state of the device user and also how that state changes while interacting with the chatbot or virtual assistant. For example, an AI accelerator 9460 in the peripheral device could detect whether an individual is frustrated or satisfied by a particular chatbot response from input device 9420 (mouse click or keyboard typing force, microphone comments, sudden mouse movement) or sensor 9430 data. The input device 9420 may detect that the force of pressing keys suddenly becomes greater or sensor 9430 collects an elevated heart rate, both indicating an increased level of frustration. This information is sent to processor 9405 and sent to the chat bot or virtual assistant program through the network port 9410. The chat bot or virtual assistant may modify their response and ask if the user needs additional help or if they would prefer a call. In this case the sensor and input device data may be used to predict the emotional state of the device user and alter the performance for chatbots and assistants by allowing context-dependent scripts and responses, as well allowing the creators of chatbots and virtual assistants a diagnostic tool for measuring the effectiveness of a chatbot or virtual assistant.

Health Embodiments

Comprehensive health data is increasingly important to healthcare professionals and active health management by the individual. The mouse-keyboard device is outfitted with sensors to collect heart rate, blood pressure, tremors, finger/body temperature and grip strength, oxygen levels and hydration levels. With more telemedicine taking place among physicians, the more data points collected to assist in evaluating the health of the patient is needed. All data can be used to make the appropriate diagnosis.

In various embodiments, body temperature may be collected. Mouse-keyboard devices are equipped with sensors to collect temperature. As the temperature is collected, spikes or increases in body temperature are sent to central controller 110 and to the user for awareness of possible infection.

In various embodiments, blood pressure may be collected. In embodiments where a mouse (or other peripheral device) has an associated glove, blood pressure can be collected and monitored. Readings that fall outside of the acceptable range can be sent to central controller 110 and the individual for awareness and action.

In various embodiments, grip strength may be collected. The mouse is equipped with a sensor to collect grip strength (dynamometer). Grip strength is a measure of upper body strength and overall muscular fitness. Furthermore, using a grip strength facilitating device regularly can reduce blood pressure. The mouse is equipped with a dynamometer and the connected device alerts the user to perform various grip strength tests throughout the day while gripping the mouse. The measurements are sent to central controller 110 and also the user. Data collected over time, in conjunction with other health data, can be used to assess the health of an individual.

In various embodiments, oxygen levels may be collected. Oxygen level is a key indicator of overall health fitness. The mouse-keyboard, according to various embodiments, could read and monitor oxygen levels. For example, a user of the mouse-keyboard could routinely have their oxygen levels monitored. Depending on the level, the device may alert them via colors, sounds, vibration or on-screen display to take deeper breaths. If oxygen levels are detected at a significantly low level, others in the area could be alerted at their mice or keyboards or other devices, or 911 calls made. All data may be sent to a central health control system.

In various embodiments, mouse movement or force data may be collected. If the mouse detects rapid movement for an extended period of time, this could be an indication of hand tremors or other more serious medical conditions. The data is collected by central controller 110 and user notified for appropriate action. In addition, if force is applied to the mouse for an extended period of time, this may indicate a seizure and data may be sent to the central health control system and user for evaluation.

In various embodiments, electrocardiogram (EKG/ECG) data may be collected. The mouse-keyboard is equipped with EKG/ECG sensors. These sensors measure heart activity and provide indications of overall heart health. Together with other health data, the EKG/ECG information may be sent to a central health control system, which may be the users insurance company or physician. The data may be collected for evaluation over time, immediate feedback/action or discarded. Various embodiments provide more data points for both the user and physician to monitor the overall health of an individual. In the case of data indicative of a possibly severe condition, immediate response can be provided to the user to take action and contact a health professional.

In various embodiments, metabolic data may be collected. A metabolite sensor can be defined as a biological molecule sensor that detects changes, presence and/or abundance of a specific metabolite. Metabolite levels may be detected within a biological system or network, such as within the human circulatory system, human organ systems, human tissue, human cells, the human body as a whole, or within any other biological networks. Metabolite levels may be indicative of a state of a biological network, such as cellular activity, cellular composition, tissue composition, tissue health, overall health, etc. In various embodiments, the metabolite sensor in the mouse-keyboard (or any other peripheral) could measure the cell activity/composition (or any other status of a biological network) and transmit the results to central controller 110 that determines the abundance of cells, nutritional status and energy status of the user (or any other aspect of user health or function). Levels determined by the controller could be used to alert the user or physician of necessary actions.

In various embodiments, electroencephalogram (EEG) data may be collected. The headband device connected could measure brain activity using EEG sensors. This data could be sent to central controller 110 and used to measure brain health both immediately and over time. This information can be used by the user or the intended physician. In the case of severe issues indicating abnormal brain activity, alerts can be sent to medical personnel or identified caregivers.

In various embodiments, electrocardiogram (EKG/ECG) data may be collected. Heart rate and the associated readings are an indication of a well-functioning heart or potential health issues. The mouse-keyboard could be used to measure the EKG/ECG signals and sent to central controller 110 for analysis. The collection of this data may give a user early indication of health issues that may lead to heart attacks or other severe heart disease that may go unnoticed.

In various embodiments, electromyography (EMG) data may be collected. The mouse-keyboard could be equipped with EMG sensors. Electromyography (EMG) measures muscle response or electrical activity in response to a nerve's stimulation of the muscle. The test is used to help detect neuromuscular abnormalities. With significant game play or mouse-keyboard activity, the nerves in the fingers, hands, wrists could become damaged or fatigued. The EMG sensor could measure this activity and send it to central controller 110 for analysis. Results could be sent to the user and medical personnel for evaluation and diagnosis.

In various embodiments, a device may render infrared (IR) therapy. The mouse-keyboard could be equipped with IR light. Infrared therapy is suggested for pain management, jaundice, eczema, wrinkles, scars, improved blood circulation, and to help wounds and burns heal faster. At the request of the user, the IR light could be turned on for a period of time to assist with conditions in the fingers, hand and wrist. If the IR therapy is used, the data regarding time used and IR wavelengths used could be sent to central controller 110 for analysis and reporting.

In various embodiments, a device may perform ultraviolet (UV) light sanitization. Controlling bacteria on surfaces is becoming more important. Bacteria are present on surfaces that are routinely used by multiple people, like a mouse-keyboard. The mouse and keyboard could be installed with UV lights that help control bacteria. For example, if the user selects a sanitizing mode on the mouse-keyboard, the UV light could illuminate for a period of time, render the mouse-keyboard unusable during this time and thoroughly clean the device. When finished, the UV lights on the keyboard and mouse are turned off and the device ready for use again.

Relaxation

Relaxation and meditation activities facilitated by physical devices are becoming increasingly more popular and important in our society as a way to control stressful activities. With biometric sensors included in a mouse to measure various physical events (heartbeat, temperature, breathing rate, moisture content), the mouse could be enabled to facilitate relaxation.

In various embodiments, a mouse may be adapted with a compression glove. Swaddling of infants provides a sense of security and calms them. In a similar manner, the use of a glove-equipped mouse could provide a sense of calm to the user when the biometric data indicates they are becoming stressed or if they elect to enable the function. As an example, if the heartbeat of the user is elevated, the glove may begin to constrict slightly to provide a more secure feel between the glove and mouse. Once the heartbeat drops to acceptable levels or the glove is disengaged by the user, the glove loosens. The compression of the glove could also cycle to promote increased blood flow through the hand.

In various embodiments, a mouse may be adapted with a vibration mechanism. If biometric sensors in the mouse indicate elevated stress levels, the mouse could begin to vibrate as a way to control stress levels. This vibration can relax the finger, hand and wrist muscles to result in less tension for the user. In addition, the mouse can detect the breathing rate and the mouse can mirror this rate with a vibration. This vibration provides the user with a conscious awareness of their breathing rate. As the user is made aware of the breathing rate, the user can take steps to decrease it, and this decrease is also reflected in the mouse.

In various embodiments, a mouse may be equipped with massage roller balls. As a user is stressed or the hand/fingers are tired from overuse of a mouse-keyboard, the massage roller ball equipped mouse could be invoked to relax the hand. If biometric sensors in the mouse-keyboard indicate elevated stress levels, or upon user invocation, the mouse could begin to move the massage roller balls as a way to control stress and simply relieve the fingers/hand of tension. These rollers could move from front to back and side to side simulating a massage action.

In various embodiments, a mouse may be equipped with a TENS unit. Pain, muscle twitches, or weak muscles brought on by overuse can sometimes be relieved by applying small electrical impulses to muscles. If the mouse-keyboard indicates stress or the user invokes the action due to muscle discomfort, the TENS unit can be activated. For example, with a glove equipped mouse, TENS electrodes can be placed at the appropriate places in the glove and when invoked, small electrical impulse can be sent to the glove while holding the mouse. The TENS unit sets a cycle time and, when complete, it turns off automatically. The mouse can continue to be used while the TENS unit is functioning or turned off at the request of the user.

In various embodiments, a mouse functions as a breathing coach ('breathing' mouse). Controlled breathing is a way to calm a person and help the person relax. Oftentimes people do not realize their breathing is elevated and find it difficult to control breathing on their own. With the sensor equipped mouse-keyboard, if the breathing rate is elevated, the mouse could display lights matching the breathing rate or vibrate accordingly. Central controller 110 could coach the individual through controlled breathing exercises. As the breathing rate decreases, the lights and/or vibration on the mouse-keyboard could change to reflect the current rate.

In various embodiments, a mouse has temperature control. The application of warmer or cooler temperatures to a user's hands can have a calming effect on them. With a mouse configured with heating and/or cooling elements, the user device or central controller 110 would be able to direct warmer or cooler temperatures to a users hands. For example, on a hot day the users computer screen could display cool images like an iceberg, while simultaneously causing the user's mouse to glow in a light blue color. At the same time the mouse may engage cooling elements such as fans or a small refrigeration element to cool the user's hand.

Behavioral Modification and Behavioral "Nudges"

Behavioral "nudges," or the use of insights gleaned from the academic fields of behavioral sciences, are tools for individuals to improve their well-being by utilizing psychological tricks. The devices according to various embodiments could facilitate behavioral nudges because users frequently spend large amounts of time using keyboards and mice, and when they are not in use, these devices often occupy prominent physical locations.

The devices according to various embodiments could be used for behavioral nudges for habit formation and making progress toward goals. For example, the device could produce visual indications of streaks of behavior or progress by lighting up keys individually as progress is made or by showing a digital timer feature (count-up or count-down) on the devices. If positive or negative behavior is detected, for example, the user could be prompted by a reminder spelled out on lit up or raised/depressed keys. If negative behavior is detected, for example, the device could output calming music, vibrate, initiate TENs stimulation of the user's hand, or use another of the devices' outputs as a form of reminder. Repeated negative behavior could result in escalating reminders.

Device users could utilize "social accountability", enabled by the devices according to various embodiments, to improve progress towards goals. Users could share goals with others, via social media, internet, or software, and the devices could help measure progress towards those goals. The devices could display to others whether the device owner has made progress toward goals. The device could also display a leaderboard of individuals' progress.

Progress towards habits or goals could result in rewards, such as unlocking device functionality, while backsliding or failing to result in progress could result in locking device functionality. Users for example could set goals, such as visiting a favorite website or playing a favorite game, and then lock the device's functionality for those goals until progress is achieved. Locking and unlocking functionality could be used for enabling third-party rewards. For example, positive behavior could result in users accumulating progress toward digital rewards, which could be redeemed by certain levels of progress toward a goal. A user might be encouraged not to redeem their progress but instead continue to earn progress points for a better digital reward.

The devices could enable users to create a "time diary," which would summarize device usage by software program, and help individuals meet their goals. For example, an individual user might be prompted to categorize different software, websites or other forms of digital interaction, and the user would receive a daily or weekly summary of time usage. For example, the user might be shown time spent on productive tasks vs non-productive tasks. By connecting individual devices and survey responses with the central controller, an AI module could be trained to provide recommendations to individuals about how to make progress toward their goals.

An AI module could be trained to detect a variety of physical and mental impediments to individual well-being, such as detecting flagging attention or whether an individual's productivity was affected by hydration, sleep, excessive sitting or excessive screen time, and other variables. The AI module could prompt the user with coaching advice. In some embodiments, the AI module could prompt the user to get up and walk around for a few minutes after a pre-set amount of time sitting has been reached.

In various embodiments, peripheral devices could be used as a timekeeper—either a count-up or count-down function could be set to visually show when a user is getting close to the end of time. A user could set a timer, for example, by turning the device clockwise or counterclockwise to add or subtract time from the timer. The timekeeping function could be useful when users have their screens occupied by tasks, such as giving a presentation. If a user, for example, has thirty minutes to give a presentation, they could set the mouse to change colors or vibrate when five minutes remain.

Power Remaining

In various embodiments, a mouse (or other peripheral) may have a limited amount of power or energy (e.g., the mouse may be battery operated). In various embodiments, different activities may consume different amounts of power. For example, playing a video game may consume a relatively large amount of power compared to browsing the Internet. Thus, it may be desirable for a user to know how much time the peripheral would be expected to last given his current or expected activities. In particular, if the user will be involved in a video game or other activity where he cannot take a break without adverse consequence (e.g., losing the game), then the user may be keen to know that his peripheral will not quit in the middle of the activity.

In various embodiments, a mouse or other peripheral provides an estimate of battery life at current or projected activity levels. An estimate may be shown in terms of an actual time remaining (e.g., a display may show 8 minutes remaining). An estimate may be shown with a colored light on the mouse (e.g., green for more than ten minutes remaining, red for less than five minutes remaining, etc.). An estimate may be shown in any other suitable fashion. In various embodiments, a mouse may provide multiple estimates, one corresponding to each type of use (e.g., one estimate for gaming activities, and one estimate for word processing activities). In various embodiments, a mouse may provide an estimate in terms of a quantity of activity that can be completed with remaining power levels. For example, a mouse may indicate that the mouse should be good for two more video games.

In various embodiments, if power levels are running low, a peripheral device may shut down one or more items (e.g., one or more modules; e.g., one or more hardware components). For example, if a mouse is low on power, it may shut off a display screen. In various embodiments, to conserve power, a peripheral may reduce functionality of one or more modules and/or of one or more components.

Automatic Completion

In various embodiments, a peripheral tracks a user's activities (e.g., clicks, mouse movements, keystrokes, etc.). The peripheral may note activities that are performed frequently and/or repetitively. For example, the user may frequently move a mouse from left to right, then quickly click the left mouse button three times. The peripheral may offer to make a script, macro, or shortcut for the user whereby the peripheral may receive a single (or condensed) instruction from the user in order to accomplish the activity that the user had been performing repetitively.

In various embodiments, a mouse or other peripheral may anticipate a user's actions. In various embodiments, the peripheral may automatically perform the anticipated actions, thereby saving the user the trouble of providing additional inputs to the peripheral. In various embodiments, the peripheral may first ask for confirmation from the user to perform the actions.

A peripheral may anticipate a user's actions based on having monitored prior actions of a user. If a pattern of actions has occurred repeatedly, and the peripheral now receives inputs consistent with the pattern, then the peripheral may anticipate that subsequent actions will conform to the pattern.

In various embodiments, a peripheral may illustrate or demonstrate actions that it intends to perform automatically on behalf of the user. For example, a mouse may show a 'ghost' or 'tracer' mouse pointer moving on a screen (e.g., on the screen of a user device) where the mouse anticipates that the user wishes the mouse pointer to go. If the user then clicks (or otherwise confirms), and then the mouse pointer may in fact follow the suggested trajectory of the mouse pointer.

In various embodiments, a mouse can show a whole series of clicks and drags (e.g., with clicks represented by circles and drags represented by arrows). In a chess example, when a user moves a mouse to a pawn's location the mouse may anticipate the next click and drag to advance the pawn 1 square. The mouse may therefore show a circle at the pawn's current location (to represent a click on the pawn), and an arrow going from the pawn's current location to the next square on the chessboard in front of the pawn (to represent dragging the pawn).

In various embodiments, a peripheral (e.g., a keyboard) may correct spelling, grammar, or any other input. The peripheral may make such corrections before any signal is transmitted to a user device (e.g., a user device running a word processing application), so that the user device receives corrected text. In various embodiments, a peripheral may alter text in other ways, such as to alter word choice, alter salutations, use preferred or local spellings, etc. For example, where a keyboard is used in the United Kingdom (or where an intended recipient of text is in the U.K.), the word "theater" may be altered to use the preferred British spelling of "theatre". In some embodiments, the peripheral may be set up to ask for confirmation before making an alteration. A peripheral device may use GPS information or other location information in order to determine what corrections to make.

In various embodiments, a peripheral may alter idioms based on location. For example, the American idiom of "putting in your two cents" may be altered, in the U.K., to read "put in your two pence worth".

Peripheral Coordination

In various embodiments, two or more peripherals may coordinate their activities. For example, a mouse or keyboard may adjust illumination to a user's face so that the user shows up better on camera (e.g., on a video conference). The illumination may adjust based on ambient lighting. In various embodiments, when one peripheral needs help from another, the first peripheral can send a message to the second peripheral requesting some action on the part of the second peripheral.

Trackpad

While trackpads are used to provide input similar to that of a mouse, various embodiments envision other functionality that could be incorporated into trackpads to enhance their functionality.

With display capability built into the trackpad, users could be guided through tutorials which teach the user how to perform trackpad gestures. For example, the trackpad could display the words "Show Desktop" with three lines below it to represent three fingers swiping to the right. This would help users to learn and remember trackpad gestures.

The trackpad surface could also be partitioned into separate sections, allowing a user to control a game character from one portion while operating a work application from another partition.

Mousepad

According to various embodiments a mousepad could perform non-traditional functions by adding the functionality of the peripherals described above.

The mousepad could include a matrix of individually addressable small lights to enable it to operate as a display screen. For example, it could represent a game map. The user's mouse could be configured with a small tip at the top, allowing the user to position the tip over a point in the map, allowing the user to click on that point and be instantly taken to that location in the game.

In another embodiment, the mousepad could be used to display the faces of game characters, and could enable other users to send images of their own game character to appear on the user's mousepad.

The mousepad with addressable lights could also display a 2d barcode that would allow an optical scanner built into the base of the user's mouse to read the barcode.

In various embodiments, a mouse functions as a barcode scanner. The mouse may be adapted to this function by taking advantage of the LED or other light on many existing mice. In various embodiments, a user may scan products he likes, or may show what he is eating, drinking, or consuming now. In various embodiments, a mousepad has different barcodes for common products you might want, e.g., soda, chips, pizza, etc. A player can roll his mouse over the right barcode and order with one click.

In various embodiments, consumption of drink may be correlated with game performance.

In various embodiments, a mouse may camouflage itself. As it traverses a patterned surface, the skin of the mouse may change to match the surface beneath. The mouse may recognize the pattern of the surface beneath using a camera or one or more light sensitive elements on its underside. Where a mouse is camouflaged, a desk or other working environment might have a more aesthetically pleasing, or less cluttered look. In various embodiments, a mouse does not necessarily attempt to camouflage itself, but may rather take on a color that is complementary to other colors or items in its vicinity.

In various embodiments, a mouse learns the pattern of the surface beneath it (e.g., of the mousepad) with use. Eventually, the mouse can be used to return an absolute position rather than simply a change in position. The mouse can do this by recognizing where on the mousepad it is.

In various embodiments, a mouse gets charged via the mouse pad. Charging may occur while the mouse is in use, or while the mouse is idle. Charging may occur via inductive charging, or via any other suitable technology.

Power Management

As devices become more sophisticated in terms of data collected via sensors and output collected from users, power needs will increase. In addition, as these devices can perform outside of a direct connection with a computer, alternative power supplies will be needed.

Physical movement of the device could generate power for Wi-Fi® connectivity or processing of software. Kinetic energy can be harnessed, conserved and stored as power for use by the device.

With respect to a mouse, use of the buttons, roller and physical movement of the device can generate kinetic energy. This energy can be used to support the functions of the mouse, including collection of sensory data, color display, skin display and connection to other devices.

With respect to a keyboard, numerous keystrokes are collected by users on a keyboard. The force applied to the keyboard can be used to power the device and provide energy to other connected devices. If the kinetic energy stored from a keyboard is collected, it could be shared with other devices (mouse, sensors) to power specific functions.

Power conservation of devices is important for overall carbon footprint management and longevity of a device. In various embodiments, if devices are not in use for a set period of time, even if connected to a computer, they automatically go in sleep mode. For example, if the device is displaying colors or continually collecting sensory information while not in use, they are consuming power. The device may turn off automatically and only support those features where alerts/messages can be received from another person. Once the device is touched, moved or message received, the device turns back on and is available for use.

In various embodiments, a device uses infrared (IR) to detect whether a user is at the device or near the device and powers on/off accordingly. A proximity sensor in the device may turn on a computer/device and other room monitored devices. For example, if the user has not been in the room for some time and the computer, lights, thermostat, and device have all been turned off, then once the user walks in the room, the proximity sensor (I R) in the device notices that they have returned and automatically turns on aforementioned and/or other devices. This reduces the amount of start up time and ancillary activities to reset the room for use. In addition, since the proximity sensor can determine the size of the object, the devices should only restart if the image is of a size comparable to previous users. For example, a pet or small child walking in the room should not restart the devices.

In various embodiments, an accelerometer detects certain patterns of movement (such as walking) and turns off the device (e.g., a device left in a backpack or briefcase gets powered off). Devices are equipped with features that make them more personal and thus more mobile. They are carried by users to different meeting rooms, classrooms, home locations and between locations (home to school, home to home, and work to home). Oftentimes these devices are quickly placed in a case and not turned off, thus reducing the lifespan of the device and using energy needlessly. The device is equipped with an accelerometer that notices movements of the device that are not consistent with owner use. If this is the case, the device will turn off automatically after a set period of time. Likewise, on a mouse, if the galvanic sensor does not get a reading, the device could also turn off after a period of time.

In various embodiments, parental control may be used for power management. Parents could control the power of a separate device by using their device to turn on or off the separate device. For example, if a child is not allowed to play games until 5 pm, after homework is done, the parent could simply set a preference in their child's device to not allow the device to be turned on until this time. In addition, if the device needs to be turned off when it is time for dinner, the parent could send a signal from their device or application to turn the device off.

Controlling the Home Via Mouse or Keyboard

As people spend a larger portion of their day at a computer, there will be more times at which they will need to initiate changes to house systems—such as changing temperature, moving shades up and down, turning lights on/off, opening a front door remotely, opening a garage door, turning on/off music, etc. Various embodiments allow for such changes to be made in an efficient manner without disrupting workflows. By allowing peripherals such as a mouse or keyboard access to house control systems, a user can make quick changes without breaking focus.

In various embodiments, users can change house lighting conditions while playing a game. For example, a user could tap three times on his mouse to bring up a sliding scale indicating a temperature range from 60 degrees to 70 degrees. The user uses one finger to identify the desired temperature and then taps the mouse three times to have that desired temperature sent to the user device which then sends the signal to the environmental controller which operates the temperature control systems. The user device could also display temperature controls in-game, so that a user could be presented with two targets in a shooting game. By shooting one target a signal is sent to the environmental controller to increase room temperature by one degree, while shooting at the other target would cause a signal to be sent decreasing the temperature by one degree. The user device could provide such in-game temperature targets upon a trigger level reached via temperature sensors on the users mouse and/or keyboard, or by an infrared temperature sensor operating in the computer's player facing camera.

Users could also adjust home or room lighting levels via a mouse, such as by shaking the mouse left and right several times to turn lights on, or turning the mouse sideways to turn lights off. In another embodiment, whenever the user is in-game, the game controller adds light switches throughout the game. The user can then use the game controls to move the light switch up to turn lights on and down to turn lights off.

A user could also turn down the volume on a television when there is an incoming phone call by tapping twice on a mouse, or turning the mouse over. This would initiate a signal to the user device which could then signal the television to decrease the volume. The volume would then return to the previous setting when the mouse is again turned over.

With players often being in complex game play situations when there is an incoming call, various embodiments allow players to answer the call without taking their hands off of the mouse and keyboard. For example, their cell phone could send a signal to the user device that there is an incoming call, and the user device could send a signal to the game controller to display an icon in game which can be clicked on to connect the call or decline it.

Connected Devices and Ergonomics

Computer users frequently suffer from overuse or repetitive use strains and injuries due to poor ergonomics and posture. Users rarely position devices, screens, and furniture in ways that consider their own anthropometry. Users tend not to vary positions over the course of long computing sessions or over multiple sessions. Over the course of a computing session, the positioning of devices, monitors and furniture may be knocked or moved from ideal alignments into sub-ideal alignments. Devices according to various embodiments could improve ergonomics and reduce overuse injuries.

The devices according to various embodiments could track the location, orientation, heights, and positioning of screens, input devices, and furniture, such as desktops, chairs, or keyboard trays. The devices could also track user anthropometry, including posture, eye gaze and neck angle, internal rotation angles of the elbows or shoulders, and other key ergonomics data. Position, orientation, and angle data could be obtained through camera tracking, such as a webcam, a camera built into a computer screen, or via other cameras. Position, orientation, or angle data could also be obtained through range finding and positioning systems, such as infrared camera, ultrasonic range finders, or "lighthouse" optical flashes.

Data on location, orientation, angles, and furniture heights, as well as user positioning relative to devices and furniture could be used to train an AI module that optimizes individual ergonomics. An AI module could detect the anthropometry of device users and alert users to device, monitor, and furniture configurations that are associated with repetitive-use strains or injuries. The AI module could prompt the user to alter specific positions, orientations, and heights of monitors, input devices or furniture to reduce the likelihood of repetitive or overuse injuries.

The AI module could also dynamically alter positions, orientations, and heights of specific devices or furniture. It could alter these devices or pieces of furniture by sending a signal to enable wheels, actuators, or other movement controls to move the devices or furniture into positions associated with improved anthropometry. The AI module could track and dynamically alter positioning to improve ergonomics or posture over the course of a computing session. People use headsets for listening to music and for providing data to computers for enabling communications. For example, headsets are commonly used to enhance the audio quality of video calls, such as business meetings, online classes, or video game team communications. Headsets are also commonly used to listen to music or video files.ve setups for different kinds of computing sessions (gaming or word processing, for example), allowing multiple individuals to use the same devices, or allowing an individual to port their ergonomic settings to any other socially-enabled work setup.

Headsets

As more and more interactions (meetings, games, social and recreational events) are held virtually, a greater number of participants are not physically present in a room. Those participants are connecting via phone, or more commonly via video meeting services such as Zoom® or WebEx® using a laptop/PC/gaming device. In these situations, it is common for participants to be wearing headsets.

According to various embodiments, headsets improve the interactions and feedback by gathering and delivering more information to participants. Various embodiments also allow for enhanced experiences in the physical world by using a headset for in-person meetings, social interactions, gaming and recreational activities.

Audio Sources

In various embodiments, a headset may be well suited to playing or broadcasting audio from one or more audio sources. Audio sources may include: meetings; other business contexts; talking with friends, family, acquaintances (vocal); gaming; audiobooks; podcasts; watching videos (entertainment); watching sounds only from videos; theatre, concerts and in-person entertainment; listening to music; making music, video editing; ambient and environmental sounds; white noise; alerts and signals; or any other audio source.

Verbal Output (Speaking into Microphone)

In various embodiments, a headset microphone may capture vocal input (e.g., from a wearer) and background information. The interpretation of the vocal and background sounds and actions are collected by the headset processor 405, sent to the user device 107*a* and transmitted to the central controller 110 for AI analysis and appropriate feedback/action/response to the user(s).

The microphone could always be listening. For participants that are on mute, once they begin to speak, the microphone detects this and automatically takes them off mute. For example, there are many occasions where meeting participants place themselves on mute or are placed on mute. Oftentimes, they do not remember to take themselves off of mute and it forces them to repeat themselves and delay the meeting. The microphone in the headset could communicate with the headset processor 405, once the headset processor 405 hears a verbal sound and sent to the central controller AI system to interpret, the central controller responds to the computer and headset processor 405 indicating to turn the microphone on. In contrast, if the central controller took the participant off mute, once they stop speaking or there is a designated pause, the headset processor 405 or central controller could put the user back on mute.

Microphones could be muted automatically if they are outside the range of the meeting or the person is no longer visible on the video screen. Remote workers take quick breaks from meetings to take care of other needs. For example, a parent's child may start screaming and need immediate attention. If the meeting controller recognizes the meeting participant has moved from the video screen or computer camera and are several feet from their display device, mute the microphone automatically. Another example may be where someone leaves the meeting to visit the restroom. The camera on the computer detects the individual is no longer in view, the user device 107*a* communicates to the headset processor 405 and the microphone is put on mute. Once the camera detects the individual is in view again, the user device 107*a* indicates to the headset processor 405 to turn the microphone on for the individual.

Various embodiments allow a wearer to speak to a controlled list of people. The headset could allow vocal commands that automatically link others for a private conversation. For example, if the user wants to initiate a quick conversation with 2 other people from a larger conference call, they could say, 'link, followed by the NAME(S)'. Those people are immediately brought into a private conversation while others remaining on the larger conference call have no indication that they left the meeting or rejoined. The headset processor 405 collects the verbal command, is transmitted to the computer and central controller AI system. The central controller AI system interprets the command and names (e.g. 'link' and participant names), sends the information to the appropriate users user device 107*a* and headset processor 405, and places them in a secure conversation. Once any participant uses the command, 'delink', the headset processor 405 transmits the command to the computer and central controller AI system and removes them from the conversation and rejoins them to the larger conference call.

Various embodiments allow a wearer to speak to a streamer or single individual over the internet. The streamer profession is growing in use and popularity. The desire to speak securely and directly to a streamer/individual could be appealing to the users of a headset as part of this invention. For example, if the user of a headset subscribed to a streamer using a headset, the user could simply 'whisper' something directly to the streamer in their headset without others hearing. The vocal command (e.g. 'whisper') by the user could initiate a secure (e.g. VPN enabled) quick conversation with the streamer/individual. If the command is accepted by the streamer/individual, the user could speak directly to the streamer securely. The user may ask the streamer/individual to repeat the last phrase in the meeting, provide another example or explain in more detail during a demo or show a particular skill while playing a game. The headset processor 405 collects the verbal command, is transmitted to the user device 107*a* and central controller AI system. The central controller AI system interprets the command (e.g. 'whisper'), opens a secure channel via VPN or shared encryption/decryption keys within the headset or in the controllers and places them in a secure conversation. Once the conversation is complete, the connection is disconnected by using an appropriate command (e.g. 'stop conversation').

Various embodiments allow a user to speak to a single individual locally. In cases where both individuals are in the same geographic location, there is no need to transmit the communication via the computer and central controller. The headset could have encryption/decryption capabilities that enable secure conversations to occur outside of the internet. For example, if two users of the headsets want to have a conversation, one of the users simply initiates a vocal command (e.g. 'whisper', local, Name) to indicate they are wanting to connect directly to another headset of the named individual. This could be useful for two people in close proximity or walking together to have a brief conversation without others knowing who you are communicating. Another use is not providing confidential information on a network or risk that someone else is attempting to listen to the conversation. The headset processor 405 collects the verbal command, is transmitted directly to the receiver's headset. The sending and receiving headsets are paired and the encryption/decryption keys are exchanged opening a secure connection. Once the conversation is complete, the connection is disconnected by using an appropriate command (e.g. 'stop conversation').

Various embodiments allow a user to broadcast audio to multiple individuals and meetings. There are times when leaders and individuals wish to communicate information simultaneously to people. Using email often slows the communication, appears less than personal and can be interpreted differently by those simply reading the content. In addition, going from meeting to meeting to communicate the same information can be time consuming and reduce productivity. The sender could transmit a message to those using the headset and those participants in meetings connected to a central controller AI system. For example, as a CEO of the company, I may wish to inform them of the latest competitive pressures within the industry. The CEO could use the headset, speak the 'broadcast' command, indicate the user audience (e.g., all employees, VPs only, named project teams; e.g., based on tagging of individuals/groups), record the message and send it immediately to the indicated group. The users with the headsets on at the time or the participants in meetings connected to the central controller AI system could immediately hear the message from the CEO. Another example may be when an SME (Subject Matter Expert) or Architect needs to communicate to various scrum teams during a PI (Program Increment) event. The verbal command (e.g. 'broadcast') is transmitted to the headset, computer and central controller AI system. The central controller AI system interprets the command and names (e.g. 'broadcast'), sends the message/information to the appropriate users' user devices (e.g., 107*a*) and headset processors (e.g., 405).

Various embodiments allow a user to speak to pay with value stored in the headset. Using cash and other forms of payment are becoming less common. In many cases, it is still necessary to authenticate and pay using a stored payment on another device. The headset could securely store payment types for the user. When purchases or transfer of cash (e.g. VENMO®, Paypal®) are made via a computer or in-person at a retailer, the device could transmit payment to the merchant. For example, the user goes to Starbucks® to order a coffee, when payment is requested, the headset could securely connect to Starbucks® and transfer funds via a push of a button or via a verbal command (e.g. 'pay Starbucks®'). Funds or forms of payment are loaded to the headset securely. The headset processor 405 communicates directly with the merchant POS device and transfers funds. Alternatively, if the headset is connected to a secure network, the central controller could also act as another form of secure transfer across the internet to the merchant.

Voice Control

Various embodiments include voice control, or use of commands to control the features of the headset or other non-human interactions. All data flows from the headset processor 405 to immediately enable/disable the function, to the user device 107*a* (if not connected via Wi-Fi®), to the central controller to record the action for future analysis purposes.

When other voice control devices are not present, the headset could allow the user to speak commands that are understood by the headset or central controller. For example, if the user is listening to music and wants to switch songs, the user could simply say, 'switch songs'. Likewise, if the user wants functions to turn on or off, they could simply state, 'turn on camera' or 'turn off assistant'.

There may be times when the user wants to disable or enable functions on a headset. For example, the user may want to turn off sensors and can simply say, 'disable all sensors' or 'disable temperature sensor'. In other cases, the user may wish to enable functions that had previously been turned off, for example, 'enable camera' when I need to record a situation and have no time to pull out my phone and record. This may include a child doing a memorable activity (first walk, laughing) or in the case of abuses (property and physical). This may also include statements like, 'mute, power off, conserve power, increase/decrease volume, turn on lights . . . .'

In various embodiments, the headset could allow for control of internet enabled devices in the home/office and automobile that are paired to the headphone for secure communication. For example, the user could speak in the headset to turn on the alarm, turn off the lights, turn on the oven to 350 degrees, turn down the thermostat in my work office prior to arriving in the summer or start my car and turn on the heat.

In various embodiments, the headset could be built with Alexa® or Siri® enabled technology or any voice activated remote controls (e.g. Nefflix®, Comcast®, AT&T® UVerse®)

Various embodiments assist with interpretation of semantic content. Semantic barriers to communication are the symbolic obstacles that distort the sent message in some other way than intended, making the message difficult to understand. The meaning of words, signs and symbols might be different from one person to another and the same word might have hundreds of meanings. Users of the headsets, when indicating confusion, could get a different representation to the comments. As more teams are formed around the globe, the semantics used in meetings can be frustrating and cause people to take actions not intended. The user of headsets could get a different interpretation of the meeting contents to remove the semantics. For example, if a meeting owner conducts a global meeting and states, 'we all need to run now', this can be interpreted differently by those listening around the world. The central controller AI system could understand the semantic differences and communicate different meanings to those on the call. The system could recognize the statement and send an alternative meaning such as, we all need to end the meeting now' removing confusion.

Various embodiments assist with interpretation of sentiment. It has been recently studied that "vocal bursts" are found to convey at least 24 kinds of emotion. These vocal sentiments and their corresponding emotions could be used to measure engagement of individuals and teams, support of an idea, frustration, embarrassment and so forth and collected by the central controller AI system for evaluation, measurement and reporting to the individual and organization. For example, on a call, a leader pitches a new idea and various individuals respond with statements like, 'great'. These can be analyzed to mean, great, another project to distract me and for me to work longer hours or great, I can't wait to get started. Each has a different sentiment. If all of these vocalizations are collected by the headset and analyzed by the central controller AI system, individuals can be informed about how their statements are perceived for improvement or reinforcement and the leader can get a collective sense of the overall presentation. This can enhance human and overall organizational performance.

Various embodiments assist with verbal tagging (e.g. new idea, good idea, up next to talk reminder), such as by using AI system action. Meetings often have varying degrees of notes or categorization of content. Using the headset, the meeting owner or individuals could state a verbal tag for the central controller 110 to collect and categorize for the meeting and make available. For example, a meeting participant describes a solution to a problem they are discussing. The meeting owner can simply say, 'good idea' and the central controller tag the last 2 minutes of the conversation for later evaluation and reporting. Another example may be for voting purposes. If the meeting owner asks for a 'vote', the central controller can tag, record and count the number of yes and no votes for later reporting in the meeting minutes.

Vocal Tags

In various embodiments, vocal statements invoke AI detection and action. During meetings or games, vocal statements could be interpreted by the central controller AI system and action taken.

For example, during a meeting, the owner may step through the agenda by providing vocal queues. When the agenda gets to the next topic, the central controller AI system could inform the agenda topic owner that they are next to speak. This could be delivered to the headset via a sound queue in the ear or a vibration on the ear bud. This improves productivity and human performance.

As another example, if a topic is generating a larger than expected/average amount of engagement or is taking more than the allotted time, it may mean the topic could be tabled or moved to a separate meeting. The central controller AI system can collect the amount of discussion by member, time spoken, ideas/solutions/resolution generated based on keywords/statements (e.g. complete, resolved, new idea, more issues, don't agree) and communicate to the meeting owner and participants that the topic could be tabled or resolved quickly.

As another example, during a meeting, if multiple ideas are being generated to solve a problem, the central controller AI system could interject and summarize the ideas and request that a vote be taken. This improves productivity and human performance.

As another example, if during a game, the player is using the controller to shoot a gun, but could use vocal commands to launch a grenade or invoke a airstrike, this provides another opportunity to engage with the game. In this case, the headset microphone and statements become another point to control the gaming experience.

Gamification of Meetings

In order to encourage meeting participants to be more engaged during meetings, a company could gamify the meeting by providing participants with points for different positive meeting behaviors. Awarding of points could be managed via the user's headset processor 405, and could be done during both virtual and physical meetings.

In some embodiments, the user's headset has a stored list of actions or behaviors that will result in an award of points that can be converted into prizes, bonus money, extra time off, etc. For example, the storage device of the headset might indicate that a user earns one point for every minute they speak during a meeting. This might apply to all meetings, or only to some designated meetings. A microphone of the headset identifies that the user is speaking, and calculates how long the user is talking. When the user stops talking, the processor of the headset saves the talking time and stores it in a point balance register in the data storage device, updating the total points earned if the user spends more time talking during the meeting. At the conclusion of the meeting the users new point balance could be transferred to the central controller, or kept within the headset data storage device so that the user could—after authenticating his identity to the headset—spend those points such as by obtaining company logo merchandise. In an alternative embodiment, the user earns points for each minute spoken during a meeting, but only when at least one other meeting participant indicates that the quality of what the user said was above a threshold amount.

In various embodiments, points could be earned by the user for other actions such as drafting meeting minutes after the meeting concludes, or for taking ownership of one or more task items. In the case where a user earns points for ownership of a task item, the headset processor 405 could store that task item in the data storage device of the headset for later review by the user. When that task item is completed, the user could be awarded with more points. The headset could also provide audio reminders to the user of any open task items and the deadlines for completion of these items.

Points could also be awarded when the user makes a decision in a meeting, or provides support for one or more options that need to be decided upon. In this embodiment, the points may be awarded not by the headset processor 405, but by the other participants in the meeting. For example, a meeting owner or participant with a headset might say "award Gary ten points for making a decision" which would then trigger that participant's headset to award ten points to the headset of Gary.

Participants could also be awarded with points for tagging content as a meeting is underway. For example, a user might receive two points every time they identify meeting content as being relevant to the accounting department.

Another valuable behavior to award points for is providing feedback to others in a meeting. For example, the user might be awarded five points for providing, via a series of taps on a microphone of the headset, a numeric evaluation of the effectiveness of the meeting owner.

Users could also receive points based on their location. For example, a user might receive five points for walking around a one mile walking path at the company, with the headset verifying that the authenticated user completed the entire walk.

Listening Via Headset

As more information becomes captured and communicated in digital form, users can easily be overwhelmed by a tidal wave of information. The headset can serve in the role of filtering out some data while enhancing other data.

In some embodiments, a user wants to review the audio from a large meeting that lasted for several hours. Rather than listening to the entire meeting, the headset could be configured to only play back the audio from the CEO. This filtering could be done by the central controller, comparing the voice of speakers on the call to voice samples from all executives of the company, and deleting all audio not produced by the CEO. The central controller would then send that CEO-only audio to the users headset for playback via speakers of the headset. In another embodiment, the user could request of his headset that the audio from a particular meeting be filtered down to only that audio related to the third and fourth agenda items as determined by tagging data provided by the meeting participants.

Users may also want to have background noise filtered out of a call or a recording of a call. For example, the users headset processor 405 could have sound samples from the user's dog stored in the data storage device, and the microphone of the headset could transmit a barking sound to the headset processor so that the barking could be deleted from the user's audio before it is sent out to other call participants. The headset could generate the sound samples for the user's dog barking by periodically asking the user during the day if a given barking sound was his dog, and then training AI within the headset on the dataset.

In various embodiments, safety information is amplified by the use of the headset. For example, with GPS capability the user's headset could determine that the user has wandered into some new construction of a new area of the third floor of the building in which the user works. This could trigger the headset processor to send a warning message such as "please leave this restricted area" to the user via the speaker of the headset. In another embodiment, the user headset instead opens up a direct channel of communication with a safety officer who can talk with the user and make sure they understand how to exit the restricted area. The GPS data could be used in conjunction with other data, such as a video feed from the users forward facing camera, to better understand the precise location of the user in the building.

At a coffee shop where the environment is quite noisy, the headset could relay messages to the user's headset from the coffee shop, such as telling the user that his coffee is ready. This message could replace any music that the user was listening to at the moment, ensuring that the user easily hears the message.

The headset could also get the users attention when the user shows signs of losing focus or engagement in a meeting. For example, an inward facing camera or accelerometer could determine that the user's head is dropping in a meeting, sending an alert (e.g. audio, vibration, light flashing) to the users headset in order to communicate that his attention to the meeting may be dropping and perhaps suggest a cup of coffee or tea.

Listening (Non-Vocal Noises)

Headset microphones inadvertently capture non-vocal noises and ambient noises. Such noises can be a distraction to conversations, and devices according to various embodiments could be used to remove these distracting noises and improve audio quality. Yet non-vocal noises and ambient noises also provide insight into headset wearers, their behavior and their environment.

The central controller 110 could record and analyze non-lexical and ambient noises. Non-lexical noises include man made noises that are not words such as guttural noises (e.g. grunts), throat clearing, vocal hesitation words (e.g. "um," "ah"), sighs, non-lexical mutter, sub vocalizations and other noises produced by exhalation. Common ambient noises include office and household appliances, HVAC systems, outdoor noises, animals, children, neighbors, track, vibrations created by electronic devices, pings, ringtones, furniture, eating and drinking sounds, weather, typing, writing noises, and paper shuffling.

An AI module could be trained to detect nonlexical noises and ambient noises. The central controller could filter or mask unwanted nonlexical noises or ambient noises to improve the audio quality of listeners. This processing, filtering and or masking could occur locally in the headset, on a connected phone or computing device, or by the central controller.

An AI module could be trained to detect nonlexical noises or gestures that indicate that an individual is ready to speak. The central controller could mute non speaking participants to reduce ambient non and unmute individuals dynamically based upon signal of intent to speak. For example, individuals could lean forward or flip down the microphone arm prior to speaking. For example, individuals could inhale sharply prior to speaking or could begin with a vocal hesitation word such as "um".

In various embodiments, the central controller could mute or prompt individuals to mute microphones that are inadvertently left on.

In various embodiments, the central controller 110 could automatically mute individuals when it detects certain noises. By using pre-recorded sounds that invoke a response by the central controller 110, the microphone could be put on mute automatically. For example, if your dog's bark is pre-recorded, the central controller could be listening for a bark and when recognized, the microphone is automatically put on mute. Similarly, if a doorbell or a cell phone ring tone is recognized, the microphone is put on mute automatically.

In various embodiments, the central controller 110 could record and analyze sub vocalizations, muttering and other forms of self-talk when individuals are working alone or when in meetings or conversation. Sighs and other forms of muttering could be analyzed as nonlexical responses to conversation that indicate the affective response of the speaker to others speech. For example, the central controller could detect excitement, disgust or other emotional responses through nonlexical noises. When working alone, the central controller could record and analyze self talk. The central controller could provide coaching based upon the content of self talk. Sometimes individuals think out loud. The central controller could record this form of self talk and transcribe it into notes. Other forms of self talk involve confusion, hesitation or other forms of uncertainty. The central controller could detect this form of self talk, the context for the self talk, and provide suggestions or recommendations from an autocomplete or recommender AI module.

In various embodiments, the central controller could record and analyze audio elements such as voice quality, rate, pitch, loudness, as well as rhythm, intonation and syllable stress.

In various embodiments, the central controller could record ambient audio from the headset even when the device owner is muted. Ambient audio could be analyzed by the central controller to indicate engagement, intent to speak, affective response and other forms of conversational diagnostics.

In various embodiments, the headset could use nonlexical noises as device inputs. Clicking, tsking, clucking and other sounds could be used as inputs.

In various embodiments, the headset could detect environmental noises requiring the device owner to perform actions such as microwave beeping, a kettle whistling or a doorbell. The central controller could place the individual on mute during a call if it detects an environment noise requiring a response. The central controller could prompt the device owner if the device owner ignores the environmental noise, such audio, video, tactile feedback either on the headset or a connected device. For example, individuals sometimes become involved with tasks and forget to respond to environment noises that are signals to engage in behavior.

Security and Authentication

Applications according to various embodiments can be enhanced with authentication protocols performed by the headset processor 405, user device 107*a*, or central controller 110. Information and cryptographic protocols can be used in communications with other users and other devices to facilitate the creation of secure communications, transfers of money, authentication of identity, and authentication of credentials. Such a headset could be provided to a user who needs access to sensitive areas of a company, or to sensitive information. The headset might be issued by the company and come with encryption and decryption keys securely stored in a storage device 445 of the headset.

In various embodiments, the user authenticates themselves to the headset by providing a password or other access token. For example, the user might enter a password or PIN via a numeric keypad presented on a display screen of the headset. In this way, the headset can be assured that the user is a legitimate user, and could provide access to stored value, passwords for access to networks, or access to particular applications within data storage of the headset.

The user could also authenticate themselves by providing a voiceprint by saying a passphrase into a microphone of the headset. For example, the user could say the phrase "Gary Smith access request for level three capabilities," which could then be compared to stored voice samples within data storage of the headset, with the headset processor 405 using stored algorithms to compare the voiceprints and then enable level three access if the voiceprint matches. In some embodiments, the headset data storage stores voiceprints from multiple users and stores digital content (like stored value of access credentials) for each user, enabling access to the stored content only if a user successfully provides a matching voiceprint. Alternatively, or in addition to the voiceprint, the user might provide a password or PIN by voice into the headset microphone, with the processor of the headset converting that voice signal into text and then comparing to a stored password or PIN with a match required in order for the user to be able to gain access to the functionality of the headset. For example, the user might say "PIN 258011" with the microphone of the headset sending the voice segment to the headset processor 405 where it is translated into the text and compared with the stored PIN value prior to allowing access.

The headset could also manage user access by an iris and/or retinal scan. In this embodiment, the user might enable a camera that is pointed toward the eyes of the user, with the headset camera sending the visual signal to the headset processor 405 which then identifies the iris/retina pattern of the user and compares it with a stored sample of that users iris/retina. For an iris based authentication, the headset processor 405 might match the image of the users iris with an iris stored with the central controller 110.

The headset can also gather biometric information from the users hands and fingers using a camera attached to the headset (or attached to the user device 107a). For example, the camera could be outward facing and pick up the geometry of the user's hands or fingers, sending that information to the headset processor 405 for processing and matching to stored values for the user. Similarly, a fingerprint could be read from a camera.

The headset camera could also read the pattern of the users veins on his face or hands.

Other biometric data that could be read by the headset includes ear shape, gait, odor, typing recognition, signature recognition, etc.

In some embodiments, a user might be authenticated when a second user is able to authenticate the face/eyes of the first user.

Headsets could communicate with each other, making frequent attempts to authenticate other users.

In various embodiments, the user may be required to authenticate via multiple forms in order to provide high enough confidence that they are who they claim to be in order to enter a restricted area, access restricted information, or use restricted resources. This is done by a point system where each authentication method is scored by its relative strength. The user must attain a score equal to or greater than the requirement for the area/data/resource. The headset will force the user to authenticate until such time as their authentication score is high enough for access or the user stops the attempts. In another embodiment, a user might need 10 points to access a particular database, but the user currently only has 8 points. The central controller might then allow access, but only if the user allows a video feed from the user's headset to be transmitted live to security personnel of the company while access to the database is taking place. If the user attempts to take his headset off in a high security location, the headset processor 405 could generate a loud warning siren, or give the user a warning that they need to put the headset back on in the next ten seconds.

When in a restricted setting, a user may be required to re-authenticate to maintain access if any of their credentials expire and their authentication score dips below the necessary level. They must regain the needed score within a threshold timeframe or have their access revoked.

When in a restricted setting, the headset may record events through the camera and microphone to keep a record of the actions taken by the user. This video can be sent to the central processor to allow for security review, either live or a later time from the stored video/audio recording.

When in a restricted setting, the functionality of the headset may be restricted to prevent the user from performing forbidden actions. For example, the internet access may be cut off when entering a restricted area to prevent sending data outside. In another embodiment, the camera on the headset may be disabled to prevent the user from taking video or photographs of confidential or secret data. Another example, the file system may be forced into a read-only mode to prevent the user from copying and storing confidential or secret information.

When in a restricted setting, if a user removes their headset, disables it, or removes or adds components, or interferes with its authentication ability the headset can take one or more actions to alert others. For example, the headset can give a verbal warning to the user to undo the action they took. In another embodiment, the headset can produce a loud alarm and/or flash lights on the headband warning others in the area of the potential security breach. Another example is the headset may communicate with company security to inform them of the situation.

A headset can log failed attempts at authorization to keep a record. This information can be stored locally on the headset and/or sent to the central controller. This log can contain the attempted method of authentication, the incorrect information provided, photo or video evidence of the attempt, audio recording of the attempt, time, location, and/or other authentication data collected by the headset, e.g., automatically. The data once collected can be used in a variety of ways: to improve the authentication methods if the person trying to authenticate was the actual person and the attempt should have been successful, to find who the person actual was if their data was in the system, or to alert security or the authorities to the attempted fraud.

By removing a headset a user can revoke all the active credentials on the headset. This prevents another from taking another's headset and gaining all accesses of another.

A headset can authenticate others in the area through facial and/or voice recognition to help ensure that unauthorized people cannot maintain access to places they do not belong. For example, when a user is walking around the office they pass others doing so the headset can take facial and/or voice samples and send them to the central controller to verify the identity. This can be done on a random sample basis or, when in times of heightened security, on every person encountered.

By authenticating himself to the headset, the headset verifies the identity of the user so that the headset processor 405 can make additional functionality of the headset available to the user. For example, the headset processor 405 could enable the user to listen to music at any time, but in order to make calls via the headset the user is required to first authenticate himself. In another embodiment, after the user successfully authenticates himself to the headset, the headset retrieves stored credentials of the user. For example, the headset processor 405 might search a credentials database stored in the data storage device of the headset (or user computer) and retrieve information indicating that the user is a licensed physician in the state of New York. This could be especially useful at the beginning of a telemedicine session in which the stored credential can be sent via text or email to a patient as proof that the physician on the other end of the call is a certified physician. Other examples of stored credentials include SAFe 4.6 instructor, Patent Agent, Heart Surgeon with more than ten years of pediatric cardiac surgery experience, Chess Grandmaster, Electrical Engineering Masters degree, fluent in German and French, licensed electrician in California and Nevada, currently active pilot's license, chef at a five star restaurant, top secret security clearance, retired police officer, member of the American Institute of Biological Sciences, Ambassador to Mexico, employee of IBM, a Subject Matter Expert on Project X at IBM, etc. These credentials could be communicated to others once the user is authenticated. For example, a user on a virtual call could authenticate himself to the headset which then emails or texts those credentials so that other participants on the virtual call can be assured that the user is a licensed heart surgeon. This credential information could include a license number of the physician. In some embodiments, the headset could display a visual indication of the credentials of a user on a display area of the headband of the headset. For example, a video game streamer could authenticate to the headset so that his insignia is illuminated on the headband of the headset.

In various embodiments, virtual calls for company XYZ could be set up where only authenticated Subject Matter Experts in microservices are allowed to join the call. Alternatively, the call could be set up so that only those authenticated Subject Matter Experts could be allowed to speak on the call, though other non-credentialed users could not be allowed to speak. A user could also be credentialed as someone who is on the list of approved participants on a given call. In this case, the user authenticates with the headset, such as by using a password spoken out loud and picked up by a microphone of the headset, with the user's name communicated to a central controller which then compares it to a list of stored invitee names for the call and allows the user on the call if his name is matched to one of the names on the list.

Once a user is authenticated to the headset, it could enable the headset processor 405 access to stored demographic information such as age, gender, race, marital status, location, income, etc. A user ordering food delivery via the headset, for example, could authenticate himself to the headset which enables the headset processor 405 to retrieve the address and age of the user and transmit that information to the food provider via email.

In various embodiments, the user provides periodic or continuous authentication information to the headset. For example, the user might initially authenticate himself to the headset processor 405 by providing a particular passphrase verbally to a microphone in the headset which then passes it to the headset processor 405 to be authenticated by comparing it to a stored passphrase for that user. Once this authentication process is complete, the headset processor 405 could frequently sample voice information from the headset's microphone, such as by taking a voice sample every five seconds, and comparing that sample to see if the characteristics of the voice matched that of the user's stored voice characteristics in the data storage device of the headset. In another embodiment, the user authenticates his identity with the headset processor 405, and then an inward facing camera controlled by the headset processor 405 continuously views the face of the user and sends still images from the video feed to a biometric processor which compares the video stills with information stored in the headset storage device related to face information of the user. The headset processor then makes a determination for each video frame whether or not the user is still the same as the user who first authenticated with the device. In such an embodiment, the headset processor could be assured that the user had not removed the headset and had someone else put on the headset. For example, a company gathering statistics relating to the television source that a user is watching could have the user wear a headset while watching television/cable/internet programs. The headset could authenticate the user at the start of the session, and the headset could engage in periodic or continuous authentication while the user was watching, ensuring that a different user had not replaced the original user during the session.

In various embodiments, the headset can sample environmental information in order to supplement ongoing authentication of a user. For example, the user could provide the headset with samples of the sound of her dog barking, with those sounds saved in a data storage device of the headset. After authenticating the user, the headset could periodically or continuously use a microphone to sample sounds from the user's environment, sending any barking sounds (identified via machine learning software of the headset processor 405) to be compared to the user's previously stored barking sounds so as to determine if it was the users dog that was barking. This information could add to the confidence of the headset processor 405 that the user's identity is known and has not changed.

The ability to authenticate a user can also be valuable in embodiments in which a user has valuable information stored in a data storage device of the headset processor 405. Valuable information could include credit/debit card info, account numbers, passwords, login data, digital currency, saved music and video and books, saved conversations, stored documents, medical data, etc. For example, the headset could be configured to transmit credit card information (including the user's name, card month and year of expiration, zip code, and ccv data) to a central controller (or directly to an online merchant) to facilitate the sale and delivery of an item. The information could be communicated in an electronic manner or it could be read out by text to speech software via a phone connection with the central controller or third party merchant. In this example, the user requests the information to be sent to the merchant, but the headset processor 405 is first required to complete a successful authentication of the user, upon which the information is then forwarded along. In this example, the user is relieved of the need to transmit the financial data, speeding up and simplifying the purchase transaction. In another example, the headset allows a user to subscribe to music stored in the storage device of the headset processor 405. Payment could be made on a monthly basis to allow the user access to the stored music.

In various embodiments, encryption is an encoding protocol used for authenticating information to and from the headset. Provided the encryption key has not been compromised, if the central controller can decrypt the encrypted communication, it is known to be authentic. Alternatively, the cryptographic technique of "one-way functions" may be used to ensure communication integrity. As used herein, a one-way function is one that outputs a unique representation of an input such that a given output is likely only to have come from its corresponding input, and such that the input cannot be readily deduced from the output. Thus, the term one-way function includes hashes, message authenticity codes (MACs—keyed one-way functions), cyclic redundancy checks (CRCs), and other techniques well known to those skilled in the art. See, for example, Bruce Schneier, "Applied Cryptography," Wiley, 1996, incorporated herein by reference. As a matter of convenience, the term "hash" will be understood to represent any of the aforementioned or other one-way functions throughout this discussion.

In various embodiments, the headset could store authentication information to make virtual meetings with people outside of the company more fluid. The user headset could store HR "rules" for communication, with required standards of authentication. All audio and video with outside people could be automatically captured and stored/encrypted/hashed in a data storage device of the headset processor 405 or a central controller. Other data that could be captured from calls (or used to manage calls) with people outside the company include work history, licenses, certifications, ratings and reviews from prior contracts, and stored lists of outsiders under NDA. In one embodiment, a user headset could initiate all calls with people outside the company by verbally declaring that "this call is "on the record."

For enhanced security applications, the user headset could include a connected security token (via USB or audio jack).

In various embodiments, audio recordings could be encrypted when stored in a data storage device of the headset processor 405.

Brainwaves

Various embodiments include a headset (e.g., headset 8000, headset 107*a*, headset 4000 and/or headset 9400) for authenticating a first user based on brain activity of the first user.

In various embodiments, a headset 8000 includes an electronic processing device (e.g., a processor 405 or 9405). In various embodiments, the headset includes a set of electrodes (e.g., two electrodes 8085), each electrode operable to detect an electrical potential at a respective point on a head of a first user (e.g., on the head of the wearer of the headset.

In various embodiments, the headset includes an amplifier (e.g., amplifier 8090) in communication with each of the set of electrodes 8085 and with the electronic processing device. The amplifier may be operable to amplify differences in electrical potentials detected at the respective electrodes. In various embodiments, the amplifier may amplify a relatively small voltage difference detected across two electrodes into a relatively larger voltage difference.

In various embodiments, headset 8000 includes a camera in communication with the electronic processing device 405. In various embodiments, headset 8000 includes a network device (e.g., network port 8010) in communication with the electronic processing device 405.

In various embodiments, headset 8000 includes a memory (e.g., storage device 8045). The memory may store image analysis instructions, which may comprise instructions for analyzing images and/or videos, and/or for determining objects or contents that appear in the images and/or videos.

The memory may store brain wave data. The brain wave data may include voltage readings from one or more individuals' brains or heads. The brain wave data may include data previously obtained from the wearer of headset 8000. The brain wave data may include EEG data. The brain wave data may include data previously obtained from users who were viewing familiar objects. The brain wave data may include data previously obtained from users who were viewing unfamiliar objects. In various embodiments, the brain wave data may serve as reference data against which new brain wave data will be compared.

The memory may store processing instructions that, when executed by the electronic processing device 405, result in one or more embodiments described herein.

Figure 103:
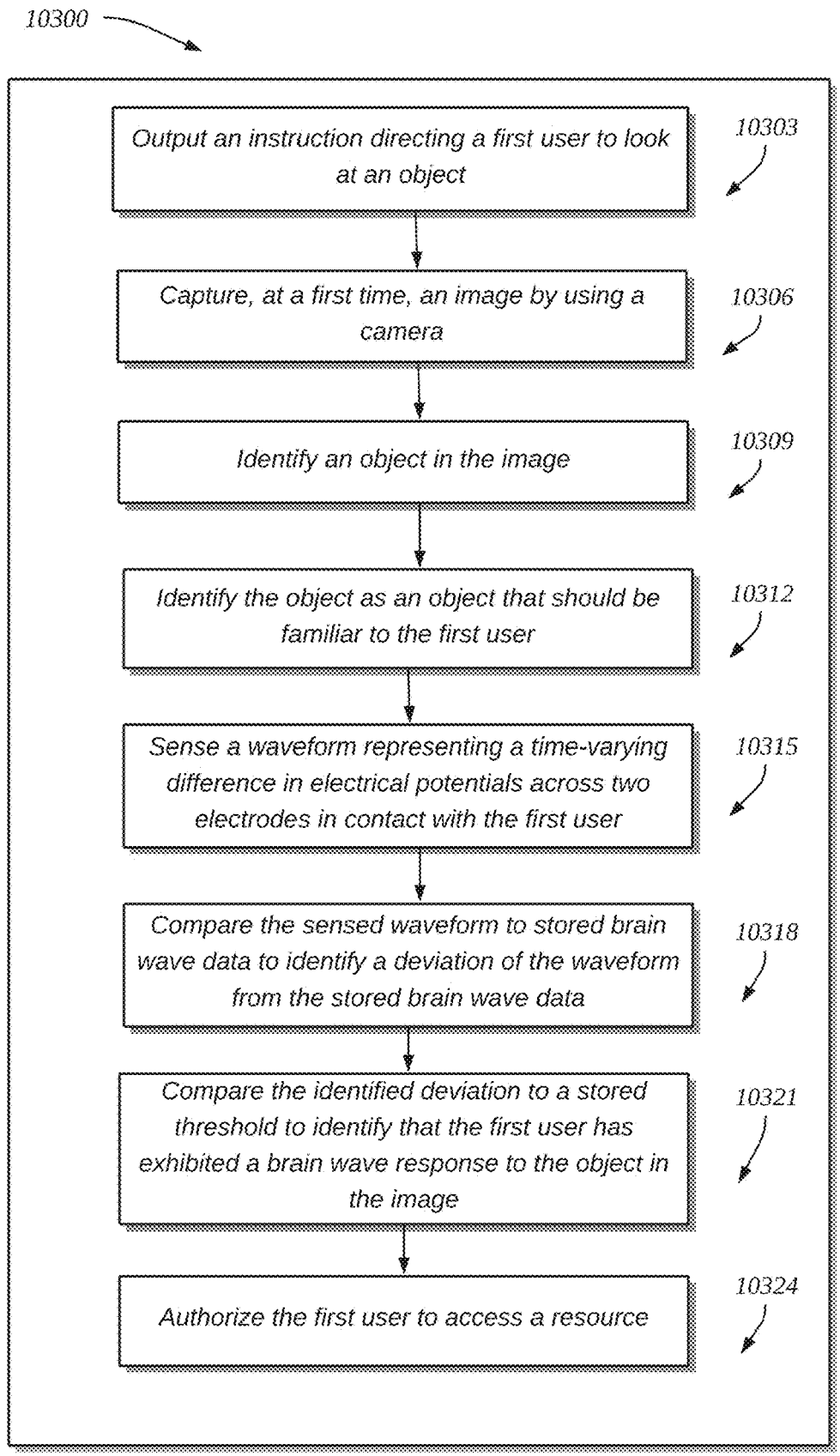
FIG. 103 shows a diagram of a process flow consistent with at least some embodiments described herein.

Turning now to FIG. 103, illustrated therein is an example process 10300 for authenticating a first user based on brain activity of the first user, which is now described according to some embodiments.

At step 10303, in various embodiments, electronic processing device 405 outputs an instruction directing the first user to look at an object.

At step 10306, in various embodiments, electronic processing device 405 captures, at a first time, an image by using the camera. The camera may be a forward facing camera (e.g., one or both of cameras 4022*a* and 4022*b*) and may thereby capture an image of an object or scene at which the user (i.e., the wearer of the headset) is currently looking. The object may be the object at which the user was instructed to look.

At step 10309, in various embodiments, electronic processing device 405 may execute the image analysis instructions to identify an object in the image. This may be accomplished via object recognition algorithms, for example.

At step 10312, in various embodiments, the electronic processing device 405 may identify the object as an object that should be familiar to the first user. Electronic processing device 405 may retrieve a portion of the stored object data. In various embodiments, electronic processing device 405 retrieves stored image(s) and/or recorded video from a database table (e.g., from peripheral sensing log table 2300; e.g., from sensor log table 7500), where the presumed user (i.e., headset wearer 8000) is known or believed to have seen such images or videos and/or the contents thereof. For example, the retrieved image may also have been recorded by headset 8000 when worn by the user. If the retrieved image(s) and/or video match the presently identified object in the image, then it may be presumed that the presently identified object is familiar to the first user.

In various embodiments, the retrieved portion of the stored object data comprises data descriptive of a location of the object. For example, the data may indicate that the object had been in a particular room, or on a particular wall. In various embodiments, the electronic processing device 405 may identify that the object should be familiar to the first user by identifying that the first user has previously been to a nearby or proximate location to the location of the object. For example, the first user has previously been to the room where the object has been located.

In various embodiments, the portion of the stored object data comprises data descriptive of a certification associated with the object. For example, the object may be a piece of machinery, and the certification may be a certification for proper use of the piece of machinery. The electronic processing device 405 may identify that the object should be familiar to the first user by verifying that the first user has obtained the certification. For example, if the first user has obtained a certification on how to use a piece of machinery, then that piece of machinery should be familiar to the user.

At step 10315, in various embodiments, electronic processing device 405 may sense a waveform representing a time-varying difference in electrical potentials across two electrodes of the set of electrodes. This waveform may be sensed, received, and/or determined by the set of electrode(s) 8085 and/or by amplifier 8090. The waveform may represent brain waves of the user wearing the headset 8000. The waveform may be an electroencephalogram. The waveform may be sensed at a second time proximate to and following the first time.

The waveform may represent the user's response or reaction to seeing the object, since it occurs right after the image of the object has been captured (and therefore, presumably, right after the user has seen the object in the image). In various embodiments, the waveform is sensed from the first time until one second after the first time. In various embodiments, the waveform is sensed from 1 millisecond after the first time until 500 milliseconds after the first time. As will be appreciated, the waveform may be sensed (and thus the second time may occur) at any suitable time and for any suitable duration of time.

In various embodiments, the electronic processing device 405 may determine that the waveform represents cognitive recognition. In other words, the user's brainwaves show that the user recognized the object he was presumed to be familiar with.

At step 10318, in various embodiments, electronic processing device 405 may compare the sensed waveform to the stored brain wave data. The electronic processing device 405 may thereby identify a deviation of the waveform from the stored brain wave data. For example, the device 405 may subtract the sensed waveform from the stored brain wave data to determine a deviation. As another example, the device 405 may determine a degree or percentage of similarity between the sensed waveform and the stored brainwave data.

At step 10321, in various embodiments, the electronic processing device 405 may compare the identified deviation to a stored threshold. Based on the comparison, the electronic processing device 405 may identify that the first user has exhibited a brain wave response to the object in the image. For example, if the stored brain wave data represents data from an individual viewing an unfamiliar object, and the sensed waveform deviates from the stored waveform by more than 20% (or by more than some other predetermined threshold), then the device 405 may identify that the user has exhibited a brain wave response representing recognition. As another example, if the stored brain wave data represents data from an individual viewing a familiar object, and the sensed waveform deviates from the stored waveform by less than 10% (or by less than some other predetermined threshold), then the device 405 may identify that the user has exhibited a brain wave response representing recognition.

In various embodiments, electronic processing device 405 identifies a brain response in the first user if the sensed waveform is closer to a stored brainwave of a user viewing a familiar object than it is to a stored brainwave of a user viewing an unfamiliar object.

In various embodiments, electronic processing device 405 identifies a brain response from the sensed waveform in relation to the stored brain wave data in any other fashion.

At step 10324, in various embodiments, electronic processing device 405 may authorize, in response to the identifying of the brain wave response to the object in the image, the first user to access a resource. The resource may be an electronically-actuated access device (e.g., an electronic door lock, a lock to a safe, an ignition for a car), a computing device, an electronic storage address, or any other resource.

Authorizing the first user to access the resource may include transmitting, by the network device, a wireless command indicative of the authorization for the first user to access the resource.

In various embodiments, electronic processing device 405 may cause an indication of the authorization to be stored in memory. In various embodiments, so long as an indication of the authorization is stored in memory, the first user may continue to access the resource.

In various embodiments, the electronic processing device 405 may detect a removal of the headset by the first user. The electronic processing device 405 may then erase the stored indication of the authorizing. Thus, upon removing the headset, the first user may lose access to the resource.

Multi-Tiered Authentication

Various embodiments include a headset (e.g., headset 8000, headset 107*a*, headset 4000 and/or headset 9400) for authenticating a first user based on an on-going, multi-tiered authentication process.

As used herein, the term "authentic user" may refer to an individual that is a true, trusted, authorized, and/or known individual. In embodiments described herein a given user, of possibly unknown or uncertain identity, may attempt to represent himself as the "authentic user", e.g., so as to be granted access to a resource. Accordingly, embodiments described herein attempt to determine whether a given user is the "authentic user".

In various embodiments, the headset 8000 may include an electronic processing device (e.g., a processor 405 or 9405), a speaker (e.g., speaker 4010*a* and 4010*b*) in communication with the electronic processing device; a microphone (e.g., microphone 4014) in communication with the electronic processing device; a positioning system (e.g., sensor 4040, which may be a GPS or other positioning sensor) in communication with the electronic processing device; an accelerometer (e.g., 4070*a* and 4070*b*) in communication with the electronic processing device; a network device in communication with the electronic processing device (e.g., network port 4060); a camera in communication with the electronic processing device (e.g., camera unit 4020, cameras 4022*a* and 4022*b*); a biometric device in communication with the electronic processing device; and a memory (e.g., storage device 8045).

The memory may store point allocation instructions, which may comprise instructions for allocating points to a user based on how much evidence the user has provided to verify his identity. The memory may store referential instructions, which may comprise reference data or instructions against which to compare identifying information provided by the user.

The memory may store processing instructions that, when executed by the electronic processing device 405, result in one or more embodiments described herein.

Figure 104A:
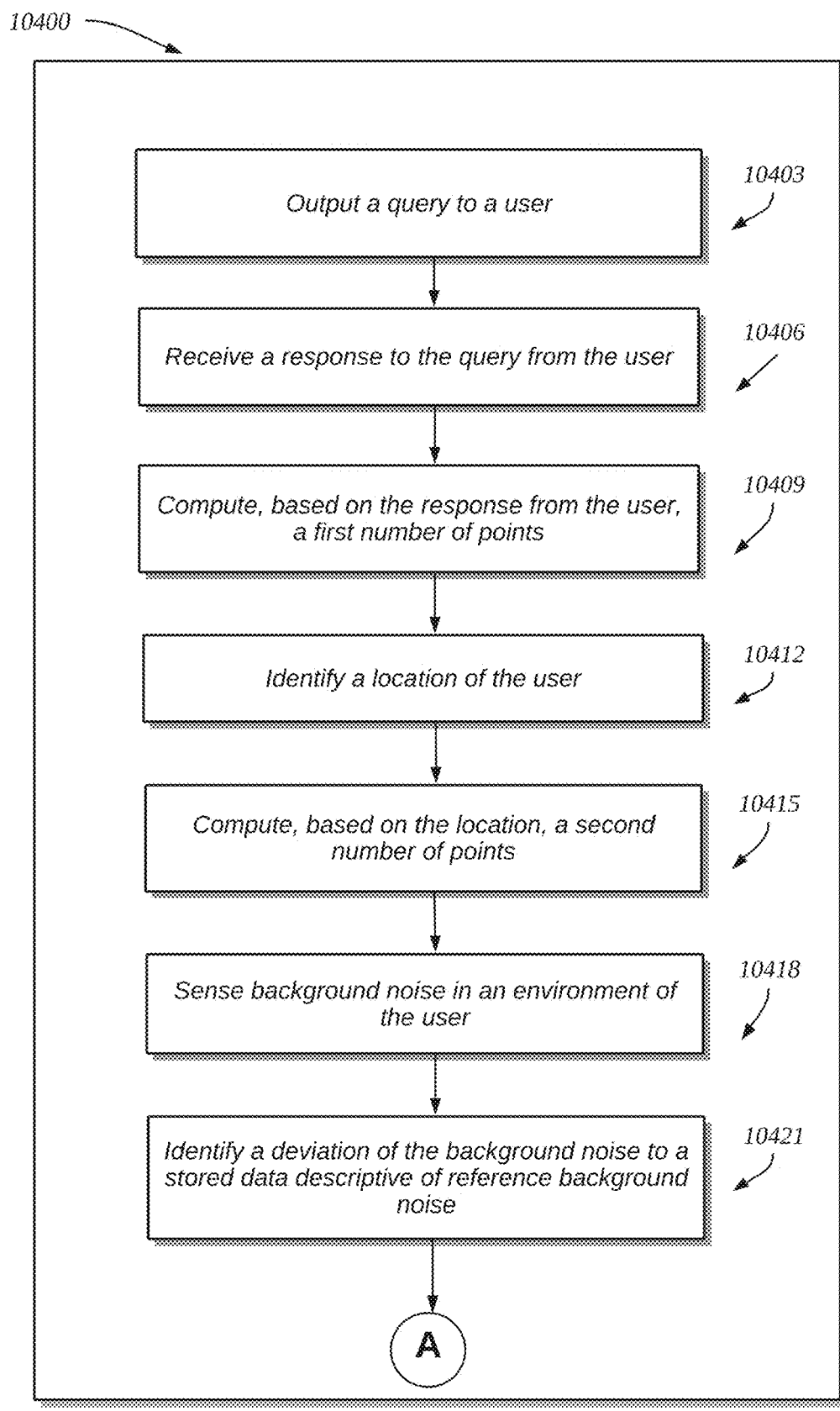
FIG. 104A and FIG. 104B, together show a diagram of a process flow consistent with at least some embodiments described herein.
Figure 104B:
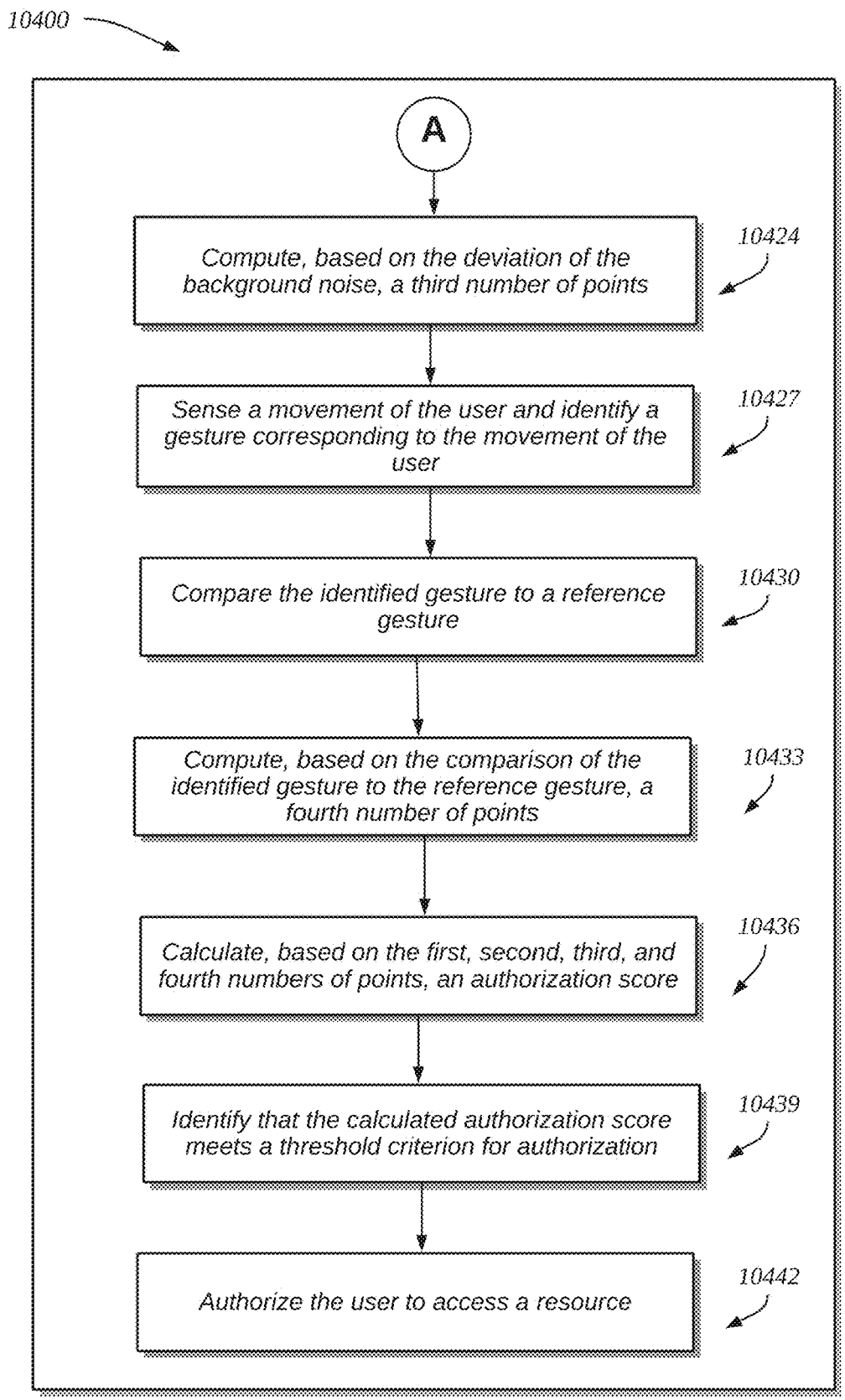

Turning now to FIG. 104, illustrated therein is an example process 10400 for authenticating a first user based on multiple factors, which is now described according to some embodiments.

At step 10403, in various embodiments, the electronic processing device 405 may output, by the speaker, a query to a user. The query may comprise a voice prompt. The query may ask the user for a personal identification number (PIN), a password, an item of personal information, a piece of information only the user would be likely to know, and/or any other query.

At step 10406, in various embodiments, the electronic processing device 405 may receive, by the microphone and in response to the query, a response from the user. For example, the user may provide an oral response spoken into the microphone. In various embodiments, the user may respond in other ways, such as with a gesture, pressing of a button, typing in a message, and/or providing a response in any other fashion.

At step 10409, in various embodiments, the electronic processing device 405 may execute the point allocation instructions to compute, based on the response from the user, a first number of points. For example, the point allocation instructions may detail a number of points to allocate to the user upon a correct or accurate response to the query. For instance, if the user correctly provides his password, then the user may receive four points. In various embodiments, the user may receive less than a maximum allowable number of points if the user provides a partially correct answer. For example, if a user provides a PIN with only three out of four digits correct, then the user may receive an allocation of only two out of a possible four points. In various embodiments, the user is allocated points based on the speed of his response. The user may receive ten points for a correct response given within one second, and may receive one fewer point for each additional second the user needs to respond. In various embodiments, point allocation instructions may provide instructions to allocate points in any other suitable fashion.

At step 10412, in various embodiments, the electronic processing device 405 may identify, by the positioning system, a location of the user. For example, device 405 may identify a latitude and longitude, a city, an intersection, a landmark, a building, an address, a room, a door, a proximity to an object, or any other indication of a location of the user.

At step 10415, in various embodiments, the electronic processing device 405 may compute, by an execution of the point allocation instructions and based on the location of the user, a second number of points. In various embodiments, point allocation instructions specify that the user is allocated a first number of points if the user is in a first location, and a second number of points if the user is in a second location. For example, if the user is in a particular room, the user is allocated five points, but the user is otherwise allocated zero points. In various embodiments, point allocation instructions may provide instructions to allocate points in any other suitable fashion. In various embodiments, it may be desirable to confirm that a user is in a particular location, because an authentic user would likely be in that location (and, e.g., an imposter would not likely be in that location).

In various embodiments, the user's location may be computed in other ways. In various embodiments, electronic processing device 405 may prompt the user to sequentially orient the camera in a plurality of directions; capture, by the camera and at each orientation, an image of an environment surrounding the user; and compute, by an execution of the referential instructions based on the images of the environment surrounding the user, the location of the user. For instance, referential instructions may cause device 405 to compare the images of the environment to known images, locations, landmarks, etc. If there is a match, it may be presumed that the user is currently located at the same location as the known images, locations, landmarks, etc.

At step 10418, in various embodiments, the electronic processing device 405 may sense, by the microphone, background noise in an environment of the user. For example, the device 405 may sense the sound of machinery in the background, the sound of a dog barking, the sound of traffic from a highway in the background, the sound of planes taking off from an airport in the background, and/or any other background noise.

Device 405 may retrieve stored data descriptive of reference background noise. The reference background noise may represent noise that is associated with the authentic user. For example, the reference background noise may be background noise that had previously been recorded in the background of the authentic user (e.g., at the authentic users house, at the authentic users office, etc.). The reference background noise may be a pre-recorded sound of a dog barking in an environment of the user.

At step 10421, in various embodiments, the electronic processing device 405 executes the referential instructions to identify a deviation of the background noise to a stored data descriptive of reference background noise. The referential instructions may instruct device 405 to determine a deviation in terms of volume level, frequency content, type of sound (e.g., cars, dogs, birds, machinery, etc.), voices heard, spoken words heard, and/or any other type of deviation.

At step 10424, in various embodiments, the electronic processing device 405 computes, by an execution of the point allocation instructions, and based on the deviation of the background noise, a third number of points. In various embodiments, point allocation instructions may specify a maximum number of points that may be allocated (e.g., 10 points), and may specify that some number of points is to be deducted from the maximum number that is proportional to the deviation of the background noise. For example, if the background noise deviates by 10% from the reference background noise, then there are 9 points allocated, e.g., 10×(1-10%) points allocated. In various embodiments, point allocation instructions may provide instructions to allocate points in any other suitable fashion.

At step 10427, in various embodiments, the electronic processing device 405 senses, by the accelerometer, a movement of the user. In various embodiments, the electronic processing device 405 identifies, by an execution of the referential instructions and based on the movement of the user, a gesture corresponding to the movement of the user. For example, referential instructions may include reference movements against which the movement of the user may be compared. Each reference movement may be associated with a reference gesture. Where the movement of the user is most closely matched to a particular reference movement, a gesture associated with the reference movement may be ascribed to the user. In various embodiments, a gesture of the user may be identified in any other suitable fashion.

In various embodiments, referential instructions include reference movements or gestures of the authentic user.

At step 10430, in various embodiments, the identified gesture and/or movement of the user may be compared to a reference movement or gesture of the authentic user. A degree of similarity or dissimilarity may be determined. An amount of deviation may be determined. In various embodiments, any other suitable comparison may be made between the identified gesture and a reference movement or gesture of the authentic user.

At step 10433, in various embodiments, the electronic processing device 405 may compute, by an execution of the point allocation instructions and based on the gesture, a fourth number of points. In various embodiments, point allocation instructions may specify a number of points to be allocated based on a degree of similarity, dissimilarity, and/or deviation of the identified gesture and a reference movement or gesture of the authentic user. For example, a maximum of 6 points (for example) may be allocated, with 1 point deducted from the maximum for each 10% deviation of the identified gesture from a reference gesture. In various embodiments, point allocation instructions specify that a predetermined number of points will be allocated if the identified gesture matches a reference gesture, and no points will be allocated otherwise. In various embodiments, point allocation instructions may provide instructions to allocate points in any other suitable fashion.

At step 10436, in various embodiments, the electronic processing device 405 may calculate, based on the first, second, third, and fourth numbers of points, an authorization score. In various embodiments, the electronic processing device 405 adds up the respective numbers of points. In various embodiments, the device 405 multiplies the respective numbers of points. In various embodiments, the device 405 adds up the three highest numbers of points (or the N highest for some number N). The device 405 may calculate an authorization score in any other suitable fashion.

In various embodiments, an authorization score may be calculated based on more or fewer numbers of points (e.g., based on only three numbers of points rather than four; e.g. based on two numbers of points; e.g., based on five numbers of points, etc.). In various embodiments, an authorization score is further calculated based on a fifth number of points. In various embodiments, an authorization score may be determined based on any other factors in addition to and/or besides the aforementioned (e.g., in addition to and/or besides query responses, location, etc.). In various embodiments, an authorization score may be determined based on any subset, superset, combination, etc., of the aforementioned factors and/or of any other factors.

In the aforementioned discussion, ordinal references such as "first", "second", etc., are made for convenience only, and do not imply that the user must take actions or receive points in any particular order. Nor do such references imply that any given action is a precondition or must occur at all in order for another action to occur. For example, in various embodiments, a user may obtain the second number of points without obtaining the first number of points (or without even having the opportunity to obtain the first number of points).

At step 10439, in various embodiments, the electronic processing device 405 identifies that the calculated authorization score meets a threshold criterion for authorization. In various embodiments, the authorization score must exceed a predetermined threshold number (e.g., must exceed the number 10). In various embodiments, the authorization score must fall below a predetermined threshold number.

At step 10442, in various embodiments, the electronic processing device 405 authorizes, in response to the identifying that the calculated authorization score meets the threshold criterion for authorization, the first user to access a resource. Authorization may include transmitting, by the network device, a wireless command indicative of the authorization for the first user to access the resource.

In various embodiments, "points" need not be numerical, but may represent any tally, record, quantity, fraction, portion, piece, component, etc. For example, in various embodiments, a user receives a piece of a puzzle for a query response, another piece of a puzzle for a movement, etc. The user may ultimately receive authorization if he receives enough pieces to complete the puzzle.

In various embodiments, the resource may be an electronically-actuated access device, a computing device, and/or an electronic storage address.

In various embodiments, the electronic processing device 405 captures, by the camera, an image of an environment surrounding the user (e.g., an image of the user's workplace, an image of the user's home, etc.). In various embodiments, the electronic processing device 405 identifies an object in the image (e.g., with object recognition algorithms). In various embodiments, the electronic processing device 405 prompts (e.g., via an audible instruction output from a speaker) the user to provide an identification of the object. In various embodiments, the electronic processing device 405 receives, in response to the prompting, a user-indicated identification of the object (e.g., a verbal response received at a microphone 4014 of the headset 8000).

In various embodiments, the electronic processing device 405 compares the user-indicated identification of the object to the identification of the object by the electronic processing device.

In various embodiments, the electronic processing device 405 computes, by an execution of the point allocation instructions and based on the comparing, a fifth number of points. In various embodiments, point allocation instructions specify that a predetermined number of points will be allocated if the user-indicated identification of the object matches the identification of the object by the electronic processing device and no points will be allocated otherwise. In various embodiments, point allocation instructions may provide instructions to allocate points in any other suitable fashion.

In various embodiments, the electronic processing device 405 senses, by the biometric device, a biometric reading of the user (e.g., a voice print, retinal image, iris image, etc.). In various embodiments, the electronic processing device 405 computes, by an execution of the point allocation instructions and based on the biometric reading, a fifth number of points. In various embodiments, point allocation instructions specify that a predetermined number of points (e.g., five points) will be allocated if the biometric reading matches a stored biometric reading from the authentic user and no points will be allocated otherwise. In various embodiments, point allocation instructions specify that a number of points will be allocated, up to a predetermined maximum number of points, based on (e.g., proportional to) the degree or confidence of a match between the biometric reading and a stored biometric reading from the authentic user. In various embodiments, point allocation instructions may provide instructions to allocate points in any other suitable fashion.

In various embodiments, the electronic processing device 405 identifies an electronic device in proximity to the location of the user (e.g., a security camera); transmits a command to the electronic device, the command being operable to cause the electronic device to output a verification (e.g., to send a wireless signal to headset 8000); detects an indication of the verification; and computes, by an execution of the point allocation instructions and based on the detecting of the indication of the verification, the fifth number of points.

Various embodiments comprise a headset for authenticating a first user based on verification of the first user by a second user. The headset may comprising an arcuate housing operable to be removably coupled to a head of a first user; an electronic processing device (e.g., processor 405) coupled to the housing; a camera in communication with the electronic processing device; a speaker in communication with the electronic processing device; a microphone in communication with the electronic processing device; a network device in communication with the electronic processing device; and a memory. The memory may store (i) human identification instructions, (ii) speech recognition instructions, and (iii) processing instructions that, when executed by the electronic processing device, result in one or more embodiments described herein.

In various embodiments, the electronic processing device (e.g., processor 405) may identify a proximity of a second user with respect to the first user. In various embodiments, the electronic processing device may identify, by an execution of the human identification instructions, the second user.

The electronic processing device may identify the second user by matching a portion of an image captured of an area proximate to the first user that is captured by the camera, to stored data descriptive of a plurality of users. Based on the matching, the electronic processing device may identify an association between the portion of the image and the second user.

In various embodiments, the electronic processing device may determine that the second user is a member of a trusted group of users.

The electronic processing device 405 may output, by the speaker, an audible instruction requesting that the second user verify an identity of the first user. Device 405 may compute a distance to the second user, and select an output volume based on the distance to the second user.

The electronic processing device may receive, by the microphone, a verbal response from the second user. The device 405 may compute, by an execution of the speech recognition instructions and based on the verbal response from the second user, an indication of a verification of the first user by the second user. The device 405 may authorize, in response to the computing of the indication of the verification of the first user by the second user, the first user to access a resource.

In various embodiments, authorizing may include transmitting, by the network device, a wireless command indicative of the authorization for the first user to access the resource.

Figure 92:
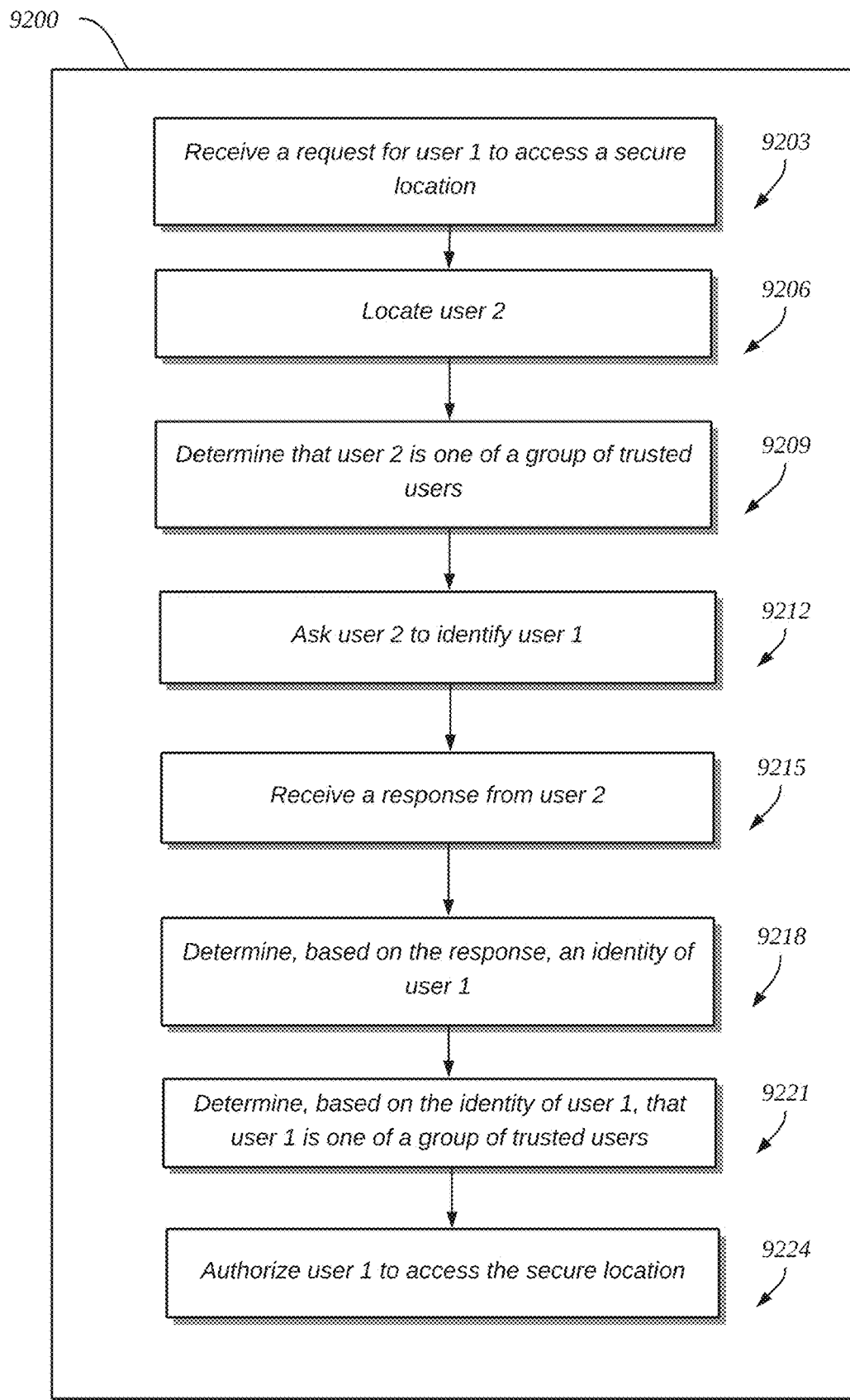
FIG. 92 shows a diagram of a process flow consistent with at least some embodiments described herein.

Turning now to FIG. 92, illustrated therein is an example process 9200 for granting access to a secure location, which is now described according to some embodiments. For purposes of illustration, process 9200 will be described in the context of room 6900 of FIG. 69, although it will be appreciated that process 9200 may occur in any applicable location. In various embodiments, process 9200 may be performed by a headset 4000 worn by a user (e.g., "user 1" 6985*b*) who is seeking access to a secure location (e.g., the "Laser facility" behind door 6905. In various embodiments, process 9200 may be performed in conjunction with one or more other devices, such as central controller 110.

At step 9203, headset 4000 may receive a request for user 1 to access a secure location, according to some embodiments. The request may come from user 1. For example, user 1 may verbally ask to open a particular door or enter a particular room. The request may be implied, e.g., because user 1 is standing next to a particular door. In various embodiments, the request may come from another device.

For example, an electronic door lock proximate to user 1 may initiate the request on behalf of user 1. The request may come from central controller 110, such as after user 1 has expressed a desire to the central controller 110 to access the secure location. For example, user 1 may interact with an app and use the app to request entry into the secure location. In various embodiments, the request may come from any applicable party and may occur in any suitable fashion.

At step 9206, headset 4000 may locate a second user ("user 2"), according to some embodiments. The purpose of locating user 2 may be so that user 2 can confirm the identity of user 1 and/or otherwise indicate approval for user 1 to receive access to the secure location.

In various embodiments, user 2 may confirm that user 1 is dressed appropriately (e.g., is not wearing a tie or other clothing that can be caught in equipment), that user 1 is wearing appropriate safety equipment, that user 1 is competent (e.g., user 1 does not appear to be intoxicated; e.g., user one does not appear to be fatigued), that user 1 is not under duress, and/or that user 1 is otherwise in a suitable state to receive access to the secure location.

In various embodiments, headset 4000 seeks to locate a second user that is proximate in location to user 1. In this way, for example, user 2 may directly observe user 1 (e.g., visually observe use 1). User 2 may also directly listen to user 1, smell user 1 (e.g., to detect the smell of alcohol), or otherwise interact with user 1.

In various embodiments, headset 4000 seeks a particular individual (e.g., a plant manager) to observe user 1. In various embodiments, headset 4000 may seek any of a group of individuals, or any individual who happens to be available (e.g., nearby).

In various embodiments, headset 4000 may locate user 2 via another headset or other device worn by user 2. Headset 4000 may pick up a Bluetooth®, Wi-Fi®, radio, or other signal (e.g., a short-range) signal from the device worn by user 2, thereby inferring the presence of user 2. In various embodiments, headset 4000 may locate user 2 via the central controller 110. For example, the central controller may be in communication with headset 4000 and with a device associated with user 2 (e.g., with user 2's headset). User 1's headset and user 2's device (e.g., headset) may each have positioning sensors (e.g., GPS). User 1 and user 2's devices may need to report their respective positions to the central controller. The central controller may thereby determine whether user 2 is proximate to user 1. If user 2 is proximate to user 1, the central controller may indicate such proximity to headset 4000.

In various embodiments, headset 4000 may detect user 2 via sensors, including a camera, image sensor, infrared sensor, motion sensor, microphone, or via any other suitable sensor. In various embodiments, camera 4022*a* and/or 4022*b* may capture an image of user 2. Processor 4055 may use face-detection or face-recognition algorithms to recognize the presence of a person (i.e., user 2) in the image.

In various embodiments, user 2 may be specifically identified from an image captured by headset 4000. Headset 4000 (or central controller 110) may scan through the authentication database table 3600 to find image data (field 3606) most closely matching a captured image. The user ID for the associated user may then be found at field 3604 for the matching row.

In a similar fashion, user 2 may be specifically identified from audio captured by the headset 4000. Audio data may be compared to stored "Voiceprint" data (field 3612), in order to determine the user ID for a matching voiceprint. In various embodiments, user 2 may be identified via iris or retinal scans (field 3610), or in any other fashion.

In various embodiments, microphone 4014 may detect user 2's voice, footsteps, or some other sign of user 2. Voice recognition or other audio processing algorithms may be used to detect or confirm the presence of user 2.

In various embodiments, user 1 may see or hear user 2 himself, and then, e.g., report the presence of user 2 to headset 4000.

In various embodiments, user 2 may be located in any suitable fashion.

In accordance with the present illustrative example, user 2 may be user 6985*a*, since this user is proximate to user 1 6985*b* and is therefore in a good position to identify user 1 and/or otherwise observe user 1.

At step 9209, headset 4000 may determine that user 2 is one of a group of trusted users, according to some embodiments. In various embodiments, a determination that user 2 is an employee of a company (e.g., user 2 is listed in user table 700 and/or in employees table 5000) is sufficient to establish that user 2 is a trusted user. In various embodiments, user groups table 1500 includes a group of trusted users (e.g., a group of users known to work at a particular facility). If user 2 is a member of this group (i.e., as indicated at field 1512), then user 2 may be deemed to be a trusted user. In various embodiments, if user 2 has at least a minimum security level (e.g., as indicated in field 5018 of employees table 5000), then user 2 may be deemed to be a trusted user. Headset 4000 may determine that user 2 is a trusted user in any other suitable fashion.

At step 9212, headset 4000 may ask user 2 to identify user 1, according to some embodiments. In various embodiments, a speaker (e.g., speaker 4010*a* and/or 4010*b*) may output audio at a sufficient volume so as to be audible to user 2, even though user 2 is not the person wearing the headset. In various embodiments, the headset may first warn user 1 to take the headset off his ears so as not to hurt his ears with the louder-than-usual output. In various embodiments, headset 4000 may include an externally directed speaker 4074 (i.e., a speaker not directed to the wearer of the headset), and may employ this speaker to output audio to be heard by user 2.

In various embodiments, headset 4000 may transmit a message to a device of user 2 (e.g., to user 2's headset). The message may be, for example, "Please look over at the person standing by the entrance to the laser room, and say their name." In various embodiments, headset 4000 may take on a noticeable appearance (e.g., headset 4000 may display flashing red lights), so it is clear to user 2 whom user 2 should identify. In such a case, a message may be, for example, "Please look over at the person with the flashing red headset, and say their name."

In various embodiments, headset 4000 may visually convey a message to user 2, such as by displaying text for user 2 to read (e.g., via display 4046).

In various embodiments, rather than asking user 2 to explicitly identify user 1, headset 4000 may ask user 2 to confirm the identity of user 1. For example, headset 4000 may ask user 2 to confirm that user 1 is "Joe Smith".

In various embodiments, user 2 is asked only to show support for (e.g., to approve) user 1's request for entry or access.

At step 9215, headset 4000 may receive a response from user 2, according to some embodiments. The response may be a verbal response from user 2, and may be received, e.g., at microphone 4014 of the headset. In various embodiments, a "thumbs up", a head nod, or other gesture showing approval for user 1's request may be received, e.g., at camera unit 4020. In various embodiments, a response may come in any other form, such as an electronically transmitted message from user 2 to headset 4000.

At step 9218, headset 4000 may determine, based on the response, an identity of user 1, according to some embodiments. Headset 4000 may use speech recognition algorithms to determine user 1's name from user 2's verbal response, which presumably contains user 1's spoken name. If user 2 has indicated approval for user 1, then headset 4000 may determine that an identity that was previously presumed for user 1 (e.g., an identity that was provided by user 1) is in fact correct. If user 2 has provided a text message with user 1's identity, then user 1's identity may be read from the text message.

In various embodiments, headset 4000 may correct for any nicknames, misspelling, mispronunciations, etc., that may be contained in user 2's response. For example, headset 4000 may compare a first name contained in user 2's response to a list of one thousand common names, and assume user 2's response represents the most closely matching name from the list. The headset 4000 may perform a similar procedure for user 1's last name, for user 1's middle name, for user 1's salutation, for user 1's suffix (e.g., "Jr.") and/or for any other names or identifiers for user 1.

At step 9221, headset 4000 may determine, based on the identity of user 1, that user 1 is one of a group of trusted users, according to some embodiments. In various embodiments, confirmation that user 1 is one of a group of trusted users may occur along the same lines as how the determination was made for user 2 at step 9209.

At step 9224, headset 4000 may authorize user 1 to access the restricted location. If the headset has determined that user 1 is one of a group of trusted users, then headset 4000 may authorize user 1 to access the restricted location. In various embodiments, final authorization is provided by a separate entity (e.g., by central controller 110). The separate entity may rely upon identification and/or confirmation provided by user 2, which may be relayed to the entity via headset 4000, in various embodiments.

In various embodiments, once user 1 has been authorized, an electronic door lock may be opened, headset 4000 may show green lights or other indications of authorization for user 1, and/or any other event may transpire.

Process of 9200 has been described herein with respect to granting authorization for user 1 to enter a secure location. Various embodiments contemplate that a similar process may be used for granting access or permission for user 1 to view a document, view a resource, listen to a conversation, speak to an individual, take possession of an item, be left in an area alone or unsupervised, access a network, access a computing system, use a piece of equipment, and/or take any other action of a sensitive nature, and/or take any other action.

Sensors

The headset could be equipped with various off the shelf sensors that allow for collection of sensory data. This sensory data could be used by the various controllers; headset, computer, game and central AI controllers to enhance the experience of the user(s) in both the virtual world (e.g. the game or virtual meeting) and physical world (e.g. exercise, meetings, physical activities, coaching, training, health management, safety, environmental and other people using headsets). The data collected from the sensors could also provide both real-time and post activity feedback for improvement. The sensors could be embedded directly in the headset or attached as an add-on accessory. The sensors could also be powered using the internal power management system of the headset or run independently using battery power. Data collected could flow from the sensor to headset processor 405 to user device 107*a* (if connected) to central controller AI where the data is stored and interpreted. Once processed the data is returned to the headset using the reverse data flow.

Examples of sensors that could be included in the headset and their uses are as follows.

Accelerometer

An accelerometer is an electromechanical device used to measure acceleration forces. Such forces may be static, like the continuous force of gravity or, as is the case with many mobile devices, dynamic to sense movement or vibrations. This sensor headset could be used to detect head movements and the information processed through the controllers which could be made available to the owners of the headset, participants and virtual players (e.g. games). Furthermore, this sensory data could also invoke responses from other accessories on the headset (e.g. lights, microphone, cameras, force, vibration). The following are examples.

In various embodiments, a headset may detect (e.g., using an accelerometer) whether or not a meeting participant is currently nodding in agreement or shaking their head from side to side to indicate disagreement. The physical movement could alert the meeting owner or participant of their vote without actually getting a verbal response or selecting a choice.

In various embodiments, a headset may detect head movements along a continuum so that the participant can indicate strong agreement, agreement, neutrality, disagreement, or strong disagreement based on the position of their head in an arc from left to right.

In various embodiments, a headset may detect whether a person is getting sleepy or bored by having their head leaned forward for a period of time.

If a head turns abruptly, this could indicate a distraction and mute the microphone automatically. When a dog enters or someone not a part of the meeting (a child), oftentimes people turn their head quickly to give them attention.

In various embodiments, a headset may detect whether someone has been sitting for long periods and the headset used to remind the wearer to take breaks and stand up.

In various embodiments, head movements coupled with other physical movements detected by the camera could be interpreted by the central controller. For example, if a participant's head turns down and their hands cup their face, this may be a sign of frustration. Fidgeting with a headset might be a sign of fatigue.

The central controller could interpret head movements and provide a visual overlay of these movements in video conferencing software. For instance, the central controller could interpret a head nod and overlay a "thumbs up" symbol. If the central controller detects an emotional reaction, it could overlay an emoji. These overlays could provide visual cues to meeting participants about the group's opinion at a given moment.

In various embodiments, movements of the head could be superimposed on an avatar in a game giving them movements similar to the player. Movements could also directly control a game characters movements, the use of objects in a game, or as a data input method.

In various embodiments, detachable accelerometers could be placed on other locations of the body to measure force during an activity. This could be applied to the leg to measure force during an exercise or used to mirror the movement of a person for superimposing on an avatar.

Thermometer

Various embodiments include a sensor to measure the wearer's temperature and the ambient temperature of the room. The headset could be equipped with sensors to collect temperature. The temperature could be collected through an in-ear thermometer or external to the body. As the temperature is collected, changes in body or ambient temperature could be sent to a central controller for user awareness and possible actions.

The central controller 110 could record the users temperature to determine if the user is healthy by comparing current temperature to a baseline measurement. If elevated, alerts could be sent to the user for possible infection. The central controller could determine if the individual is hot or cold and send a signal to environmental controls to change the temperature of the room. The central controller could use temperature to determine fatigue or hunger and send a signal to the wearer or the meeting owner to schedule breaks or order food. The central controller could use ambient temperature information to alert the user to dress warmer or remove clothing to cool.

The central controller could use body and ambient temperature data to mirror game play. If the player is cold, the avatar could dress in a coat. If the room temperature is hot, the avatar could sweat and dress in shorts. Likewise, the ambient temperature could determine the landscape of the environment the game is played. A warm room could have the avatar playing in the desert.

Visual Motion

Visual motion can be used to indicate position and physical movement that invokes functions on a headset or its other connected devices.

In various embodiments, the headset could have a camera that detects whether or not the user's mouth is moving and then check with virtual meeting technology to determine whether or not that user is currently muted. If they are currently muted, the headset could send a signal to unmute the user after a period of time (such as 10 seconds), or it could trigger the virtual meeting technology to output a warning that it appears the user is talking but that they are currently muted.

The headset could have a camera that detects if a person is quickly approaching and alerts the user to move out of the way.

The headset could have a camera that detects the movement of a person and displays the movements on the avatar in a game setting.

The headset could have a camera that detects physical movements that are interpreted by the central controller. If a person is frustrated, they may throw up their hands, cross their arms, clinch their fists or not smile. This information could be interpreted by the central controller to inform the user how their movements are being portrayed or to the meeting owner to modify their approach for the user.

The visual motions could be captured and used as virtual coaching in various activities. If two people have cameras and participate in a dance, the virtual coach could, through the central controller, could provide feedback to both participants on corrections to the dance movements.

Chemical Diffuser

Smells evoke strong memories, mask other scents and can be used as relaxation therapy. The headset could contain a chemical diffuser to produce a scent. This diffuser could counteract a smell in the room, use aromatherapy to calm an individual, evoke a particular memory or experience, or evoke a particular physical place or environment.

For example, during a meeting, participants become agitated about a change in scope. The central controller or meeting owner may recognize this and produce a scent of fresh baked cookies or lavender to calm the individuals or cause them to think about more pleasant things.

Travelling in a confined space could put the user in surroundings with unpleasant smells. The headset or owner could recognize this and diffuse a cleaner aroma, such as freshly washed linens.

Accessory to Headset Sensor

Other external accessories could be paired with the headset to work together to produce a response that could be used as behavior modification or collection of data for reporting and measuring to the user.

In various embodiments, the headset could be paired with a Wi-Fi® ring/smart watch which could set off an alarm in the headset (e.g. vibration, cooling/heating, sound) when the user's hand approached their face. This could allow presenters to avoid distracting an audience by touching their face, or it could be used to remind participants not to touch their face when flu season is in full swing.

Some users have habits of tapping their feet during meetings or while waiting causing distractions around them. A sensor in their shoe could produce an alert in the headset when the user's foot is tapping excessively.

The headset could be paired with an electronic pen that recognizes when someone is writing too much during a meeting and indicating a lack of attention or using the pen to tap the table as a nervous behavior. In both cases, the headset could produce an alarm/alert to notify the user to stop the behavior.

Galvanic Sensor

The headset could contain galvanic skin response sensors or sweat sensors. The central controller could record the galvanic skin response or the rate of sweat to determine whether the wearer is healthy by comparing the current measurement to a baseline measurement.

In various embodiments, an athlete uses the headset during a workout. During the workout, the galvanic sensor could collect data to determine that the athlete is not sweating to the same degree as previous exercises of similar intensity. The information is sent to the central controller and results provided to the athlete letting the user know they could drink more electrolytes or take a break.

In various embodiments, a headset may create awareness of nervousness. During a presentation the user of a headset may not recognize they are sweating prior to a presentation. The central controller could inform the user that this is taking place so they can engage in relaxation exercises to get control of their emotions.

A user plays a game using a headset and the intensity of the game increases causing the user to sweat. This reaction could be displayed on the avatar, causing the avatar to sweat. In addition, the other players of the game could be made aware so they know to keep up the pressure in an effort to win the game.

As women age, hot flashes occur regularly, but seldom are tracked for medical intervention. The headset and central controller could measure the random sweats for analysis. The quantity and intensity of the hot flashes could be made available to medical personnel for evaluation and treatment.

Electroencephalography (EEG) Sensor

An EEG measures brain wave activity of a person and is used as a first-line method of diagnosis for tumors, stroke and other focal brain disorders. Mental faculties also measured through EEG include cognitive skills such as language, perception, memory, attention, reasoning, and emotion. The headset device could measure brain wave activity using EEG sensors. This data could be sent to a central controller and used to measure brain health both immediately and overtime. It could also be used to measure activity during activities, both while awake and asleep. This information could be used by the user for awareness, to dynamically modify responses or provided to the intended physician. In the case of severe issues indicating abnormal brain activity, alerts could be sent to medical personnel or identified caregivers. For example:

Further details on how headsets can be used as an EEG can be found in U.S. Pat. No. 10,076,279, entitled "System and method for a compact EEG headset" to Nahum issued Sep. 18, 2018, at columns 11-14, which is hereby incorporated by reference.

In one example, a worker using the headset consistently attends strategy meetings in the early morning. While work may be done, the sensors detect areas of the brain that are not functioning as well when compared to other times of the day. While there is no health issue, the information collected by the central controller could inform the user that conducting these types of meetings later in the day may provide better results.

Oftentimes people must recall images, facts and experiences, but it is difficult. Using the headset, the user could be informed through the central controller that areas of the brain responsible for memory are not functioning to the level needed. The central controller could suggest exercises to improve memory for improved performance and recall.

Games provide an experience that could be dynamically adjusted based on EEG data. If a user is playing a game (or has played the same game multiple times), the headset and central controller could determine that the user is bored or the game is not giving the level of excitement as expected. The brain activity may be much less than expected. In this case, the game could dynamically change to add a more challenging task or introduce environmental stimulus in the game. Furthermore, the environment itself could change to dim or brighten room lights, introduce noise in the headset or provide force/vibrations to the user.

Many times people exhibit emotions that are not observed. The headset could measure if a person is happy, sad or even angry. In the case of a status update or performance review, if someone is having a tad' day, the employee's boss could have information and determine if rescheduling is more appropriate. The headset could inform the boss through audio alerts or information sent prior to the meeting.

During a town hall meeting an executive delivers information about a new program for employee development. While the creators of the program believe this is what the employees want and need, they do not know how well it will be perceived. The headsets on each employee could provide immediate information as to how well the new program is perceived by the employees. If the program is not perceived well, the EEG data collected and analyzed by the central controller could immediately be sent to the creators. The delivery of information could change or additional feedback gathered from employees to make the program more appealing.

Heart Rate Sensor

The heart rate sensor could measure heart activity and provide indications of overall heart health or level of excitement. With all health data, the heart rate information could be sent to the central controller 110 and to the user's insurance company, physician, games or others the person is engaged. The data could be collected for evaluation over time, immediate feedback/action or discarded. It provides more data points for both the user and physician to monitor the overall health of an individual or other parties and games. In the case of severe data, immediate response can be provided to the user to take action and contact a health professional. For more casual uses, the heart rate data may be used as a way to gauge excitement in an activity (game, performance, meeting) or engagement overall (conversation) with recommendations for relaxation or to influence player strategy. Furthermore, to create a more connected experience, the user participating in games or other activities could sense the heart rate of other people.

In various embodiments, a user may not realize the variation of their heart rate during times of sedentary activity. The heart rate could be collected by the headset and analyzed by the central controller 110. If the variation in heart rate is significant, the user and associated health provider could be informed for awareness and corrective action.

Workers may be put in stressful situations causing the heart rate to increase, but they are unaware. If the heart rate increases before or during a task, the headset could inform the user that this is taking place and provide calming background noises or recommendations for relaxation techniques.

Gamers could sense the heart rate of other players. If a person is playing a war game and their opponent is being attacked, their heart rate could be elevated indicating excitement or nervousness. The player, with a headset could receive the heart rate of the opponent through a pulse in their ear, a force in the headset or a blinking light. The game itself could also reflect the same heart rate on the avatar.

Irregular heart rates can lead to serious health issues. The continual heart rate of the user could be collected through the headset. If the rate changes are recognized by the central controller as being abnormal, the information is sent to medical personnel and the user for immediate action.

Metabolite Sensor

A metabolite sensor is defined as a biological molecule sensor that detects the changes/presence of a specific metabolite and transmits the information of metabolite abundance into biological networks. The headset could contain metabolite sensors. The central controller could record the metabolite generation to determine whether the wearer is healthy by comparing the current measurement to a baseline measurement. The metabolite sensor in the headset could measure the cell activity/composition and transmit the results to a central controller that determines the abundance of cells, nutritional status and energy status of the user. Levels determined by the controller could be used to alert the user or physician of necessary actions.

In one example, the user of the headset may feel a bit worn out. The headset could inform the user that their nutritional levels responsible for cellular/molecular health are at levels lower than expected. Recommendations of proper eating to improve the user's health could be sent.

Gamers spend many hours sitting and engaging with others in computer games. Over time, they may forget to eat which could impact their playing skills. The headset could evaluate the player's metabolism and provide information on eating to improve attention and skill.

Someone taking prescription or over the counter drugs may not realize they are impaired. The user wearing the headset could be alerted if the sensor detects they have been taking a drug for which they may be impaired. This alert could protect the user and others.

Oxygen Sensor

Sensor to measure oxygen levels. Oxygen level is a key indicator of overall health fitness. The headset could read and monitor oxygen levels. Depending on the level, the device may alert them via colors, sounds, vibration or on-screen display to take deeper breaths. If oxygen levels are detected at a significantly low level, others in the area with mouse-keyboard enabled devices could be alerted or 911 calls made. All data is sent to a central controller. For example:

People may feel fatigued or tired during normal day to day activities. This could be a result of low oxygen levels. The headset is continually monitoring oxygen levels. If these drop or show a progressive drop over a period of time, the headset could inform the user to take deep breaths to increase oxygen levels.

During exercise, people will sometimes forget to breathe and cause them to get light headed and faint or fall. The headset could monitor oxygen levels during this activity and prompt the user to breath if levels are decreased.

Photoplethysmography Sensor

Photoplethysmography (PPG) is a simple optical technique used to detect volumetric changes in blood in peripheral circulation. It is a low cost and non-invasive method that makes measurements at the surface of the skin. The sensor could be enabled through the headset touching the skin or remotely using the camera.

For example, the photoplethysmography sensor could be included in the headset to measure cardiac health. If the sensor, through the central controller, indicates low blood volumetric flow, the user could be notified that they may have a heart condition or other health related conditions that require medical attention.

Impairment

In various embodiments, a person may be considered impaired under one or more conditions. When considered impaired, a person may be denied access (e.g., to a location; e.g., to the use of equipment; e.g., to sensitive information) or privileges and/or any other abilities.

In various embodiments, a person is considered impaired if their blood alcohol level (BAC) is above a certain threshold (e.g., above 0.05%; e.g., above 0.08%); if blood oxygen levels are below a certain threshold (e.g., below 88%); if carbon dioxide levels are below a certain threshold, e.g., 23 mEq/L (milliequivalent units per liter of blood) or above a certain threshold, e.g., 29 mEq/L; if opioid levels above a certain level (e.g., blood serum oxycodone levels above 50 ng/ml); if delta9-THC-COOH (a metabolite of marijuana) levels in urine are above 50 ng/mL; and/or if any other applicable criteria are met.

Force Sensor

Headphones according to various embodiments, are equipped with sensors to adjust the force (e.g. squeezing) or vibration (e.g. buzzing, vibrating) or electrical sensation in the padding on a headphone/headband. There could be situations where a user wants a more passive approach to alerting someone or enhancing an experience (e.g. computer game) where a typical audio voice may be disruptive. The headset/presentation controller could be used to not only deliver the intended force to someone else, but also receive a force signal.

The presentation controller could be used for the meeting owner to contact the meeting participant. For example, a meeting owner may need to ask a question specific to another person without others hearing in the room. They could speak the user's name in the presentation controller and it could get the attention of the other person via the intended sensation (e.g. buzz, vibration, apply force as a squeeze) Also, they could use the same capability to request the meeting participant to engage in the discussion.

Game players could alert/contact other players to challenges in the game via sounds, vibrations and forces with headsets.

Game players could feel the vibration of a gun shoot, movement of another player, explosion by having the headset vibrate.

Game players could sense through vibration, pulsing or headset squeezing the breathing rate and heart rate of another player. This could intensify the excitement level and connectedness of the players. In addition, the force/pressure sensor could adjust as well to provide a sense of feeling the breathing rate.

Game players could feel the force/pressure of the headset when a gun is fired, explosion heard or intensity of a game increases.

In cases where a user is wanting to eliminate a bad behavior, the headset could vibrate, buzz or provide force when the headset recognizes they are engaging in the bad behavior. If the attached camera recognizes the person is reaching for a cigarette, the headset could buzz to remind them to not smoke. Likewise, If a meeting participant has consumed a considerable amount of time speaking in a meeting, or feedback was collected from other participants, the person could be alerted. The microphone could pick up on the voice of the intended speaker and immediately vibrate reminding them to not speak or carefully consider their contribution in the meeting.

The headset could act as a reminder to complete tasks or collect items. For example, if the central controller recognizes patterns of an individual it could store these and remind users if they miss collecting items or completing tasks. If the user leaves work each day and collects their ID badge, lunch, briefcase, laptop, cell phone, gym clothes and kids backpacks, the headset could recognize each day if any of these items are not collected and remind the user through alerts (e.g. audio, pictures, vibrations, forces or buzzes). The items not collected could be gathered and the central controller recognizes if the user has completed all tasks/gathered items before departing.

Environmental Light-Time of Day Sensor

Light is a guide for people to determine time of day and also enhance the mood of an individual. Natural light is used as sensory input and for a user and also provides a reference for people. The light and cues assists people in performing functions and engaging others. Without visual light cues, people could feel a sense of isolation or not give others an understanding of the time of day a person is engaging (e.g. day, night, dusk, dawn). Various embodiments, through the headset, could simulate light for the user and provide an indication to the user of someone else's time of day.

A gaming user may be playing a game in the middle of the day when it is sunny. Their opponent, on the other side of the world, may be playing the game at night, in the dark. The headset could automatically provide a light to the person playing in the day while the person at night receives no light. Each player could have the game environment change to match the lighting conditions of the real environment.

Various embodiments include sound cues to match time of day. Light provides users with indications of time of day, but there are other auditory cues that can indicate time of day or support the time of day. For example, if a user is on a conference call early in the morning, the user could have auditory cues provided through the headset such as chirping of birds, school buses moving, coffee brewing, showers starting to name a few. Later in the day, around noon, the user may hear a noon siren that is common in many cities, bells ringing from a church to indicate time, rustling of lunch plates, or the mailman delivering mail. In the evening, the user may have more silence and calming noises, lullabies, rush hour traffic, or sporting event noises. These sounds, in combination with the light to simulate the outdoors, could provide the user with a more realistic experience of what is taking place around them throughout the day.

In various embodiments, a light controller monitors the lighting conditions and provides increased light where needed, automatically. For example, a user is working at home during the day with sunlight in their office. As the evening approaches, the light headset could automatically detect the room is getting darker and provide the light gradually to assist in the tasks being performed.

In various embodiments, a virtual display changes color to simulate local time for remote participants. Global conference calls are common in different time zones. As part of each participant's background, the headset could communicate to the central controller to lighten backgrounds for people working during the day and provide darker backgrounds for those working at night. This dynamically changing background environment could provide everyone with a visual cue regarding the time of day each person is working and a deeper appreciation for their surroundings.

In various embodiments, a headset may determine individual time-of-day productivity and use light control to extend productive periods. As people work at different times of the day, the headset could gather biometric feedback to determine the time of day a person is most productive. This time of day could be simulated using light for an individual using the headset. For example, if the headset collected biometric data indicates the person is most productive from 1:00 pm-3:00 pm in the day, but is forced to work from 8:00 pm-10:00 pm, the headset could simulate light from 1:00 pm. The light at 1:00 pm, even though it is 8:00 pm, could stimulate or trick the brain into thinking it was earlier and improve user productivity. This light could be enabled through both the inward and outward facing lights.

A headset according to various embodiments may include a task light. Users performing certain tasks need more lighting. For example, reading, sewing, cooking, routine home maintenance or cleaning require task specific light. The headset could recognize the task being performed (through the central controller) and automatically switch light on the headset for the user. The person sewing may need very targeted lighting, while the person doing routine home maintenance may need broad lighting with a wide angle.

Air Quality Sensor

Air quality is key to the health and productivity of people, in a work and recreational environment. Continually monitoring and measuring air quality in the form of pollutants, particles and levels, and alerting users to the conditions through the headset could assist in allowing the user to make different choices and protect their overall health.

In one example, a user is walking a baby through a crowded street at rush hour, they typically walk in the mid-morning when traffic is light and pollution is minimal. At rush hour, the headset could inform the user that the air quality is poor and recognizes high levels of CO/$CO_2$ and other carbon emissions. The headset could also instruct the user on a different path allowing them to avoid the highly polluted area at that time.

In one example, a headset reports high levels of ozone. A user of the headset decides to go to the beach for a run. They have mild asthma and routinely run this path. On this day, the headset could inform the user that running should not take place as the levels of ozone could harm their lungs.

In one example, a headset reports carbon monoxide. The headset could detect high levels of carbon monoxide. Users of the headset could be alerted if carbon monoxide reaches dangerous levels in their home. The headset could provide audible alerts, messages in the earphones or light signals to warn the user to get out of the house.

Pliable Sensing Fabric

Headsets equipped with pliable sensing fabric could inform the device to turn on, off or adjust various controls. The pliable fabric contains small connected electronic signals that recognize when a device is moved or bent. As an example, when the headset is picked up and stretched apart to put on the ears, the sensor could detect this and automatically turn the device on and connect to the network. This saves time for the user. When the headset is removed, the reverse could occur and the device turned off.

Ambient Noise Sensors

Ambient noise level is the collection of all noise at one time. Given the sensors provide instructions and feedback in terms of audible announcements, it is important to measure the ambient noise levels, adjust the levels or provide instructions for the user. The headset microphone could have an ambient noise detector and continually provide this data to the central controller for analysis. In addition the overall collection of sounds being heard could be collected from the headset and processed by the central controller.

In various embodiments, a headset may adjust volume. There may be times when the headset and central controller need to inform the user of an impending danger. The ambient noise could be lowered so the announcement to the user is heard and the volume overall is acceptable to the user. There may be times when the user is listening to games, music and other sounds that are above dangerous hearing level. The headset could dynamically change sound levels to protect the hearing of the individual.

In various embodiments, a headset may filter sounds. The headset and central controller could detect ambient noise in the background and filter out the sounds before presenting the audio to other listeners. An example could be a dog barking or a baby crying while on a conference call.

In various embodiments, a headset may inform companies about situations regarding ambient noise. During periods of construction, a worker may be presented with sounds from many pieces of equipment (e.g. dump truck, loader, concrete mixing, welding) and activities. The headset could monitor the volume of all ambient sounds in the area for the user. If the sound level is too high for a period of time, the company could be informed by the central controller of the dangerous levels for the employee or reported to a governing agency. The user could also be informed by the headset to protect ears or leave the area.

Thermal Camera Enabled Sensor

The camera could include a thermal sensor to collect thermal readings from the user's surroundings and alert them accordingly.

In one example, a user with a headset enters their place of employment. As they greet various coworkers, the thermal sensor could measure the body temperature of those around them. If the sensor collects information and sends it to the central controller for analysis, it could indicate the body temperature is high. This may mean the person has a fever. The user is alerted through the headset (audio message/ sound or forced alert like a buzz) of the condition of the person around them. The user could inform a person without a headset that they may be ill or simply avoid the individual to protect their health.

A person playing a game with a headset could involve others in the room in the game. A user may wish to display a character and their motions in a game which they are not playing. The thermal enabled camera on the headset could discover people in the physical room and display their character on the screen using their thermal image. The motions and avatar could represent the images collected by the headset and processed through the central controller.

360 Degree Camera

A 360 degree camera included in the headset invention allows for complete viewing of all activities of the user. This could be useful for detecting objects, people and movement from all angles supporting many of the embodiments from safety, recreation and exercise and gaming to name a few. Companies manufacturing 360 degree cameras include Ricoh (THeta Z1 as an example) and Insta360 (One X as an example).

In one example, a person may be working with little distraction. Someone walking up behind the person may cause them significant fear. The headset with the 360 degree camera could alert the user that someone is approaching them from behind and alert them sooner.

A person running, walking, biking or any activity in a public area may want to be aware if someone is approaching them quickly from behind. Many accidents are caused due to people moving in front of an object/person that is approaching them from the rear (e.g. runner being hit by a bike or car, dog approaching pedestrians from the rear or someone walking to their car alone at night).

Light in Earphone

Lights in earphones could be used as indicators to others around a user or internal as a sensor to measure light absorption in the ear. Light absorption in the ear could be a way to determine wax buildup and inform the user of possible ear infections.

Ear wax is normal in most people, but the coloration of ear wax can indicate more serious issues. Dark brown/red wax could indicate an infection or bleeding, while clear or light yellow is acceptable. The color of wax absorbs light differently. Darker colors absorb more light while lighter colors reflect more light. The headset with a light in the earphone could produce a light to measure absorption and communicate the information to the central controller AI system. If the light is absorbed in the range for dark brown/colors, the user could be notified that they may have wax build up and to clean their ears or seek medical attention. The reading could indicate an infection or the onset of an infection.

The headphone colors could change to indicate to others if they are available or are participating in an activity that can be interrupted. For example, a user may be on a conference call and the central controller understands they are actively participating based on the amount of dialogue. The headphones could change to red indicating they can't be interrupted. If the meeting is on break, the headphones could change to yellow indicating to others that they are on a break and can talk briefly. If the user is listening to music, a podcast or an audiobook, the headphones could flash yellow indicating it is fine for someone to interrupt them. Finally, if the user is listening to white noise, the headset could be turned green allowing interruptions.

Form Factor

The physical device of the headset could accommodate/ connect the various features including sensors and other named features: Accelerometer, Thermometer, Visual/Camera, Chemical, Accessory to headset, Galvanic, Electroencephalography, Metabolite, Oxygen, Force Sensor, Force Feedback, Environmental Light Controller, Air Quality, Photoplethysmograpghy (PPG) Sensor, Pliable sensing fabric, Heating and cooling, Thermal camera, 360 degree camera, headphone with light, water resistance, knobs, slide controllers, power input, microphone(s), cameras (inward, outward and 360 degree), flexible arm(s), plug and play, speakers, lights (camera, illumination, ultraviolet), ear cushions, ear lobe clip, volume controls, detachables/add-ons (e.g. sensors, accessories), laser, video screen, mouth protection guard, air diffuser, headset holder/clip, elastic headband, plug and play with game controllers, connections for USB, audio and micro-USB, and internal and external power supply.

The flow of information for these scenarios is from the headset processor 405 to the user device 107a (if connected to a computer) or central controller AI systems for interpretation and analysis. The analysis of results and response could be returned from the central controller to the user device 107a (if connected) and the headset processor 405 for response to the user. The connection directly to the central controller from the headset processor 405 can occur if there is not a connection to the user device 107a and a cellular connection exists. Likewise, the headset processor 405 can be used to collect sensory data and stored until uploaded to the central controller once a connection is established.

The collection of sensors and other functioning devices could be integrated to form a lightweight wearing headset. This lightweight device could make it more appealing for users of the device.

In various embodiments, a headset may be a modular device. In various embodiments, a headset may have wireless connectivity, such as with Bluetooth® Connectivity. There may be times when a user needs to share functions of their headset with others. This could include the sharing of audio (speaker content) or video content from a camera. In addition, the user may want to have another person participate in a conversation with their microphone audio or provide sensor information. These devices could be add-ons and connected to another person's device via Bluetooth® with connection and facilitation of communication enabled through the Bluetooth® enabled add-on device, the headset processor 405 and central controller AI system.

Various embodiments include a share function (e.g., to deliver information). For example, the owner of the headset device is on a conference call. The owner wishes to share their audio of the meeting with another person nearby. The owner could give the other person an add-on that is connected to their phone via Bluetooth® and listen to the conference call.

Headset Arm

In various embodiments, a headset has a flip up/down small display on the voice arm. The display screen could be used to view short video clips, communication chats with individuals or as an extra way to observe what the camera is displaying.

In various embodiments, an audio arm could act as a joystick, laser pointer or electronic pen. This could be a detachable arm that could be used as a pointer/presentation controller to be used in meetings, an electronic pen to be used for taking notes on electronic material or as a joystick to be used in various games.

In various embodiments, flipping down the flexible arm without talking starts a count up clock and increases priority overlays during a call. The functions of the arm could be used for more than holding the microphone or other accessories. They could also be used to invoke a timer, when moved down, the timer starts, when it is moved up, the timer is stopped. This could be useful during meetings when control of the agenda timing is necessary. Move the arm to the left and this mutes the person talking, move to the right and it advances the slide on the presentation. Flipping down the arm could also initiate a countdown timer of five minutes when a break has been called for a meeting.

In various embodiments, the headset arm has a camera facing the user (it could focus on the user's face, eyes, lips, jaw, or other parts of the face as required by various embodiments, and could even be pointed up to a ceiling or down to a floor)

In various embodiments, the headset arm contains a camera that could be pointed to the user to assist the hearing impaired to read lips. Many people with hearing loss read lips. A camera placed close to the lips and displayed for those with hearing loss and the ability to read lips provides a more complete experience for the hearing impaired. The user's lips could have a substance applied—such as a lipstick of a color that helps the lips stand out from the background of the user's face) which makes it easier for the camera to accurately measure the lip movements.

In various embodiments, a user may speak silently (i.e., uses lip movement which gets processed which then generates output as audio). There could be situations where the user wants to move their lips forming words and statements but does not want others around them to hear. The camera on the arm could collect the lip movements, process them through the headset processor 405 to user device 107a and the central controller AI system. The AI engine could interpret the lip movements and translate them to the listener in audio format, keeping the comments private. The AI engine could also create a running text transcript while reading the users lips and scroll that text on a display screen of the user device 107a or on a display screen of the headset.

In various embodiments, a headset arm includes lights (forward and inward facing) are attached to the arm for use by the camera(s) or as illumination for the user during an activity.

Headband/Earphones

In various embodiments, the headband connects the two earphones across the top of the head. They are adjustable and provide various functions for the user.

In various embodiments, detachable headband/earphones becomes a speaker for others to hear.

When others without a headset want to listen to the audio, the earphone on the headband could be detached and used by the other person. This earphone could have a moveable loop that could hang directly on the ear of the person so their hands are free to perform other tasks.

In various embodiments, the color and/or shape of the headband/earphone display indicates an employee's function/role at a company. The role of the employee, favorite sports team, name of the project, or other items could be established and sent from the central controller 110 or user device 107a and displayed on the headband/earphone display. For example, if I am a graduate of Cornell, the school mascot could display on the headband. Also, if I am an IT architect in a company, this role could be displayed on the headband and earphones.

In various embodiments, headbands/earphones create visible status indicators for others on a call or meeting. For example, if the meeting owner has completed a presentation and requests decision makers to vote on an option, the user could vote using the on device controller or computer and the headband/earphone displays the color of the vote, green for approval and red for denial.

Various embodiments include lights on or over the headband/earphone. These lights could be used to illuminate a document for reading, for security/safety in a dimly lit area of a city or parking lot, etc. The lights could be on flexible stalks to allow for pointing them in any direction.

In various embodiments, a headband may be bendable. Because the headsets have to fit over heads, the material could be pliable enough to stretch.

In various embodiments, the headset could contain a heating and/or cooling device to signal useful information to the wearer by a change in temperature. The device could turn cold to indicate they are next in line to speak, whether a prediction or answer to a question is accurate ("hotter/colder" guessing and response), becoming warm if the user is close to completing a level in a virtual setting or signal time remaining or other countdown function using temperature control. These temperature indications could be less disruptive than a sound or hearing a voice to signal these changes and give a gradient of awareness as well.

In various embodiments, the headband could be constructed of an elastic material that could be worn anywhere on the head.

In various embodiments, a headset may include a face/mouth guard. A mouth protection guard may include a plexiglass or plastic mouth shield (which could be made transparent or opaque). The protection guard could be moved from the top or side of the headset or to shield people from exhaled breath and protect from potential airborne pathogens.

In various embodiments, a headset may include a face/mouth guard that functions to hide part of the face or mouth. People have a need to conduct conversations on conference calls and in open spaces in a private setting, but there is a risk that such conversations might be compromised if people could read lips. The mouth guard could be pulled down from above or from the side of the headset to visually distort the mouth/lips and prevent people from reading lips. The guard could also be created to isolate the user's voice to only project into their headset's microphone and not to those around the user, thus creating a more secure conversation.

In various embodiments, speakers are included in the earphones for amplification of sounds received to the headset. In addition, speakers could take the form of conduction devices that allow for sound to be heard through placing the device on the bone behind the ear. Speakers could also be disconnected from the headset and used for external listening or placed in another object (e.g. chair, pillow).

Various embodiments include a headset in a pillow. A pillow is used for many functions and throughout different parts of the day. The headset could be fitted in a pillow, allowing a user to watch TV or a movie, participate in a conference call, engage in a video game, listen to music or audiobook without disturbing anyone.

The headset pillow could include a microphone and allow for a user to also engage in conversations (e.g. conference calls, friendly social chats or gaming activities) while using.

In various embodiments, a microphone in a pillow could be used for detecting the characteristic sounds of sleep apnea, snoring, or teeth grinding. The microphone in the headset could be detached and placed in a pillow or placed on any surface near the user to record sounds of the individual during their sleep or waking activity. The central controller AI analysis could provide feedback on potential sleep and dental issues.

In various embodiments, a headset with detachables could be in a contoured pillow allowing for both listening, speaking, viewing, sensing and recording (microphone). The pillow could take the form of a neck pillow or sleep pillow containing the mentioned accessories that could be contoured to the individual's head as needed. As an example, this form could be useful during times of rest where the user wants to listen while resting and also allows continued monitoring of sensory data for feedback and analysis from the central controller AI system.

The headset in a pillow could project an image/video on the ceiling and allow the user to engage with the video (e.g. conference call or game) using the microphone, speaker and other sensors included in the device. The central controller could collect and deliver needed content.

Various embodiments include a headset in a desk chair. The sensors and devices included in a headset (with the exception of a holder) could be built in the chair including, the back, head rest, seat, and arms. The cameras, lights, microphone could be attached/detached from the chair but collect the same information as a worn headset. The chair could also be powered and supply the needed power to the functions of the headset. The communication of the collected information from the chair replaces the headset processor 405 and could be thought of as a 'chair controller'.

Various embodiments include a headset in hat form. Hats are popular forms of fashion and clothing. The headset functions could be available in a hat form.

Various embodiments include clip cameras or display screens for attachment to the bill of the cap. The detachable camera(s) could be placed on the bill of the hat or attached wherever the user could secure the device.

Various embodiments include electroencephalography (EEG) sensors in cap. The EEG sensors measure brain waves from various locations on the head. Placing these sensors in a hat more closely resembles those used in medical practice making the information collected more reliable.

The hat may include microphones in the seam of the hat running alongside the side of the hat. The hat may include all other sensors (as mentioned above) around the rim of the hat that could be detached.

Various embodiments include Transcranial Direct-Current Stimulation (tDCS) in a cap. Stimulating the brain has proven to increase various chemical responses and improvements in associated physical human performance. The small stimulation of the brain via the hat could be measured and associated to task completion for reporting.

Various embodiments include Transcranial magnetic stimulation (TMS) in a cap. Stimulating the brain has proven to increase various chemical responses and improvements in associated physical human performance. The small stimulation of the brain via the hat could be measured and associated to task completion for reporting.

Various embodiments include a built-in heat dissipating function. Use of sensors and other powered devices in the hat could cause heat buildup. The hats could be made of heat dissipating material which is a self-regulating fabric from infrared-sensitive yarn that reacts to temperature and humidity assisting to dissipate heat.

Microphone

Various embodiments contemplate alternate form factors for microphones. Form factors could include cavity microphones in teeth or detachable microphones to be used on other parts of the body to capture sounds (e.g. foot, nose, stomach, knees or hips). The microphones could also be flexible to assist in attaching to objects.

Detachable microphone (dual mic) or an earbud to share. The headset could be fitted with two microphones on each side of the face. As an example, if a person is on a call and wishes to have someone without a headset listen and contribute, the user could detach the earphone and microphone and provide it to the other person for temporary use. Another example is when someone makes a call and others want to participate. Today, a speakerphone is often used but reduces clarity. The use of a secondary microphone that could be shared improves the listening and speaking experience.

Various embodiments contemplate switching between two microphones. A user could switch between single and omnidirectional microphone functions to include, in the latter case, someone standing next to the user and speaking. At times, the microphone could only be enabled to pick up the voice of the headset owner/wearer (single person) and not others around you. This could take place in meetings, in public places or where background noise is being filtered. In other cases, the microphone could allow omnidirectional input for people wanting to contribute to a conversation. The omnidirectional mode could have a wider field of sound to pick up on the voices and sounds around the headset owner.

A microphone could be set to allow for multiple modes, i.e., functions or combinations of functions. A "talk only" mode is where the microphone is only detecting and sending verbal content to the headset processor 405, user device 107a and central controller AI for analysis. Background noise, non-verbal is excluded from the collected audio information to provide feedback to the user(s).

A "listen only" mode is where the microphone is listening for audio (non-verbal sounds, background noise) on behalf of the user and not during active engagement (e.g. a meeting, game) where continual feedback from the central controller AI system is taking place. This is a mode where the microphone is in stealth mode and will wake up and collect information that is not part of a normal activity. For example, a user may have the headset on and the microphone continues to measure the number of times you cough, produce a short burst of air in exasperation and later provide analysis to the user for awareness as a way to help the user lower their risk of transmitting a disease to someone else.

In a "bot mode", the user may have the headset and microphone respond to routine questions as a bot. For example, a customer service agent may initially discuss an account with a person. As they progress through the conversation, the bot may continue the interview process (e.g. routine collection of personal data) on behalf of the headset owner and later come back to finish the inquiry in person.

There may be times when the headset owner experiences a soundscape they wish to share with others. This could include a concert experience, nature noises (e.g. birds, waterfall, ocean waves) or a loud neighbor. The headset owner could collect these soundscapes through the microphone and make them available to any other person using a headset in real-time, recorded or as part of a gaming experience.

In various embodiments, a headset may include a clip. Headphones are routinely placed on a desk or table and take up valuable space. When not in use, headphones are routinely hung on various pieces of furniture, specialized holders, the side of a monitor, a laptop or thrown in a drawer. If placed on the corner of the monitor, it could obstruct the display itself. The headphones could be designed with a padded flip clip that could be used to easily engage and attach over the back of a monitor/laptop, on a desk/drawer handle or the edge of a table/desk serving to hold the headset and conserve space on the desk/table.

A headset may include a camera. A headset may include one or more of an inward facing camera, outward facing camera and 360 degree cameras. A camera may be situated on a boom/telescoping arm, on the cord with a microphone, or on top of the headband (360 degree camera). Having a camera on the headset could allow the user and central control AI system to collect and interpret facial visual information for feedback to the user and others. If the user looks confused, the facial expressions are interpreted by the central AI controller and the meeting owner alerted to help address the confusion. In addition, an outward facing camera allows the central controller AI system to collect information about the user's environment and provide feedback to the user, both immediately and after the fact. An example includes the person running could have the camera detect a biker quickly passing on the right side of them and alerting the runner so there is not a collision.

Camera functions may provide hybrid between phone call and video call with the ability to switch from one to the other. A camera may increase or decrease video quality, or otherwise manage video quality in response to the connection bandwidth (e.g., the camera may reduce video quality where there is a low bandwidth connection).

In various embodiments, the user has the ability to engage or disengage the camera for protection of privacy and/or other sensitive information In a multi-tasking embodiment, the camera could be engaged to monitor external environmental factors like exercising while the other functions are focused on other tasks, like meetings. The user could have the ability to define the preferences based on activity or priority of activities.

In various embodiments, a camera may participate in object detection, e.g., detection of cars, people, pets, trash, potholes, uneven sidewalks and alerting the user of the headset of potential issues and feedback for user action.

Further details on object detection and classification in images can be found in U.S. Pat. No. 9,858,496, entitled "Object detection and classification in images" to Sun et al., issued Jan. 2, 2018, e.g., at columns 12-16, which is hereby incorporated by reference.

In various embodiments, a camera could inform the 'tuning' of a microphone, such as by instructing the microphone as to which audio source to pick up. For example, if the camera has a particular person in its field of view, the user is presumably listening to that person, so the microphone may tune itself to the sound (e.g., to the direction) of that person.

A camera may maintain a steady focus on a subject (e.g., on another person's face) even if the users head changes direction (e.g., looks to the side).

In various embodiments, various form factors such as knobs, sliders, and buttons, could be used to control headset functions. The functions of the controls may be customizable for the user.

Controls may be on a wire (e.g., on a headset connector). Sliders on the wire may allow for volume, light control, camera placement, sensor control (on/off), etc. Beads on a slider may be used as a controller, such as for volume, light control, camera placement, sensor control (on/off)

In various embodiments, an LED colored wire has visual controls of volume. As fingers are moved over the wire and heat generated, the wire absorbs the heat and the colors change to reflect the volume change.

Controls on Headband

Various embodiments include controls on the headband of a headset and/or on any other part of a headset. Controls may be located on earbuds, earphones, and/or on any other wearable device, and/or on any other device. Controls may be used to control attachable/detachable sensors or other components (e.g., the headset may communicate control signals wirelessly to sensors, such as when the sensors are detached from the headset). In various embodiments, attachable/detachable sensors may include built-in on/off controls. Sensors (e.g., attachable/detachable sensors) may include: cameras, lights, mouth guards, microphones, microphones with arms, etc. Other components may include displays, speakers, etc. In various embodiments, controls may include knobs (e.g., to control microphone volume, speaker volume, light intensity, power to a sensor or device, etc.). In various embodiments, controls may include a connection and power indicator. In various embodiments, controls may include a screen display.

Headsets could have various functions, from meeting/corporate use, exercise enthusiasts, gamers or bloggers/streamers, or casual internet surfers. The form factor of the headset could allow for add-ons to support the needs of the user. A base version of the headset could be developed to support minimal function and collection of data. Add-ons that the headset could support include: forward facing camera; inward facing camera; any and all sensors described herein; a secondary microphone; lights, etc.

In various embodiments, a headset may include a screen display for viewing by a user. Such a screen could allow a user to view teleprompter text which includes the agenda of a meeting or a small copy of each PowerPoint slide from the user's presentation.

Add-ons on a headset may include collectables for games played, gamer status, accomplishments (e.g. agile certification, college degree) or other status symbols could be collected and attached to the headband, earphones In various embodiments, a MOLLE (Modular Lightweight Load-carry Equipment) device could be attached to the earphones or the headband to carry all of the add-ons and collectables. These could be used by the headset owner when switching between tasks. Adding those devices to the headset while exercising, but removing them when simply browsing the internet and later others attached for a remote video conference call.

Various embodiments include a frame-based headset (e.g., a glasses headset). Sensors, cameras and microphones could be fitted in or on the frame of glasses. The glasses could support a limited number of sensors and functions to provide a more specialized use. For example, the exercise glasses could include a galvanic sensor, heart rate monitor, accelerometer, camera, speaker, microphone and lights. They could be rechargeable with additional ports that allow for connecting of other devices and add-ons. The glasses could be provided with prescription lenses or without and allow for external charging and uploading of data (Wi-Fi® connected).

Multiple Audio Channels and Subchannels

As communications become more integrated into the way we do work and communicate with friends, there is a need for technologies that can allow for more fluid consumption of multiple audio channels.

In various embodiments, the user's headset is configured to allow access to multiple audio channels at the same time. For example, the processor of the headset processor 405 could direct two incoming channels of sound to the user's ears. The speaker associated with one ear gets a first audio feed while the speaker of the other ear gets a second audio feed. The user could listen to both at the same time, moving her attention from one to the other as needed. For example, the first audio feed might be the sound of an audio conference call, while the second audio feed was light background music. The second audio feed could be ambient office sounds, the audio feed from a different call that is of interest to the user, the sound of the user's own voice, etc. The second audio feed could be continuous, as in a music feed, or it could be intermittent, such as periodic traffic or weather updates. This would allow a user to participate in a call while getting access to information relevant to whether or not the user needs to begin her commute home early due to bad weather or traffic, for example. The processor of the headset could access GPS data while the user was on the call, and automatically end the weather or traffic audio feed (but keep the meeting audio) if the user appears to be heading to the location of her car in the company parking lot for an early return home.

The user could also juggle multiple audio streams at the same time. For example, the user could press a button on the headset to instruct the headset processor to swap one audio feed with a second audio feed, or replace two current audio feeds with two different audio feeds. The user could similarly press a button, or provide a voice command, to switch the right ear audio feed with the left ear audio feed. When two audio feeds are directed to two ears, the user could adjust the relative volumes of those audio feeds, such as by saying the voice command "louder in left ear" or by simply saying "new balance" and tipping her head left or right, generating a signal from an accelerometer of the headset that would go to the headset processor to initiate more volume in the left ear if the user tilts her head to the left.

In embodiments where the user is receiving a single audio feed to both ears, the user could elect to sample a number of other audio feeds by saying "next audio feed." For example, the user might be listening to classical music and then say "next audio feed" and get a jazz music audio feed instead. Alternatively, the user could select a desired audio feed, such as by the user saying "play 80s music" into the microphone of the headset, with the headset processor using voice to text software to generate a command that could be sent to the central controller where a search could be conducted for audio feeds matching the phrase "80s music." If a match is found, the central controller initiates access to that audio feed to the user's headset processor 405.

Meeting participants sometimes want to have small side conversations with others in different locations of the meeting room (or with those virtually dialed in) without disturbing others or interrupting the meeting. In this embodiment, the headset could allow the user to invite a subset of participants to join a concurrent meeting sub-channel. As other participants are invited and accept the invitation, their headphones (or gallery view boxes) could light up in a different color. The users of the sub-channel can now speak in low tones with each other to exchange information without disrupting others. When communication via the sub-channel is finished, or if a participant wishes to leave the group, a button could be pressed on the headset to instruct the processor of that headset to terminate that user's access to the sub-channel. Alternatively, sub-channel communications could be made permanent. Sub-channels could also be established by default, such as by two employees who designate that they always want to be connected in a sub-channel in any meetings that they are both attending.

In various embodiments, the user is on mute for a video call, but not on mute for two other participants. For example, the user can press a "mute" button or press a "mute except for Gary and Jennifer" button. Or the user could mute themselves to everyone except for all of the Architects on the call.

Setting up sub-channels under a main call could be especially useful in cases where a large number of people are on a call on an emergency basis to determine the cause of a system outage or software failure. In cases like these, it could be helpful to create one or more sub-channels for groups with a particular area of expertise to have side conversations. For example, on a main call of 75 people, a group of 12 network engineers might establish a sub-channel for communication amongst themselves and have their left ear follow the main call while their right ear follows the sub-channel for discussions of the network engineers. There could be many sub-channel groups created, and some people might be members of many sub-channel groups at the same time. In this example, the owner of the call could have the ability to bring a sub-channel conversation back up into the main call, and then later push that conversation back down to the sub-channel from which it came.

In various embodiments, large calls could also allow the call owner to mute groups of participants by function or role. For example, all software developers could be muted, or everyone except for decision makers could be muted. Participants could also elect to mute one or more groups of participants by function or role. In the case of education, a teacher could be allowed to mute groups of kids by age level or grade level.

Coaching could be done through the use of sub-channels, with one user in a large video meeting having a sub-channel open with a coach so they can talk about the call and about the performance of the first user in the call.

Sub-channels could also be used to share content to a subset of the participants on a video call. For example, a financial presentation could be shared with the entire group, but a particular slide with more sensitive financial information could be shared only with a sub-channel consisting of Directors and VPs.

In various embodiments, users could switch between different types of audio feeds. For example, dispatchers could switch between radio and phone feeds. The headset processor 405 would include software capable of processing each type of audio input and switch to the appropriate software as the user selected a particular audio feed.

In various embodiments, an audio feed could be selected based on the location of the user. For example, a user with a GPS headset might go on a walking tour of a large city, subscribing to tour information that is delivered when the user gets to a particular location. The user's headset could store in a data storage device 50 modules of short audio segments by a tour guide. Each of the 50 modules would have corresponding GPS data of the location of each of those segments, and when the users headset GPS readings indicated that the user was in one of these 50 locations, the headset processor would retrieve the corresponding audio segment and play it back to the user via a speaker of the headset.

Headsets could also be used for direct headset to headset communication, functioning like a walkie-talkie half duplex communication system. This could be a good communication option for individuals in a family house who want easy communications with others in the house without interrupting their current gameplay or music listening.

In various embodiments, one or more audio feeds may be transcribed (e.g., in real time) and presented to a user. In this way, for example, a user may follow the transcript of one audio feed while listening to the other.

Inward Facing Camera

Headset functionality can be greatly enhanced with the use of an inward facing camera that is able to capture video of a user's face, hands, arms, fingers, shoulders, clothing, and details of the room behind him. This visual data feed can be used by the headset processor 405 in many ways to make communication via the headset more efficient, more fun, and more secure. In some embodiments inward facing video feeds can also be used to improve a users health, such as by monitoring blood flow levels in the face or detecting that a user seems to be sleep deprived.

Forward Facing Camera

A forward facing camera can also enhance the effectiveness of a user headset, such as by allowing others to be able to "see through the eyes" of the user as they attempt a complex repair of an engine. The forward facing camera can also enable lots of functionality which requires seeing the user type, such as allowing for smarter typographical error correction.

Eye Gaze and Head Orientation Tracker

Conventional eye gaze systems often rely on cameras facing the individual. Eye gaze tracking systems thus are either limited to fixed settings such as in-front of a television or particular setting arrangements, or require large numbers of cameras to track gaze as individuals move within environments. The device according to various embodiments could facilitate eye gaze or head orientation tracking in mobile settings or without the use of large numbers of games. Eye gaze or head orientation tracking enables improved functionality for device wearers such as more precise advertising, user experience functionality, workplace monitoring, or insurance pricing.

A headset could be used as an eye gaze or head orientation tracker. The headset could contain a camera oriented toward the device owners face, located either in the microphone arm or in another location. The camera could be used to detect patterns of gaze, eye fixation, pupil dilation, blink rate, and other information about the device owners visual patterns. The headset could be used as a head orientation tracker. Accelerometers located in the headband, ear cups, or other locations in the device could be used to detect head orientation in X, Y, Z coordinates, as well as tilt, pitch, velocity and acceleration of the head. The orientation of the head could be used alone, in combination with eye tracking, or combined with a forward facing camera, to detect what the device wearer is looking at.

Data on head orientation or eye tracking could be combined with other eye data such as patterns of fixation, blink rate. Data on head orientation or eye tracking could be combined with other device inputs such as audio or biometric data. Eye gaze, head orientation, and correlated audio, biometric and behavioral data could be stored by the central controller. Access to the data could be made available to the device owner or to third parties through an API.

Signing into the device, authenticating the device owner's identity, or other biometric patterns could allow the central controller to solve the disambiguation problem of multiple users on televisions, computers and other devices. Shared devices present a difficult tracking and user identity problem for security, advertising and other uses that rely on knowing the identity of who is using the device. Individuals are commonly served ads that are targeted to them based upon other users of the device. For example if a woman's voice is recognized, the marketer could not send advertisements to them regarding male hair baldness products. Additionally, knowing the identity of the headset could allow the central controller to track an individual's eye gaze and other data across multiple devices such as computers, phones, and televisions. Knowing the identity of the device owner could allow tracking of individual data across physical and digital environments. For example, the central controller could track eye gaze in a physical store as well as in an online store.

Mobile eye gaze or head orientation tracking could be used to improve the measurement and effectiveness of advertising. Devices could facilitate the measurement of the number of individuals viewing advertising such as billboards, signs, flyers, and other forms of physical advertising. Devices could be used to measure the number of individuals viewing digital advertising on television shows, movies, digital videos, games, internet pages, within apps and software on mobile or computing devices and other forms of digital advertising. devices could be used to measure the number of people viewing product placement and other promotional materials either in physical or digital settings. In addition to measuring the number of people viewing ads, devices could be used to measure individual engagement with particular ads—through eye fixation, blink rates, and other visual data. Other data, such as audio or biometric data, could also be used to measure individual engagement with particular ads. Combining eye gaze, head tracking, and other forms of data from the headset could allow advertising to measure how an individual's affective state responds to particular forms of advertising.

Devices according to various embodiments could allow an AI module to be trained that predicts key demographic, lifestyle and potential spending data for marketing purposes such as age, gender, education level, occupation type, income bracket, housing and household attributes, spending patterns, patterns of life, daily locational movements, beliefs, ideologies, daily activities, interests, and media consumption of the device wearer.

Headsets could allow ads to be customized to the device wearer—either physical or digital advertising—using demographic, lifestyle, and potential spending level. By combining location data and other data on the wearer with eye gaze or engagement data, the central controller could allow micro-targeting of advertising to very specific segments.

Inputs of vocal statements, emotions and gender could be interpreted by the central controller AI system and used to deliver content or not deliver content. The central controller 110 could detect whether an individual is tired, fatigued, or has a particular affective state. The central controller could detect whether certain kinds of emotional valence in ads is effective and determine under what conditions a particular kind of ad is likely to be effective. For example, it could determine that a negative valence ad is unlikely to be effective based upon certain times of day, fatigue levels, or health conditions.

The central controller 110 could detect the type of activity an individual is engaging in and allow advertising to be customized by activity. For example, the central controller could allow advertisers to place contextual advertising when an individual is engaged in an activity. For example, if it detected that an individual was jogging, it could allow advertising to place contextual ads for running clothes. For example, if the individual sneezed, it could place an antihistamine ad.

The central controller 110 could detect if an individual was shown an ad and then engaged in intent-to-purchase behavior, such as looking up a particular product after being shown an ad, browsing the company's website, or looking at similar products within a category.

The central controller 110 could detect if the user has purchased an item recently and thus should not be shown ads within that category.

The central controller 110 could detect if an individual is engaged in intent-to-purchase behavior and then display appropriate ads. For example, it could detect whether an individual has asked a friend about something she is wearing and then display an ad for that product or product category.

A headset could allow physical advertising to change dynamically based upon the kinds of users within vicinity of the ad or who is looking at the ad. The central controller could communicate with the billboard or other form of advertising to display different types of ads, target the ad toward high value individuals, or use different techniques or valances based upon who is in the vicinity. The central controller could play audio ads to accompany visual advertising when individuals come within physical proximity to the ad, sight line of an ad or look at the ad. Individuals could interact with the ad through vocal commands. For example, individuals could tell the central controller that they are not interested in particular kinds of ads or they could ask for more information or "remind me later".

If the central controller 110 detects that a device wearer makes positive or negative comments about a product, it could use that information to adjust ad delivery. For example, if a wearer makes negative comments about a product, the central controller could serve an ad for a competing or substitute product.

The pricing of billboards and other physical ads could change based upon data captured by the central controller 110, such as the number of impressions as measured by eye gaze, the value of particular demographics looking at the ad, or whether individuals who viewed the ad then display intent-to-buy or actually purchase the product.

The pricing of digital ads could change based upon data captured by the central controller such as the number of impressions as measured by eye gaze, the value of particular demographics looking at the ad, or whether individuals who viewed the ad then display intent-to-buy or actually purchase the product. headsets could be used to authenticate ad impressions to defeat ad viewing bots, ad click bots and other forms of advertising fraud.

Many websites, apps, and other software prohibit online reviews, posts, or comments which are posted by bots or other automated means. The devices according to various embodiments could be used to authenticate that online reviews, posts, or comments were made by an actual individual.

Headsets could allow tracking of eye gaze, engagement, and other forms of nonverbal behavioral information as individuals browse stores, look at shelves and displays, or interact with sales people. Eye gaze, engagement and other forms of nonverbal behavioral information could be used to optimize store layouts, shelving and display layouts. The central controller could inform sales people of which shoppers to concentrate their attention on (based on intent-to-purchase, eye gaze, or other markers) and which marketing approaches would be likely to result in a purchase or positive interaction.

Headsets could allow adaptive pricing based, for example, upon intent to purchase, eye gaze, or other data recorded by the central controller. For example, if an individual fixates on a particular item but looks as if they are walking away, the central controller could communicate with the store's software or with a smart pricing display to alter the price.

Headsets could allow dynamic software, app, and website designs. For example some individuals could be more engaged with ads or buy buttons displayed in certain areas of the screen. The central controller could communicate with the site owner to display ads, buy buttons, or other aspects of website arrangement to increase engagement, buy conversion, or other metrics. For example, apps or software to rearrange windows, menus, and other aspects of user experience to improve functionality for individuals based upon their eye gaze and engagement levels.

Headsets could improve cashier-less checkout processes in physical stores by tracking device owners' eye gaze and tracking which products they take off of shelves without installing extensive camera systems in store.

Headsets could be used for monitoring, auditing, and regulating workplaces and monitoring worker safety. Eye tracking functionality, combined with authentication and data recording, could create auditable data on the wearers eye gaze and attention. For example, a headset could be used to detect workplace safety issues such as inattention drivers or machine operators. The central controller could prompt the user of their inattentiveness, alert a supervisor, regulator or law enforcement, or could disable the ability of the wearer to operate a vehicle or a machine. If a workplace accident occurred, the headset wearer's data could be reviewable to determine whether the wearer engaged in appropriate behavior.

Headsets could be used for monitoring whether employee functionality is impaired. Alcohol, THC, opioids and other psychoactive substances can cause changes to individuals' visual movement, such as speed of eye tracking, blink rate, and pupil dilation. An AI module could be trained to detect whether dimensions of an individual's visual activity correspond to an impaired individual. The central controller 110 could prompt the device wearer, inform the wearers manager, or disable functionality of vehicles, equipment or other work equipment.

In some embodiments, eye gaze tracking, combined with other device functionality, could be used to better price insurance risks—whether the device wearer engages or does not engage in certain kinds of risk. Device wearers could receive improved insurance pricing as increased information allows insurers to remove sources of uncertainty regarding individual behavior from their pricing models.

Micro-Expressions and Nonverbal Signals

Individuals frequently engage in micro-expressions and other nonverbal signals of emotion. These signals however are often difficult to detect. Devices according to various embodiments could enable the detection of micro-expressions, nonverbal signals of emotion and other "tells."

Micro-expressions are nearly imperceptible facial movements that result from simultaneous voluntary and involuntary emotional responses. Micro expressions occur when amygdala responds to stimuli in a genuine manner, while other areas of the brain attempt to conceal the specific emotional response. Micro-expressions are often not discernible under ordinary circumstances because they may last a fraction of a second and may be masked by other facial expressions. In addition to microexpressions, individuals may provide other visual cues as to their emotional state such as eye contact, gaze, frequency of eye movement, patterns of fixation, pupil dilation and blink rate. Likewise, audio elements such as voice quality, rate, pitch, loudness, as well as rhythm, intonation and syllable stress could provide cues about a speaker's emotional state. Additionally, individuals may have "micro-head movements" or changes in their head orientation, body positioning, or pose that may correspond with particular cognitive or affective states, such as head tilting.

A major challenge for measuring microexpressions is the use of a single channel of information—facial expressions—without other context information such as nonverbal communication data such as tone, rate, pitch, loudness and speaking style. By combining cameras, accelerometer data, and nonverbal elements of audio data, an AI module could be trained to detect micro-expressions and other "tells". The devices according to various embodiments could enable the detection of micro-expressions through several sensors, such as cameras, microphones, accelerometers, and strain gauges. The device could be enabled to detect microexpressions of the device owner through a camera located in the microphone arm. Expressions could be associated with particular head or facial movements which could be detected by accelerometers or strain gauges located in the headset's headband or ear cups. Micro expressions could also be detected using lidar, light pulses, or lasers. These types of expression data could be supplemented with camera data of eye movements and audio data. An AI module could be trained with these types of data to detect microexpressions and the affective state of the device owner. Insights from this AI module could be shared with the device owner—whether the device owner has a "tell" or exhibits certain forms of micro-expressions. For example, while negotiating, the device owner may subtly reveal information via an emotional response during negotiations. The AI module might prompt the device owner to modulate their "tell". Insights into the device owner's emotional state could also be stored by the central controller and be made available via an API.

Devices according to various embodiments may detect the microexpressions and "tells" of individuals with whom the device owner is interacting. Forward facing cameras could be used to detect facial expressions. Expression data could be combined with imagery of eye movements and audio data. An AI module could be trained utilizing these kinds of data to detect micro-expressions, nonverbal cues, and other "tells". The central controller could communicate to the device owner its prediction of the affective state of individuals with whom the device owner is interacting. Insights from the AI module could also be stored for later review by the device owner or be made available via an API.

In some embodiments, the micro-expressions of the device owner or others with whom the device owner is interacting could be used to gain insight into creativity or learning by detecting "glimmers" of surprise or moments of intuition, discovery or mastery. The central controller could record audio and video before and after that insight, as well as flagging those clips for review by the device owner. Micro-expressions could be used as a non-test method of measuring learning outcomes. Micro-expressions could be used to facilitate cross-cultural interactions by helping device owners interpret non-verbal communication and reduce misunderstandings.

Adaptive Technologies

Each person has unique physical characteristics that can be considered. These are in the form of vision, hearing, and other sensory items that could be learned and known by the headset device to improve the experience of the user.

Various embodiments contemplate lip reading on video chat. Many people lose their hearing over time to varying degrees. For those people with a reduction in hearing, the central controller AI system could remember this and adapt the headset experience. The camera/video recording the speaker could automatically adjust for the individual user with hearing loss so that the lips are presented in a magnified manner. In this case, since the lips are larger, the person with hearing loss and ability to read lips could more easily understand what is being said and contribute to the conversation. This is an example of ADA (Americans Disability Act) function.

For those with hearing loss, the central control system could automatically transcribe the conversation in real time, allowing it to be presented on the screen for reading or later published for review.

Various embodiments include light illumination for those with poor vision. Those with poor vision could be known by the central controller AI system. The lights on the headset could illuminate the workspace to improve the vision capabilities of the user.

Various embodiments include sensory feedback adaptation. The sensory information for each individual is unique. The central controller AI system could learn the individual's sensory levels and adjust the responses accordingly or suppress feedback. For example, if the heart rate of a typical person of similar size/age/gender is 65 beats per minute, but the headset owner has a rate of 45 beats per minute, the central control AI system could not continue to warn the individual. Likewise, if a person that exercises has an unusually high galvanic skin response, this may not indicate any hydration concerns, but the responses adapted to the individual.

Various embodiments include an adaptive cloth covering. The adaptive cloth covering could compensate for heat generated by the headset and/or by the user. The headset could be created or wrapped in adaptive cloth over the headphone, headband or other devices touching the skin. The adaptive cloth could adjust to allow heat dissipation and for the skin to cool.

Health Awareness

Comprehensive health data is increasingly important to healthcare professionals and active health management by the individual. The headset device according to various embodiments is equipped with sensors to collect heart rate, head movement, temperature, hydration, brainwave activity, metabolite, blood flow and air quality levels. With more telemedicine taking place among physicians, the more data points collected and analyzed by the central controller AI system to assist in evaluating the health of the patient is needed. All data could be used to make the appropriate diagnosis. The collection and process flow of data occurs from the headset processor 405 to the user device 107a (if connected) to the central controller AI system. Once evaluated, the feedback from the central controller AI system could be sent to subscribers of the information (healthcare provider or insurance company) and the headset owner.

Hearing Evaluation and Control

Hearing loss is sometimes a progressive condition that is not recognized by the user. This could occur due to various factors. The headset and central controller could monitor various conditions and behaviors to alert the user of potential hearing loss with corrective actions.

Various embodiments include volume controls, which may include system and/or user generated volume controls.

The user may increase the volume of the headset over time. This could be an early indication of hearing loss and the central controller could alert the user to seek medical attention. The central controller could also suggest lowering the volume to acceptable levels or taking the headset off to protect the users hearing.

If the user has known hearing loss and the volume needs to be at a certain level, the central controller or headset processor 405 could establish this volume level in advance of the activity, based on the preference of the user (higher level for meetings or less for games).

Various embodiments permit the fixing or locking of volume levels. The user preference or via a parental control could set a volume level on the headset that is not allowed to be adjusted without permission. This fixed volume level using the headset could protect the hearing of the user.

Various embodiments include ambient noise control. In various embodiments, ambient noise can be removed. Those with hearing loss can be distracted by ambient noises. The central controller 110 and headset processor 405 equipped with an ambient noise sensor could remove ambient noises if the person is known to have hearing loss. This could improve the overall hearing experience.

In various embodiments, volume may be adjusted based on ambient noise. Users may turn up the volume when ambient noises are loud or in the background. When the person leaves the area, the user does not adjust the headphone volume and it remains high. The headset processor 405 could detect from the ambient noise sensor that the noise has been reduced. If this is the case, the user could be alerted via the headset to reduce the volume or this could be done automatically, thus protecting the hearing of the user In various embodiments, headphones may function as hearing aids and assistants. In various embodiments, a headset may perform a digital transformation to move audio into range that people can hear. There are certain auditory ranges that individuals have difficulty hearing. The central controller AI system, in conjunction with the headset, could understand this and modify the audio to a range that is more easily heard by the user. For example, as you age, it is more difficult to hear higher frequency ranges, the headset could amplify these making it easier for those with hearing disabilities.

In various embodiments, a headset may provide in-bone conduction hearing functionality. The use of the headset could allow the user to replace the speakers with in-bone conduction devices. This modified use allows those with hearing loss the ability to use the functions of the headset.

In various embodiments, a headset may detect whether people are struggling with listening. A headset may include cameras and accelerometers. There are subtle indications that people are struggling to hear. These may include someone making facial expressions (micro-expressions as well) of intensity while trying to listen, leaning forward in the direction of sound or someone speaking, having no response when spoken to, tilting the head or asking some to 'repeat the question', saying 'what', or pausing for lengthy periods of time as a few examples. These visual and auditory clues are collected from the microphone and camera and sent to the headset processor 405 and central controller AI system. The analysis of this information can be provided to the headset user with suggestions on volume control or to seek medical attention.

In various embodiments, a headset may create 'white' noise to create the cocktail effect. People can focus on a single conversation in a crowded, noisy environment. This is the 'cocktail effect'. However, for some people, this is difficult. The headset could allow the user to initiate a 'cocktail effect' by introducing white noise in the headset by selecting on a knob or control and selecting the single voice they are wanting to listen to. This could improve the hearing capabilities of the user.

Sensor Based Hearing Evaluation

EEG Brain waves can indicate hearing loss. In various embodiments, a headset is equipped with an EEG sensor to measure brain waves. As people age, the alpha brain waves are modified. The central controller AI system could evaluate the brain waves of individuals and compare to the hearing performance of others. If there is a change in brain wave activity affecting hearing, the central controller 110 could alert the user via the headset to adjust volume or seek medical attention.

EEG brain waves may indicate signal perception (where a sound is originating). At each ear, a slightly different signal (sound) will be perceived and by analyzing these differences, the brain can determine where the sound originated. The two most important localization cues are the Interaural Time Difference, or ITD, and the Interaural Intensity Difference or HD. The headset equipped with an EEG sensor can measure the brain waves during a sound test. For example, the headset processor 405 could initiate a hearing test to measure signal perception. The sound could be generated and brain waves measured. The ITD and HD results could be evaluated by the central controller AI system and provide the user with an indication of hearing loss or recommendations. Furthermore, if the user has a deficiency in one of the ears, the headset processor 405 could adjust the output of the sound to adjust for this impairment.

In various embodiments, a camera can measure head acoustics. The shape of the head can affect the hearing of an individual due to head shadows and obstruction of sound to the ear. The headset equipped with a camera could measure facial features and the central controller AI system compares it to others with similar features and hearing loss. The central controller could provide recommendations to turn up the volume in one of the earphones or seek medical attention.

Various embodiments assist with sensing and hearing sounds above and below a user. Individuals have difficulty recognizing sounds coming from above and below you (Z Direction). The headset could adjust sounds to provide the user with a clearer sense of where the sounds are coming from. For example, if the user is playing a video game and an airplane is flying above to drop a bomb, the audio in the headset could adjust the sound of the airplane to give a more realistic experience that the plane was flying above the user.

In various embodiments, an earbud may serve as an in-ear thermometer. An in-ear temperature sensor can be an accurate way of collecting body temperature. The in-ear thermometer could actively monitor the body temperature throughout the day. If the body temperature appears to change, the central controller could inform the user to take necessary steps.

Various embodiments may facilitate home hearing tests. Hearing tests are indications of hearing impairment. The user of the headset could initiate a hearing test by selecting a function on the headphone or with the application. The headphone could generate sounds of different frequencies and request the user to acknowledge those sounds by touching the headphone screen sensor or pressing an enabled button. The collected information is sent to the central controller AI system for analysis. The results of the test could be provided to the user and medical professional for review. Signs of hearing loss could generate preventative action by the user.

In various embodiments, earbuds convert to earplugs. Oftentimes hearing could be protected or external, ambient noises blocked with the use of earplugs. Using the sensory data in the headset, the earbuds/earphones could automatically change form to act like an earplug.

In one example, a person is using the earbuds in bed to listen to music and falls asleep. The music turns off and the earbuds remain in the users ears. Later in the night, the headset with a microphone picks up on the sound of a snore. The earbuds could automatically convert to earplugs to not disturb the user from sleeping.

In one example, during construction work sounds of heavy construction vehicles or construction noise (e.g. placing steel beams in the ground). These noises can damage the ear and hearing. The headset could listen for sudden changes in ambient noise and send the single to the central controller for analysis. If the noise is in a range to damage hearing, the earbud/headphone could automatically change to an earplug, protecting the construction workers hearing.

Health Evaluations

Health evaluations can be provided using the headset sensors to collect information, which may then be analyzed by the central controller AI system. These evaluations and recommendations can provide users with immediate information to change behaviors and avoid long term health issues.

A microphone can be used as an active or passive listener to alert users of potential health issues. In various embodiments, the microphone can detect when a person is grinding their teeth. This sound could be communicated to the central controller AI system via the headset processor 405 to determine if teeth grinding is occurring. If this is the case, the headset could deliver calming music, a vibration to stop the user or recommendations to prevent teeth grinding.

In various embodiments, a microphone can detect sleep apnea or other sleep noises. Sleep apnea and snoring are key health concerns. The microphone on the headset could collect and deliver these sounds to the central controller AI system via the headset processor 405 to determine if sleep apnea or snoring is occurring. If this is the case, the headset could deliver calming music or a vibration to stop snoring or a more forceful vibration or sound (e.g. alarm) to awaken the user in the case of sleep apnea. The collection and analysis of the sounds could provide the user and medical representative with the information to further diagnose the condition.

In various embodiments, a camera and accelerometer may be used in combination to detect health issues. One such issue is Temporomandibular (TMJ)/Jaw tension, i.e., pain in the TMJ joint associated with stress and other health conditions. The headset with a camera and accelerometer can monitor and measure the clenching of teeth, tension in the face and jaw, movement of the mouth from side to side and other micro facial expressions. The collection and analysis of the collected information by the central controller AI system could provide the user and medical representative with the information to further diagnose the condition. The system could also provide remediation steps to prevent or reduce the TMJ pain.

A camera and accelerometer may be used to identify headaches and strain. Headaches are caused by various conditions, poor lighting, eye strain, length of time in an activity to name a few. The headset and sensors could collect the various forms of data. If, for example, the user indicates to the central controller AI system that they have a headache, the system could immediately produce a report showing the biometric sensor feedback with possible remediation steps to alleviate the headache. For example, a user that has spent 10 hours on the computer with the headset, shows signs of dehydration and facial expression of fatigue and eyes turning red may be indications that the user could drink water, take a break and use relaxation techniques.

A camera and accelerometer may be used to identify posture and ergonomics related to neck strain. The headset with accelerometer and cameras could notice the movement of the head, posture of the user in the sitting position, walking posture or continual focus of the head (e.g. in a downward position). The central controller AI system could compare these images and movements to users with good posture in similar positions and provide recommendations. The system could also alert you if your posture or head position is good. For example, if a user is sitting in a chair on a conference call for 2 hours, the camera and accelerometer could notice that the user's head is dropping over time and the user is moving further down the chair in a slouching position. The headset could alert the user to sit up straight and light their head. These recommendations could prevent fatigue and pain in the future.

In various embodiments, a headset equipped with cameras can record and monitor the surroundings of the patient and the patient himself to predict and prevent health concerns.

A headset may facilitate fall prevention. The camera could continually look for potential fall hazards in a home. For example, if the camera notices a rug with an upturned edge or a toy in the middle of the stairway, it could send an alert to the user to address. The camera could also evaluate the pathway a runner is taking and alert them if there is a branch, an uneven sidewalk or pot hole so they can alter their run/bike direction.

A headset may facilitate proprioception training (out of the rehab setting into the home setting). The camera could be used to monitor the rehabilitation of an individual at home. The camera could record the movement of individuals for the prescribed exercises or general movement and provide feedback to the patient for encouragement or correction. In addition, the results could be delivered to the health care professional for evaluation of the patient.

A forward facing camera/screen, rangefinder may facilitate home eye tests. The gradual decline of vision is common. The headset can be used to administer an eye test. The headset could initiate a vision test requiring the user to observe images on the screen in different lighting. In addition, the camera could measure the physical characteristics of the eye as additional pieces of information used in the exam. The collected information sent to the central controller AI system for analysis. The results of the test could be provided to the user and medical professional for review. Indications of vision loss could generate preventative action by the user.

In various embodiments, a headset equipped with an accelerometer could monitor movement over a period of time. If the central controller does not notice movement, it could provide a message for the user to move, stand up or take a break.

In various embodiments, a headset equipped with an accelerometer could facilitate fall prevention. The headset with accelerometer could continually monitor movement and more specifically, abrupt movement. If the central controller AI system notices frequent abrupt movements, this could indicate the user is at a greater risk of falling or a more serious health condition like Parkinson's disease.

Cleaning—Sterilization

Headphones rarely get cleaned by most users and collect germs. The headphones could be made of a plastic where a ultraviolet (UV) light can be installed and powered on for sterilization by the user. The sterilization process is set for a designated period of time (for example 5 minutes) to disinfect the headphones.

Telemedicine Facilitated by Headset

The use of telemedicine is becoming more prevalent. The headset could be used to collect information in real time and provide it to the medical professional for evaluation. Today, the only view a medical professional receives is from a camera on the computer and audio. The sensor headset, along with other cameras and lights can provide the medical professional with a more complete picture of the patient's health. The sensory data collected can be delivered to the medical professional over a secure connection from the central controller AI system. For example, if the patient is using a telemedicine connection with their physician, the headset could provide the doctor with the patient's temperature, hydration levels, heart rate and if needed focus on a particular part of the body with movable cameras and lights. If the doctor wanted to look at the patient's throat, the user could move the camera closer to their mouth, turn on the light and allow the doctor to example the throat. All of this information collected from the sensors and using devices (e.g. microphone, camera) to provide the doctor with more complete information to diagnose and assist the patient.

Brain Data and Stimulation

In various embodiments, a headset may gather EEG brain data. Brain waves could be measured by the EEG sensor placed in the headset. EEG measurements could be a first-line method to diagnose tumors, stroke and other focal brain disorders. The data collected by the EEG sensor could be transmitted from the headset to the central controller AI system to evaluate the brain waves and compare it to other brain waves. If the brain waves indicate a potential stroke, tumor or other brain disorder, the information can be delivered to the user immediately to the headset with a verbal update or provided in the form of a text report In various embodiments, a headset may facilitate brain stimulation. Transcranial Direct Current Stimulation (tDCS) are devices used to deliver low levels of constant current for neurostimulation. Scientific studies have shown that tDCS has the ability to enhance language and mathematical ability, attention span, problem solving, memory, and coordination. These are key contributors to improving human performance. In addition, tDCS has also been documented as having impressive potential to treat depression, anxiety, PTSD, as well as chronic pain. The headset could be equipped with tDCS stimulators to deliver the current to the user over a specific period of time and current level. These devices could be turned on and intensity established using control knobs. The duration and current levels could be collected and provided to the central controller AI system along with the associated brain waves to measure the long term impact on the brain and associated activities (working; learning, brainstorming, decision making, aligning; exercising, gaming and casual engagements). Improvements or recommendations could be provided to the user for alignment to skills or further stimulation.

Transcutaneous Electrical Nerve Stimulation (TENS) is a noninvasive device placed on the skin that can help control pain. Use of this device can block pain signals from reaching the brain and potentially reduce pain medication. The headset could be equipped with a removable TENs unit allowing the user to place the device wherever pain may be occurring. The duration and intensity of the TENs unit can be controlled by the headset. Information collected from the headset can be delivered to the central controller AI system for ongoing monitoring and reporting to the user.

Audio Management, Mixing, Smart Sound Producer, Tracks

Audio is used to hear sounds from another person, game, music or artificial sounds. In this invention with a headset, controllers and AI system, the management of the audio experience is enhanced and made available, before, during and after the activity. Vocal commands (e.g. in the form of 'hey, Siri') and non-vocal actions (buttons, knobs, user selections) could be used to enhance audio content delivery, establish and control connections, categorize audio content, and use and control non-audio content.

Enhanced Audio Content Delivery

Sounds could be used to set a mood that is personalized by the individual or owner in any setting; exercise, meetings, games or casual use. Users of the headset could layer sounds together to enhance their overall experience by using a pre-programmed soundscape or adding, removing or adjusting the musicals layers in a soundscape and storing on the central controller AI system or within the headset or user device 107a. For example, a meeting owner is conducting a learning meeting and establishes a very energetic soundscape with modern tones. Users of the headset could hear this at the start of the meeting once they authenticate. If the user wants to modify the soundscape, they could use their headset to dynamically adjust the various tones (or volume) and remove specific sounds/layers using knobs/buttons. In addition, they could introduce new tones not provided based on their individual preference. The sounds could be made available in the central controller, computer or headset processor 405. As another example, a user playing a computer game could alter the soundscape provided by the game by removing, adding or adjusting the soundscape of the game based on their preferences. The personalized soundscapes could be stored on the central controller AI system and made available to other gamers as add-ons to enhance their experience.

Various embodiments may include soundboard functionality, which may permit such things as injecting clips, music, laugh tracks, etc. Enhancing the audio and overall experience of an activity (meeting, game, exercise, casual event) could be made available to users of the headset This could be controlled by the owner of the activity or a participant. Audio clips in the form of music, vocal feedback, non-vocal sounds and pre-programmed tracks could be used at the appropriate time. For example, in a learning meeting, the meeting owner may be introducing a topic and use a joke to establish rapport with the audience. When the joke is finished, the meeting owner could use the headset to layer on laughter to enhance the experience and get people more comfortable in the meeting setting. As another example, during a decision making meeting, a meeting participant could ask in the headset to find the latest revenue numbers for the APAC region. This information is found and delivered to the participants through the central controller AI system and the headsets. Furthermore, if a meeting owner schedules a break, they could indicate in their headset by saying, 'break'. The central controller AI system could deliver the personalized audio content for each individual using the headset. For some, it may be Rock, Jazz or Country. For others, it may be resuming their favorite podcast.

In various embodiments, a headset may facilitate a "Laugh track" effect. Laugh tracks are effective ways to make people feel more comfortable, safe and secure and feel they are part of a group. This is increasingly important as more teams work virtually and may feel disconnected. The central controller AI system could listen to laughter from an individual(s) when a funny statement is made and immediately layer in a laugh track to mimic the intensity and volume of laughter. This injection of laughter could provide support to the meeting owner and provide the team with a sense of levity and comradery. Likewise, the meeting owner or user could turn off the laugh track as well through the headset and AI system.

In various embodiments, a headset may facilitate equalization of volume, such as with a smart audio mixer. Users of various equipment (microphones, headsets, speakers, computers) in unique settings (e.g. home, offices, outside) can cause sound to be distorted for each listener, sometimes without the speaker being aware. At times, the non-uniformity of sound from all participants makes it difficult for the listener to continually refocus on the content being delivered. The central controller AI system, along with the headset could remove these differences and deliver a uniform listening experience. For example, in a meeting, a user could be speaking in an open space with a lot of reverberation using a low setting on the clip-on microphone, while another user may be in an office space using a computer microphone picking up every sound very loudly. The listeners of each have completely different experiences and hear each person uniquely, making it difficult to focus or hear every statement in some cases. The central controller AI system could analyze each audio input and compare the difference (volume, sound quality, reverberation). The audio content could be delivered to the headset with the correct volume and equalization based on the current headset settings of the listener. Because each listener using a different headset has a unique setting, the audio could be personalized and delivered to each individual so that the varying inputs from each speaker were normalized and all sounded the same. This could reduce distractions and allow listeners to focus on the actual content.

In various embodiments, an indication of the microphone, camera, headset, and speaker make/model, along with connection type (e.g. phone, computer, laptop, game system), could be provided to the central controller AI for a record of how the user is listening to audio at any given time.

In various embodiments, speaker settings, make and model may be provided to the central controller AI system. Each user speaker system (computer connected) is controlled to deliver the sound unique to their preferences. The central controller 110 and user device 107a could interpret the sounds delivered to the user and the speakers optimized to provide the highest quality listening experience that matches the users preference. The central controller could also maintain the speaker specifications (make and model) and listening settings (EQ and volume) for the user based on connection type (on a computer, from a phone, via wireless speakers). For example, the user is listening to friends on a conference call using wireless Bose speakers. The user has tuned the speaker to a volume level of '5', with the bass turned up to the highest level. Each friend is speaking into their individual device and the quality of audio does not match the output the user prefers. The central controller has saved the Bose speaker model and preferred audio settings for the user. When the sound of each user is collected, the sound waves are transformed by the central controller before sending to the users Bose speaker to match their listening preference and previous experience on other calls (music, games, conference).

Establish and Manage Connections

In various embodiments, a headset facilitates walkie talkie functoriality for communicating with a door bell or door camera. The user could communicate to objects to manage their function using a headset without communicating over the Internet. For example, the user's door camera could be paired to the headset. The user could simply say to the door camera to begin recording by using a simple command. The headset understands the users voice and is able to manage the functions of objects in their surrounding that are paired.

In various embodiments, a meeting is locked to individuals who do not have appropriate clearance for confidential information. Each headset is owned by a specific individual and can only be allowed access to meetings to which the headset owner has been invited, or otherwise only to prerecorded content. For example, a meeting owner plans to discuss a sensitive HR topic and only wants two people to attend the call. The owner invites the two people to the call. Each user accesses the call from their headset. The central controller knows that the specified user was invited and is using their unique headset. So, they are allowed to access the confidential call and information. However, one of the users forwarded the invite to another person not allowed to attend or have access to the confidential information. While they have the meeting passcode, the headset is not recognized by the central controller and they are not allowed permission to join the meeting. The meeting organizer is informed and can determine if the person could be allowed and override the system.

Various embodiments may facilitate anonymous contribution of content, even if contributed vocally. Various embodiments may prevent recording or facilitate masking of voices for anonymity purposes. There may be times when a person's anonymity could be maintained, but the content delivered. This can come in the form of masking someone's voice or not displaying the name/title or affiliation of the member. For example, a speaker is delivering feedback to a senior officer in the company and does not want to be identified. The user with the headset could provide their comments and the central controller AI system masks their voice, job title and name before sending the audio to others. This masking could be in the form of changing the modularity of the voice so that the content is understood, but the voice is not recognizable.

In various embodiments, a headset could allow the user to select specific people that they want to listen to on their audio feed. For example, the user of the device indicates to the headset (verbally) that they only wish to listen to the meeting owner, James and Mary. The central controller knows these individuals and only provides their audio content to the owner. It could save a favorite people list and only get their audio feed. Another example, a meeting owner tells the participants to go on a break. The users of the headset only want to talk/listen to their friends. This friends list was previously stored in the central controller. Once the central controller knows the user is on break, it automatically connects them to their friends for listening or active conversation. Once the break ends or the user indicates through pushing the disconnect button, the user is automatically rejoined to the meeting.

Various embodiments facilitate prank calling, or spontaneously connecting headset users (headset phreaking). Users may want to hear and engage in a prank call scenario, wherever that may be taking place. If the user of the headset indicates they are available for this type of activity, the central controller could store this information. The central controller could determine a prank call is starting and automatically connect the intended users to listen to the call. If the user is the person playing a prank, they could schedule a prank call type with the central controller and this be the indication when others wanting to join are connected.

Various embodiments allow users to control multiple audio channels on a headset. There may be times users want to listen to multiple channels simultaneously. The user could select the various meetings, audio content (music, white noise, podcast) or games by selecting buttons or knobs to have information delivered.

Various embodiments allow parental control to communicate to headphones. Controlling time spent on games and social media is a challenge for parents. The headset could have time of day or time limits established in the central controller by the parents. If the child attempts to access the headset outside of an allowed time or exceeds time spent on the headphones, the device will not power on. In addition, parents may want to interject a comment on the headsets. They could press a button on their headset and inform other connected headsets that dinner is ready or it is time to do homework. This is acting like an intercom device.

Meeting owners may want to change audio controls for meeting participants. As an example, if a meeting owner wants individuals to have a few minutes break to think, they may push 'white noise' to all headsets. In addition, the meeting owners only want architects to discuss a topic in a meeting. The headsets for architects are connected so a conversation can only take place with those key participants. When complete, the connection is closed and the architects rejoin the meeting.

Various embodiments may facilitate audio sharing with someone else on a headset via Bluetooth®. There are times users want to share an audio experience. A user may be listening to a new recording of their favorite artist. The user on the headset could press a button and their other friend's Bluetooth® enabled device could immediately receive the audio stream. Both are able to share the same audio experience. In addition, someone in a meeting may only want to make a quick comment to another person. In the same manner, the person on the headset could press a button and be immediately connected via Bluetooth® to another headset to make a comment.

Headset Swap Control

Various embodiments facilitate the swapping of headphones between devices. As a user, I may want to remove my headset in the middle of a game or meeting. The motion of removing the headphones could allow a different device to automatically connect. For example, I am using my headphones for a period of time at my desk. At some point, I decide I want to remove my headphones. The device could understand I'm removing and swap my listening device and microphone to my computer (my next connected device).

Various embodiments facilitate switching of headset between devices (laptop, phone, car, PC/desktop, in-room conference). Switching between devices is common, but the management and seamless transition between devices is cumbersome. The central controller 110/headset processor 405/user device 107a could know which device the headset is connected to. If the connected device (e.g. computer, car, iPhone®) changes or is outside of range (Wi-Fi®/Bluetooth®), the device could automatically connect to the selected or available paired device. For example, a user of a headset is connected to a meeting at home on their laptop. When the user leaves for the office and enters their car, the headset could automatically join the cellular network or in-car Wi-Fi® network without dropping the call. Later, the person walks from the parking lot to their office. The headset could automatically connect via the users phone network and again, without losing a connection to the call. Once in the office and they enter the meeting room, the headset is connected to the meeting room for completion of the call.

Various embodiments include pre-programmed channels, which may allow ease of movement between each (button press, knob, etc.). The switch between various channels (music, games, podcast, book audio, conference call or, favorite people lists, white noise, coaching session or any listening activity) should be as easy as tuning to a different channel like on a car radio. For example, the user of the headset is playing a game with friends and discussing strategy, sometime during the game the user decides to join a phone call with friends. The user could simply select a button/knob or vocal command and the channel is immediately connected to the friend's call. Likewise, if the user is listening to a podcast and a conference call begins, the headset could automatically know (via the central controller) that the conference call should be connected and with no intervention from the user. At the end of the call, the headset could transfer the user back to the podcast or any other preferred channel.

Categorize and Edit Audio Content

Audio collected from users could be stored with hash values making searching for content easier. The central controller could mark each audio file with a unique user, event type and subject/content. The audio could later be searched by any index (audio, visual or text) and results provided to the user. For example, The headset could provide hash values for a subject matter expert (SME named 'John') providing a discussion on microservices and stored on the central controller 110. Much later in time, a person with an interest in learning about microservices (or any person) with a headset could make an inquiry to the central controller and ask to provide the SME John discussion of microservices. The central controller could retrieve the audio content and provide from John recorded earlier and provide to the user. Another example may be to retrieve decisions made by a team that occurred years earlier to understand how a project failed. Collection, assigning a hash value to audio and retrieving from the central controller provides a way to easily, quickly and securely obtain information for evaluation in the context needed by users of a headset.

Various embodiments facilitate instant replay of audio from the last 60 seconds (or any duration) into one ear. Oftentimes people are asked to repeat something that was just said. This is because the listener was distracted or was simply not paying attention. Instead of stopping everyone else in a meeting or looking foolish, the user of the headset could ask the central controller to repeat a portion of the missed conversation. For example, during a call, the presenter discusses a complex topic. The listener of a headset did not quite understand the statement and could request the central controller, either via a verbal command (not heard by others while on mute) or selection of a knob (to dial in the amount of time needed for the replay)/button (default time), to replay the content in one ear. Another example, a meeting owner hears a terrific explanation to solving a problem. Instead of asking the person to restate it and provide focus for the entire team on the idea, the user simply makes a request to the central controller to replay the last comments over 2 minutes.

Editing the Audio

Various embodiments allow audio content to be edited before being submitted to listeners, in case it needs to be deleted. For example, on a call with investors, the executive committee may be responding to investor questions. An executive using a headset through a central controller may provide an answer that gives insight into a future strategy for their competition using a key phrase. Since the audio is delayed and not sent, the user or designee could immediately delete the key phrase from the audio before being sent thus protecting the company and market position.

Various embodiments facilitate editing people out. There are comments that are sometimes not meant for all listeners on a call or game and the invention could allow the blocking of people from the audio. For example, during a decision making meeting, the actual decision makers may want to have a brief discussion before bringing in all other listeners. Instead of dropping the call or having another meeting with only those decision makers, the users (the decision makers in this case) could inform the central controller that only the decision makers need to communicate. Once the communication occurs, they are placed back in the call to resume the meeting by simply requesting the central controller to join the call.

Various embodiments facilitate editing people out or including only certain people. For example, a user could only listen to certain people that spoke during a call. It may not be possible to attend a conference call but the user of the headset wants to listen to key portions from certain people. The user with the headset could request the central controller to replay the meeting and edit out all discussions that did not include the Architects. During the replay, the central controller could provide the audio content for only those Architects and save time for the listener.

There may be times when sudden noises consume large amounts of time in a meeting and are not needed for archival or replay. Various embodiments allow the headset to recognize the content and the central controller 110 to edit out the non-essential audio for storing and replay. For example, each time a dog barks, someone apologizes, a child screams in the background, the doorbell rings or a siren is heard, the meeting is disrupted and time is lost. The central controller could take those noises and edit them from the overall meeting content making them more efficient and less distracting.

Various embodiments facilitate the ability to delay comments on a call. In some cases, a user wishes to retract or rephrase statements he wishes he did not say. Various embodiments allow content to be delayed in its submission to listeners in case it needs to be deleted. For example, on a call with investors, the executive committee may be responding to investor questions. An executive using a headset through a central controller may provide answers that give insight into a future strategy for their competition. Since the audio is delayed and not sent, the user or designee could immediately prevent the audio from being sent and allow another response to be provided.

Various embodiments facilitate clarification of comments. Various embodiments facilitate putting multiple audio clips together. Various embodiments facilitate smart transcripts with tagging. The headset and central controller could allow the user to combine clips to make for a cohesive response. A subject matter expert may have provided an explanation for the use of a new technology to multiple teams, but in a slightly different way or with some revisions along the way, making their original comments outdated. Instead of meeting with all teams again, the subject matter expert using a headset could retrieve the tagged comments from all team discussions via the central controller, edit the most relevant and best explanations and provide corrected statements where needed and resend to all teams. In this case, all teams could now have the most current information at the same time and add efficiency for the subject matter expert.

Various embodiments facilitate speeding up audio to catch up. Users are oftentimes late for meetings. Instead of asking for a recap of the meeting to get them up to speed and delay everyone else, the user of the device could request the central controller play them the portion of the meeting missed and in an accelerated manner. The user could slow the audio down with the headset device if there is a particular piece that interests them the most before catching up to the meeting.

In some situations, for example, a user has not adequately prepared prior to a meeting, and requests a summary. The central controller 110 could analyze the content uploaded for a meeting (video, audio, presentation content or other supporting content) and summarize for the user that failed to do prep work prior to a meeting. For example, if a user of a device is attending a meeting, they could request the central controller provide a summary of the content. The audio provided could scour the content and previous meeting content and provide a verbal summary. If the meeting was in regards to financial update on a project, the attendee could be presented with bottom line financials, key points of contention, comparison of financial information from the previous meeting and submitter as an example. The central controller could also begin to learn the patterns (questions asked, context, learning style (written verbal, pictures) to help provide feedback in these types of situations). This could give the user quick information to be effective in the meeting.

Various embodiments facilitate music that can be broken into constituent instruments. A user may be interested in hearing the different instruments on a recording for purposes of learning or mimicking. For example, the user of a headset may want to learn to play a specific piano piece, the chords, rhythms and meter. The users could request the central controller 110 to only play the piano portion of the recording which could allow the user to more closely match their playing to the recording. In addition, there may be situations where audio mistakes on recordings are made and a user needs to correct (e.g. sound engineer). In this case, the sound engineer could inquire with the central controller via the headset and request only certain instruments be played on the device. This could give the engineer quick attention to these parts for feedback and corrective action.

Use and Control Non-Audio Content

Various embodiments facilitate voting to move on to the next topic, slide, image or video. There may be times when meeting attendees need to move quickly through presentation material due to time constraints or familiarity with a topic. In this case, the user of the headset could signal (audio vote, selection on headset) and indicate to the presenter to move to the next topic, slide, image or video. This invention could allow for a dramatic improvement in meeting efficiency or allow for more time to be spent on topics of most interest to the attendees.

Various embodiments facilitate picking up on social cues or signals. One cue may be to pause and not move on during a presentation. Non-verbal signals may be given to people during a presentation that should delay moving on to a new topic but are often not picked up on by a presenter. For example, some presenters want to quickly move through slides and not allow people to digest content for meaningful questions or dialogue. Sometimes this is a nervous habit or a strategy so no questions are asked, when listeners really need time to formulate their questions. This is especially true for complex topics. For example, a junior marketer may be pitching a new product to a group of executives that includes a lot of background market data and a complex product. While the marketer is open to questions and asks for feedback, there is silence and the user quickly moves to the next slide/topic. The user of the headset/central controller could get visual feedback from the attendees that indicate an inquisitive look on their faces. The central controller could inform the marketer to pause and allow them to think or rephrase a topic. Once the central controller recognizes these expressions have changed to a more accepting look, or questions have been asked, the marketer could move on.

One cue may be to leave a person alone. Sometimes people do not want to be engaged in a conversation but their social cues are not interpreted correctly by others. Users of a headset could interpret the other person's non-verbal cues from the camera, such as not making eye contact, moving their body in the opposite direction, blank facial expression or shrugging to indicate they do not want to be engaged in conversation. The users headset could inform them to not engage the person and to leave them alone at that time.

Visual Alerts

There are times when the user of a headset wants to communicate information to others without having to speak or actively communicate—letting others understand the user's state of mind without having to address them directly.

In some embodiments, the user establishes his status (such as "busy", "available to talk", "free to talk at 11 AM", "can talk if the question is important", "do not interrupt", "email me if you have a question") which is then saved in a data storage device of the headset. The user's current status could be entered into the headset by saying the phrase "busy" into a speaker of the headset which is then transmitted to the headset processor and converted via voice to text software and then stored in a data storage device of the headset as a status of "busy." Alternatively, the user could indicate that he is busy by pressing an input button or setting a switch on the headset processor 405 that indicates a status of "busy." The user could also use an application on his computer to indicate his status and have that transmitted to the headset processor 405, or the user could send a text from a mobile phone directly to a communication device of the headset processor 405 indicating a current status. Once a status has been identified, lights controlled by the headset processor could be used to communicate that status on a persistent basis to others.

In some embodiments, communication of the users status could take the form of light, motion, or sound from the user's headset. For example, the ear coverings of the headset could contain one or more LED lights (under the control of the headset processor) which light up when the user is busy. The headset headband could also contain one or more display areas that communicate the exact status of the user to others. A color scheme could be used such as Green, Yellow, and Red to indicate whether or not the user is comfortable with being interrupted. In this scheme green could indicate that the user is free to talk, yellow indicates that they are willing to talk if something is important, and red means that the user could prefer not to talk unless there is an emergency of some kind.

The status of the user could also be determined based on actions taken by the user. For example, when a user is on a video call the headset processor stores a status of "yellow" when the user is currently on mute, with the headband of the headset automatically displaying a yellow color indicating to others on the call or to passersby that they can communicate with the user. If the user is actively engaged in the call/meeting/game, the outer ring of the headband could display a different color (red for example) to indicate to others on the call or passersby that the user should not be interrupted.

Users could also update their status to indicate a request to others. For example, it is often difficult to speak on a conference call (video or audio) when participants vocally overlap each other, causing frustration. In one embodiment, a user in a conference call could use the headphones to display a different color or display a text request in order to get the attention of a meeting owner/moderator to request that the moderator mute everyone else and allow the user to speak, thus providing opportunities for everyone to engage in conversation in a more managed way. The Central Controller could also know which participants have been waiting the longest to speak, and send information to the meeting owner to help them moderate who is able to speak next. At any time, the meeting participant could elect to withdraw their question/comment and the color or the headphone returns to a normal color.

Social Connectedness

While many employees now spend more and more time working remotely from home, video calls with co-workers sometimes do not have quite the same level of social connectedness that in-person meetings have. Workers can spend time connecting via video calls, but they often miss having people drop by their office to chat, engaging in small talk with a coworker while getting coffee, bumping into someone in the company parking lot, eating together at the company cafeteria, and the like. Some of the sounds that help to give an office space its character may be rarely heard by remote workers from home, resulting in reduced social connection to employees in the office.

In some embodiments, the headset is able to simulate sounds from an office environment to supplement the experience of remote workers. For example, while a user is on a video call the headset processor could periodically retrieve from data storage a sound associated with an office and present it to the user via a speaker of the users headset. For example, the headset might periodically play the sound of water dispensers gurgling as users get water, low level conversations among worker, windows being opened, phones ringing, doors opening and shutting, air conditioning units going on or off, footsteps on a floor, coffee pots boiling, airplanes flying overhead, cars honking, etc. Such sounds could help a remote worker to feel as though they were at the office rather than working from home, and could help the remote worker to feel more connected to the other workers on the call who were in the office.

In some embodiments, the remote user's headset could receive samples of actual sounds from a physical office. For example, the physical office could be outfitted with a number of microphones which pick up audio throughout the office—including the sounds of phones ringing, doors closing, air conditioners turning on, etc. These sound feeds would be transmitted to a central controller which would then relay the sounds to the speaker of the user's headset during video calls. The central controller could also store a map of employee locations in the physical office relative to the microphones so that when a remote user is on a video call with a group of employees from a particular location in the physical office, during those calls the audio feed would represent sounds that the office workers might be currently hearing, allowing remote viewers to share in the sound experience of the office workers.

In some embodiments, a remote user can log into a particular location in a physical office, connecting directly to a microphone that is currently receiving sounds from that area. For example, the remote user could connect via her headset to a microphone and/or camera in the break room where employees often make coffee in the morning. While listening to those sounds and conversation, the remote user could make coffee at her own home and feel more connected to the office. In this example, employees present in the break room could activate forward facing cameras on their headsets with the video feed going to the headsets of employees working from home.

After transmitting a live video or audio feed from a physical office location to the central controller, the central controller could transform that data into a more generic form. For example, a live video feed of office workers making coffee could be converted into more of a cartoonish or abstract version in which the identities of individuals in the video could not be determined, though the abstract representation would still give the remote user at hone a sense of being by the coffee machine without knowing exactly who was currently there. The cartoon version of employees could also identify the employee by name, and could include information about that employee that could be helpful in starting a conversation, such as an identification of a key project that they are working on, their to do list for the day, or a technology issue that they are currently struggling with. A company could also allocate physical rooms for the purpose of helping remote workers informally interact with workers physically present at a location. For example, a company could paint a room with a beach theme and connect employees entering the room with virtual attendees from remote locations. The room would enable physical and virtual employees wearing headsets to engage each other in a relaxing environment as a way to motivate social bonding and collaboration.

Pairing, Organizing Teams and Managing

Organizing teams, pairing individuals to work together and connecting teams with experts within or without the organization are central challenges for businesses and organization. Devices according to various embodiments could facilitate team formation, pairing individuals, connect teams with appropriate experts, and connecting organizations with contractors or other forms of expertise outside of the organization.

Within meetings, devices could be used to pair individuals on opposite sides of an argument or on opposite sides of a decision to be made. Meeting owner or central controller could poll meeting participants and match them based upon their responses to a poll. The meeting owner or central controller could assign individuals to particular roles, positions or arguments and pair them with similar or dissimilar individuals. For example, the central controller could ask to pair two individuals together and ask them to defend the opposite position from the one they agree with.

Within meetings, the meeting owner or central controller 110 could pair individuals by engagement level, mood, length of time at the company or in a particular role, or by skill levels. For example, a new employee or a new team member could be paired with an experienced employee or team member. A participant with high levels of engagement could be paired with someone with a low level of engagement to encourage the low engagement employee. The central controller could use employment history, CVs, 360 evaluations, post-meeting evaluations, post-project evaluations, or other more holistic measures of experience and skills to pair employees on other dimensions. The central controller could for example pair employees from different backgrounds or different parts of the company.

The central controller 110 could detect the cognitive type of individuals based upon cognitive task batteries such as the rationality quotient or the elastic thinking measurement. The central controller could use cognitive type to pair individuals or to organize small teams. The central controller could pair individuals to balance out each other's weaknesses or to ensure that the team has a certain threshold number of individuals of particular types. The central controller could utilize the meeting agenda or other criteria supplied by the meeting owner or project manager to discern which types of individuals would be suited for the meeting or project. The central controller could attempt to ensure cognitive diversity by balancing types, or it could use the cognitive types to avoid staffing individuals to certain kinds of meetings or tasks. For example, an individual that is low on a rationality quotient score could be excluded from a decision making meeting.

A common problem in meetings is that the meeting lacks a subject matter expert for a particular technical issue that arises during the meeting. The central controller 110 could provide meeting owners or meeting participants with a list of subject matter experts who have availability on their calendar to be patched into the meeting. The central controller could record, tag and make available throughout the project or enterprise the questions asked of the SME and how the SME answered those questions to disseminate those answers and avoid re-asking those questions of an SME at a later date.

A common problem during meetings is that an outside expert, consultant, contractor, or vendor is not invited to meetings and their expertise is required. The central controller 110 could provide meeting owners or meeting participants with a list of relevant individuals outside of the firm who have availability on their calendar to be patched into the meeting. The central controller could record, tag and make available throughout the project or enterprise the questions asked of the outsider and how the expert answered those questions to disseminate those answers and avoid re-asking those questions of the outsider at a later date.

Outside of meetings, the central controller 110 could detect members of the organization have free time. The central controller could check calendar availability and then detect down time or inactivity beyond a certain threshold. The central controller could then pair a manager with an inactive team member or two inactive team members. The central controller or the project manager could provide conversation prompts for the pair to discuss or could ask a team member to update the other half pair of their work. The central could also pair a busy employee with an inactive employee on a similar project to facilitate the work of the busy employee.

Outside of the meeting, the central controller 110 could pair individuals or organize teams of individuals who work well together. An AI module could be trained based upon audio of prior meetings, 360 evaluations, post-meeting evaluations, post-project evaluations, or other data to determine how well employees interact with each and their contributions to team performance. The AI module could pair or assemble teams or make staffing suggestions to a hiring manager or project manager about the optimal composition of a pair or a team.

Hiring contractors, consultants, vendors and other individuals from outside of the organization is often a high-friction task. Consequently organizations face hurdles to assembling a temporary team designed for specific tasks or projects. Individual contractors, consultants, vendors and other individuals from outside of the organization could store in their headset their work history, CV, licenses, reviews from previous employers or review from previous interactions with the business, as well as their work authorization and financial information. When a manager is looking to staff a project or hire an outsider, the manager could post an opening and receive authorization from the headset owner to review these forms of confidential information. The central controller could then display these forms of confidential information to the manager and expedite hiring. The central controller could facilitate pay or contract negotiation by allowing contractors to set reservation wages or stipulations, by allowing contractors to engage in a Dutch auction for the contract, or through other market design mechanisms. The contractor could be onboarded and sign a non-disclosure agreement and a contract through a biometric signature. The company could release payment to the contractor and use the stored financial information of the device owner to transfer payment. After the contract is completed, the manager could leave feedback for the contractor to facilitate future hiring.

Devices could allow for leaders of an organization to hold office hours or create availability for employees to ask quick questions. A leader could designate certain calendar availability for office hours. The central controller could determine if the leader has calendar availability and then determine if the leader is inactive. An individual with a question could then ask to be added to a queue to speak with the leader. The queue could be prioritized by the leader or by the individual inputting a description, rationale, or ranking of importance of the need for their access to the leader holding office hours. Based upon the queue, the central controller could connect the leader and the individual seeking office hours. The central controller could allocate time to individuals based upon time slots or dynamically depending on the priority of the conversation or number of others in the queue.

The central controller 110 could create a "peek inside" function for organization leaders, allowing them to drop into ongoing meetings in an observer or participant mode. The leader could be visible or not visible to meeting participants in order to not disturb or interrupt the meeting, or to indicate that someone was monitoring the meeting. The leader could choose which meetings to "peek inside." The central controller could suggest meetings for the leader to review, based upon several criteria such as the agenda items, the cost of the meeting as measured by salaries of individuals involved, the type of meeting, meetings that receive high or low post-meeting evaluations.

Headsets according to various embodiments could facilitate a snippet view, allowing meeting owners, project managers, or organizational leadership to poll or survey select employees and theme review audio responses to the poll or survey questions. Individuals could hear the question or take the poll or survey and have a chance to record an audio snippet. Those snippets could be analyzed by the central controller or the leader could review those snippets directly.
De-Biasing Group Interactions and Improving Group Behavior Business and organizations seek to reduce discrimination and social biases in the workforce. Many biases however are subtle and unintentional. Headsets could be used to reduce biases through detecting biases, providing bias metrics at team or enterprise levels, coaching, or through signals processing that could alter some biased cues that individuals use to process information about other individuals.

Within a meeting or video conferencing session, the central controller 110 could record the amount of time each person speaks. The central controller could detect how much time each headset wearer spends in different conversational roles such as speaker, direct addressee, audience, and bystander roles. The central controller could provide descriptive statistics about the amount of time individuals of legally protected groups or other groups of interest speak during meetings or the amount of time spent in particular conversational roles. The central controller could allow individuals to access their own speaking data and compare their metrics to other members of the team or enterprise, or compare averages for similar roles within the organization. The central controller could also allow individuals to access project or enterprise aggregate data broken down by legally protected groups.

Audio and other device inputs could be used to train an AI module that detects how speakers engage with one another based upon sentiment content in verbal audio content. This module could be trained using verbal content or it could be combined with other device inputs such as facial imagery to detect facial expressions or microexpression or biometric data to detect biophysical responses to stimuli during conversations. Likewise, audio elements such as voice quality, rate, pitch, loudness, as well as rhythm, intonation and syllable stress could be used to train an AI module that analyzes how individuals react to the speech of others. A module could be trained using eye contact, gaze, frequency of eye movement, patterns of fixation, pupil dilation, blink rate and other eye movement data to detect how individuals respond to the speech of others. A module could be trained to detect patterns of interaction utilizing 360 degree reviews, post-meeting performance surveys, in-meeting tagging, in-meeting rating of participants, or other metrics supplied by other members of a group.

These modules individually or as an ensemble could be used to detect biases, discrimination and common patterns of negative by individuals toward members of legally protected groups or toward other groups of interest. These modules individually or as an ensemble could be used to detect how individuals engage with other members along positive dimensions of interest to the organization such as cooperativeness, helpfulness, and thoughtfulness. These modules individually or as an ensemble could be used to detect how individuals interact with others along negative dimensions such as dismissiveness, aggression, or hostility. The central controller could allow individuals to access AI insights for themselves or aggregate behavior for a team, project or the enterprise as a whole.

The central controller 110 could track patterns of interaction by individuals or between individuals across meetings and across time. The central controller could identify trends in interaction over time, detecting whether relationships were improving or deteriorating. The central controller could provide data, insights and trends to individuals, team leaders, HR, organization leadership, or 3rd parties. These insights could be available at the level of individuals, teams, the project-level, clusters within networks, the whole network, or the whole enterprise level. The central controller could identify individuals who work well with particular teammates or who do not work well with particular teams to inform project or team staffing. The central controller could identify problematic relationships for a manager or HR member to intervene and could also identify managers who are adept at managing problematic relationships or reducing negative behavior among subordinates.

During or after meetings, the central controller 110 could detect problematic spoken behavior and prompt the individual with alternative language, framings of problems, or other language. During or after meetings, the central controller could prompt a speaker to apologize to particular individuals or suggest that the individual receive additional coaching or training. Prior to meetings, the central controller could prompt an individual with a history of biased interaction with particular individuals with coaching prior to the meeting.

The central controller 110 could use signals processing techniques to alter the audio or video content of a meeting to reduce biases. Just as orchestras often hold auditions behind a screen, the central controller could hide the face of a speaker, genericize their audio output, or use other visual or audio masking techniques to hide potentially bias-inducing or non-relevant information such as the gender or race of a meeting speaker.

Using masking techniques could also improve how groups use non-relevant (but potentially non-discriminatory) information as cues for information processing. Individuals within groups do not independently form beliefs about information but instead use cues from others about how they should think about information, such as taking cues from authority figures, what they perceive the majority of the group to think, what they think the group believes to be appropriate. These and other forms of social cues can lead to distorted information processing and compromised decision making. The central controller could utilize masking techniques to reduce the ability of individuals to use cues from other group members and increase the individuals reliance on their own judgement. For example, it could turn off visual output from devices and mask all voices. For example it could ask participants to record their opinions and then display them anonymously as text in video or in chat. This feature could be enabled as a default or certain kinds of meetings, such as in high stakes decision making meetings.

Pitch, loudness, quality of audio and other facets of speech have been shown to induce bias in group interactions. Studies have shown for example that louder or deeper voices are perceived as more confident or more authoritative than quieter or higher pitch voices. The central controller could use equalizers, masking or other signal processing techniques to amplify or reduce the volume of quiet/loud voices or increase or decrease the pitch of voices.

Genericizing, anonymizing, masking and other signals processing techniques could be controlled by an individual headset wearer, the meeting owner, enterprise leadership, or the central controller. An individual, meeting owner, leader, or central controller could place some or all output channels as masked or anonymized. For example, a leader might want to reduce their own biases and mask the audio and video content for themselves but allow other participants to be unmasked. The central controller could detect biased behavior on the part of some individuals and mask audio or video output for the remainder of the meeting for some or all participants.

Mood Contagion

Businesses and other organizations often seek to improve the performance of small teams by creating social environments that enhance employee engagement and individual performance. The devices according to various embodiments could facilitate improved social dynamics in small groups by harnessing a social psychological phenomenon known as "mood contagion" or "affective transfer." The behavior of individuals within groups is shaped by their perception of the mood, emotions, or affective state of other members of the group. Through the data generated by the device, an AI module could be trained that could provide feedback to the device owner on the affective states of others, how others perceive the device owners mood, and through coaching or signals processing, subtly alter the emotional state of the group to improve group performance.

Recent research in social psychology and cognitive neuroscience finds that mood is contagious. More specifically, listeners may mirror the emotional or affective state of a speaker. Individual listeners process aspects of spoken language such as volume, tone, and word cadence as signals of the speaker's affective state. In turn, listeners subtly mirror the speaker's emotional state. That is, unintentional vocal signals of mood can induce a congruent mood on the part of the listener.

Additionally, cognitive neuroscience research has shown that affective states influence group behavior by shaping cooperativeness and information processing. When groups have a positive affective state, they may be more creative, make better decisions and be more thorough in performing a task. They may also be more risk averse, less likely to discern between strong and weak evidence, and more easily persuaded by peripheral cues and irrelevant data. When groups have a negative affective state, they have higher levels of pessimism and negative judgements of others, more likely to engage in in-group/out-group reasoning, and increase risk tolerance. They may also be more likely to use a structured decision making protocol and less likely to rely on peripheral cues and irrelevant data. Depending on the group task, particular group affective states may be more or less optimal.

A headset could improve team behavioral dynamics by altering, inducing or counteracting mood contagion effects. The central controller could detect whether the affective states of individuals in the group correspond to desirable affective states for performing group dynamics. Individuals such as the device owner, meeting owner, or members of the group could input information about the group's task and/or the desired affective state. Alternatively, the central controller could detect a desired affective state from a meeting agenda, the vocal or visual content of a group interaction, or other contextual information. Data generated by the device, such as audio, biometric or visual data could be shared with the central controller. This data could be used to train an AI module that detects the mood of the device owner or other participants in a call, video conference meeting, or other group interaction. The AI module could compare the affective state of individual group members against the group's task. The module then could provide audio, visual, or tactile prompts to the device owner to alter their tone, volume, cadence or other aspects of communication to induce the desired affective state. Likewise, the module could provide feedback to the device owner on whether mood contagion effects were occurring or being used successfully. The central controller could also use signals processing techniques to automatically alter tone, volume, cadence or other aspects of communication to induce the desired affective state. For example, when if it detects that a speaker is angry and is causing other members of the group to have a negative affective state while the group's task required a positive affective state, the central controller could reduce the volume of the speakers voice or shift the pitch of the speaker's voice to modulate how other group members perceive the speaker's voice.

Integration of Audio, Content, and Messaging

A headset according to various embodiments is well suited to allow users to integrate voice notes into content being reviewed. Many business conference calls involve multiple participants reviewing a presentation deck on a shared screen. While there can be a lot of discussion on the content, those discussions are sometimes lost when the meeting is concluded.

In some embodiments, users on a video conference call are able to append voice notes to the content being discussed. For example, while discussing slide three of a presentation, one user might mention to all call participants that the new product prototype might require more engineering review of the metal casing. The headset could be configured such that the user could say "apply the last five minutes of audio to slide three" at which point the processor of the user's headset retrieves the last five minutes of audio from the user headset data storage device and sends the sound file to the central controller where it could be integrated into slide three of the presentation. After all such sound files are appended, the meeting owner could email the slides with appended audio notes out to all call participants who could pull up slide three and then click any audio files associated with that slide. Audio files could also be associated and stored with particular portions of the slide. For example, the audio clip regarding the need for more engineering review of the metal casing might be associated with a bullet point mentioning the steel casing. That would allow others on the call to review the audio notes for a particular slide (or portion of a slide) of interest later. In addition, the slide presentation could be sent to a representative from the engineering group for review, with the appended audio notes providing substantial additional information. In another embodiment, the user could apply a tag to the appended audio file such as "engineering" or "metal." In this example, the user could say the expression "tag audio comment with engineering" which would be picked up by a microphone controlled by the headset processor, translated to text, and then parsed into a command that associates the tag "engineering" with the stored five minute audio clip. In this way, a representative from engineering could do a search of all presentations stored within data storage of the central controller for the tag "engineering" and then pull up all of the audio files and presentation files which included that tag. This tag could also trigger the central controller to automatically send any audio file with the tag of "engineer" to a particular engineering representative of the company.

Audio files could be recorded and stored before, during, or after a presentation. For example, a user could review a presentation file before a meeting and then add several audio notes to the presentation as described above, sending the presentation file with the audio notes back to the meeting owner who could then aggregate audio files from other meeting participants who had done a similar pre-meeting review of the presentation. During the meeting, the meeting owner could have the option to play one or more of the audio files during the presentation. Users with headsets could also request to privately hear an audio file, or request to privately hear all of those audio files including a tag connected to their area of expertise or interest. Participants could also add audio files to a presentation after the presentation was over. Such post-meeting appended audio files could include suggestions for improvement of the presenter, or could include reminders of action items to be completed by other participants.

In various embodiments, a user listening on a video conference call could send an audio file to another person talking on the call. For example, a user might be listening to a participant and realize that the participant is missing a critical piece of information. Rather than trying to interrupt the participant, the user could instead command the headset processor to take a message by saying "begin message." The user then records an audio file via the microphone of the headset processor 405, and finishes by saying "end message." This triggers the headset processor to end the recording. The user then says "send to Gary Jones" and the headset processor emails the file to Gary Jones for later review.

Appending of audio files could also be used in gaming embodiments. For example, a game character could record an audio comment (such as a suggested new game strategy) and append it to a location on a game for later review by a team member, or it could be sent to all of the users team members or later review.

Gaming Embodiments

Game audio is central to video gaming experience—facilitating player communication, providing information to players, and heightening immersiveness. Headsets however also could be utilized as game controllers, as enabling dynamic forms of game play and changes to the game environment, facilitating player functionality of transaction and controlling game settings, and enabling social interactions between game players.

In various embodiments, headsets could be used as game controllers. The headset could include accelerometers or tension strain gauges in the headband or the earcups which could detect head orientation, positioning, turning, tilting, or facial expressions. These inputs could be utilized in games for example to control character visual fields, control camera angles, control vehicles. Turning the head for example could be used as a steering wheel in a racing game. Devices could allow for in-game character movements to mirror changes in head or torso orientation. For example, a player might look around the corner of a wall by leaning forward and turning the head. headsets could also include eye tracking cameras which could be used to change the visual field of a character or control in-game functionality. For example, a player might be able to switch inventory items by tracking their gaze across different items. Cameras directed toward the player's mouth might allow games to be controlled by subvocalization. For example, a player could move their mouth in ways that the central controller could interpret as in-game actions.

Eye gaze and head orientation captured by devices could be used for gaming analytics. For example, a player could review how quickly their eyes track to new in-game stimuli. For example, a player could review what parts of the screen they do and not engage with.

Headsets could facilitate a game controller dynamically changing in-game content to increase excitement, difficulty level, game play time, amount of money spent in-game, the amount of social interaction among players, or another goal of the game controller. Attributes of the game could change dynamically in response to head orientation or eye gaze. The game controller for example could path enemies in ways that surprise players by directing their paths through areas of low eye gaze. For example, valuable rewards could be placed in screen locations that players are less likely to view. Attributes of the game could also change in response to engagement levels, affective state, and other nonverbal signals of emotional response such as changes in heart rate, blink rate, galvanic response and other biophysical responses to gameplay.

Verbal and non-verbal auditory data created during gameplay could be recorded by the central controller 110 or game controller. For example, a player could be required to speak certain lines or read from a script during a game. For example, a player speaking with another player could enable game play. For example player to player communication—either with teams, between teams, or between non-team players—could be recorded and used as inputs for metrics. A player for example could be scored on communication skills or one a sub dimension of interpersonal skills such as cooperativeness, helpfulness, coaching other players through game scenarios. These metrics could be used to unlock game functionality—for example, a helpful player could receive certain skills, rewards, or other in-game functionality. Likewise, a game could reward treachery, misinformation, or deceitfulness with in-game skills or rewards. Player spoken audio could transform storylines or alter gameplay. Player spoken inputs captured by the game could be reviewed after a game or made into a transcript.

Non-verbal auditory data such as muttering, exclamations, or breathing rates could be used to enable game functionality. For example, a player muttering under their breath could be mirrored by an in-game character. The respiration rate of the player could also be mirrored in game. The central controller could utilize non-verbal auditory data (e.g. tone, cadence, breathing rates) to detect the sentiment and engagement level of the player and dynamically change game content. Non-verbal audio data could also be used as a metric for reviewing player performance post-game.

Players often use visual skins to customize their characters. Devices according to various embodiments could facilitate "audio skins" or customization of in-game character voices. For example, players could speak character vocal lines or scripts. For example, a voice track could be generated based upon a player's voice. A player could be prompted to provide a training set for an AI module by speaking particular lines or vocal cues. The AI module could then generate in-game audio based upon their voice. Players could modify character voices through audio filters. Players could purchase audio filters of either their own voice or of in-game characters. Players could utilize game character voices within their own player-to-player audio channels.

Attributes of gameplay could alter a players or game character's voice, either in-game audio or in player-to-player audio channels. For example, a loot drop box could contain items that change the pitch or volume of a player's voice, alter the comprehensibility of a players voice, or alter the player's ability to speak. For example, game functions could create a helium-like filter for a player or it could make the player slur their words.

Attributes of the game environment could shape audio functionality. For example, the ability of players to communicate with other players or non-player characters could be affected by loud in-game noises. For example, an in-game waterfall or thunderstorm could drown out audio or intermittently mask audio. For example if I am playing a game in an open field you could hear sounds of nature or the sound is digitized to sound like you are outside. Another example is the sound if you are being shot at and hear the bullet go past you. Another example is that if you are in an open room (concrete room) you may hear reverb. If players are inside buildings or around corners from each other, game communication could be disabled to match the performance of radios or communication devices.

Devices according to various embodiments could enable players to interact with other player's headsets—to communicate, alter the functionality or otherwise interact via the devices' outputs. For example, a player could make another players headset vibrate or change color. If you are getting close to your opponent, you may want to send noises or comments that make them more anxious. This is in an effort to make your opponent be on edge a bit more and make mistakes. If for example you are killed in-game by another player, they could temporarily control your headsets audio, visual or tactile outputs. For example, the headset could output an audio clip of the other players choice or have their name displayed on your devices.

The central controller 110 could detect the sentiment of player communications, prompt or coach players on their tone, or control access to the game or chat functions. For example, it could send messages to a player when it detects aggressive language, tone or intensity. The central controller could prompt the player to calm down, apologize, or suggest alternative language. If the player continues to engage in inappropriate behavior, the central controller could remove the player's communication abilities, pause the player's inputs (allowing other players to take advantage of the non-responsive controls), remove the player from the game, add the player to a ban list, or otherwise punish the player. Positive behavior could be incentivized. The game controller, the central controller, or a third party such as a parent or regulator could set a list of particular words, phrases, or behaviors to encourage or discourage. The game controller, the central controller or third parties such as parents could set a threshold of behavior that triggers positive or negative consequences. Positive in-game behavior could be used to offset negative behavior.

Devices could allow offline modes for games or for headset-to-headset gaming. In some embodiments, game software could be installed in the headset's memory and/or could run using the headset's processor. Games could be played via the headset, with or without additional controllers, when players are not connected to phones, computers, or other computing devices. Headset based localization of games could be useful when players have limited connectivity to networks, such as while driving in rural areas or playing inside subways or dense urban areas. headsets could be connected to each other via Bluetooth®, local area networks, Wi-Fi®, cell data, or other networking methods. In some embodiments, headsets could communicate directly with other headsets. Connecting headsets with other headsets could enable location-based game functionality. Connecting headsets with other headsets could also enable social discovery—connecting players within an area with other players playing the same game or gaming in general. Connecting headsets with other headsets could create hybrid or blended real and game environments, such as live action role playing.

Headsets could connect with cars, vehicles and other modes of transportation, allow players to continue playing games while moving or allow new forms of game functionality, such as location-based game modes. For example, while playing a game while moving, a headset could permit the in-game character to move using an analogous form of transportation. If I am driving a car, then I could be driving a wagon in game.

Physical movement, visiting a particular real world location or travel in the real world could be required to move a character in-game, unlock particular game items, skills or functionalities. Actions taken in the real world could be detected by the headset based upon location data from GPS, Bluetooth® beacons, or other form of positioning system. Accelerometer data could be used to detect particular forms of physical movement. headsets could use location information to dynamically change the game based upon location context. For instance, to unlock a new area of the game, I could be required to visit a particular store or location in the real world. The game controller could detect that I had visited a physical location or performed a particular activity and then unlock in-game functionality. For example, visiting a particular store could unlock a customized digital skin or in-game loot. For example, I could be required to exercise or go outside of my home before a character could level up.

Headsets could allow for the manipulation of information and communication as a controllable aspect of gameplay. In some embodiments, a player might control another's headset, listen in on another's communication in whole or in part, insert disinformation, encrypt or decrypt another's communication, jam or disrupt, or otherwise manipulate another player's in-game audio. For example, a player might use an in-game listening device, such as planting a bug, to spy on another team and gain access to their physical headsets. For example, if a character is killed in game, a player might be able to pick up that characters radio and listen in or send broadcasts. For example, a game might temporarily provide tidbits of radio chatter or team audio as part of a scenario or as in-game loot or reward.

In-game microtransactions could be enabled by the headsets in accordance with various embodiments. The headset could store identity and financial details of the device user. The device owner could set a pin, passphrase, or other form of authentication to unlock in-game purchasing ability. In-game purchases could be enabled by voice command. For example, a player could purchase a temporary level-up, skill, or functionality during a boss fight by saying "buy a potion."

In-game audio controls, such as the volume of player communication, game music, or ambient game noises, could be controlled via inputs on the headset. Buttons, sliders and toggles either on the headset or located on the headset wires could be used to control these functionalities. The headset could control these audio settings via voice recognition. Setting preferences for individual device users could be saved in the headset, either overall preferences or preferences based upon particular games, game scenarios, or types of games. The device could remember these settings or utilize preloaded settings based upon the type of gaming being played. The device could manipulate these settings based upon game play performance, engagement or affective state. For example, when a player is performing poorly, it could increase the game audio and reduce music audio. Game music tracks could be controlled dynamically by the headset, game controller, or central controller based engagement levels or affective states. For example, the game controller could change music genre to create new stimuli or because it detects that a player doesn't like a particular genre of in-game music.

Avatar Management

Video conferencing calls often have participants in a gallery view so that you can see most or all of the participants. Participants can decide to enable a video feed of themselves if they have a camera, or they can have a still photo of themselves to represent them, or they can have a blank representation typically with only a name or telephone number shown. There are situations, however, when a user would like a greater amount of control in how they are represented in a video call.

In various embodiments, a user can create a cartoon character as a video call avatar that embodies elements of the user without revealing all of the details of the users face or clothing. For example, the user could be represented in the call as a less distinct cartoon character that provided a generic looking face and simplified arms and hands. The character could be animated and controlled by the users headset. A user might create a cartoon character, but have his headset track movement of his head, eyes, and mouth. In this embodiment, when the user tilts his head to the left an accelerometer in his headset registers the movement and sends the movement data to the headset's processor which is in control of the users animated avatar, tilting the avatar's head to the left to mirror the head motion of the user. In this way, the user is able to communicate an essence of himself without requiring a full video stream. The user could also provide a verbal command to his headset processor to make his avatar nod, even though the user himself is not nodding. One of the benefits to using an avatar is that it would require significantly less bandwidth to achieve (another way to reduce bandwidth used is to show a user in black and white or grayscale). The user's headset processor could also use data from an inward looking video camera to capture movement of the users eyes and mouth, with the processor managing to control the users avatar to reflect the actual facial movements of the user. In this way, the user is able to communicate some emotion via the user's avatar without using a full video feed.

In various embodiments, the user headset includes detachable sensors that can be clipped to the clothing of the user in order to feed whole body movements into the control of the avatar. For example, the user might clip one sensor on each leg and one sensor on each arm. These sensors would provide position data with Bluetooth® or Wi-Fi® to the user's headset processor so as to allow the processor to generate the user's avatar to reflect the arm and leg motions of the user. For example, this would enable the user to be able to raise his right arm and see his avatar raise its corresponding right arm as well. By employing a larger number of sensors, the user could enable the creation of an avatar with a greater level of position control.

The user's avatar could be created to look something like the user, such as by matching the user's hair color, hair style, color of eyes, color of clothing, height, etc. Clothing color could be picked up by an inward facing camera of the user's headset and reflected in the clothing color of the users avatar. Users could also have several different avatars, selecting the one that they want to use before a call, or switching avatars during the call. Alternatively, the user could define triggers which automatically change his avatar, such as changing the avatar whenever the user is speaking. The owner of the call could also change a users avatar, or even substitute one of the meeting owner's avatars for the one that the user is currently employing.

Avatars could be licensed characters, and could include catch phrases or motions that are associated with that character.

Users might have one avatar for use in game playing, another avatar for use in school online lessons, and another avatar for video calls with friends and family. The user could also deploy his game avatar while participating in a video call with friends.

Avatars could also be used as ice breakers in video meetings. For example, a user might have an avatar that can add or remove a college football helmet of his alma mater. The owner of the call might also be able to add a helmet to each meeting participant based on their alma mater. The user could have a separate avatar for his dog which appears whenever the dog begins to bark.

In various embodiments, the user is able to have control of the space that appears behind her on a video call. Instead of putting up a photo as a virtual backdrop behind her, the user could use her headset to create a more dynamic background that could entertain or inform other call participants. For example, the user might speak into a microphone of the user's headset, with the audio signal being processed by the processor of the headset with speech to text software. The resulting text could be displayed in the space behind the user on the video call.

In various embodiments, the user creates small drawings or doodles using a mouse that is wirelessly connected to the headset. The headset processor 405 then sends these images to the meeting video feed so that they appear behind the user during a video call. Users could create a "thought bubble" to the right or left of their image on a call. Alternatively, the user could do a drawing but have it overlaid on top of the image of another call participant's head. For example, the user could sketch a pair of eyeglasses to appear on the face of another call participant.

Users could also direct the headset processor to alter the images of other participants on a video call, flipping the images upside down or sideways, or invert the image right to left. Such alterations could be done to appear only in the call video feed that the user sees, or in the call video feed that every call participant sees.

In various embodiments, the user employs degrees of blurring of their face during a video call. For example, a user just waking up might not want other call participants to see that their hair was not combed and elect to blur out their image somewhat, or elect to blur out just their hair.

Non-Player Character Management

While call participants are used to dealing with photos and videos of other call participants, along with the occasional backdrop image, various embodiments provide options for far greater interactivity and creativity in the way the traditional video call gallery looks.

In various embodiments, software used to host online calls is enabled to allow non-player characters to move about in a gallery view of call participants. For example, a non-player character could be a cartoon image of a sheriff which shows up randomly on the backdrops of users in a video call. For example, a user might have a video feed of himself displayed to all of the other users on a video call when the sheriff character shows up next to the image of the user. These non-player characters could appear on some user backgrounds but not others. They could be programmed to only show up during breaks or in between agenda items when users are looking for a moment to have fun and relax.

In various embodiments, two non-player characters could interact with each other. For example, a sheriff character and a thief character might show up in the backgrounds of two different users. The sheriff character then throws a lasso over to the thief character and reels him into the background in which the sheriff is currently positioned.

Non-player characters could add some fun to calls, but could also serve useful roles on a call and could help to improve the behaviors of users on the call. For example, a librarian character could show up in the background of a user who seemed to have forgotten to go off mute, with the librarian character telling the user to be quiet. The participants on a call could have the option to double click on the image of a participant who they think should be on mute, summoning the librarian character to appear and give a warning to the offending user. In this way, a light hearted and anonymous measure can be taken to improve call behaviors.

Non-player characters could also be associated with particular roles on a call. For example, the call owner could have a dragon character by the side of his video image as a reminder to the rest of the users that he holds a lot of power on the call. A character with a wooden hook could "pull" a user out of a gallery frame when they speak too long.

Non-player characters could be used to amplify or exaggerate the emotional state of a call participant, such as by having a devil character appear next to the image of a user who has been speaking loudly.

These characters could appear to walk by, appear behind a user, or peak out from behind a user.

Examples of non-player characters include a Sheriff (who might appear when the meeting is drifting away from the agenda), Barkeep (when someone is listening and fully engaged according to that users headset), Villain, "Damsel" in distress (for a user who is struggling with the call software), Fire fighter, Trickster, Snake oil salesman, Time keeper, round keeper, Master of Ceremonies, DJ, Boxing announcer, Messenger (when one user wants to initiate a sub-channel communication with another user), Ambassador, etc.

Non-player characters could also be licensed characters that are purchased from the central controller. Examples include Simpsons characters, King Kong, the Godfather character, Disney princesses, Star Wars characters who can have light saber battles during a call, and the like. These licensed characters could also have associated sound bite catch phrases or short video clips of licensed content.

Appearance of non-player characters could be determined by a vote of the call participants, or an appearance could be triggered by the request of a single call participant. In another embodiment, a user not currently on the call could initiate the appearance of a character to explain why the user was late for the call.

These characters do not have to be characters. In some embodiments, the non-player character is a lightning strike that hits a call participant who was identified by the meeting owner as having a good brainstorming idea. There could be a conch shell object that a user "hands over" to another user when the first user is done talking.

Non-player characters can interact with user images, such as a firefighter character pouring water on a user who has been talking for more than five minutes continuously.

Games could be facilitated to entertain users on a call or serve as a warm up exercise. The call platform could prompt everyone at the start of a call to say a word that begins with "R." Or the call platform randomly picks a first user and requests that they say a word or sentence beginning with the letter "A", and then picks a second user at random to start a word or sentence with the letter "B", and so on until "Z." In an improv game of Count to Twenty, users could start by shouting out the number 1, then 2, then 3, etc. But if two users say the same number at the same time, the platform determines that a word collision has occurred, and the users have to start back at number 1. A non-player character could introduce the rules to the users.

Non-player characters could be awarded to call participants for tagging content, taking notes, helping others on the call, being supportive, or encouraging a shy participant to speak up. Meeting owners could also award participants coins for good behavior, with users buying non-player characters with those coins.

In some embodiments, call participants could buy a subscription to licensed characters, or buy clothing that would trigger the appearance of non-player characters.

Heating, Cooling and Power Management

The inclusion of sensors and other accessories may consume power and generate heat. The management of these devices and controlling the heat may be beneficial, e.g., to make the headset more comfortable.

Heat dissipation may be accomplished in various ways. A fan may be used for cooling the headset and person. Liquid cooling may be utilized, such as cooling that allows for the flow of a supercooled substance to regulate the temperature of the device. In various embodiments, adaptive fabrics are used on the covering of the headset to release heat more efficiently and at the same time cool the user. In various embodiments, a headset may be adaptive to outdoor and body temperature. If the outside temperature is cold or the body is cold, the sensors could continue to function and provide body warmth.

In various embodiments, sensors may be controlled with a view to heat dissipation. A headset may control processes to regulate sensor/processing to reduce heat. There may be times that sensors need to be turned off in the case of malfunction or to reduce heat. The central controller 110 could monitor the temperature of the overall headset and once it reaches a level or if a sensor is malfunctioning, begin to turn off the appropriate sensor. The order the sensors are turned off could be a preference the user sets based on their use. For example, a casual user on a walk may prefer that all biometric sensors be turned off, but the camera, microphone and light feature be left on for safety purposes. In the event that all sensors are turned off, the user could be notified for corrective action (repair, removal or to get to a cooler place).

Sensors may switch on and off dynamically, altering which is recording. The use of some sensors may be prioritized over the use of other sensors. If the headset reaches temperatures in excess of the stated limits, the headset could turn off sensors and other functions to reduce thermal output. For example, the inward camera could be turned off, the various sensors turned off in order (e.g. EEG, Oxygen, temperature) but leave core functions like the microphone enabled. Once the temperature returns to a normal state, the sensors could be automatically turned on and the user informed.

In various embodiments, the headset may control the use of the sensors and other functions based on the power level (0% to 100%) of the headset.

A headset may employ equalizer-like controls. The headset could be equipped with knobs/buttons/sliding wire controls that allow the user to dynamically manage the power consumption and function of the sensors when the overall power level is low. For example, the user may use a control knob to reduce the video quality of the camera, turn the inward camera off or stop recording the EEG and temperature readings.

Various embodiments may facilitate prioritization of sensors, quality of or frequency of input readings, and/or mode (connected or not). The central controller 110 could allow the user to set power consumption preferences related to the priority of senor use and level (more or less sensor readings), quality of reading and recordings or connectivity (cellular, Wi-Fi® or no connectivity). As the power is consumed, the headset and central controller could alert the user which sensor and functions are reduced in capability or turned off. At a certain point in power consumption, the user could be informed that the device is turning off and to recharge.

The headset could be powered by a direct wired connection, USB connection, magnetic connection or any other computer or device where sharing of power is available.

A headset according to various embodiments may offload processing to another device or PC. Using headset processing to enable the device could consume power. The headset could have the ability to connect to another processing device (e.g. computer, cell phone, tablet, watch, central controller) and use their processing power to collect and analyze data collected from the headset. This could reduce the power consumption needs of the headset.

A headset according to various embodiments could be outfitted to allow for wireless charging. An example could be the use of magnetic charging.

Various embodiments facilitate power generation from head movement. Kinetic energy may be generated from the movement of the head while a user is wearing a headset. The kinetic energy generated could be stored in the headset and used to power the various sensors and functions.

A headset could have a power supply (e.g., batteries) that could be swapped and recharged for use at a later time. The power pack could be put in a rechargeable device and used later when power is depleted on the headset.

In various embodiments, sensors/modules have their own batteries. The sensors or any supported function/add-on in the headset could be powered by their own batteries. This could offload power consumption from the main headset power.

In various embodiments, a headset (or any sensor or other component thereof) may be solar powered. The headband on the headset could be equipped with a solar panel. The energy collected from the solar panel could be used to power the headset and sensors on the headset.

Based on a users activity (start and end), the headset could go from sleep mode to active mode. For example, prior to a meeting, the headset could be sitting on the user's desk and in sleep mode. Once the meeting begins and the headset is placed on the head, the headset could automatically go into active mode with all sensors and functions activated. If the user is a participant only and not playing a defined role (e.g. decision maker, innovator, SME, meeting owner), the headset power could go into conservation mode and disable power consumption for specified sensors (e.g. EEG, EKG, outward camera) or based on the preferences of the user.

In various embodiments, geofencing controls power modes. The headset device could enable/disable sensors and functions based on the established geography of the device. For example, if a company owned headset is to be used only for on-property purposes, the headset could be powered only when the device is in the geography of the company. In addition, if a runner wants to have exercise-type sensors function for a running path, the user could establish the route in a preference and only those sensors would then be powered by the headset in the defined geography.

Emergency and Safety

The use of devices to alert emergency personnel or prevent accidents from occurring is a potential benefit in various embodiments. The headset, e.g., via its sensors and cameras, could continually monitor the user's environment and respond to vocal/non-vocal events to provide emergency services and feedback.

Various embodiments facilitate alerts to complete activities. There are times when users are distracted and forget to complete a task. The headset equipped with a camera can record the activity, send the information to the central controller AI system and alert them if the task was not completed. This can help with improving human performance and focus on a task to completion.

For example, a parent may put a child in the car during a hot summer day to go to daycare. The parent is distracted with conference calls and mental wandering and drives to work, forgetting to drop off the child. When the user arrives at work and closes the door, the headset and central control AI system recognizes the task of removing the child from the car seat did not take place and alerts the user via the headphone audio Net child from car) or emergency vibration.

As another example, a user may decide to cook a steak on the grill. They place the steak on the grill and leave the patio. They are distracted by someone coming to the door and starting a conversation. 15 minutes later they recall the steak was left on the grill and burned. With the headset, the camera could record the user putting a steak on the grill. The central controller AI system knows the steak is being grilled, in 7 minutes of cooking does not record movement to the grill and alerts the user to complete the activity and move to the grill to turn the steak.

As another example, in business, interruptions occur all the time. The camera could record a user preparing an expense report, but is interrupted. The central controller AI system could later alert the user that the activity was not completed.

Various embodiments facilitate voice activated connections. For example, a user could request to be connected with "poison control". The headset could respond to vocal commands and call the appropriate emergency department. Examples included 9-1-1, Poison Control or Animal Control.

Various embodiments facilitate voice activated feedback, such as emergency feedback. The headset could recognize that any emergency call has been placed and immediately provide helpful feedback. Examples include directing the user to begin CPR, not induce vomiting for ingestion of certain cleaners, applying pressure to a cut or providing calming sounds if the headset notices a spike in heart rate or blood pressure.

Various embodiments facilitate sound enabled connections. Various embodiments facilitate providing useful information to emergency authorities. In an exemplary situation, a user says "Contact Security, active threat". The headset could understand these types of statements and call a company's security department and local authorities. While connected, all sounds could be recorded and delivered. These may be gunshots, statements made by the people involved in the incident, video of the actual event and global positioning. All of this information collected by the central controller AI system, in combination with the actual layout of the facility, could be made available to emergency responders and analyzed for the best plan of action prior to arriving at the scene.

In the event of someone falling while they are alone, the headset could contact emergency responders, record the user's vital signs using the enabled sensors and provide authorities with video footage of the incident. Furthermore, the responders could also deliver information to the person as a way to help them regain consciousness or inform them that assistance is on the way Various embodiments facilitate telling a person where to go and how to get there. In the case of a fire or places that are unfamiliar to a user when an emergency begins, the headset could provide guidance. For example, if a fire started in a building that is unfamiliar to the user, the headset could use information from the central controller (with access to public information) to inform the user how to exit. The emergency responders could inform the user which path to take to avoid closures or where there is impending danger.

Various embodiments facilitate coaching a user through a Heimlich maneuver or CPR. Bystanders are often used to engage in emergency procedures while waiting on emergency responders. At times, users do not have immediate recall or lack the basic understanding to perform the emergency function without some coaching. The headset could coach the user through emergency procedures. For example, if a person is choking at a restaurant, a user of a headset could request coaching on the Heimlich maneuver. The central controller could respond with the steps or a video. In addition, since the camera is enabled, it could inform the user of any corrections needed during the maneuver.

Various embodiments facilitate engaging emergency lights on top of the headset. There may be situations where a user is stranded and need to inform others. For example, if a car is broken down on the side of a road, the user could enable the lights on the headset to signal an emergency. Likewise, if a biker is wearing the headset and falls or is hit, the headset could also light up automatically. Headset sensors could be automatically enabled to collect data and send to emergency responders through the central control AI system.

In various embodiments, an inbound emergency headset contact number and conditions get patched through immediately. Users participate in activities by themselves (e.g. biking, running, walking, shopping) or with people that do not have headsets. If an emergency occurs the headset may contact the users emergency contacts immediately and inform them of the location and connect them to the individual. In addition, the emergency contact information and health data of the individual is immediately provided via the central controller 110 to the emergency personnel during the dispatching process.

Various embodiments facilitate overriding a users phone settings, e.g., with respect to blocked calls or with respect to a silent mode. There are situations where people do not answer cell phone calls after repeated attempts because they do not have their phone, silence their phone or leave it in their office/home. But, they need to be contacted. For example, a mother leaves their child at daycare and the child becomes ill. The mother, a user of a headset, is attending an important meeting and silences her cell phone or leaves it in her office. The daycare needs to desperately contact her, but fails. After repeated attempts to the phone, the phone call can be immediately transferred to the headset for connection. The list of priority individuals where a call can be automatically transferred and event interrupted could be maintained in the user's preference on the central controller (e.g. daycare, school child, spouse, parents).

Various embodiments facilitate use of a headset as a driving assistant. There are examples where headsets can prevent accidents. For example, with the accelerometer and inward/outward camera, the headset could notice the head dropping and determine the user is falling asleep while driving. In this case, the headset could alert the user via vibration alerts and vocal alerts to stop the car. In cases where there are environmental distractions, the headset could inform the driver to take corrective action. For example, the headset could notice it is raining outside, there are multiple people in the car speaking/yelling/singing, visibility is reduced, the music is turned up to excessive levels and the biometric sensor data collected notices a high heart rate, irregular EEG and reduced breathing. In this case the headset could inform the user to slow down, turn down the music, encourage people to stop talking and take a few deep breaths to avoid an accident.

Situational (Environmental) Awareness

Environmental conditions, sounds and images are constantly collected by the user to take action or ignore. Many of these indicators are but casually observed, overlooked or not even noticed given other senses are fully engaged. The headset can provide ongoing environmental awareness and alert the user, even when they are not engaged mentally.

In various embodiments, a headset microphone collects audio information from the environment. In various embodiments, audio collection of siren (emergency) noise causes runners/bikers to be alerted for action. For example, if a person on a bike wearing a headset hears a siren (via the microphone), the biker is alerted in the headphone (e.g. 'emergency vehicles approaching') or the headphones vibrate.

A microphone may collect audio from animals. The headset could listen for animal noises to alert the user in advance. For example, if a person is walking, listening to music, they may not hear a dog approaching them (angry or friendly). This could startle the user and create panic in the animal with unintended consequences. The headset could listen for the barking dog running toward the walker. The headset could notify the user that a dog is approaching.

In various embodiments, a headset camera collects visual information from the environment. Consistent with some examples, footsteps/bicycle images behind (or in front of) the user are collected from the camera(s). If the user attempts to move to the left or right and the microphone or camera notices someone approaching quickly, vibrate the earphone so the user does not move over in front of them or give you an opportunity to alert those behind you.

In various embodiments, a forward facing camera can provide the user with the distance to an identified point (e.g., the camera can serve as a rangefinder). For example, a runner wants to know how far down the path until they run 0.5 miles. The user could speak into the microphone of the headset and make a request (e.g. 'show location in 0.5 miles'), the camera could be engaged and headset respond from the central controller AI system with the landmark in front of the user (e.g. 'to the red brick house on the right' or show on the display screen).

In various embodiments, a camera can trigger a volume adjustment. Users in public often listen to other audio (e.g. books, podcast, music, telephone calls). When the camera on a headset notices another user approach and begin to speak, the volume could be turned down or muted for listening. In addition, if the camera notices heavy traffic before the user wants to cross in the intersection, the audio volume could automatically be turned off or reduced.

Various embodiments facilitate litter control. Those searching for litter to clean the environment could be alerted by the headset. Using the forward facing camera, the camera could continually monitor the environmental surroundings and detect trash. The display screen or audio alert could notify the user of trash in proximity so it can be picked up and disposed of. This could be considered the 'metal detector for trash' using a camera.

Various embodiments facilitate sharing and/or evaluation of images (e.g., among large groups of people). Groups of people with headsets equipped with cameras, audio and sensors could share information with others via the central controller AI system and relay this to others when appropriate. For example, if a person goes for a walk on a path and discovers that it is covered with rain from the night before, the GPS, camera and audio could pick up this information and store it in the central controller AI system. Later that morning, another person on the same path using a headset could be alerted in advance that the path is covered with water and to reroute their walk.

Air Quality Sensor

A headset according to various embodiments may include an air quality sensor. The sensor may detect pollution and alert one or more people as to the presence of the pollution. People desire to breathe clean air while outside or inside. The sensor equipped headset could continually monitor air particulates, volatile organic compounds, pollen levels, ozone levels or other aspects of air quality. The headset could alert the user if they reach unacceptable levels. For example, if the family is outside on a casual bike ride and ventures past a paper processing plant, the headset could alert the user that they are entering a zone with high levels of methane gas. The alert could be in the form of an audio announcement or vibration. When the family exits the area and air quality improves, another announcement is made through the headset.

Various embodiments facilitate obtaining crowd-sourced data about pollution. If multiple people with headsets pick up the pollution, the information could be sent to the EPA (Environmental Protection Agency) or appropriate local authorities. For example, each morning, people drive cars to offices and are routinely stuck in traffic creating CO2 and other pollutants. The headset picks up the pollutants and informs the central controller AI system. The central controller AI system could know the traffic patterns of drivers and alert them to avoid the area due to pollution. This could be sent to their audio headset or in report format. In addition, the local authorities or EPA could be informed by the central controller of high pollution levels for notification to the community at large. Crowd sourced pollution data could also be shared via an API. For example, crowd sourced data could be integrated into mapping software to route walking, running or cycling individuals away from point sources of pollution or prompt users to avoid using human mobility during certain times of day. For example, crowd sourced pollution data could be integrated into health and exercise software to inform individuals about their exposures to different sources of pollution across different time scales, such as daily exposure to small particulates or VOCs. Air quality data could be integrated with other sensor data such as respiration or heart rate data to model how air quality impacts different aspects of exercise or health such as running performance, asthma risks, or lung cancer risks. Crowd sourced pollution data from headsets could be used to inform advertising, insurance or other commercial purposes. For example, if an individual has been exposed to outdoor pollen, the central controller via an API could share that data with companies marketing antihistamines. A company might improve insurance models by utilizing crowd sourced pollution data. For example, a company might increase insurance rates for a business if distributed pollution sensors such as headsets reveal that individuals downwind of the business are exposed to higher levels of pollution.

In various embodiments, a headset, e.g., using a microphone, may monitor ambient noise, such as to measure noise pollution. Individuals are continually exposed to ambient noise levels that may damage their hearing, reduce cognitive performance or otherwise affect their health. The device could utilize the main microphones as an ambient sound sensor or could include an ambient noise sensor. A headset could communicate ambient noise data to a connected cell phone, computing device, other headsets in a local network, or to the central controller. Ambient noise data from the central controller could be made available via an API. The device could be enabled to collect ambient noise data when the device is not being worn. Device owners could be prompted with visual, tactile, or audio alerts about high levels of noise pollution or dangerous forms of ambient noise, such as particular frequencies. The central controller could collect aggregate noise exposure data for individuals. The central controller could also collect ambient noise data to develop crowdsourced geospatial data on noise pollution. The central controller could prompt local government authorities about high levels of ambient noise. For example, the central controller could contact the government about noise complaints from loud parties, construction work, or overhead aircraft. Crowd sourced noise data from headsets could be used to inform real estate, advertising, insurance or other commercial purposes. For example, ambient noise data could be used in real estate to gauge the desirability of living in a particular neighborhood or whether an individual apartment within an apartment building is noisy.

Public Health Embodiments

Many public health issues require collecting fine-grained, disaggregated data about individuals' health and their social contacts. Obtaining high levels of resolution both spatially and temporally, while respecting the privacy of individuals whose data is being collected, is a difficult challenge. The devices according to various embodiments could detect individual level health data, could anonymize and share that data with public authorities, healthcare workers and researchers, and could enable social contact tracing for communicable diseases.

Devices could contain many sensors that could be used to aid in the detection of disease symptoms for the device owner and symptoms in others, such as thermal cameras, ear thermometers, forward facing RGB cameras and other sensors. For communicable diseases such as SARs-2 Covid 19, an AI module could be trained that could detect common symptoms such as coughing, elevated temperature, and muscle rigors (shaking from chills) using forward facing thermal cameras or RGB cameras in the device. The central controller could compare an individual's temperature with baseline readings and prompt the individual with an alert if they had an elevated temperature. An AI module could be trained to detect whether the device owner was sick, detecting for example sneezing, coughing or muscle rigors from accelerometer data or through an inward-facing camera in the microphone arm. The central controller could then prompt the device owner through an alert that the device owner was likely to be sick.

Devices could also aid in detecting whether others around the device owner were likely to be sick and aid in contact tracing. The device for example could record when others sneeze, cough, or display visual indications of a disease. The device could also record the identity of others in the vicinity through for example facial imagery, through Bluetooth® proximity data or through a token protocol. The device could communicate with other devices and/or the central controller to share both the symptoms and the identity of individuals who had been likely to be exposed. The central controller could prompt the owners of devices that they had been in the vicinity of individuals displaying symptoms and suggest they engage self-quarantine and also prompt public health officials with an alert to test the individuals who had potentially been exposed. Health and social contact data shared with the central controller could be made available to public health officials, medical personnel or researchers via an API.

By logging into the device or otherwise authenticating the identity of the wearer, the headset could enable public health authorities to detect whether individuals were observing a quarantine. Using a location geofence around the wearers place of residence, the central controller could detect whether an individual had left their home and broken the quarantine. Likewise, the central controller could detect whether individuals had visited a quarantined individual.

Headsets for Exercise

Comprehensive exercise data is increasingly important to athletes, both novice and professional. The data is used to improve endurance, form and to reduce injuries. Many devices (e.g. Smart Watch) currently collect data for observation during the activity and analysis after the exercise, but provide limited immediate feedback to improve the athlete. The headset device is equipped with sensors to collect heart rate, oxygen levels, galvanic (sweat/hydration levels), accelerometer and temperature. In addition, the use of the camera on the headset is used to gather visual data for immediate/post analysis of the exercise for feedback to the athlete.

Real-time monitoring and feedback of athletic performance to athletes. A runner, biker, weightlifter, basketball player, soccer player or athlete of any type may have varying degrees of performance at various times, but not enough comprehensive data to make the needed adjustments. These can be the time of day, type of exercise, length of exercise or physical condition of the athlete. The headset, with sensors and cameras can collect the following information, process via the headset processor 405 and feedback provided to the athlete during the exercise activity.

Various embodiments facilitate monitoring oxygen levels. Measuring oxygen levels is important feedback to provide the athlete as a reminder to intake more air and breath. The headset oxygen sensor monitors the oxygen levels in the body, transmits this to the headset processor 405 which is sent to the central controller for AI analysis. If the oxygen level is low, the results are transmitted to the athlete via the central controller to the headset processor 405.

Various embodiments facilitate monitoring heart rate. The heart rate is something done in devices today, but analysis of the data and feedback to the athlete is minimal. The headset heart rate monitor measures the heart rate, transmits this to the headset processor 405 which is sent to the central controller for AI analysis. If the heart rate level is too low or high, the results are transmitted to the athlete via the central controller to the headset processor 405 with a reminder to slow the heart rate or increase the pace to increase the heart rate if that is the goal of the athlete.

Various embodiments facilitate monitoring galvanic/hydration levels. Dehydration is a serious concern for many athletes, especially in a location with high temperature/humidity, and is sometimes a dangerous condition. The headset galvanic sensor measures the hydration level of the athlete, transmits this to the headset processor 405 which is sent to the central controller for AI analysis. If the hydration level is too low, the results are transmitted to the athlete via the central controller to the headset processor 405 with a reminder to drink more fluids.

Various embodiments facilitate monitoring acceleration, e.g., via an accelerometer. Measuring acceleration for runners, walkers, bikers or other activities with forward motion may help with improving performance. Many devices measure average speed over a distance, but few provide real time information of acceleration during the exercise activity. The headset accelerometer measures the athlete's acceleration, transmits this to the headset processor 405 which is sent to the central controller for AI analysis. The results are transmitted to the athlete via the central controller to the headset processor 405 with information indicating that the acceleration is consistent with the athlete's desired goal or to increase their acceleration or to adjust their gait to increase/decrease acceleration.

Various embodiments facilitate monitoring temperature. Athlete temperature is a serious concern for many athletes, especially in locations with high temperature/humidity or cold/dry climates. The temperature sensor measures the body/skin temperature of the athlete, transmits this to the headset processor 405 which is sent to the central controller for AI analysis. If the temperature of the athlete is too low, the results are transmitted to the athlete via the central controller to the headset processor 405 with a reminder to dress warmer or indications of other issues, like dehydration. If the results indicate the body temperature is too high, the reminder to the athlete from the central controller may be to remove clothing, slow/stop the exercise, drink more fluids, get to shade or assist in contacting emergency personnel.

In various embodiments, athletic form is captured and evaluated by using a forward facing camera. Proper form is a key element to preventing injury and improving athletic performance, but is rarely captured unless you have a coach observing and providing feedback or you have access to a mirror to observe yourself. The forward facing camera as part of the headset invention could capture movement of the athlete during the exercise for arm movement, stride/leg extension, foot placement, posture and vertical motion. For example, during a run, the camera could capture the stride of the runner and placement of the foot on the ground. If the stride is too long and the leg fully extended, this could cause injury to the knee. Whereas, a shorter stride, where the leg is not fully extended and the stride length reduced could result in lesser injuries. This information could be collected by the headset processor 405 via the forward facing camera, transmitted to the central controller and feedback provided to the runner, real-time or after the fact. This allows the runner to be coached immediately for improved performance. Another example is for weightlifters. Incorrect form could cause serious injuries. If someone is performing a deadlift with an arched back, incorrect hand placement on the weight when bent over, or incorrect stance, The forward facing camera, as part of the headset invention, could provide feedback to the user for weight lifting form and movement of the athlete during the exercise. This information could be collected by the headset processor 405 via the forward facing camera, transmitted to the central controller and feedback provided to the weight lifter, real-time or after the fact. This allows the weightlifter to be coached immediately for improved performance with feedback to pull your shoulders back and not arch your back, place your feet shoulder width apart or place your hand closer together on the weights. Another example could be for use in yoga. As these moves can be complex, the headset with camera could monitor the move and provide feedback if the yoga position were incorrect. This could result in improved performance and less injury.

Various embodiments facilitate monitoring rehabilitation (e.g., compliance with rehabilitation exercises). For example, if the physical therapist provides a list of stretching exercises in the form of a piece of paper with written instructions, the execution of those at home and on your own is not continually observed by the therapist for immediate correction. With the forward facing camera, the therapy movements could be captured by the camera via the headset processor 405, transmitted to the central controller for AI analysis and immediate corrective feedback or encouragement sent to the individual. This could accelerate the therapeutic impacts and reduce healing time as well as provide confirmation to the therapist that the patient performed the exercises correctly.

In various embodiments, a headset may flash or glow to alert bystanders or signal turns. indicator. Many people are using the same space to exercise (run, bike, walk), walk with pets, ride motorized vehicles (e-bikes, scooters) at various speeds and response patterns. This is increasing the rate of accidents between these various people and activities. The headset could be equipped with a flashing light/glowing symbol to indicate to those in front of you and behind you of your intention and movement direction. For example, with the voice, accelerator and camera headset, if you are approaching another person, you could move your head to the left or say 'left move' which could light the headset symbol on the front and back indicating you are moving to the left. If you are intending to stop, you could shake your head multiple times or say 'stop' and the headset symbol on the front and back could display a stop sign symbol. The information could be facilitated by the sensor collecting information, transmitting to the headset processor 405 and the headset activating the light, glow or symbol.

In various embodiments, a headset may include a path light for exercise or other activity. People that exercise at the end of the day or evening are oftentimes met with changing conditions from dusk to full darkness. The light headset could activate the light when the outside conditions turn dark or cloudy, thus increasing visibility. If the camera senses that visibility is reduced, the lights on the headset could turn on automatically providing visibility to the individual.

In various embodiments, a 360 degree camera on the headset could be configured to provide continual feedback to users. For example, suppose a runner is on a path and decides to move to the left. The 360 degree camera could see a biker or car coming up quickly behind them and inform them to not move to the left, avoiding a collision.

The collection of the sensor data from the headset could also be stored locally during the exercise and analysis/feedback not performed real time. The headset processor 405 with sensors could collect the data, the user connects the headset to the user device 107*a*, the user device transmits the data to the central controller 110 for AI analysis and feedback provided to the individual of the activity they complete. The feedback could be in the form of audio coaching, video coaching showing your activity overtime using the enabled camera, or text of results and improvement opportunities post the activity.

Keyword Review

There are many communications (such as meetings, one-on-one sessions, or inbound calls) in which one participant is operating under regulations or guidelines that restrict what he or she can say in that session.

In some embodiments, a user saying a particular keyword or key phrase into a microphone of the user headset triggers immediate intervention from an authorized representative of a company or a regulatory body. For example, an employee conducting a job interview who asks the interviewee an impermissible question might trigger the headset to initiate a call to an HR representative of the company to provide guidance on what the employee needs to do next, or tells the employee to wait until an HR representative comes to the interview room. In this embodiment, the user headset might also provide audio warnings during the interview when such impermissible questions are asked.

Users might also be able to initiate a sub-channel call during an inbound call from a customer. This could be initiated by a user who is not sure about what he should be telling the customer. For example, the user could press a button on his headset when a call comes in asking about warranty options for a new product. The headset then opens a call with the user's supervisor, but only the user can hear the supervisor, and the customer is not able to hear the communication between the user and the supervisor.

A call regarding an employee reference might also be monitored for particular keywords so as to ensure compliance with company policy. For example, the company might have a policy not to verify a previous employee's salary level. If a reference call comes in, the headset could listen to the call content and then generate an audible warning to the employee answering the call if the caller used the word "salary" during the call.

In various embodiments, meeting transcripts could be searched for keywords after the meeting was concluded. For example, a transcript with the word "regulations" could be flagged for further review by a representative of the regulatory department.

In various embodiments, the stress levels of a user during a call, such as an elevated heart rate picked up by a heart rate monitor of the user's headset, could trigger a sub-channel call with someone from HR.

Education

Education, courses, training, examinations and other forms of learning increasingly use software, take place in digital environments, occur over videoconferencing, or utilize telepresence technologies. The devices according to various embodiments could enable improved measurement and feedback of learning and teaching outcomes, as well as provide coaching to students and teachers. devices could allow for personalized educational content or methods of instruction.

Devices according to various embodiments could be used for verification of student identity and ensuring integrity for teaching, courses, and online examinations. Verifying that the correct individual is taking an exam and ensuring that individuals don't cut, copy, or paste material from outside of the exam into the exam software are challenges to replacing in-person exams with online exams. The functionality of exam software could depend on the device owner wearing a headset. A headset according to various embodiments could use authentication, passwords, biometrics sensors or other stored identity information to verify that the individual using the input device is the individual supposed to be taking the exam. Additionally, a forward facing camera in the headset could be used to track the visual field of the device owner and could be used to detect cheating behaviors. For example, it could detect whether individuals were typing answers or whether individuals are cutting, copying, or pasting material into the exam. For example, it could detect individuals were looking at material outside of the exam software. The headset could also be used to detect whether individuals had biometric data consistent with someone taking an exam on their own rather than reading notes or communicating with someone. The exam software could use micro-expressions as an anti-cheat measure. For example, the exam software could ask a question such as "are you cheating?" and then the central controller could use the individual's micro-expressions to detect whether the individual is attempting to conceal information.

During classes, training, or exams, the central controller 110 could detect whether the device owner is utilizing non-education software or whether the device owner is present in front of the computing device through the use of a forward facing camera. The central controller could prompt the device owner to return to the educational software or could lock the functionality of the devices for non-education purposes during classes; until a task, assignment, or homework has been completed; or until the teacher permits a class break.

Devices according to various embodiments could provide a real time measure of student engagement and learning outcomes through an AI module that is trained using the device's inputs, such as camera, audio and biometric sensors. A forward facing camera or the audio data could allow the AI module to detect what kind of learning task or type of material the student is attempting to learn. A camera in the microphone arm or an external camera could provide eye tracking data. In addition, the device could utilize head accelerometer data or tension strain sensors located in the device headband or ear cups to measure head orientation, angles and movements, as well as hand gestures such as a head tilt, facepalming, or intertwining of hands in hair. Other sensors such as galvanic skin responses, heart rate data, thermal cameras, and other biometric sensors could be used to detect physiological responses to different kinds of learning tasks or material. Using these kinds of inputs, an AI module could be trained to detect: engagement levels, affective or emotional states, and microexpressions or other "tells." For example, the AI module could detect excited, apathetic, confused, stressed, or other emotional responses by learning material.

A headset and AI module could be utilized in many ways. Devices could be used to measure learning processes and outcomes during classes, during homework, or during exams. For example, it could provide real time feedback to both learners and teachers about student's engagement levels. For example, an AI module could provide coaching to students about material they find difficult or frustrating. Or an AI module could detect material students find stimulating and give supplemental or additional course material. Additionally, an AI module could measure over time the effectiveness of different teaching strategies for teachers. The AI module could prompt teachers to alter ineffective teaching strategies, reinforce effective teaching strategies, or individualize strategies to different types of students. devices could be used to coach teachers on more effective instruction techniques, the proportion of students with different learning styles, and how to customize material students' learning styles and speeds.

The AI module could track over time student responses to similar material to measure learning outcomes or to enable improved material presentation. An AI module could choose among multiple versions of teaching material to individualize learning to an individual student by dynamically matching versions with a student's learning history, or the module could offer another version if the AI module detects that student is not learning from a particular version.

Devices according to various embodiments could be used to train an AI module that predicts the difficulty of learning material and would allow a teacher or educational software to "dial in" the difficulty of learning material to individualize learning content—either to decrease difficulty or increase difficulty. Devices could also allow the creation of customized syllabi or learning modules, which present the material to students in different sequences depending on learning styles and engagement levels.

Devices according to various embodiments could be used to train an AI module that combines device inputs and sensor inputs to ascertain whether documents, presentations, or other material are challenging to read or comprehend. A headset containing a camera in the microphone arm or in another location that focuses on the wearers eyes or a headset that contains an accelerometer could be used as an eye tracker or head orientation tracker. This data could be combined with a forward facing camera to detect what the device owner is looking at. By tracking eye gaze or head orientation, an AI module could be trained to detect what material individuals spend time looking at and what they do not. By combining eye gaze or head orientation data with other device sensor data such as biometric data, an AI module could be trained that detects micro-expressions, affective states, or other nonverbal "tells" related to viewing material. These insights could be provided to the device owner, the meeting owner or stored in the central controller. These insights could be used to create a coaching tool to improve the quality of presentations and presentation materials.

An eye gaze or head orientation tracker 110 could allow the central controller to measure how much time students are spending on homework or practice outside of the classroom and whether they are engaged with the material ("effective practice").

Devices according to various embodiments could allow third parties such as parents, tutors, school administrators, or auditors to review engagement and learning data as measured by the central controller. Learning data and AI insights could be made available via an API. For example, because a headset could allow measurement of learning outside of traditional testing environments, continual measurement might defeat "teaching to the test." Educational testing could be replaced with engagement levels or other learning metrics from devices. School administrators or other third parties could develop metrics of which teachers are effective from learning data derived from the central controller rather than relying upon existing systems of measurement and evaluation.

Headsets according to various embodiments could permit teachers to pair students for practice session small tasks, assignments, or group projects based upon student's engagement levels, proficiency with the material or other dimension. Students could be able to communicate on an audio channel within the group which the instructor could access.

The inputs of the device could allow for quick quizzes, polls, or answers without students raising a head and waiting to be called on. Students could digitally shout out the answer, which could or could not be shared on the main audio channel of the class, and receive feedback from the teacher or software. Similarly, a student could ask a question out loud and the central controller would recognize the question and not share it with the main audio channel. Consequently, a student would be able to ask a question without waiting for the teacher to ask for questions or raise their hand. Any question could be displayed to the teacher in real time or collected for a later moment. The central controller could store the questions for analysis either by the teacher or by an AI module.

The outputs of the devices according to various embodiments could be utilized for providing feedback to students in the form of visual, tactile, or audio feedback. This feedback can be controlled by the teacher, the central controller, the game or software controller, or an AI module. For example, a student could receive feedback, in the form of visual, vibration, or temperature changes, after they input an answer to the question. The teacher, software, central controller, or AI module could identify whether the question is correct and output a visual signal if correct ("yes", "thumbs up,"), if incorrect, ("no", "thumbs down.")

Students could utilize a tagging or clipping feature to take notes during classes. Students could tag content using keywords, themes, sentiments ("I didn't understand") or action items ("review this" or "ask a question about this"). Additionally, they could clip portions of a class audio and/or presentation material. These tags and clips could be overlaid with audio or text notes generated by the student. These tags, clips, and notes could be made available to the teacher or used by the central controller for analysis.

Devices according to various embodiments could be used for learning a language. For example, it could allow software to detect whether students pronounce words correctly or visually detect whether words are formed using the correct part of the mouth. Gamification of language practice could be enabled by these devices. For example, language practice software could be installed locally on the device hard drive and run using local processors allowing a student to learn while wearing the device but away from a computer, phone, or connected device. For example, while practicing language skills, the central controller could detect whether the speaker is using correct pronunciation, word choice, grammar, and word ordering and give audio or tactical feedback to the speaker. A student or teacher could customize the type of feedback (e.g. vocabulary or grammar rather than both) and also the level of feedback (during a conversation or after the conversation for example). The central controller could detect language errors and then create focused practice to help the learner.

Childcare

Parents are often overwhelmed by the parenting process, especially when they have multiple small children who require a lot of attention. Any help that they can get in making this process easier to manage would be greatly appreciated.

In various embodiments, sensors of a parent's headset can help to make visible issues that previously went unseen. By making the invisible more visible, the parent is able to make more informed decisions and is better able to understand the needs of children.

In one example, the parent's headset includes a sensitive microphone that can pick up sounds outside of the normal human hearing range, or sounds so soft that an aging parent would normally completely miss it. For example, a baby might have an upset stomach that is making very soft gurgling sounds that might easily be missed by a parent. But by wearing a headset with a sensitive microphone, the headset processor could detect these sounds and amplify them for replay into a speaker of the headset, enabling the parent to become aware of the sounds and perhaps alter their behavior in some way as a result.

With a thermal camera attached to a parent's headset, it would be possible for the headset processor 405 to generate a heatmap of a baby which indicated where the baby was warm or cool. This map could be emailed to the parent, or presented to the parent on a display screen of the parent's headset.

With an outward facing camera, the headset could be programmed to detect changes in skin color which might be a precursor to the onset of Jaundice. The video/photo data collected could also be used to detect the earliest stages of the onset of a rash, or reveal how a cut has been healing over time. Data related to the health of the child could be stored in a data storage device of the parent's headset, and it could be transmitted to a physician for review. Video clips, for example, could be shown to a physician via a telemedicine session relating to the child's health.

In various embodiments, the parent could detach a Bluetooth® paired motion sensor from their headset and attach it to an arm or leg of the baby so that the headset could detect small changes in the baby's mobility over time, which could allow a parent to be able to better predict in advance when a baby is going to get sick.

Babies make a lot of movements that are often mistaken for seizures, including having a quivering chin, trembling hands, and jerky arm movements. The outward camera could detect these micro-movements and assure the parent there is nothing to worry about or compare to babies of similar age and alert the parent if they should take the baby for further diagnosis.

The parent's headset could include a camera and microphone that could record and tag the emotions of a child. For example, parents want to capture the development of their children, including laughing, cooing, and new movements like clapping and rolling over. These emotions and movements could be captured more quickly than retrieving a cell phone and tag these for storage and retrieval. The parents could also compare responses from a child over time (from night to day) and compare to see if emotions are getting stronger.

With an outward camera and microphone, the parent could capture if the baby is in pain or which body part is affected. The emotions, movements and complete body scanning could be captured and compared to a bank of other baby responses. This comparison could assist the parent and indicate if the emotion is common among babies or if there is a need for further diagnosis. Parents could be relieved from overeating to conditions typical in children. These sounds and images could also be shared with medical professionals for evaluation.

Audiobooks and Podcasts

Listening to audiobooks and podcasts is a popular pastime, with sales growing significantly as people consume more and more content digitally.

In various embodiments, the headset processor 405 allows for easier and more adaptive means of controlling the rate at which the audiobook audio is presented to the user. For example, the headset could automate the regulation of playback speed by having the headset processor 405 detect the level of engagement of the user as she listens, such as by a camera of the headset processor 405 determining that the user is yawning above a fixed threshold of frequency. In this example, when the user yawns more the playback rate of the audio is automatically slowed down. EEG data read from the headband of the users headset could also provide base data on which an engagement level could be determined and used to adjust playback speed up or down.

Playback speed could also be adjusted based on verbal requests from the user. For example, users could listen to an audiobook and say "slower" or "faster" at any point in the book to change the speed of the audio. Data from multiple users aggregated at the central controller could allow users to elect to have the audiobook playback slow down or speed up based on an average of the data collected by the central controller for that page of the audiobook.

Volume level could be adjusted via an audible request from the user, or pressing an up/down volume indicator on the headband or ear cup of the user's headset. Volume changes could also be made automatically based on the level of sound in the users environment. For example, the audio might be at a medium level while a user walks down a quiet street towards a coffee shop, but increases in volume if the headset detects that the coffee shop is a noisier environment.

Audiobook content could also automatically be stopped based on the headset picking up what seems to be a verbal request from someone. For example, a user in line to buy coffee might listen to an audiobook, but when a camera and microphone of the headset detect that a question has been asked of the user, such as an employee asking for an order, the headset processor temporarily stops the audio feed of the audiobook.

Audio content such as audiobooks or podcasts could also be stored within the data storage device of the headset, allowing users to pay for and access content without having to make a purchase at a third party merchant. The headset could also be sold with bundled content stored within, available to a user as long as they are able to authenticate themselves to the headset.

Audiobook content could also be made more dynamic by having the content change based on where the user was when she listened to it or the time of day. For example, the audio content could avoid the words "car accident" if it was determined by the headset that the user was traveling more than 40 miles per hour.

In various embodiments, audio content such as an audiobook or audioplay could be customized to the individual. Akin to a "choose your own adventure story," the audio content could allow the listener to make decisions between different aspects of a plot tree or storyline. The audiobook or play would prompt the listener to make a decision from several options, the listener could use device buttons or voice commands to choose an option, and the audiobook could deliver the branch of the plot tree associated with that choice.

Music

Currently digital media use masking and other forms of information reduction as a form of compression. Music could be provided in an unmixed, multichannel form allowing individuals to customize their own mix or equalizer settings for instrumental and vocal parts. The headset could record the equalizer settings, store these settings for playback of the song at a later time, or enable sharing of these settings as "remixes" with others.

Musicians, producers, and labels could release filters that could enable the headset to alter their audio inputs or outputs to match the style of their favorite artists. Using equalizer settings, masking and signals processing technique, the filter could alter my audio input or output. I could alter all music or audio through a particular filter, or my microphone output could be transformed by the filter. For example, I could buy a licensed filter from my favorite producer or band. I could have all of my vocal output put through a Rick Rubin filter, or my voice could sound like Kanye West's.

The headset could facilitate improved sing-along and karaoke functionality. The central controller 110 could detect whether the headset wearer is singing along to the song and then display lyrics on connected devices with a screen output or the headsets visual outputs. The central controller could also provide upcoming lyrics in an audio channel in one ear to provide coaching on the next lyrics. The central controller could detect when individuals are singing incorrect lyrics, signing off pitch or off tempo.

The devices according to various embodiments could provide feedback or coaching for individuals learning to play music. The central controller could detect what piece of music you are practicing and correct mistakes such as inappropriate changes in tempo, missing noises, inappropriate dynamic range or other musical mistakes. For certain instruments, the central controller could provide audio coaching about changes to finger positioning, vocal embouchure or other physical aspects of the instrument. When it detects repetition of particular errors, the central controller could suggest particular forms of practice or drills to improve weak areas. The central controller could track the amount of deliberate practice (focused repetition) that the wearer is engaging in. For group musical compositions, the headset could play the other musical parts or provide the vocal equivalent of a conductor, telling the wearer when to perform certain musical actions.

Individuals enjoy dancing to music but sometimes struggle to find an appropriate rhythm. The central controller 110 could detect dancing movements through an accelerometer in the headband of the headset, in the ear cups, or located elsewhere in the device. The central controller could enable a metronome or provide feedback on whether the wearer is dancing to the beat of the song.

The central controller 110 could dynamically create playlists depending on contextual information from the headsets inputs. Dynamic playlists could be created depending on time of day, activity, the affective state or mode of the device owner (to counteract affective states or to amplify affective states), sleep, fatigue levels, and location. For example, the central controller could detect that I am lifting weights, am low energy, and am surrounded by other individuals in a gym. It could then create a playlist designed to increase performance by playing loud heavy metal.

Soundtracks may be important audio elements of shows, movies, and digital movies. They are often designed to evoke particular feelings. Yet different types of music produce different affective states in different individuals. TV, movie and video creators could insert metadata into videos that allow the central controller to determine what kind of emotion the creator intended to create and dynamically choose appropriate music for that scene, taking into account the individual's past affective responses to music. Or creators could choose a small number of musical clips and allow the central controller to choose the best option.

Individuals often have pieces or phrases of music "stuck in their head" but can't remember the rest of the song or the name of the song or artist. The wearer could sing or describe the phrase stuck in their head, and the central controller could make suggestions about which piece of music the wearer has stuck in their head. The controller could play clips and the wearer could search using vocal or button controls until they hear the piece or phrase they were thinking of.

Individuals could trade songs or playlists with other wearers of headsets. Often people wearing headsets look as if they are listening to a particularly compelling song or playlist. If they are wearing a headset, another person could query them for permission to listen to their music or they could set permissions to allow individuals around them to sample their audio. Individuals could set a friends list or permission list that allows select other headset wearers to sample their audio. One person could subscribe to someone else's headset, such as a celebrity, a musician or band, or a DJ. Permissions could be geofenced so a first person could make anyone in their vicinity able to hear the first person's playlist. The headset could also suggest songs or playlists to be based upon what other people on a person's friend list or within the person's vicinity are listening to. The central controller could suggest social connections to the person based on the correspondence of his/her musical tastes and the tastes of other individuals in his/her location/area.

In various embodiments, headsets could allow individuals on friends or permissions list to control the music playing in other devices. For example, one person could make a playlist or choose songs for a particular friend.

Individuals feel a sense of pride for discovering obscure or unfollowed music. The central controller could curate a playlist of unpopular songs either in the wearer vicinity or in their friend list. As songs become listened to more and more, the central controller could suggest new obscure music. Some obscure music is obscure for a reason. The central controller could optimize obscurity with other metrics based upon music that the wearer enjoys. For example, the playlist could be the most obscure things that sound like songs I already like.

Headsets could allow musicians to stream concerts and live music directly to headset wearers. Individuals could receive a notification if a musician they like is about to go live, and they could pay for a concert ticket using stored value in the headset. Individuals could use buttons or voice control to tip the musician during the concert.

Individuals could store music in the headset in order to listen to music when they are not connected to other devices or to a network connection.

The central controller 110 could suggest local bands or upcoming concerts based upon the wearers location data and music listening history. The headset could show me what concerts other people in my vicinity are going to attend, so I don't miss a show that will be attended by my peers. The headset could prompt me if I come into contact with other future attendees to facilitate finding a "concert buddy" to go to a show together.

A venue could communicate with the headset to authenticate that an individual had attended an event. Individuals could visually display "social proof" of their attendance on their headset or other connected devices. Headsets could exchange tokens with other headsets in their vicinity or on the same network. People who attend the same concert or event could be prompted when they come in contact with someone else who attended the concert or event, facilitating discovery of individuals with shared interests.

Tickets for a concert, festival, or event could be purchased or traded from headset to headset. I could use voice command or button functionality to find a concert, find available tickets either from the venue or on the secondary market, and purchases or trade for those tickets. Tickets could use the devices authentication and encryption capabilities so that individuals could verify they have purchased valid tickets on the secondary market. My headset could contain my ticket, which would allow me to enter a concert, festival or event without scanning a physical ticket. Headset ticket holders for example could have a shorter queue into a venue. Venues could re-sell tickets based upon event capacity if authenticated ticket holders do not show up to the show at a certain time. I could be prompted if a ticket becomes available during the opening act.

Preferences/Customization

A headset according to various embodiments can become personalized by the user so that the users preferences are reflected in the functionality of the headset and the way that the headset can be employed by the user. Various embodiments allow users participating in virtual calls to customize many aspects of how those communications are heard, seen, and managed. Game players can customize their gameplay experience. The present invention allows users to store information about desired customizations for use in customizing headset experiences. Customizations could be for digital actions, or for physical changes of the headset.

Game players could store their identity for use across games, computers, and operating systems. For example, the headset could store player logins and passwords associated with all of their favorite game characters. This could enable a player to take their headset from their home and go to a friend's house to use it during game play there. The computer or game console owned by their friend could then read in data from the users headset processor 405, enabling the user to log in with any of their characters (such as by having the headset processor 405 retrieve the appropriate login and password from the storage device of the headset, sending that information to the computer of the users friend to be used to initiate a game session for the user) and have access to things like saved inventory items such as a +5 sword or a magic healing potion. The user's mouse could display the items in inventory on a display screen of the user's headset, allowing the user to touch an item on the display screen to select it for use, with the headset processor 405 transmitting the selection to the user device 107*a* or central controller 110. The user could also have access to stored preferences and customization for things like custom light patterns on their headset. The user's headset might also have stored game value that could allow a user to buy game skins during a game session at their friend's house.

The headphone owner could be given options to personalize their headphones visually on the physical headset display device for viewing by other users—such as by designating a lighting pattern on a series of LED lights across the headband of the headset. Such lighting patterns could be done to demonstrate the user's mood for the day (green for happy, blue for sad, red for energetic, etc.), a special event (e.g. the users birth day, month and year scroll across one or more display screens on the headset headband), a recent accomplishment (certification, graduation, birth of a child), or any topic to discuss (such as something in the news that day) or any emoji of interest. If it was the user's birthday that day, the user may want to have the sides of the headphones display a party hat or cake with a candle. Likewise, if the user just received their Agile Certification, the headphone could display their certification badge. In a meeting setting, the meeting owner could call on the person or highlight the person based on the headset display.

Attendees on a conference call are often presented with 'canned' music. In various embodiments, the headphones could automatically retrieve from the data storage device of the headset the type of music that the user prefers, and play that via speakers of the headset that music to the participant while they are waiting. Preferences can be stored with the central controller 110 or made available via the headset data storage device. The headphones can also be used to select different music channels by simply hitting a button on the arm of the headset, or tapping one or more times on the ear cup of the headset.

Similarly to a green screen or background image, a user could be enabled to modify the virtual display of her headphones to be visible to others during a meeting. For example, if the weather is cold outside, I may want to select a headphone background/image to show as ear muffs to others in the meeting.

Physical customization that a user might establish could include elements like the length of the headset band, the tension of the headset band, the direction of one or more cameras, the sensitivity of one or more microphones, the angle of view of a camera, and the like.

Customization of a headset could also include the location of display areas, sensors, cameras, lights, foam padding, length of the headset arm, preferred color patterns, the weight of the headset, etc.

Virtual customization could allow players to establish preferences for a wide range of enhancements. For example, the player might save a preference that when his headset signals that he is away from his computer that any other connected users are alerted that he will return in ten minutes time. Customizations could also include a list of friends who are desired team members for a particular game, or a list of co-workers for virtual business meetings. These other people could automatically be added to a chat stream when that particular game or business call was initiated.

Customizations could be stored in a data storage device of the headset, in a detachable token that can be plugged into the headset processor 405, in the user device 107*a*, or at the central controller 110.

Customization could also be tied to the location of the user. For example, information in a data storage device of the headset might be unlocked for a user only when he is within a particular geographical area. The functionality of the headset could also vary depending on the location of the user. For example, a user who steps away from his desk while on a call could trigger the headset processor to automatically mute the user.

Nudges

Nudges may include brief reminders to users to be aware of their current behavior for possible modification. These nudges are more passive in nature and various embodiments can assist the user in correcting and improving the desired behavior.

Nudges may help people stop the use of phrases. Some people have bad habits they try to stop, and the headset could provide alerts (audio, visual or movement) when the phrase or habit is recognized. In some embodiments, if someone uses phrases like, 'you always act like . . . ' or 'stop yelling at me', the virtual assistant could provide audio coaching and tell the user to stop the use of the phrase. This could be in the form of an audio announcement or audio cue (e.g. vibration, beep). In other embodiments, the user may use too casual of word choices for a conversation and need to be informed to correct. These could include using the term 'bro' with people in authority or in a more formal discussion. Furthermore, the assistant could provide alternative steps to correct the action based on available resources.

In some embodiments, nudges may help avoid vocal hesitations and distractions. For example, delivering a presentation or content to another person can be distracting if there are overuses of phrases or delay tactics. Examples include using the words, 'um,' ah', 'like; or use of slang and stalling. The headset could inform or nudge the user of these words for immediate correction or provide a summary feedback (via the central controller) to the user after the event (e.g., number of times a word was used, amount of delay).

In some embodiments, nudges may serve as human performance reminders. There are times that users fail to recall the coaching provided by their managers, peers or professional coaches and need to be reminded. Headset 4000 could allow those individuals ('coaches') the ability to 'nudge' the user to take some action or improve based on observations. In some embodiments, if a manager has coached an employee to be more assertive in meetings, when there is a meeting taking place where the employee is being perceived as passive, the manager could simply send a reminder through the headset that alerts the employee to exhibit more assertive behavior. These could take the form of non-verbal or verbal reminders. This real-time coaching reminder is valuable to increase the chances of modifying behavior and improving human performance in a way that is not distracting to others or calls attention to the person needing to improve.

Coaching and Training

Coaching and training are key developmental activities that both employees and employers are continually looking to deliver. Individuals also desire coaches for both recreational activities, self-help studies and those are or are perceived as successful in their field of expertise. Coaching and training requires investment in time and resources to not only observe the behavior of a person, but also the skills to deliver effective feedback, suggest improvements and motivate them to continue. In many cases, timely delivery of feedback is not possible and hence the effectiveness diminishes. The headset and central controller AI system could allow the users to subscribe (or receive) to coaching and training based on their level of interest or goals, observe the behavior and provide feedback on improvements or encouragement on performing the activity and match the feedback to the learning style of the user. This coaching and training is dynamic and could be provided in real time when the activity occurs or after the fact.

Various embodiments include a headset equipped with a virtual assistant. Users sometimes need to be coached through a task or simply inquire about an issue. In various embodiments, a headset could not only provide audio feedback, but also video. For example, if the user is refinishing a piece of furniture and needs to see instructions for removing varnish, the user could simply say to the headset to coach me through refinishing. Both audio and video cues could be delivered to the user.

In various embodiments, micromovements and/or voice commands turn on an assistant. The headset equipped with a camera/microphone could always be monitoring the user for physical movements, vocal commands and biometrics If the user's heart rate, facial expression (e.g. scowling or perplexed look) or comments (e.g. 'I'm not sure about this', 'how do I do this', 'this doesn't feel right') indicates there is an opportunity for assistance, the virtual assistant could automatically offer coaching and training.

Various embodiments include voice controls and/or a virtual assistant. The central controller could be aware of the task or activity the user is participating in, or the user simply requests the virtual assistant for help. For example, a user is wanting to bake a chocolate cake and requests assistance from the virtual assistant. Instead of simply delivering a static version of a recipe, the virtual assistant could walk through each step of the recipe with the user, observe the step and approve before moving on using the headset with camera(s). The headset with camera could see that the dry ingredients were not mixed thoroughly and provide the user with feedback to continue mixing. In addition, if the user was supposed to use two eggs and the assistant observes only one egg, feedback could be provided that only one egg was used. In this way, the user could not only get verbal instructions, but also observation of the task, making coaching and training more effective.

In various embodiments, a virtual assistant could remind users of behavioral issues, such as talking over each other. Coaching people for behavioral corrections is difficult because they need to occur at the time the behavior is noticed and not after the fact. In a business setting or conference call, this is not always possible or appropriate during a professional setting. The virtual assistant could remind users of behavioral issues in real time. In addition, various embodiments could allow a message to appear on a screen indicating that people are speaking over each other. For example, if a person is always interrupting others on a call, the headset could notice this behavior and inform the user to be more conscious and wait until others are finished talking. Likewise, a message on their screen could say, 'wait your turn, others are speaking' as a reminder.

Various embodiments facilitate a prompter. The central controller 110 could provide prompts to the user regarding content being delivered. For example, a user may be delivering key updates using summary slides. The slides may contain details in the notes section but are not easily accessible during a presentation. If the presenter is asked a question, the central controller could interpret the question and provide the user with prompts regarding relevant details in the notes section or other sources of information.

In various embodiments, a virtual assistant can help a manager to provide coaching to an employee or other individual. Managers may observe behaviors (good and bad) that need to be delivered to an employee, but full schedules by both do not allow for timely feedback and discussion. The headset could allow a manager to record feedback for the employee. The central controller 110 could tag the feedback and make it available to both parties for review at a convenient time. In addition, the central controller could edit the feedback to be more succinct and use words that are more coaching oriented (start with positive feedback, provide specific examples referencing the audio/video/content recorded) to achieve increased employee performance and acceptance of the feedback.

In various embodiments, coaching and training may be delivered in a user's preferred learning style. Users may desire a coach that gives them commands on how to perform better, while others may respond better to feedback from a more encouraging style. Still others may prefer to receive feedback as areas of opportunity and not corrections/errors. The headset and central controller could allow the user to select their preferred learning style and the feedback adapted to match the style.

In various embodiments, coaching may be provided based on goals and desired feedback levels. Users performing activities may have different goals. Some may desire to achieve a level of improvement in a certain time period while others are just interested in some helpful techniques. The headset and central controller could allow the user to specify their goals and tailor the amount of feedback during or after an activity accordingly. For example, if a person is wanting to compete in a 5K running race in one month, the central controller could provide a coach that is frequently telling the user to run certain distances, start eating healthier and set a pace goal, while at the same time giving feedback during the activity on progress and corrections in more of a militant style. On the other hand, another user may want to simply run a 5K sometime in the next 6 months and do so casually. In this case, the virtual coach may provide helpful techniques on running durations, food items to each and in a more encouraging tone.

Various embodiments facilitate coaching a user for or during a game. There is increased interest in the gaming community to improve skills and learn from others. Various embodiments could use the camera(s) and headset to provide coaching advice to gamers during the game or after the game. The user of the head set could act as a coach or student at any point in time. For example, the headset with a camera could show the hand position while playing a game so that others on my team can learn from the players style and see how the keyboard is laid out. Or, as an in game option, the observers could click on a character to see what the keyboard layout of the player looks like.

Various embodiments facilitate provision of feedback to a user regarding the user's current coaches. People often enlist the help of coaches and trainers that have little impact on the users performance over a given period of time. In this case, various embodiments could use the camera, microphone and headset to give feedback to the user that after observing the interactions of their coach, there are other alternatives that could help them improve. If the user hires a coach for delivering effective presentations, but the coach rarely provides actionable points or does not engage the presenter, the headset could provide the user with a list of more qualified coaches. Moreover, if the coach is providing good feedback, the headset could tell the user to continue and to work harder or listen to the coach's feedback.

Various embodiments facilitate training a user to ignore factors and people. There may be individuals or behaviors that are disruptive to the user. The headset with a central controller could learn the people and behaviors and remind the user at times to ignore this until they no longer are distracted. For example, there may be an executive who attends a weekly update meeting that is continually making negative facial expressions which throw off the presenter. The central controller with headset/camera could recognize the individual and coach the user to ignore the face or look beyond them or beside them. These coaching tips could help to improve the overall performance of the individual.

Various embodiments facilitate comparison coaching. There are people who are competitive and are motivated by knowing where they rank in a class or people of similar skill. The headset could provide them ongoing feedback as to their ranking and improvement within the collective benchmark. For example, if a person is trying to achieve a perfect score on the ACT, the coach may provide insight into the person's relative ranking based on the results of each practice exam and provide helpful coaching on sections to study more.

Various embodiments facilitate coach matching. There are times when a person makes a connection with a coach based on factors other than pure skill. Various embodiments could facilitate the matching of coaches with students by providing short term coaching engagements on a trial basis. The headset could monitor the biometric data of the student and provide feedback if there is a match where they are exhibiting signs of general favorability.

Various embodiments facilitate coaching on audio and headset set-up. The set up of technology can be difficult for some users or they don't enable all capabilities. The headset could instruct the user how to set-up the audio for the environment they are in or how to enable all functions of the headset.

Various embodiments facilitate coaching on conversation coach, such as how to handle awkward pauses. Awkward pauses are challenging for individuals that are not versed in conversation. The headset could realize this by measuring pauses and assist in prompting individuals with discussion topics that are unique to the individual and previously learned by the central controller. For example, the user finishes some introductory comments with an individual and their mind goes blank and there is a pause. The headset, at the prompting of the user or automatically, could provide the user with topics unique to the other person. The central controller could know the individual is interested in NBA basketball and prompts the user to ask them about their favorite team. This type of assistant can help the user learn to engage others and improve overall human performance. Other examples of information that could be provided include the Individual's name, role, how the user met the individual, etc. The headset could also provide factual information including news articles, information in their current context (e.g. school subject, game attending, project being worked), and so on.

Various embodiments provide coaching on conversations, including coaching on social awareness. There are people who do not notice the minor verbal/non-verbal feedback from others to help guide the conversation. When the headset notices these, coaching or non-verbal feedback could be given to the user to assist them in moving to another topic or ending the conversation. Social cues could include total time spoken in relation to the entire conversation. Social cues may include biometric feedback collected from the other person to measure engagement, including smiling, eye contact, micro-expressions. Social cues may include tone and meter of speech. Social cues may include vocal variety and modulation of voice.

Digital Audio Ads

Digital audio advertising is a growing segment as users switch from radio listening to digital audio, music, audiobooks, and podcasts. Headsets described according to various embodiments could improve ad targeting for digital audio and allow customization of digital ads based upon data collected by the device such as the wearer's affective state, the wearer's current activity, engagement or attention level, sleep, fatigue, or health status.

Devices of according to various embodiments could allow an AI module to be trained that predicts key demographic, lifestyle and potential spending data for marketing purposes such as age, gender, education level, occupation type, income bracket, housing and household attributes, spending patterns, patterns of life, daily locational movements, social embeddedness, beliefs, ideologies, daily activities, interests, and media consumption of the device wearer. headsets could allow ads to be customized to the device wearer—either physical or digital advertising—using demographic, lifestyle, and potential spending level. By combining location data and other data on the wearer with eye gaze or engagement data, the central controller could allow micro-targeting of advertising to very specific segments.

Devices according to various embodiments could allow an AI module to be trained that predicts the device owner's engagement level, mood, and level of alertness or attention. Headsets could be equipped with such as heart rate sensors, galvanic skin response sensors, sweat and metabolite sensors, or other biometric sensors. The data generated by these biometric sensors could be. The devices according to various embodiments could send biometric data to the owners computing device or an external server. An AI module could be trained using these inputs which would predict dimensions about the physical and mental state of the device user, such as engagement, affective state, or persuadability.

By gathering information about the activities that a wearer is engaging in, the central controller could dynamically serve ads or price ads. The central controller could detect competing stimuli such as visual distractions or whether the wearer is engaged in a physical task such as running or typing either to improve ad targeting based upon contextual information or price ads based upon whether audio ads would be competing with other sources of stimuli.

Headsets could allow the central controller 110 to record, sample, or analyze audio played by the device wearer such as music, audiobooks, digital radio, digital music, podcasts, digital videos played in the background as audio, spoken conversations and ambient environmental noise. The central controller could use information gleaned from sampling or analyzing device audio inputs and outputs to increase granularity of advertising segmentation, to provide more relevant advertising based upon contingent and contextual information, or to customize the kinds of messaging and advertising techniques to individuals prefer.

An AI module of user engagement could permit advertisers to target ads optimally to the user's mental and physical state and dynamically target ads based upon these states. For example, an advertiser might predict that their ad is more likely to be effective when users are alert or when users are hungry. The devices according to various embodiments could enable dynamic pricing of advertisements, for example, based upon what activity a device is being used for or based upon individual users mental and physical states. For example, an ad placement might be less valuable if a user is typing, which indicates that they may not be paying attention to the ad.

By combining device data from sensors such as the forward facing camera, the central controller 110 can gain insights into aspects of the marketing funnel such as conversion of ads from impressions into behavior.

The central controller 110 could help optimize the insertion of digital audio ads into audio content by measuring engagement, intent-to-buy and purchasing behavior in response to different types of ads. Many attributes of inserting audio ads could be tailored to individual device wearers such as whether individuals prefer clustered or spaced out ads, whether certain lengths of ads are more or less effective, or whether certain aspects of the audio such as volume, tone, word cadence, etc., should be tailored to the device wearer.

Paste Before Copy

During word processing and other common tasks (e.g., computer-related tasks), a conventional method for copying and pasting is to first copy (e.g., copy a stretch of text), then paste (e.g., paste the stretch of text previously copied). According to various embodiments, the sequence of copy and paste is reversed. A user first indicates a desire to "paste" at a first location (e.g., at a first location in a document). For example, the user hits ctrl-v. The user subsequently highlights text, or otherwise selects text or some object (e.g., at a second location in the document) and hits ctrl-c. The computer (or other device), thereupon automatically pastes the selected text (or other object) into the first location. Advantageously, if a user starts the process with his cursor at a location where pasting is desired, the user can immediately indicate his desire to paste without first having to move the cursor to copy, and then return the cursor to the starting location to paste.

Rules of Interpretation

Throughout the description herein and unless otherwise specified, the following terms may include and/or encompass the example meanings provided. These terms and illustrative example meanings are provided to clarify the language selected to describe embodiments both in the specification and in the appended claims, and accordingly, are not intended to be generally limiting. While not generally limiting and while not limiting for all described embodiments, in some embodiments, the terms are specifically limited to the example definitions and/or examples provided. Other terms are defined throughout the present description.

Some embodiments described herein are associated with a "user device" or a "network device". As used herein, the terms "user device" and "network device" may be used interchangeably and may generally refer to any device that can communicate via a network. Examples of user or network devices include a PC, a workstation, a server, a printer, a scanner, a facsimile machine, a copier, a Personal Digital Assistant (PDA), a storage device (e.g., a disk drive), a hub, a router, a switch, and a modem, a video game console, or a wireless phone. User and network devices may comprise one or more communication or network components. As used herein, a "user" may generally refer to any individual and/or entity that operates a user device. Users may comprise, for example, customers, consumers, product underwriters, product distributors, customer service representatives, agents, brokers, etc.

As used herein, the term "network component" may refer to a user or network device, or a component, piece, portion, or combination of user or network devices. Examples of network components may include a Static Random Access Memory (SRAM) device or module, a network processor, and a network communication path, connection, port, or cable.

In addition, some embodiments are associated with a "network" or a "communication network". As used herein, the terms "network" and "communication network" may be used interchangeably and may refer to any object, entity, component, device, and/or any combination thereof that permits, facilitates, and/or otherwise contributes to or is associated with the transmission of messages, packets, signals, and/or other forms of information between and/or within one or more network devices. Networks may be or include a plurality of interconnected network devices. In some embodiments, networks may be hard-wired, wireless, virtual, neural, and/or any other configuration of type that is or becomes known. Communication networks may include, for example, one or more networks configured to operate in accordance with the Fast Ethernet LAN transmission standard 802.3-2002® published by the Institute of Electrical and Electronics Engineers (IEEE). In some embodiments, a network may include one or more wired and/or wireless networks operated in accordance with any communication standard or protocol that is or becomes known or practicable.

As used herein, the terms "information" and "data" may be used interchangeably and may refer to any data, text, voice, video, image, message, bit, packet, pulse, tone, waveform, and/or other type or configuration of signal and/or information. Information may comprise information packets transmitted, for example, in accordance with the Internet Protocol Version 6 (IPv6) standard as defined by "Internet Protocol Version 6 (IPv6) Specification" RFC 1883, published by the Internet Engineering Task Force (IETF), Network Working Group, S. Deering et al. (December 1995). Information may, according to some embodiments, be compressed, encoded, encrypted, and/or otherwise packaged or manipulated in accordance with any method that is or becomes known or practicable.

In addition, some embodiments described herein are associated with an "indication". As used herein, the term "indication" may be used to refer to any indicia and/or other information indicative of or associated with a subject, item, entity, and/or other object and/or idea. As used herein, the phrases "information indicative of" and "indicia" may be used to refer to any information that represents, describes, and/or is otherwise associated with a related entity, subject, or object. Indicia of information may include, for example, a code, a reference, a link, a signal, an identifier, and/or any combination thereof and/or any other informative representation associated with the information. In some embodiments, indicia of information (or indicative of the information) may be or include the information itself and/or any portion or component of the information. In some embodiments, an indication may include a request, a solicitation, a broadcast, and/or any other form of information gathering and/or dissemination.

Numerous embodiments are described in this patent application, and are presented for illustrative purposes only. The described embodiments are not, and are not intended to be, limiting in any sense. The presently disclosed invention(s) are widely applicable to numerous embodiments, as is readily apparent from the disclosure. One of ordinary skill in the art will recognize that the disclosed invention(s) may be practiced with various modifications and alterations, such as structural, logical, software, and electrical modifications. Although particular features of the disclosed invention(s) may be described with reference to one or more particular embodiments and/or drawings, it should be understood that such features are not limited to usage in the one or more particular embodiments or drawings with reference to which to are described, unless expressly specified otherwise.

"Determining" something can be performed in a variety of manners and therefore the term "determining" (and like terms) includes calculating, computing, deriving, looking up (e.g., in a table, database or data structure), ascertaining and the like. The term "computing" as utilized herein may generally refer to any number, sequence, and/or type of electronic processing activities performed by an electronic device, such as, but not limited to looking up (e.g., accessing a lookup table or array), calculating (e.g., utilizing multiple numeric values in accordance with a mathematical formula), deriving, and/or defining.

Numerous embodiments have been described, and are presented for illustrative purposes only. The described embodiments are not intended to be limiting in any sense. The invention is widely applicable to numerous embodiments, as is readily apparent from the disclosure herein. These embodiments are described in sufficient detail to enable those skilled in the art to practice the invention, and it is to be understood that other embodiments may be utilized and that structural, logical, software, electrical and other changes may be made without departing from the scope of the present invention. Accordingly, those skilled in the art will recognize that the present invention may be practiced with various modifications and alterations. Although particular features of the present invention may be described with reference to one or more particular embodiments or figures that form a part of the present disclosure, and in which are shown, by way of illustration, specific embodiments of the invention, it should be understood that such features are not limited to usage in the one or more particular embodiments or figures with reference to which they are described. The present disclosure is thus neither a literal description of all embodiments of the invention nor a listing of features of the invention that must be present in all embodiments.

The terms "an embodiment", "embodiment", "embodiments", "the embodiment", "the embodiments", "an embodiment", "some embodiments", "an example embodiment", "at least one embodiment", "one or more embodiments" and "one embodiment" mean "one or more (but not necessarily all) embodiments of the present invention(s)" unless expressly specified otherwise.

The terms "including", "comprising" and variations thereof mean "including but not limited to", unless expressly specified otherwise.

The term "consisting of" and variations thereof mean "including and limited to", unless expressly specified otherwise.

The enumerated listing of items does not imply that any or all of the items are mutually exclusive. The enumerated listing of items does not imply that any or all of the items are collectively exhaustive of anything, unless expressly specified otherwise. The enumerated listing of items does not imply that the items are ordered in any manner according to the order in which they are enumerated.

The term "comprising at least one of" followed by a listing of items does not imply that a component or sub-component from each item in the list is required. Rather, it means that one or more of the items listed may comprise the item specified. For example, if it is said "wherein A comprises at least one of: a, b and c" it is meant that (i) A may comprise a, (ii) A may comprise b, (iii) A may comprise c, (iv) A may comprise a and b, (v) A may comprise a and c, (vi) A may comprise b and c, or (vii) A may comprise a, b and c.

The terms "a", "an" and "the" mean "one or more", unless expressly specified otherwise.

The term "based on" means "based at least on", unless expressly specified otherwise.

The methods described herein (regardless of whether they are referred to as methods, processes, algorithms, calculations, and the like) inherently include one or more steps. Therefore, all references to a "step" or "steps" of such a method have antecedent basis in the mere recitation of the term 'method' or a like term. Accordingly, any reference in a claim to a 'step' or 'steps' of a method is deemed to have sufficient antecedent basis.

Headings of sections provided in this document and the title are for convenience only, and are not to be taken as limiting the disclosure in any way.

Devices that are in communication with each other need not be in continuous communication with each other, unless expressly specified otherwise. In addition, devices that are in communication with each other may communicate directly or indirectly through one or more intermediaries.

A description of an embodiment with several components in communication with each other does not imply that all such components are required, or that each of the disclosed components must communicate with every other component. On the contrary a variety of optional components are described to illustrate the wide variety of possible embodiments of the present invention.

Further, although process steps, method steps, algorithms or the like may be described in a sequential order, such processes, methods and algorithms may be configured to work in alternate orders. In other words, any sequence or order of steps that may be described in this document does not, in and of itself, indicate a requirement that the steps be performed in that order. The steps of processes described herein may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to the invention, and does not imply that the illustrated process is preferred.

It will be readily apparent that the various methods and algorithms described herein may be implemented by, e.g., appropriately programmed general purpose computers and computing devices.

A "processor" generally means any one or more microprocessors, CPU devices, computing devices, microcontrollers, digital signal processors, or like devices, as further described herein.

Typically a processor (e.g., a microprocessor or controller device) will receive instructions from a memory or like storage device, and execute those instructions, thereby performing a process defined by those instructions. Further, programs that implement such methods and algorithms may be stored and transmitted using a variety of known media.

When a single device or article is described herein, it will be readily apparent that more than one device/article (whether or not they cooperate) may be used in place of a single device/article. Similarly, where more than one device or article is described herein (whether or not they cooperate), it will be readily apparent that a single device/article may be used in place of the more than one device or article.

The functionality and/or the features of a device may be alternatively embodied by one or more other devices which are not explicitly described as having such functionality/features. Thus, other embodiments of the present invention need not include the device itself.

The term "computer-readable medium" as used herein refers to any medium that participates in providing data (e.g., instructions) that may be read by a computer, a processor or a like device. Such a medium may take many forms, including but not limited to, non-volatile media, volatile media, and transmission media. Non-volatile media include, for example, optical or magnetic disks and other persistent memory. Volatile media may include dynamic random access memory (DRAM), which typically constitutes the main memory. Transmission media may include coaxial cables, copper wire and fiber optics, including the wires or other pathways that comprise a system bus coupled to the processor. Transmission media may include or convey acoustic waves, light waves and electromagnetic emissions, such as those generated during radio frequency (RF) and infrared (IR) data communications. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge, a carrier wave as described hereinafter, or any other medium from which a computer can read.

The term "computer-readable memory" may generally refer to a subset and/or class of computer-readable medium that does not include transmission media such as waveforms, carrier waves, electromagnetic emissions, etc. Computer-readable memory may typically include physical media upon which data (e.g., instructions or other information) are stored, such as optical or magnetic disks and other persistent memory, DRAM, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge, computer hard drives, backup tapes, Universal Serial Bus (USB) memory devices, and the like.

Various forms of computer readable media may be involved in carrying sequences of instructions to a processor. For example, sequences of instruction (i) may be delivered from RAM to a processor, (ii) may be carried over a wireless transmission medium, and/or (iii) may be formatted according to numerous formats, standards or protocols, such as Transmission Control Protocol, Internet Protocol (TCP/IP), Wi-Fi®, Bluetooth®, TDMA, CDMA, and 3G.

Where databases are described, it will be understood by one of ordinary skill in the art that (i) alternative database structures to those described may be readily employed, and (ii) other memory structures besides databases may be readily employed. Any schematic illustrations and accompanying descriptions of any sample databases presented herein are illustrative arrangements for stored representations of information. Any number of other arrangements may be employed besides those suggested by the tables shown. Similarly, any illustrated entries of the databases represent exemplary information only; those skilled in the art will understand that the number and content of the entries can be different from those illustrated herein. Further, despite any depiction of the databases as tables, other formats (including relational databases, object-based models and/or distributed databases) could be used to store and manipulate the data types described herein.

Likewise, object methods or behaviors of a database can be used to implement the processes of the present invention. In addition, the databases may, in a known manner, be stored locally or remotely from a device that accesses data in such a database.

For example, as an example alternative to a database structure for storing information, a hierarchical electronic file folder structure may be used. A program may then be used to access the appropriate information in an appropriate file folder in the hierarchy based on a file path named in the program.

The present invention can be configured to work in a network environment including a computer that is in communication, via a communications network, with one or more devices. The computer may communicate with the devices directly or indirectly, via a wired or wireless medium such as the Internet, LAN, WAN or Ethernet, Token Ring, or via any appropriate communications means or combination of communications means. Each of the devices may comprise computers, such as those based on the Intel® Pentium® or Centrino™ processor, that are adapted to communicate with the computer. Any number and type of machines may be in communication with the computer.

It should also be understood that, to the extent that any term recited in the claims is referred to elsewhere in this document in a manner consistent with a single meaning, that is done for the sake of clarity only, and it is not intended that any such term be so restricted, by implication or otherwise, to that single meaning.

In a claim, a limitation of the claim which includes the phrase "means for" or the phrase "step for" means that 35 U.S.C. § 112, paragraph 6, applies to that limitation.

In a claim, a limitation of the claim which does not include the phrase "means for" or the phrase "step for" means that 35 U.S.C. § 112, paragraph 6 does not apply to that limitation, regardless of whether that limitation recites a function without recitation of structure, material or acts for performing that function. For example, in a claim, the mere use of the phrase "step of" or the phrase "steps of" in referring to one or more steps of the claim or of another claim does not mean that 35 U.S.C. § 112, paragraph 6, applies to that step(s).

With respect to a means or a step for performing a specified function in accordance with 35 U.S.C. § 112, paragraph 6, the corresponding structure, material or acts described in the specification, and equivalents thereof, may perform additional functions as well as the specified function.

Computers, processors, computing devices and like products are structures that can perform a wide variety of functions. Such products can be operable to perform a specified function by executing one or more programs, such as a program stored in a memory device of that product or in a memory device which that product accesses. Unless expressly specified otherwise, such a program need not be based on any particular algorithm, such as any particular algorithm that might be disclosed in the present application. It is well known to one of ordinary skill in the art that a specified function may be implemented via different algorithms, and any of a number of different algorithms would be a mere design choice for carrying out the specified function.

Therefore, with respect to a means or a step for performing a specified function in accordance with 35 U.S.C. § 112, paragraph 6, structure corresponding to a specified function includes any product programmed to perform the specified function. Such structure includes programmed products which perform the function, regardless of whether such product is programmed with (i) a disclosed algorithm for performing the function, (ii) an algorithm that is similar to a disclosed algorithm, or (iii) a different algorithm for performing the function.

The present disclosure provides, to one of ordinary skill in the art, an enabling description of several embodiments and/or inventions. Some of these embodiments and/or inventions may not be claimed in the present application, but may nevertheless be claimed in one or more continuing applications that claim the benefit of priority of the present application. Applicants intend to file additional applications to pursue patents for subject matter that has been disclosed and enabled but not claimed in the present application.

While various embodiments have been described herein, it should be understood that the scope of the present invention is not limited to the particular embodiments explicitly described. Many other variations and embodiments would be understood by one of ordinary skill in the art upon reading the present description.

What is claimed is:

1. A headset for authenticating a first user based on brain activity of the first user, the headset comprising:
   an electronic processing device;
   a set of electrodes, each electrode operable to detect an electrical potential at a respective point on a head of a first user;
   an amplifier in communication with each of the electrodes and with the electronic processing device, the amplifier operable to amplify differences in the electrical potentials detected at the respective electrodes;
   a camera in communication with the electronic processing device; and
   a memory storing (i) image analysis instructions, (ii) stored object data, (iii) stored brain wave data, and (iv) processing instructions that, when executed by the electronic processing device, result in:
      capturing, at a first time and by the camera, an image;
      identifying, by an execution of the image analysis instructions by the electronic processing device, an object in the image;
      identifying, by the electronic processing device and by matching the identified object to a portion of the stored object data, the object as an object that should be familiar to the first user;
      sensing, by the set of electrodes and at a second time proximate to and following the first time, a waveform representing a time-varying difference in electrical potentials across the set of electrodes;
      identifying, by the electronic processing device and by comparing the sensed waveform to the stored brain wave data, a deviation of the waveform from the stored brain wave data;
      identifying, by the electronic processing device and by comparing the identified deviation to a stored threshold, that the first user has exhibited a brain wave response to the object in the image; and
      authorizing, in response to the identifying of the brain wave response to the object in the image, the first user to access a resource.

2. The headset of claim 1, further comprising:
   a network device in communication with the electronic processing device.

3. The headset of claim 2, wherein the authorizing, comprises:
   transmitting, by the network device, a wireless command indicative of the authorization for the first user to access the resource.

4. The headset of claim 1, wherein the processing instructions, when executed by the electronic processing device, further result in:

outputting an instruction directing the first user to look at the object.

5. The headset of claim 1, wherein the waveform comprises an electroencephalogram.

6. The headset of claim 1, wherein the portion of the stored object data comprises data descriptive of a location of the object and wherein the identifying that the object should be familiar to the first user comprises identifying a previous location of the first user that is proximate to the location of the object.

7. The headset of claim 1, wherein the portion of the stored object data comprises data descriptive of a certification associated with the object and wherein the identifying that the object should be familiar to the first user comprises verifying that the first user has obtained the certification.

8. The headset of claim 1, wherein the resource comprises an electronically-actuated access device.

9. The headset of claim 1, wherein the resource comprises a computing device.

10. The headset of claim 1, wherein the resource comprises an electronic storage address.

11. A headset for authenticating a first user based on verification of the first user by a second user, the headset comprising:
an arcuate housing operable to be removably coupled to a head of a first user;
an electronic processing device coupled to the housing;
a speaker in communication with the electronic processing device;
a microphone in communication with the electronic processing device; and
a memory storing (i) human identification instructions, (ii) speech recognition instructions, and (iii) processing instructions that, when executed by the electronic processing device, result in:
identifying, by the electronic processing device, a proximity of a second user with respect to the first user;
identifying, by an execution of the human identification instructions by the electronic processing device, the second user;
determining, by the electronic processing device, that the second user is a member of a trusted group of users;
outputting, by the speaker, an audible instruction requesting that the second user verify an identify of the first user;
receiving, by the microphone, a verbal response from the second user;
computing, by an execution of the speech recognition instructions by the electronic processing device and based on the verbal response from the second user, an indication of a verification of the first user by the second user; and
authorizing, in response to the computing of the indication of the verification of the first user by the second user, the first user to access a resource.

12. The headset of claim 11, further comprising:
a network device in communication with the electronic processing device.

13. The headset of claim 12, wherein the authorizing, comprises:
transmitting, by the network device, a wireless command indicative of the authorization for the first user to access the resource.

14. The headset of claim 11, wherein the outputting, comprises:

computing a distance to the second user; and
selecting an output volume based on the distance to the second user.

15. The headset of claim 11, wherein the identifying of the second user, comprises:
matching, by an execution of the human identification instructions by the electronic processing device, a portion of an image captured of an area proximate to the first user that is captured by the camera to stored data descriptive of a plurality of users; and
identifying, based on the matching, an association between the portion of the image and the second user.

16. The headset of claim 11, wherein the processing instructions, when executed by the electronic processing device, further result in:
storing, by the memory, an indication of the authorizing.

17. The headset of claim 16, wherein the processing instructions, when executed by the electronic processing device, further result in:
detecting a removal of the headset from the head of the first user; and
erasing the stored indication of the authorizing.

18. The headset of claim 11, further comprising:
a camera in communication with the electronic processing device.

19. The headset of claim 18, wherein the identifying of the proximity of the second user with respect to the first user, comprises:
capturing, by the camera, an image of an area proximate to the first user; and
matching, by an execution of the human identification instructions by the electronic processing device, a portion of the image to stored data descriptive of a human.

20. The headset of claim 18, wherein the identifying of the second user, comprises:
capturing, by the camera, an image of an area proximate to the first user; and
matching, by an execution of the human identification instructions by the electronic processing device, a portion of the image to stored data descriptive of the second user.

21. A headset for authenticating a first user based on an on-going, multi-tiered authentication process, the headset comprising:
an electronic processing device;
a speaker in communication with the electronic processing device;
a microphone in communication with the electronic processing device;
a positioning system in communication with the electronic processing device;
an accelerometer in communication with the electronic processing device; and
a memory storing (i) point allocation instructions, (ii) referential instructions, and (iii) processing instructions that, when executed by the electronic processing device, result in:
outputting, by the speaker, a query to a user;
receiving, by the microphone and in response to the query, a response from the user;
computing, by an execution of the point allocation instructions by the electronic processing device and based on the response from the user, a first number of points;
identifying, by the positioning system, a location of the user;

computing, by an execution of the point allocation instructions by the electronic processing device and based on the location of the user, a second number of points;
sensing, by the microphone, background noise in an environment of the user;
identifying, by an execution of the referential instructions by the electronic processing device and based on the background noise, a deviation of the background noise to a stored data descriptive of reference background noise;
computing, by an execution of the point allocation instructions by the electronic processing device and based on the deviation of the background noise, a third number of points;
sensing, by the accelerometer, a movement of the user;
identifying, by an execution of the referential instructions by the electronic processing device and based on the movement of the user, a gesture corresponding to the movement of the user;
computing, by an execution of the point allocation instructions by the electronic processing device and based on the gesture, a fourth number of points;
calculating, based on the first, second, third, and fourth numbers of points, an authorization score;
identifying that the calculated authorization score meets a threshold criterion for authorization; and
authorizing, in response to the identifying that the calculated authorization score meets the threshold criterion for authorization, the first user to access a resource.

22. The headset of claim 21, further comprising:
a network device in communication with the electronic processing device.

23. The headset of claim 22, wherein the authorizing, comprises:
transmitting, by the network device, a wireless command indicative of the authorization for the first user to access the resource.

24. The headset of claim 21, wherein the reference background noise comprises a pre-recorded sound of a dog barking in an environment of the user.

25. The headset of claim 21, wherein the query comprises a voice prompt for a password.

26. The headset of claim 21, further comprising:
a camera in communication with the electronic processing device.

27. The headset of claim 26, wherein the calculating of the authorization score is further based on a fifth number of points and wherein the processing instructions, when executed by the electronic processing device, further result in:
capturing, by the camera, an image of an environment surrounding the user;
identifying, by the electronic processing device, an object in the image;
prompting, by the electronic processing device, the user to provide an identification of the object;
receiving, in response to the prompting, a user-indicated identification of the object;
comparing, by the electronic processing device, the user-indicated identification of the object to the identification of the object by the electronic processing device; and
computing, by an execution of the point allocation instructions by the electronic processing device and based on the comparing, the fifth number of points.

28. The headset of claim 26, wherein the calculating of the authorization score is further based on a fifth number of points and wherein the processing instructions, when executed by the electronic processing device, further result in:
prompting the user to sequentially orient the camera in a plurality of directions;
capturing, by the camera and at each orientation, an image of an environment surrounding the user;
computing, by an execution of the referential instructions by the electronic processing device and based on the images of the environment surrounding the user, the location of the user; and
computing, by an execution of the point allocation instructions by the electronic processing device and based on the computing of the location, the fifth number of points.

29. The headset of claim 21, further comprising a biometric device in communication with the electronic processing device, and wherein the calculating of the authorization score is further based on a fifth number of points and wherein the processing instructions, when executed by the electronic processing device, further result in:
sensing, by the biometric device, a biometric reading of the user; and
computing, by an execution of the point allocation instructions by the electronic processing device and based on the biometric reading of the user, the fifth number of points.

30. The headset of claim 21, wherein the calculating of the authorization score is further based on a fifth number of points and wherein the processing instructions, when executed by the electronic processing device, further result in:
identifying an electronic device in proximity to the location of the user;
transmitting a command to the electronic device, the command being operable to cause the electronic device to output a verification;
detecting an indication of the verification; and
computing, by an execution of the point allocation instructions by the electronic processing device and based on the detecting of the indication of the verification, the fifth number of points.

* * * * *